US010647993B2

(12) United States Patent
Grossi De Sa et al.

(10) Patent No.: US 10,647,993 B2
(45) Date of Patent: May 12, 2020

(54) GENETIC CONSTRUCT EXPRESSING INSECTICIDAL TOXIN AND THE METHOD OF USING THEREOF

(75) Inventors: Maria Fatima Grossi De Sa, Brasilia (BR); Gustavo Ramos De Oliveira, Brasilia (BR); Maria Cristina Mattar Da Silva, Brasilia (BR); Thales Lima Rocha, Brasilia (BR); Mariana Torquato Quezado De Magalhaes, Brasilia (BR)

(73) Assignee: EMPRESA BRASILEIRA DE PESQUISA AGROPECUARIA—EMBRAPA, Brasilia-DF (BR)

( * ) Notice: Subject to any disclaimer, the term of this patent is extended or adjusted under 35 U.S.C. 154(b) by 786 days.

(21) Appl. No.: 13/386,796

(22) PCT Filed: Jul. 26, 2010

(86) PCT No.: PCT/BR2010/000242

§ 371 (c)(1), (2), (4) Date: May 23, 2012

(87) PCT Pub. No.: WO2011/009182

PCT Pub. Date: Jan. 27, 2011

(65) Prior Publication Data

US 2012/0272404 A1 Oct. 25, 2012

(30) Foreign Application Priority Data

Jul. 24, 2009 (BR) ..................................... 0906128

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01); *Y02A 40/162* (2018.01)

(58) Field of Classification Search
None
See application file for complete search history.

(56) References Cited

U.S. PATENT DOCUMENTS

2004/0210963 A1* 10/2004 Abad .................. C07K 14/325
800/279

FOREIGN PATENT DOCUMENTS

WO WO 2005/066349 A2 7/2005
WO WO 2009/158470 A2 12/2009
WO WO 2009158470 A2 * 12/2009 ........... C07K 14/325

OTHER PUBLICATIONS

De Magged et al. Identification of Bacillus thuringiensis Delta-Endotoxin Cry1C Domain III Amino Acid Residues Involve in Insect Specificity. Appl Environ Microbiol. 65:4369-74, Oct. 1999.*
Friedberg (Automated protein function prediction—the genomic challenge. Brief. Bioinformatics. 7:225-242, 2006).*
Van Frankenhuyzen (Insecticidal activity of Bacillus thuringiensis crystal proteins. Journal of Invertebrate Pathology 101: 1-16, 2009).*
De Maaged et al (Identification of Bacillus thuringiensis Delta-Endotoxin Cry1C Domain III Amino Acid Residues Involve in Insect Specificity. Appl Environ Microbiol. 65:4369-74, Oct. 1999).*
Tounsi et al (Cloning and study of the expression of a novel cry1la-type gene from *Bacillus thuringiensis* subsp. kurstaki. J Appl Microbiol. 95:23-8, Jan. 2003).*

(Continued)

*Primary Examiner* — Medina A Ibrahim
*Assistant Examiner* — Wayne Zhong
(74) *Attorney, Agent, or Firm* — Sughrue Mion, PLLC

(57) ABSTRACT

The present invention belongs to an insecticide compound derived from a strain of *Bacillus thuringiensis* and refers to the field of controlling plant pests, particularly to the control of the boll weevil—*Anthonomus grandis*. More specifically, the object of the invention refers to a new gene for the new delta-endotoxin designated Cry8Ha and to the cloning and expression of the gene that encodes for the protein Cry8Ha in *Escherichia coli*. There is provided the nucleotide sequence and encoding protein of the new delta-endotoxin, recombinant vectors and host cells. There is also provided processes and means for recombinant production and the use of the new delta-endotoxin for application in the control of the boll weevil. Additionally, the invention also provides an optimized synthetic gene for expression in cotton plants. Using the gene described herein, it is possible to transform plants based on techniques known by specialists in the art, for the expression of the endotoxin active against the boll weevil.

18 Claims, 132 Drawing Sheets

Figure 1:
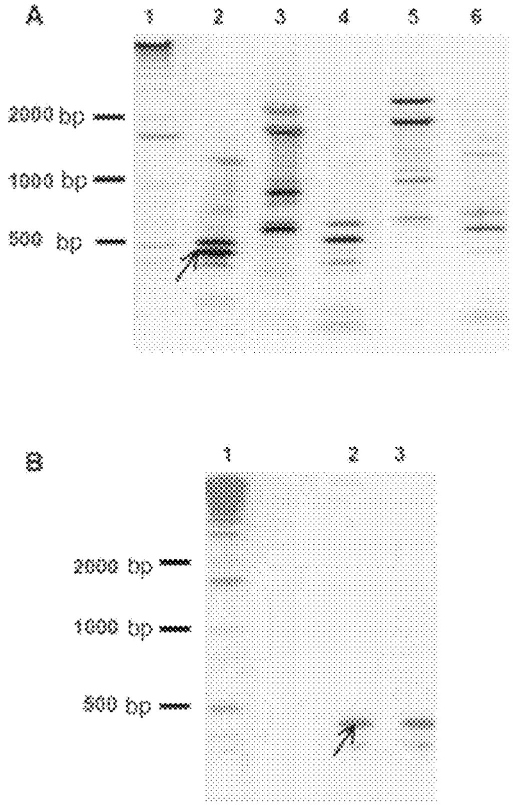

Specification includes a Sequence Listing.

(56) References Cited

OTHER PUBLICATIONS

Van Frankenhuyzen (Insecticidal activity of Bacillus thuringiensis crystal proteins. Journal of Invertebrate Pathology 101: 1-16, 2009) (Year: 2009).*
Grossi-De-Sa, Maria F., et al., "Susceptibility of Anthonomus grandis (Cotton Boll Weevil) and Spodoptera frugiperda (Fall Armyworm) to a Cry1la-type Toxin from a Brazilian Bacillus thuringiensis Strain," Journal of Biochemistry and Molecular Biology, Sep. 2007, pp. 773-782, vol. 40, No. 5.
Magalhaes, M.T.Q., "Toxinas Cry: Perspectivas Para Obtencao De Algodao Transgenico Brasileiro," Internet Citation, Apr. 11, 2006, p. 104, XP009142654.
Martins, E.S., et al., "Recombinant Cry1la Protein is Highly Toxic to Cotton Boll Weevil (Anthonomus grandis Boheman) and Fall Armywork (Spodoptera Frugiperda)," Journal of Applied Microbiology, May 2008, pp. 1363-1371, vol. 104, No. 5.
Martins, Erica Soares, et al., "Characterization of Bacillus thuringiensis Isolates Toxic to Cotton Boll Weevil (Anthonomus grandis)," Biological Control, Dec. 12, 2006, pp. 65-68, vol. 40, No. 1.

* cited by examiner

```
Cry8Bb1_Seq_15      ATGAGTCCAAATAATCAAAATGAATATGAAATTATAGATGCGACACCTTCTACTTCTGTA 60  (SEQ ID NO:17)
Cry8Bb1_Seq_17      ATGAGTCCAAATAATCAAAATGAATATGAAATTATAGATGCGACACCTTCTACTTCTGTA 60  (SEQ ID NO:18)
Cry8AB00.1_Seq_5    ATGAGTCCAAATAATCAAAATGAATATGAAATTATAGATGCGACACCTTCTACTTCTGTA 60  (SEQ ID NO:19)
50C_b               ATGAGTCCAAATAATCAAAATGAATATGAAATTATAGATGCGACACCTTCTACATCTGTA 60  (SEQ ID NO:20)
Cry8AB00.1_Seq_3    ATGAGTCCAAATAATCAAAATGAATATGAAATTATAGATGCGACACCTTCTACTTCTGTA 60  (SEQ ID NO:21)
Cry8Ka1             ATGAGTCCAAATAATCTAAATGAATATGAAATTATAGATGCGACACCTTCTACATCTGTA 60  (SEQ ID NO:22)
                    **************** ************************************ ******

Cry8Bb1_Seq_15      TCCAATGATTCTAACAGATACCCTTTTGCGAATGAGCCAACAAATGCGCTACAAAATATG 120
Cry8Bb1_Seq_17      TCCAATGATTCTAACAGATACCCTTTTGCGAATGAGCCAACAAATGCGCTACAAAATATG 120
Cry8AB00.1_Seq_5    TCCAATGATTCTAACAGATACCCTTTTGCGAATGAGCCAACAAATGCGCTACAAAATATG 120
50C_b               TCCAATGATTCTAACAGATACCCTTTTGCGAATGAGCCAACAAATGCGCTACAAAATATG 120
Cry8AB00.1_Seq_3    TCCAATGATTCTAACAGATACCCTTTTGCGAATGAGCCAACAAATGCATTACAAAATATG 120
Cry8Ka1             TCTAATGATTCTACCAGATACCCTTATGCGAATGAGCCCACAAATGCGTTACAAAATATG 120
                    ** ********** *********** ************ ********  ***********

Cry8Bb1_Seq_15      GATTATAAAGATTATTTAAAAATGTCTGCGGGAAATGCTAGTGAATACCCTGGTTCACCT 180
Cry8Bb1_Seq_17      GATTATAAAGATTATTTAAAAATGTCTGCGGGAAATGCTAGTGAATACCCTGGTTCACCT 180
Cry8AB00.1_Seq_5    GATTATAAAGATTATTTAAAAATGTCTGCGGGAAATGCTAGTGAATACCCTGGTTCACCT 180
50C_b               GATTATAAAGATTATTTAAAAATGTCTGCGGGAAATGTTAGTGAATACCCTGGTTCACCT 180
Cry8AB00.1_Seq_3    AATTATAAGGATTATTTAAGAATGTCTGAGGGGTATGATAGTGAATATTCTGGTTCACCT 180
Cry8Ka1             AATTATAAGGATTATTTAAGAATGTCTGAAGGTTACGATAATAAATATTTTGCAAATCCT 180
                     ******* ********** ********  **  * * ** * ****   **     ***
```

To Fig. 15B

Fig. 15A

From Fig. 15A

```
Cry8Bb1_Seq_15    GAAGTACTTGTTAGCGGACAAGATGCAGCTAAGGCCGCAATTGATATAGTAGGTAAATTA 240
Cry8Bb1_Seq_17    GAAGTACTTGTTAGCGGACAAGATGCAGCTAAGGCCGCAATTGATATAGTAGGTAAATTA 240
Cry8AB00.1_Seq_5  GAAGTACTTGTTAGCGGACAAGATGCAGCTAAGGCCGCAATTGATATAGTAGGTAAATTA 240
50C_b             GAGGTATTTCTAAGCGAGCAAGATGCAGTTAAGGCCGCAATTGATATAGTAGGTAAATTA 240
Cry8AB00.1_Seq_3  GGAGCACTTGTTAGTGGAAAACAAGCAATTAAGGTTGGAATCGATATTGTCGGCAACATA 240
Cry8Ka1           GAAGTGTTTGCT---GCACCAGGTGGATTACAACTGGAATTACTATAGTTACTAAATTA 237
                  *  *   **      *    *    *    **     * ***    *** **     **  **

Cry8Bb1_Seq_15    CTATCAGGTTTAGGGGTCCCATTTGTTGGGCCGATAGTGAGTCTTTATACTCAACTTATT 300
Cry8Bb1_Seq_17    CTATCAGGTTTAGGGGTCCCATTTGTTGGGCCGATAGTGAGTCTTTATACTCAACTTATT 300
Cry8AB00.1_Seq_5  CTATCAGGTTTAGGGGTCCCATTTGTTGGGCCGATAGTGAGTCTTTATACTCAACTTATT 300
50C_b             CTAACAGGTTTAGGGGTTCCATTTGTTGGGCCGATAGTGAGTCTTTATACTCAACTTATT 300
Cry8AB00.1_Seq_3  TTAGGTAAGTTAGGAGTTCCGTTTGCTAGTCAGATAGTAAGTTTTTATAATTTTATTCTC 300
Cry8Ka1           CTGGGGTGGTTAGGACTTCCATTTGCTGGGGAAACAGGGATGGCTCTTAATTTCATTCTA 297
                   *        *****  * ** **** * *    * **  *     *  ** *     ** *

Cry8Bb1_Seq_15    GATATTCTGTGGCCTTCAGGGGAAAAGAGTCAATGGGAAATTTTTATGGAACAAGTAGAA 360
Cry8Bb1_Seq_17    GATATTCTGTGGCCTTCAGGGGAAAAGAGTCAATGGGAAATTTTTATGGAACAAGTAGAA 360
Cry8AB00.1_Seq_5  GATATTCTGTGGCCTTCAGGGGAAAAGAGTCAATGGGAAATTTTTATGGAACAAGTAGAA 360
50C_b             GATATTCTGTGGCCTTCAAAACAAAAGAGTCAATGGGAAATTTTTATGGAACAAGTAGAA 360
Cry8AB00.1_Seq_3  GATCAGCTATGGCCATCAAATTCTGTGAGTGTATGGGAACAGATTATGACGCTAGTGGAA 360
Cry8Ka1           GGTCTATTATGGCCAACA---TCAGGAAACCCGTGGGCTGAACTAATGATATTGGTAGAA 354
                  * *    * *****  **          *      ****      * ***      ** ***

Cry8Bb1_Seq_15    GAACTCATTAATCAAAAAATAGCAGAATATGCAAGGAATAAAGCGCTTTCGGAATTAGAA 420
Cry8Bb1_Seq_17    GAACTCATTAATCAAAAAATAGCAGAATATGCAAGGAATAAAGCGCTTTCGGAATTAGAA 420
Cry8AB00.1_Seq_5  GAACTCATTAATCAAAAAATAGCAGAATATGCAAGGAATAAAGCGCTTTCGGAATTAGAA 420
50C_b             GAACTCATTAATCAAAAAATAGCAGAATATGCAAGGAATAAAGCGCTTTCGGAATTGGAA 420
Cry8AB00.1_Seq_3  GAACTTGTAGATCAAAAAATAACAGAATATGCAAGAAATAAAGCACTCGCTGAATTAAAA 420
Cry8Ka1           GAACTCATAAATCAAAAAATAGAAGAGACTGTAAGAAACAAAGCACTAGCGGATTTGGGC 414
                  *****  *  ***********  ***    ** *** ** ***** **   * ** **

Cry8Bb1_Seq_15    GGATTAGGTAATAATTACCAATTATATCTAACTGCGCTTGAAGAATGGGAAGAAAATCCA 480
Cry8Bb1_Seq_17    GGATTAGGTAATAATTACCAATTATATCTAACTGCGCTTGAAGAATGGGAAGAAAATCCA 480
Cry8AB00.1_Seq_5  GGATTAGGTAATAATTACCAATTATATCTAACTGCGCTTGAAGAATGGGAAGAAAATCCA 480
50C_b             GGGCTAGGGAATAATTACCAATTATATCTAACTGCGCTTGAAGAGTGGAAAGAAAATCCA 480
Cry8AB00.1_Seq_3  GGATTAGGAGATGCTTTGGGTGTATATCAGCAATCACTTGAAGCTTGGTTGGAAAATCGC 480
Cry8Ka1           AATTCAGGTAGAGCCTTACGATCCTATTTAAACGCATTTGAAGATTGGCAAAAAAACCCT 474
                       ***       *        ***       *  ******  ***     **** *

Cry8Bb1_Seq_15    TTTCGACGAGGTTTTCGACGAGGTGCCTTACGAGATGTGCGAAATCGATTTGAAATCCTG 540
Cry8Bb1_Seq_17    TTTCGACGAGGTTTTCGACGAGGTGCCTTACGAGATGTGCGAAATCGATTTGAAATCCTG 540
Cry8AB00.1_Seq_5  AAT------GGTTC------AAGAGCCTTACGAGATGTGCGAAATCGATTTGAAATCCTG 528
50C_b             AAT------GGTTC------AAGAGCCTTACGAGATGTTCGAAATCGATTTGAAATCCTG 528
Cry8AB00.1_Seq_3  AAT------GACAC------GAGAGCTAGAAGTGTTGTTTCTAATCAATTTATAGCCTTA 528
Cry8Ka1           AAT------ATCTTT-----CGGAGTAAAGAGTTA-GTAAAAGAAAGATTTTCAAACGCG 522
                    *                     * *       *     **       *    ****   *
```

Fig. 15B

To Fig. 15C

From Fig. 15B

```
Cry8Bb1_Seq_15      GATAGTTTATTTACGCAATATATGCCATCTTTTAGAGTGACAAATTTTGAAGTACCATTC 600
Cry8Bb1_Seq_17      GATAGTTTATTTACGCAATATATGCCATCTTTTAGAGTGACAAATTTTGAAGTACCATTC 600
Cry8AB00.1_Seq_5    GATAGTTTATTTACGCAATATATGCCATCTTTTAGAGTGACAAATTTTGAAGTACCATTC 588
50C_b               GATAGTTTATTTACGCAATATATGCCATCTTTTCGAGTGACAAATTTTGAAGTACCATTC 588
Cry8AB00.1_Seq_3    GAACTGGATTTTGTTGGAGCAATTCCATCCTTTGCAGTATCCGGGCAGGAAGTACCATTA 588
Cry8Ka1             GAACATTCATTACGTACCGAAATGAGTTCTTTTGCCATAAGAGGATTTGAAATTCCTCTT 582
                    **       **          **    ** ***    *          *** * **  *

Cry8Bb1_Seq_15      CTTACTGTATATGCAATGGCAGCCAACCTTCATTTACTGTTATTAAAGGACGCGTCAATT 660
Cry8Bb1_Seq_17      CTTACTGTATATGCAATGGCAGCCAACCTTCATTTACTGTTATTAAAGGACGCGTCAATT 660
Cry8AB00.1_Seq_5    CTTACTGTATATGCAATGGCAGCCAACCTTCATTTACTGTTATTAAAGGACGCGTCAATT 648
50C_b               CTTACAGTATATACAATGGCAGCAAACCTACATTTACTTTTATTAAGGGACGCATCAATT 648
Cry8AB00.1_Seq_3    TTAGCAGTATATGCACAGGCTGTGAACATGCACTTATTGTTACTAAGAGACGCTTCTATT 648
Cry8Ka1             TTAGCAACATATGCACAAGCTGCGAATTTACATTTATTTCTAATTAAAGATATTCAAATT 642
                     *  *   **** **    ** *  **  * ** *** *  ** * *  **       ***

Cry8Bb1_Seq_15      TTTGGAGAAGAATGGGGATGGTCAACAACTACTATTAATAACTATTATGATCGTCAAATG 720
Cry8Bb1_Seq_17      TTTGGAGAAGAATGGGGATGGTCAACAACTACTATTAATAACTATTATGATCGTCAAATG 720
Cry8AB00.1_Seq_5    TTTGGAGAAGAATGGGGATGGTCAACAACTACTATTAATAACTATTATGATCGTCAAATG 708
50C_b               TTTGGAGAAGAATGGGGATTGTCTACAAGCACTATTAATAACTACTATAATCGTCAAATG 708
Cry8AB00.1_Seq_3    TTTGGAGAAGAGTGGGGATTCACATCATCTGAAATTTCCACTTACTACAACCGTCAAGTG 708
Cry8Ka1             TATGGAAAAGAATGGGGATATACTCAAGCCGATATTGACTTATTTTATAGAGAACAAGTA 702
                    * **** **** *******   *   *      ***      *  **       *** *

Cry8Bb1_Seq_15      AAACTTACTGCAGAATATTCTGATCACTGTGTAAAGTGGTATGAAACTGGTTTAGCAAAA 780
Cry8Bb1_Seq_17      AAACTTACTGCAGAATATTCTGATCACTGTGTAAAGTGGTATGAAACTGGTTTAGCAAAA 780
Cry8AB00.1_Seq_5    AAACTTACTGCAGAATATTCTGATCACTGTGTAAAGTGGTATGAAACTGGTTTAGCAAAA 768
50C_b               AAACTTACTGCAGAATATTCTGACCACTGTGTAAAGTGGTATGAAACTGGTTTAGCAAAA 768
Cry8AB00.1_Seq_3    CAACTCACTTCTCAATATTCCGATTATTGTGTGAAGTGGTACGATACCGGTTTACAGAAA 768
Cry8Ka1             GAGTTTACGAAAGAATACACCGAACACTGTATTAATATTTATAATGATGGTTTAAATCAA 762
                     *  * **     ****  * **  * *** * **    **   *    ******    **

Cry8Bb1_Seq_15      TTAAAAGGCACGAGCGCTAAACAATGGGTTGACTATAACCAATTCCGTAGAGAAATGACA 840
Cry8Bb1_Seq_17      TTAAAAGGCACGAGCGCTAAACAATGGGTTGACTATAACCAATTCCGTAGAGAAATGACA 840
Cry8AB00.1_Seq_5    TTAAAAGGCACGAGCGCTAAACAATGGGTTGACTATAACCAATTCCGTAGAGAAATGACA 828
50C_b               TTAAAAGGCTCGAGCGCTAAACAATGGATTGACTATAACCAATTCCGTAGAGAAATGACA 828
Cry8AB00.1_Seq_3    TTAAAAGGTACGAGCGCTGAGAGTTGGCTGGAGTATCATCAATTCCGCAGAGAGATGACT 828
Cry8Ka1             TTAAAAGGTTCGAATGCTAAGCAATGGATTGCATTTAATCGCTTCCGTAGAGAAATGACA 822
                    ********  ***  *** *    *** * *  * * * *  ***** ***** *****

Cry8Bb1_Seq_15      CTGGCGGTTTTAGATGTTGTTGCATTATTCCCAAATTATGACACACGCACGTACCCAATG 900
Cry8Bb1_Seq_17      CTGGCGGTTTTAGATGTTGTTGCATTATTCCCAAATTATGACACACGCACGTACCCAATG 900
Cry8AB00.1_Seq_5    CTGGCGGTTTTAGATGTTGTTGCATTATTCCCAAATTATGACACACGCACGTACCCAATG 888
50C_b               TTGACGGTGTTAGACGTTGTTGCATTATTTTCAAACTATGATACGCGTACGTATCCACTG 888
Cry8AB00.1_Seq_3    TTCATGGTATTAGATTTGGTTGCATTATTTCCAAACTACGATACACACACGTATCCACTT 888
Cry8Ka1             TTGACGGTACTGGATGTAGTTGCATTATTCCCGAACTATGATGTACGTATGTACCCTATA 882
                     *   *** *  **  * ***********  * ** ** **    *  * *** **  *
```

Fig. 15C

To Fig. 15D

From Fig. 15C

```
Cry8Bb1_Seq_15    GAAACGAAAGCACAACTAACAAGGGAAGTATATACAGATCCACTGGGCG---------CG 951
Cry8Bb1_Seq_17    GAAACGAAAGCACAACTAACAAGGGAAGTATATACAGATCCACTGGGCG---------CG 951
Cry8AB00.1_Seq_5  GAAACGAAAGCACAACTAACAAGGGAAGTATATACAGATCCACTGGGCG---------CG 939
50C_b             GCAACAACAGCTCAGCTTACAAGGGAAGTATATACAGATCCACTTGGCG---------CG 939
Cry8AB00.1_Seq_3  GAAACAAAGGCTCAACTTACACGAGAAGTATATACGGATCCGATCGCCTTTAATCTTTCT 948
Cry8Ka1           AAAACAACTACAGAGCTAACGAGAACAATTTATACCGATCCACTTGGTTACA------CG 936
                    *** *   *  * ** **  *   * * ***** *****  * *            *

Cry8Bb1_Seq_15    GTAAACGTGTCTTCAATTGGTTCCTGGT---ATGACAAAGCACCTTCTTTCGGAGTGATA 1008
Cry8Bb1_Seq_17    GTAAACGTGTCTTCAATTGGTTCCTGGT---ATGACAAAGCACCTTCTTTCGGAGTGATA 1008
Cry8AB00.1_Seq_5  GTAAACGTGTCTTCAATTGGTTCCTGGT---ATGACAAAGCACCTTCTTTCGGAGTGATA 996
50C_b             GTAGATGTGCCTAATATTGGCTCCTGGT---ATGACAAAGCACCTTCTTTCTCAGAAATA 996
Cry8AB00.1_Seq_3  GGGGCAGCGGGTTTTTGTAGCCCTTGGTCAAAGTATACTGGTATTTCCTTTTCGGAGATT 1008
Cry8Ka1           AAAACGGGTTCTAGTAGTACACCACCATGGTATAATTATGGATCTAGTTTCTCATATATA 996
                        *    *     *    *    *   *  *    *    *   **       **

Cry8Bb1_Seq_15    GAATCATCCGTTATTCGACCACCCCATGTATTTGATTATATAACGGGACTCACAGTGTAT 1068
Cry8Bb1_Seq_17    GAATCATCCGTTATTCGACCACCCCATGTATTTGATTATATAACGGGACTCACAGTGTAT 1068
Cry8AB00.1_Seq_5  GAATCATCCGTTATTCGACCACCCCATGTATTTGATTATATAACGGGACTCACAGTGTAT 1056
50C_b             GAAAAAGCGGCTATTCGTCCACCTCATGTGTTTGATTATATAACGGGACTCACAGTTTAT 1056
Cry8AB00.1_Seq_3  GAAAATGATGTAATTCGTCCGCCTCATTTATTTAATCTACTCAGAAGTTTAGAGATTAAT 1068
Cry8Ka1           GAAAGTGTAGCGATTCCAGCCCCTAGTCTGGTTAAGTGGTTAAGTCAGATTGAAATTTAT 1056
                  ***      *  ****   * **   * *  ** *     * *      *     *  **

Cry8Bb1_Seq_15    ACACAATCAAGAAGCATTTC------TTCCGCTCGCTATATAAGACATTGGGCTGGTCAT 1122
Cry8Bb1_Seq_17    ACACAATCAAGAAGCATTTC------TTCCGCTCGCTATATAAGACATTGGGCTGGTCAT 1122
Cry8AB00.1_Seq_5  ACACAATCAAGAAGCATTTC------TTCCGCTCGCTATATAAGACATTGGGCTGGTCAT 1110
50C_b             ACAAAAAAACGTAGCTTCAC------TTCTGATCGTTATATGAGATATTGGGCTGGTCAT 1110
Cry8AB00.1_Seq_3  ACAGTTAGGGGGACAATTTTAGGTAATACTAAAGATTACCTAAACTATTGGTCAGGTCAT 1128
Cry8Ka1           TCGAAATCCGCAAGGGCTAC-------ACCGCAAAGTGC--GGATTATTGGCAGGACAT 1107
                   *          *               *       *         ***** * ** ***

Cry8Bb1_Seq_15    CAAATAAGCTACCATCGTGTCAGTAGGGGTAGTAATCTTCAACAA-ATGTATGGAACTAA 1181
Cry8Bb1_Seq_17    CAAATAAGCTACCATCGTGTCAGTAGGGGTAGTAATCTTCAACAA-ATGTATGGAACTAA 1181
Cry8AB00.1_Seq_5  CAAATAAGCTACCATCGTGTCAGTAGGGGTAGTAATCTTCAACAA-ATGTATGGAACTAA 1169
50C_b             CAAATAAGCTATAAGCATATCGGTACGAGTAGTACCTTTACACAG-ATGTATGGAACCAA 1169
Cry8AB00.1_Seq_3  TCTCTACAATATAATTTTATAGGTAAGA-CAATAGTCAGGGAAAGTAATTATGGAT---A 1184
Cry8Ka1           ACAATAACATATCACTATAGTGGAGATGATGGTCAAGCAGTACCT-AATTATGGAGATAG 1166
                      **   **  *   *    *         *        *    *  ******

Cry8Bb1_Seq_15    TCAAAATCTACACAGCACTAGTACCTTTGATTTTACGAATTATGATATTTACAAGACTCT 1241
Cry8Bb1_Seq_17    TCAAAATCTACACAGCACTAGTACCTTTGATTTTACGAATTATGATATTTACAAGACTCT 1241
Cry8AB00.1_Seq_5  TCAAAATCTACACAGCACTAGTACCTTTGATTTTACGAATTATGATATTTACAAGACTCT 1229
50C_b             TCAAAATTTACAAAGTACTAGCAATTTTGATTTTACGAATTACGATATTTACAAGACTTT 1229
Cry8AB00.1_Seq_3  TCTTACTTCAGAAAAAACTAGGA---TTGAATTAGACACTAGAGATATTTTTGAAATTAA 1241
Cry8Ka1           AACGAATCCTGTAATTGTAAATCGTTATAATTTTGAGCAGGCTGACATTTATAGAGTTTC 1226
                      * *      *     *       * * **          ** ****       *
```

To Fig. 15E

Fig. 15D

From Fig. 15D

```
Cry8Bb1_Seq_15     ATCAAAGGATGCAGTACTCCTTGATATTGTTTACCCTGGTTATACGTATATATTTTTTGG 1301
Cry8Bb1_Seq_17     ATCAAAGGATGCAGTACTCCTTGATATTGTTTACCCTGGTTATACGTATATATTTTTTGG 1301
Cry8AB00.1_Seq_5   ATCAAAGGATGCAGTACTCCTTGATATTGTTTACCCTGGTTATACGTATATATTTTTTGG 1289
50C_b              ATCAAATGGTGCAGTACTCCTTGATATAGTTTACCCTGGTTATACGTATACATTTTTTGG 1289
Cry8AB00.1_Seq_3   TTCAACTGCCGCAA--------------GCTTAGCG-AATTACTATCAAGAGACTTATGG 1286
Cry8Ka1            ATCATCTGTTGCT----------------TCAAGTACAACTAGTGGTGTTAAATTATTAA 1270
                    ***   *  **                    *       **            *  *

Cry8Bb1_Seq_15     AATGCCAGAAGTCGAGTTTTTCATGGTAA-ACCAAT-TGAATAATACCAGAAAGACGTTA 1359
Cry8Bb1_Seq_17     AATGCCAGAAGTCGAGTTTTTCATGGTAA-ACCAAT-TGAATAATACCAGAAAGACGTTA 1359
Cry8AB00.1_Seq_5   AATGCCAGAAGTCGAGTTTTTCATGGTAA-ACCAAT-TGAATAATACCAGAAAGACGTTA 1347
50C_b              AATGCCAGAAACCGAGTTTTTTATGGTAA-ATCAAT-TGAATAATACCAGAAAGACGTTA 1347
Cry8AB00.1_Seq_3   TGTGCCAGAATCTAGGCTCCATTTGGTGAGATGGGC-TAGCCCATATTATACATCATCTC 1345
Cry8Ka1            C-TACTA------AGGCTATATTTGATGGCATAAGTACAAACAATGGACTAGTGAGTTAC 1323
                     * * *        * *     ** *      *         **     *

Cry8Bb1_Seq_15     AAGTATAATCCAGTTTCCAAAGA--TATTATAGCGAGTACAAGAGATT-CGGAATTA--- 1413
Cry8Bb1_Seq_17     AAGTATAATCCAGTTTCCAAAGA--TATTATAGCGAGTACAAGAGATT-CGGAATTA--- 1413
Cry8AB00.1_Seq_5   AAGTATAATCCAGTTTCCAAAGA--TATTATAGCGAGTACAAGAGATT-CGGAATTA--- 1401
50C_b              ACGTATAAACCAGCTTCCAAAGA--TATTATAGATCGGACAAGAGATT-CGGAATTA--- 1401
Cry8AB00.1_Seq_3   ATCTTTATTCTAAAACACATACAACTGGAGAAGGTTGTACACAAGTTT-ATGAATCAAGT 1404
Cry8Ka1            ATGTATGAAAAATTATCGAACTTTTTAATGAACTAAAAGATACAATTACAGAGCTACCT 1383
                   *  * *     *      *      *     *      * *     **   **   *

Cry8Bb1_Seq_15     GAATTACCTCCAGAAACTTCAGATCAACCAAATTATGAGTCATATAGCCATAGATTATGT 1473
Cry8Bb1_Seq_17     GAATTACCTCCAGAAACTTCAGATCAACCAAATTATGAGTCATATAGCCATAGATTATGT 1473
Cry8AB00.1_Seq_5   GAATTACCTCCAGAAACTTCAGATCAACCAAATTATGAGTCATATAGCCATAGATTATGT 1461
50C_b              GAATTGCCTCCAGAAACTTCAGGTCAACCAAATTACGAGTCATATAGCCATAGATTAGGT 1461
Cry8AB00.1_Seq_3   GAGGAAATACCTGTAGACAGAACCGTACCGATAAATGAAGGTTATAGTCACAGACTATCG 1464
Cry8Ka1            GTTCAGATATCCAGTCCTCCTACCTACGGGGATGCTGAACAGTACAGTCATCGGCTATCC 1443
                   *         *                         **     ** ** **  *  **

Cry8Bb1_Seq_15     CATATCACAAGTATTCCCGCG------ACGGGTAACACT---------ACCGGATTAGTA 1518
Cry8Bb1_Seq_17     CATATCACAAGTATTCCCGCG------ACGGGTAACACT---------ACCGGATTAGTA 1518
Cry8AB00.1_Seq_5   CATATCACAAGTATTCCCGCG------ACGGGTAACACT---------ACCGGATTAGTA 1506
50C_b              CATATTACATTTATTTACTCC------A---GTTCAACT---------AGCACGTATGTA 1503
Cry8AB00.1_Seq_3   TATGTCACCGCTCTCTTTTTCCAGAAAATTATTAATACTTTTTATAGAAATGGAACTCTA 1524
Cry8Ka1            TATGTTTCTAATGCTCCAACAGAGTACTCTTCGGGCGGACATTTAATTTTGGGACTAATC 1503
                    ** *  *   *                                               *

Cry8Bb1_Seq_15     CCTGTATTTTCTTGGACACATCGAAGTGCAGATTTAAACAATACAATATATTCAGATAAA 1578
Cry8Bb1_Seq_17     CCTGTATTTTCTTGGACACATCGAAGTGCAGATTTAAACAATACAATATATTCAGATAAA 1578
Cry8AB00.1_Seq_5   CCTGTATTTTCTTGGACACATCGAAGTGCAGATTTAAACAATACAATATATTCAGATAAA 1566
50C_b              CCTGTATTTTCTTGGACACATCGGAGTGCAGATCTAACAAATACAGTTAAAAGTGGCGAA 1563
Cry8AB00.1_Seq_3   CCTGTCTTTGTTTGGACACATCGAAGTGCAGATCTTACAAATACAATTTATCCAGATGTA 1584
Cry8Ka1            CCAGTACTGGGTTGGACGCATACTAGTTTAACTCAAACAAATCAGATACATTCTGACTCA 1563
                   ** **  *   ****** ***   ***  *  *   *  ***    *  *    *    *
```

Fig. 15E

To Fig. 15F

From Fig. 15E

```
Cry8Bb1_Seq_15    ATCACTCAAATTCCGGCCGTTAAATGTTGGGA------------TAATTTACCGTT-TGT 1625
Cry8Bb1_Seq_17    ATCACTCAAATTCCGGCCGTTAAATGTTGGGA------------TAATTTACCGTT-TGT 1625
Cry8AB00.1_Seq_5  ATCACTCAAATTCCGGCCGTTAAATGTTGGGA------------TAATTTACCGTT-TGT 1613
50C_b             ATCACCCAAATACCAGGGGGCAAGT-CTAGCA------------CCATAGGCAGAAATAC 1610
Cry8AB00.1_Seq_3  ATTACTCAAATACCAGTGGTAAAGGCCTATGAATTGGGTAGCTCCATCTTACCAGATAGT 1644
Cry8Ka1           ATTACTCAAATTCCAGCTGTTAAAGCAAATAG------------TGTTAGTTCTTATGT 1610
                  ** ** ***** ** *  *  **

Cry8Bb1_Seq_15    TC--------CAGTGGTAAAAGGACCAGGACATACAGGAGGGGATTTATT-------ACA 1670
Cry8Bb1_Seq_17    TC--------CAGTGGTAAAAGGACCAGGACATACAGGAGGGGATTTATT-------ACA 1670
Cry8AB00.1_Seq_5  TC--------CAGTGGTAAAAGGACCAGGACATACAGGAGGGGATTTATT-------ACA 1658
50C_b             TT--------ATATAATAAAAGGGCGTGGTTATACAGGGGGAGACTTAGTGGCTTTAACG 1662
Cry8AB00.1_Seq_3  CCATCACCTACTATTGTGCCAGGGCCTGGATTTACAGGGGGGGATATAATACAATTACTG 1704
Cry8Ka1           TA--------CTGTTGAAAAGGGAACAGGCTTTACAGGTGGAGATTTAGTG------AAA 1656
                               *       **    **    ****** ** **  ** *

Cry8Bb1_Seq_15    G--TATAATAGAAGTACTGGTTCTGTAG-GAACCTTATTTCTAGCTCGATATGGCCTA-G 1726
Cry8Bb1_Seq_17    G--TATAATAGAAGTACTGGTTCTGTAG-GAACCTTATTTCTAGCTCGATATGGCCTA-G 1726
Cry8AB00.1_Seq_5  G--TATAATAGAAGTACTGGTTCTGTAG-GAACCTTATTTCTAGCTCGATATGGCCTA-G 1714
50C_b             GACCGCATCGGAAGTTGTGAGTTTCAGA-TGATCTT--TCCAGAGTCTCAACGATTCC-G 1718
Cry8AB00.1_Seq_3  GCGAATACAAAAGGTATAGCAAATATGA-ATTTTGAAATTCAAGACATTAATAAAGAATA 1763
Cry8Ka1           TTCTCCACTGGATTCATGTCTACAGGAATACAGTTTAATTTAAAGATAGAAGAAAGAAAG 1716
                        *    *                          *           *

Cry8Bb1_Seq_15    CATTAGAAAAAGCAGGGAAATATCGTGTAAGACTGAGATATGCTA-CTGATGCAGAT--- 1782
Cry8Bb1_Seq_17    CATTAGAAAAAGCAGGGAAATATCGTGTAAGACTGAGATATGCTA-CTGATGCAGAT--- 1782
Cry8AB00.1_Seq_5  CATTAGAAAAAGCAGGGAAATATCGTGTAAGACTGAGATATGCTA-CTGATGCAGAT--- 1770
50C_b             TATTCGGA---TTCGTTACGCTTCTAATGAAACT-AGTTATATTAGTTTATACGGACTAA 1774
Cry8AB00.1_Seq_3  TATTATGAGAATTCGGTATGCTTCCGCTGCAAAT--CCTGAATTC---AATATAGCT--- 1815
Cry8Ka1           CGTTA------TCGTATCCGTATACGATATGCCG--CTGATGTTA----ATGCTACTCTA 1764
                    **                  *    *               *      **

Cry8Bb1_Seq_15    ATTGTATTGCATGTAAACGATGCTCAGATTCAGATGCCAAAAACAATGAACCCAGGTGAG 1842
Cry8Bb1_Seq_17    ATTGTATTGCATGTAAACGATGCTCAGATTCAGATGCCAAAAACAATGAACCCAGGTGAG 1842
Cry8AB00.1_Seq_5  ATTGTATTGCATGTAAACGATGCTCAGATTCAGATGCCAAAAACAATGAACCCAGGTGAG 1830
50C_b             ACCAAAGCGGAACTTTAAAATTCAACCAGACATATTCTAATAAAAATGAA-------AAT 1827
Cry8AB00.1_Seq_3  GTTGGTACTAGTGGAGAAAGAGTTAGTACTAGTGCTCAAAAAACTATGAATCCAGGGGAT 1875
Cry8Ka1           TCTGCACTTGGATTAAATGATGCATTTATTAACATTAAATCGACAATGTCTCAAGACACA 1824
                                  *          *          *   *   ***

Cry8Bb1_Seq_15    GATCTGACATCTAAAACTTTTAAAGTTGCAGATGCTATCACAACAGTAAATTTAG--CAA 1900
Cry8Bb1_Seq_17    GATCTGACATCTAAAACTTTTAAAGTTGCAGATGCTATCACAACAGTAAATTTAG--CAA 1900
Cry8AB00.1_Seq_5  GATCTGACATCTAAAACTTTTAAAGTTGCAGATGCTATCACAACATTAAATTTAG--CAA 1888
50C_b             GATTTAACATATAATGATTTCAAATATATAGAA--TATC-CAAGAGTCATTTCAG--TAA 1882
Cry8AB00.1_Seq_3  ATTTTAACATTTAATAAATTTAATTACGCAACT--TTCCCTCCCATTAAATTTAATTCAA 1933
Cry8Ka1           CCATTGAAGTATAACGATTTCCAATATGCAGAAGCTGACAAAACAGTGCATTTATACAAT 1884
                      * *  * ***   ** *      *     *  *     * *   ** *    *
```

Fig. 15F

To Fig. 15G

From Fig. 15F

```
Cry8Bb1_Seq_15    CAGATAGTTCGGTAGCAGTGAAACATAATTTAGGTGAAGACCCTAATTCAACATTATCTG 1960
Cry8Bb1_Seq_17    CAGATAGTTCGGTAGCAGTGAAACATAATGTAGGTGAAGACCCTAATTCAACATTATCTG 1960
Cry8AB00.1_Seq_5  CAGATAGTTCGCTAGCATTGAAACATAATTTAGGTGAAGACCCTAATTCAACATTATCTG 1948
50C_b             ATGCTTCTTCAAACATACAGAGGTTATCTATAGGTATACAAACGAATACAAATTTATTTA 1942
Cry8AB00.1_Seq_3  CTAAAATTTCGATAATGTTAACAGCAAGATTGGCTGCTTTTGCAAGCACA---TTATTGG 1990
Cry8Ka1           CCTCGTTTTTCTTTATATTTAGA--AAATTCAGATCAATCCGGGAAAAG-----TATTTA 1937
                         **           *           * *         *         ***

Cry8Bb1_Seq_15    GTATAGTTTACGTTGACCGAATCGAATTCATCCCAGTAGATGAGACATATGAAGCGGAAT 2020
Cry8Bb1_Seq_17    GTATAGTTTACGTTGACCGAATCGAATTCATCCCAGTAGATGAGACATATGAAGCGGAAT 2020
Cry8AB00.1_Seq_5  GTATAGTTTACGTTGACCGAATCGAATTCATCCCAGTAGATGAGACATATGAAGCGGAAC 2008
50C_b             TTTTAG---------ACCGAATCGAATTCATCCCAGTAGATGAGACATATGAAGCGGAAA 1993
Cry8AB00.1_Seq_3  A---AACCTATATAGATAGAATCGAATTCATCCCAGTAGATGAAACATACGAGGCGGAGA 2047
Cry8Ka1           T----------ATAGATCGAATCGAATTCATCCCAGTAGATGAGACCTATGAAGCAGAAC 1987
                                 * ************************* ** ** ** ** **

Cry8Bb1_Seq_15    AA---------------------------------------------------------- 2022
Cry8Bb1_Seq_17    AA---------------------------------------------------------- 2022
Cry8AB00.1_Seq_5  AAGATTTAGAAGCAGCGAAGAAAGCAGTGAATGCCTTGTTTACGAATACAAAAGATGGCT 2068
50C_b             CGGATTTAGAAGCGGCAAAGAAAGCAGTGAATGCCTTGTTTACGAATACAAAAGATGGAT 2053
Cry8AB00.1_Seq_3  CAGATTTAGAAACGGCGAAGAAAGCAGTGAATGCCTTGTTTACGAATACAAAAGATGGCT 2107
Cry8Ka1           AAGAT------------------------------------------------------- 1992
```

Fig. 15G

```
Sequence_1      -----------------------------------------------------ATGAGTC 7
Sequence_17     AAAAGAAAGTGTAAAAAATCTTTGTATCTTGTATATGTATAGGAGGAAAATAGATGAGTC 737
Sequence_3      -----------------------------------------------------ATGAGTC 7
Sequence_13     -----------------------------------------------------ATGAGTC 7
Sequence_18     TTAAAAAAAGTGTAAGAAATTTTATATCTTTTGTATGTATAGGAGGAAAATAGATGAGTC 1260
Cry8Ha1         -----------------------------------------------------ATGAGTC 7
                                                                     *******

Sequence_71     CAAATAATCAAAATGAATATGAAATTATAGATGCGACACCTTCTACTTCTGTATCCAATG 67 (SEQ ID NO:47)
Sequence_73     CAAATAATCAAAATGAATATGAAATTATAGATGCGACACCTTCTACTTCTGTATCCAATG 67 (SEQ ID NO:48)
Sequence_21     CAAATAATCAAAATGAATATGAAATTATAGATGCGACACCTTCTACTTCTGTATCCAATG 67 (SEQ ID NO:32)
Sequence_67     CAAATAATCAAAATGAATATGAAATTATAGATGCGACACCTTCTACTTCTGTATCCAATG 67 (SEQ ID NO:45)
Sequence_61     CAAATAATCAAAATGAATATGAAATTATAGATGCGACACCTTCTACTTCTGTATCCAATG 67 (SEQ ID NO:44)
Sequence_93     CAAATAATCAAAATGAATATGAAATTATAGATGCGACACCTTCTACTTCTGTATCCAATG 67 (SEQ ID NO:55)
Sequence_59     CAAATAATCAAAATGAATATGAAATTATAGATGCGACACCTTCTACTTCTGTATCCAATG 67 (SEQ ID NO:43)
Sequence_91     CAAATAATCAAAATGAATATGAAATTATAGATGCGACACCTTCTACTTCTGTATCCAATG 67 (SEQ ID NO:54)
Sequence_39     CAAATAATCAAAATGAATATGAAATTATAGATGCGACACCTTCTACTTCTGTATCCAATG 67 (SEQ ID NO:36)
Sequence_41     CAAATAATCAAAATGAATATGAAATTATAGATGCGACACCTTCTACTTCTGTATCCAATG 67 (SEQ ID NO:37)
Sequence_49     CAAATAATCAAAATGAATATGAAATTATAGATGCGACACCTTCTACTTCTGTATCCAATG 67 (SEQ ID NO:41)
Sequence_81     CAAATAATCAAAATGAATATGAAATTATAGATGCGACACCTTCTACTTCTGTATCCAATG 67 (SEQ ID NO:52)
Sequence_45     CAAATAATCAAAATGAATATGAAATTATAGATGCGACACCTTCTACTTCTGTATCCAATG 67 (SEQ ID NO:39)
Sequence_77     CAAATAATCAAAATGAATATGAAATTATAGATGCGACACCTTCTACTTCTGTATCCAATG 67 (SEQ ID NO:50)
Sequence_75     CAAATAATCAAAATGAATATGAAATTATAGATGCGACACCTTCTACTTCTGTATCCAATG 67 (SEQ ID NO:49)
```

To Fig. 16B

Fig. 16A

From Fig. 16A

```
Sequence_43     CAAATAATCAAAATGAATATGAAATTATAGATGCGACACCTTCTACTTCTGTATCCAATG 67  (SEQ ID NO:38)
Sequence_47     CAAATAATCAAAATGAATATGAAATTATAGATGCGACACCTTCTACTTCTGTATCCAATG 67  (SEQ ID NO:40)
Sequence_79     CAAATAATCAAAATGAATATGAAATTATAGATGCGACACCTTCTACTTCTGTATCCAATG 67  (SEQ ID NO:51)
Sequence_51     CAAATAATCAAAATGAATATGAAATTATAGATGCGACACCTTCTACTTCTGTATCCAATG 67  (SEQ ID NO:42)
Sequence_83     CAAATAATCAAAATGAATATGAAATTATAGATGCGACACCTTCTACTTCTGTATCCAATG 67  (SEQ ID NO:53)
Sequence_7      CAAATAATCAAAATGAATATGAAATTATAGATGCGACACCTTCTACTTCTGTATCCAATG 67  (SEQ ID NO:27)
Sequence_25     CAAATAATCAAAATGAATATGAAATTATAGATGCGACACCTTCTACTTCTGTATCCAATG 67  (SEQ ID NO:33)
Sequence_29     CAAATAATCAAAATGAATATGAAATTATAGATGCGACACCTTCTACTTCTGTATCCAATG 67  (SEQ ID NO:34)
Sequence_33     CAAATAATCAAAATGAATATGAAATTATAGATGCGACACCTTCTACTTCTGTATCCAATG 67  (SEQ ID NO:35)
Sequence_69     CAAATAATCAAAATGAATATGAAATTATAGATGCGACACCTTCTACTTCTGTATCCAATG 67  (SEQ ID NO:46)
Sequence_11     CAAATAATCAAAATGAATATGAAATTATAGATGCGACACCTTCTACTTCTGTATCCAATG 67  (SEQ ID NO:28)
Sequence_5      CAAATAATCAAAATGAATATGAAATTATAGATGCGACACCTTCTACTTCTGTATCCAATG 67  (SEQ ID NO:26)
Sequence_1      CAAATAATCAAAATGAATATGAAATTATAGATGCGACACCTTCTACTTCTGTATCCAATG 67  (SEQ ID NO:24)
Sequence_17     CAAATAATCAAAATGAATATGAAATTATAGATGCGACACCTTCTACTTCTGTATCCAATG 797 (SEQ ID NO:30)
Sequence_3      CAAATAATCAAAATGAATATGAAATTATAGATGCGACACCTTCTACTTCTGTATCCAATG 67  (SEQ ID NO:25)
Sequence_13     CAAATAATCAAAATGAATATGAAATTATAGATGCGACACCTTCTACTTCTGTATCCAATG 67  (SEQ ID NO:29)
Sequence_18     CAAATAATCAAAATGAATATGAAATTATAGATGCGACACCTTCTACTTCTGTATCCAATG 1320(SEQ ID NO:31)
Cry8Ha1         CAAATAATCTAAATGAATATGAAATTATAGATGCGACACCTTCTACATCTGTATCTAATG 67  (SEQ ID NO:23)
                ********* ************************************ ******** ****
```

To Fig. 16C

Fig. 16B

From Fig. 16B

```
Sequence_71     ATTCTAACAGATACCCTTTTGCGAATGAGCCAACAAATGCGCTACAAAATATGGATTATA 127
Sequence_73     ATTCTAACAGATACCCTTTTGCGAATGAGCCAACAAATGCGCTACAAAATATGGATTATA 127
Sequence_21     ATTCTAACAGATACCCTTTTGCGAATGAGCCAACAAATGCGCTACAAAATATGGATTATA 127
Sequence_67     ATTCTAACAGATACCCTTTTGCGAATGAGCCAACAAATGCGCTACAAAATATGGATTATA 127
Sequence_61     ATTCTAACAGATACCCTTTTGCGAATGAGCCAACAAATGCGCTACAAAATATGGATTATA 127
Sequence_93     ATTCTAACAGATACCCTTTTGCGAATGAGCCAACAAATGCGCTACAAAATATGGATTATA 127
Sequence_59     ATTCTAACAGATACCCTTTTGCGAATGAGCCAACAAATGCGCTACAAAATATGGATTATA 127
Sequence_91     ATTCTAACAGATACCCTTTTGCGAATGAGCCAACAAATGCGCTACAAAATATGGATTATA 127
Sequence_39     ATTCTAACAGATACCCTTTTGCGAATGAGCCAACAAATGCGCTACAAAATATGGATTATA 127
Sequence_41     ATTCTAACAGATACCCTTTTGCGAATGAGCCAACAAATGCGCTACAAAATATGGATTATA 127
Sequence_49     ATTCTAACAGATACCCTTTTGCGAATGAGCCAACAAATGCGCTACAAAATATGGATTATA 127
Sequence_81     ATTCTAACAGATACCCTTTTGCGAATGAGCCAACAAATGCGCTACAAAATATGGATTATA 127
Sequence_45     ATTCTAACAGATACCCTTTTGCGAATGAGCCAACAAATGCGCTACAAAATATGGATTATA 127
Sequence_77     ATTCTAACAGATACCCTTTTGCGAATGAGCCAACAAATGCGCTACAAAATATGGATTATA 127
Sequence_75     ATTCTAACAGATACCCTTTTGCGAATGAGCCAACAAATGCGCTACAAAATATGGATTATA 127
Sequence_43     ATTCTAACAGATACCCTTTTGCGAATGAGCCAACAAATGCGCTACAAAATATGGATTATA 127
Sequence_47     ATTCTAACAGATACCCTTTTGCGAATGAGCCAACAAATGCGCTACAAAATATGGATTATA 127
Sequence_79     ATTCTAACAGATACCCTTTTGCGAATGAGCCAACAAATGCGCTACAAAATATGGATTATA 127
Sequence_51     ATTCTAACAGATACCCTTTTGCGAATGAGCCAACAAATGCGCTACAAAATATGGATTATA 127
Sequence_83     ATTCTAACAGATACCCTTTTGCGAATGAGCCAACAAATGCGCTACAAAATATGGATTATA 127
Sequence_7      ATTCTAACAGATACCCTTTTGCGAATGAGCCAACAAATGCGCTACAAAATATGGATTATA 127
Sequence_25     ATTCTAACAGATACCCTTTTGCGAATGAGCCAACAAATGCGCTACAAAATATGGATTATA 127
Sequence_29     ATTCTAACAGATACCCTTTTGCGAATGAGCCAACAAATGCGCTACAAAATATGGATTATA 127
Sequence_33     ATTCTAACAGATACCCTTTTGCGAATGAGCCAACAAATGCGCTACAAAATATGGATTATA 127
Sequence_69     ATTCTAACAGATACCCTTTTGCGAATGAGCCAACAAATGCGCTACAAAATATGGATTATA 127
Sequence_11     ATTCTAACAGATACCCTTTTGCGAATGAGCCAACAAATGCGCTACAAAATATGGATTATA 127
Sequence_5      ATTCTAACAGATACCCTTTTGCGAATGAGCCAACAAATGCGCTACAAAATATGGATTATA 127
Sequence_1      ATTCTAACAGATACCCTTTTGCGAATGAGCCAACAAATGCGCTACAAAATATGGATTATA 127
Sequence_17     ATTCTAACAGATACCCTTTTGCGAATGAGCCAACAAATGCGCTACAAAATATGGATTATA 857
Sequence_3      ATTCTAACAGATACCCTTTTGCGAATGAGCCAACAAATGCGCTACAAAATATGGATTATA 127
Sequence_13     ATTCTAACAGATACCCTTTTGCGAATGAGCCAACAAATGCGCTACAAAATATGGATTATA 127
Sequence_18     ATTCTAACAGATACCCTTTTGCGAATGAGCCAACAAATGCGCTACAAAATATGGATTATA 1380
Cry8Ha1_        ATTCTACCAGATACCCTTATGCGAATGAGCCCACAAATGCGTTACAAAATATGAATTATA 127
                ****** *********** ************ ********* *********** ******
```

To Fig. 16D

Fig. 16C

From Fig. 16C

```
Sequence_71    AAGATTATTTAAAAATGTCTGCGGGAAATGCTAGTGAATACCCTGGTTCACCTGAAGTAC 187
Sequence_73    AAGATTATTTAAAAATGTCTGCGGGAAATGCTAGTGAATACCCTGGTTCACCTGAAGTAC 187
Sequence_21    AAGATTATTTAAAAATGTCTGCGGGAAATGCTAGTGAATACCCTGGTTCACCTGAAGTAC 187
Sequence_67    AAGATTATTTAAAAATGTCTGCGGGAAATGCTAGTGAATACCCTGGTTCACCTGAAGTAC 187
Sequence_61    AAGATTATTTAAAAATGTCTGCGGGAAATGCTAGTGAATACCCTGGTTCACCTGAAGTAC 187
Sequence_93    AAGATTATTTAAAAATGTCTGCGGGAAATGCTAGTGAATACCCTGGTTCACCTGAAGTAC 187
Sequence_59    AAGATTATTTAAAAATGTCTGCGGGAAATGCTAGTGAATACCCTGGTTCACCTGAAGTAC 187
Sequence_91    AAGATTATTTAAAAATGTCTGCGGGAAATGCTAGTGAATACCCTGGTTCACCTGAAGTAC 187
Sequence_39    AAGATTATTTAAAAATGTCTGCGGGAAATGCTAGTGAATACCCTGGTTCACCTGAAGTAC 187
Sequence_41    AAGATTATTTAAAAATGTCTGCGGGAAATGCTAGTGAATACCCTGGTTCACCTGAAGTAC 187
Sequence_49    AAGATTATTTAAAAATGTCTGCGGGAAATGCTAGTGAATACCCTGGTTCACCTGAAGTAC 187
Sequence_81    AAGATTATTTAAAAATGTCTGCGGGAAATGCTAGTGAATACCCTGGTTCACCTGAAGTAC 187
Sequence_45    AAGATTATTTAAAAATGTCTGCGGGAAATGCTAGTGAATACCCTGGTTCACCTGAAGTAC 187
Sequence_77    AAGATTATTTAAAAATGTCTGCGGGAAATGCTAGTGAATACCCTGGTTCACCTGAAGTAC 187
Sequence_75    AAGATTATTTAAAAATGTCTGCGGGAAATGCTAGTGAATACCCTGGTTCACCTGAAGTAC 187
Sequence_43    AAGATTATTTAAAAATGTCTGCGGGAAATGCTAGTGAATACCCTGGTTCACCTGAAGTAC 187
Sequence_47    AAGATTATTTAAAAATGTCTGCGGGAAATGCTAGTGAATACCCTGGTTCACCTGAAGTAC 187
Sequence_79    AAGATTATTTAAAAATGTCTGCGGGAAATGCTAGTGAATACCCTGGTTCACCTGAAGTAC 187
Sequence_51    AAGATTATTTAAAAATGTCTGCGGGAAATGCTAGTGAATACCCTGGTTCACCTGAAGTAC 187
Sequence_83    AAGATTATTTAAAAATGTCTGCGGGAAATGCTAGTGAATACCCTGGTTCACCTGAAGTAC 187
Sequence_7     AAGATTATTTAAAAATGTCTGCGGGAAATGCTAGTGAATACCCTGGTTCACCTGAAGTAC 187
Sequence_25    AAGATTATTTAAAAATGTCTGCGGGAAATGCTAGTGAATACCCTGGTTCACCTGAAGTAC 187
Sequence_29    AAGATTATTTAAAAATGTCTGCGGGAAATGCTAGTGAATACCCTGGTTCACCTGAAGTAC 187
Sequence_33    AAGATTATTTAAAAATGTCTGCGGGAAATGCTAGTGAATACCCTGGTTCACCTGAAGTAC 187
Sequence_69    AAGATTATTTAAAAATGTCTGCGGGAAATGCTAGTGAATACCCTGGTTCACCTGAAGTAC 187
Sequence_11    AAGATTATTTAAAAATGTCTGCGGGAAATGCTAGTGAATACCCTGGTTCACCTGAAGTAC 187
Sequence_5     AAGATTATTTAAAAATGTCTGCGGGAAATGCTAGTGAATACCCTGGTTCACCTGAAGTAC 187
Sequence_1     AAGATTATTTAAAAATGTCTGCGGGAAATGCTAGTGAATACCCTGGTTCACCTGAAGTAC 187
Sequence_17    AAGATTATTTAAAAATGTCTGCGGGAAATGCTAGTGAATACCCTGGTTCACCTGAAGTAC 917
Sequence_3     AAGATTATTTAAAAATGTCTGCGGGAAATGCTAGTGAATACCCTGGTTCACCTGAAGTAC 187
Sequence_13    AAGATTATTTAAAAATGTCTGCGGGAAATGCTAGTGAATACCCTGGTTCACCTGAAGTAC 187
Sequence_18    AAGATTATTTAAAAATGTCTGCGGGAAATGCTAGTGAATACCCTGGTTCACCTGAAGTAC 1440
Cry8Ha1_       AGGATTATTTAAGAATGTCTGAAGGTTACGATAATAAATATTTTGCAAATCCTGAAGTGT 187
               * ********** ********   **   * * ** * ****    **      *******
```

To Fig. 16E

Fig. 16D

From Fig. 16D

```
Sequence_71        TTGTTAGCGGACAAGATGCAGCTAAGGCCGCAATTGATATAGTAGGTAAATTACTATCAG 247
Sequence_73        TTGTTAGCGGACAAGATGCAGCTAAGGCCGCAATTGATATAGTAGGTAAATTACTATCAG 247
Sequence_21        TTGTTAGCGGACAAGATGCAGCTAAGGCCGCAATTGATATAGTAGGTAAATTACTATCAG 247
Sequence_67        TTGTTAGCGGACAAGATGCAGCTAAGGCCGCAATTGATATAGTAGGTAAATTACTATCAG 247
Sequence_61        TTGTTAGCGGACAAGATGCAGCTAAGGCCGCAATTGATATAGTAGGTAAATTACTATCAG 247
Sequence_93        TTGTTAGCGGACAAGATGCAGCTAAGGCCGCAATTGATATAGTAGGTAAATTACTATCAG 247
Sequence_59        TTGTTAGCGGACAAGATGCAGCTAAGGCCGCAATTGATATAGTAGGTAAATTACTATCAG 247
Sequence_91        TTGTTAGCGGACAAGATGCAGCTAAGGCCGCAATTGATATAGTAGGTAAATTACTATCAG 247
Sequence_39        TTGTTAGCGGACAAGATGCAGCTAAGGCCGCAATTGATATAGTAGGTAAATTACTATCAG 247
Sequence_41        TTGTTAGCGGACAAGATGCAGCTAAGGCCGCAATTGATATAGTAGGTAAATTACTATCAG 247
Sequence_49        TTGTTAGCGGACAAGATGCAGCTAAGGCCGCAATTGATATAGTAGGTAAATTACTATCAG 247
Sequence_81        TTGTTAGCGGACAAGATGCAGCTAAGGCCGCAATTGATATAGTAGGTAAATTACTATCAG 247
Sequence_45        TTGTTAGCGGACAAGATGCAGCTAAGGCCGCAATTGATATAGTAGGTAAATTACTATCAG 247
Sequence_77        TTGTTAGCGGACAAGATGCAGCTAAGGCCGCAATTGATATAGTAGGTAAATTACTATCAG 247
Sequence_75        TTGTTAGCGGACAAGATGCAGCTAAGGCCGCAATTGATATAGTAGGTAAATTACTATCAG 247
Sequence_43        TTGTTAGCGGACAAGATGCAGCTAAGGCCGCAATTGATATAGTAGGTAAATTACTATCAG 247
Sequence_47        TTGTTAGCGGACAAGATGCAGCTAAGGCCGCAATTGATATAGTAGGTAAATTACTATCAG 247
Sequence_79        TTGTTAGCGGACAAGATGCAGCTAAGGCCGCAATTGATATAGTAGGTAAATTACTATCAG 247
Sequence_51        TTGTTAGCGGACAAGATGCAGCTAAGGCCGCAATTGATATAGTAGGTAAATTACTATCAG 247
Sequence_83        TTGTTAGCGGACAAGATGCAGCTAAGGCCGCAATTGATATAGTAGGTAAATTACTATCAG 247
Sequence_7         TTGTTAGCGGACAAGATGCAGCTAAGGCCGCAATTGATATAGTAGGTAAATTACTATCAG 247
Sequence_25        TTGTTAGCGGACAAGATGCAGCTAAGGCCGCAATTGATATAGTAGGTAAATTACTATCAG 247
Sequence_29        TTGTTAGCGGACAAGATGCAGCTAAGGCCGCAATTGATATAGTAGGTAAATTACTATCAG 247
Sequence_33        TTGTTAGCGGACAAGATGCAGCTAAGGCCGCAATTGATATAGTAGGTAAATTACTATCAG 247
Sequence_69        TTGTTAGCGGACAAGATGCAGCTAAGGCCGCAATTGATATAGTAGGTAAATTACTATCAG 247
Sequence_11        TTGTTAGCGGACAAGATGCAGCTAAGGCCGCAATTGATATAGTAGGTAAATTACTATCAG 247
Sequence_5         TTGTTAGCGGACAAGATGCAGCTAAGGCCGCAATTGATATAGTAGGTAAATTACTATCAG 247
Sequence_1         TTGTTAGCGGACAAGATGCAGCTAAGGCCGCAATTGATATAGTAGGTAAATTACTATCAG 247
Sequence_17        TTGTTAGCGGACAAGATGCAGCTAAGGCCGCAATTGATATAGTAGGTAAATTACTATCAG 977
Sequence_3         TTGTTAGCGGACAAGATGCAGCTAAGGCCGCAATTGATATAGTAGGTAAATTACTATCAG 247
Sequence_13        TTGTTAGCGGACAAGATGCAGCTAAGGCCGCAATTGATATAGTAGGTAAATTACTATCAG 247
Sequence_18        TTGTTAGCGGACAAGATGCAGCTAAGGCCGCAATTGATATAGTAGGTAAATTACTATCAG 1500
Cry8Ha1            TTGCT---GCACCAGGTGGGATTACAACTGGAATTACTATAGTTACTAAATTACTGGGT 244
                   *** *   * ** ** **    **   * * ****  ******   *********
```

To Fig. 16F

Fig. 16E

From Fig. 16E

```
Sequence_71      GTTTAGGGGTCCCATTTGTTGGGCCGATAGTGAGTCTTTATACTCAACTTATTGATATTC 307
Sequence_73      GTTTAGGGGTCCCATTTGTTGGGCCGATAGTGAGTCTTTATACTCAACTTATTGATATTC 307
Sequence_21      GTTTAGGGGTCCCATTTGTTGGGCCGATAGTGAGTCTTTATACTCAACTTATTGATATTC 307
Sequence_67      GTTTAGGGGTCCCATTTGTTGGGCCGATAGTGAGTCTTTATACTCAACTTATTGATATTC 307
Sequence_61      GTTTAGGGGTCCCATTTGTTGGGCCGATAGTGAGTCTTTATACTCAACTTATTGATATTC 307
Sequence_93      GTTTAGGGGTCCCATTTGTTGGGCCGATAGTGAGTCTTTATACTCAACTTATTGATATTC 307
Sequence_59      GTTTAGGGGTCCCATTTGTTGGGCCGATAGTGAGTCTTTATACTCAACTTATTGATATTC 307
Sequence_91      GTTTAGGGGTCCCATTTGTTGGGCCGATAGTGAGTCTTTATACTCAACTTATTGATATTC 307
Sequence_39      GTTTAGGGGTCCCATTTGTTGGGCCGATAGTGAGTCTTTATACTCAACTTATTGATATTC 307
Sequence_41      GTTTAGGGGTCCCATTTGTTGGGCCGATAGTGAGTCTTTATACTCAACTTATTGATATTC 307
Sequence_49      GTTTAGGGGTCCCATTTGTTGGGCCGATAGTGAGTCTTTATACTCAACTTATTGATATTC 307
Sequence_81      GTTTAGGGGTCCCATTTGTTGGGCCGATAGTGAGTCTTTATACTCAACTTATTGATATTC 307
Sequence_45      GTTTAGGGGTCCCATTTGTTGGGCCGATAGTGAGTCTTTATACTCAACTTATTGATATTC 307
Sequence_77      GTTTAGGGGTCCCATTTGTTGGGCCGATAGTGAGTCTTTATACTCAACTTATTGATATTC 307
Sequence_75      GTTTAGGGGTCCCATTTGTTGGGCCGATAGTGAGTCTTTATACTCAACTTATTGATATTC 307
Sequence_43      GTTTAGGGGTCCCATTTGTTGGGCCGATAGTGAGTCTTTATACTCAACTTATTGATATTC 307
Sequence_47      GTTTAGGGGTCCCATTTGTTGGGCCGATAGTGAGTCTTTATACTCAACTTATTGATATTC 307
Sequence_79      GTTTAGGGGTCCCATTTGTTGGGCCGATAGTGAGTCTTTATACTCAACTTATTGATATTC 307
Sequence_51      GTTTAGGGGTCCCATTTGTTGGGCCGATAGTGAGTCTTTATACTCAACTTATTGATATTC 307
Sequence_83      GTTTAGGGGTCCCATTTGTTGGGCCGATAGTGAGTCTTTATACTCAACTTATTGATATTC 307
Sequence_7       GTTTAGGGGTCCCATTTGTTGGGCCGATAGTGAGTCTTTATACTCAACTTATTGATATTC 307
Sequence_25      GTTTAGGGGTCCCATTTGTTGGGCCGATAGTGAGTCTTTATACTCAACTTATTGATATTC 307
Sequence_29      GTTTAGGGGTCCCATTTGTTGGGCCGATAGTGAGTCTTTATACTCAACTTATTGATATTC 307
Sequence_33      GTTTAGGGGTCCCATTTGTTGGGCCGATAGTGAGTCTTTATACTCAACTTATTGATATTC 307
Sequence_69      GTTTAGGGGTCCCATTTGTTGGGCCGATAGTGAGTCTTTATACTCAACTTATTGATATTC 307
Sequence_11      GTTTAGGGGTCCCATTTGTTGGGCCGATAGTGAGTCTTTATACTCAACTTATTGATATTC 307
Sequence_5       GTTTAGGGGTCCCATTTGTTGGGCCGATAGTGAGTCTTTATACTCAACTTATTGATATTC 307
Sequence_1       GTTTAGGGGTCCCATTTGTTGGGCCGATAGTGAGTCTTTATACTCAACTTATTGATATTC 307
Sequence_17      GTTTAGGGGTCCCATTTGTTGGGCCGATAGTGAGTCTTTATACTCAACTTATTGATATTC 1037
Sequence_3       GTTTAGGGGTCCCATTTGTTGGGCCGATAGTGAGTCTTTATACTCAACTTATTGATATTC 307
Sequence_13      GTTTAGGGGTCCCATTTGTTGGGCCGATAGTGAGTCTTTATACTCAACTTATTGATATTC 307
Sequence_18      GTTTAGGGGTCCCATTTGTTGGGCCGATAGTGAGTCTTTATACTCAACTTATTGATATTC 1560
Cry8Ha1          GGTTAGGACTTCCATTTGCTGGGGAAACAGGGATGGCTCTTAATTTCATTCTAGGTCTAT 304
                 * *****  * ******* ****   * ** **    *  ** *    ** * * * *
```

To Fig. 16G

Fig. 16F

From Fig. 16F

```
Sequence_71    TGTGGCCTTCAGGGGAAAAGAGTCAATGGGAAATTTTTATGGAACAAGTAGAAGAACTCA 367
Sequence_73    TGTGGCCTTCAGGGGAAAAGAGTCAATGGGAAATTTTTATGGAACAAGTAGAAGAACTCA 367
Sequence_21    TGTGGCCTTCAGGGGAAAAGAGTCAATGGGAAATTTTTATGGAACAAGTAGAAGAACTCA 367
Sequence_67    TGTGGCCTTCAGGGGAAAAGAGTCAATGGGAAATTTTTATGGAACAAGTAGAAGAACTCA 367
Sequence_61    TGTGGCCTTCAGGGGAAAAGAGTCAATGGGAAATTTTTATGGAACAAGTAGAAGAACTCA 367
Sequence_93    TGTGGCCTTCAGGGGAAAAGAGTCAATGGGAAATTTTTATGGAACAAGTAGAAGAACTCA 367
Sequence_59    TGTGGCCTTCAGGGGAAAAGAGTCAATGGGAAATTTTTATGGAACAAGTAGAAGAACTCA 367
Sequence_91    TGTGGCCTTCAGGGGAAAAGAGTCAATGGGAAATTTTTATGGAACAAGTAGAAGAACTCA 367
Sequence_39    TGTGGCCTTCAGGGGAAAAGAGTCAATGGGAAATTTTTATGGAACAAGTAGAAGAACTCA 367
Sequence_41    TGTGGCCTTCAGGGGAAAAGAGTCAATGGGAAATTTTTATGGAACAAGTAGAAGAACTCA 367
Sequence_49    TGTGGCCTTCAGGGGAAAAGAGTCAATGGGAAATTTTTATGGAACAAGTAGAAGAACTCA 367
Sequence_81    TGTGGCCTTCAGGGGAAAAGAGTCAATGGGAAATTTTTATGGAACAAGTAGAAGAACTCA 367
Sequence_45    TGTGGCCTTCAGGGGAAAAGAGTCAATGGGAAATTTTTATGGAACAAGTAGAAGAACTCA 367
Sequence_77    TGTGGCCTTCAGGGGAAAAGAGTCAATGGGAAATTTTTATGGAACAAGTAGAAGAACTCA 367
Sequence_75    TGTGGCCTTCAGGGGAAAAGAGTCAATGGGAAATTTTTATGGAACAAGTAGAAGAACTCA 367
Sequence_43    TGTGGCCTTCAGGGGAAAAGAGTCAATGGGAAATTTTTATGGAACAAGTAGAAGAACTCA 367
Sequence_47    TGTGGCCTTCAGGGGAAAAGAGTCAATGGGAAATTTTTATGGAACAAGTAGAAGAACTCA 367
Sequence_79    TGTGGCCTTCAGGGGAAAAGAGTCAATGGGAAATTTTTATGGAACAAGTAGAAGAACTCA 367
Sequence_51    TGTGGCCTTCAGGGGAAAAGAGTCAATGGGAAATTTTTATGGAACAAGTAGAAGAACTCA 367
Sequence_83    TGTGGCCTTCAGGGGAAAAGAGTCAATGGGAAATTTTTATGGAACAAGTAGAAGAACTCA 367
Sequence_7     TGTGGCCTTCAGGGGAAAAGAGTCAATGGGAAATTTTTATGGAACAAGTAGAAGAACTCA 367
Sequence_25    TGTGGCCTTCAGGGGAAAAGAGTCAATGGGAAATTTTTATGGAACAAGTAGAAGAACTCA 367
Sequence_29    TGTGGCCTTCAGGGGAAAAGAGTCAATGGGAAATTTTTATGGAACAAGTAGAAGAACTCA 367
Sequence_33    TGTGGCCTTCAGGGGAAAAGAGTCAATGGGAAATTTTTATGGAACAAGTAGAAGAACTCA 367
Sequence_69    TGTGGCCTTCAGGGGAAAAGAGTCAATGGGAAATTTTTATGGAACAAGTAGAAGAACTCA 367
Sequence_11    TGTGGCCTTCAGGGGAAAAGAGTCAATGGGAAATTTTTATGGAACAAGTAGAAGAACTCA 367
Sequence_5     TGTGGCCTTCAGGGGAAAAGAGTCAATGGGAAATTTTTATGGAACAAGTAGAAGAACTCA 367
Sequence_1     TGTGGCCTTCAGGGGAAAAGAGTCAATGGGAAATTTTTATGGAACAAGTAGAAGAACTCA 367
Sequence_17    TGTGGCCTTCAGGGGAAAAGAGTCAATGGGAAATTTTTATGGAACAAGTAGAAGAACTCA 1097
Sequence_3     TGTGGCCTTCAGGGCAAAAGAGTCAATGGGAGATTTTTATGGAACAAGTAGAAGAACTCA 367
Sequence_13    TGTGGCCTTCAGGGCAAAAGAGTCAATGGGAGATTTTTATGGAACAAGTAGAAGAACTCA 367
Sequence_18    TGTGGCCTTCAGGGCAAAAGAGTCAATGGGAGATTTTTATGGAACAAGTAGAAGAACTCA 1620
Cry8Ha1        TATGGCCAACA---TCAGGAAACCCGTGGGCTGAACTAATGATATTGGTAGAAGAACTCA 361
               * *****  **     *   *  *  ****      * ***  *   *************
```

To Fig. 16H

Fig. 16G

From Fig. 16G

```
Sequence_71     TTAATCAAAAAATAGCAGAATATGCAAGGAATAAAGCGCTTTCGGAATTAGAAGGATTAG 427
Sequence_73     TTAATCAAAAAATAGCAGAATATGCAAGGAATAAAGCGCTTTCGGAATTAGAAGGATTAG 427
Sequence_21     TTAATCAAAAAATAGCAGAATATGCAAGGAATAAAGCGCTTTCGGAATTAGAAGGATTAG 427
Sequence_67     TTAATCAAAAAATAGCAGAATATGCAAGGAATAAAGCGCTTTCGGAATTAGAAGGATTAG 427
Sequence_61     TTAATCAAAAAATAGCAGAATATGCAAGGAATAAAGCGCTTTCGGAATTAGAAGGATTAG 427
Sequence_93     TTAATCAAAAAATAGCAGAATATGCAAGGAATAAAGCGCTTTCGGAATTAGAAGGATTAG 427
Sequence_59     TTAATCAAAAAATAGCAGAATATGCAAGGAATAAAGCGCTTTCGGAATTAGAAGGATTAG 427
Sequence_91     TTAATCAAAAAATAGCAGAATATGCAAGGAATAAAGCGCTTTCGGAATTAGAAGGATTAG 427
Sequence_39     TTAATCAAAAAATAGCAGAATATGCAAGGAATAAAGCGCTTTCGGAATTAGAAGGATTAG 427
Sequence_41     TTAATCAAAAAATAGCAGAATATGCAAGGAATAAAGCGCTTTCGGAATTAGAAGGATTAG 427
Sequence_49     TTAATCAAAAAATAGCAGAATATGCAAGGAATAAAGCGCTTTCGGAATTAGAAGGATTAG 427
Sequence_81     TTAATCAAAAAATAGCAGAATATGCAAGGAATAAAGCGCTTTCGGAATTAGAAGGATTAG 427
Sequence_45     TTAATCAAAAAATAGCAGAATATGCAAGGAATAAAGCGCTTTCGGAATTAGAAGGATTAG 427
Sequence_77     TTAATCAAAAAATAGCAGAATATGCAAGGAATAAAGCGCTTTCGGAATTAGAAGGATTAG 427
Sequence_75     TTAATCAAAAAATAGCAGAATATGCAAGGAATAAAGCGCTTTCGGAATTAGAAGGATTAG 427
Sequence_43     TTAATCAAAAAATAGCAGAATATGCAAGGAATAAAGCGCTTTCGGAATTAGAAGGATTAG 427
Sequence_47     TTAATCAAAAAATAGCAGAATATGCAAGGAATAAAGCGCTTTCGGAATTAGAAGGATTAG 427
Sequence_79     TTAATCAAAAAATAGCAGAATATGCAAGGAATAAAGCGCTTTCGGAATTAGAAGGATTAG 427
Sequence_51     TTAATCAAAAAATAGCAGAATATGCAAGGAATAAAGCGCTTTCGGAATTAGAAGGATTAG 427
Sequence_83     TTAATCAAAAAATAGCAGAATATGCAAGGAATAAAGCGCTTTCGGAATTAGAAGGATTAG 427
Sequence_7      TTAATCAAAAAATAGCAGAATATGCAAGGAATAAAGCGCTTTCGGAATTAGAAGGATTAG 427
Sequence_25     TTAATCAAAAAATAGCAGAATATGCAAGGAATAAAGCGCTTTCGGAATTAGAAGGATTAG 427
Sequence_29     TTAATCAAAAAATAGCAGAATATGCAAGGAATAAAGCGCTTTCGGAATTAGAAGGATTAG 427
Sequence_33     TTAATCAAAAAATAGCAGAATATGCAAGGAATAAAGCGCTTTCGGAATTAGAAGGATTAG 427
Sequence_69     TTAATCAAAAAATAGCAGAATATGCAAGGAATAAAGCGCTTTCGGAATTAGAAGGATTAG 427
Sequence_11     TTAATCAAAAAATAGCAGAATATGCAAGGAATAAAGCGCTTTCGGAATTAGAAGGATTAG 427
Sequence_5      TTAATCAAAAAATAGCAGAATATGCAAGGAATAAAGCGCTTTCGGAATTAGAAGGATTAG 427
Sequence_1      TTAATCAAAAAATAGCAGAATATGCAAGGAATAAAGCGCTTTCGGAATTAGAAGGATTAG 427
Sequence_17     TTAATCAAAAAATAGCAGAATATGCAAGGAATAAAGCGCTTTCGGAATTAGAAGGATTAG 1157
Sequence_3      TAAATCAAAAAATAGCAGAATATGCAAGGAATAAAGCGCTTTCGGAATTAGAAGGATTAG 427
Sequence_13     TAAATCAAAAAATAGCAGAATATGCAAGGAATAAAGCGCTTTCGGAATTAGAAGGATTAG 427
Sequence_18     TAAATCAAAAAATAGCAGAATATGCAAGGAATAAAGCGCTTTCGGAATTAGAAGGATTAG 1680
Cry8Ha1         TAAATCAAAAAATAGAAGAGACTGTAAGAAACAAAGCACTAGCGGATTTGGGCAATTCAG 421
                * ************* ***   ** *** ** ***** **  **** ** *     * **
```

To Fig. 16I

Fig. 16H

From Fig. 16H

```
Sequence_71     GTAATAATTACCAATTATATCTAACTGCGCTTGAAGAATGGGAAGAAAATCCATTTCGAA 487
Sequence_73     GTAATAATTACCAATTATATCTAACTGCGCTTGAAGAATGGGAAGAAAATCCATTTCGAA 487
Sequence_21     GTAATAATTACCAATTATATCTAACTGCGCTTGAAGAATGGGAAGAAAATCCATTTCGA- 486
Sequence_67     GTAATAATTACCAATTATATCTAACTGCGCTTGAAGAATGGGAAGAAAATCCATTTCGA- 486
Sequence_61     GTAATAATTACCAATTATATCTAACTGCGCTTGAAGAATGGGAAGAAAATCCATTTCGA- 486
Sequence_93     GTAATAATTACCAATTATATCTAACTGCGCTTGAAGAATGGGAAGAAAATCCATTTCGA- 486
Sequence_59     GTAATAATTACCAATTATATCTAACTGCGCTTGAAGAATGGGAAGAAAATCCATTTCGA- 486
Sequence_91     GTAATAATTACCAATTATATCTAACTGCGCTTGAAGAATGGGAAGAAAATCCATTTCGA- 486
Sequence_39     GTAATAATTACCAATTATATCTAACTGCGCTTGAAGAATGGGAAGAAAATCCATTTCGAA 487
Sequence_41     GTAATAATTACCAATTATATCTAACTGCGCTTGAAGAATGGGAAGAAAATCCATTTCGAA 487
Sequence_49     GTAATAATTACCAATTATATCTAACTGCGCTTGAAGAATGGGAAGAAAATCCAAATGGTT 487
Sequence_81     GTAATAATTACCAATTATATCTAACTGCGCTTGAAGAATGGGAAGAAAATCCAAATGGTT 487
Sequence_45     GTAATAATTACCAATTATATCTAACTGCGCTTGAAGAATGGGAAGAAAATCCAAATGGTT 487
Sequence_77     GTAATAATTACCAATTATATCTAACTGCGCTTGAAGAATGGGAAGAAAATCCAAATGGTT 487
Sequence_75     GTAATAATTACCAATTATATCTAACTGCGCTTGAAGAATGGGAAGAAAATCCAAATGGTT 487
Sequence_43     GTAATAATTACCAATTATATCTAACTGCGCTTGAAGAATGGGAAGAAAATCCAAATGGTT 487
Sequence_47     GTAATAATTACCAATTATATCTAACTGCGCTTGAAGAATGGGAAGAAAATCCATTTCGAA 487
Sequence_79     GTAATAATTACCAATTATATCTAACTGCGCTTGAAGAATGGGAAGAAAATCCATTTCGAA 487
Sequence_51     GTAATAATTACCAATTATATCTAACTGCGCTTGAAGAATGGGAAGAAAATCCATTTCGAA 487
Sequence_83     GTAATAATTACCAATTATATCTAACTGCGCTTGAAGAATGGGAAGAAAATCCATTTCGAA 487
Sequence_7      GTAATAATTACCAATTATATCTAACTGCGCTTGAAGAATGGGAAGAAAATCCAAATGGT- 486
Sequence_25     GTAATAATTACCAATTATATCTAACTGCGCTTGAAGAATGGGAAGAAAATCCAAATGGT- 486
Sequence_29     GTAATAATTACCAATTATATCTAACTGCGCTTGAAGAATGGGAAGAAAATCCAAATGGT- 486
Sequence_33     GTAATAATTACCAATTATATCTAACTGCGCTTGAAGAATGGGAAGAAAATCCAAATGGT- 486
Sequence_69     GTAATAATTACCAATTATATCTAACTGCGCTTGAAGAATGGGAAGAAAATCCAAATGGT- 486
Sequence_11     GTAATAATTACCAATTATATCTAACTGCGCTTGAAGAATGGGAAGAAAATCCAAATGGT- 486
Sequence_5      GTAATAATTACCAATTATATCTAACTGCGCTTGAAGAATGGGAAGAAAATCCAAATGGT- 486
Sequence_1      GTAATAATTACCAATTATATCTAACTGCGCTTGAAGAATGGGAAGAAAATCCAAATGGT- 486
Sequence_17     GTAATAATTACCAATTATATCTAACTGCGCTTGAAGAATGGGAAGAAAATCCAAATGGT- 1216
Sequence_3      GTAATAATTACCAATTATATCTAACTGCGCTTGAAGAATGGAAAGAAAATCCAAATGGT- 486
Sequence_13     GTAATAATTACCAATTATATCTAACTGCGCTTGAAGAATGGAAAGAAAATCCAAATGGT- 486
Sequence_18     GTAATAATTACCAATTATATCTAACTGCGCTTGAAGAATGGAAAGAAAATCCAAATGGT- 1739
Cry8Ha1         GTAGAGCCTTACGATCCTATTTAACGCATTTGAAGATTGGCAAAAAAACCCTAATATCT 481
                ***     *  * **  *** ***  **  ******* *** ** **** **   *
```

To Fig. 16J

Fig. 16I

From Fig. 16I

```
Sequence_71     GTCGAGGTTTTCGAAGTCGAGGTCCA---GCCTTACGAGAT-GTGCGAAATCGATTTGAA 543
Sequence_73     GTCGAGGTTTTCGAAGTCGAGGT------GCCTTACGAGAT-GTGCGAAATCGATTTGAA 540
Sequence_21     --CGAGGTTTTCGA---CGAGGT------GCCTTACGAGAT-GTGCGAAATCGATTTGAA 534
Sequence_67     --CGAGGTTTTCGA---CGAGGT------GCCTTACGAGAT-GTGCGAAATCGATTTGAA 534
Sequence_61     --CGAGGTTTTCGA---CGAGGT------GCCTTACGAGAT-GTGCGAAATCGATTTGAA 534
Sequence_93     --CGAGGTTTTCGA---CGAGGT------GCCTTACGAGAT-GTGCGAAATCGATTTGAA 534
Sequence_59     --CGAGGTTTTCGA---CGAGGT------GCCTTACGAGAT-GTGCGAAATCGATTTGAA 534
Sequence_91     --CGAGGTTTTCGA---CGAGGT------GCCTTACGAGAT-GTGCGAAATCGATTTGAA 534
Sequence_39     GTCGAGGTTTTCGAAGTCGAGGTCCA---GCCTTACGAGAT-GTGCGAAATCGATTTGAA 543
Sequence_41     GTCGAGGTTTTCGAAGTCGAGGT------GCCTTACGAGAT-GTGCGAAATCGATTTGAA 540
Sequence_49     CCCGG---TTTCGAAGTCGA---CAA---GCCTTACGAGAT-GTGCGAAATCGATTTGAA 537
Sequence_81     CCCGG---TTTCGAAGTCGA---CAA---GCCTTACGAGAT-GTGCGAAATCGATTTGAA 537
Sequence_45     CCCGG---TTTCGAAGTCGAGGTCCA---GCCTTACGAGAT-GTGCGAAATCGATTTGAA 540
Sequence_77     CCCGG---TTTCGAAGTCGAGGTCCA---GCCTTACGAGAT-GTGCGAAATCGATTTGAA 540
Sequence_75     CCCGG---TTTCGAAGTCGAG---GT---GCCTTACGAGAT-GTGCGAAATCGATTTGAA 537
Sequence_43     CCCGG---TTTCGAAGTCGAG---GT---GCCTTACGAGAT-GTGCGAAATCGATTTGAA 537
Sequence_47     GTCGAGGT---CCAAATGGTTCCCGG---GCCTTACGAGAT-GTGCGAAATCGATTTGAA 540
Sequence_79     GTCGAGGT---CCAAATGGTTCCCGG---GCCTTACGAGAT-GTGCGAAATCGATTTGAA 540
Sequence_51     GTCGAGGTAGTTTAAATGGTTCCCGGCCAGCCTTACGAGAT-GTGCGAAATCGATTTGAA 546
Sequence_83     GTCGAGGTAGTTTAAATGGTTCCCGGCCAGCCTTACGAGAT-GTGCGAAATCGATTTGAA 546
Sequence_7      -TCAA-------GAAATGGTTCCCGG---GCCTTACGAGAT-GTGCGAAATCGATTTGAA 534
Sequence_25     -TCAA-------GAAATGGTTCCCGG---GCCTTACGAGAT-GTGCGAAATCGATTTGAA 534
Sequence_29     -TCAA-------GAAATGGTTCCCGG---GCCTTACGAGAT-GTGCGAAATCGATTTGAA 534
Sequence_33     -TCAA-------GAAATGGTTCCCGG---GCCTTACGAGAT-GTGCGAAATCGATTTGAA 534
Sequence_69     -TCAA-------GAAATGGTTCCCGG---GCCTTACGAGAT-GTGCGAAATCGATTTGAA 534
Sequence_11     -TCAA-------GA---------------GCCTTACGAGAT-GTGCGAAATCGATTTGAA 522
Sequence_5      -TCAA-------GA---------------GCCTTACGAGAT-GTGCGAAATCGATTTGAA 522
Sequence_1      -TCAA-------GA---------------GCCTTACGAGAT-GTGCGAAATCGATTTGAA 522
Sequence_17     -TCAA-------GA---------------GCCTTACGAGAT-GTGCGAAATCGATTTGAA 1252
Sequence_3      -TCAA-------GA---------------GCCTTACGAGAT-GTGCGAAATCGATTTGAA 522
Sequence_13     -TCAA-------GA---------------GCCTTACGAGAT-GTGCGAAATCGATTTGAA 522
Sequence_18     -TCAA-------GA---------------GCCTTACGAGAT-GTGCGAAATCGATTTGAA 1775
Cry8Ha1         TTCG-------------------------GAGTAAAGAGTTAGTAAAAGAAAGATTTCA 516
                  *                          *  * * *** * **   * *  *****  *
```

To Fig. 16K

Fig. 16J

From Fig. 16J

```
Sequence_71    ATCCTGGATAGTTTATTTACGCAAT-ATATGCCATCTTTTAGAGTGACAAATTTTGAAGT 602
Sequence_73    ATCCTGGATAGTTTATTTACGCAAT-ATATGCCATCTTTTAGAGTGACAAATTTTGAAGT 599
Sequence_21    ATCCTGGATAGTTTATTTACGCAAT-ATATGCCATCTTTTAGAGTGACAAATTTTGAAGT 593
Sequence_67    ATCCTGGATAGTTTATTTACGCAAT-ATATGCCATCTTTTAGAGTGACAAATTTTGAAGT 593
Sequence_61    ATCCTGGATAGTTTATTTACGCAAT-ATATGCCATCTTTTAGAGTGACAAATTTTGAAGT 593
Sequence_93    ATCCTGGATAGTTTATTTACGCAAT-ATATGCCATCTTTTAGAGTGACAAATTTTGAAGT 593
Sequence_59    ATCCTGGATAGTTTATTTACGCAAT-ATATGCCATCTTTTAGAGTGACAAATTTTGAAGT 593
Sequence_91    ATCCTGGATAGTTTATTTACGCAAT-ATATGCCATCTTTTAGAGTGACAAATTTTGAAGT 593
Sequence_39    ATCCTGGATAGTTTATTTACGCAAT-ATATGCCATCTTTTAGAGTGACAAATTTTGAAGT 602
Sequence_41    ATCCTGGATAGTTTATTTACGCAAT-ATATGCCATCTTTTAGAGTGACAAATTTTGAAGT 599
Sequence_49    ATCCTGGATAGTTTATTTACGCAAT-ATATGCCATCTTTTAGAGTGACAAATTTTGAAGT 596
Sequence_81    ATCCTGGATAGTTTATTTACGCAAT-ATATGCCATCTTTTAGAGTGACAAATTTTGAAGT 596
Sequence_45    ATCCTGGATAGTTTATTTACGCAAT-ATATGCCATCTTTTAGAGTGACAAATTTTGAAGT 599
Sequence_77    ATCCTGGATAGTTTATTTACGCAAT-ATATGCCATCTTTTAGAGTGACAAATTTTGAAGT 599
Sequence_75    ATCCTGGATAGTTTATTTACGCAAT-ATATGCCATCTTTTAGAGTGACAAATTTTGAAGT 596
Sequence_43    ATCCTGGATAGTTTATTTACGCAAT-ATATGCCATCTTTTAGAGTGACAAATTTTGAAGT 596
Sequence_47    ATCCTGGATAGTTTATTTACGCAAT-ATATGCCATCTTTTAGAGTGACAAATTTTGAAGT 599
Sequence_79    ATCCTGGATAGTTTATTTACGCAAT-ATATGCCATCTTTTAGAGTGACAAATTTTGAAGT 599
Sequence_51    ATCCTGGATAGTTTATTTACGCAAT-ATATGCCATCTTTTAGAGTGACAAATTTTGAAGT 605
Sequence_83    ATCCTGGATAGTTTATTTACGCAAT-ATATGCCATCTTTTAGAGTGACAAATTTTGAAGT 605
Sequence_7     ATCCTGGATAGTTTATTTACGCAAT-ATATGCCATCTTTTAGAGTGACAAATTTTGAAGT 593
Sequence_25    ATCCTGGATAGTTTATTTACGCAAT-ATATGCCATCTTTTAGAGTGACAAATTTTGAAGT 593
Sequence_29    ATCCTGGATAGTTTATTTACGCAAT-ATATGCCATCTTTTAGAGTGACAAATTTTGAAGT 593
Sequence_33    ATCCTGGATAGTTTATTTACGCAAT-ATATGCCATCTTTTAGAGTGACAAATTTTGAAGT 593
Sequence_69    ATCCTGGATAGTTTATTTACGCAAT-ATATGCCATCTTTTAGAGTGACAAATTTTGAAGT 593
Sequence_11    ATCCTGGATAGTTTATTTACGCAAT-ATATGCCATCTTTTAGAGTGACAAATTTTGAAGT 581
Sequence_5     ATCCTGGATAGTTTATTTACGCAAT-ATATGCCATCTTTTAGAGTGACAAATTTTGAAGT 581
Sequence_1     ATCCTGGATAGTTTATTTACGCAAT-ATATGCCATCTTTTAGAGTGACAAATTTTGAAGT 581
Sequence_17    ATCCTGGATAGTTTATTTACGCAAT-ATATGCCATCTTTTAGAGTGACAAATTTTGAAGT 1311
Sequence_3     ATCCTGGATAGTTTATTTACGCAAT-ACATGCCATCTTTTCGAGTGACAAATTTTGAAGT 581
Sequence_13    ATCCTGGATAGTTTATTTACGCAAT-ACATGCCATCTTTTCGAGTGACAAATTTTGAAGT 581
Sequence_18    ATCCTGGATAGTTTATTTACGCAAT-ACATGCCATCTTTTCGAGTGACAAATTTTGAAGT 1834
Cry8Ha1        AACGCGGAACATTCATT-ACGTACCGAAATGAGTTCTTTTGCCATAAGAGGATTTGAAAT 575
               * *  ***   ** *** *** *   * ***   ******    * * *   ****** *
```

To Fig. 16L

Fig. 16K

From Fig. 16K

```
Sequence_71      ACCATTCCTTACTGTATATGCAATGGCAGCCAACCTTCATTTACTGTTATTAAAGGACGC 662
Sequence_73      ACCATTCCTTACTGTATATGCAATGGCAGCCAACCTTCATTTACTGTTATTAAAGGACGC 659
Sequence_21      ACCATTCCTTACTGTATATGCAATGGCAGCCAACCTTCATTTACTGTTATTAAAGGACGC 653
Sequence_67      ACCATTCCTTACTGTATATGCAATGGCAGCCAACCTTCATTTACTGTTATTAAAGGACGC 653
Sequence_61      ACCATTCCTTACTGTATATGCAATGGCAGCCAACCTTCATTTACTGTTATTAAAGGACGC 653
Sequence_93      ACCATTCCTTACTGTATATGCAATGGCAGCCAACCTTCATTTACTGTTATTAAAGGACGC 653
Sequence_59      ACCATTCCTTACTGTATATGCAATGGCAGCCAACCTTCATTTACTGTTATTAAAGGACGC 653
Sequence_91      ACCATTCCTTACTGTATATGCAATGGCAGCCAACCTTCATTTACTGTTATTAAAGGACGC 653
Sequence_39      ACCATTCCTTACTGTATATGCAATGGCAGCCAACCTTCATTTACTGTTATTAAAGGACGC 662
Sequence_41      ACCATTCCTTACTGTATATGCAATGGCAGCCAACCTTCATTTACTGTTATTAAAGGACGC 659
Sequence_49      ACCATTCCTTACTGTATATGCAATGGCAGCCAACCTTCATTTACTGTTATTAAAGGACGC 656
Sequence_81      ACCATTCCTTACTGTATATGCAATGGCAGCCAACCTTCATTTACTGTTATTAAAGGACGC 656
Sequence_45      ACCATTCCTTACTGTATATGCAATGGCAGCCAACCTTCATTTACTGTTATTAAAGGACGC 659
Sequence_77      ACCATTCCTTACTGTATATGCAATGGCAGCCAACCTTCATTTACTGTTATTAAAGGACGC 659
Sequence_75      ACCATTCCTTACTGTATATGCAATGGCAGCCAACCTTCATTTACTGTTATTAAAGGACGC 656
Sequence_43      ACCATTCCTTACTGTATATGCAATGGCAGCCAACCTTCATTTACTGTTATTAAAGGACGC 656
Sequence_47      ACCATTCCTTACTGTATATGCAATGGCAGCCAACCTTCATTTACTGTTATTAAAGGACGC 659
Sequence_79      ACCATTCCTTACTGTATATGCAATGGCAGCCAACCTTCATTTACTGTTATTAAAGGACGC 659
Sequence_51      ACCATTCCTTACTGTATATGCAATGGCAGCCAACCTTCATTTACTGTTATTAAAGGACGC 665
Sequence_83      ACCATTCCTTACTGTATATGCAATGGCAGCCAACCTTCATTTACTGTTATTAAAGGACGC 665
Sequence_7       ACCATTCCTTACTGTATATGCAATGGCAGCCAACCTTCATTTACTGTTATTAAAGGACGC 653
Sequence_25      ACCATTCCTTACTGTATATGCAATGGCAGCCAACCTTCATTTACTGTTATTAAAGGACGC 653
Sequence_29      ACCATTCCTTACTGTATATGCAATGGCAGCCAACCTTCATTTACTGTTATTAAAGGACGC 653
Sequence_33      ACCATTCCTTACTGTATATGCAATGGCAGCCAACCTTCATTTACTGTTATTAAAGGACGC 653
Sequence_69      ACCATTCCTTACTGTATATGCAATGGCAGCCAACCTTCATTTACTGTTATTAAAGGACGC 653
Sequence_11      ACCATTCCTTACTGTATATGCAATGGCAGCCAACCTTCATTTACTGTTATTAAAGGACGC 641
Sequence_5       ACCATTCCTTACTGTATATGCAATGGCAGCCAACCTTCATTTACTGTTATTAAAGGACGC 641
Sequence_1       ACCATTCCTTACTGTATATGCAATGGCAGCCAACCTTCATTTACTGTTATTAAAGGACGC 641
Sequence_17      ACCATTCCTTACTGTATATGCAATGGCAGCCAACCTTCATTTACTGTTATTAAAGGACGC 1371
Sequence_3       ACCATTCCTTACAGTATATACACAGGCAGCCAACCTTCATTTACTGTTATTAAAGGACGC 641
Sequence_13      ACCATTCCTTACAGTATATACACAGGCAGCCAACCTTCATTTACTGTTATTAAAGGACGC 641
Sequence_18      ACCATTCCTTACAGTATATACACAGGCAGCCAACCTTCATTTACTGTTATTAAAGGACGC 1894
Cry8Ha1          TCCTCTTTTAGCAACATATGCACAAGCTGCGAATTTACATTTATTTCTAATTAAAGATAT 635
                  **  *  *  *   **** **   ** ** **  * ****** *  ** * ** **
```

To Fig. 16M

Fig. 16L

From Fig. 16L

```
Sequence_71      GTCAATTTTTGGAGAAGAATGGGGATGGTCAACAACTACTATTAATAACTATTATGATCG 722
Sequence_73      GTCAATTTTTGGAGAAGAATGGGGATGGTCAACAACTACTATTAATAACTATTATGATCG 719
Sequence_21      GTCAATTTTTGGAGAAGAATGGGGATGGTCAACAACTACTATTAATAACTATTATGATCG 713
Sequence_67      GTCAATTTTTGGAGAAGAATGGGGATGGTCAACAACTACTATTAATAACTATTATGATCG 713
Sequence_61      GTCAATTTTTGGAGAAGAATGGGGATGGTCAACAACTACTATTAATAACGTGGTGGATCG 713
Sequence_93      GTCAATTTTTGGAGAAGAATGGGGATGGTCAACAACTACTATTAATAACGTGGTGGATCG 713
Sequence_59      GTCAATTTTTGGAGAAGAATGGGGATGGTCAACAACTACTATTAATAACTATTATGATCG 713
Sequence_91      GTCAATTTTTGGAGAAGAATGGGGATGGTCAACAACTACTATTAATAACTATTATGATCG 713
Sequence_39      GTCAATTTTTGGAGAAGAATGGGGATGGTCAACAACTACTATTAATAACTATTATGATCG 722
Sequence_41      GTCAATTTTTGGAGAAGAATGGGGATGGTCAACAACTACTATTAATAACTATTATGATCG 719
Sequence_49      GTCAATTTTTGGAGAAGAATGGGGATGGTCAACAACTACTATTAATAACTATTATGATCG 716
Sequence_81      GTCAATTTTTGGAGAAGAATGGGGATGGTCAACAACTACTATTAATAACTATTATGATCG 716
Sequence_45      GTCAATTTTTGGAGAAGAATGGGGATGGTCAACAACTACTATTAATAACTATTATGATCG 719
Sequence_77      GTCAATTTTTGGAGAAGAATGGGGATGGTCAACAACTACTATTAATAACTATTATGATCG 719
Sequence_75      GTCAATTTTTGGAGAAGAATGGGGATGGTCAACAACTACTATTAATAACTATTATGATCG 716
Sequence_43      GTCAATTTTTGGAGAAGAATGGGGATGGTCAACAACTACTATTAATAACTATTATGATCG 716
Sequence_47      GTCAATTTTTGGAGAAGAATGGGGATGGTCAACAACTACTATTAATAACTATTATGATCG 719
Sequence_79      GTCAATTTTTGGAGAAGAATGGGGATGGTCAACAACTACTATTAATAACTATTATGATCG 719
Sequence_51      GTCAATTTTTGGAGAAGAATGGGGATGGTCAACAACTACTATTAATAACTATTATGATCG 725
Sequence_83      GTCAATTTTTGGAGAAGAATGGGGATGGTCAACAACTACTATTAATAACTATTATGATCG 725
Sequence_7       GTCAATTTTTGGAGAAGAATGGGGATGGTCAACAACTACTATTAATAACTATTATGATCG 713
Sequence_25      GTCAATTTTTGGAGAAGAATGGGGATGGTCAACAACTACTATTAATAACTATTATGATCG 713
Sequence_29      GTCAATTTTTGGAGAAGAATGGGGATGGTCAACAACTACTATTAATAACTATTATGATCG 713
Sequence_33      GTCAATTTTTGGAGAAGAATGGGGATGGTCAACAACTACTATTAATAACTATTATGATCG 713
Sequence_69      GTCAATTTTTGGAGAAGAATGGGGATGGTCAACAACTACTATTAATAACTATTATGATCG 713
Sequence_11      GTCAATTTTTGGAGAAGAATGGGGATGGTCAACAACTACTATTAATAACTATTATGATCG 701
Sequence_5       GTCAATTTTTGGAGAAGAATGGGGATGGTCAACAACTACTATTAATAACTATTATGATCG 701
Sequence_1       GTCAATTTTTGGAGAAGAATGGGGATGGTCAACAACTACTATTAATAACTATTATGATCG 701
Sequence_17      GTCAATTTTTGGAGAAGAATGGGGATGGTCAACAACTACTATTAATAACTATTATGATCG 1431
Sequence_3       TTCAATTTTTGGAGAAGAATGGGGATGGTCTACAACCACTATTAATAACTATTATGATCG 701
Sequence_13      TTCAATTTTTGGAGAAGAATGGGGATGGTCTACAACCACTATTAATAACTATTATGATCG 701
Sequence_18      TTCAATTTTTGGAGAAGAATGGGGATGGTCTACAACCACTATTAATAACTATTATGATCG 1954
Cry8Ha1          TCAAATTTATGGAAAAGAATGGGGATATACTCAAGCCGATATTGACTTATTTTATAGAGA 695
                    ***** **** ************   *   * *   **** *
```

To Fig. 16N

Fig. 16M

From Fig. 16M

```
Sequence_71     TCAAATGAAACTTACTGCAGAATATTCTGATCACTGTGTAAAGTGGTATGAAACTGGTTT 782
Sequence_73     TCAAATGAAACTTACTGCAGAATATTCTGATCACTGTGTAAAGTGGTATGAAACTGGTTT 779
Sequence_21     TCAAATGAAACTTACTGCAGAATATTCTGATCACTGTGTAAAGTGGTATGAAACTGGTTT 773
Sequence_67     TCAAATGAAACTTACTGCAGAATATTCTGATCACTGTGTAAAGTGGTATGAAACTGGTTT 773
Sequence_61     TCAAATGAAACTTACTGCAGAATATTCTGATCACTGTGTAAAGTGGTATGAAACTGGTTT 773
Sequence_93     TCAAATGAAACTTACTGCAGAATATTCTGATCACTGTGTAAAGTGGTATGAAACTGGTTT 773
Sequence_59     TCAAATGAAACTTACTGCAGAATATTCTGATCACTGTGTAAAGTGGTATGAAACTGGTTT 773
Sequence_91     TCAAATGAAACTTACTGCAGAATATTCTGATCACTGTGTAAAGTGGTATGAAACTGGTTT 773
Sequence_39     TCAAATGAAACTTACTGCAGAATATTCTGATCACTGTGTAAAGTGGTATGAAACTGGTTT 782
Sequence_41     TCAAATGAAACTTACTGCAGAATATTCTGATCACTGTGTAAAGTGGTATGAAACTGGTTT 779
Sequence_49     TCAAATGAAACTTACTGCAGAATATTCTGATCACTGTGTAAAGTGGTATGAAACTGGTTT 776
Sequence_81     TCAAATGAAACTTACTGCAGAATATTCTGATCACTGTGTAAAGTGGTATGAAACTGGTTT 776
Sequence_45     TCAAATGAAACTTACTGCAGAATATTCTGATCACTGTGTAAAGTGGTATGAAACTGGTTT 779
Sequence_77     TCAAATGAAACTTACTGCAGAATATTCTGATCACTGTGTAAAGTGGTATGAAACTGGTTT 779
Sequence_75     TCAAATGAAACTTACTGCAGAATATTCTGATCACTGTGTAAAGTGGTATGAAACTGGTTT 776
Sequence_43     TCAAATGAAACTTACTGCAGAATATTCTGATCACTGTGTAAAGTGGTATGAAACTGGTTT 776
Sequence_47     TCAAATGAAACTTACTGCAGAATATTCTGATCACTGTGTAAAGTGGTATGAAACTGGTTT 779
Sequence_79     TCAAATGAAACTTACTGCAGAATATTCTGATCACTGTGTAAAGTGGTATGAAACTGGTTT 779
Sequence_51     TCAAATGAAACTTACTGCAGAATATTCTGATCACTGTGTAAAGTGGTATGAAACTGGTTT 785
Sequence_83     TCAAATGAAACTTACTGCAGAATATTCTGATCACTGTGTAAAGTGGTATGAAACTGGTTT 785
Sequence_7      TCAAATGAAACTTACTGCAGAATATTCTGATCACTGTGTAAAGTGGTATGAAACTGGTTT 773
Sequence_25     TCAAATGAAACTTACTGCAGAATATTCTGATCACTGTGTAAAGTGGTATGAAACTGGTTT 773
Sequence_29     TCAAATGAAACTTACTGCAGAATATTCTGATCACTGTGTAAAGTGGTATGAAACTGGTTT 773
Sequence_33     TCAAATGAAACTTACTGCAGAATATTCTGATCACTGTGTAAAGTGGTATGAAACTGGTTT 773
Sequence_69     TCAAATGAAACTTACTGCAGAATATTCTGATCACTGTGTAAAGTGGTATGAAACTGGTTT 773
Sequence_11     TCAAATGAAACTTACTGCAGAATATTCTGATCACTGTGTAAAGTGGTATGAAACTGGTTT 761
Sequence_5      TCAAATGAAACTTACTGCAGAATATTCTGATCACTGTGTAAAGTGGTATGAAACTGGTTT 761
Sequence_1      TCAAATGAAACTTACTGCAGAATATTCTGATCACTGTGTAAAGTGGTATGAAACTGGTTT 761
Sequence_17     TCAAATGAAACTTACTGCAGAATATTCTGATCACTGTGTAAAGTGGTATGAAACTGGTTT 1491
Sequence_3      TCAAATGAAACTTACTGCAGAATATTCTGATCACTGTGTAAAGTGGTATGAAACTGGTTT 761
Sequence_13     TCAAATGAAACTTACTGCAGAATATTCTGATCACTGTGTAAAGTGGTATGAAACTGGTTT 761
Sequence_18     TCAAATGAAACTTACTGCAGAATATTCTGATCACTGTGTAAAGTGGTATGAAACTGGTTT 2014
Cry8Ha1         ACAAGTAGAGTTTACGAAAGAATACACCGAACACTGTATTAATATTTATAATGATGGTTT 755
                 *** *  *  ****   ******  * ** ****** * **    *** *   ******
```

To Fig. 16O

Fig. 16N

From Fig. 16N

```
Sequence_71     AGCAAAATTAAAAGGCACGAGCGCTAAACAATGGGTTGACTATAACCAATTCCGTAGAGA 842
Sequence_73     AGCAAAATTAAAAGGCACGAGCGCTAAACAATGGGTTGACTATAACCAATTCCGTAGAGA 839
Sequence_21     AGCAAAATTAAAAGGCACGAGCGCTAAACAATGGGTTGACTATAACCAATTCCGTAGAGA 833
Sequence_67     AGCAAAATTAAAAGGCACGAGCGCTAAACAATGGGTTGACTATAACCAATTCCGTAGAGA 833
Sequence_61     AGCAAAATTAAAAGGCACGAGCGCTAAACAATGGGTTGACTATAACCAATTCCGTAGAGA 833
Sequence_93     AGCAAAATTAAAAGGCACGAGCGCTAAACAATGGGTTGACTATAACCAATTCCGTAGAGA 833
Sequence_59     AGCAAAATTAAAAGGCACGAGCGCTAAACAATGGGTTGACTATAACCAATTCCGTAGAGA 833
Sequence_91     AGCAAAATTAAAAGGCACGAGCGCTAAACAATGGGTTGACTATAACCAATTCCGTAGAGA 833
Sequence_39     AGCAAAATTAAAAGGCACGAGCGCTAAACAATGGGTTGACTATAACCAATTCCGTAGAGA 842
Sequence_41     AGCAAAATTAAAAGGCACGAGCGCTAAACAATGGGTTGACTATAACCAATTCCGTAGAGA 839
Sequence_49     AGCAAAATTAAAAGGCACGAGCGCTAAACAATGGGTTGACTATAACCAATTCCGTAGAGA 836
Sequence_81     AGCAAAATTAAAAGGCACGAGCGCTAAACAATGGGTTGACTATAACCAATTCCGTAGAGA 836
Sequence_45     AGCAAAATTAAAAGGCACGAGCGCTAAACAATGGGTTGACTATAACCAATTCCGTAGAGA 839
Sequence_77     AGCAAAATTAAAAGGCACGAGCGCTAAACAATGGGTTGACTATAACCAATTCCGTAGAGA 839
Sequence_75     AGCAAAATTAAAAGGCACGAGCGCTAAACAATGGGTTGACTATAACCAATTCCGTAGAGA 836
Sequence_43     AGCAAAATTAAAAGGCACGAGCGCTAAACAATGGGTTGACTATAACCAATTCCGTAGAGA 836
Sequence_47     AGCAAAATTAAAAGGCACGAGCGCTAAACAATGGGTTGACTATAACCAATTCCGTAGAGA 839
Sequence_79     AGCAAAATTAAAAGGCACGAGCGCTAAACAATGGGTTGACTATAACCAATTCCGTAGAGA 839
Sequence_51     AGCAAAATTAAAAGGCACGAGCGCTAAACAATGGGTTGACTATAACCAATTCCGTAGAGA 845
Sequence_83     AGCAAAATTAAAAGGCACGAGCGCTAAACAATGGGTTGACTATAACCAATTCCGTAGAGA 845
Sequence_7      AGCAAAATTAAAAGGCACGAGCGCTAAACAATGGGTTGACTATAACCAATTCCGTAGAGA 833
Sequence_25     AGCAAAATTAAAAGGCACGAGCGCTAAACAATGGGTTGACTATAACCAATTCCGTAGAGA 833
Sequence_29     AGCAAAATTAAAAGGCACGAGCGCTAAACAATGGGTTGACTATAACCAATTCCGTAGAGA 833
Sequence_33     AGCAAAATTAAAAGGCACGAGCGCTAAACAATGGGTTGACTATAACCAATTCCGTAGAGA 833
Sequence_69     AGCAAAATTAAAAGGCACGAGCGCTAAACAATGGGTTGACTATAACCAATTCCGTAGAGA 833
Sequence_11     AGCAAAATTAAAAGGCACGAGCGCTAAACAATGGGTTGACTATAACCAATTCCGTAGAGA 821
Sequence_5      AGCAAAATTAAAAGGCACGAGCGCTAAACAATGGGTTGACTATAACCAATTCCGTAGAGA 821
Sequence_1      AGCAAAATTAAAAGGCACGAGCGCTAAACAATGGGTTGACTATAACCAATTCCGTAGAGA 821
Sequence_17     AGCAAAATTAAAAGGCACGAGCGCTAAACAATGGGTTGACTATAACCAATTCCGTAGAGA 1551
Sequence_3      AGCAAAATTAAAAGGCACGAGCGCTAAACAATGGGTCGACTATAACCAATTCCGTAGAGA 821
Sequence_13     AGCAAAATTAAAAGGCACGAGCGCTAAACAATGGGTCGACTATAACCAATTCCGTAGAGA 821
Sequence_18     AGCAAAATTAAAAGGCACGAGCGCTAAACAATGGGTCGACTATAACCAATTCCGTAGAGA 2074
Cry8Ha1_        AAATCAATTAAAAGGTTCGAATGCTAAGCAATGGATTGCATTTAATCGCTTCCGTAGAGA 815
                *    **********  ***  ***** ****** * *  * *** *  ***********
```

To Fig. 16P

Fig. 16O

From Fig. 16O

```
Sequence_71     AATGACACTGGCGGTTTTAGATGTTGTTGCATTATTCCCAAATTATGACACACGCACGTA 902
Sequence_73     AATGACACTGGCGGTTTTAGATGTTGTTGCATTATTCCCAAATTATGACACACGCACGTA 899
Sequence_21     AATGACACTGGCGGTTTTAGATGTTGTTGCATTATTCCCAAATTATGACACACGCACGTA 893
Sequence_67     AATGACACTGGCGGTTTTAGATGTTGTTGCATTATTCCCAAATTATGACACACGCACGTA 893
Sequence_61     AATGACACTGGCGGTTTTAGATGTTGTTGCATTATTCCCAAATTATGACACAATAACGTA 893
Sequence_93     AATGACACTGGCGGTTTTAGATGTTGTTGCATTATTCCCAAATTATGACACAATAACGTA 893
Sequence_59     AATGACACTGGCGGTTTTAGATGTTGTTGCATTATTCCCAAATTATGACACAATAACGTA 893
Sequence_91     AATGACACTGGCGGTTTTAGATGTTGTTGCATTATTCCCAAATTATGACACAATAACGTA 893
Sequence_39     AATGACACTGGCGGTTTTAGATGTTGTTGCATTATTCCCAAATTATGACACACGCACGTA 902
Sequence_41     AATGACACTGGCGGTTTTAGATGTTGTTGCATTATTCCCAAATTATGACACACGCACGTA 899
Sequence_49     AATGACACTGGCGGTTTTAGATGTTGTTGCATTATTCCCAAATTATGACACACGCACGTA 896
Sequence_81     AATGACACTGGCGGTTTTAGATGTTGTTGCATTATTCCCAAATTATGACACACGCACGTA 896
Sequence_45     AATGACACTGGCGGTTTTAGATGTTGTTGCATTATTCCCAAATTATGACACACGCACGTA 899
Sequence_77     AATGACACTGGCGGTTTTAGATGTTGTTGCATTATTCCCAAATTATGACACACGCACGTA 899
Sequence_75     AATGACACTGGCGGTTTTAGATGTTGTTGCATTATTCCCAAATTATGACACACGCACGTA 896
Sequence_43     AATGACACTGGCGGTTTTAGATGTTGTTGCATTATTCCCAAATTATGACACACGCACGTA 896
Sequence_47     AATGACACTGGCGGTTTTAGATGTTGTTGCATTATTCCCAAATTATGACACACGCACGTA 899
Sequence_79     AATGACACTGGCGGTTTTAGATGTTGTTGCATTATTCCCAAATTATGACACACGCACGTA 899
Sequence_51     AATGACACTGGCGGTTTTAGATGTTGTTGCATTATTCCCAAATTATGACACACGCACGTA 905
Sequence_83     AATGACACTGGCGGTTTTAGATGTTGTTGCATTATTCCCAAATTATGACACACGCACGTA 905
Sequence_7      AATGACACTGGCGGTTTTAGATGTTGTTGCATTATTCCCAAATTATGACACACGCACGTA 893
Sequence_25     AATGACACTGGCGGTTTTAGATGTTGTTGCATTATTCCCAAATTATGACACACGCACGTA 893
Sequence_29     AATGACACTGGCGGTTTTAGATGTTGTTGCATTATTCCCAAATTATGACACACGCACGTA 893
Sequence_33     AATGACACTGGCGGTTTTAGATGTTGTTGCATTATTCCCAAATTATGACACACGCACGTA 893
Sequence_69     AATGACACTGGCGGTTTTAGATGTTGTTGCATTATTCCCAAATTATGACACACGCACGTA 893
Sequence_11     AATGACACTGGCGGTTTTAGATGTTGTTGCATTATTCCCAAATTATGACACACGCACGTA 881
Sequence_5      AATGACACTGGCGGTTTTAGATGTTGTTGCATTATTCCCAAATTATGACACACGCACGTA 881
Sequence_1      AATGACACTGGCGGTTTTAGATGTTGTTGCATTATTCCCAAATTATGACACACGCACGTA 881
Sequence_17     AATGACACTGGCGGTTTTAGATGTTGTTGCATTATTCCCAAATTATGACACACGCACGTA 1611
Sequence_3      AATGACACTGACGGTTTTAGATGTTGTTGCATTATTCCCAAATTATGACACACGCACGTA 881
Sequence_13     AATGACACTGACGGTTTTAGATGTTGTTGCATTATTCCCAAATTATGACACACGCACGTA 881
Sequence_18     AATGACACTGACGGTTTTAGATGTTGTTGCATTATTCCCAAATTATGACACACGCACGTA 2134
Cry8Ha1         AATGACATTGACGGTACTGGATGTAGTTGCATTATTCCCGAACTATGATGTACGTATGTA 875
                ******* ** ****  * ***** ************** ** *****   *   * ***
```

To Fig. 16Q

Fig. 16P

From Fig. 16P

```
Sequence_71       CCCAATGGAAACGAAAGCACAACTAACAAGGGAAGTATATACAGATCCACTGGGCGCGGT 962
Sequence_73       CCCAATGGAAACGAAAGCACAACTAACAAGGGAAGTATATACAGATCCACTGGGCGCGGT 959
Sequence_21       CCCAATGGAAACGAAAGCACAACTAACAAGGGAAGTATATACAGATCCACTGGGCGCGGT 953
Sequence_67       CCCAATGGAAACGAAAGCACAACTAACAAGGGAAGTATATACAGATCCACTGGGCGCGGT 953
Sequence_61       CCCAATAGAAACGAAAGCACAACTAACAAGGGAAGTATATACAGATCCACTGGGCGCGGT 953
Sequence_93       CCCAATAGAAACGAAAGCACAACTAACAAGGGAAGTATATACAGATCCACTGGGCGCGGT 953
Sequence_59       CCCAATGGAAACGAAAGCACAACTAACAAGGGAAGTATATACAGATCCACTGGGCGCGGT 953
Sequence_91       CCCAATGGAAACGAAAGCACAACTAACAAGGGAAGTATATACAGATCCACTGGGCGCGGT 953
Sequence_39       CCCAATGGAAACGAAAGCACAACTAACAAGGGAAGTATATACAGATCCACTGGGCGCGGT 962
Sequence_41       CCCAATGGAAACGAAAGCACAACTAACAAGGGAAGTATATACAGATCCACTGGGCGCGGT 959
Sequence_49       CCCAATGGAAACGAAAGCACAACTAACAAGGGAAGTATATACAGATCCACTGGGCGCGGT 956
Sequence_81       CCCAATGGAAACGAAAGCACAACTAACAAGGGAAGTATATACAGATCCACTGGGCGCGGT 956
Sequence_45       CCCAATGGAAACGAAAGCACAACTAACAAGGGAAGTATATACAGATCCACTGGGCGCGGT 959
Sequence_77       CCCAATGGAAACGAAAGCACAACTAACAAGGGAAGTATATACAGATCCACTGGGCGCGGT 959
Sequence_75       CCCAATGGAAACGAAAGCACAACTAACAAGGGAAGTATATACAGATCCACTGGGCGCGGT 956
Sequence_43       CCCAATGGAAACGAAAGCACAACTAACAAGGGAAGTATATACAGATCCACTGGGCGCGGT 956
Sequence_47       CCCAATGGAAACGAAAGCACAACTAACAAGGGAAGTATATACAGATCCACTGGGCGCGGT 959
Sequence_79       CCCAATGGAAACGAAAGCACAACTAACAAGGGAAGTATATACAGATCCACTGGGCGCGGT 959
Sequence_51       CCCAATGGAAACGAAAGCACAACTAACAAGGGAAGTATATACAGATCCACTGGGCGCGGT 965
Sequence_83       CCCAATGGAAACGAAAGCACAACTAACAAGGGAAGTATATACAGATCCACTGGGCGCGGT 965
Sequence_7        CCCAATGGAAACGAAAGCACAACTAACAAGGGAAGTATATACAGATCCACTGGGCGCGGT 953
Sequence_25       CCCAATGGAAACGAAAGCACAACTAACAAGGGAAGTATATACAGATCCACTGGGCGCGGT 953
Sequence_29       CCCAATGGAAACGAAAGCACAACTAACAAGGGAAGTATATACAGATCCACTGGGCGCGGT 953
Sequence_33       CCCAATGGAAACGAAAGCACAACTAACAAGGGAAGTATATACAGATCCACTGGGCGCGGT 953
Sequence_69       CCCAATGGAAACGAAAGCACAACTAACAAGGGAAGTATATACAGATCCACTGGGCGCGGT 953
Sequence_11       CCCAATGGAAACGAAAGCACAACTAACAAGGGAAGTATATACAGATCCACTGGGCGCGGT 941
Sequence_5        CCCAATGGAAACGAAAGCACAACTAACAAGGGAAGTATATACAGATCCACTGGGCGCGGT 941
Sequence_1        CCCAATGGAAACGAAAGCACAACTAACAAGGGAAGTATATACAGATCCACTGGGCGCGGT 941
Sequence_17       CCCAATGGAAACGAAAGCACAACTAACAAGGGAAGTATATACAGATCCACTGGGCGCGGT 1671
Sequence_3        CCCAATGGAAACGAAAGCACAACTAACAAGGGAAGTATATACAGATCCACTGGGCGCGGT 941
Sequence_13       CCCAATGGAAACGAAAGCACAACTAACAAGGGAAGTATATACAGATCCACTGGGCGCGGT 941
Sequence_18       CCCAATGGAAACGAAAGCACAACTAACAAGGGAAGTATATACAGATCCACTGGGCGCGGT 2194
Cry8Ha1           CCCTATAAAAACAACTACAGAGCTAACGAGAACAATTTATACCGATCCACTTGGTTACAC 935
                  *** **  **** *   ** * ***** **   * * ***** ******** **
```

To Fig. 16R

Fig. 16Q

From Fig. 16Q

```
Sequence_71      AAACGTGTCTTCAATTGGT------TCCTGGTATGACAAAGCACCTTCTTTCGGAGTGAT 1016
Sequence_73      AAACGTGTCTTCAATTGGT------TCCTGGTATGACAAAGCACCTTCTTTCGGAGTGAT 1013
Sequence_21      AAACGTGTCTTCAATTGGT------TCCTGGTATGACAAAGCACCTTCTTTCGGAGTGAT 1007
Sequence_67      AAACGTGTCTTCAATTGGT------TCCTGGTATGACAAAGCACCTTCTTTCGGAGTGAT 1007
Sequence_61      AAACGTGTCTTCAATTGGT------TCCTGGTATGACAAAGCACCTTCTTTCGGAGTGAT 1007
Sequence_93      AAACGTGTCTTCAATTGGT------TCCTGGTATGACAAAGCACCTTCTTTCGGAGTGAT 1007
Sequence_59      AAACGTGTCTTCAATTGGT------TCCTGGTATGACAAAGCACCTTCTTTCGGAGTGAT 1007
Sequence_91      AAACGTGTCTTCAATTGGT------TCCTGGTATGACAAAGCACCTTCTTTCGGAGTGAT 1007
Sequence_39      AAACGTGTCTTCAATTGGT------TCCTGGTATGACAAAGCACCTTCTTTCGGAGTGAT 1016
Sequence_41      AAACGTGTCTTCAATTGGT------TCCTGGTATGACAAAGCACCTTCTTTCGGAGTGAT 1013
Sequence_49      AAACGTGTCTTCAATTGGT------TCCTGGTATGACAAAGCACCTTCTTTCGGAGTGAT 1010
Sequence_81      AAACGTGTCTTCAATTGGT------TCCTGGTATGACAAAGCACCTTCTTTCGGAGTGAT 1010
Sequence_45      AAACGTGTCTTCAATTGGT------TCCTGGTATGACAAAGCACCTTCTTTCGGAGTGAT 1013
Sequence_77      AAACGTGTCTTCAATTGGT------TCCTGGTATGACAAAGCACCTTCTTTCGGAGTGAT 1013
Sequence_75      AAACGTGTCTTCAATTGGT------TCCTGGTATGACAAAGCACCTTCTTTCGGAGTGAT 1010
Sequence_43      AAACGTGTCTTCAATTGGT------TCCTGGTATGACAAAGCACCTTCTTTCGGAGTGAT 1010
Sequence_47      AAACGTGTCTTCAATTGGT------TCCTGGTATGACAAAGCACCTTCTTTCGGAGTGAT 1013
Sequence_79      AAACGTGTCTTCAATTGGT------TCCTGGTATGACAAAGCACCTTCTTTCGGAGTGAT 1013
Sequence_51      AAACGTGTCTTCAATTGGT------TCCTGGTATGACAAAGCACCTTCTTTCGGAGTGAT 1019
Sequence_83      AAACGTGTCTTCAATTGGT------TCCTGGTATGACAAAGCACCTTCTTTCGGAGTGAT 1019
Sequence_7       AAACGTGTCTTCAATTGGT------TCCTGGTATGACAAAGCACCTTCTTTCGGAGTGAT 1007
Sequence_25      AAACGTGTCTTCAATTGGT------TCCTGGTATGACAAAGCACCTTCTTTCGGAGTGAT 1007
Sequence_29      AAACGTGTCTTCAATTGGT------TCCTGGTATGACAAAGCACCTTCTTTCGGAGTGAT 1007
Sequence_33      AAACGTGTCTTCAATTGGT------TCCTGGTATGACAAAGCACCTTCTTTCGGAGTGAT 1007
Sequence_69      AAACGTGTCTTCAATTGGT------TCCTGGTATGACAAAGCACCTTCTTTCGGAGTGAT 1007
Sequence_11      AAACGTGTCTTCAATTGGT------TCCTGGTATGACAAAGCACCTTCTTTCGGAGTGAT 995
Sequence_5       AAACGTGTCTTCAATTGGT------TCCTGGTATGACAAAGCACCTTCTTTCGGAGTGAT 995
Sequence_1       AAACGTGTCTTCAATTGGT------TCCTGGTATGACAAAGCACCTTCTTTCGGAGTGAT 995
Sequence_17      AAACGTGTCTTCAATTGGT------TCCTGGTATGACAAAGCACCTTCTTTCGGAGTGAT 1725
Sequence_3       AAACGTGTCTTCAATTGGT------TCCTGGTATGACAAAGCACCTTCTTTCGGAGTGAT 995
Sequence_13      AAACGTGTCTTCAATTGGT------TCCTGGTATGACAAAGCACCTTCTTTCGGAGTGAT 995
Sequence_18      AAACGTGTCTTCAATTGGT------TCCTGGTATGACAAAGCACCTTCTTTCGGAGTGAT 2248
Cry8Ha1_         GAAAACGGGTTCTAGTAGTACACCACCATGGTATAATTATGGATCTAGTTTCTCATATAT 995
                  **   *  *** * * **         * ****** *  * * * **  ****  *   **
```

To Fig. 16S

Fig. 16R

From Fig. 16R

```
Sequence_71     AGAATCATCCGTTATTCGACCACCCCATGTATTTGATTATATAACGGGACTCACAGTGTA 1076
Sequence_73     AGAATCATCCGTTATTCGACCACCCCATGTATTTGATTATATAACGGGACTCACAGTGTA 1073
Sequence_21     AGAATCATCCGTTATTCGACCACCCCATGTATTTGATTATATAACGGGACTCACAGTGTA 1067
Sequence_67     AGAATCATCCGTTATTCGACCACCCCATGTATTTGATTATATAACGGGACTCACAGTGTA 1067
Sequence_61     AGAATCATCCGTTATTCGACCACCCCATGTATTTGATTATATAACGGGACTCACAGTGTA 1067
Sequence_93     AGAATCATCCGTTATTCGACCACCCCATGTATTTGATTATATAACGGGACTCACAGTGTA 1067
Sequence_59     AGAATCATCCGTTATTCGACCACCCCATGTATTTGATTATATAACGGGACTCACAGTGTA 1067
Sequence_91     AGAATCATCCGTTATTCGACCACCCCATGTATTTGATTATATAACGGGACTCACAGTGTA 1067
Sequence_39     AGAATCATCCGTTATTCGACCACCCCATGTATTTGATTATATAACGGGACTCACAGTGTA 1076
Sequence_41     AGAATCATCCGTTATTCGACCACCCCATGTATTTGATTATATAACGGGACTCACAGTGTA 1073
Sequence_49     AGAATCATCCGTTATTCGACCACCCCATGTATTTGATTATATAACGGGACTCACAGTGTA 1070
Sequence_81     AGAATCATCCGTTATTCGACCACCCCATGTATTTGATTATATAACGGGACTCACAGTGTA 1070
Sequence_45     AGAATCATCCGTTATTCGACCACCCCATGTATTTGATTATATAACGGGACTCACAGTGTA 1073
Sequence_77     AGAATCATCCGTTATTCGACCACCCCATGTATTTGATTATATAACGGGACTCACAGTGTA 1073
Sequence_75     AGAATCATCCGTTATTCGACCACCCCATGTATTTGATTATATAACGGGACTCACAGTGTA 1070
Sequence_43     AGAATCATCCGTTATTCGACCACCCCATGTATTTGATTATATAACGGGACTCACAGTGTA 1070
Sequence_47     AGAATCATCCGTTATTCGACCACCCCATGTATTTGATTATATAACGGGACTCACAGTGTA 1073
Sequence_79     AGAATCATCCGTTATTCGACCACCCCATGTATTTGATTATATAACGGGACTCACAGTGTA 1073
Sequence_51     AGAATCATCCGTTATTCGACCACCCCATGTATTTGATTATATAACGGGACTCACAGTGTA 1079
Sequence_83     AGAATCATCCGTTATTCGACCACCCCATGTATTTGATTATATAACGGGACTCACAGTGTA 1079
Sequence_7      AGAATCATCCGTTATTCGACCACCCCATGTATTTGATTATATAACGGGACTCACAGTGTA 1067
Sequence_25     AGAATCATCCGTTATTCGACCACCCCATGTATTTGATTATATAACGGGACTCACAGTGTA 1067
Sequence_29     AGAATCATCCGTTATTCGACCACCCCATGTATTTGATTATATAACGGGACTCACAGTGTA 1067
Sequence_33     AGAATCATCCGTTATTCGACCACCCCATGTATTTGATTATATAACGGGACTCACAGTGTA 1067
Sequence_69     AGAATCATCCGTTATTCGACCACCCCATGTATTTGATTATATAACGGGACTCACAGTGTA 1067
Sequence_11     AGAATCATCCGTTATTCGACCACCCCATGTATTTGATTATATAACGGGACTCACAGTGTA 1055
Sequence_5      AGAATCATCCGTTATTCGACCACCCCATGTATTTGATTATATAACGGGACTCACAGTGTA 1055
Sequence_1      AGAATCATCCGTTATTCGACCACCCCATGTATTTGATTATATAACGGGACTCACAGTGTA 1055
Sequence_17     AGAATCATCCGTTATTCGACCACCCCATGTATTTGATTATATAACGGGACTCACAGTGTA 1785
Sequence_3      AGAATCATCCGTTATTCGACCACCCCATGTATTTGATTATATAACGGGACTCACAGTGTA 1055
Sequence_13     AGAATCATCCGTTATTCGACCACCCCATGTATTTGATTATATAACGGGACTCACAGTGTA 1055
Sequence_18     AGAATCATCCGTTATTCGACCACCCCATGTATTTGATTATATAACGGGACTCACAGTGTA 2308
Cry8Ha1         AGAAAGTGTAGCGATTCCAGCCCCTAGTCTGGTTAAGTGGTTAAGTCAGATTGAAATTTA 1055
                ****      *  **** * * **   * *  ** * *   ***      *   * * **
```

To Fig. 16T

Fig. 16S

From Fig. 16S

```
Sequence_71      TACACAATCAAGAAGCATTTCTTCCGCTCGCTATATAAGACATTGGGCTGGTCATCAAAT 1136
Sequence_73      TACACAATCAAGAAGCATTTCTTCCGCTCGCTATATAAGACATTGGGCTGGTCATCAAAT 1133
Sequence_21      TACACAATCAAGAAGCATTTCTTCCGCTCGCTATATAAGACATTGGGCTGGTCATCAAAT 1127
Sequence_67      TACACAATCAAGAAGCATTTCTTCCGCTCGCTATATAAGACATTGGGCTGGTCATCAAAT 1127
Sequence_61      TACACAATCAAGAAGCATTTCTTCCGCTCGCTATATAAGACATTGGGCTGGTCATCAAAT 1127
Sequence_93      TACACAATCAAGAAGCATTTCTTCCGCTCGCTATATAAGACATTGGGCTGGTCATCAAAT 1127
Sequence_59      TACACAATCAAGAAGCATTTCTTCCGCTCGCTATATAAGACATTGGGCTGGTCATCAAAT 1127
Sequence_91      TACACAATCAAGAAGCATTTCTTCCGCTCGCTATATAAGACATTGGGCTGGTCATCAAAT 1127
Sequence_39      TACACAATCAAGAAGCATTTCTTCCGCTCGCTATATAAGACATTGGGCTGGTCATCAAAT 1136
Sequence_41      TACACAATCAAGAAGCATTTCTTCCGCTCGCTATATAAGACATTGGGCTGGTCATCAAAT 1133
Sequence_49      TACACAATCAAGAAGCATTTCTTCCGCTCGCTATATAAGACATTGGGCTGGTCATCAAAT 1130
Sequence_81      TACACAATCAAGAAGCATTTCTTCCGCTCGCTATATAAGACATTGGGCTGGTCATCAAAT 1130
Sequence_45      TACACAATCAAGAAGCATTTCTTCCGCTCGCTATATAAGACATTGGGCTGGTCATCAAAT 1133
Sequence_77      TACACAATCAAGAAGCATTTCTTCCGCTCGCTATATAAGACATTGGGCTGGTCATCAAAT 1133
Sequence_75      TACACAATCAAGAAGCATTTCTTCCGCTCGCTATATAAGACATTGGGCTGGTCATCAAAT 1130
Sequence_43      TACACAATCAAGAAGCATTTCTTCCGCTCGCTATATAAGACATTGGGCTGGTCATCAAAT 1130
Sequence_47      TACACAATCAAGAAGCATTTCTTCCGCTCGCTATATAAGACATTGGGCTGGTCATCAAAT 1133
Sequence_79      TACACAATCAAGAAGCATTTCTTCCGCTCGCTATATAAGACATTGGGCTGGTCATCAAAT 1133
Sequence_51      TACACAATCAAGAAGCATTTCTTCCGCTCGCTATATAAGACATTGGGCTGGTCATCAAAT 1139
Sequence_83      TACACAATCAAGAAGCATTTCTTCCGCTCGCTATATAAGACATTGGGCTGGTCATCAAAT 1139
Sequence_7       TACACAATCAAGAAGCATTTCTTCCGCTCGCTATATAAGACATTGGGCTGGTCATCAAAT 1127
Sequence_25      TACACAATCAAGAAGCATTTCTTCCGCTCGCTATATAAGACATTGGGCTGGTCATCAAAT 1127
Sequence_29      TACACAATCAAGAAGCATTTCTTCCGCTCGCTATATAAGACATTGGGCTGGTCATCAAAT 1127
Sequence_33      TACACAATCAAGAAGCATTTCTTCCGCTCGCTATATAAGACATTGGGCTGGTCATCAAAT 1127
Sequence_69      TACACAATCAAGAAGCATTTCTTCCGCTCGCTATATAAGACATTGGGCTGGTCATCAAAT 1127
Sequence_11      TACACAATCAAGAAGCATTTCTTCCGCTCGCTATATAAGACATTGGGCTGGTCATCAAAT 1115
Sequence_5       TACACAATCAAGAAGCATTTCTTCCGCTCGCTATATAAGACATTGGGCTGGTCATCAAAT 1115
Sequence_1       TACACAATCAAGAAGCATTTCTTCCGCTCGCTATATAAGACATTGGGCTGGTCATCAAAT 1115
Sequence_17      TACACAATCAAGAAGCATTTCTTCCGCTCGCTATATAAGACATTGGGCTGGTCATCAAAT 1845
Sequence_3       TACACAATCAAGAAGCATTTCTTCCGCTCGCTATATAAGACATTGGGCTGGTCATCAAAT 1115
Sequence_13      TACACAATCAAGAAGCATTTCTTCCGCTCGCTATATAAGACATTGGGCTGGTCATCAAAT 1115
Sequence_18      TACACAATCAAGAAGCATTTCTTCCGCTCGCTATATAAGACATTGGGCTGGTCATCAAAT 2368
Cry8Ha1          TTCGAAATCCGCAAGGGCTACACC---GCAAAGTGCGGATTATTGGGCAGGACATACAAT 1112
                 * *  ****   ***   * *  *    *    *       ******* ** ***  ***
```

To Fig. 16U

Fig. 16T

From Fig. 16T

```
Sequence_71     AAGCTACCATCGTGTCAGTAGGGGTAGTAATCTTCAACAAATGTATGGAACTAATCAAAA 1196
Sequence_73     AAGCTACCATCGTGTCAGTAGGGGTAGTAATCTTCAACAAATGTATGGAACTAATCAAAA 1193
Sequence_21     AAGCTACCATCGTGTCAGTAGGGGTAGTAATCTTCAACAAATGTATGGAACTAATCAAAA 1187
Sequence_67     AAGCTACCATCGTGTCAGTAGGGGTAGTAATCTTCAACAAATGTATGGAACTAATCAAAA 1187
Sequence_61     AAGCTACCATCGTGTCAGTAGGGGTAGTAATCTTCAACAAATGTATGGAACTAATCAAAA 1187
Sequence_93     AAGCTACCATCGTGTCAGTAGGGGTAGTAATCTTCAACAAATGTATGGAACTAATCAAAA 1187
Sequence_59     AAGCTACCATCGTGTCAGTAGGGGTAGTAATCTTCAACAAATGTATGGAACTAATCAAAA 1187
Sequence_91     AAGCTACCATCGTGTCAGTAGGGGTAGTAATCTTCAACAAATGTATGGAACTAATCAAAA 1187
Sequence_39     AAGCTACCATCGTGTCAGTAGGGGTAGTAATCTTCAACAAATGTATGGAACTAATCAAAA 1196
Sequence_41     AAGCTACCATCGTGTCAGTAGGGGTAGTAATCTTCAACAAATGTATGGAACTAATCAAAA 1193
Sequence_49     AAGCTACCATCGTGTCAGTAGGGGTAGTAATCTTCAACAAATGTATGGAACTAATCAAAA 1190
Sequence_81     AAGCTACCATCGTGTCAGTAGGGGTAGTAATCTTCAACAAATGTATGGAACTAATCAAAA 1190
Sequence_45     AAGCTACCATCGTGTCAGTAGGGGTAGTAATCTTCAACAAATGTATGGAACTAATCAAAA 1193
Sequence_77     AAGCTACCATCGTGTCAGTAGGGGTAGTAATCTTCAACAAATGTATGGAACTAATCAAAA 1193
Sequence_75     AAGCTACCATCGTGTCAGTAGGGGTAGTAATCTTCAACAAATGTATGGAACTAATCAAAA 1190
Sequence_43     AAGCTACCATCGTGTCAGTAGGGGTAGTAATCTTCAACAAATGTATGGAACTAATCAAAA 1190
Sequence_47     AAGCTACCATCGTGTCAGTAGGGGTAGTAATCTTCAACAAATGTATGGAACTAATCAAAA 1193
Sequence_79     AAGCTACCATCGTGTCAGTAGGGGTAGTAATCTTCAACAAATGTATGGAACTAATCAAAA 1193
Sequence_51     AAGCTACCATCGTGTCAGTAGGGGTAGTAATCTTCAACAAATGTATGGAACTAATCAAAA 1199
Sequence_83     AAGCTACCATCGTGTCAGTAGGGGTAGTAATCTTCAACAAATGTATGGAACTAATCAAAA 1199
Sequence_7      AAGCTACCATCGTGTCAGTAGGGGTAGTAATCTTCAACAAATGTATGGAACTAATCAAAA 1187
Sequence_25     AAGCTACCATCGTGTCAGTAGGGGTAGTAATCTTCAACAAATGTATGGAACTAATCAAAA 1187
Sequence_29     AAGCTACCATCGTGTCAGTAGGGGTAGTAATCTTCAACAAATGTATGGAACTAATCAAAA 1187
Sequence_33     AAGCTACCATCGTGTCAGTAGGGGTAGTAATCTTCAACAAATGTATGGAACTAATCAAAA 1187
Sequence_69     AAGCTACCATCGTGTCAGTAGGGGTAGTAATCTTCAACAAATGTATGGAACTAATCAAAA 1187
Sequence_11     AAGCTACCATCGTGTCAGTAGGGGTAGTAATCTTCAACAAATGTATGGAACTAATCAAAA 1175
Sequence_5      AAGCTACCATCGTGTCAGTAGGGGTAGTAATCTTCAACAAATGTATGGAACTAATCAAAA 1175
Sequence_1      AAGCTACCATCGTGTCAGTAGGGGTAGTAATCTTCAACAAATGTATGGAACTAATCAAAA 1175
Sequence_17     AAGCTACCATCGTGTCAGTAGGGGTAGTAATCTTCAACAAATGTATGGAACTAATCAAAA 1905
Sequence_3      AAGCTATCATCGGATTTTTAGTGATAATATTATAAAACAGATGTATGGAACTAATCAAAA 1175
Sequence_13     AAGCTATCATCGGATTTTTAGTGATAATATTATAAAACAGATGTATGGAACTAATCAAAA 1175
Sequence_18     AAGCTATCATCGGATTTTTAGTGATAATATTATAAAACAGATGTATGGAACTAATCAAAA 2428
Cry8Ha1         AACATATCACTATAGTGGAGATGATGGTCAAGCAGTACCTAATTATGGAGATAGAACGAA 1172
                **  ** **             * *  *        **  *  ******  **     **
```

To Fig. 16V

Fig. 16U

From Fig. 16U

| | | |
|---|---|---|
| Sequence_71 | TCTACACAGCACTAGTACCTTTGATTTTACGAATTATGATATTTACAAGACTCTATCAAA | 1256 |
| Sequence_73 | TCTACACAGCACTAGTACCTTTGATTTTACGAATTATGATATTTACAAGACTCTATCAAA | 1253 |
| Sequence_21 | TCTACACAGCACTAGTACCTTTGATTTTACGAATTATGATATTTACAAGACTCTATCAAA | 1247 |
| Sequence_67 | TCTACACAGCACTAGTACCTTTGATTTTACGAATTATGATATTTACAAGACTCTATCAAA | 1247 |
| Sequence_61 | TCTACACAGCACTAGTACCTTTGATTTTACGAATTATGATATTTACAAGACTCTATCAAA | 1247 |
| Sequence_93 | TCTACACAGCACTAGTACCTTTGATTTTACGAATTATGATATTTACAAGACTCTATCAAA | 1247 |
| Sequence_59 | TCTACACAGCACTAGTACCTTTGATTTTACGAATTATGATATTTACAAGACTCTATCAAA | 1247 |
| Sequence_91 | TCTACACAGCACTAGTACCTTTGATTTTACGAATTATGATATTTACAAGACTCTATCAAA | 1247 |
| Sequence_39 | TCTACACAGCACTAGTACCTTTGATTTTACGAATTATGATATTTACAAGACTCTATCAAA | 1256 |
| Sequence_41 | TCTACACAGCACTAGTACCTTTGATTTTACGAATTATGATATTTACAAGACTCTATCAAA | 1253 |
| Sequence_49 | TCTACACAGCACTAGTACCTTTGATTTTACGAATTATGATATTTACAAGACTCTATCAAA | 1250 |
| Sequence_81 | TCTACACAGCACTAGTACCTTTGATTTTACGAATTATGATATTTACAAGACTCTATCAAA | 1250 |
| Sequence_45 | TCTACACAGCACTAGTACCTTTGATTTTACGAATTATGATATTTACAAGACTCTATCAAA | 1253 |
| Sequence_77 | TCTACACAGCACTAGTACCTTTGATTTTACGAATTATGATATTTACAAGACTCTATCAAA | 1253 |
| Sequence_75 | TCTACACAGCACTAGTACCTTTGATTTTACGAATTATGATATTTACAAGACTCTATCAAA | 1250 |
| Sequence_43 | TCTACACAGCACTAGTACCTTTGATTTTACGAATTATGATATTTACAAGACTCTATCAAA | 1250 |
| Sequence_47 | TCTACACAGCACTAGTACCTTTGATTTTACGAATTATGATATTTACAAGACTCTATCAAA | 1253 |
| Sequence_79 | TCTACACAGCACTAGTACCTTTGATTTTACGAATTATGATATTTACAAGACTCTATCAAA | 1253 |
| Sequence_51 | TCTACACAGCACTAGTACCTTTGATTTTACGAATTATGATATTTACAAGACTCTATCAAA | 1259 |
| Sequence_83 | TCTACACAGCACTAGTACCTTTGATTTTACGAATTATGATATTTACAAGACTCTATCAAA | 1259 |
| Sequence_7 | TCTACACAGCACTAGTACCTTTGATTTTACGAATTATGATATTTACAAGACTCTATCAAA | 1247 |
| Sequence_25 | TCTACACAGCACTAGTACCTTTGATTTTACGAATTATGATATTTACAAGACTCTATCAAA | 1247 |
| Sequence_29 | TCTACACAGCACTAGTACCTTTGATTTTACGAATTATGATATTTACAAGACTCTATCAAA | 1247 |
| Sequence_33 | TCTACACAGCACTAGTACCTTTGATTTTACGAATTATGATATTTACAAGACTCTATCAAA | 1247 |
| Sequence_69 | TCTACACAGCACTAGTACCTTTGATTTTACGAATTATGATATTTACAAGACTCTATCAAA | 1247 |
| Sequence_11 | TCTACACAGCACTAGTACCTTTGATTTTACGAATTATGATATTTACAAGACTCTATCAAA | 1235 |
| Sequence_5 | TCTACACAGCACTAGTACCTTTGATTTTACGAATTATGATATTTACAAGACTCTATCAAA | 1235 |
| Sequence_1 | TCTACACAGCACTAGTACCTTTGATTTTACGAATTATGATATTTACAAGACTCTATCAAA | 1235 |
| Sequence_17 | TCTACACAGCACTAGTACCTTTGATTTTACGAATTATGATATTTACAAGACTCTATCAAA | 1965 |
| Sequence_3 | TCTACACAGCACTAGTACCTTTGATTTTACGAATTATGATATTTACAAGACGTTATCAAA | 1235 |
| Sequence_13 | TCTACACAGCACTAGTACCTTTGATTTTACGAATTATGATATTTACAAGACGTTATCAAA | 1235 |
| Sequence_18 | TCTACACAGCACTAGTACCTTTGATTTTACGAATTATGATATTTACAAGACGTTATCAAA | 2488 |
| Cry8Ha1 | TCCTGTAATTGTAAATCGTTATAATTTTGAGCAGGCTGACATTTATAGAGTTTCATCATC | 1232 |
| | ** * * * * * ***** * * *** ***** * **** | |

To Fig. 16W

Fig. 16V

From Fig. 16V

```
Sequence_71    GGATGCAGTACTCCTTGATATTGTT-TACCCTGGTTATACGTATATATTTTTTGGAATGC 1315
Sequence_73    GGATGCAGTACTCCTTGATATTGTT-TACCCTGGTTATACGTATATATTTTTTGGAATGC 1312
Sequence_21    GGATGCAGTACTCCTTGATATTGTT-TACCCTGGTTATACGTATATATTTTTTGGAATGC 1306
Sequence_67    GGATGCAGTACTCCTTGATATTGTT-TACCCTGGTTATACGTATATATTTTTTGGAATGC 1306
Sequence_61    GGATGCAGTACTCCTTGATATTGTT-TACCCTGGTTATACGTATATATTTTTTGGAATGC 1306
Sequence_93    GGATGCAGTACTCCTTGATATTGTT-TACCCTGGTTATACGTATATATTTTTTGGAATGC 1306
Sequence_59    GGATGCAGTACTCCTTGATATTGTT-TACCCTGGTTATACGTATATATTTTTTGGAATGC 1306
Sequence_91    GGATGCAGTACTCCTTGATATTGTT-TACCCTGGTTATACGTATATATTTTTTGGAATGC 1306
Sequence_39    GGATGCAGTACTCCTTGATATTGTT-TACCCTGGTTATACGTATATATTTTTTGGAATGC 1315
Sequence_41    GGATGCAGTACTCCTTGATATTGTT-TACCCTGGTTATACGTATATATTTTTTGGAATGC 1312
Sequence_49    GGATGCAGTACTCCTTGATATTGTT-TACCCTGGTTATACGTATATATTTTTTGGAATGC 1309
Sequence_81    GGATGCAGTACTCCTTGATATTGTT-TACCCTGGTTATACGTATATATTTTTTGGAATGC 1309
Sequence_45    GGATGCAGTACTCCTTGATATTGTT-TACCCTGGTTATACGTATATATTTTTTGGAATGC 1312
Sequence_77    GGATGCAGTACTCCTTGATATTGTT-TACCCTGGTTATACGTATATATTTTTTGGAATGC 1312
Sequence_75    GGATGCAGTACTCCTTGATATTGTT-TACCCTGGTTATACGTATATATTTTTTGGAATGC 1309
Sequence_43    GGATGCAGTACTCCTTGATATTGTT-TACCCTGGTTATACGTATATATTTTTTGGAATGC 1309
Sequence_47    GGATGCAGTACTCCTTGATATTGTT-TACCCTGGTTATACGTATATATTTTTTGGAATGC 1312
Sequence_79    GGATGCAGTACTCCTTGATATTGTT-TACCCTGGTTATACGTATATATTTTTTGGAATGC 1312
Sequence_51    GGATGCAGTACTCCTTGATATTGTT-TACCCTGGTTATACGTATATATTTTTTGGAATGC 1318
Sequence_83    GGATGCAGTACTCCTTGATATTGTT-TACCCTGGTTATACGTATATATTTTTTGGAATGC 1318
Sequence_7     GGATGCAGTACTCCTTGATATTGTT-TACCCTGGTTATACGTATATATTTTTTGGAATGC 1306
Sequence_25    GGATGCAGTACTCCTTGATATTGTT-TACCCTGGTTATACGTATATATTTTTTGGAATGC 1306
Sequence_29    GGATGCAGTACTCCTTGATATTGTT-TACCCTGGTTATACGTATATATTTTTTGGAATGC 1306
Sequence_33    GGATGCAGTACTCCTTGATATTGTT-TACCCTGGTTATACGTATATATTTTTTGGAATGC 1306
Sequence_69    GGATGCAGTACTCCTTGATATTGTT-TACCCTGGTTATACGTATATATTTTTTGGAATGC 1306
Sequence_11    GGATGCAGTACTCCTTGATATTGTT-TACCCTGGTTATACGTATATATTTTTTGGAATGC 1294
Sequence_5     GGATGCAGTACTCCTTGATATTGTT-TACCCTGGTTATACGTATATATTTTTTGGAATGC 1294
Sequence_1     GGATGCAGTACTCCTTGATATTGTT-TACCCTGGTTATACGTATATATTTTTTGGAATGC 1294
Sequence_17    GGATGCAGTACTCCTTGATATTGTT-TACCCTGGTTATACGTATATATTTTTTGGAATGC 2024
Sequence_3     AGATGCGGTGCTCCTTGATATTGTT-TTTCCTGGTTATACGTATATATTTTTTGGAATGC 1294
Sequence_13    AGATGCGGTGCTCCTTGATATTGTT-TTTCCTGGTTATACGTATATATTTTTTGGAATGC 1294
Sequence_18    AGATGCGGTGCTCCTTGATATTGTT-TTTCCTGGTTATACGTATATATTTTTTGGAATGC 2547
Cry8Hal_       TGTTGCTTCAAGTACAACTAGTGGTGTTAAATTATTAACTACTAAGGCTATATTTGATGG 1292
                * ***         ** ** * *    *  ***       *    * * *   ***
```

To Fig. 16X

Fig. 16W

From Fig. 16W

```
Sequence_71         CAGAAGTCGAGTTTTTCATGGTAAACCAATTGAATA-ATACCAGAAAGAC-GTTAAAGTA 1373
Sequence_73         CAGAAGTCGAGTTTTTCATGGTAAACCAATTGAATA-ATACCAGAAAGAC-GTTAAAGTA 1370
Sequence_21         CAGAAGTCGAGTTTTTCATGGTAAACCAATTGAATA-ATACCAGAAAGAC-GTTAAAGTA 1364
Sequence_67         CAGAAGTCGAGTTTTTCATGGTAAACCAATTGAATA-ATACCAGAAAGAC-GTTAAAGTA 1364
Sequence_61         CAGAAGTCGAGTTTTTCATGGTAAACCAATTGAATA-ATACCAGAAAGAC-GTTAAAGTA 1364
Sequence_93         CAGAAGTCGAGTTTTTCATGGTAAACCAATTGAATA-ATACCAGAAAGAC-GTTAAAGTA 1364
Sequence_59         CAGAAGTCGAGTTTTTCATGGTAAACCAATTGAATA-ATACCAGAAAGAC-GTTAAAGTA 1364
Sequence_91         CAGAAGTCGAGTTTTTCATGGTAAACCAATTGAATA-ATACCAGAAAGAC-GTTAAAGTA 1364
Sequence_39         CAGAAGTCGAGTTTTTCATGGTAAACCAATTGAATA-ATACCAGAAAGAC-GTTAAAGTA 1373
Sequence_41         CAGAAGTCGAGTTTTTCATGGTAAACCAATTGAATA-ATACCAGAAAGAC-GTTAAAGTA 1370
Sequence_49         CAGAAGTCGAGTTTTTCATGGTAAACCAATTGAATA-ATACCAGAAAGAC-GTTAAAGTA 1367
Sequence_81         CAGAAGTCGAGTTTTTCATGGTAAACCAATTGAATA-ATACCAGAAAGAC-GTTAAAGTA 1367
Sequence_45         CAGAAGTCGAGTTTTTCATGGTAAACCAATTGAATA-ATACCAGAAAGAC-GTTAAAGTA 1370
Sequence_77         CAGAAGTCGAGTTTTTCATGGTAAACCAATTGAATA-ATACCAGAAAGAC-GTTAAAGTA 1370
Sequence_75         CAGAAGTCGAGTTTTTCATGGTAAACCAATTGAATA-ATACCAGAAAGAC-GTTAAAGTA 1367
Sequence_43         CAGAAGTCGAGTTTTTCATGGTAAACCAATTGAATA-ATACCAGAAAGAC-GTTAAAGTA 1367
Sequence_47         CAGAAGTCGAGTTTTTCATGGTAAACCAATTGAATA-ATACCAGAAAGAC-GTTAAAGTA 1370
Sequence_79         CAGAAGTCGAGTTTTTCATGGTAAACCAATTGAATA-ATACCAGAAAGAC-GTTAAAGTA 1370
Sequence_51         CAGAAGTCGAGTTTTTCATGGTAAACCAATTGAATA-ATACCAGAAAGAC-GTTAAAGTA 1376
Sequence_83         CAGAAGTCGAGTTTTTCATGGTAAACCAATTGAATA-ATACCAGAAAGAC-GTTAAAGTA 1376
Sequence_7          CAGAAGTCGAGTTTTTCATGGTAAACCAATTGAATA-ATACCAGAAAGAC-GTTAAAGTA 1364
Sequence_25         CAGAAGTCGAGTTTTTCATGGTAAACCAATTGAATA-ATACCAGAAAGAC-GTTAAAGTA 1364
Sequence_29         CAGAAGTCGAGTTTTTCATGGTAAACCAATTGAATA-ATACCAGAAAGAC-GTTAAAGTA 1364
Sequence_33         CAGAAGTCGAGTTTTTCATGGTAAACCAATTGAATA-ATACCAGAAAGAC-GTTAAAGTA 1364
Sequence_69         CAGAAGTCGAGTTTTTCATGGTAAACCAATTGAATA-ATACCAGAAAGAC-GTTAAAGTA 1364
Sequence_11         CAGAAGTCGAGTTTTTCATGGTAAACCAATTGAATA-ATACCAGAAAGAC-GTTAAAGTA 1352
Sequence_5          CAGAAGTCGAGTTTTTCATGGTAAACCAATTGAATA-ATACCAGAAAGAC-GTTAAAGTA 1352
Sequence_1          CAGAAGTCGAGTTTTTCATGGTAAACCAATTGAATA-ATACCAGAAAGAC-GTTAAAGTA 1352
Sequence_17         CAGAAGTCGAGTTTTTCATGGTAAACCAATTGAATA-ATACCAGAAAGAC-GTTAAAGTA 2082
Sequence_3          CAGAAGTCGAGTTTTTCATGGTAAACCAATTGAATA-ATACCAGAAAGAC-GTTAAAGTA 1352
Sequence_13         CAGAAGTCGAGTTTTTCATGGTAAACCAATTGAATA-ATACCAGAAAGAC-GTTAAAGTA 1352
Sequence_18         CAGAAGTCGAGTTTTTCATGGTAAACCAATTGAATA-ATACCAGAAAGAC-GTTAAAGTA 2605
Cry8Ha1_            CATAAGTACAA------ACAATGGACTAGTGAGTTACATGTATGAAAAATTATCGAACTT 1346
                    * ****  *       *   *  ** * *    ** **    **** *   *  ** *
```

To Fig. 16Y

Fig. 16X

From Fig. 16X

```
Sequence_71    TAATCCAGTTTCCAAAGATATTATAGCGAGTACAAGAGATTCGGAATTAGAAT----TAC 1429
Sequence_73    TAATCCAGTTTCCAAAGATATTATAGCGAGTACAAGAGATTCGGAATTAGAAT----TAC 1426
Sequence_21    TAATCCAGTTTCCAAAGATATTATAGCGAGTACAAGAGATTCGGAATTAGAAT----TAC 1420
Sequence_67    TAATCCAGTTTCCAAAGATATTATAGCGAGTACAAGAGATTCGGAATTAGAAT----TAC 1420
Sequence_61    TAATCCAGTTTCCAAAGATATTATAGCGAGTACAAGAGATTCGGAATTAGAAT----TAC 1420
Sequence_93    TAATCCAGTTTCCAAAGATATTATAGCGAGTACAAGAGATTCGGAATTAGAAT----TAC 1420
Sequence_59    TAATCCAGTTTCCAAAGATATTATAGCGAGTACAAGAGATTCGGAATTAGAAT----TAC 1420
Sequence_91    TAATCCAGTTTCCAAAGATATTATAGCGAGTACAAGAGATTCGGAATTAGAAT----TAC 1420
Sequence_39    TAATCCAGTTTCCAAAGATATTATAGCGAGTACAAGAGATTCGGAATTAGAAT----TAC 1429
Sequence_41    TAATCCAGTTTCCAAAGATATTATAGCGAGTACAAGAGATTCGGAATTAGAAT----TAC 1426
Sequence_49    TAATCCAGTTTCCAAAGATATTATAGCGAGTACAAGAGATTCGGAATTAGAAT----TAC 1423
Sequence_81    TAATCCAGTTTCCAAAGATATTATAGCGAGTACAAGAGATTCGGAATTAGAAT----TAC 1423
Sequence_45    TAATCCAGTTTCCAAAGATATTATAGCGAGTACAAGAGATTCGGAATTAGAAT----TAC 1426
Sequence_77    TAATCCAGTTTCCAAAGATATTATAGCGAGTACAAGAGATTCGGAATTAGAAT----TAC 1426
Sequence_75    TAATCCAGTTTCCAAAGATATTATAGCGAGTACAAGAGATTCGGAATTAGAAT----TAC 1423
Sequence_43    TAATCCAGTTTCCAAAGATATTATAGCGAGTACAAGAGATTCGGAATTAGAAT----TAC 1423
Sequence_47    TAATCCAGTTTCCAAAGATATTATAGCGAGTACAAGAGATTCGGAATTAGAAT----TAC 1426
Sequence_79    TAATCCAGTTTCCAAAGATATTATAGCGAGTACAAGAGATTCGGAATTAGAAT----TAC 1426
Sequence_51    TAATCCAGTTTCCAAAGATATTATAGCGAGTACAAGAGATTCGGAATTAGAAT----TAC 1432
Sequence_83    TAATCCAGTTTCCAAAGATATTATAGCGAGTACAAGAGATTCGGAATTAGAAT----TAC 1432
Sequence_7     TAATCCAGTTTCCAAAGATATTATAGCGAGTACAAGAGATTCGGAATTAGAAT----TAC 1420
Sequence_25    TAATCCAGTTTCCAAAGATATTATAGCGAGTACAAGAGATTCGGAATTAGAAT----TAC 1420
Sequence_29    TAATCCAGTTTCCAAAGATATTATAGCGAGTACAAGAGATTCGGAATTAGAAT----TAC 1420
Sequence_33    TAATCCAGTTTCCAAAGATATTATAGCGAGTACAAGAGATTCGGAATTAGAAT----TAC 1420
Sequence_69    TAATCCAGTTTCCAAAGATATTATAGCGAGTACAAGAGATTCGGAATTAGAAT----TAC 1420
Sequence_11    TAATCCAGTTTCCAAAGATATTATAGCGAGTACAAGAGATTCGGAATTAGAAT----TAC 1408
Sequence_5     TAATCCAGTTTCCAAAGATATTATAGCGAGTACAAGAGATTCGGAATTAGAAT----TAC 1408
Sequence_1     TAATCCAGTTTCCAAAGATATTATAGCGAGTACAAGAGATTCGGAATTAGAAT----TAC 1408
Sequence_17    TAATCCAGTTTCCAAAGATATTATAGCGAGTACAAGAGATTCGGAATTAGAAT----TAC 2138
Sequence_3     TAATCCGGTTTCCAAAGATATTATAGCGGGGACAAGAGATTCGGAATTAGAAT----TAC 1408
Sequence_13    TAATCCGGTTTCCAAAGATATTATAGCGGGGACAAGAGATTCGGAATTAGAAT----TAC 1408
Sequence_18    TAATCCGGTTTCCAAAGATATTATAGCGGGGACAAGAGATTCGGAATTAGAAT----TAC 2661
Cry8Ha1        TTTTAATGAACTAAAAGATACAATTACAGAGCTACCTGTTCAGATATCCAGTCCTCCTAC 1406
               *  *   *     *******  **  *      *   * *  *  **          ***
```

To Fig. 16Z

Fig. 16Y

From Fig. 16Y

```
Sequence_71   CTCCAGAAACTTCAGATCAACCAAATTATGAGTCATATAGCCATAGATTATGTCATATCA 1489
Sequence_73   CTCCAGAAACTTCAGATCAACCAAATTATGAGTCATATAGCCATAGATTATGTCATATCA 1486
Sequence_21   CTCCAGAAACTTCAGATCAACCAAATTATGAGTCATATAGCCATAGATTATGTCATATCA 1480
Sequence_67   CTCCAGAAACTTCAGATCAACCAAATTATGAGTCATATAGCCATAGATTATGTCATATCA 1480
Sequence_61   CTCCAGAAACTTCAGATCAACCAAATTATGAGTCATATAGCCATAGATTATGTCATATCA 1480
Sequence_93   CTCCAGAAACTTCAGATCAACCAAATTATGAGTCATATAGCCATAGATTATGTCATATCA 1480
Sequence_59   CTCCAGAAACTTCAGATCAACCAAATTATGAGTCATATAGCCATAGATTATGTCATATCA 1480
Sequence_91   CTCCAGAAACTTCAGATCAACCAAATTATGAGTCATATAGCCATAGATTATGTCATATCA 1480
Sequence_39   CTCCAGAAACTTCAGATCAACCAAATTATGAGTCATATAGCCATAGATTATGTCATATCA 1489
Sequence_41   CTCCAGAAACTTCAGATCAACCAAATTATGAGTCATATAGCCATAGATTATGTCATATCA 1486
Sequence_49   CTCCAGAAACTTCAGATCAACCAAATTATGAGTCATATAGCCATAGATTATGTCATATCA 1483
Sequence_81   CTCCAGAAACTTCAGATCAACCAAATTATGAGTCATATAGCCATAGATTATGTCATATCA 1483
Sequence_45   CTCCAGAAACTTCAGATCAACCAAATTATGAGTCATATAGCCATAGATTATGTCATATCA 1486
Sequence_77   CTCCAGAAACTTCAGATCAACCAAATTATGAGTCATATAGCCATAGATTATGTCATATCA 1486
Sequence_75   CTCCAGAAACTTCAGATCAACCAAATTATGAGTCATATAGCCATAGATTATGTCATATCA 1483
Sequence_43   CTCCAGAAACTTCAGATCAACCAAATTATGAGTCATATAGCCATAGATTATGTCATATCA 1483
Sequence_47   CTCCAGAAACTTCAGATCAACCAAATTATGAGTCATATAGCCATAGATTATGTCATATCA 1486
Sequence_79   CTCCAGAAACTTCAGATCAACCAAATTATGAGTCATATAGCCATAGATTATGTCATATCA 1486
Sequence_51   CTCCAGAAACTTCAGATCAACCAAATTATGAGTCATATAGCCATAGATTATGTCATATCA 1492
Sequence_83   CTCCAGAAACTTCAGATCAACCAAATTATGAGTCATATAGCCATAGATTATGTCATATCA 1492
Sequence_7    CTCCAGAAACTTCAGATCAACCAAATTATGAGTCATATAGCCATAGATTATGTCATATCA 1480
Sequence_25   CTCCAGAAACTTCAGATCAACCAAATTATGAGTCATATAGCCATAGATTATGTCATATCA 1480
Sequence_29   CTCCAGAAACTTCAGATCAACCAAATTATGAGTCATATAGCCATAGATTATGTCATATCA 1480
Sequence_33   CTCCAGAAACTTCAGATCAACCAAATTATGAGTCATATAGCCATAGATTATGTCATATCA 1480
Sequence_69   CTCCAGAAACTTCAGATCAACCAAATTATGAGTCATATAGCCATAGATTATGTCATATCA 1480
Sequence_11   CTCCAGAAACTTCAGATCAACCAAATTATGAGTCATATAGCCATAGATTATGTCATATCA 1468
Sequence_5    CTCCAGAAACTTCAGATCAACCAAATTATGAGTCATATAGCCATAGATTATGTCATATCA 1468
Sequence_1    CTCCAGAAACTTCAGATCAACCAAATTATGAGTCATATAGCCATAGATTATGTCATATCA 1468
Sequence_17   CTCCAGAAACTTCAGATCAACCAAATTATGAGTCATATAGCCATAGATTATGTCATATCA 2198
Sequence_3    CTCCAGAAACTTCAGATCAACCAAATTATGAGTCATATAGCCATAGATTATGTCATATCA 1468
Sequence_13   CTCCAGAAACTTCAGATCAACCAAATTATGAGTCATATAGCCATAGATTATGTCATATCA 1468
Sequence_18   CTCCAGAAACTTCAGATCAACCAAATTATGAGTCATATAGCCATAGATTATGTCATATCA 2721
Cry8Ha1       CTACGGGGA-TGCTGAACAGTACAGTCATCGGCTATCCTAT-GTTTCTAATGCTCCAACA 1464
              **  *  *   *  **  **      *  **   *  **       *   * ***   * **
```

To Fig. 16AA

Fig. 16Z

From Fig. 16Z

```
Sequence_71     CAAGTATTCCCGCGACGGG--TAACACTACCGGATTAGTACCTGTATTTTCTTGGACACA 1547
Sequence_73     CAAGTATTCCCGCGACGGG--TAACACTACCGGATTAGTACCTGTATTTTCTTGGACACA 1544
Sequence_21     CAAGTATTCCCGCGACGGG--TAACACTACCGGATTAGTACCTGTATTTTCTTGGACACA 1538
Sequence_67     CAAGTATTCCCGCGACGGG--TAACACTACCGGATTAGTACCTGTATTTTCTTGGACACA 1538
Sequence_61     CAAGTATTCCCGCGACGGG--TAACACTACCGGATTAGTACCTGTATTTTCTTGGACACA 1538
Sequence_93     CAAGTATTCCCGCGACGGG--TAACACTACCGGATTAGTACCTGTATTTTCTTGGACACA 1538
Sequence_59     CAAGTATTCCCGCGACGGG--TAACACTACCGGATTAGTACCTGTATTTTCTTGGACACA 1538
Sequence_91     CAAGTATTCCCGCGACGGG--TAACACTACCGGATTAGTACCTGTATTTTCTTGGACACA 1538
Sequence_39     CAAGTATTCCCGCGACGGG--TAACACTACCGGATTAGTACCTGTATTTTCTTGGACACA 1547
Sequence_41     CAAGTATTCCCGCGACGGG--TAACACTACCGGATTAGTACCTGTATTTTCTTGGACACA 1544
Sequence_49     CAAGTATTCCCGCGACGGG--TAACACTACCGGATTAGTACCTGTATTTTCTTGGACACA 1541
Sequence_81     CAAGTATTCCCGCGACGGG--TAACACTACCGGATTAGTACCTGTATTTTCTTGGACACA 1541
Sequence_45     CAAGTATTCCCGCGACGGG--TAACACTACCGGATTAGTACCTGTATTTTCTTGGACACA 1544
Sequence_77     CAAGTATTCCCGCGACGGG--TAACACTACCGGATTAGTACCTGTATTTTCTTGGACACA 1544
Sequence_75     CAAGTATTCCCGCGACGGG--TAACACTACCGGATTAGTACCTGTATTTTCTTGGACACA 1541
Sequence_43     CAAGTATTCCCGCGACGGG--TAACACTACCGGATTAGTACCTGTATTTTCTTGGACACA 1541
Sequence_47     CAAGTATTCCCGCGACGGG--TAACACTACCGGATTAGTACCTGTATTTTCTTGGACACA 1544
Sequence_79     CAAGTATTCCCGCGACGGG--TAACACTACCGGATTAGTACCTGTATTTTCTTGGACACA 1544
Sequence_51     CAAGTATTCCCGCGACGGG--TAACACTACCGGATTAGTACCTGTATTTTCTTGGACACA 1550
Sequence_83     CAAGTATTCCCGCGACGGG--TAACACTACCGGATTAGTACCTGTATTTTCTTGGACACA 1550
Sequence_7      CAAGTATTCCCGCGACGGG--TAACACTACCGGATTAGTACCTGTATTTTCTTGGACACA 1538
Sequence_25     CAAGTATTCCCGCGACGGG--TAACACTACCGGATTAGTACCTGTATTTTCTTGGACACA 1538
Sequence_29     CAAGTATTCCCGCGACGGG--TAACACTACCGGATTAGTACCTGTATTTTCTTGGACACA 1538
Sequence_33     CAAGTATTCCCGCGACGGG--TAACACTACCGGATTAGTACCTGTATTTTCTTGGACACA 1538
Sequence_69     CAAGTATTCCCGCGACGGG--TAACACTACCGGATTAGTACCTGTATTTTCTTGGACACA 1538
Sequence_11     CAAGTATTCCCGCGACGGG--TAACACTACCGGATTAGTACCTGTATTTTCTTGGACACA 1526
Sequence_5      CAAGTATTCCCGCGACGGG--TAACACTACCGGATTAGTACCTGTATTTTCTTGGACACA 1526
Sequence_1      CAAGTATTCCCGCGACGGG--TAACACTACCGGATTAGTACCTGTATTTTCTTGGACACA 1526
Sequence_17     CAAGTATTCCCGCGACGGG--TAACACTACCGGATTAGTACCTGTATTTTCTTGGACACA 2256
Sequence_3      CAAGTATTCCCGCGACGGG--TTCAACTACCGGATTAGTACCTGTATTTTCTTGGACACA 1526
Sequence_13     CAAGTATTCCCGCGACGGG--TTCAACTACCGGATTAGTACCTGTATTTTCTTGGACACA 1526
Sequence_18     CAAGTATTCCCGCGACGGG--TTCAACTACCGGATTAGTACCTGTATTTTCTTGGACACA 2779
Cry8Ha1         -GAGTACTCTTCGGGCGGACATTTAATTTTGGGACTAATCCCAGTACTGGGTTGGACGCA 1523
                  **** **    * ***   *   * *   *** ** * ** *** *   ****** **
```

To Fig. 16AB

Fig. 16AA

From Fig. 16AA

```
Sequence_71     TCGAAGTGCAGATTTAAACAATACAATATATTCAGATAAAATCACTCAAATTCCGGCCGT 1607
Sequence_73     TCGAAGTGCAGATTTAAACAATACAATATATTCAGATAAAATCACTCAAATTCCGGCCGT 1604
Sequence_21     TCGAAGTGCAGATTTAAACAATACAATATATTCAGATAAAATCACTCAAATTCCGGCCGT 1598
Sequence_67     TCGAAGTGCAGATTTAAACAATACAATATATTCAGATAAAATCACTCAAATTCCGGCCGT 1598
Sequence_61     TCGAAGTGCAGATTTAAACAATACAATATATTCAGATAAAATCACTCAAATTCCGGCCGT 1598
Sequence_93     TCGAAGTGCAGATTTAAACAATACAATATATTCAGATAAAATCACTCAAATTCCGGCCGT 1598
Sequence_59     TCGAAGTGCAGATTTAAACAATACAATATATTCAGATAAAATCACTCAAATTCCGGCCGT 1598
Sequence_91     TCGAAGTGCAGATTTAAACAATACAATATATTCAGATAAAATCACTCAAATTCCGGCCGT 1598
Sequence_39     TCGAAGTGCAGATTTAAACAATACAATATATTCAGATAAAATCACTCAAATTCCGGCCGT 1607
Sequence_41     TCGAAGTGCAGATTTAAACAATACAATATATTCAGATAAAATCACTCAAATTCCGGCCGT 1604
Sequence_49     TCGAAGTGCAGATTTAAACAATACAATATATTCAGATAAAATCACTCAAATTCCGGCCGT 1601
Sequence_81     TCGAAGTGCAGATTTAAACAATACAATATATTCAGATAAAATCACTCAAATTCCGGCCGT 1601
Sequence_45     TCGAAGTGCAGATTTAAACAATACAATATATTCAGATAAAATCACTCAAATTCCGGCCGT 1604
Sequence_77     TCGAAGTGCAGATTTAAACAATACAATATATTCAGATAAAATCACTCAAATTCCGGCCGT 1604
Sequence_75     TCGAAGTGCAGATTTAAACAATACAATATATTCAGATAAAATCACTCAAATTCCGGCCGT 1601
Sequence_43     TCGAAGTGCAGATTTAAACAATACAATATATTCAGATAAAATCACTCAAATTCCGGCCGT 1601
Sequence_47     TCGAAGTGCAGATTTAAACAATACAATATATTCAGATAAAATCACTCAAATTCCGGCCGT 1604
Sequence_79     TCGAAGTGCAGATTTAAACAATACAATATATTCAGATAAAATCACTCAAATTCCGGCCGT 1604
Sequence_51     TCGAAGTGCAGATTTAAACAATACAATATATTCAGATAAAATCACTCAAATTCCGGCCGT 1610
Sequence_83     TCGAAGTGCAGATTTAAACAATACAATATATTCAGATAAAATCACTCAAATTCCGGCCGT 1610
Sequence_7      TCGAAGTGCAGATTTAAACAATACAATATATTCAGATAAAATCACTCAAATTCCGGCCGT 1598
Sequence_25     TCGAAGTGCAGATTTAAACAATACAATATATTCAGATAAAATCACTCAAATTCCGGCCGT 1598
Sequence_29     TCGAAGTGCAGATTTAAACAATACAATATATTCAGATAAAATCACTCAAATTCCGGCCGT 1598
Sequence_33     TCGAAGTGCAGATTTAAACAATACAATATATTCAGATAAAATCACTCAAATTCCGGCCGT 1598
Sequence_69     TCGAAGTGCAGATTTAAACAATACAATATATTCAGATAAAATCACTCAAATTCCGGCCGT 1598
Sequence_11     TCGAAGTGCAGATTTAAACAATACAATATATTCAGATAAAATCACTCAAATTCCGGCCGT 1586
Sequence_5      TCGAAGTGCAGATTTAAACAATACAATATATTCAGATAAAATCACTCAAATTCCGGCCGT 1586
Sequence_1      TCGAAGTGCAGATTTAAACAATACAATATATTCAGATAAAATCACTCAAATTCCGGCCGT 1586
Sequence_17     TCGAAGTGCAGATTTAAACAATACAATATATTCAGATAAAATCACTCAAATTCCGGCCGT 2316
Sequence_3      TCGGAGTGCCGATCTTATAAATGCAGTTCATTCAGATAAAATTACTCAGATTCCGGTCGT 1586
Sequence_13     TCGGAGTGCCGATCTTATAAATGCAGTTCATTCAGATAAAATTACTCAGATTCCGGTCGT 1586
Sequence_18     TCGGAGTGCCGATCTTATAAATGCAGTTCATTCAGATAAAATTACTCAGATTCCGGTCGT 2839
Cry8Ha1         TACTAGTTTAACTCAAACAAATCAGATACATTCTGACTCAATTACTCAAATTCCAGCTGT 1583
                *   ***     *   *  ***    *  **** **   *** ***** ***** *  **
```

To Fig. 16AC

Fig. 16AB

From Fig. 16AB

```
Sequence_71     TAAATGTTGGGATAATTTACCGTTTGTTCCAGTGGT----AAAAGGACCAGGACATACAG 1663
Sequence_73     TAAATGTTGGGATAATTTACCGTTTGTTCCAGTGGT----AAAAGGACCAGGACATACAG 1660
Sequence_21     TAAATGTTGGGATAATTTACCGTTTGTTCCAGTGGT----AAAAGGACCAGGACATACAG 1654
Sequence_67     TAAATGTTGGGATAATTTACCGTTTGTTCCAGTGGT----AAAAGGACCAGGACATACAG 1654
Sequence_61     TAAATGTTGGGATAATTTACCGTTTGTTCCAGTGGT----AAAAGGACCAGGACATACAG 1654
Sequence_93     TAAATGTTGGGATAATTTACCGTTTGTTCCAGTGGT----AAAAGGACCAGGACATACAG 1654
Sequence_59     TAAATGTTGGGATAATTTACCGTTTGTTCCAGTGGT----AAAAGGACCAGGACATACAG 1654
Sequence_91     TAAATGTTGGGATAATTTACCGTTTGTTCCAGTGGT----AAAAGGACCAGGACATACAG 1654
Sequence_39     TAAATGTTGGGATAATTTACCGTTTGTTCCAGTGGT----AAAAGGACCAGGACATACAG 1663
Sequence_41     TAAATGTTGGGATAATTTACCGTTTGTTCCAGTGGT----AAAAGGACCAGGACATACAG 1660
Sequence_49     TAAATGTTGGGATAATTTACCGTTTGTTCCAGTGGT----AAAAGGACCAGGACATACAG 1657
Sequence_81     TAAATGTTGGGATAATTTACCGTTTGTTCCAGTGGT----AAAAGGACCAGGACATACAG 1657
Sequence_45     TAAATGTTGGGATAATTTACCGTTTGTTCCAGTGGT----AAAAGGACCAGGACATACAG 1660
Sequence_77     TAAATGTTGGGATAATTTACCGTTTGTTCCAGTGGT----AAAAGGACCAGGACATACAG 1660
Sequence_75     TAAATGTTGGGATAATTTACCGTTTGTTCCAGTGGT----AAAAGGACCAGGACATACAG 1657
Sequence_43     TAAATGTTGGGATAATTTACCGTTTGTTCCAGTGGT----AAAAGGACCAGGACATACAG 1657
Sequence_47     TAAATGTTGGGATAATTTACCGTTTGTTCCAGTGGT----AAAAGGACCAGGACATACAG 1660
Sequence_79     TAAATGTTGGGATAATTTACCGTTTGTTCCAGTGGT----AAAAGGACCAGGACATACAG 1660
Sequence_51     TAAATGTTGGGATAATTTACCGTTTGTTCCAGTGGT----AAAAGGACCAGGACATACAG 1666
Sequence_83     TAAATGTTGGGATAATTTACCGTTTGTTCCAGTGGT----AAAAGGACCAGGACATACAG 1666
Sequence_7      TAAATGTTGGGATAATTTACCGTTTGTTCCAGTGGT----AAAAGGACCAGGACATACAG 1654
Sequence_25     TAAATGTTGGGATAATTTACCGTTTGTTCCAGTGGT----AAAAGGACCAGGACATACAG 1654
Sequence_29     TAAATGTTGGGATAATTTACCGTTTGTTCCAGTGGT----AAAAGGACCAGGACATACAG 1654
Sequence_33     TAAATGTTGGGATAATTTACCGTTTGTTCCAGTGGT----AAAAGGACCAGGACATACAG 1654
Sequence_69     TAAATGTTGGGATAATTTACCGTTTGTTCCAGTGGT----AAAAGGACCAGGACATACAG 1654
Sequence_11     TAAATGTTGGGATAATTTACCGTTTGTTCCAGTGGT----AAAAGGACCAGGACATACAG 1642
Sequence_5      TAAATGTTGGGATAATTTACCGTTTGTTCCAGTGGT----AAAAGGACCAGGACATACAG 1642
Sequence_1      TAAATGTTGGGATAATTTACCGTTTGTTCCAGTGGT----AAAAGGACCAGGACATACAG 1642
Sequence_17     TAAATGTTGGGATAATTTACCGTTTGTTCCAGTGGT----AAAAGGACCAGGACATACAG 2372
Sequence_3      AAAGGTTTCTGATTTGGCTCCCTCTATAACAGGAGGGCCAAATAATACCGTTGTATCGGG 1646
Sequence_13     AAAGGTTTCTGATTTGGCTCCCTCTATAACAGGAGGGCCAAATAATACCGTTGTATCGGG 1646
Sequence_18     AAAGGTTTCTGATTTGGCTCCCTCTATAACAGGAGGGCCAAATAATACCGTTGTATCGGG 2899
Cry8Ha1         TAAAGCAAATAGTGTTAGTTCTTATGT------------------TACTGTTGAAAAGGG 1625
                 **         *       * * * *                 **       *    *
```

To Fig. 16AD

Fig. 16AC

From Fig. 16AC

```
Sequence_71     GAGGGGATTTATTACAGT----ATAATAGAAGTACTG-GTTCTGTAGGAACCTTATTTCT 1718
Sequence_73     GAGGGGATTTATTACAGT----ATAATAGAAGTACTG-GTTCTGTAGGAACCTTATTTCT 1715
Sequence_21     GAGGGGATTTATTACAGT----ATAATAGAAGTACTG-GTTCTGTAGGAACCTTATTTCT 1709
Sequence_67     GAGGGGATTTATTACAGT----ATAATAGAAGTACTG-GTTCTGTAGGAACCTTATTTCT 1709
Sequence_61     GAGGGGATTTATTACAGT----ATAATAGAAGTACTG-GTTCTGTAGGAACCTTATTTCT 1709
Sequence_93     GAGGGGATTTATTACAGT----ATAATAGAAGTACTG-GTTCTGTAGGAACCTTATTTCT 1709
Sequence_59     GAGGGGATTTATTACAGT----ATAATAGAAGTACTG-GTTCTGTAGGAACCTTATTTCT 1709
Sequence_91     GAGGGGATTTATTACAGT----ATAATAGAAGTACTG-GTTCTGTAGGAACCTTATTTCT 1709
Sequence_39     GAGGGGATTTATTACAGT----ATAATAGAAGTACTG-GTTCTGTAGGAACCTTATTTCT 1718
Sequence_41     GAGGGGATTTATTACAGT----ATAATAGAAGTACTG-GTTCTGTAGGAACCTTATTTCT 1715
Sequence_49     GAGGGGATTTATTACAGT----ATAATAGAAGTACTG-GTTCTGTAGGAACCTTATTTCT 1712
Sequence_81     GAGGGGATTTATTACAGT----ATAATAGAAGTACTG-GTTCTGTAGGAACCTTATTTCT 1712
Sequence_45     GAGGGGATTTATTACAGT----ATAATAGAAGTACTG-GTTCTGTAGGAACCTTATTTCT 1715
Sequence_77     GAGGGGATTTATTACAGT----ATAATAGAAGTACTG-GTTCTGTAGGAACCTTATTTCT 1715
Sequence_75     GAGGGGATTTATTACAGT----ATAATAGAAGTACTG-GTTCTGTAGGAACCTTATTTCT 1712
Sequence_43     GAGGGGATTTATTACAGT----ATAATAGAAGTACTG-GTTCTGTAGGAACCTTATTTCT 1712
Sequence_47     GAGGGGATTTATTACAGT----ATAATAGAAGTACTG-GTTCTGTAGGAACCTTATTTCT 1715
Sequence_79     GAGGGGATTTATTACAGT----ATAATAGAAGTACTG-GTTCTGTAGGAACCTTATTTCT 1715
Sequence_51     GAGGGGATTTATTACAGT----ATAATAGAAGTACTG-GTTCTGTAGGAACCTTATTTCT 1721
Sequence_83     GAGGGGATTTATTACAGT----ATAATAGAAGTACTG-GTTCTGTAGGAACCTTATTTCT 1721
Sequence_7      GAGGGGATTTATTACAGT----ATAATAGAAGTACTG-GTTCTGTAGGAACCTTATTTCT 1709
Sequence_25     GAGGGGATTTATTACAGT----ATAATAGAAGTACTG-GTTCTGTAGGAACCTTATTTCT 1709
Sequence_29     GAGGGGATTTATTACAGT----ATAATAGAAGTACTG-GTTCTGTAGGAACCTTATTTCT 1709
Sequence_33     GAGGGGATTTATTACAGT----ATAATAGAAGTACTG-GTTCTGTAGGAACCTTATTTCT 1709
Sequence_69     GAGGGGATTTATTACAGT----ATAATAGAAGTACTG-GTTCTGTAGGAACCTTATTTCT 1709
Sequence_11     GAGGGGATTTATTACAGT----ATAATAGAAGTACTG-GTTCTGTAGGAACCTTATTTCT 1697
Sequence_5      GAGGGGATTTATTACAGT----ATAATAGAAGTACTG-GTTCTGTAGGAACCTTATTTCT 1697
Sequence_1      GAGGGGATTTATTACAGT----ATAATAGAAGTACTG-GTTCTGTAGGAACCTTATTTCT 1697
Sequence_17     GAGGGGATTTATTACAGT----ATAATAGAAGTACTG-GTTCTGTAGGAACCTTATTTCT 2427
Sequence_3      TCCTGGATTTACAGGGGGGGGATAATAAAAGTAATAAGAAATGGAGTAATTATATCACA 1706
Sequence_13     TCCTGGATTTACAGGGGGGGGATAATAAAAGTAATAAGAAATGGAGTAATTATATCACA 1706
Sequence_18     TCCTGGATTTACAGGGGGGGGATAATAAAAGTAATAAGAAATGGAGTAATTATATCACA 2959
Cry8Ha1_        AACAGGCTTTACAGGTGGAGATTTAGTGAAATTCTCC---ACTGGATTCATGTCTACAGG 1682
                    ** ****     *      ** *  ** *         ** *   *
```

To Fig. 16AE

Fig. 16AD

From Fig. 16AD

```
Sequence_71      AGCTCGATATGGCCTAGCATTAGAAAAAGCAGGGAAATATCGTGTAAGACTGAGATATGC 1778
Sequence_73      AGCTCGATATGGCCTAGCATTAGAAAAAGCAGGGAAATATCGTGTAAGACTGAGATATGC 1775
Sequence_21      AGCTCGATATGGCCTAGCATTAGAAAAAGCAGGGAAATATCGTGTAAGACTGAGATATGC 1769
Sequence_67      AGCTCGATATGGCCTAGCATTAGAAAAAGCAGGGAAATATCGTGTAAGACTGAGATATGC 1769
Sequence_61      AGCTCGATATGGCCTAGCATTAGAAAAAGCAGGGAAATATCGTGTAAGACTGAGATATGC 1769
Sequence_93      AGCTCGATATGGCCTAGCATTAGAAAAAGCAGGGAAATATCGTGTAAGACTGAGATATGC 1769
Sequence_59      AGCTCGATATGGCCTAGCATTAGAAAAAGCAGGGAAATATCGTGTAAGACTGAGATATGC 1769
Sequence_91      AGCTCGATATGGCCTAGCATTAGAAAAAGCAGGGAAATATCGTGTAAGACTGAGATATGC 1769
Sequence_39      AGCTCGATATGGCCTAGCATTAGAAAAAGCAGGGAAATATCGTGTAAGACTGAGATATGC 1778
Sequence_41      AGCTCGATATGGCCTAGCATTAGAAAAAGCAGGGAAATATCGTGTAAGACTGAGATATGC 1775
Sequence_49      AGCTCGATATGGCCTAGCATTAGAAAAAGCAGGGAAATATCGTGTAAGACTGAGATATGC 1772
Sequence_81      AGCTCGATATGGCCTAGCATTAGAAAAAGCAGGGAAATATCGTGTAAGACTGAGATATGC 1772
Sequence_45      AGCTCGATATGGCCTAGCATTAGAAAAAGCAGGGAAATATCGTGTAAGACTGAGATATGC 1775
Sequence_77      AGCTCGATATGGCCTAGCATTAGAAAAAGCAGGGAAATATCGTGTAAGACTGAGATATGC 1775
Sequence_75      AGCTCGATATGGCCTAGCATTAGAAAAAGCAGGGAAATATCGTGTAAGACTGAGATATGC 1772
Sequence_43      AGCTCGATATGGCCTAGCATTAGAAAAAGCAGGGAAATATCGTGTAAGACTGAGATATGC 1772
Sequence_47      AGCTCGATATGGCCTAGCATTAGAAAAAGCAGGGAAATATCGTGTAAGACTGAGATATGC 1775
Sequence_79      AGCTCGATATGGCCTAGCATTAGAAAAAGCAGGGAAATATCGTGTAAGACTGAGATATGC 1775
Sequence_51      AGCTCGATATGGCCTAGCATTAGAAAAAGCAGGGAAATATCGTGTAAGACTGAGATATGC 1781
Sequence_83      AGCTCGATATGGCCTAGCATTAGAAAAAGCAGGGAAATATCGTGTAAGACTGAGATATGC 1781
Sequence_7       AGCTCGATATGGCCTAGCATTAGAAAAAGCAGGGAAATATCGTGTAAGACTGAGATATGC 1769
Sequence_25      AGCTCGATATGGCCTAGCATTAGAAAAAGCAGGGAAATATCGTGTAAGACTGAGATATGC 1769
Sequence_29      AGCTCGATATGGCCTAGCATTAGAAAAAGCAGGGAAATATCGTGTAAGACTGAGATATGC 1769
Sequence_33      AGCTCGATATGGCCTAGCATTAGAAAAAGCAGGGAAATATCGTGTAAGACTGAGATATGC 1769
Sequence_69      AGCTCGATATGGCCTAGCATTAGAAAAAGCAGGGAAATATCGTGTAAGACTGAGATATGC 1769
Sequence_11      AGCTCGATATGGCCTAGCATTAGAAAAAGCAGGGAAATATCGTGTAAGACTGAGATATGC 1757
Sequence_5       AGCTCGATATGGCCTAGCATTAGAAAAAGCAGGGAAATATCGTGTAAGACTGAGATATGC 1757
Sequence_1       AGCTCGATATGGCCTAGCATTAGAAAAAGCAGGGAAATATCGTGTAAGACTGAGATATGC 1757
Sequence_17      AGCTCGATATGGCCTAGCATTAGAAAAAGCAGGGAAATATCGTGTAAGACTGAGATATGC 2487
Sequence_3       TATGCG---TGTTAAAATTTCAGACATTAACAAAGAATATAGTATGAGGATTCGGTATGC 1763
Sequence_13      TATGCG---TGTTAAAATTTCAGACATTAACAAAGAATATAGTATGAGGATTCGGTATGC 1763
Sequence_18      TATGCG---TGTTAAAATTTCAGACATTAACAAAGAATATAGTATGAGGATTCGGTATGC 3016
Cry8Ha1_         AATACAGTTTAATTTAAAGATAGAAGAAAGAAAGCGTTATCGTATCCGTATACGATATGC 1742
                     *    *     *     ***             *** ** *  *  *  * *****
```

To Fig. 16AF

Fig. 16AE

From Fig. 16AE

```
Sequence_71    TACTGATGCAGATATTGTATTGCATGTAAAC------------GATGCTCAGATTCAGAT 1826
Sequence_73    TACTGATGCAGATATTGTATTGCATGTAAAC------------GATGCTCAGATTCAGAT 1823
Sequence_21    TACTGATGCAGATATTGTATTGCATGTAAAC------------GATGCTCAGATTCAGAT 1817
Sequence_67    TACTGATGCAGATATTGTATTGCATGTAAAC------------GATGCTCAGATTCAGAT 1817
Sequence_61    TACTGATGCAGATATTGTATTGCATGTAAAC------------GATGCTCAGATTCAGAT 1817
Sequence_93    TACTGATGCAGATATTGTATTGCATGTAAAC------------GATGCTCAGATTCAGAT 1817
Sequence_59    TACTGATGCAGATATTGTATTGCATGTAAAC------------GATGCTCAGATTCAGAT 1817
Sequence_91    TACTGATGCAGATATTGTATTGCATGTAAAC------------GATGCTCAGATTCAGAT 1817
Sequence_39    TACTGATGCAGATATTGTATTGCATGTAAAC------------GATGCTCAGATTCAGAT 1826
Sequence_41    TACTGATGCAGATATTGTATTGCATGTAAAC------------GATGCTCAGATTCAGAT 1823
Sequence_49    TACTGATGCAGATATTGTATTGCATGTAAAC------------GATGCTCAGATTCAGAT 1820
Sequence_81    TACTGATGCAGATATTGTATTGCATGTAAAC------------GATGCTCAGATTCAGAT 1820
Sequence_45    TACTGATGCAGATATTGTATTGCATGTAAAC------------GATGCTCAGATTCAGAT 1823
Sequence_77    TACTGATGCAGATATTGTATTGCATGTAAAC------------GATGCTCAGATTCAGAT 1823
Sequence_75    TACTGATGCAGATATTGTATTGCATGTAAAC------------GATGCTCAGATTCAGAT 1820
Sequence_43    TACTGATGCAGATATTGTATTGCATGTAAAC------------GATGCTCAGATTCAGAT 1820
Sequence_47    TACTGATGCAGATATTGTATTGCATGTAAAC------------GATGCTCAGATTCAGAT 1823
Sequence_79    TACTGATGCAGATATTGTATTGCATGTAAAC------------GATGCTCAGATTCAGAT 1823
Sequence_51    TACTGATGCAGATATTGTATTGCATGTAAAC------------GATGCTCAGATTCAGAT 1829
Sequence_83    TACTGATGCAGATATTGTATTGCATGTAAAC------------GATGCTCAGATTCAGAT 1829
Sequence_7     TACTGATGCAGATATTGTATTGCATGTAAAC------------GATGCTCAGATTCAGAT 1817
Sequence_25    TACTGATGCAGATATTGTATTGCATGTAAAC------------GATGCTCAGATTCAGAT 1817
Sequence_29    TACTGATGCAGATATTGTATTGCATGTAAAC------------GATGCTCAGATTCAGAT 1817
Sequence_33    TACTGATGCAGATATTGTATTGCATGTAAAC------------GATGCTCAGATTCAGAT 1817
Sequence_69    TACTGATGCAGATATTGTATTGCATGTAAAC------------GATGCTCAGATTCAGAT 1817
Sequence_11    TACTGATGCAGATATTGTATTGCATGTAAAC------------GATGCTCAGATTCAGAT 1805
Sequence_5     TACTGATGCAGATATTGTATTGCATGTAAAC------------GATGCTCAGATTCAGAT 1805
Sequence_1     TACTGATGCAGATATTGTATTGCATGTAAAC------------GATGCTCAGATTCAGAT 1805
Sequence_17    TACTGATGCAGATATTGTATTGCATGTAAAC------------GATGCTCAGATTCAGAT 2535
Sequence_3     TTCCGCTAATAATACTGAATTTTATATAAATCCTTCTGAAGAAAACGTTAAATCTCACGC 1823
Sequence_13    TTCCGCTAATAATACTGAATTTTATATAAATCCTTCTGAAGAAAACGTTAAATCTCACGC 1823
Sequence_18    TTCCGCTAATAATACTGAATTTTATATAAATCCTTCTGAAGAAAACGTTAAATCTCACGC 3076
Cry8Ha1        CGCTGATGTTAATGCT--ACTCTATCTGCACTTGGATTAA-ATGATGCATTTATTAACAT 1799
                 * * *    **  *  * *  ** *  *              * *       *
```

To Fig. 16AG

Fig. 16AF

From Fig. 16AF

```
Sequence_71      GCCAAAAACAATGAACCCAGGTGAGGATCTGACATCTAAAACTTTTAAAGTTGCAGATGC 1886
Sequence_73      GCCAAAAACAATGAACCCAGGTGAGGATCTGACATCTAAAACTTTTAAAGTTGCAGATGC 1883
Sequence_21      GCCAAAAACAATGAACCCAGGTGAGGATCTGACATCTAAAACTTTTAAAGTTGCAGATGC 1877
Sequence_67      GCCAAAAACAATGAACCCAGGTGAGGATCTGACATCTAAAACTTTTAAAGTTGCAGATGC 1877
Sequence_61      GCCAAAAACAATGAACCCAGGTGAGGATCTGACATCTAAAACTTTTAAAGTTGCAGATGC 1877
Sequence_93      GCCAAAAACAATGAACCCAGGTGAGGATCTGACATCTAAAACTTTTAAAGTTGCAGATGC 1877
Sequence_59      GCCAAAAACAATGAACCCAGGTGAGGATCTGACATCTAAAACTTTTAAAGTTGCAGATGC 1877
Sequence_91      GCCAAAAACAATGAACCCAGGTGAGGATCTGACATCTAAAACTTTTAAAGTTGCAGATGC 1877
Sequence_39      GCCAAAAACAATGAACCCAGGTGAGGATCTGACATCTAAAACTTTTAAAGTTGCAGATGC 1886
Sequence_41      GCCAAAAACAATGAACCCAGGTGAGGATCTGACATCTAAAACTTTTAAAGTTGCAGATGC 1883
Sequence_49      GCCAAAAACAATGAACCCAGGTGAGGATCTGACATCTAAAACTTTTAAAGTTGCAGATGC 1880
Sequence_81      GCCAAAAACAATGAACCCAGGTGAGGATCTGACATCTAAAACTTTTAAAGTTGCAGATGC 1880
Sequence_45      GCCAAAAACAATGAACCCAGGTGAGGATCTGACATCTAAAACTTTTAAAGTTGCAGATGC 1883
Sequence_77      GCCAAAAACAATGAACCCAGGTGAGGATCTGACATCTAAAACTTTTAAAGTTGCAGATGC 1883
Sequence_75      GCCAAAAACAATGAACCCAGGTGAGGATCTGACATCTAAAACTTTTAAAGTTGCAGATGC 1880
Sequence_43      GCCAAAAACAATGAACCCAGGTGAGGATCTGACATCTAAAACTTTTAAAGTTGCAGATGC 1880
Sequence_47      GCCAAAAACAATGAACCCAGGTGAGGATCTGACATCTAAAACTTTTAAAGTTGCAGATGC 1883
Sequence_79      GCCAAAAACAATGAACCCAGGTGAGGATCTGACATCTAAAACTTTTAAAGTTGCAGATGC 1883
Sequence_51      GCCAAAAACAATGAACCCAGGTGAGGATCTGACATCTAAAACTTTTAAAGTTGCAGATGC 1889
Sequence_83      GCCAAAAACAATGAACCCAGGTGAGGATCTGACATCTAAAACTTTTAAAGTTGCAGATGC 1889
Sequence_7       GCCAAAAACAATGAACCCAGGTGAGGATCTGACATCTAAAACTTTTAAAGTTGCAGATGC 1877
Sequence_25      GCCAAAAACAATGAACCCAGGTGAGGATCTGACATCTAAAACTTTTAAAGTTGCAGATGC 1877
Sequence_29      GCCAAAAACAATGAACCCAGGTGAGGATCTGACATCTAAAACTTTTAAAGTTGCAGATGC 1877
Sequence_33      GCCAAAAACAATGAACCCAGGTGAGGATCTGACATCTAAAACTTTTAAAGTTGCAGATGC 1877
Sequence_69      GCCAAAAACAATGAACCCAGGTGAGGATCTGACATCTAAAACTTTTAAAGTTGCAGATGC 1877
Sequence_11      GCCAAAAACAATGAACCCAGGTGAGGATCTGACATCTAAAACTTTTAAAGTTGCAGATGC 1865
Sequence_5       GCCAAAAACAATGAACCCAGGTGAGGATCTGACATCTAAAACTTTTAAAGTTGCAGATGC 1865
Sequence_1       GCCAAAAACAATGAACCCAGGTGAGGATCTGACATCTAAAACTTTTAAAGTTGCAGATGC 1865
Sequence_17      GCCAAAAACAATGAACCCAGGTGAGGATCTGACATCTAAAACTTTTAAAGTTGCAGATGC 2595
Sequence_3       TCAAAAAACTATGAATAGAGGTGAAGCTTTAACATATAATAAATTTAATTATGC-GACTT 1882
Sequence_13      TCAAAAAACTATGAATAGAGGTGAAGCTTTAACATATAATAAATTTAATTATGC-GACTT 1882
Sequence_18      TCAAAAAACTATGAATAGAGGTGAAGCTTTAACATATAATAAATTTAATTATGC-GACTT 3135
Cry8Ha1          TAAATCGACAATGTCTCAAGACACACCATTGAAGTATAACGATTTCCAATATGCAGAAGC 1859
                    *   ** ***     **         * *  * ***    **  *   *** **
```

To Fig. 16AH

Fig. 16AG

From Fig. 16AG

```
Sequence_71    TATCACAACAGTTAATTTA--GCAACAGATAGTTCGGTTGCAGTTAAA--CATAATTTAG 1942
Sequence_73    TATCACAACAGTTAATTTA--GCAACAGATAGTTCGGTTGCAGTTAAA--CATAATTTAG 1939
Sequence_21    TATCACAACAGTAAATTTA--GCAACAGATAGTTCGGTAGCAGTGAAA--CATAATGTAG 1933
Sequence_67    TATCACAACAGTAAATTTA--GCAACAGATAGTTCGGTAGCAGTGAAA--CATAATTTAG 1933
Sequence_61    TATCACAACAGTTAATTTA--GCAACAGATAGTTCGGTTGCAGTTAAA--CATAATGTAG 1933
Sequence_93    TATCACAACAGTTAATTTA--GCAACAGATAGTTCGGTTGCAGTTAAA--CATAATTTAG 1933
Sequence_59    TATCACAACAGTTAATTTA--GCAACAGATAGTTCGGTTGCAGTTAAA--CATAATGTAG 1933
Sequence_91    TATCACAACAGTTAATTTA--GCAACAGATAGTTCGGTTGCAGTTAAA--CATAATTTAG 1933
Sequence_39    TATCACAACAGTTAATTTA--GCAACAGATAGTTCGGTTGCAGTTAAA--CATAATGTAG 1942
Sequence_41    TATCACAACAGTTAATTTA--GCAACAGATAGTTCGGTTGCAGTTAAA--CATAATGTAG 1939
Sequence_49    TATCACAACAGTTAATTTA--GCAACAGATAGTTCGGTTGCAGTTAAA--CATAATGTAG 1936
Sequence_81    TATCACAACAGTTAATTTA--GCAACAGATAGTTCGGTTGCAGTTAAA--CATAATTTAG 1936
Sequence_45    TATCACAACAGTTAATTTA--GCAACAGATAGTTCGGTTGCAGTTAAA--CATAATGTAG 1939
Sequence_77    TATCACAACAGTTAATTTA--GCAACAGATAGTTCGGTTGCAGTTAAA--CATAATTTAG 1939
Sequence_75    TATCACAACAGTTAATTTA--GCAACAGATAGTTCGGTTGCAGTTAAA--CATAATTTAG 1936
Sequence_43    TATCACAACAGTTAATTTA--GCAACAGATAGTTCGGTTGCAGTTAAA--CATAATGTAG 1936
Sequence_47    TATCACAACAGTTAATTTA--GCAACAGATAGTTCGGTTGCAGTTAAA--CATAATGTAG 1939
Sequence_79    TATCACAACAGTTAATTTA--GCAACAGATAGTTCGGTTGCAGTTAAA--CATAATTTAG 1939
Sequence_51    TATCACAACAGTTAATTTA--GCAACAGATAGTTCGGTTGCAGTTAAA--CATAATGTAG 1945
Sequence_83    TATCACAACAGTTAATTTA--GCAACAGATAGTTCGGTTGCAGTTAAA--CATAATTTAG 1945
Sequence_7     TATCACAACATTAAATTTA--GCAACAGATAGTTCGCTAGCATTGAAA--CATAATTTAG 1933
Sequence_25    TATCACAACATTAAATTTA--GCAACAGATAGTTCGCTAGCATTGAAA--CATAATGTAG 1933
Sequence_29    TATCACAACATTAAATTTA--GCAACAGATAGTTCGCTAGCAGTGAAA--CATAATGTAG 1933
Sequence_33    TATCACAACAGTAAATTTA--GCAACAGATAGTTCGGTAGCAGTGAAA--CATAATGTAG 1933
Sequence_69    TATCACAACAGTAAATTTA--GCAACAGATAGTTCGGTAGCAGTGAAA--CATAATTTAG 1933
Sequence_11    TATCACAACATTAAATTTA--GCAACAGATAGTTCGCTAGCATTGAAA--CATAATTTAG 1921
Sequence_5     TATCACAACATTAAATTTA--GCAACAGATAGTTCGCTAGCATTGAAA--CATAATTTAG 1921
Sequence_1     TATCACAACATTAAATTTA--GCAACAGATAGTTCGCTAGCATTGAAA--CATAATTTAG 1921
Sequence_17    TATCACAACATTAAATTTA--GCAACAGATAGTTCGCTAGCATTGAAA--CATAATTTAG 2651
Sequence_3     TGCCCCC-TATTAAATTTACGACAACCGAACCTTTCATTACTCTAGGGGCTATATTTGAA 1941
Sequence_13    TGCCCCC-TATTAAATTTACGACAACCGAACCTTTCATTACTCTAGGGGCTATATTTGAA 1941
Sequence_18    TGCCCCC-TATTAAATTTACGACAACCGAACCTTTCATTACTCTAGGGGCTATATTTGAA 3194
Cry8Ha1        TGACAAAACAGTGCATTTA-----TACAATCCTCGTTTTTCTTTA-----TATTTAGAAA 1909
               *  *     * *  *****         *   *    *  *  *       **     *
```

To Fig. 16AI

Fig. 16AH

From Fig. 16AH

```
Sequence_71      GTGAAGACCCTAATTCAACATTATCTGGTATAGTTTACGTTGACCGAATCGAATTCATCC 2002
Sequence_73      GTGAAGACCCTAATTCAACATTATCTGGTATAGTTTACGTTGACCGAATCGAATTCATCC 1999
Sequence_21      GTGAAGACCCTAATTCAACATTATCTGGTATAGTTTACGTTGACCGAATCGAATTCATCC 1993
Sequence_67      GTGAAGACCCTAATTCAACATTATCTGGTATAGTTTACGTTGACCGAATCGAATTCATCC 1993
Sequence_61      GTGAAGACCCTAATTCAACATTATCTGGTATAGTTTACGTTGACCGAATCGAATTCATCC 1993
Sequence_93      GTGAAGACCCTAATTCAACATTATCTGGTATAGTTTACGTTGACCGAATCGAATTCATCC 1993
Sequence_59      GTGAAGACCCTAATTCAACATTATCTGGTATAGTTTACGTTGACCGAATCGAATTCATCC 1993
Sequence_91      GTGAAGACCCTAATTCAACATTATCTGGTATAGTTTACGTTGACCGAATCGAATTCATCC 1993
Sequence_39      GTGAAGACCCTAATTCAACATTATCTGGTATAGTTTACGTTGACCGAATCGAATTCATCC 2002
Sequence_41      GTGAAGACCCTAATTCAACATTATCTGGTATAGTTTACGTTGACCGAATCGAATTCATCC 1999
Sequence_49      GTGAAGACCCTAATTCAACATTATCTGGTATAGTTTACGTTGACCGAATCGAATTCATCC 1996
Sequence_81      GTGAAGACCCTAATTCAACATTATCTGGTATAGTTTACGTTGACCGAATCGAATTCATCC 1996
Sequence_45      GTGAAGACCCTAATTCAACATTATCTGGTATAGTTTACGTTGACCGAATCGAATTCATCC 1999
Sequence_77      GTGAAGACCCTAATTCAACATTATCTGGTATAGTTTACGTTGACCGAATCGAATTCATCC 1999
Sequence_75      GTGAAGACCCTAATTCAACATTATCTGGTATAGTTTACGTTGACCGAATCGAATTCATCC 1996
Sequence_43      GTGAAGACCCTAATTCAACATTATCTGGTATAGTTTACGTTGACCGAATCGAATTCATCC 1996
Sequence_47      GTGAAGACCCTAATTCAACATTATCTGGTATAGTTTACGTTGACCGAATCGAATTCATCC 1999
Sequence_79      GTGAAGACCCTAATTCAACATTATCTGGTATAGTTTACGTTGACCGAATCGAATTCATCC 1999
Sequence_51      GTGAAGACCCTAATTCAACATTATCTGGTATAGTTTACGTTGACCGAATCGAATTCATCC 2005
Sequence_83      GTGAAGACCCTAATTCAACATTATCTGGTATAGTTTACGTTGACCGAATCGAATTCATCC 2005
Sequence_7       GTGAAGACCCTAATTCAACATTATCTGGTATAGTTTACGTTGACCGAATCGAATTCATCC 1993
Sequence_25      GTGAAGACCCTAATTCAACATTATCTGGTATAGTTTACGTTGACCGAATCGAATTCATCC 1993
Sequence_29      GTGAAGACCCTAATTCAACATTATCTGGTATAGTTTACGTTGACCGAATCGAATTCATCC 1993
Sequence_33      GTGAAGACCCTAATTCAACATTATCTGGTATAGTTTACGTTGACCGAATCGAATTCATCC 1993
Sequence_69      GTGAAGACCCTAATTCAACATTATCTGGTATAGTTTACGTTGACCGAATCGAATTCATCC 1993
Sequence_11      GTGAAGACCCTAATTCAACATTATCTGGTATAGTTTACGTTGACCGAATCGAATTCATCC 1981
Sequence_5       GTGAAGACCCTAATTCAACATTATCTGGTATAGTTTACGTTGACCGAATCGAATTCATCC 1981
Sequence_1       GTGAAGACCCTAATTCAACATTATCTGGTATAGTTTACGTTGACCGAATCGAATTCATCC 1981
Sequence_17      GTGAAGACCCTAATTCAACATTATCTGGTATAGTTTACGTTGACCGAATCGAATTCATCC 2711
Sequence_3       GCGGAAGACTTTCTTGGAATTGA--------AGCTTATATAGACCGAATCGAATTTATCC 1993
Sequence_13      GCGGAAGACTTTCTTGGAATTGA--------AGCTTATATAGACCGAATCGAATTTATCC 1993
Sequence_18      GCGGAAGACTTTCTTGGAATTGA--------AGCTTATATAGACCGAATCGAATTTATCC 3246
Cry8Ha1_         ATTCAGATCAATCCGGGAAAAGT---------ATTTATATAGATCGAATCGAATTCATCC 1960
                     *   *        *                ***  * ** *********** ****
```

To Fig. 16AJ

Fig. 16AI

From Fig. 16AI

```
Sequence_71      CAGTAGATGAGACATATGAAGCGGAA---------------------------------- 2028
Sequence_73      CAGTAGATGAGACATATGAAGCGGAA---------------------------------- 2025
Sequence_21      CAGTAGATGAGACATATGAAGCGGAATAA------------------------------- 2022
Sequence_67      CAGTAGATGAGACATATGAAGCGGAATAA------------------------------- 2022
Sequence_61      CAGTAGATGAGACATATGAAGCGGAA---------------------------------- 2019
Sequence_93      CAGTAGATGAGACATATGAAGCGGAA---------------------------------- 2019
Sequence_59      CAGTAGATGAGACATATGAAGCGGAA---------------------------------- 2019
Sequence_91      CAGTAGATGAGACATATGAAGCGGAA---------------------------------- 2019
Sequence_39      CAGTAGATGAGACATATGAAGCGGAA---------------------------------- 2028
Sequence_41      CAGTAGATGAGACATATGAAGCGGAA---------------------------------- 2025
Sequence_49      CAGTAGATGAGACATATGAAGCGGAA---------------------------------- 2022
Sequence_81      CAGTAGATGAGACATATGAAGCGGAA---------------------------------- 2022
Sequence_45      CAGTAGATGAGACATATGAAGCGGAA---------------------------------- 2025
Sequence_77      CAGTAGATGAGACATATGAAGCGGAA---------------------------------- 2025
Sequence_75      CAGTAGATGAGACATATGAAGCGGAA---------------------------------- 2022
Sequence_43      CAGTAGATGAGACATATGAAGCGGAA---------------------------------- 2022
Sequence_47      CAGTAGATGAGACATATGAAGCGGAA---------------------------------- 2025
Sequence_79      CAGTAGATGAGACATATGAAGCGGAA---------------------------------- 2025
Sequence_51      CAGTAGATGAGACATATGAAGCGGAA---------------------------------- 2031
Sequence_83      CAGTAGATGAGACATATGAAGCGGAA---------------------------------- 2031
Sequence_7       CAGTAGATGAGACATATGAAGCGGAATAA------------------------------- 2022
Sequence_25      CAGTAGATGAGACATATGAAGCGGAATAA------------------------------- 2022
Sequence_29      CAGTAGATGAGACATATGAAGCGGAATAA------------------------------- 2022
Sequence_33      CAGTAGATGAGACATATGAAGCGGAATAA------------------------------- 2022
Sequence_69      CAGTAGATGAGACATATGAAGCGGAATAA------------------------------- 2022
Sequence_11      CAGTAGATGAGACATATGAAGCGGAATAA------------------------------- 2010
Sequence_5       CAGTAGATGAGACATATGAAGCGGAACAAGATTTAGAAGCAGCGAAGAAAGCAGTGAATG 2041
Sequence_1       CAGTAGATGAGACATATGAAGCGGAACAAGATTTAGAAGCAGCGAAGAAAGCAGTGAATG 2041
Sequence_17      CAGTAGATGAGACATATGAAGCGGAACAAGATTTAGAAGCAGCGAAGAAAGCAGTGAATG 2771
Sequence_3       CAGTAGATGAGACATATGAAGCGGAACAAGATTTAGAAGCAGCGAAGAAAGCAGTGAATG 2053
Sequence_13      CAGTAGATGAGACATATGAAGCGGAATAA------------------------------- 2022
Sequence_18      CAGTAGATGAGACATATGAAGCGGAACAAGATTTAGAAGCAGCGAAGAAAGCAGTGAATG 3306
Cry8Ha1          CAGTAGATGAGACCTATGAAGCAGAACAAGAT---------------------------- 1992
                 ************* ******** ***
```

Fig. 16AJ

```
Sequence_71    CAAATAATCAAAATGAATATGAAATTATAGATGCGACACCTTCTACTTCTGTATCCAATG 67  (SEQ ID NO:47)
Sequence_73    CAAATAATCAAAATGAATATGAAATTATAGATGCGACACCTTCTACTTCTGTATCCAATG 67  (SEQ ID NO:48)
Sequence_21    CAAATAATCAAAATGAATATGAAATTATAGATGCGACACCTTCTACTTCTGTATCCAATG 67  (SEQ ID NO:32)
Sequence_67    CAAATAATCAAAATGAATATGAAATTATAGATGCGACACCTTCTACTTCTGTATCCAATG 67  (SEQ ID NO:45)
Sequence_61    CAAATAATCAAAATGAATATGAAATTATAGATGCGACACCTTCTACTTCTGTATCCAATG 67  (SEQ ID NO:44)
Sequence_93    CAAATAATCAAAATGAATATGAAATTATAGATGCGACACCTTCTACTTCTGTATCCAATG 67  (SEQ ID NO:55)
Sequence_59    CAAATAATCAAAATGAATATGAAATTATAGATGCGACACCTTCTACTTCTGTATCCAATG 67  (SEQ ID NO:43)
Sequence_91    CAAATAATCAAAATGAATATGAAATTATAGATGCGACACCTTCTACTTCTGTATCCAATG 67  (SEQ ID NO:54)
Sequence_39    CAAATAATCAAAATGAATATGAAATTATAGATGCGACACCTTCTACTTCTGTATCCAATG 67  (SEQ ID NO:36)
Sequence_41    CAAATAATCAAAATGAATATGAAATTATAGATGCGACACCTTCTACTTCTGTATCCAATG 67  (SEQ ID NO:37)
Sequence_49    CAAATAATCAAAATGAATATGAAATTATAGATGCGACACCTTCTACTTCTGTATCCAATG 67  (SEQ ID NO:41)
Sequence_81    CAAATAATCAAAATGAATATGAAATTATAGATGCGACACCTTCTACTTCTGTATCCAATG 67  (SEQ ID NO:52)
Sequence_45    CAAATAATCAAAATGAATATGAAATTATAGATGCGACACCTTCTACTTCTGTATCCAATG 67  (SEQ ID NO:39)
Sequence_77    CAAATAATCAAAATGAATATGAAATTATAGATGCGACACCTTCTACTTCTGTATCCAATG 67  (SEQ ID NO:50)
Sequence_75    CAAATAATCAAAATGAATATGAAATTATAGATGCGACACCTTCTACTTCTGTATCCAATG 67  (SEQ ID NO:49)
Sequence_43    CAAATAATCAAAATGAATATGAAATTATAGATGCGACACCTTCTACTTCTGTATCCAATG 67  (SEQ ID NO:38)
```

To Fig. 17B

Fig. 17A

From Fig. 17A

```
Sequence_47    CAAATAATCAAAATGAATATGAAATTATAGATGCGACACCTTCTACTTCTGTATCCAATG 67   (SEQ ID NO:40)
Sequence_79    CAAATAATCAAAATGAATATGAAATTATAGATGCGACACCTTCTACTTCTGTATCCAATG 67   (SEQ ID NO:51)
Sequence_51    CAAATAATCAAAATGAATATGAAATTATAGATGCGACACCTTCTACTTCTGTATCCAATG 67   (SEQ ID NO:42)
Sequence_83    CAAATAATCAAAATGAATATGAAATTATAGATGCGACACCTTCTACTTCTGTATCCAATG 67   (SEQ ID NO:53)
Sequence_7     CAAATAATCAAAATGAATATGAAATTATAGATGCGACACCTTCTACTTCTGTATCCAATG 67   (SEQ ID NO:27)
Sequence_25    CAAATAATCAAAATGAATATGAAATTATAGATGCGACACCTTCTACTTCTGTATCCAATG 67   (SEQ ID NO:33)
Sequence_29    CAAATAATCAAAATGAATATGAAATTATAGATGCGACACCTTCTACTTCTGTATCCAATG 67   (SEQ ID NO:34)
Sequence_33    CAAATAATCAAAATGAATATGAAATTATAGATGCGACACCTTCTACTTCTGTATCCAATG 67   (SEQ ID NO:35)
Sequence_69    CAAATAATCAAAATGAATATGAAATTATAGATGCGACACCTTCTACTTCTGTATCCAATG 67   (SEQ ID NO:46)
Sequence_11    CAAATAATCAAAATGAATATGAAATTATAGATGCGACACCTTCTACTTCTGTATCCAATG 67   (SEQ ID NO:28)
Sequence_1     CAAATAATCAAAATGAATATGAAATTATAGATGCGACACCTTCTACTTCTGTATCCAATG 67   (SEQ ID NO:24)
Sequence_17    CAAATAATCAAAATGAATATGAAATTATAGATGCGACACCTTCTACTTCTGTATCCAATG 797  (SEQ ID NO:30)
Sequence_3     CAAATAATCAAAATGAATATGAAATTATAGATGCGACACCTTCTACTTCTGTATCCAATG 67   (SEQ ID NO:25)
Sequence_13    CAAATAATCAAAATGAATATGAAATTATAGATGCGACACCTTCTACTTCTGTATCCAATG 67   (SEQ ID NO:29)
Sequence_18    CAAATAATCAAAATGAATATGAAATTATAGATGCGACACCTTCTACTTCTGTATCCAATG 1320 (SEQ ID NO:31)
Cry8Ka1        CAAATAATCTAAATGAATATGAAATTATAGATGCGACACCTTCTACATCTGTATCTAATG 67   (SEQ ID NO:22)
               ********* ************************************ ******** ****
```

To Fig. 17C

Fig. 17B

From Fig. 17B

```
Sequence_71      ATTCTAACAGATACCCTTTTGCGAATGAGCCAACAAATGCGCTACAAAATATGGATTATA 127
Sequence_73      ATTCTAACAGATACCCTTTTGCGAATGAGCCAACAAATGCGCTACAAAATATGGATTATA 127
Sequence_21      ATTCTAACAGATACCCTTTTGCGAATGAGCCAACAAATGCGCTACAAAATATGGATTATA 127
Sequence_67      ATTCTAACAGATACCCTTTTGCGAATGAGCCAACAAATGCGCTACAAAATATGGATTATA 127
Sequence_61      ATTCTAACAGATACCCTTTTGCGAATGAGCCAACAAATGCGCTACAAAATATGGATTATA 127
Sequence_93      ATTCTAACAGATACCCTTTTGCGAATGAGCCAACAAATGCGCTACAAAATATGGATTATA 127
Sequence_59      ATTCTAACAGATACCCTTTTGCGAATGAGCCAACAAATGCGCTACAAAATATGGATTATA 127
Sequence_91      ATTCTAACAGATACCCTTTTGCGAATGAGCCAACAAATGCGCTACAAAATATGGATTATA 127
Sequence_39      ATTCTAACAGATACCCTTTTGCGAATGAGCCAACAAATGCGCTACAAAATATGGATTATA 127
Sequence_41      ATTCTAACAGATACCCTTTTGCGAATGAGCCAACAAATGCGCTACAAAATATGGATTATA 127
Sequence_49      ATTCTAACAGATACCCTTTTGCGAATGAGCCAACAAATGCGCTACAAAATATGGATTATA 127
Sequence_81      ATTCTAACAGATACCCTTTTGCGAATGAGCCAACAAATGCGCTACAAAATATGGATTATA 127
Sequence_45      ATTCTAACAGATACCCTTTTGCGAATGAGCCAACAAATGCGCTACAAAATATGGATTATA 127
Sequence_77      ATTCTAACAGATACCCTTTTGCGAATGAGCCAACAAATGCGCTACAAAATATGGATTATA 127
Sequence_75      ATTCTAACAGATACCCTTTTGCGAATGAGCCAACAAATGCGCTACAAAATATGGATTATA 127
Sequence_43      ATTCTAACAGATACCCTTTTGCGAATGAGCCAACAAATGCGCTACAAAATATGGATTATA 127
Sequence_47      ATTCTAACAGATACCCTTTTGCGAATGAGCCAACAAATGCGCTACAAAATATGGATTATA 127
Sequence_79      ATTCTAACAGATACCCTTTTGCGAATGAGCCAACAAATGCGCTACAAAATATGGATTATA 127
Sequence_51      ATTCTAACAGATACCCTTTTGCGAATGAGCCAACAAATGCGCTACAAAATATGGATTATA 127
Sequence_83      ATTCTAACAGATACCCTTTTGCGAATGAGCCAACAAATGCGCTACAAAATATGGATTATA 127
Sequence_7       ATTCTAACAGATACCCTTTTGCGAATGAGCCAACAAATGCGCTACAAAATATGGATTATA 127
Sequence_25      ATTCTAACAGATACCCTTTTGCGAATGAGCCAACAAATGCGCTACAAAATATGGATTATA 127
Sequence_29      ATTCTAACAGATACCCTTTTGCGAATGAGCCAACAAATGCGCTACAAAATATGGATTATA 127
Sequence_33      ATTCTAACAGATACCCTTTTGCGAATGAGCCAACAAATGCGCTACAAAATATGGATTATA 127
Sequence_69      ATTCTAACAGATACCCTTTTGCGAATGAGCCAACAAATGCGCTACAAAATATGGATTATA 127
Sequence_11      ATTCTAACAGATACCCTTTTGCGAATGAGCCAACAAATGCGCTACAAAATATGGATTATA 127
Sequence_1       ATTCTAACAGATACCCTTTTGCGAATGAGCCAACAAATGCGCTACAAAATATGGATTATA 127
Sequence_17      ATTCTAACAGATACCCTTTTGCGAATGAGCCAACAAATGCGCTACAAAATATGGATTATA 857
Sequence_3       ATTCTAACAGATACCCTTTTGCGAATGAGCCAACAAATGCGCTACAAAATATGGATTATA 127
Sequence_13      ATTCTAACAGATACCCTTTTGCGAATGAGCCAACAAATGCGCTACAAAATATGGATTATA 127
Sequence_18      ATTCTAACAGATACCCTTTTGCGAATGAGCCAACAAATGCGCTACAAAATATGGATTATA 1380
Cry8Ka1          ATTCTACCAGATACCCTTATGCGAATGAGCCCACAAATGCGTTACAAAATATGAATTATA 127
                 ****** *********** ************ ********* *********** ******
```

To Fig. 17D

Fig. 17C

From Fig. 17C

```
Sequence_71     AAGATTATTTAAAAATGTCTGCGGGAAATGCTAGTGAATACCCTGGTTCACCTGAAGTAC 187
Sequence_73     AAGATTATTTAAAAATGTCTGCGGGAAATGCTAGTGAATACCCTGGTTCACCTGAAGTAC 187
Sequence_21     AAGATTATTTAAAAATGTCTGCGGGAAATGCTAGTGAATACCCTGGTTCACCTGAAGTAC 187
Sequence_67     AAGATTATTTAAAAATGTCTGCGGGAAATGCTAGTGAATACCCTGGTTCACCTGAAGTAC 187
Sequence_61     AAGATTATTTAAAAATGTCTGCGGGAAATGCTAGTGAATACCCTGGTTCACCTGAAGTAC 187
Sequence_93     AAGATTATTTAAAAATGTCTGCGGGAAATGCTAGTGAATACCCTGGTTCACCTGAAGTAC 187
Sequence_59     AAGATTATTTAAAAATGTCTGCGGGAAATGCTAGTGAATACCCTGGTTCACCTGAAGTAC 187
Sequence_91     AAGATTATTTAAAAATGTCTGCGGGAAATGCTAGTGAATACCCTGGTTCACCTGAAGTAC 187
Sequence_39     AAGATTATTTAAAAATGTCTGCGGGAAATGCTAGTGAATACCCTGGTTCACCTGAAGTAC 187
Sequence_41     AAGATTATTTAAAAATGTCTGCGGGAAATGCTAGTGAATACCCTGGTTCACCTGAAGTAC 187
Sequence_49     AAGATTATTTAAAAATGTCTGCGGGAAATGCTAGTGAATACCCTGGTTCACCTGAAGTAC 187
Sequence_81     AAGATTATTTAAAAATGTCTGCGGGAAATGCTAGTGAATACCCTGGTTCACCTGAAGTAC 187
Sequence_45     AAGATTATTTAAAAATGTCTGCGGGAAATGCTAGTGAATACCCTGGTTCACCTGAAGTAC 187
Sequence_77     AAGATTATTTAAAAATGTCTGCGGGAAATGCTAGTGAATACCCTGGTTCACCTGAAGTAC 187
Sequence_75     AAGATTATTTAAAAATGTCTGCGGGAAATGCTAGTGAATACCCTGGTTCACCTGAAGTAC 187
Sequence_43     AAGATTATTTAAAAATGTCTGCGGGAAATGCTAGTGAATACCCTGGTTCACCTGAAGTAC 187
Sequence_47     AAGATTATTTAAAAATGTCTGCGGGAAATGCTAGTGAATACCCTGGTTCACCTGAAGTAC 187
Sequence_79     AAGATTATTTAAAAATGTCTGCGGGAAATGCTAGTGAATACCCTGGTTCACCTGAAGTAC 187
Sequence_51     AAGATTATTTAAAAATGTCTGCGGGAAATGCTAGTGAATACCCTGGTTCACCTGAAGTAC 187
Sequence_83     AAGATTATTTAAAAATGTCTGCGGGAAATGCTAGTGAATACCCTGGTTCACCTGAAGTAC 187
Sequence_7      AAGATTATTTAAAAATGTCTGCGGGAAATGCTAGTGAATACCCTGGTTCACCTGAAGTAC 187
Sequence_25     AAGATTATTTAAAAATGTCTGCGGGAAATGCTAGTGAATACCCTGGTTCACCTGAAGTAC 187
Sequence_29     AAGATTATTTAAAAATGTCTGCGGGAAATGCTAGTGAATACCCTGGTTCACCTGAAGTAC 187
Sequence_33     AAGATTATTTAAAAATGTCTGCGGGAAATGCTAGTGAATACCCTGGTTCACCTGAAGTAC 187
Sequence_69     AAGATTATTTAAAAATGTCTGCGGGAAATGCTAGTGAATACCCTGGTTCACCTGAAGTAC 187
Sequence_11     AAGATTATTTAAAAATGTCTGCGGGAAATGCTAGTGAATACCCTGGTTCACCTGAAGTAC 187
Sequence_1      AAGATTATTTAAAAATGTCTGCGGGAAATGCTAGTGAATACCCTGGTTCACCTGAAGTAC 187
Sequence_17     AAGATTATTTAAAAATGTCTGCGGGAAATGCTAGTGAATACCCTGGTTCACCTGAAGTAC 917
Sequence_3      AAGATTATTTAAAAATGTCTGCGGGAAATGCTAGTGAATACCCTGGTTCACCTGAAGTAC 187
Sequence_13     AAGATTATTTAAAAATGTCTGCGGGAAATGCTAGTGAATACCCTGGTTCACCTGAAGTAC 187
Sequence_18     AAGATTATTTAAAAATGTCTGCGGGAAATGCTAGTGAATACCCTGGTTCACCTGAAGTAC 1440
Cry8Ka1         AGGATTATTTAAGAATGTCTGAAGGTTACGATAATAAATATTTTGCAAATCCTGAAGTGT 187
                * ********** ********  **  * * ** * ****   **     ******* 
```

To Fig. 17E

Fig. 17D

From Fig. 17D

```
Sequence_71   TTGTTAGCGGACAAGATGCAGCTAAGGCCGCAATTGATATAGTAGGTAAATTACTATCAG  247
Sequence_73   TTGTTAGCGGACAAGATGCAGCTAAGGCCGCAATTGATATAGTAGGTAAATTACTATCAG  247
Sequence_21   TTGTTAGCGGACAAGATGCAGCTAAGGCCGCAATTGATATAGTAGGTAAATTACTATCAG  247
Sequence_67   TTGTTAGCGGACAAGATGCAGCTAAGGCCGCAATTGATATAGTAGGTAAATTACTATCAG  247
Sequence_61   TTGTTAGCGGACAAGATGCAGCTAAGGCCGCAATTGATATAGTAGGTAAATTACTATCAG  247
Sequence_93   TTGTTAGCGGACAAGATGCAGCTAAGGCCGCAATTGATATAGTAGGTAAATTACTATCAG  247
Sequence_59   TTGTTAGCGGACAAGATGCAGCTAAGGCCGCAATTGATATAGTAGGTAAATTACTATCAG  247
Sequence_91   TTGTTAGCGGACAAGATGCAGCTAAGGCCGCAATTGATATAGTAGGTAAATTACTATCAG  247
Sequence_39   TTGTTAGCGGACAAGATGCAGCTAAGGCCGCAATTGATATAGTAGGTAAATTACTATCAG  247
Sequence_41   TTGTTAGCGGACAAGATGCAGCTAAGGCCGCAATTGATATAGTAGGTAAATTACTATCAG  247
Sequence_49   TTGTTAGCGGACAAGATGCAGCTAAGGCCGCAATTGATATAGTAGGTAAATTACTATCAG  247
Sequence_81   TTGTTAGCGGACAAGATGCAGCTAAGGCCGCAATTGATATAGTAGGTAAATTACTATCAG  247
Sequence_45   TTGTTAGCGGACAAGATGCAGCTAAGGCCGCAATTGATATAGTAGGTAAATTACTATCAG  247
Sequence_77   TTGTTAGCGGACAAGATGCAGCTAAGGCCGCAATTGATATAGTAGGTAAATTACTATCAG  247
Sequence_75   TTGTTAGCGGACAAGATGCAGCTAAGGCCGCAATTGATATAGTAGGTAAATTACTATCAG  247
Sequence_43   TTGTTAGCGGACAAGATGCAGCTAAGGCCGCAATTGATATAGTAGGTAAATTACTATCAG  247
Sequence_47   TTGTTAGCGGACAAGATGCAGCTAAGGCCGCAATTGATATAGTAGGTAAATTACTATCAG  247
Sequence_79   TTGTTAGCGGACAAGATGCAGCTAAGGCCGCAATTGATATAGTAGGTAAATTACTATCAG  247
Sequence_51   TTGTTAGCGGACAAGATGCAGCTAAGGCCGCAATTGATATAGTAGGTAAATTACTATCAG  247
Sequence_83   TTGTTAGCGGACAAGATGCAGCTAAGGCCGCAATTGATATAGTAGGTAAATTACTATCAG  247
Sequence_7    TTGTTAGCGGACAAGATGCAGCTAAGGCCGCAATTGATATAGTAGGTAAATTACTATCAG  247
Sequence_25   TTGTTAGCGGACAAGATGCAGCTAAGGCCGCAATTGATATAGTAGGTAAATTACTATCAG  247
Sequence_29   TTGTTAGCGGACAAGATGCAGCTAAGGCCGCAATTGATATAGTAGGTAAATTACTATCAG  247
Sequence_33   TTGTTAGCGGACAAGATGCAGCTAAGGCCGCAATTGATATAGTAGGTAAATTACTATCAG  247
Sequence_69   TTGTTAGCGGACAAGATGCAGCTAAGGCCGCAATTGATATAGTAGGTAAATTACTATCAG  247
Sequence_11   TTGTTAGCGGACAAGATGCAGCTAAGGCCGCAATTGATATAGTAGGTAAATTACTATCAG  247
Sequence_1    TTGTTAGCGGACAAGATGCAGCTAAGGCCGCAATTGATATAGTAGGTAAATTACTATCAG  247
Sequence_17   TTGTTAGCGGACAAGATGCAGCTAAGGCCGCAATTGATATAGTAGGTAAATTACTATCAG  977
Sequence_3    TTGTTAGCGGACAAGATGCAGCTAAGGCCGCAATTGATATAGTAGGTAAATTACTATCAG  247
Sequence_13   TTGTTAGCGGACAAGATGCAGCTAAGGCCGCAATTGATATAGTAGGTAAATTACTATCAG  247
Sequence_18   TTGTTAGCGGACAAGATGCAGCTAAGGCCGCAATTGATATAGTAGGTAAATTACTATCAG  1500
Cry8Ka1       TTGCT---GCACCAGGTGGGATTACAACTGGAATTACTATAGTTACTAAATTACTGGGGT  244
              *** *   * ** ** **    **   * * ***  *****    ********
```

To Fig. 17F

Fig. 17E

From Fig. 17E

```
Sequence_71       GTTTAGGGGTCCCATTTGTTGGGCCGATAGTGAGTCTTTATACTCAACTTATTGATATTC 307
Sequence_73       GTTTAGGGGTCCCATTTGTTGGGCCGATAGTGAGTCTTTATACTCAACTTATTGATATTC 307
Sequence_21       GTTTAGGGGTCCCATTTGTTGGGCCGATAGTGAGTCTTTATACTCAACTTATTGATATTC 307
Sequence_67       GTTTAGGGGTCCCATTTGTTGGGCCGATAGTGAGTCTTTATACTCAACTTATTGATATTC 307
Sequence_61       GTTTAGGGGTCCCATTTGTTGGGCCGATAGTGAGTCTTTATACTCAACTTATTGATATTC 307
Sequence_93       GTTTAGGGGTCCCATTTGTTGGGCCGATAGTGAGTCTTTATACTCAACTTATTGATATTC 307
Sequence_59       GTTTAGGGGTCCCATTTGTTGGGCCGATAGTGAGTCTTTATACTCAACTTATTGATATTC 307
Sequence_91       GTTTAGGGGTCCCATTTGTTGGGCCGATAGTGAGTCTTTATACTCAACTTATTGATATTC 307
Sequence_39       GTTTAGGGGTCCCATTTGTTGGGCCGATAGTGAGTCTTTATACTCAACTTATTGATATTC 307
Sequence_41       GTTTAGGGGTCCCATTTGTTGGGCCGATAGTGAGTCTTTATACTCAACTTATTGATATTC 307
Sequence_49       GTTTAGGGGTCCCATTTGTTGGGCCGATAGTGAGTCTTTATACTCAACTTATTGATATTC 307
Sequence_81       GTTTAGGGGTCCCATTTGTTGGGCCGATAGTGAGTCTTTATACTCAACTTATTGATATTC 307
Sequence_45       GTTTAGGGGTCCCATTTGTTGGGCCGATAGTGAGTCTTTATACTCAACTTATTGATATTC 307
Sequence_77       GTTTAGGGGTCCCATTTGTTGGGCCGATAGTGAGTCTTTATACTCAACTTATTGATATTC 307
Sequence_75       GTTTAGGGGTCCCATTTGTTGGGCCGATAGTGAGTCTTTATACTCAACTTATTGATATTC 307
Sequence_43       GTTTAGGGGTCCCATTTGTTGGGCCGATAGTGAGTCTTTATACTCAACTTATTGATATTC 307
Sequence_47       GTTTAGGGGTCCCATTTGTTGGGCCGATAGTGAGTCTTTATACTCAACTTATTGATATTC 307
Sequence_79       GTTTAGGGGTCCCATTTGTTGGGCCGATAGTGAGTCTTTATACTCAACTTATTGATATTC 307
Sequence_51       GTTTAGGGGTCCCATTTGTTGGGCCGATAGTGAGTCTTTATACTCAACTTATTGATATTC 307
Sequence_83       GTTTAGGGGTCCCATTTGTTGGGCCGATAGTGAGTCTTTATACTCAACTTATTGATATTC 307
Sequence_7        GTTTAGGGGTCCCATTTGTTGGGCCGATAGTGAGTCTTTATACTCAACTTATTGATATTC 307
Sequence_25       GTTTAGGGGTCCCATTTGTTGGGCCGATAGTGAGTCTTTATACTCAACTTATTGATATTC 307
Sequence_29       GTTTAGGGGTCCCATTTGTTGGGCCGATAGTGAGTCTTTATACTCAACTTATTGATATTC 307
Sequence_33       GTTTAGGGGTCCCATTTGTTGGGCCGATAGTGAGTCTTTATACTCAACTTATTGATATTC 307
Sequence_69       GTTTAGGGGTCCCATTTGTTGGGCCGATAGTGAGTCTTTATACTCAACTTATTGATATTC 307
Sequence_11       GTTTAGGGGTCCCATTTGTTGGGCCGATAGTGAGTCTTTATACTCAACTTATTGATATTC 307
Sequence_1        GTTTAGGGGTCCCATTTGTTGGGCCGATAGTGAGTCTTTATACTCAACTTATTGATATTC 307
Sequence_17       GTTTAGGGGTCCCATTTGTTGGGCCGATAGTGAGTCTTTATACTCAACTTATTGATATTC 1037
Sequence_3        GTTTAGGGGTCCCATTTGTTGGGCCGATAGTGAGTCTTTATACTCAACTTATTGATATTC 307
Sequence_13       GTTTAGGGGTCCCATTTGTTGGGCCGATAGTGAGTCTTTATACTCAACTTATTGATATTC 307
Sequence_18       GTTTAGGGGTCCCATTTGTTGGGCCGATAGTGAGTCTTTATACTCAACTTATTGATATTC 1560
Cry8Ka1           GGTTAGGACTTCCATTTGCTGGGGAAACAGGGATGGCTCTTAATTTCATTCTAGGTCTAT 304
                  * *****  * ******* ****   * ** **    *  ** *    ** * * * *
```

To Fig. 17G

Fig. 17F

From Fig. 17F

```
Sequence_71     TGTGGCCTTCAGGGGAAAAGAGTCAATGGGAAATTTTTATGGAACAAGTAGAAGAACTCA 367
Sequence_73     TGTGGCCTTCAGGGGAAAAGAGTCAATGGGAAATTTTTATGGAACAAGTAGAAGAACTCA 367
Sequence_21     TGTGGCCTTCAGGGGAAAAGAGTCAATGGGAAATTTTTATGGAACAAGTAGAAGAACTCA 367
Sequence_67     TGTGGCCTTCAGGGGAAAAGAGTCAATGGGAAATTTTTATGGAACAAGTAGAAGAACTCA 367
Sequence_61     TGTGGCCTTCAGGGGAAAAGAGTCAATGGGAAATTTTTATGGAACAAGTAGAAGAACTCA 367
Sequence_93     TGTGGCCTTCAGGGGAAAAGAGTCAATGGGAAATTTTTATGGAACAAGTAGAAGAACTCA 367
Sequence_59     TGTGGCCTTCAGGGGAAAAGAGTCAATGGGAAATTTTTATGGAACAAGTAGAAGAACTCA 367
Sequence_91     TGTGGCCTTCAGGGGAAAAGAGTCAATGGGAAATTTTTATGGAACAAGTAGAAGAACTCA 367
Sequence_39     TGTGGCCTTCAGGGGAAAAGAGTCAATGGGAAATTTTTATGGAACAAGTAGAAGAACTCA 367
Sequence_41     TGTGGCCTTCAGGGGAAAAGAGTCAATGGGAAATTTTTATGGAACAAGTAGAAGAACTCA 367
Sequence_49     TGTGGCCTTCAGGGGAAAAGAGTCAATGGGAAATTTTTATGGAACAAGTAGAAGAACTCA 367
Sequence_81     TGTGGCCTTCAGGGGAAAAGAGTCAATGGGAAATTTTTATGGAACAAGTAGAAGAACTCA 367
Sequence_45     TGTGGCCTTCAGGGGAAAAGAGTCAATGGGAAATTTTTATGGAACAAGTAGAAGAACTCA 367
Sequence_77     TGTGGCCTTCAGGGGAAAAGAGTCAATGGGAAATTTTTATGGAACAAGTAGAAGAACTCA 367
Sequence_75     TGTGGCCTTCAGGGGAAAAGAGTCAATGGGAAATTTTTATGGAACAAGTAGAAGAACTCA 367
Sequence_43     TGTGGCCTTCAGGGGAAAAGAGTCAATGGGAAATTTTTATGGAACAAGTAGAAGAACTCA 367
Sequence_47     TGTGGCCTTCAGGGGAAAAGAGTCAATGGGAAATTTTTATGGAACAAGTAGAAGAACTCA 367
Sequence_79     TGTGGCCTTCAGGGGAAAAGAGTCAATGGGAAATTTTTATGGAACAAGTAGAAGAACTCA 367
Sequence_51     TGTGGCCTTCAGGGGAAAAGAGTCAATGGGAAATTTTTATGGAACAAGTAGAAGAACTCA 367
Sequence_83     TGTGGCCTTCAGGGGAAAAGAGTCAATGGGAAATTTTTATGGAACAAGTAGAAGAACTCA 367
Sequence_7      TGTGGCCTTCAGGGGAAAAGAGTCAATGGGAAATTTTTATGGAACAAGTAGAAGAACTCA 367
Sequence_25     TGTGGCCTTCAGGGGAAAAGAGTCAATGGGAAATTTTTATGGAACAAGTAGAAGAACTCA 367
Sequence_29     TGTGGCCTTCAGGGGAAAAGAGTCAATGGGAAATTTTTATGGAACAAGTAGAAGAACTCA 367
Sequence_33     TGTGGCCTTCAGGGGAAAAGAGTCAATGGGAAATTTTTATGGAACAAGTAGAAGAACTCA 367
Sequence_69     TGTGGCCTTCAGGGGAAAAGAGTCAATGGGAAATTTTTATGGAACAAGTAGAAGAACTCA 367
Sequence_11     TGTGGCCTTCAGGGGAAAAGAGTCAATGGGAAATTTTTATGGAACAAGTAGAAGAACTCA 367
Sequence_1      TGTGGCCTTCAGGGGAAAAGAGTCAATGGGAAATTTTTATGGAACAAGTAGAAGAACTCA 367
Sequence_17     TGTGGCCTTCAGGGGAAAAGAGTCAATGGGAAATTTTTATGGAACAAGTAGAAGAACTCA 1097
Sequence_3      TGTGGCCTTCAGGGCAAAAGAGTCAATGGGAGATTTTTATGGAACAAGTAGAAGAACTCA 367
Sequence_13     TGTGGCCTTCAGGGCAAAAGAGTCAATGGGAGATTTTTATGGAACAAGTAGAAGAACTCA 367
Sequence_18     TGTGGCCTTCAGGGCAAAAGAGTCAATGGGAGATTTTTATGGAACAAGTAGAAGAACTCA 1620
Cry8Ka1         TATGGCCAACA---TCAGGAAACCCGTGGGCTGAACTAATGATATTGGTAGAAGAACTCA 361
                * *****  **     *   *  *  ****      * ***  *   *************
```

To Fig. 17H

Fig. 17G

From Fig. 17G

```
Sequence_71     TTAATCAAAAAATAGCAGAATATGCAAGGAATAAAGCGCTTTCGGAATTAGAAGGATTAG 427
Sequence_73     TTAATCAAAAAATAGCAGAATATGCAAGGAATAAAGCGCTTTCGGAATTAGAAGGATTAG 427
Sequence_21     TTAATCAAAAAATAGCAGAATATGCAAGGAATAAAGCGCTTTCGGAATTAGAAGGATTAG 427
Sequence_67     TTAATCAAAAAATAGCAGAATATGCAAGGAATAAAGCGCTTTCGGAATTAGAAGGATTAG 427
Sequence_61     TTAATCAAAAAATAGCAGAATATGCAAGGAATAAAGCGCTTTCGGAATTAGAAGGATTAG 427
Sequence_93     TTAATCAAAAAATAGCAGAATATGCAAGGAATAAAGCGCTTTCGGAATTAGAAGGATTAG 427
Sequence_59     TTAATCAAAAAATAGCAGAATATGCAAGGAATAAAGCGCTTTCGGAATTAGAAGGATTAG 427
Sequence_91     TTAATCAAAAAATAGCAGAATATGCAAGGAATAAAGCGCTTTCGGAATTAGAAGGATTAG 427
Sequence_39     TTAATCAAAAAATAGCAGAATATGCAAGGAATAAAGCGCTTTCGGAATTAGAAGGATTAG 427
Sequence_41     TTAATCAAAAAATAGCAGAATATGCAAGGAATAAAGCGCTTTCGGAATTAGAAGGATTAG 427
Sequence_49     TTAATCAAAAAATAGCAGAATATGCAAGGAATAAAGCGCTTTCGGAATTAGAAGGATTAG 427
Sequence_81     TTAATCAAAAAATAGCAGAATATGCAAGGAATAAAGCGCTTTCGGAATTAGAAGGATTAG 427
Sequence_45     TTAATCAAAAAATAGCAGAATATGCAAGGAATAAAGCGCTTTCGGAATTAGAAGGATTAG 427
Sequence_77     TTAATCAAAAAATAGCAGAATATGCAAGGAATAAAGCGCTTTCGGAATTAGAAGGATTAG 427
Sequence_75     TTAATCAAAAAATAGCAGAATATGCAAGGAATAAAGCGCTTTCGGAATTAGAAGGATTAG 427
Sequence_43     TTAATCAAAAAATAGCAGAATATGCAAGGAATAAAGCGCTTTCGGAATTAGAAGGATTAG 427
Sequence_47     TTAATCAAAAAATAGCAGAATATGCAAGGAATAAAGCGCTTTCGGAATTAGAAGGATTAG 427
Sequence_79     TTAATCAAAAAATAGCAGAATATGCAAGGAATAAAGCGCTTTCGGAATTAGAAGGATTAG 427
Sequence_51     TTAATCAAAAAATAGCAGAATATGCAAGGAATAAAGCGCTTTCGGAATTAGAAGGATTAG 427
Sequence_83     TTAATCAAAAAATAGCAGAATATGCAAGGAATAAAGCGCTTTCGGAATTAGAAGGATTAG 427
Sequence_7      TTAATCAAAAAATAGCAGAATATGCAAGGAATAAAGCGCTTTCGGAATTAGAAGGATTAG 427
Sequence_25     TTAATCAAAAAATAGCAGAATATGCAAGGAATAAAGCGCTTTCGGAATTAGAAGGATTAG 427
Sequence_29     TTAATCAAAAAATAGCAGAATATGCAAGGAATAAAGCGCTTTCGGAATTAGAAGGATTAG 427
Sequence_33     TTAATCAAAAAATAGCAGAATATGCAAGGAATAAAGCGCTTTCGGAATTAGAAGGATTAG 427
Sequence_69     TTAATCAAAAAATAGCAGAATATGCAAGGAATAAAGCGCTTTCGGAATTAGAAGGATTAG 427
Sequence_11     TTAATCAAAAAATAGCAGAATATGCAAGGAATAAAGCGCTTTCGGAATTAGAAGGATTAG 427
Sequence_1      TTAATCAAAAAATAGCAGAATATGCAAGGAATAAAGCGCTTTCGGAATTAGAAGGATTAG 427
Sequence_17     TTAATCAAAAAATAGCAGAATATGCAAGGAATAAAGCGCTTTCGGAATTAGAAGGATTAG 1157
Sequence_3      TAAATCAAAAAATAGCAGAATATGCAAGGAATAAAGCGCTTTCGGAATTAGAAGGATTAG 427
Sequence_13     TAAATCAAAAAATAGCAGAATATGCAAGGAATAAAGCGCTTTCGGAATTAGAAGGATTAG 427
Sequence_18     TAAATCAAAAAATAGCAGAATATGCAAGGAATAAAGCGCTTTCGGAATTAGAAGGATTAG 1680
Cry8Ka1         TAAATCAAAAAATAGAAGAGACTGTAAGAAACAAAGCACTAGCGGATTTGGGCAATTCAG 421
                * ************* ***   ** *** ** ***** **  **** ** *     * **
```

To Fig. 17I

Fig. 17H

From Fig. 17H

```
Sequence_71    GTAATAATTACCAATTATATCTAACTGCGCTTGAAGAATGGGAAGAAAATCCATTTCGAA 487
Sequence_73    GTAATAATTACCAATTATATCTAACTGCGCTTGAAGAATGGGAAGAAAATCCATTTCGAA 487
Sequence_21    GTAATAATTACCAATTATATCTAACTGCGCTTGAAGAATGGGAAGAAAATCCATTTCGA- 486
Sequence_67    GTAATAATTACCAATTATATCTAACTGCGCTTGAAGAATGGGAAGAAAATCCATTTCGA- 486
Sequence_61    GTAATAATTACCAATTATATCTAACTGCGCTTGAAGAATGGGAAGAAAATCCATTTCGA- 486
Sequence_93    GTAATAATTACCAATTATATCTAACTGCGCTTGAAGAATGGGAAGAAAATCCATTTCGA- 486
Sequence_59    GTAATAATTACCAATTATATCTAACTGCGCTTGAAGAATGGGAAGAAAATCCATTTCGA- 486
Sequence_91    GTAATAATTACCAATTATATCTAACTGCGCTTGAAGAATGGGAAGAAAATCCATTTCGA- 486
Sequence_39    GTAATAATTACCAATTATATCTAACTGCGCTTGAAGAATGGGAAGAAAATCCATTTCGAA 487
Sequence_41    GTAATAATTACCAATTATATCTAACTGCGCTTGAAGAATGGGAAGAAAATCCATTTCGAA 487
Sequence_49    GTAATAATTACCAATTATATCTAACTGCGCTTGAAGAATGGGAAGAAAATCCAAATGGTT 487
Sequence_81    GTAATAATTACCAATTATATCTAACTGCGCTTGAAGAATGGGAAGAAAATCCAAATGGTT 487
Sequence_45    GTAATAATTACCAATTATATCTAACTGCGCTTGAAGAATGGGAAGAAAATCCAAATGGTT 487
Sequence_77    GTAATAATTACCAATTATATCTAACTGCGCTTGAAGAATGGGAAGAAAATCCAAATGGTT 487
Sequence_75    GTAATAATTACCAATTATATCTAACTGCGCTTGAAGAATGGGAAGAAAATCCAAATGGTT 487
Sequence_43    GTAATAATTACCAATTATATCTAACTGCGCTTGAAGAATGGGAAGAAAATCCAAATGGTT 487
Sequence_47    GTAATAATTACCAATTATATCTAACTGCGCTTGAAGAATGGGAAGAAAATCCATTTCGAA 487
Sequence_79    GTAATAATTACCAATTATATCTAACTGCGCTTGAAGAATGGGAAGAAAATCCATTTCGAA 487
Sequence_51    GTAATAATTACCAATTATATCTAACTGCGCTTGAAGAATGGGAAGAAAATCCATTTCGAA 487
Sequence_83    GTAATAATTACCAATTATATCTAACTGCGCTTGAAGAATGGGAAGAAAATCCATTTCGAA 487
Sequence_7     GTAATAATTACCAATTATATCTAACTGCGCTTGAAGAATGGGAAGAAAATCCAAATGGT- 486
Sequence_25    GTAATAATTACCAATTATATCTAACTGCGCTTGAAGAATGGGAAGAAAATCCAAATGGT- 486
Sequence_29    GTAATAATTACCAATTATATCTAACTGCGCTTGAAGAATGGGAAGAAAATCCAAATGGT- 486
Sequence_33    GTAATAATTACCAATTATATCTAACTGCGCTTGAAGAATGGGAAGAAAATCCAAATGGT- 486
Sequence_69    GTAATAATTACCAATTATATCTAACTGCGCTTGAAGAATGGGAAGAAAATCCAAATGGT- 486
Sequence_11    GTAATAATTACCAATTATATCTAACTGCGCTTGAAGAATGGGAAGAAAATCCAAATGGT- 486
Sequence_1     GTAATAATTACCAATTATATCTAACTGCGCTTGAAGAATGGGAAGAAAATCCAAATGGT- 486
Sequence_17    GTAATAATTACCAATTATATCTAACTGCGCTTGAAGAATGGGAAGAAAATCCAAATGGT- 1216
Sequence_3     GTAATAATTACCAATTATATCTAACTGCGCTTGAAGAATGGAAAGAAAATCCAAATGGT- 486
Sequence_13    GTAATAATTACCAATTATATCTAACTGCGCTTGAAGAATGGAAAGAAAATCCAAATGGT- 486
Sequence_18    GTAATAATTACCAATTATATCTAACTGCGCTTGAAGAATGGAAAGAAAATCCAAATGGT- 1739
Cry8Ka1        GTAGAGCCTTACGATCCTATTTAAACGCATTTGAAGATTGGCAAAAAAACCCTAATATCT 481
               ***     *  * **  *** ***  **  ******* *** ** **** **   *
```

To Fig. 17J

Fig. 17I

From Fig. 17I

```
Sequence_71     GTCGAGGTTTTCGAAGTCGAGGTCCA---GCCTTACGAGAT-GTGCGAAATCGATTTGAA 543
Sequence_73     GTCGAGGTTTTCGAAGTCGAGGT------GCCTTACGAGAT-GTGCGAAATCGATTTGAA 540
Sequence_21     --CGAGGTTTTCGA---CGAGGT------GCCTTACGAGAT-GTGCGAAATCGATTTGAA 534
Sequence_67     --CGAGGTTTTCGA---CGAGGT------GCCTTACGAGAT-GTGCGAAATCGATTTGAA 534
Sequence_61     --CGAGGTTTTCGA---CGAGGT------GCCTTACGAGAT-GTGCGAAATCGATTTGAA 534
Sequence_93     --CGAGGTTTTCGA---CGAGGT------GCCTTACGAGAT-GTGCGAAATCGATTTGAA 534
Sequence_59     --CGAGGTTTTCGA---CGAGGT------GCCTTACGAGAT-GTGCGAAATCGATTTGAA 534
Sequence_91     --CGAGGTTTTCGA---CGAGGT------GCCTTACGAGAT-GTGCGAAATCGATTTGAA 534
Sequence_39     GTCGAGGTTTTCGAAGTCGAGGTCCA---GCCTTACGAGAT-GTGCGAAATCGATTTGAA 543
Sequence_41     GTCGAGGTTTTCGAAGTCGAGGT------GCCTTACGAGAT-GTGCGAAATCGATTTGAA 540
Sequence_49     CCCGG---TTTCGAAGTCGA---CAA---GCCTTACGAGAT-GTGCGAAATCGATTTGAA 537
Sequence_81     CCCGG---TTTCGAAGTCGA---CAA---GCCTTACGAGAT-GTGCGAAATCGATTTGAA 537
Sequence_45     CCCGG---TTTCGAAGTCGAGGTCCA---GCCTTACGAGAT-GTGCGAAATCGATTTGAA 540
Sequence_77     CCCGG---TTTCGAAGTCGAGGTCCA---GCCTTACGAGAT-GTGCGAAATCGATTTGAA 540
Sequence_75     CCCGG---TTTCGAAGTCGAG---GT---GCCTTACGAGAT-GTGCGAAATCGATTTGAA 537
Sequence_43     CCCGG---TTTCGAAGTCGAG---GT---GCCTTACGAGAT-GTGCGAAATCGATTTGAA 537
Sequence_47     GTCGAGGT---CCAAATGGTTCCCGG---GCCTTACGAGAT-GTGCGAAATCGATTTGAA 540
Sequence_79     GTCGAGGT---CCAAATGGTTCCCGG---GCCTTACGAGAT-GTGCGAAATCGATTTGAA 540
Sequence_51     GTCGAGGTAGTTTAAATGGTTCCCGGCCAGCCTTACGAGAT-GTGCGAAATCGATTTGAA 546
Sequence_83     GTCGAGGTAGTTTAAATGGTTCCCGGCCAGCCTTACGAGAT-GTGCGAAATCGATTTGAA 546
Sequence_7      -TCAA-------GAAATGGTTCCCGG---GCCTTACGAGAT-GTGCGAAATCGATTTGAA 534
Sequence_25     -TCAA-------GAAATGGTTCCCGG---GCCTTACGAGAT-GTGCGAAATCGATTTGAA 534
Sequence_29     -TCAA-------GAAATGGTTCCCGG---GCCTTACGAGAT-GTGCGAAATCGATTTGAA 534
Sequence_33     -TCAA-------GAAATGGTTCCCGG---GCCTTACGAGAT-GTGCGAAATCGATTTGAA 534
Sequence_69     -TCAA-------GAAATGGTTCCCGG---GCCTTACGAGAT-GTGCGAAATCGATTTGAA 534
Sequence_11     -TCAA-------GA---------------GCCTTACGAGAT-GTGCGAAATCGATTTGAA 522
Sequence_1      -TCAA-------GA---------------GCCTTACGAGAT-GTGCGAAATCGATTTGAA 522
Sequence_17     -TCAA-------GA---------------GCCTTACGAGAT-GTGCGAAATCGATTTGAA 1252
Sequence_3      -TCAA-------GA---------------GCCTTACGAGAT-GTGCGAAATCGATTTGAA 522
Sequence_13     -TCAA-------GA---------------GCCTTACGAGAT-GTGCGAAATCGATTTGAA 522
Sequence_18     -TCAA-------GA---------------GCCTTACGAGAT-GTGCGAAATCGATTTGAA 1775
Cry8Ka1         TTCG-------------------------GAGTAAAGAGTTAGTAAAAGAAAGATTTTCA 516
                  *                          *  * * *** * **   * *  *****  *
```

To Fig. 17K

Fig. 17J

From Fig. 17J

```
Sequence_71         ATCCTGGATAGTTTATTTACGCAAT-ATATGCCATCTTTTAGAGTGACAAATTTTGAAGT 602
Sequence_73         ATCCTGGATAGTTTATTTACGCAAT-ATATGCCATCTTTTAGAGTGACAAATTTTGAAGT 599
Sequence_21         ATCCTGGATAGTTTATTTACGCAAT-ATATGCCATCTTTTAGAGTGACAAATTTTGAAGT 593
Sequence_67         ATCCTGGATAGTTTATTTACGCAAT-ATATGCCATCTTTTAGAGTGACAAATTTTGAAGT 593
Sequence_61         ATCCTGGATAGTTTATTTACGCAAT-ATATGCCATCTTTTAGAGTGACAAATTTTGAAGT 593
Sequence_93         ATCCTGGATAGTTTATTTACGCAAT-ATATGCCATCTTTTAGAGTGACAAATTTTGAAGT 593
Sequence_59         ATCCTGGATAGTTTATTTACGCAAT-ATATGCCATCTTTTAGAGTGACAAATTTTGAAGT 593
Sequence_91         ATCCTGGATAGTTTATTTACGCAAT-ATATGCCATCTTTTAGAGTGACAAATTTTGAAGT 593
Sequence_39         ATCCTGGATAGTTTATTTACGCAAT-ATATGCCATCTTTTAGAGTGACAAATTTTGAAGT 602
Sequence_41         ATCCTGGATAGTTTATTTACGCAAT-ATATGCCATCTTTTAGAGTGACAAATTTTGAAGT 599
Sequence_49         ATCCTGGATAGTTTATTTACGCAAT-ATATGCCATCTTTTAGAGTGACAAATTTTGAAGT 596
Sequence_81         ATCCTGGATAGTTTATTTACGCAAT-ATATGCCATCTTTTAGAGTGACAAATTTTGAAGT 596
Sequence_45         ATCCTGGATAGTTTATTTACGCAAT-ATATGCCATCTTTTAGAGTGACAAATTTTGAAGT 599
Sequence_77         ATCCTGGATAGTTTATTTACGCAAT-ATATGCCATCTTTTAGAGTGACAAATTTTGAAGT 599
Sequence_75         ATCCTGGATAGTTTATTTACGCAAT-ATATGCCATCTTTTAGAGTGACAAATTTTGAAGT 596
Sequence_43         ATCCTGGATAGTTTATTTACGCAAT-ATATGCCATCTTTTAGAGTGACAAATTTTGAAGT 596
Sequence_47         ATCCTGGATAGTTTATTTACGCAAT-ATATGCCATCTTTTAGAGTGACAAATTTTGAAGT 599
Sequence_79         ATCCTGGATAGTTTATTTACGCAAT-ATATGCCATCTTTTAGAGTGACAAATTTTGAAGT 599
Sequence_51         ATCCTGGATAGTTTATTTACGCAAT-ATATGCCATCTTTTAGAGTGACAAATTTTGAAGT 605
Sequence_83         ATCCTGGATAGTTTATTTACGCAAT-ATATGCCATCTTTTAGAGTGACAAATTTTGAAGT 605
Sequence_7          ATCCTGGATAGTTTATTTACGCAAT-ATATGCCATCTTTTAGAGTGACAAATTTTGAAGT 593
Sequence_25         ATCCTGGATAGTTTATTTACGCAAT-ATATGCCATCTTTTAGAGTGACAAATTTTGAAGT 593
Sequence_29         ATCCTGGATAGTTTATTTACGCAAT-ATATGCCATCTTTTAGAGTGACAAATTTTGAAGT 593
Sequence_33         ATCCTGGATAGTTTATTTACGCAAT-ATATGCCATCTTTTAGAGTGACAAATTTTGAAGT 593
Sequence_69         ATCCTGGATAGTTTATTTACGCAAT-ATATGCCATCTTTTAGAGTGACAAATTTTGAAGT 593
Sequence_11         ATCCTGGATAGTTTATTTACGCAAT-ATATGCCATCTTTTAGAGTGACAAATTTTGAAGT 581
Sequence_1          ATCCTGGATAGTTTATTTACGCAAT-ATATGCCATCTTTTAGAGTGACAAATTTTGAAGT 581
Sequence_17         ATCCTGGATAGTTTATTTACGCAAT-ATATGCCATCTTTTAGAGTGACAAATTTTGAAGT 1311
Sequence_3          ATCCTGGATAGTTTATTTACGCAAT-ACATGCCATCTTTTCGAGTGACAAATTTTGAAGT 581
Sequence_13         ATCCTGGATAGTTTATTTACGCAAT-ACATGCCATCTTTTCGAGTGACAAATTTTGAAGT 581
Sequence_18         ATCCTGGATAGTTTATTTACGCAAT-ACATGCCATCTTTTCGAGTGACAAATTTTGAAGT 1834
Cry8Ka1             AACGCGGAACATTCATT-ACGTACCGAAATGAGTTCTTTTGCCATAAGAGGATTTGAAAT 575
                    * *  ***   ** *** *** *   * ***   ******    * * *   ****** *
```

To Fig. 17L

Fig. 17K

From Fig. 17K

```
Sequence_71     ACCATTCCTTACTGTATATGCAATGGCAGCCAACCTTCATTTACTGTTATTAAAGGACGC 662
Sequence_73     ACCATTCCTTACTGTATATGCAATGGCAGCCAACCTTCATTTACTGTTATTAAAGGACGC 659
Sequence_21     ACCATTCCTTACTGTATATGCAATGGCAGCCAACCTTCATTTACTGTTATTAAAGGACGC 653
Sequence_67     ACCATTCCTTACTGTATATGCAATGGCAGCCAACCTTCATTTACTGTTATTAAAGGACGC 653
Sequence_61     ACCATTCCTTACTGTATATGCAATGGCAGCCAACCTTCATTTACTGTTATTAAAGGACGC 653
Sequence_93     ACCATTCCTTACTGTATATGCAATGGCAGCCAACCTTCATTTACTGTTATTAAAGGACGC 653
Sequence_59     ACCATTCCTTACTGTATATGCAATGGCAGCCAACCTTCATTTACTGTTATTAAAGGACGC 653
Sequence_91     ACCATTCCTTACTGTATATGCAATGGCAGCCAACCTTCATTTACTGTTATTAAAGGACGC 653
Sequence_39     ACCATTCCTTACTGTATATGCAATGGCAGCCAACCTTCATTTACTGTTATTAAAGGACGC 662
Sequence_41     ACCATTCCTTACTGTATATGCAATGGCAGCCAACCTTCATTTACTGTTATTAAAGGACGC 659
Sequence_49     ACCATTCCTTACTGTATATGCAATGGCAGCCAACCTTCATTTACTGTTATTAAAGGACGC 656
Sequence_81     ACCATTCCTTACTGTATATGCAATGGCAGCCAACCTTCATTTACTGTTATTAAAGGACGC 656
Sequence_45     ACCATTCCTTACTGTATATGCAATGGCAGCCAACCTTCATTTACTGTTATTAAAGGACGC 659
Sequence_77     ACCATTCCTTACTGTATATGCAATGGCAGCCAACCTTCATTTACTGTTATTAAAGGACGC 659
Sequence_75     ACCATTCCTTACTGTATATGCAATGGCAGCCAACCTTCATTTACTGTTATTAAAGGACGC 656
Sequence_43     ACCATTCCTTACTGTATATGCAATGGCAGCCAACCTTCATTTACTGTTATTAAAGGACGC 656
Sequence_47     ACCATTCCTTACTGTATATGCAATGGCAGCCAACCTTCATTTACTGTTATTAAAGGACGC 659
Sequence_79     ACCATTCCTTACTGTATATGCAATGGCAGCCAACCTTCATTTACTGTTATTAAAGGACGC 659
Sequence_51     ACCATTCCTTACTGTATATGCAATGGCAGCCAACCTTCATTTACTGTTATTAAAGGACGC 665
Sequence_83     ACCATTCCTTACTGTATATGCAATGGCAGCCAACCTTCATTTACTGTTATTAAAGGACGC 665
Sequence_7      ACCATTCCTTACTGTATATGCAATGGCAGCCAACCTTCATTTACTGTTATTAAAGGACGC 653
Sequence_25     ACCATTCCTTACTGTATATGCAATGGCAGCCAACCTTCATTTACTGTTATTAAAGGACGC 653
Sequence_29     ACCATTCCTTACTGTATATGCAATGGCAGCCAACCTTCATTTACTGTTATTAAAGGACGC 653
Sequence_33     ACCATTCCTTACTGTATATGCAATGGCAGCCAACCTTCATTTACTGTTATTAAAGGACGC 653
Sequence_69     ACCATTCCTTACTGTATATGCAATGGCAGCCAACCTTCATTTACTGTTATTAAAGGACGC 653
Sequence_11     ACCATTCCTTACTGTATATGCAATGGCAGCCAACCTTCATTTACTGTTATTAAAGGACGC 641
Sequence_1      ACCATTCCTTACTGTATATGCAATGGCAGCCAACCTTCATTTACTGTTATTAAAGGACGC 641
Sequence_17     ACCATTCCTTACTGTATATGCAATGGCAGCCAACCTTCATTTACTGTTATTAAAGGACGC 1371
Sequence_3      ACCATTCCTTACAGTATATACACAGGCAGCCAACCTTCATTTACTGTTATTAAAGGACGC 641
Sequence_13     ACCATTCCTTACAGTATATACACAGGCAGCCAACCTTCATTTACTGTTATTAAAGGACGC 641
Sequence_18     ACCATTCCTTACAGTATATACACAGGCAGCCAACCTTCATTTACTGTTATTAAAGGACGC 1894
Cry8Ka1         TCCTCTTTTAGCAACATATGCACAAGCTGCGAATTTACATTTATTTCTAATTAAAGATAT 635
                 **  *  *  *   **** **   ** ** **  * ****** *  ** * ** **
```

To Fig. 17M

Fig. 17L

From Fig. 17L

```
Sequence_71        GTCAATTTTTGGAGAAGAATGGGGATGGTCAACAACTACTATTAATAACTATTATGATCG 722
Sequence_73        GTCAATTTTTGGAGAAGAATGGGGATGGTCAACAACTACTATTAATAACTATTATGATCG 719
Sequence_21        GTCAATTTTTGGAGAAGAATGGGGATGGTCAACAACTACTATTAATAACTATTATGATCG 713
Sequence_67        GTCAATTTTTGGAGAAGAATGGGGATGGTCAACAACTACTATTAATAACTATTATGATCG 713
Sequence_61        GTCAATTTTTGGAGAAGAATGGGGATGGTCAACAACTACTATTAATAACGTGGTGGATCG 713
Sequence_93        GTCAATTTTTGGAGAAGAATGGGGATGGTCAACAACTACTATTAATAACGTGGTGGATCG 713
Sequence_59        GTCAATTTTTGGAGAAGAATGGGGATGGTCAACAACTACTATTAATAACTATTATGATCG 713
Sequence_91        GTCAATTTTTGGAGAAGAATGGGGATGGTCAACAACTACTATTAATAACTATTATGATCG 713
Sequence_39        GTCAATTTTTGGAGAAGAATGGGGATGGTCAACAACTACTATTAATAACTATTATGATCG 722
Sequence_41        GTCAATTTTTGGAGAAGAATGGGGATGGTCAACAACTACTATTAATAACTATTATGATCG 719
Sequence_49        GTCAATTTTTGGAGAAGAATGGGGATGGTCAACAACTACTATTAATAACTATTATGATCG 716
Sequence_81        GTCAATTTTTGGAGAAGAATGGGGATGGTCAACAACTACTATTAATAACTATTATGATCG 716
Sequence_45        GTCAATTTTTGGAGAAGAATGGGGATGGTCAACAACTACTATTAATAACTATTATGATCG 719
Sequence_77        GTCAATTTTTGGAGAAGAATGGGGATGGTCAACAACTACTATTAATAACTATTATGATCG 719
Sequence_75        GTCAATTTTTGGAGAAGAATGGGGATGGTCAACAACTACTATTAATAACTATTATGATCG 716
Sequence_43        GTCAATTTTTGGAGAAGAATGGGGATGGTCAACAACTACTATTAATAACTATTATGATCG 716
Sequence_47        GTCAATTTTTGGAGAAGAATGGGGATGGTCAACAACTACTATTAATAACTATTATGATCG 719
Sequence_79        GTCAATTTTTGGAGAAGAATGGGGATGGTCAACAACTACTATTAATAACTATTATGATCG 719
Sequence_51        GTCAATTTTTGGAGAAGAATGGGGATGGTCAACAACTACTATTAATAACTATTATGATCG 725
Sequence_83        GTCAATTTTTGGAGAAGAATGGGGATGGTCAACAACTACTATTAATAACTATTATGATCG 725
Sequence_7         GTCAATTTTTGGAGAAGAATGGGGATGGTCAACAACTACTATTAATAACTATTATGATCG 713
Sequence_25        GTCAATTTTTGGAGAAGAATGGGGATGGTCAACAACTACTATTAATAACTATTATGATCG 713
Sequence_29        GTCAATTTTTGGAGAAGAATGGGGATGGTCAACAACTACTATTAATAACTATTATGATCG 713
Sequence_33        GTCAATTTTTGGAGAAGAATGGGGATGGTCAACAACTACTATTAATAACTATTATGATCG 713
Sequence_69        GTCAATTTTTGGAGAAGAATGGGGATGGTCAACAACTACTATTAATAACTATTATGATCG 713
Sequence_11        GTCAATTTTTGGAGAAGAATGGGGATGGTCAACAACTACTATTAATAACTATTATGATCG 701
Sequence_1         GTCAATTTTTGGAGAAGAATGGGGATGGTCAACAACTACTATTAATAACTATTATGATCG 701
Sequence_17        GTCAATTTTTGGAGAAGAATGGGGATGGTCAACAACTACTATTAATAACTATTATGATCG 1431
Sequence_3         TTCAATTTTTGGAGAAGAATGGGGATGGTCTACAACCACTATTAATAACTATTATGATCG 701
Sequence_13        TTCAATTTTTGGAGAAGAATGGGGATGGTCTACAACCACTATTAATAACTATTATGATCG 701
Sequence_18        TTCAATTTTTGGAGAAGAATGGGGATGGTCTACAACCACTATTAATAACTATTATGATCG 1954
Cry8Ka1            TCAAATTTATGGAAAAGAATGGGGATATACTCAAGCCGATATTGACTTATTTTATAGAGA 695
                      ***** **** ************   *   * *   **** *
```

To Fig. 17N

Fig. 17M

From Fig. 17M

```
Sequence_71    TCAAATGAAACTTACTGCAGAATATTCTGATCACTGTGTAAAGTGGTATGAAACTGGTTT 782
Sequence_73    TCAAATGAAACTTACTGCAGAATATTCTGATCACTGTGTAAAGTGGTATGAAACTGGTTT 779
Sequence_21    TCAAATGAAACTTACTGCAGAATATTCTGATCACTGTGTAAAGTGGTATGAAACTGGTTT 773
Sequence_67    TCAAATGAAACTTACTGCAGAATATTCTGATCACTGTGTAAAGTGGTATGAAACTGGTTT 773
Sequence_61    TCAAATGAAACTTACTGCAGAATATTCTGATCACTGTGTAAAGTGGTATGAAACTGGTTT 773
Sequence_93    TCAAATGAAACTTACTGCAGAATATTCTGATCACTGTGTAAAGTGGTATGAAACTGGTTT 773
Sequence_59    TCAAATGAAACTTACTGCAGAATATTCTGATCACTGTGTAAAGTGGTATGAAACTGGTTT 773
Sequence_91    TCAAATGAAACTTACTGCAGAATATTCTGATCACTGTGTAAAGTGGTATGAAACTGGTTT 773
Sequence_39    TCAAATGAAACTTACTGCAGAATATTCTGATCACTGTGTAAAGTGGTATGAAACTGGTTT 782
Sequence_41    TCAAATGAAACTTACTGCAGAATATTCTGATCACTGTGTAAAGTGGTATGAAACTGGTTT 779
Sequence_49    TCAAATGAAACTTACTGCAGAATATTCTGATCACTGTGTAAAGTGGTATGAAACTGGTTT 776
Sequence_81    TCAAATGAAACTTACTGCAGAATATTCTGATCACTGTGTAAAGTGGTATGAAACTGGTTT 776
Sequence_45    TCAAATGAAACTTACTGCAGAATATTCTGATCACTGTGTAAAGTGGTATGAAACTGGTTT 779
Sequence_77    TCAAATGAAACTTACTGCAGAATATTCTGATCACTGTGTAAAGTGGTATGAAACTGGTTT 779
Sequence_75    TCAAATGAAACTTACTGCAGAATATTCTGATCACTGTGTAAAGTGGTATGAAACTGGTTT 776
Sequence_43    TCAAATGAAACTTACTGCAGAATATTCTGATCACTGTGTAAAGTGGTATGAAACTGGTTT 776
Sequence_47    TCAAATGAAACTTACTGCAGAATATTCTGATCACTGTGTAAAGTGGTATGAAACTGGTTT 779
Sequence_79    TCAAATGAAACTTACTGCAGAATATTCTGATCACTGTGTAAAGTGGTATGAAACTGGTTT 779
Sequence_51    TCAAATGAAACTTACTGCAGAATATTCTGATCACTGTGTAAAGTGGTATGAAACTGGTTT 785
Sequence_83    TCAAATGAAACTTACTGCAGAATATTCTGATCACTGTGTAAAGTGGTATGAAACTGGTTT 785
Sequence_7     TCAAATGAAACTTACTGCAGAATATTCTGATCACTGTGTAAAGTGGTATGAAACTGGTTT 773
Sequence_25    TCAAATGAAACTTACTGCAGAATATTCTGATCACTGTGTAAAGTGGTATGAAACTGGTTT 773
Sequence_29    TCAAATGAAACTTACTGCAGAATATTCTGATCACTGTGTAAAGTGGTATGAAACTGGTTT 773
Sequence_33    TCAAATGAAACTTACTGCAGAATATTCTGATCACTGTGTAAAGTGGTATGAAACTGGTTT 773
Sequence_69    TCAAATGAAACTTACTGCAGAATATTCTGATCACTGTGTAAAGTGGTATGAAACTGGTTT 773
Sequence_11    TCAAATGAAACTTACTGCAGAATATTCTGATCACTGTGTAAAGTGGTATGAAACTGGTTT 761
Sequence_1     TCAAATGAAACTTACTGCAGAATATTCTGATCACTGTGTAAAGTGGTATGAAACTGGTTT 761
Sequence_17    TCAAATGAAACTTACTGCAGAATATTCTGATCACTGTGTAAAGTGGTATGAAACTGGTTT 1491
Sequence_3     TCAAATGAAACTTACTGCAGAATATTCTGATCACTGTGTAAAGTGGTATGAAACTGGTTT 761
Sequence_13    TCAAATGAAACTTACTGCAGAATATTCTGATCACTGTGTAAAGTGGTATGAAACTGGTTT 761
Sequence_18    TCAAATGAAACTTACTGCAGAATATTCTGATCACTGTGTAAAGTGGTATGAAACTGGTTT 2014
Cry8Ka1        ACAAGTAGAGTTTACGAAAGAATACACCGAACACTGTATTAATATTTATAATGATGGTTT 755
                *** *  *  ***    ******  * ** ****** * **    *** *   ******
```

To Fig. 17O

Fig. 17N

From Fig. 17N

```
Sequence_71    AGCAAAATTAAAAGGCACGAGCGCTAAACAATGGGTTGACTATAACCAATTCCGTAGAGA 842
Sequence_73    AGCAAAATTAAAAGGCACGAGCGCTAAACAATGGGTTGACTATAACCAATTCCGTAGAGA 839
Sequence_21    AGCAAAATTAAAAGGCACGAGCGCTAAACAATGGGTTGACTATAACCAATTCCGTAGAGA 833
Sequence_67    AGCAAAATTAAAAGGCACGAGCGCTAAACAATGGGTTGACTATAACCAATTCCGTAGAGA 833
Sequence_61    AGCAAAATTAAAAGGCACGAGCGCTAAACAATGGGTTGACTATAACCAATTCCGTAGAGA 833
Sequence_93    AGCAAAATTAAAAGGCACGAGCGCTAAACAATGGGTTGACTATAACCAATTCCGTAGAGA 833
Sequence_59    AGCAAAATTAAAAGGCACGAGCGCTAAACAATGGGTTGACTATAACCAATTCCGTAGAGA 833
Sequence_91    AGCAAAATTAAAAGGCACGAGCGCTAAACAATGGGTTGACTATAACCAATTCCGTAGAGA 833
Sequence_39    AGCAAAATTAAAAGGCACGAGCGCTAAACAATGGGTTGACTATAACCAATTCCGTAGAGA 842
Sequence_41    AGCAAAATTAAAAGGCACGAGCGCTAAACAATGGGTTGACTATAACCAATTCCGTAGAGA 839
Sequence_49    AGCAAAATTAAAAGGCACGAGCGCTAAACAATGGGTTGACTATAACCAATTCCGTAGAGA 836
Sequence_81    AGCAAAATTAAAAGGCACGAGCGCTAAACAATGGGTTGACTATAACCAATTCCGTAGAGA 836
Sequence_45    AGCAAAATTAAAAGGCACGAGCGCTAAACAATGGGTTGACTATAACCAATTCCGTAGAGA 839
Sequence_77    AGCAAAATTAAAAGGCACGAGCGCTAAACAATGGGTTGACTATAACCAATTCCGTAGAGA 839
Sequence_75    AGCAAAATTAAAAGGCACGAGCGCTAAACAATGGGTTGACTATAACCAATTCCGTAGAGA 836
Sequence_43    AGCAAAATTAAAAGGCACGAGCGCTAAACAATGGGTTGACTATAACCAATTCCGTAGAGA 836
Sequence_47    AGCAAAATTAAAAGGCACGAGCGCTAAACAATGGGTTGACTATAACCAATTCCGTAGAGA 839
Sequence_79    AGCAAAATTAAAAGGCACGAGCGCTAAACAATGGGTTGACTATAACCAATTCCGTAGAGA 839
Sequence_51    AGCAAAATTAAAAGGCACGAGCGCTAAACAATGGGTTGACTATAACCAATTCCGTAGAGA 845
Sequence_83    AGCAAAATTAAAAGGCACGAGCGCTAAACAATGGGTTGACTATAACCAATTCCGTAGAGA 845
Sequence_7     AGCAAAATTAAAAGGCACGAGCGCTAAACAATGGGTTGACTATAACCAATTCCGTAGAGA 833
Sequence_25    AGCAAAATTAAAAGGCACGAGCGCTAAACAATGGGTTGACTATAACCAATTCCGTAGAGA 833
Sequence_29    AGCAAAATTAAAAGGCACGAGCGCTAAACAATGGGTTGACTATAACCAATTCCGTAGAGA 833
Sequence_33    AGCAAAATTAAAAGGCACGAGCGCTAAACAATGGGTTGACTATAACCAATTCCGTAGAGA 833
Sequence_69    AGCAAAATTAAAAGGCACGAGCGCTAAACAATGGGTTGACTATAACCAATTCCGTAGAGA 833
Sequence_11    AGCAAAATTAAAAGGCACGAGCGCTAAACAATGGGTTGACTATAACCAATTCCGTAGAGA 821
Sequence_1     AGCAAAATTAAAAGGCACGAGCGCTAAACAATGGGTTGACTATAACCAATTCCGTAGAGA 821
Sequence_17    AGCAAAATTAAAAGGCACGAGCGCTAAACAATGGGTTGACTATAACCAATTCCGTAGAGA 1551
Sequence_3     AGCAAAATTAAAAGGCACGAGCGCTAAACAATGGGTCGACTATAACCAATTCCGTAGAGA 821
Sequence_13    AGCAAAATTAAAAGGCACGAGCGCTAAACAATGGGTCGACTATAACCAATTCCGTAGAGA 821
Sequence_18    AGCAAAATTAAAAGGCACGAGCGCTAAACAATGGGTCGACTATAACCAATTCCGTAGAGA 2074
Cry8Ka1        AAATCAATTAAAAGGTTCGAATGCTAAGCAATGGATTGCATTTAATCGCTTCCGTAGAGA 815
               *    **********  ***  ***** ****** * *  * *** *  ***********
```

To Fig. 17P

Fig. 17O

From Fig. 17O

```
Sequence_71      AATGACACTGGCGGTTTTAGATGTTGTTGCATTATTCCCAAATTATGACACACGCACGTA 902
Sequence_73      AATGACACTGGCGGTTTTAGATGTTGTTGCATTATTCCCAAATTATGACACACGCACGTA 899
Sequence_21      AATGACACTGGCGGTTTTAGATGTTGTTGCATTATTCCCAAATTATGACACACGCACGTA 893
Sequence_67      AATGACACTGGCGGTTTTAGATGTTGTTGCATTATTCCCAAATTATGACACACGCACGTA 893
Sequence_61      AATGACACTGGCGGTTTTAGATGTTGTTGCATTATTCCCAAATTATGACACAATAACGTA 893
Sequence_93      AATGACACTGGCGGTTTTAGATGTTGTTGCATTATTCCCAAATTATGACACAATAACGTA 893
Sequence_59      AATGACACTGGCGGTTTTAGATGTTGTTGCATTATTCCCAAATTATGACACAATAACGTA 893
Sequence_91      AATGACACTGGCGGTTTTAGATGTTGTTGCATTATTCCCAAATTATGACACAATAACGTA 893
Sequence_39      AATGACACTGGCGGTTTTAGATGTTGTTGCATTATTCCCAAATTATGACACACGCACGTA 902
Sequence_41      AATGACACTGGCGGTTTTAGATGTTGTTGCATTATTCCCAAATTATGACACACGCACGTA 899
Sequence_49      AATGACACTGGCGGTTTTAGATGTTGTTGCATTATTCCCAAATTATGACACACGCACGTA 896
Sequence_81      AATGACACTGGCGGTTTTAGATGTTGTTGCATTATTCCCAAATTATGACACACGCACGTA 896
Sequence_45      AATGACACTGGCGGTTTTAGATGTTGTTGCATTATTCCCAAATTATGACACACGCACGTA 899
Sequence_77      AATGACACTGGCGGTTTTAGATGTTGTTGCATTATTCCCAAATTATGACACACGCACGTA 899
Sequence_75      AATGACACTGGCGGTTTTAGATGTTGTTGCATTATTCCCAAATTATGACACACGCACGTA 896
Sequence_43      AATGACACTGGCGGTTTTAGATGTTGTTGCATTATTCCCAAATTATGACACACGCACGTA 896
Sequence_47      AATGACACTGGCGGTTTTAGATGTTGTTGCATTATTCCCAAATTATGACACACGCACGTA 899
Sequence_79      AATGACACTGGCGGTTTTAGATGTTGTTGCATTATTCCCAAATTATGACACACGCACGTA 899
Sequence_51      AATGACACTGGCGGTTTTAGATGTTGTTGCATTATTCCCAAATTATGACACACGCACGTA 905
Sequence_83      AATGACACTGGCGGTTTTAGATGTTGTTGCATTATTCCCAAATTATGACACACGCACGTA 905
Sequence_7       AATGACACTGGCGGTTTTAGATGTTGTTGCATTATTCCCAAATTATGACACACGCACGTA 893
Sequence_25      AATGACACTGGCGGTTTTAGATGTTGTTGCATTATTCCCAAATTATGACACACGCACGTA 893
Sequence_29      AATGACACTGGCGGTTTTAGATGTTGTTGCATTATTCCCAAATTATGACACACGCACGTA 893
Sequence_33      AATGACACTGGCGGTTTTAGATGTTGTTGCATTATTCCCAAATTATGACACACGCACGTA 893
Sequence_69      AATGACACTGGCGGTTTTAGATGTTGTTGCATTATTCCCAAATTATGACACACGCACGTA 893
Sequence_11      AATGACACTGGCGGTTTTAGATGTTGTTGCATTATTCCCAAATTATGACACACGCACGTA 881
Sequence_1       AATGACACTGGCGGTTTTAGATGTTGTTGCATTATTCCCAAATTATGACACACGCACGTA 881
Sequence_17      AATGACACTGGCGGTTTTAGATGTTGTTGCATTATTCCCAAATTATGACACACGCACGTA 1611
Sequence_3       AATGACACTGACGGTTTTAGATGTTGTTGCATTATTCCCAAATTATGACACACGCACGTA 881
Sequence_13      AATGACACTGACGGTTTTAGATGTTGTTGCATTATTCCCAAATTATGACACACGCACGTA 881
Sequence_18      AATGACACTGACGGTTTTAGATGTTGTTGCATTATTCCCAAATTATGACACACGCACGTA 2134
Cry8Ka1          AATGACATTGACGGTACTGGATGTAGTTGCATTATTCCCGAACTATGATGTACGTATGTA 875
                 ******* ** ****  * ***** ************** ** *****   *   * ***
```

To Fig. 17Q

Fig. 17P

From Fig. 17P

```
Sequence_71     CCCAATGGAAACGAAAGCACAACTAACAAGGGAAGTATATACAGATCCACTGGGCGCGGT 962
Sequence_73     CCCAATGGAAACGAAAGCACAACTAACAAGGGAAGTATATACAGATCCACTGGGCGCGGT 959
Sequence_21     CCCAATGGAAACGAAAGCACAACTAACAAGGGAAGTATATACAGATCCACTGGGCGCGGT 953
Sequence_67     CCCAATGGAAACGAAAGCACAACTAACAAGGGAAGTATATACAGATCCACTGGGCGCGGT 953
Sequence_61     CCCAATAGAAACGAAAGCACAACTAACAAGGGAAGTATATACAGATCCACTGGGCGCGGT 953
Sequence_93     CCCAATAGAAACGAAAGCACAACTAACAAGGGAAGTATATACAGATCCACTGGGCGCGGT 953
Sequence_59     CCCAATGGAAACGAAAGCACAACTAACAAGGGAAGTATATACAGATCCACTGGGCGCGGT 953
Sequence_91     CCCAATGGAAACGAAAGCACAACTAACAAGGGAAGTATATACAGATCCACTGGGCGCGGT 953
Sequence_39     CCCAATGGAAACGAAAGCACAACTAACAAGGGAAGTATATACAGATCCACTGGGCGCGGT 962
Sequence_41     CCCAATGGAAACGAAAGCACAACTAACAAGGGAAGTATATACAGATCCACTGGGCGCGGT 959
Sequence_49     CCCAATGGAAACGAAAGCACAACTAACAAGGGAAGTATATACAGATCCACTGGGCGCGGT 956
Sequence_81     CCCAATGGAAACGAAAGCACAACTAACAAGGGAAGTATATACAGATCCACTGGGCGCGGT 956
Sequence_45     CCCAATGGAAACGAAAGCACAACTAACAAGGGAAGTATATACAGATCCACTGGGCGCGGT 959
Sequence_77     CCCAATGGAAACGAAAGCACAACTAACAAGGGAAGTATATACAGATCCACTGGGCGCGGT 959
Sequence_75     CCCAATGGAAACGAAAGCACAACTAACAAGGGAAGTATATACAGATCCACTGGGCGCGGT 956
Sequence_43     CCCAATGGAAACGAAAGCACAACTAACAAGGGAAGTATATACAGATCCACTGGGCGCGGT 956
Sequence_47     CCCAATGGAAACGAAAGCACAACTAACAAGGGAAGTATATACAGATCCACTGGGCGCGGT 959
Sequence_79     CCCAATGGAAACGAAAGCACAACTAACAAGGGAAGTATATACAGATCCACTGGGCGCGGT 959
Sequence_51     CCCAATGGAAACGAAAGCACAACTAACAAGGGAAGTATATACAGATCCACTGGGCGCGGT 965
Sequence_83     CCCAATGGAAACGAAAGCACAACTAACAAGGGAAGTATATACAGATCCACTGGGCGCGGT 965
Sequence_7      CCCAATGGAAACGAAAGCACAACTAACAAGGGAAGTATATACAGATCCACTGGGCGCGGT 953
Sequence_25     CCCAATGGAAACGAAAGCACAACTAACAAGGGAAGTATATACAGATCCACTGGGCGCGGT 953
Sequence_29     CCCAATGGAAACGAAAGCACAACTAACAAGGGAAGTATATACAGATCCACTGGGCGCGGT 953
Sequence_33     CCCAATGGAAACGAAAGCACAACTAACAAGGGAAGTATATACAGATCCACTGGGCGCGGT 953
Sequence_69     CCCAATGGAAACGAAAGCACAACTAACAAGGGAAGTATATACAGATCCACTGGGCGCGGT 953
Sequence_11     CCCAATGGAAACGAAAGCACAACTAACAAGGGAAGTATATACAGATCCACTGGGCGCGGT 941
Sequence_1      CCCAATGGAAACGAAAGCACAACTAACAAGGGAAGTATATACAGATCCACTGGGCGCGGT 941
Sequence_17     CCCAATGGAAACGAAAGCACAACTAACAAGGGAAGTATATACAGATCCACTGGGCGCGGT 1671
Sequence_3      CCCAATGGAAACGAAAGCACAACTAACAAGGGAAGTATATACAGATCCACTGGGCGCGGT 941
Sequence_13     CCCAATGGAAACGAAAGCACAACTAACAAGGGAAGTATATACAGATCCACTGGGCGCGGT 941
Sequence_18     CCCAATGGAAACGAAAGCACAACTAACAAGGGAAGTATATACAGATCCACTGGGCGCGGT 2194
Cry8Ka1         CCCTATAAAAACAACTACAGAGCTAACGAGAACAATTTATACCGATCCACTTGGTTACAC 935
                *** **  **** *   ** * ***** **   * * ***** ******** **
```

To Fig. 17R

Fig. 17Q

From Fig. 17Q

```
Sequence_71     AAACGTGTCTTCAATTGGT------TCCTGGTATGACAAAGCACCTTCTTTCGGAGTGAT 1016
Sequence_73     AAACGTGTCTTCAATTGGT------TCCTGGTATGACAAAGCACCTTCTTTCGGAGTGAT 1013
Sequence_21     AAACGTGTCTTCAATTGGT------TCCTGGTATGACAAAGCACCTTCTTTCGGAGTGAT 1007
Sequence_67     AAACGTGTCTTCAATTGGT------TCCTGGTATGACAAAGCACCTTCTTTCGGAGTGAT 1007
Sequence_61     AAACGTGTCTTCAATTGGT------TCCTGGTATGACAAAGCACCTTCTTTCGGAGTGAT 1007
Sequence_93     AAACGTGTCTTCAATTGGT------TCCTGGTATGACAAAGCACCTTCTTTCGGAGTGAT 1007
Sequence_59     AAACGTGTCTTCAATTGGT------TCCTGGTATGACAAAGCACCTTCTTTCGGAGTGAT 1007
Sequence_91     AAACGTGTCTTCAATTGGT------TCCTGGTATGACAAAGCACCTTCTTTCGGAGTGAT 1007
Sequence_39     AAACGTGTCTTCAATTGGT------TCCTGGTATGACAAAGCACCTTCTTTCGGAGTGAT 1016
Sequence_41     AAACGTGTCTTCAATTGGT------TCCTGGTATGACAAAGCACCTTCTTTCGGAGTGAT 1013
Sequence_49     AAACGTGTCTTCAATTGGT------TCCTGGTATGACAAAGCACCTTCTTTCGGAGTGAT 1010
Sequence_81     AAACGTGTCTTCAATTGGT------TCCTGGTATGACAAAGCACCTTCTTTCGGAGTGAT 1010
Sequence_45     AAACGTGTCTTCAATTGGT------TCCTGGTATGACAAAGCACCTTCTTTCGGAGTGAT 1013
Sequence_77     AAACGTGTCTTCAATTGGT------TCCTGGTATGACAAAGCACCTTCTTTCGGAGTGAT 1013
Sequence_75     AAACGTGTCTTCAATTGGT------TCCTGGTATGACAAAGCACCTTCTTTCGGAGTGAT 1010
Sequence_43     AAACGTGTCTTCAATTGGT------TCCTGGTATGACAAAGCACCTTCTTTCGGAGTGAT 1010
Sequence_47     AAACGTGTCTTCAATTGGT------TCCTGGTATGACAAAGCACCTTCTTTCGGAGTGAT 1013
Sequence_79     AAACGTGTCTTCAATTGGT------TCCTGGTATGACAAAGCACCTTCTTTCGGAGTGAT 1013
Sequence_51     AAACGTGTCTTCAATTGGT------TCCTGGTATGACAAAGCACCTTCTTTCGGAGTGAT 1019
Sequence_83     AAACGTGTCTTCAATTGGT------TCCTGGTATGACAAAGCACCTTCTTTCGGAGTGAT 1019
Sequence_7      AAACGTGTCTTCAATTGGT------TCCTGGTATGACAAAGCACCTTCTTTCGGAGTGAT 1007
Sequence_25     AAACGTGTCTTCAATTGGT------TCCTGGTATGACAAAGCACCTTCTTTCGGAGTGAT 1007
Sequence_29     AAACGTGTCTTCAATTGGT------TCCTGGTATGACAAAGCACCTTCTTTCGGAGTGAT 1007
Sequence_33     AAACGTGTCTTCAATTGGT------TCCTGGTATGACAAAGCACCTTCTTTCGGAGTGAT 1007
Sequence_69     AAACGTGTCTTCAATTGGT------TCCTGGTATGACAAAGCACCTTCTTTCGGAGTGAT 1007
Sequence_11     AAACGTGTCTTCAATTGGT------TCCTGGTATGACAAAGCACCTTCTTTCGGAGTGAT 995
Sequence_1      AAACGTGTCTTCAATTGGT------TCCTGGTATGACAAAGCACCTTCTTTCGGAGTGAT 995
Sequence_17     AAACGTGTCTTCAATTGGT------TCCTGGTATGACAAAGCACCTTCTTTCGGAGTGAT 1725
Sequence_3      AAACGTGTCTTCAATTGGT------TCCTGGTATGACAAAGCACCTTCTTTCGGAGTGAT 995
Sequence_13     AAACGTGTCTTCAATTGGT------TCCTGGTATGACAAAGCACCTTCTTTCGGAGTGAT 995
Sequence_18     AAACGTGTCTTCAATTGGT------TCCTGGTATGACAAAGCACCTTCTTTCGGAGTGAT 2248
Cry8Ka1         GAAAACGGGTTCTAGTAGTACACCACCATGGTATAATTATGGATCTAGTTTCTCATATAT 995
                 **   *  *** * * **       * ****** *  * * * **  ****  *   **
```

To Fig. 17S

Fig. 17R

From Fig. 17R

```
Sequence_71     AGAATCATCCGTTATTCGACCACCCCATGTATTTGATTATATAACGGGACTCACAGTGTA 1076
Sequence_73     AGAATCATCCGTTATTCGACCACCCCATGTATTTGATTATATAACGGGACTCACAGTGTA 1073
Sequence_21     AGAATCATCCGTTATTCGACCACCCCATGTATTTGATTATATAACGGGACTCACAGTGTA 1067
Sequence_67     AGAATCATCCGTTATTCGACCACCCCATGTATTTGATTATATAACGGGACTCACAGTGTA 1067
Sequence_61     AGAATCATCCGTTATTCGACCACCCCATGTATTTGATTATATAACGGGACTCACAGTGTA 1067
Sequence_93     AGAATCATCCGTTATTCGACCACCCCATGTATTTGATTATATAACGGGACTCACAGTGTA 1067
Sequence_59     AGAATCATCCGTTATTCGACCACCCCATGTATTTGATTATATAACGGGACTCACAGTGTA 1067
Sequence_91     AGAATCATCCGTTATTCGACCACCCCATGTATTTGATTATATAACGGGACTCACAGTGTA 1067
Sequence_39     AGAATCATCCGTTATTCGACCACCCCATGTATTTGATTATATAACGGGACTCACAGTGTA 1076
Sequence_41     AGAATCATCCGTTATTCGACCACCCCATGTATTTGATTATATAACGGGACTCACAGTGTA 1073
Sequence_49     AGAATCATCCGTTATTCGACCACCCCATGTATTTGATTATATAACGGGACTCACAGTGTA 1070
Sequence_81     AGAATCATCCGTTATTCGACCACCCCATGTATTTGATTATATAACGGGACTCACAGTGTA 1070
Sequence_45     AGAATCATCCGTTATTCGACCACCCCATGTATTTGATTATATAACGGGACTCACAGTGTA 1073
Sequence_77     AGAATCATCCGTTATTCGACCACCCCATGTATTTGATTATATAACGGGACTCACAGTGTA 1073
Sequence_75     AGAATCATCCGTTATTCGACCACCCCATGTATTTGATTATATAACGGGACTCACAGTGTA 1070
Sequence_43     AGAATCATCCGTTATTCGACCACCCCATGTATTTGATTATATAACGGGACTCACAGTGTA 1070
Sequence_47     AGAATCATCCGTTATTCGACCACCCCATGTATTTGATTATATAACGGGACTCACAGTGTA 1073
Sequence_79     AGAATCATCCGTTATTCGACCACCCCATGTATTTGATTATATAACGGGACTCACAGTGTA 1073
Sequence_51     AGAATCATCCGTTATTCGACCACCCCATGTATTTGATTATATAACGGGACTCACAGTGTA 1079
Sequence_83     AGAATCATCCGTTATTCGACCACCCCATGTATTTGATTATATAACGGGACTCACAGTGTA 1079
Sequence_7      AGAATCATCCGTTATTCGACCACCCCATGTATTTGATTATATAACGGGACTCACAGTGTA 1067
Sequence_25     AGAATCATCCGTTATTCGACCACCCCATGTATTTGATTATATAACGGGACTCACAGTGTA 1067
Sequence_29     AGAATCATCCGTTATTCGACCACCCCATGTATTTGATTATATAACGGGACTCACAGTGTA 1067
Sequence_33     AGAATCATCCGTTATTCGACCACCCCATGTATTTGATTATATAACGGGACTCACAGTGTA 1067
Sequence_69     AGAATCATCCGTTATTCGACCACCCCATGTATTTGATTATATAACGGGACTCACAGTGTA 1067
Sequence_11     AGAATCATCCGTTATTCGACCACCCCATGTATTTGATTATATAACGGGACTCACAGTGTA 1055
Sequence_1      AGAATCATCCGTTATTCGACCACCCCATGTATTTGATTATATAACGGGACTCACAGTGTA 1055
Sequence_17     AGAATCATCCGTTATTCGACCACCCCATGTATTTGATTATATAACGGGACTCACAGTGTA 1785
Sequence_3      AGAATCATCCGTTATTCGACCACCCCATGTATTTGATTATATAACGGGACTCACAGTGTA 1055
Sequence_13     AGAATCATCCGTTATTCGACCACCCCATGTATTTGATTATATAACGGGACTCACAGTGTA 1055
Sequence_18     AGAATCATCCGTTATTCGACCACCCCATGTATTTGATTATATAACGGGACTCACAGTGTA 2308
Cry8Ka1         AGAAAGTGTAGCGATTCCAGCCCCTAGTCTGGTTAAGTGGTTAAGTCAGATTGAAATTTA 1055
                ****      *  **** * * **   * *  ** * *   ***      *   * * **
```

To Fig. 17T

Fig. 17S

From Fig. 17S

```
Sequence_71    TACACAATCAAGAAGCATTTCTTCCGCTCGCTATATAAGACATTGGGCTGGTCATCAAAT 1136
Sequence_73    TACACAATCAAGAAGCATTTCTTCCGCTCGCTATATAAGACATTGGGCTGGTCATCAAAT 1133
Sequence_21    TACACAATCAAGAAGCATTTCTTCCGCTCGCTATATAAGACATTGGGCTGGTCATCAAAT 1127
Sequence_67    TACACAATCAAGAAGCATTTCTTCCGCTCGCTATATAAGACATTGGGCTGGTCATCAAAT 1127
Sequence_61    TACACAATCAAGAAGCATTTCTTCCGCTCGCTATATAAGACATTGGGCTGGTCATCAAAT 1127
Sequence_93    TACACAATCAAGAAGCATTTCTTCCGCTCGCTATATAAGACATTGGGCTGGTCATCAAAT 1127
Sequence_59    TACACAATCAAGAAGCATTTCTTCCGCTCGCTATATAAGACATTGGGCTGGTCATCAAAT 1127
Sequence_91    TACACAATCAAGAAGCATTTCTTCCGCTCGCTATATAAGACATTGGGCTGGTCATCAAAT 1127
Sequence_39    TACACAATCAAGAAGCATTTCTTCCGCTCGCTATATAAGACATTGGGCTGGTCATCAAAT 1136
Sequence_41    TACACAATCAAGAAGCATTTCTTCCGCTCGCTATATAAGACATTGGGCTGGTCATCAAAT 1133
Sequence_49    TACACAATCAAGAAGCATTTCTTCCGCTCGCTATATAAGACATTGGGCTGGTCATCAAAT 1130
Sequence_81    TACACAATCAAGAAGCATTTCTTCCGCTCGCTATATAAGACATTGGGCTGGTCATCAAAT 1130
Sequence_45    TACACAATCAAGAAGCATTTCTTCCGCTCGCTATATAAGACATTGGGCTGGTCATCAAAT 1133
Sequence_77    TACACAATCAAGAAGCATTTCTTCCGCTCGCTATATAAGACATTGGGCTGGTCATCAAAT 1133
Sequence_75    TACACAATCAAGAAGCATTTCTTCCGCTCGCTATATAAGACATTGGGCTGGTCATCAAAT 1130
Sequence_43    TACACAATCAAGAAGCATTTCTTCCGCTCGCTATATAAGACATTGGGCTGGTCATCAAAT 1130
Sequence_47    TACACAATCAAGAAGCATTTCTTCCGCTCGCTATATAAGACATTGGGCTGGTCATCAAAT 1133
Sequence_79    TACACAATCAAGAAGCATTTCTTCCGCTCGCTATATAAGACATTGGGCTGGTCATCAAAT 1133
Sequence_51    TACACAATCAAGAAGCATTTCTTCCGCTCGCTATATAAGACATTGGGCTGGTCATCAAAT 1139
Sequence_83    TACACAATCAAGAAGCATTTCTTCCGCTCGCTATATAAGACATTGGGCTGGTCATCAAAT 1139
Sequence_7     TACACAATCAAGAAGCATTTCTTCCGCTCGCTATATAAGACATTGGGCTGGTCATCAAAT 1127
Sequence_25    TACACAATCAAGAAGCATTTCTTCCGCTCGCTATATAAGACATTGGGCTGGTCATCAAAT 1127
Sequence_29    TACACAATCAAGAAGCATTTCTTCCGCTCGCTATATAAGACATTGGGCTGGTCATCAAAT 1127
Sequence_33    TACACAATCAAGAAGCATTTCTTCCGCTCGCTATATAAGACATTGGGCTGGTCATCAAAT 1127
Sequence_69    TACACAATCAAGAAGCATTTCTTCCGCTCGCTATATAAGACATTGGGCTGGTCATCAAAT 1127
Sequence_11    TACACAATCAAGAAGCATTTCTTCCGCTCGCTATATAAGACATTGGGCTGGTCATCAAAT 1115
Sequence_1     TACACAATCAAGAAGCATTTCTTCCGCTCGCTATATAAGACATTGGGCTGGTCATCAAAT 1115
Sequence_17    TACACAATCAAGAAGCATTTCTTCCGCTCGCTATATAAGACATTGGGCTGGTCATCAAAT 1845
Sequence_3     TACACAATCAAGAAGCATTTCTTCCGCTCGCTATATAAGACATTGGGCTGGTCATCAAAT 1115
Sequence_13    TACACAATCAAGAAGCATTTCTTCCGCTCGCTATATAAGACATTGGGCTGGTCATCAAAT 1115
Sequence_18    TACACAATCAAGAAGCATTTCTTCCGCTCGCTATATAAGACATTGGGCTGGTCATCAAAT 2368
Cry8Ka1        TTCGAAATCCGCAAGGGCTACACC---GCAAAGTGCGGATTATTGGGCAGGACATACAAT 1112
               * *  ****   ***   * *  *    *    *       ******* ** ***  ***
```

To Fig. 17U

Fig. 17T

From Fig. 17T

```
Sequence_71      AAGCTACCATCGTGTCAGTAGGGGTAGTAATCTTCAACAAATGTATGGAACTAATCAAAA 1196
Sequence_73      AAGCTACCATCGTGTCAGTAGGGGTAGTAATCTTCAACAAATGTATGGAACTAATCAAAA 1193
Sequence_21      AAGCTACCATCGTGTCAGTAGGGGTAGTAATCTTCAACAAATGTATGGAACTAATCAAAA 1187
Sequence_67      AAGCTACCATCGTGTCAGTAGGGGTAGTAATCTTCAACAAATGTATGGAACTAATCAAAA 1187
Sequence_61      AAGCTACCATCGTGTCAGTAGGGGTAGTAATCTTCAACAAATGTATGGAACTAATCAAAA 1187
Sequence_93      AAGCTACCATCGTGTCAGTAGGGGTAGTAATCTTCAACAAATGTATGGAACTAATCAAAA 1187
Sequence_59      AAGCTACCATCGTGTCAGTAGGGGTAGTAATCTTCAACAAATGTATGGAACTAATCAAAA 1187
Sequence_91      AAGCTACCATCGTGTCAGTAGGGGTAGTAATCTTCAACAAATGTATGGAACTAATCAAAA 1187
Sequence_39      AAGCTACCATCGTGTCAGTAGGGGTAGTAATCTTCAACAAATGTATGGAACTAATCAAAA 1196
Sequence_41      AAGCTACCATCGTGTCAGTAGGGGTAGTAATCTTCAACAAATGTATGGAACTAATCAAAA 1193
Sequence_49      AAGCTACCATCGTGTCAGTAGGGGTAGTAATCTTCAACAAATGTATGGAACTAATCAAAA 1190
Sequence_81      AAGCTACCATCGTGTCAGTAGGGGTAGTAATCTTCAACAAATGTATGGAACTAATCAAAA 1190
Sequence_45      AAGCTACCATCGTGTCAGTAGGGGTAGTAATCTTCAACAAATGTATGGAACTAATCAAAA 1193
Sequence_77      AAGCTACCATCGTGTCAGTAGGGGTAGTAATCTTCAACAAATGTATGGAACTAATCAAAA 1193
Sequence_75      AAGCTACCATCGTGTCAGTAGGGGTAGTAATCTTCAACAAATGTATGGAACTAATCAAAA 1190
Sequence_43      AAGCTACCATCGTGTCAGTAGGGGTAGTAATCTTCAACAAATGTATGGAACTAATCAAAA 1190
Sequence_47      AAGCTACCATCGTGTCAGTAGGGGTAGTAATCTTCAACAAATGTATGGAACTAATCAAAA 1193
Sequence_79      AAGCTACCATCGTGTCAGTAGGGGTAGTAATCTTCAACAAATGTATGGAACTAATCAAAA 1193
Sequence_51      AAGCTACCATCGTGTCAGTAGGGGTAGTAATCTTCAACAAATGTATGGAACTAATCAAAA 1199
Sequence_83      AAGCTACCATCGTGTCAGTAGGGGTAGTAATCTTCAACAAATGTATGGAACTAATCAAAA 1199
Sequence_7       AAGCTACCATCGTGTCAGTAGGGGTAGTAATCTTCAACAAATGTATGGAACTAATCAAAA 1187
Sequence_25      AAGCTACCATCGTGTCAGTAGGGGTAGTAATCTTCAACAAATGTATGGAACTAATCAAAA 1187
Sequence_29      AAGCTACCATCGTGTCAGTAGGGGTAGTAATCTTCAACAAATGTATGGAACTAATCAAAA 1187
Sequence_33      AAGCTACCATCGTGTCAGTAGGGGTAGTAATCTTCAACAAATGTATGGAACTAATCAAAA 1187
Sequence_69      AAGCTACCATCGTGTCAGTAGGGGTAGTAATCTTCAACAAATGTATGGAACTAATCAAAA 1187
Sequence_11      AAGCTACCATCGTGTCAGTAGGGGTAGTAATCTTCAACAAATGTATGGAACTAATCAAAA 1175
Sequence_1       AAGCTACCATCGTGTCAGTAGGGGTAGTAATCTTCAACAAATGTATGGAACTAATCAAAA 1175
Sequence_17      AAGCTACCATCGTGTCAGTAGGGGTAGTAATCTTCAACAAATGTATGGAACTAATCAAAA 1905
Sequence_3       AAGCTATCATCGGATTTTTAGTGATAATATTATAAAACAGATGTATGGAACTAATCAAAA 1175
Sequence_13      AAGCTATCATCGGATTTTTAGTGATAATATTATAAAACAGATGTATGGAACTAATCAAAA 1175
Sequence_18      AAGCTATCATCGGATTTTTAGTGATAATATTATAAAACAGATGTATGGAACTAATCAAAA 2428
Cry8Ka1_         AACATATCACTATAGTGGAGATGATGGTCAAGCAGTACCTAATTATGGAGATAGAACGAA 1172
                 **  ** **             * *  *        **  *  ******  **     **
```

To Fig. 17V

Fig. 17U

From Fig. 17U

```
Sequence_71    TCTACACAGCACTAGTACCTTTGATTTTACGAATTATGATATTTACAAGACTCTATCAAA 1256
Sequence_73    TCTACACAGCACTAGTACCTTTGATTTTACGAATTATGATATTTACAAGACTCTATCAAA 1253
Sequence_21    TCTACACAGCACTAGTACCTTTGATTTTACGAATTATGATATTTACAAGACTCTATCAAA 1247
Sequence_67    TCTACACAGCACTAGTACCTTTGATTTTACGAATTATGATATTTACAAGACTCTATCAAA 1247
Sequence_61    TCTACACAGCACTAGTACCTTTGATTTTACGAATTATGATATTTACAAGACTCTATCAAA 1247
Sequence_93    TCTACACAGCACTAGTACCTTTGATTTTACGAATTATGATATTTACAAGACTCTATCAAA 1247
Sequence_59    TCTACACAGCACTAGTACCTTTGATTTTACGAATTATGATATTTACAAGACTCTATCAAA 1247
Sequence_91    TCTACACAGCACTAGTACCTTTGATTTTACGAATTATGATATTTACAAGACTCTATCAAA 1247
Sequence_39    TCTACACAGCACTAGTACCTTTGATTTTACGAATTATGATATTTACAAGACTCTATCAAA 1256
Sequence_41    TCTACACAGCACTAGTACCTTTGATTTTACGAATTATGATATTTACAAGACTCTATCAAA 1253
Sequence_49    TCTACACAGCACTAGTACCTTTGATTTTACGAATTATGATATTTACAAGACTCTATCAAA 1250
Sequence_81    TCTACACAGCACTAGTACCTTTGATTTTACGAATTATGATATTTACAAGACTCTATCAAA 1250
Sequence_45    TCTACACAGCACTAGTACCTTTGATTTTACGAATTATGATATTTACAAGACTCTATCAAA 1253
Sequence_77    TCTACACAGCACTAGTACCTTTGATTTTACGAATTATGATATTTACAAGACTCTATCAAA 1253
Sequence_75    TCTACACAGCACTAGTACCTTTGATTTTACGAATTATGATATTTACAAGACTCTATCAAA 1250
Sequence_43    TCTACACAGCACTAGTACCTTTGATTTTACGAATTATGATATTTACAAGACTCTATCAAA 1250
Sequence_47    TCTACACAGCACTAGTACCTTTGATTTTACGAATTATGATATTTACAAGACTCTATCAAA 1253
Sequence_79    TCTACACAGCACTAGTACCTTTGATTTTACGAATTATGATATTTACAAGACTCTATCAAA 1253
Sequence_51    TCTACACAGCACTAGTACCTTTGATTTTACGAATTATGATATTTACAAGACTCTATCAAA 1259
Sequence_83    TCTACACAGCACTAGTACCTTTGATTTTACGAATTATGATATTTACAAGACTCTATCAAA 1259
Sequence_7     TCTACACAGCACTAGTACCTTTGATTTTACGAATTATGATATTTACAAGACTCTATCAAA 1247
Sequence_25    TCTACACAGCACTAGTACCTTTGATTTTACGAATTATGATATTTACAAGACTCTATCAAA 1247
Sequence_29    TCTACACAGCACTAGTACCTTTGATTTTACGAATTATGATATTTACAAGACTCTATCAAA 1247
Sequence_33    TCTACACAGCACTAGTACCTTTGATTTTACGAATTATGATATTTACAAGACTCTATCAAA 1247
Sequence_69    TCTACACAGCACTAGTACCTTTGATTTTACGAATTATGATATTTACAAGACTCTATCAAA 1247
Sequence_11    TCTACACAGCACTAGTACCTTTGATTTTACGAATTATGATATTTACAAGACTCTATCAAA 1235
Sequence_1     TCTACACAGCACTAGTACCTTTGATTTTACGAATTATGATATTTACAAGACTCTATCAAA 1235
Sequence_17    TCTACACAGCACTAGTACCTTTGATTTTACGAATTATGATATTTACAAGACTCTATCAAA 1965
Sequence_3     TCTACACAGCACTAGTACCTTTGATTTTACGAATTATGATATTTACAAGACGTTATCAAA 1235
Sequence_13    TCTACACAGCACTAGTACCTTTGATTTTACGAATTATGATATTTACAAGACGTTATCAAA 1235
Sequence_18    TCTACACAGCACTAGTACCTTTGATTTTACGAATTATGATATTTACAAGACGTTATCAAA 2488
Cry8Ka1        TCCTGTAATTGTAAATCGTTATAATTTTGAGCAGGCTGACATTTATAGAGTTTCATCATC 1232
               **     *     * *   * * *****  * *   *** ***** *       ****
```

To Fig. 17W

Fig. 17V

From Fig. 17V

```
Sequence_71     GGATGCAGTACTCCTTGATATTGTT-TACCCTGGTTATACGTATATATTTTTTGGAATGC 1315
Sequence_73     GGATGCAGTACTCCTTGATATTGTT-TACCCTGGTTATACGTATATATTTTTTGGAATGC 1312
Sequence_21     GGATGCAGTACTCCTTGATATTGTT-TACCCTGGTTATACGTATATATTTTTTGGAATGC 1306
Sequence_67     GGATGCAGTACTCCTTGATATTGTT-TACCCTGGTTATACGTATATATTTTTTGGAATGC 1306
Sequence_61     GGATGCAGTACTCCTTGATATTGTT-TACCCTGGTTATACGTATATATTTTTTGGAATGC 1306
Sequence_93     GGATGCAGTACTCCTTGATATTGTT-TACCCTGGTTATACGTATATATTTTTTGGAATGC 1306
Sequence_59     GGATGCAGTACTCCTTGATATTGTT-TACCCTGGTTATACGTATATATTTTTTGGAATGC 1306
Sequence_91     GGATGCAGTACTCCTTGATATTGTT-TACCCTGGTTATACGTATATATTTTTTGGAATGC 1306
Sequence_39     GGATGCAGTACTCCTTGATATTGTT-TACCCTGGTTATACGTATATATTTTTTGGAATGC 1315
Sequence_41     GGATGCAGTACTCCTTGATATTGTT-TACCCTGGTTATACGTATATATTTTTTGGAATGC 1312
Sequence_49     GGATGCAGTACTCCTTGATATTGTT-TACCCTGGTTATACGTATATATTTTTTGGAATGC 1309
Sequence_81     GGATGCAGTACTCCTTGATATTGTT-TACCCTGGTTATACGTATATATTTTTTGGAATGC 1309
Sequence_45     GGATGCAGTACTCCTTGATATTGTT-TACCCTGGTTATACGTATATATTTTTTGGAATGC 1312
Sequence_77     GGATGCAGTACTCCTTGATATTGTT-TACCCTGGTTATACGTATATATTTTTTGGAATGC 1312
Sequence_75     GGATGCAGTACTCCTTGATATTGTT-TACCCTGGTTATACGTATATATTTTTTGGAATGC 1309
Sequence_43     GGATGCAGTACTCCTTGATATTGTT-TACCCTGGTTATACGTATATATTTTTTGGAATGC 1309
Sequence_47     GGATGCAGTACTCCTTGATATTGTT-TACCCTGGTTATACGTATATATTTTTTGGAATGC 1312
Sequence_79     GGATGCAGTACTCCTTGATATTGTT-TACCCTGGTTATACGTATATATTTTTTGGAATGC 1312
Sequence_51     GGATGCAGTACTCCTTGATATTGTT-TACCCTGGTTATACGTATATATTTTTTGGAATGC 1318
Sequence_83     GGATGCAGTACTCCTTGATATTGTT-TACCCTGGTTATACGTATATATTTTTTGGAATGC 1318
Sequence_7      GGATGCAGTACTCCTTGATATTGTT-TACCCTGGTTATACGTATATATTTTTTGGAATGC 1306
Sequence_25     GGATGCAGTACTCCTTGATATTGTT-TACCCTGGTTATACGTATATATTTTTTGGAATGC 1306
Sequence_29     GGATGCAGTACTCCTTGATATTGTT-TACCCTGGTTATACGTATATATTTTTTGGAATGC 1306
Sequence_33     GGATGCAGTACTCCTTGATATTGTT-TACCCTGGTTATACGTATATATTTTTTGGAATGC 1306
Sequence_69     GGATGCAGTACTCCTTGATATTGTT-TACCCTGGTTATACGTATATATTTTTTGGAATGC 1306
Sequence_11     GGATGCAGTACTCCTTGATATTGTT-TACCCTGGTTATACGTATATATTTTTTGGAATGC 1294
Sequence_1      GGATGCAGTACTCCTTGATATTGTT-TACCCTGGTTATACGTATATATTTTTTGGAATGC 1294
Sequence_17     GGATGCAGTACTCCTTGATATTGTT-TACCCTGGTTATACGTATATATTTTTTGGAATGC 2024
Sequence_3      AGATGCGGTGCTCCTTGATATTGTT-TTTCCTGGTTATACGTATATATTTTTTGGAATGC 1294
Sequence_13     AGATGCGGTGCTCCTTGATATTGTT-TTTCCTGGTTATACGTATATATTTTTTGGAATGC 1294
Sequence_18     AGATGCGGTGCTCCTTGATATTGTT-TTTCCTGGTTATACGTATATATTTTTTGGAATGC 2547
Cry8Ka1         TGTTGCTTCAAGTACAACTAGTGGTGTTAAATTATTAACTACTAAGGCTATATTTGATGG 1292
                 * ***            ** ** * *    *  ***       *   * * *   ***
```

To Fig. 17X

Fig. 17W

From Fig. 17W

```
Sequence_71     CAGAAGTCGAGTTTTTCATGGTAAACCAATTGAATA-ATACCAGAAAGAC-GTTAAAGTA 1373
Sequence_73     CAGAAGTCGAGTTTTTCATGGTAAACCAATTGAATA-ATACCAGAAAGAC-GTTAAAGTA 1370
Sequence_21     CAGAAGTCGAGTTTTTCATGGTAAACCAATTGAATA-ATACCAGAAAGAC-GTTAAAGTA 1364
Sequence_67     CAGAAGTCGAGTTTTTCATGGTAAACCAATTGAATA-ATACCAGAAAGAC-GTTAAAGTA 1364
Sequence_61     CAGAAGTCGAGTTTTTCATGGTAAACCAATTGAATA-ATACCAGAAAGAC-GTTAAAGTA 1364
Sequence_93     CAGAAGTCGAGTTTTTCATGGTAAACCAATTGAATA-ATACCAGAAAGAC-GTTAAAGTA 1364
Sequence_59     CAGAAGTCGAGTTTTTCATGGTAAACCAATTGAATA-ATACCAGAAAGAC-GTTAAAGTA 1364
Sequence_91     CAGAAGTCGAGTTTTTCATGGTAAACCAATTGAATA-ATACCAGAAAGAC-GTTAAAGTA 1364
Sequence_39     CAGAAGTCGAGTTTTTCATGGTAAACCAATTGAATA-ATACCAGAAAGAC-GTTAAAGTA 1373
Sequence_41     CAGAAGTCGAGTTTTTCATGGTAAACCAATTGAATA-ATACCAGAAAGAC-GTTAAAGTA 1370
Sequence_49     CAGAAGTCGAGTTTTTCATGGTAAACCAATTGAATA-ATACCAGAAAGAC-GTTAAAGTA 1367
Sequence_81     CAGAAGTCGAGTTTTTCATGGTAAACCAATTGAATA-ATACCAGAAAGAC-GTTAAAGTA 1367
Sequence_45     CAGAAGTCGAGTTTTTCATGGTAAACCAATTGAATA-ATACCAGAAAGAC-GTTAAAGTA 1370
Sequence_77     CAGAAGTCGAGTTTTTCATGGTAAACCAATTGAATA-ATACCAGAAAGAC-GTTAAAGTA 1370
Sequence_75     CAGAAGTCGAGTTTTTCATGGTAAACCAATTGAATA-ATACCAGAAAGAC-GTTAAAGTA 1367
Sequence_43     CAGAAGTCGAGTTTTTCATGGTAAACCAATTGAATA-ATACCAGAAAGAC-GTTAAAGTA 1367
Sequence_47     CAGAAGTCGAGTTTTTCATGGTAAACCAATTGAATA-ATACCAGAAAGAC-GTTAAAGTA 1370
Sequence_79     CAGAAGTCGAGTTTTTCATGGTAAACCAATTGAATA-ATACCAGAAAGAC-GTTAAAGTA 1370
Sequence_51     CAGAAGTCGAGTTTTTCATGGTAAACCAATTGAATA-ATACCAGAAAGAC-GTTAAAGTA 1376
Sequence_83     CAGAAGTCGAGTTTTTCATGGTAAACCAATTGAATA-ATACCAGAAAGAC-GTTAAAGTA 1376
Sequence_7      CAGAAGTCGAGTTTTTCATGGTAAACCAATTGAATA-ATACCAGAAAGAC-GTTAAAGTA 1364
Sequence_25     CAGAAGTCGAGTTTTTCATGGTAAACCAATTGAATA-ATACCAGAAAGAC-GTTAAAGTA 1364
Sequence_29     CAGAAGTCGAGTTTTTCATGGTAAACCAATTGAATA-ATACCAGAAAGAC-GTTAAAGTA 1364
Sequence_33     CAGAAGTCGAGTTTTTCATGGTAAACCAATTGAATA-ATACCAGAAAGAC-GTTAAAGTA 1364
Sequence_69     CAGAAGTCGAGTTTTTCATGGTAAACCAATTGAATA-ATACCAGAAAGAC-GTTAAAGTA 1364
Sequence_11     CAGAAGTCGAGTTTTTCATGGTAAACCAATTGAATA-ATACCAGAAAGAC-GTTAAAGTA 1352
Sequence_1      CAGAAGTCGAGTTTTTCATGGTAAACCAATTGAATA-ATACCAGAAAGAC-GTTAAAGTA 1352
Sequence_17     CAGAAGTCGAGTTTTTCATGGTAAACCAATTGAATA-ATACCAGAAAGAC-GTTAAAGTA 2082
Sequence_3      CAGAAGTCGAGTTTTTCATGGTAAACCAATTGAATA-ATACCAGAAAGAC-GTTAAAGTA 1352
Sequence_13     CAGAAGTCGAGTTTTTCATGGTAAACCAATTGAATA-ATACCAGAAAGAC-GTTAAAGTA 1352
Sequence_18     CAGAAGTCGAGTTTTTCATGGTAAACCAATTGAATA-ATACCAGAAAGAC-GTTAAAGTA 2605
Cry8Ka1         CATAAGTACAA------ACAATGGACTAGTGAGTTACATGTATGAAAAATTATCGAACTT 1346
                ** ****  *       *   *  ** * *     ** **    **** *   *  ** *
```

To Fig. 17Y

Fig. 17X

From Fig. 17X

```
Sequence_71      TAATCCAGTTTCCAAAGATATTATAGCGAGTACAAGAGATTCGGAATTAGAAT----TAC 1429
Sequence_73      TAATCCAGTTTCCAAAGATATTATAGCGAGTACAAGAGATTCGGAATTAGAAT----TAC 1426
Sequence_21      TAATCCAGTTTCCAAAGATATTATAGCGAGTACAAGAGATTCGGAATTAGAAT----TAC 1420
Sequence_67      TAATCCAGTTTCCAAAGATATTATAGCGAGTACAAGAGATTCGGAATTAGAAT----TAC 1420
Sequence_61      TAATCCAGTTTCCAAAGATATTATAGCGAGTACAAGAGATTCGGAATTAGAAT----TAC 1420
Sequence_93      TAATCCAGTTTCCAAAGATATTATAGCGAGTACAAGAGATTCGGAATTAGAAT----TAC 1420
Sequence_59      TAATCCAGTTTCCAAAGATATTATAGCGAGTACAAGAGATTCGGAATTAGAAT----TAC 1420
Sequence_91      TAATCCAGTTTCCAAAGATATTATAGCGAGTACAAGAGATTCGGAATTAGAAT----TAC 1420
Sequence_39      TAATCCAGTTTCCAAAGATATTATAGCGAGTACAAGAGATTCGGAATTAGAAT----TAC 1429
Sequence_41      TAATCCAGTTTCCAAAGATATTATAGCGAGTACAAGAGATTCGGAATTAGAAT----TAC 1426
Sequence_49      TAATCCAGTTTCCAAAGATATTATAGCGAGTACAAGAGATTCGGAATTAGAAT----TAC 1423
Sequence_81      TAATCCAGTTTCCAAAGATATTATAGCGAGTACAAGAGATTCGGAATTAGAAT----TAC 1423
Sequence_45      TAATCCAGTTTCCAAAGATATTATAGCGAGTACAAGAGATTCGGAATTAGAAT----TAC 1426
Sequence_77      TAATCCAGTTTCCAAAGATATTATAGCGAGTACAAGAGATTCGGAATTAGAAT----TAC 1426
Sequence_75      TAATCCAGTTTCCAAAGATATTATAGCGAGTACAAGAGATTCGGAATTAGAAT----TAC 1423
Sequence_43      TAATCCAGTTTCCAAAGATATTATAGCGAGTACAAGAGATTCGGAATTAGAAT----TAC 1423
Sequence_47      TAATCCAGTTTCCAAAGATATTATAGCGAGTACAAGAGATTCGGAATTAGAAT----TAC 1426
Sequence_79      TAATCCAGTTTCCAAAGATATTATAGCGAGTACAAGAGATTCGGAATTAGAAT----TAC 1426
Sequence_51      TAATCCAGTTTCCAAAGATATTATAGCGAGTACAAGAGATTCGGAATTAGAAT----TAC 1432
Sequence_83      TAATCCAGTTTCCAAAGATATTATAGCGAGTACAAGAGATTCGGAATTAGAAT----TAC 1432
Sequence_7       TAATCCAGTTTCCAAAGATATTATAGCGAGTACAAGAGATTCGGAATTAGAAT----TAC 1420
Sequence_25      TAATCCAGTTTCCAAAGATATTATAGCGAGTACAAGAGATTCGGAATTAGAAT----TAC 1420
Sequence_29      TAATCCAGTTTCCAAAGATATTATAGCGAGTACAAGAGATTCGGAATTAGAAT----TAC 1420
Sequence_33      TAATCCAGTTTCCAAAGATATTATAGCGAGTACAAGAGATTCGGAATTAGAAT----TAC 1420
Sequence_69      TAATCCAGTTTCCAAAGATATTATAGCGAGTACAAGAGATTCGGAATTAGAAT----TAC 1420
Sequence_11      TAATCCAGTTTCCAAAGATATTATAGCGAGTACAAGAGATTCGGAATTAGAAT----TAC 1408
Sequence_1       TAATCCAGTTTCCAAAGATATTATAGCGAGTACAAGAGATTCGGAATTAGAAT----TAC 1408
Sequence_17      TAATCCAGTTTCCAAAGATATTATAGCGAGTACAAGAGATTCGGAATTAGAAT----TAC 2138
Sequence_3       TAATCCGGTTTCCAAAGATATTATAGCGGGGACAAGAGATTCGGAATTAGAAT----TAC 1408
Sequence_13      TAATCCGGTTTCCAAAGATATTATAGCGGGGACAAGAGATTCGGAATTAGAAT----TAC 1408
Sequence_18      TAATCCGGTTTCCAAAGATATTATAGCGGGGACAAGAGATTCGGAATTAGAAT----TAC 2661
Cry8Ka1_         TTTTAATGAACTAAAAGATACAATTACAGAGCTACCTGTTCAGATATCCAGTCCTCCTAC 1406
                 *  *   *     *******  **  *      *   * *  *  **          ***
```

To Fig. 17Z

Fig. 17Y

From Fig. 17Y

```
Sequence_71    CTCCAGAAACTTCAGATCAACCAAATTATGAGTCATATAGCCATAGATTATGTCATATCA 1489
Sequence_73    CTCCAGAAACTTCAGATCAACCAAATTATGAGTCATATAGCCATAGATTATGTCATATCA 1486
Sequence_21    CTCCAGAAACTTCAGATCAACCAAATTATGAGTCATATAGCCATAGATTATGTCATATCA 1480
Sequence_67    CTCCAGAAACTTCAGATCAACCAAATTATGAGTCATATAGCCATAGATTATGTCATATCA 1480
Sequence_61    CTCCAGAAACTTCAGATCAACCAAATTATGAGTCATATAGCCATAGATTATGTCATATCA 1480
Sequence_93    CTCCAGAAACTTCAGATCAACCAAATTATGAGTCATATAGCCATAGATTATGTCATATCA 1480
Sequence_59    CTCCAGAAACTTCAGATCAACCAAATTATGAGTCATATAGCCATAGATTATGTCATATCA 1480
Sequence_91    CTCCAGAAACTTCAGATCAACCAAATTATGAGTCATATAGCCATAGATTATGTCATATCA 1480
Sequence_39    CTCCAGAAACTTCAGATCAACCAAATTATGAGTCATATAGCCATAGATTATGTCATATCA 1489
Sequence_41    CTCCAGAAACTTCAGATCAACCAAATTATGAGTCATATAGCCATAGATTATGTCATATCA 1486
Sequence_49    CTCCAGAAACTTCAGATCAACCAAATTATGAGTCATATAGCCATAGATTATGTCATATCA 1483
Sequence_81    CTCCAGAAACTTCAGATCAACCAAATTATGAGTCATATAGCCATAGATTATGTCATATCA 1483
Sequence_45    CTCCAGAAACTTCAGATCAACCAAATTATGAGTCATATAGCCATAGATTATGTCATATCA 1486
Sequence_77    CTCCAGAAACTTCAGATCAACCAAATTATGAGTCATATAGCCATAGATTATGTCATATCA 1486
Sequence_75    CTCCAGAAACTTCAGATCAACCAAATTATGAGTCATATAGCCATAGATTATGTCATATCA 1483
Sequence_43    CTCCAGAAACTTCAGATCAACCAAATTATGAGTCATATAGCCATAGATTATGTCATATCA 1483
Sequence_47    CTCCAGAAACTTCAGATCAACCAAATTATGAGTCATATAGCCATAGATTATGTCATATCA 1486
Sequence_79    CTCCAGAAACTTCAGATCAACCAAATTATGAGTCATATAGCCATAGATTATGTCATATCA 1486
Sequence_51    CTCCAGAAACTTCAGATCAACCAAATTATGAGTCATATAGCCATAGATTATGTCATATCA 1492
Sequence_83    CTCCAGAAACTTCAGATCAACCAAATTATGAGTCATATAGCCATAGATTATGTCATATCA 1492
Sequence_7     CTCCAGAAACTTCAGATCAACCAAATTATGAGTCATATAGCCATAGATTATGTCATATCA 1480
Sequence_25    CTCCAGAAACTTCAGATCAACCAAATTATGAGTCATATAGCCATAGATTATGTCATATCA 1480
Sequence_29    CTCCAGAAACTTCAGATCAACCAAATTATGAGTCATATAGCCATAGATTATGTCATATCA 1480
Sequence_33    CTCCAGAAACTTCAGATCAACCAAATTATGAGTCATATAGCCATAGATTATGTCATATCA 1480
Sequence_69    CTCCAGAAACTTCAGATCAACCAAATTATGAGTCATATAGCCATAGATTATGTCATATCA 1480
Sequence_11    CTCCAGAAACTTCAGATCAACCAAATTATGAGTCATATAGCCATAGATTATGTCATATCA 1468
Sequence_1     CTCCAGAAACTTCAGATCAACCAAATTATGAGTCATATAGCCATAGATTATGTCATATCA 1468
Sequence_17    CTCCAGAAACTTCAGATCAACCAAATTATGAGTCATATAGCCATAGATTATGTCATATCA 2198
Sequence_3     CTCCAGAAACTTCAGATCAACCAAATTATGAGTCATATAGCCATAGATTATGTCATATCA 1468
Sequence_13    CTCCAGAAACTTCAGATCAACCAAATTATGAGTCATATAGCCATAGATTATGTCATATCA 1468
Sequence_18    CTCCAGAAACTTCAGATCAACCAAATTATGAGTCATATAGCCATAGATTATGTCATATCA 2721
Cry8Ka1_       CTACGGGGA-TGCTGAACAGTACAGTCATCGGCTATCCTAT-GTTTCTAATGCTCCAACA 1464
               ** * *  * * * ** **    * * **  *  **       *   * ***    * **
```

To Fig. 17AA

Fig. 17Z

From Fig. 17Z

```
Sequence_71      CAAGTATTCCCGCGACGGG--TAACACTACCGGATTAGTACCTGTATTTTCTTGGACACA 1547
Sequence_73      CAAGTATTCCCGCGACGGG--TAACACTACCGGATTAGTACCTGTATTTTCTTGGACACA 1544
Sequence_21      CAAGTATTCCCGCGACGGG--TAACACTACCGGATTAGTACCTGTATTTTCTTGGACACA 1538
Sequence_67      CAAGTATTCCCGCGACGGG--TAACACTACCGGATTAGTACCTGTATTTTCTTGGACACA 1538
Sequence_61      CAAGTATTCCCGCGACGGG--TAACACTACCGGATTAGTACCTGTATTTTCTTGGACACA 1538
Sequence_93      CAAGTATTCCCGCGACGGG--TAACACTACCGGATTAGTACCTGTATTTTCTTGGACACA 1538
Sequence_59      CAAGTATTCCCGCGACGGG--TAACACTACCGGATTAGTACCTGTATTTTCTTGGACACA 1538
Sequence_91      CAAGTATTCCCGCGACGGG--TAACACTACCGGATTAGTACCTGTATTTTCTTGGACACA 1538
Sequence_39      CAAGTATTCCCGCGACGGG--TAACACTACCGGATTAGTACCTGTATTTTCTTGGACACA 1547
Sequence_41      CAAGTATTCCCGCGACGGG--TAACACTACCGGATTAGTACCTGTATTTTCTTGGACACA 1544
Sequence_49      CAAGTATTCCCGCGACGGG--TAACACTACCGGATTAGTACCTGTATTTTCTTGGACACA 1541
Sequence_81      CAAGTATTCCCGCGACGGG--TAACACTACCGGATTAGTACCTGTATTTTCTTGGACACA 1541
Sequence_45      CAAGTATTCCCGCGACGGG--TAACACTACCGGATTAGTACCTGTATTTTCTTGGACACA 1544
Sequence_77      CAAGTATTCCCGCGACGGG--TAACACTACCGGATTAGTACCTGTATTTTCTTGGACACA 1544
Sequence_75      CAAGTATTCCCGCGACGGG--TAACACTACCGGATTAGTACCTGTATTTTCTTGGACACA 1541
Sequence_43      CAAGTATTCCCGCGACGGG--TAACACTACCGGATTAGTACCTGTATTTTCTTGGACACA 1541
Sequence_47      CAAGTATTCCCGCGACGGG--TAACACTACCGGATTAGTACCTGTATTTTCTTGGACACA 1544
Sequence_79      CAAGTATTCCCGCGACGGG--TAACACTACCGGATTAGTACCTGTATTTTCTTGGACACA 1544
Sequence_51      CAAGTATTCCCGCGACGGG--TAACACTACCGGATTAGTACCTGTATTTTCTTGGACACA 1550
Sequence_83      CAAGTATTCCCGCGACGGG--TAACACTACCGGATTAGTACCTGTATTTTCTTGGACACA 1550
Sequence_7       CAAGTATTCCCGCGACGGG--TAACACTACCGGATTAGTACCTGTATTTTCTTGGACACA 1538
Sequence_25      CAAGTATTCCCGCGACGGG--TAACACTACCGGATTAGTACCTGTATTTTCTTGGACACA 1538
Sequence_29      CAAGTATTCCCGCGACGGG--TAACACTACCGGATTAGTACCTGTATTTTCTTGGACACA 1538
Sequence_33      CAAGTATTCCCGCGACGGG--TAACACTACCGGATTAGTACCTGTATTTTCTTGGACACA 1538
Sequence_69      CAAGTATTCCCGCGACGGG--TAACACTACCGGATTAGTACCTGTATTTTCTTGGACACA 1538
Sequence_11      CAAGTATTCCCGCGACGGG--TAACACTACCGGATTAGTACCTGTATTTTCTTGGACACA 1526
Sequence_1       CAAGTATTCCCGCGACGGG--TAACACTACCGGATTAGTACCTGTATTTTCTTGGACACA 1526
Sequence_17      CAAGTATTCCCGCGACGGG--TAACACTACCGGATTAGTACCTGTATTTTCTTGGACACA 2256
Sequence_3       CAAGTATTCCCGCGACGGG--TTCAACTACCGGATTAGTACCTGTATTTTCTTGGACACA 1526
Sequence_13      CAAGTATTCCCGCGACGGG--TTCAACTACCGGATTAGTACCTGTATTTTCTTGGACACA 1526
Sequence_18      CAAGTATTCCCGCGACGGG--TTCAACTACCGGATTAGTACCTGTATTTTCTTGGACACA 2779
Cry8Ka1_         -GAGTACTCTTCGGGCGGACATTTAATTTTGGGACTAATCCCAGTACTGGGTTGGACGCA 1523
                   **** **    * ***   *   * *   *** ** * ** *** *   ****** **
```

To Fig. 17AB

Fig. 17AA

From Fig. 17AA

```
Sequence_71    TCGAAGTGCAGATTTAAACAATACAATATATTCAGATAAAATCACTCAAATTCCGGCCGT 1607
Sequence_73    TCGAAGTGCAGATTTAAACAATACAATATATTCAGATAAAATCACTCAAATTCCGGCCGT 1604
Sequence_21    TCGAAGTGCAGATTTAAACAATACAATATATTCAGATAAAATCACTCAAATTCCGGCCGT 1598
Sequence_67    TCGAAGTGCAGATTTAAACAATACAATATATTCAGATAAAATCACTCAAATTCCGGCCGT 1598
Sequence_61    TCGAAGTGCAGATTTAAACAATACAATATATTCAGATAAAATCACTCAAATTCCGGCCGT 1598
Sequence_93    TCGAAGTGCAGATTTAAACAATACAATATATTCAGATAAAATCACTCAAATTCCGGCCGT 1598
Sequence_59    TCGAAGTGCAGATTTAAACAATACAATATATTCAGATAAAATCACTCAAATTCCGGCCGT 1598
Sequence_91    TCGAAGTGCAGATTTAAACAATACAATATATTCAGATAAAATCACTCAAATTCCGGCCGT 1598
Sequence_39    TCGAAGTGCAGATTTAAACAATACAATATATTCAGATAAAATCACTCAAATTCCGGCCGT 1607
Sequence_41    TCGAAGTGCAGATTTAAACAATACAATATATTCAGATAAAATCACTCAAATTCCGGCCGT 1604
Sequence_49    TCGAAGTGCAGATTTAAACAATACAATATATTCAGATAAAATCACTCAAATTCCGGCCGT 1601
Sequence_81    TCGAAGTGCAGATTTAAACAATACAATATATTCAGATAAAATCACTCAAATTCCGGCCGT 1601
Sequence_45    TCGAAGTGCAGATTTAAACAATACAATATATTCAGATAAAATCACTCAAATTCCGGCCGT 1604
Sequence_77    TCGAAGTGCAGATTTAAACAATACAATATATTCAGATAAAATCACTCAAATTCCGGCCGT 1604
Sequence_75    TCGAAGTGCAGATTTAAACAATACAATATATTCAGATAAAATCACTCAAATTCCGGCCGT 1601
Sequence_43    TCGAAGTGCAGATTTAAACAATACAATATATTCAGATAAAATCACTCAAATTCCGGCCGT 1601
Sequence_47    TCGAAGTGCAGATTTAAACAATACAATATATTCAGATAAAATCACTCAAATTCCGGCCGT 1604
Sequence_79    TCGAAGTGCAGATTTAAACAATACAATATATTCAGATAAAATCACTCAAATTCCGGCCGT 1604
Sequence_51    TCGAAGTGCAGATTTAAACAATACAATATATTCAGATAAAATCACTCAAATTCCGGCCGT 1610
Sequence_83    TCGAAGTGCAGATTTAAACAATACAATATATTCAGATAAAATCACTCAAATTCCGGCCGT 1610
Sequence_7     TCGAAGTGCAGATTTAAACAATACAATATATTCAGATAAAATCACTCAAATTCCGGCCGT 1598
Sequence_25    TCGAAGTGCAGATTTAAACAATACAATATATTCAGATAAAATCACTCAAATTCCGGCCGT 1598
Sequence_29    TCGAAGTGCAGATTTAAACAATACAATATATTCAGATAAAATCACTCAAATTCCGGCCGT 1598
Sequence_33    TCGAAGTGCAGATTTAAACAATACAATATATTCAGATAAAATCACTCAAATTCCGGCCGT 1598
Sequence_69    TCGAAGTGCAGATTTAAACAATACAATATATTCAGATAAAATCACTCAAATTCCGGCCGT 1598
Sequence_11    TCGAAGTGCAGATTTAAACAATACAATATATTCAGATAAAATCACTCAAATTCCGGCCGT 1586
Sequence_1     TCGAAGTGCAGATTTAAACAATACAATATATTCAGATAAAATCACTCAAATTCCGGCCGT 1586
Sequence_17    TCGAAGTGCAGATTTAAACAATACAATATATTCAGATAAAATCACTCAAATTCCGGCCGT 2316
Sequence_3     TCGGAGTGCCGATCTTATAAATGCAGTTCATTCAGATAAAATTACTCAGATTCCGGTCGT 1586
Sequence_13    TCGGAGTGCCGATCTTATAAATGCAGTTCATTCAGATAAAATTACTCAGATTCCGGTCGT 1586
Sequence_18    TCGGAGTGCCGATCTTATAAATGCAGTTCATTCAGATAAAATTACTCAGATTCCGGTCGT 2839
Cry8Ka1        TACTAGTTTAACTCAAACAAATCAGATACATTCTGACTCAATTACTCAAATTCCAGCTGT 1583
               *   ***     *   *  ***    *  **** **   *** ***** ***** *  **
```

To Fig. 17AC

Fig. 17AB

From Fig. 17AB

```
Sequence_71      TAAATGTTGGGATAATTTACCGTTTGTTCCAGTGGT----AAAAGGACCAGGACATACAG 1663
Sequence_73      TAAATGTTGGGATAATTTACCGTTTGTTCCAGTGGT----AAAAGGACCAGGACATACAG 1660
Sequence_21      TAAATGTTGGGATAATTTACCGTTTGTTCCAGTGGT----AAAAGGACCAGGACATACAG 1654
Sequence_67      TAAATGTTGGGATAATTTACCGTTTGTTCCAGTGGT----AAAAGGACCAGGACATACAG 1654
Sequence_61      TAAATGTTGGGATAATTTACCGTTTGTTCCAGTGGT----AAAAGGACCAGGACATACAG 1654
Sequence_93      TAAATGTTGGGATAATTTACCGTTTGTTCCAGTGGT----AAAAGGACCAGGACATACAG 1654
Sequence_59      TAAATGTTGGGATAATTTACCGTTTGTTCCAGTGGT----AAAAGGACCAGGACATACAG 1654
Sequence_91      TAAATGTTGGGATAATTTACCGTTTGTTCCAGTGGT----AAAAGGACCAGGACATACAG 1654
Sequence_39      TAAATGTTGGGATAATTTACCGTTTGTTCCAGTGGT----AAAAGGACCAGGACATACAG 1663
Sequence_41      TAAATGTTGGGATAATTTACCGTTTGTTCCAGTGGT----AAAAGGACCAGGACATACAG 1660
Sequence_49      TAAATGTTGGGATAATTTACCGTTTGTTCCAGTGGT----AAAAGGACCAGGACATACAG 1657
Sequence_81      TAAATGTTGGGATAATTTACCGTTTGTTCCAGTGGT----AAAAGGACCAGGACATACAG 1657
Sequence_45      TAAATGTTGGGATAATTTACCGTTTGTTCCAGTGGT----AAAAGGACCAGGACATACAG 1660
Sequence_77      TAAATGTTGGGATAATTTACCGTTTGTTCCAGTGGT----AAAAGGACCAGGACATACAG 1660
Sequence_75      TAAATGTTGGGATAATTTACCGTTTGTTCCAGTGGT----AAAAGGACCAGGACATACAG 1657
Sequence_43      TAAATGTTGGGATAATTTACCGTTTGTTCCAGTGGT----AAAAGGACCAGGACATACAG 1657
Sequence_47      TAAATGTTGGGATAATTTACCGTTTGTTCCAGTGGT----AAAAGGACCAGGACATACAG 1660
Sequence_79      TAAATGTTGGGATAATTTACCGTTTGTTCCAGTGGT----AAAAGGACCAGGACATACAG 1660
Sequence_51      TAAATGTTGGGATAATTTACCGTTTGTTCCAGTGGT----AAAAGGACCAGGACATACAG 1666
Sequence_83      TAAATGTTGGGATAATTTACCGTTTGTTCCAGTGGT----AAAAGGACCAGGACATACAG 1666
Sequence_7       TAAATGTTGGGATAATTTACCGTTTGTTCCAGTGGT----AAAAGGACCAGGACATACAG 1654
Sequence_25      TAAATGTTGGGATAATTTACCGTTTGTTCCAGTGGT----AAAAGGACCAGGACATACAG 1654
Sequence_29      TAAATGTTGGGATAATTTACCGTTTGTTCCAGTGGT----AAAAGGACCAGGACATACAG 1654
Sequence_33      TAAATGTTGGGATAATTTACCGTTTGTTCCAGTGGT----AAAAGGACCAGGACATACAG 1654
Sequence_69      TAAATGTTGGGATAATTTACCGTTTGTTCCAGTGGT----AAAAGGACCAGGACATACAG 1654
Sequence_11      TAAATGTTGGGATAATTTACCGTTTGTTCCAGTGGT----AAAAGGACCAGGACATACAG 1642
Sequence_1       TAAATGTTGGGATAATTTACCGTTTGTTCCAGTGGT----AAAAGGACCAGGACATACAG 1642
Sequence_17      TAAATGTTGGGATAATTTACCGTTTGTTCCAGTGGT----AAAAGGACCAGGACATACAG 2372
Sequence_3       AAAGGTTTCTGATTTGGCTCCCTCTATAACAGGAGGGCCAAATAATACCGTTGTATCGGG 1646
Sequence_13      AAAGGTTTCTGATTTGGCTCCCTCTATAACAGGAGGGCCAAATAATACCGTTGTATCGGG 1646
Sequence_18      AAAGGTTTCTGATTTGGCTCCCTCTATAACAGGAGGGCCAAATAATACCGTTGTATCGGG 2899
Cry8Ka1          TAAAGCAAATAGTGTTAGTTCTTATGT------------------TACTGTTGAAAAGGG 1625
                  **          *        * * * *                  **       *    *
```

To Fig. 17AD

Fig. 17AC

From Fig. 17AC

```
Sequence_71         GAGGGGATTTATTACAGT----ATAATAGAAGTACTG-GTTCTGTAGGAACCTTATTTCT 1718
Sequence_73         GAGGGGATTTATTACAGT----ATAATAGAAGTACTG-GTTCTGTAGGAACCTTATTTCT 1715
Sequence_21         GAGGGGATTTATTACAGT----ATAATAGAAGTACTG-GTTCTGTAGGAACCTTATTTCT 1709
Sequence_67         GAGGGGATTTATTACAGT----ATAATAGAAGTACTG-GTTCTGTAGGAACCTTATTTCT 1709
Sequence_61         GAGGGGATTTATTACAGT----ATAATAGAAGTACTG-GTTCTGTAGGAACCTTATTTCT 1709
Sequence_93         GAGGGGATTTATTACAGT----ATAATAGAAGTACTG-GTTCTGTAGGAACCTTATTTCT 1709
Sequence_59         GAGGGGATTTATTACAGT----ATAATAGAAGTACTG-GTTCTGTAGGAACCTTATTTCT 1709
Sequence_91         GAGGGGATTTATTACAGT----ATAATAGAAGTACTG-GTTCTGTAGGAACCTTATTTCT 1709
Sequence_39         GAGGGGATTTATTACAGT----ATAATAGAAGTACTG-GTTCTGTAGGAACCTTATTTCT 1718
Sequence_41         GAGGGGATTTATTACAGT----ATAATAGAAGTACTG-GTTCTGTAGGAACCTTATTTCT 1715
Sequence_49         GAGGGGATTTATTACAGT----ATAATAGAAGTACTG-GTTCTGTAGGAACCTTATTTCT 1712
Sequence_81         GAGGGGATTTATTACAGT----ATAATAGAAGTACTG-GTTCTGTAGGAACCTTATTTCT 1712
Sequence_45         GAGGGGATTTATTACAGT----ATAATAGAAGTACTG-GTTCTGTAGGAACCTTATTTCT 1715
Sequence_77         GAGGGGATTTATTACAGT----ATAATAGAAGTACTG-GTTCTGTAGGAACCTTATTTCT 1715
Sequence_75         GAGGGGATTTATTACAGT----ATAATAGAAGTACTG-GTTCTGTAGGAACCTTATTTCT 1712
Sequence_43         GAGGGGATTTATTACAGT----ATAATAGAAGTACTG-GTTCTGTAGGAACCTTATTTCT 1712
Sequence_47         GAGGGGATTTATTACAGT----ATAATAGAAGTACTG-GTTCTGTAGGAACCTTATTTCT 1715
Sequence_79         GAGGGGATTTATTACAGT----ATAATAGAAGTACTG-GTTCTGTAGGAACCTTATTTCT 1715
Sequence_51         GAGGGGATTTATTACAGT----ATAATAGAAGTACTG-GTTCTGTAGGAACCTTATTTCT 1721
Sequence_83         GAGGGGATTTATTACAGT----ATAATAGAAGTACTG-GTTCTGTAGGAACCTTATTTCT 1721
Sequence_7          GAGGGGATTTATTACAGT----ATAATAGAAGTACTG-GTTCTGTAGGAACCTTATTTCT 1709
Sequence_25         GAGGGGATTTATTACAGT----ATAATAGAAGTACTG-GTTCTGTAGGAACCTTATTTCT 1709
Sequence_29         GAGGGGATTTATTACAGT----ATAATAGAAGTACTG-GTTCTGTAGGAACCTTATTTCT 1709
Sequence_33         GAGGGGATTTATTACAGT----ATAATAGAAGTACTG-GTTCTGTAGGAACCTTATTTCT 1709
Sequence_69         GAGGGGATTTATTACAGT----ATAATAGAAGTACTG-GTTCTGTAGGAACCTTATTTCT 1709
Sequence_11         GAGGGGATTTATTACAGT----ATAATAGAAGTACTG-GTTCTGTAGGAACCTTATTTCT 1697
Sequence_1          GAGGGGATTTATTACAGT----ATAATAGAAGTACTG-GTTCTGTAGGAACCTTATTTCT 1697
Sequence_17         GAGGGGATTTATTACAGT----ATAATAGAAGTACTG-GTTCTGTAGGAACCTTATTTCT 2427
Sequence_3          TCCTGGATTTACAGGGGGGGGGATAATAAAAGTAATAAGAAATGGAGTAATTATATCACA 1706
Sequence_13         TCCTGGATTTACAGGGGGGGGGATAATAAAAGTAATAAGAAATGGAGTAATTATATCACA 1706
Sequence_18         TCCTGGATTTACAGGGGGGGGGATAATAAAAGTAATAAGAAATGGAGTAATTATATCACA 2959
Cry8Ka1             AACAGGCTTTACAGGTGGAGATTTAGTGAAATTCTCC---ACTGGATTCATGTCTACAGG 1682
                        ** ****     *      ** *  ** *         ** *   *
```

To Fig. 17AE

Fig. 17AD

From Fig. 17AD

```
Sequence_71       AGCTCGATATGGCCTAGCATTAGAAAAAGCAGGGAAATATCGTGTAAGACTGAGATATGC 1778
Sequence_73       AGCTCGATATGGCCTAGCATTAGAAAAAGCAGGGAAATATCGTGTAAGACTGAGATATGC 1775
Sequence_21       AGCTCGATATGGCCTAGCATTAGAAAAAGCAGGGAAATATCGTGTAAGACTGAGATATGC 1769
Sequence_67       AGCTCGATATGGCCTAGCATTAGAAAAAGCAGGGAAATATCGTGTAAGACTGAGATATGC 1769
Sequence_61       AGCTCGATATGGCCTAGCATTAGAAAAAGCAGGGAAATATCGTGTAAGACTGAGATATGC 1769
Sequence_93       AGCTCGATATGGCCTAGCATTAGAAAAAGCAGGGAAATATCGTGTAAGACTGAGATATGC 1769
Sequence_59       AGCTCGATATGGCCTAGCATTAGAAAAAGCAGGGAAATATCGTGTAAGACTGAGATATGC 1769
Sequence_91       AGCTCGATATGGCCTAGCATTAGAAAAAGCAGGGAAATATCGTGTAAGACTGAGATATGC 1769
Sequence_39       AGCTCGATATGGCCTAGCATTAGAAAAAGCAGGGAAATATCGTGTAAGACTGAGATATGC 1778
Sequence_41       AGCTCGATATGGCCTAGCATTAGAAAAAGCAGGGAAATATCGTGTAAGACTGAGATATGC 1775
Sequence_49       AGCTCGATATGGCCTAGCATTAGAAAAAGCAGGGAAATATCGTGTAAGACTGAGATATGC 1772
Sequence_81       AGCTCGATATGGCCTAGCATTAGAAAAAGCAGGGAAATATCGTGTAAGACTGAGATATGC 1772
Sequence_45       AGCTCGATATGGCCTAGCATTAGAAAAAGCAGGGAAATATCGTGTAAGACTGAGATATGC 1775
Sequence_77       AGCTCGATATGGCCTAGCATTAGAAAAAGCAGGGAAATATCGTGTAAGACTGAGATATGC 1775
Sequence_75       AGCTCGATATGGCCTAGCATTAGAAAAAGCAGGGAAATATCGTGTAAGACTGAGATATGC 1772
Sequence_43       AGCTCGATATGGCCTAGCATTAGAAAAAGCAGGGAAATATCGTGTAAGACTGAGATATGC 1772
Sequence_47       AGCTCGATATGGCCTAGCATTAGAAAAAGCAGGGAAATATCGTGTAAGACTGAGATATGC 1775
Sequence_79       AGCTCGATATGGCCTAGCATTAGAAAAAGCAGGGAAATATCGTGTAAGACTGAGATATGC 1775
Sequence_51       AGCTCGATATGGCCTAGCATTAGAAAAAGCAGGGAAATATCGTGTAAGACTGAGATATGC 1781
Sequence_83       AGCTCGATATGGCCTAGCATTAGAAAAAGCAGGGAAATATCGTGTAAGACTGAGATATGC 1781
Sequence_7        AGCTCGATATGGCCTAGCATTAGAAAAAGCAGGGAAATATCGTGTAAGACTGAGATATGC 1769
Sequence_25       AGCTCGATATGGCCTAGCATTAGAAAAAGCAGGGAAATATCGTGTAAGACTGAGATATGC 1769
Sequence_29       AGCTCGATATGGCCTAGCATTAGAAAAAGCAGGGAAATATCGTGTAAGACTGAGATATGC 1769
Sequence_33       AGCTCGATATGGCCTAGCATTAGAAAAAGCAGGGAAATATCGTGTAAGACTGAGATATGC 1769
Sequence_69       AGCTCGATATGGCCTAGCATTAGAAAAAGCAGGGAAATATCGTGTAAGACTGAGATATGC 1769
Sequence_11       AGCTCGATATGGCCTAGCATTAGAAAAAGCAGGGAAATATCGTGTAAGACTGAGATATGC 1757
Sequence_1        AGCTCGATATGGCCTAGCATTAGAAAAAGCAGGGAAATATCGTGTAAGACTGAGATATGC 1757
Sequence_17       AGCTCGATATGGCCTAGCATTAGAAAAAGCAGGGAAATATCGTGTAAGACTGAGATATGC 2487
Sequence_3        TATGCG---TGTTAAAATTTCAGACATTAACAAAGAATATAGTATGAGGATTCGGTATGC 1763
Sequence_13       TATGCG---TGTTAAAATTTCAGACATTAACAAAGAATATAGTATGAGGATTCGGTATGC 1763
Sequence_18       TATGCG---TGTTAAAATTTCAGACATTAACAAAGAATATAGTATGAGGATTCGGTATGC 3016
Cry8Ka1           AATACAGTTTAATTTAAAGATAGAAGAAAGAAAGCGTTATCGTATCCGTATACGATATGC 1742
                      *    *     *     ***             *** ** *  *  *  * *****
```

To Fig. 17AF

Fig. 17AE

From Fig. 17AE

```
Sequence_71     TACTGATGCAGATATTGTATTGCATGTAAAC------------GATGCTCAGATTCAGAT 1826
Sequence_73     TACTGATGCAGATATTGTATTGCATGTAAAC------------GATGCTCAGATTCAGAT 1823
Sequence_21     TACTGATGCAGATATTGTATTGCATGTAAAC------------GATGCTCAGATTCAGAT 1817
Sequence_67     TACTGATGCAGATATTGTATTGCATGTAAAC------------GATGCTCAGATTCAGAT 1817
Sequence_61     TACTGATGCAGATATTGTATTGCATGTAAAC------------GATGCTCAGATTCAGAT 1817
Sequence_93     TACTGATGCAGATATTGTATTGCATGTAAAC------------GATGCTCAGATTCAGAT 1817
Sequence_59     TACTGATGCAGATATTGTATTGCATGTAAAC------------GATGCTCAGATTCAGAT 1817
Sequence_91     TACTGATGCAGATATTGTATTGCATGTAAAC------------GATGCTCAGATTCAGAT 1817
Sequence_39     TACTGATGCAGATATTGTATTGCATGTAAAC------------GATGCTCAGATTCAGAT 1826
Sequence_41     TACTGATGCAGATATTGTATTGCATGTAAAC------------GATGCTCAGATTCAGAT 1823
Sequence_49     TACTGATGCAGATATTGTATTGCATGTAAAC------------GATGCTCAGATTCAGAT 1820
Sequence_81     TACTGATGCAGATATTGTATTGCATGTAAAC------------GATGCTCAGATTCAGAT 1820
Sequence_45     TACTGATGCAGATATTGTATTGCATGTAAAC------------GATGCTCAGATTCAGAT 1823
Sequence_77     TACTGATGCAGATATTGTATTGCATGTAAAC------------GATGCTCAGATTCAGAT 1823
Sequence_75     TACTGATGCAGATATTGTATTGCATGTAAAC------------GATGCTCAGATTCAGAT 1820
Sequence_43     TACTGATGCAGATATTGTATTGCATGTAAAC------------GATGCTCAGATTCAGAT 1820
Sequence_47     TACTGATGCAGATATTGTATTGCATGTAAAC------------GATGCTCAGATTCAGAT 1823
Sequence_79     TACTGATGCAGATATTGTATTGCATGTAAAC------------GATGCTCAGATTCAGAT 1823
Sequence_51     TACTGATGCAGATATTGTATTGCATGTAAAC------------GATGCTCAGATTCAGAT 1829
Sequence_83     TACTGATGCAGATATTGTATTGCATGTAAAC------------GATGCTCAGATTCAGAT 1829
Sequence_7      TACTGATGCAGATATTGTATTGCATGTAAAC------------GATGCTCAGATTCAGAT 1817
Sequence_25     TACTGATGCAGATATTGTATTGCATGTAAAC------------GATGCTCAGATTCAGAT 1817
Sequence_29     TACTGATGCAGATATTGTATTGCATGTAAAC------------GATGCTCAGATTCAGAT 1817
Sequence_33     TACTGATGCAGATATTGTATTGCATGTAAAC------------GATGCTCAGATTCAGAT 1817
Sequence_69     TACTGATGCAGATATTGTATTGCATGTAAAC------------GATGCTCAGATTCAGAT 1817
Sequence_11     TACTGATGCAGATATTGTATTGCATGTAAAC------------GATGCTCAGATTCAGAT 1805
Sequence_1      TACTGATGCAGATATTGTATTGCATGTAAAC------------GATGCTCAGATTCAGAT 1805
Sequence_17     TACTGATGCAGATATTGTATTGCATGTAAAC------------GATGCTCAGATTCAGAT 2535
Sequence_3      TTCCGCTAATAATACTGAATTTTATATAAATCCTTCTGAAGAAAACGTTAAATCTCACGC 1823
Sequence_13     TTCCGCTAATAATACTGAATTTTATATAAATCCTTCTGAAGAAAACGTTAAATCTCACGC 1823
Sequence_18     TTCCGCTAATAATACTGAATTTTATATAAATCCTTCTGAAGAAAACGTTAAATCTCACGC 3076
Cry8Ka1         CGCTGATGTTAATGCT--ACTCTATCTGCACTTGGATTAA-ATGATGCATTTATTAACAT 1799
                  * * *    **  *  * *  ** *  *              * *       * *
```

To Fig. 17AG

Fig. 17AF

From Fig. 17AF

```
Sequence_71      GCCAAAAACAATGAACCCAGGTGAGGATCTGACATCTAAAACTTTTAAAGTTGCAGATGC 1886
Sequence_73      GCCAAAAACAATGAACCCAGGTGAGGATCTGACATCTAAAACTTTTAAAGTTGCAGATGC 1883
Sequence_21      GCCAAAAACAATGAACCCAGGTGAGGATCTGACATCTAAAACTTTTAAAGTTGCAGATGC 1877
Sequence_67      GCCAAAAACAATGAACCCAGGTGAGGATCTGACATCTAAAACTTTTAAAGTTGCAGATGC 1877
Sequence_61      GCCAAAAACAATGAACCCAGGTGAGGATCTGACATCTAAAACTTTTAAAGTTGCAGATGC 1877
Sequence_93      GCCAAAAACAATGAACCCAGGTGAGGATCTGACATCTAAAACTTTTAAAGTTGCAGATGC 1877
Sequence_59      GCCAAAAACAATGAACCCAGGTGAGGATCTGACATCTAAAACTTTTAAAGTTGCAGATGC 1877
Sequence_91      GCCAAAAACAATGAACCCAGGTGAGGATCTGACATCTAAAACTTTTAAAGTTGCAGATGC 1877
Sequence_39      GCCAAAAACAATGAACCCAGGTGAGGATCTGACATCTAAAACTTTTAAAGTTGCAGATGC 1886
Sequence_41      GCCAAAAACAATGAACCCAGGTGAGGATCTGACATCTAAAACTTTTAAAGTTGCAGATGC 1883
Sequence_49      GCCAAAAACAATGAACCCAGGTGAGGATCTGACATCTAAAACTTTTAAAGTTGCAGATGC 1880
Sequence_81      GCCAAAAACAATGAACCCAGGTGAGGATCTGACATCTAAAACTTTTAAAGTTGCAGATGC 1880
Sequence_45      GCCAAAAACAATGAACCCAGGTGAGGATCTGACATCTAAAACTTTTAAAGTTGCAGATGC 1883
Sequence_77      GCCAAAAACAATGAACCCAGGTGAGGATCTGACATCTAAAACTTTTAAAGTTGCAGATGC 1883
Sequence_75      GCCAAAAACAATGAACCCAGGTGAGGATCTGACATCTAAAACTTTTAAAGTTGCAGATGC 1880
Sequence_43      GCCAAAAACAATGAACCCAGGTGAGGATCTGACATCTAAAACTTTTAAAGTTGCAGATGC 1880
Sequence_47      GCCAAAAACAATGAACCCAGGTGAGGATCTGACATCTAAAACTTTTAAAGTTGCAGATGC 1883
Sequence_79      GCCAAAAACAATGAACCCAGGTGAGGATCTGACATCTAAAACTTTTAAAGTTGCAGATGC 1883
Sequence_51      GCCAAAAACAATGAACCCAGGTGAGGATCTGACATCTAAAACTTTTAAAGTTGCAGATGC 1889
Sequence_83      GCCAAAAACAATGAACCCAGGTGAGGATCTGACATCTAAAACTTTTAAAGTTGCAGATGC 1889
Sequence_7       GCCAAAAACAATGAACCCAGGTGAGGATCTGACATCTAAAACTTTTAAAGTTGCAGATGC 1877
Sequence_25      GCCAAAAACAATGAACCCAGGTGAGGATCTGACATCTAAAACTTTTAAAGTTGCAGATGC 1877
Sequence_29      GCCAAAAACAATGAACCCAGGTGAGGATCTGACATCTAAAACTTTTAAAGTTGCAGATGC 1877
Sequence_33      GCCAAAAACAATGAACCCAGGTGAGGATCTGACATCTAAAACTTTTAAAGTTGCAGATGC 1877
Sequence_69      GCCAAAAACAATGAACCCAGGTGAGGATCTGACATCTAAAACTTTTAAAGTTGCAGATGC 1877
Sequence_11      GCCAAAAACAATGAACCCAGGTGAGGATCTGACATCTAAAACTTTTAAAGTTGCAGATGC 1865
Sequence_1       GCCAAAAACAATGAACCCAGGTGAGGATCTGACATCTAAAACTTTTAAAGTTGCAGATGC 1865
Sequence_17      GCCAAAAACAATGAACCCAGGTGAGGATCTGACATCTAAAACTTTTAAAGTTGCAGATGC 2595
Sequence_3       TCAAAAAACTATGAATAGAGGTGAAGCTTTAACATATAATAAATTTAATTATGC-GACTT 1882
Sequence_13      TCAAAAAACTATGAATAGAGGTGAAGCTTTAACATATAATAAATTTAATTATGC-GACTT 1882
Sequence_18      TCAAAAAACTATGAATAGAGGTGAAGCTTTAACATATAATAAATTTAATTATGC-GACTT 3135
Cry8Ka1          TAAATCGACAATGTCTCAAGACACACCATTGAAGTATAACGATTTCCAATATGCAGAAGC 1859
                     *    ** ***      **            * *  * ***     **  *    *** **
```

To Fig. 17AH

Fig. 17AG

From Fig. 17AG

```
Sequence_71    TATCACAACAGTTAATTTA--GCAACAGATAGTTCGGTTGCAGTTAAA--CATAATTTAG 1942
Sequence_73    TATCACAACAGTTAATTTA--GCAACAGATAGTTCGGTTGCAGTTAAA--CATAATTTAG 1939
Sequence_21    TATCACAACAGTAAATTTA--GCAACAGATAGTTCGGTAGCAGTGAAA--CATAATGTAG 1933
Sequence_67    TATCACAACAGTAAATTTA--GCAACAGATAGTTCGGTAGCAGTGAAA--CATAATTTAG 1933
Sequence_61    TATCACAACAGTTAATTTA--GCAACAGATAGTTCGGTTGCAGTTAAA--CATAATGTAG 1933
Sequence_93    TATCACAACAGTTAATTTA--GCAACAGATAGTTCGGTTGCAGTTAAA--CATAATTTAG 1933
Sequence_59    TATCACAACAGTTAATTTA--GCAACAGATAGTTCGGTTGCAGTTAAA--CATAATGTAG 1933
Sequence_91    TATCACAACAGTTAATTTA--GCAACAGATAGTTCGGTTGCAGTTAAA--CATAATTTAG 1933
Sequence_39    TATCACAACAGTTAATTTA--GCAACAGATAGTTCGGTTGCAGTTAAA--CATAATGTAG 1942
Sequence_41    TATCACAACAGTTAATTTA--GCAACAGATAGTTCGGTTGCAGTTAAA--CATAATGTAG 1939
Sequence_49    TATCACAACAGTTAATTTA--GCAACAGATAGTTCGGTTGCAGTTAAA--CATAATGTAG 1936
Sequence_81    TATCACAACAGTTAATTTA--GCAACAGATAGTTCGGTTGCAGTTAAA--CATAATTTAG 1936
Sequence_45    TATCACAACAGTTAATTTA--GCAACAGATAGTTCGGTTGCAGTTAAA--CATAATGTAG 1939
Sequence_77    TATCACAACAGTTAATTTA--GCAACAGATAGTTCGGTTGCAGTTAAA--CATAATTTAG 1939
Sequence_75    TATCACAACAGTTAATTTA--GCAACAGATAGTTCGGTTGCAGTTAAA--CATAATTTAG 1936
Sequence_43    TATCACAACAGTTAATTTA--GCAACAGATAGTTCGGTTGCAGTTAAA--CATAATGTAG 1936
Sequence_47    TATCACAACAGTTAATTTA--GCAACAGATAGTTCGGTTGCAGTTAAA--CATAATGTAG 1939
Sequence_79    TATCACAACAGTTAATTTA--GCAACAGATAGTTCGGTTGCAGTTAAA--CATAATTTAG 1939
Sequence_51    TATCACAACAGTTAATTTA--GCAACAGATAGTTCGGTTGCAGTTAAA--CATAATGTAG 1945
Sequence_83    TATCACAACAGTTAATTTA--GCAACAGATAGTTCGGTTGCAGTTAAA--CATAATTTAG 1945
Sequence_7     TATCACAACATTAAATTTA--GCAACAGATAGTTCGCTAGCATTGAAA--CATAATTTAG 1933
Sequence_25    TATCACAACATTAAATTTA--GCAACAGATAGTTCGCTAGCATTGAAA--CATAATGTAG 1933
Sequence_29    TATCACAACATTAAATTTA--GCAACAGATAGTTCGCTAGCAGTGAAA--CATAATGTAG 1933
Sequence_33    TATCACAACAGTAAATTTA--GCAACAGATAGTTCGGTAGCAGTGAAA--CATAATGTAG 1933
Sequence_69    TATCACAACAGTAAATTTA--GCAACAGATAGTTCGGTAGCAGTGAAA--CATAATTTAG 1933
Sequence_11    TATCACAACATTAAATTTA--GCAACAGATAGTTCGCTAGCATTGAAA--CATAATTTAG 1921
Sequence_1     TATCACAACATTAAATTTA--GCAACAGATAGTTCGCTAGCATTGAAA--CATAATTTAG 1921
Sequence_17    TATCACAACATTAAATTTA--GCAACAGATAGTTCGCTAGCATTGAAA--CATAATTTAG 2651
Sequence_3     TGCCCCC-TATTAAATTTACGACAACCGAACCTTTCATTACTCTAGGGGCTATATTTGAA 1941
Sequence_13    TGCCCCC-TATTAAATTTACGACAACCGAACCTTTCATTACTCTAGGGGCTATATTTGAA 1941
Sequence_18    TGCCCCC-TATTAAATTTACGACAACCGAACCTTTCATTACTCTAGGGGCTATATTTGAA 3194
Cry8Ka1        TGACAAAACAGTGCATTTA-----TACAATCCTCGTTTTTCTTTA-----TATTTAGAAA 1909
               *  *    * *  *****        *    *    *  *  *       **     *
```

To Fig. 17AI

Fig. 17AH

From Fig. 17AH

```
Sequence_71     GTGAAGACCCTAATTCAACATTATCTGGTATAGTTTACGTTGACCGAATCGAATTCATCC 2002
Sequence_73     GTGAAGACCCTAATTCAACATTATCTGGTATAGTTTACGTTGACCGAATCGAATTCATCC 1999
Sequence_21     GTGAAGACCCTAATTCAACATTATCTGGTATAGTTTACGTTGACCGAATCGAATTCATCC 1993
Sequence_67     GTGAAGACCCTAATTCAACATTATCTGGTATAGTTTACGTTGACCGAATCGAATTCATCC 1993
Sequence_61     GTGAAGACCCTAATTCAACATTATCTGGTATAGTTTACGTTGACCGAATCGAATTCATCC 1993
Sequence_93     GTGAAGACCCTAATTCAACATTATCTGGTATAGTTTACGTTGACCGAATCGAATTCATCC 1993
Sequence_59     GTGAAGACCCTAATTCAACATTATCTGGTATAGTTTACGTTGACCGAATCGAATTCATCC 1993
Sequence_91     GTGAAGACCCTAATTCAACATTATCTGGTATAGTTTACGTTGACCGAATCGAATTCATCC 1993
Sequence_39     GTGAAGACCCTAATTCAACATTATCTGGTATAGTTTACGTTGACCGAATCGAATTCATCC 2002
Sequence_41     GTGAAGACCCTAATTCAACATTATCTGGTATAGTTTACGTTGACCGAATCGAATTCATCC 1999
Sequence_49     GTGAAGACCCTAATTCAACATTATCTGGTATAGTTTACGTTGACCGAATCGAATTCATCC 1996
Sequence_81     GTGAAGACCCTAATTCAACATTATCTGGTATAGTTTACGTTGACCGAATCGAATTCATCC 1996
Sequence_45     GTGAAGACCCTAATTCAACATTATCTGGTATAGTTTACGTTGACCGAATCGAATTCATCC 1999
Sequence_77     GTGAAGACCCTAATTCAACATTATCTGGTATAGTTTACGTTGACCGAATCGAATTCATCC 1999
Sequence_75     GTGAAGACCCTAATTCAACATTATCTGGTATAGTTTACGTTGACCGAATCGAATTCATCC 1996
Sequence_43     GTGAAGACCCTAATTCAACATTATCTGGTATAGTTTACGTTGACCGAATCGAATTCATCC 1996
Sequence_47     GTGAAGACCCTAATTCAACATTATCTGGTATAGTTTACGTTGACCGAATCGAATTCATCC 1999
Sequence_79     GTGAAGACCCTAATTCAACATTATCTGGTATAGTTTACGTTGACCGAATCGAATTCATCC 1999
Sequence_51     GTGAAGACCCTAATTCAACATTATCTGGTATAGTTTACGTTGACCGAATCGAATTCATCC 2005
Sequence_83     GTGAAGACCCTAATTCAACATTATCTGGTATAGTTTACGTTGACCGAATCGAATTCATCC 2005
Sequence_7      GTGAAGACCCTAATTCAACATTATCTGGTATAGTTTACGTTGACCGAATCGAATTCATCC 1993
Sequence_25     GTGAAGACCCTAATTCAACATTATCTGGTATAGTTTACGTTGACCGAATCGAATTCATCC 1993
Sequence_29     GTGAAGACCCTAATTCAACATTATCTGGTATAGTTTACGTTGACCGAATCGAATTCATCC 1993
Sequence_33     GTGAAGACCCTAATTCAACATTATCTGGTATAGTTTACGTTGACCGAATCGAATTCATCC 1993
Sequence_69     GTGAAGACCCTAATTCAACATTATCTGGTATAGTTTACGTTGACCGAATCGAATTCATCC 1993
Sequence_11     GTGAAGACCCTAATTCAACATTATCTGGTATAGTTTACGTTGACCGAATCGAATTCATCC 1981
Sequence_1      GTGAAGACCCTAATTCAACATTATCTGGTATAGTTTACGTTGACCGAATCGAATTCATCC 1981
Sequence_17     GTGAAGACCCTAATTCAACATTATCTGGTATAGTTTACGTTGACCGAATCGAATTCATCC 2711
Sequence_3      GCGGAAGACTTTCTTGGAATTGA--------AGCTTATATAGACCGAATCGAATTTATCC 1993
Sequence_13     GCGGAAGACTTTCTTGGAATTGA--------AGCTTATATAGACCGAATCGAATTTATCC 1993
Sequence_18     GCGGAAGACTTTCTTGGAATTGA--------AGCTTATATAGACCGAATCGAATTTATCC 3246
Cry8Ka1         ATTCAGATCAATCCGGGAAAAGT---------ATTTATATAGATCGAATCGAATTCATCC 1960
                    *   *        *                ***  * ** *********** ****
```

To Fig. 17AJ

Fig. 17AI

From Fig. 17AI

```
Sequence_71    CAGTAGATGAGACATATGAAGCGGAA---------------------------------- 2028
Sequence_73    CAGTAGATGAGACATATGAAGCGGAA---------------------------------- 2025
Sequence_21    CAGTAGATGAGACATATGAAGCGGAATAA------------------------------- 2022
Sequence_67    CAGTAGATGAGACATATGAAGCGGAATAA------------------------------- 2022
Sequence_61    CAGTAGATGAGACATATGAAGCGGAA---------------------------------- 2019
Sequence_93    CAGTAGATGAGACATATGAAGCGGAA---------------------------------- 2019
Sequence_59    CAGTAGATGAGACATATGAAGCGGAA---------------------------------- 2019
Sequence_91    CAGTAGATGAGACATATGAAGCGGAA---------------------------------- 2019
Sequence_39    CAGTAGATGAGACATATGAAGCGGAA---------------------------------- 2028
Sequence_41    CAGTAGATGAGACATATGAAGCGGAA---------------------------------- 2025
Sequence_49    CAGTAGATGAGACATATGAAGCGGAA---------------------------------- 2022
Sequence_81    CAGTAGATGAGACATATGAAGCGGAA---------------------------------- 2022
Sequence_45    CAGTAGATGAGACATATGAAGCGGAA---------------------------------- 2025
Sequence_77    CAGTAGATGAGACATATGAAGCGGAA---------------------------------- 2025
Sequence_75    CAGTAGATGAGACATATGAAGCGGAA---------------------------------- 2022
Sequence_43    CAGTAGATGAGACATATGAAGCGGAA---------------------------------- 2022
Sequence_47    CAGTAGATGAGACATATGAAGCGGAA---------------------------------- 2025
Sequence_79    CAGTAGATGAGACATATGAAGCGGAA---------------------------------- 2025
Sequence_51    CAGTAGATGAGACATATGAAGCGGAA---------------------------------- 2031
Sequence_83    CAGTAGATGAGACATATGAAGCGGAA---------------------------------- 2031
Sequence_7     CAGTAGATGAGACATATGAAGCGGAATAA------------------------------- 2022
Sequence_25    CAGTAGATGAGACATATGAAGCGGAATAA------------------------------- 2022
Sequence_29    CAGTAGATGAGACATATGAAGCGGAATAA------------------------------- 2022
Sequence_33    CAGTAGATGAGACATATGAAGCGGAATAA------------------------------- 2022
Sequence_69    CAGTAGATGAGACATATGAAGCGGAATAA------------------------------- 2022
Sequence_11    CAGTAGATGAGACATATGAAGCGGAATAA------------------------------- 2010
Sequence_1     CAGTAGATGAGACATATGAAGCGGAACAAGATTTAGAAGCAGCGAAGAAAGCAGTGAATG 2041
Sequence_17    CAGTAGATGAGACATATGAAGCGGAACAAGATTTAGAAGCAGCGAAGAAAGCAGTGAATG 2771
Sequence_3     CAGTAGATGAGACATATGAAGCGGAACAAGATTTAGAAGCAGCGAAGAAAGCAGTGAATG 2053
Sequence_13    CAGTAGATGAGACATATGAAGCGGAATAA------------------------------- 2022
Sequence_18    CAGTAGATGAGACATATGAAGCGGAACAAGATTTAGAAGCAGCGAAGAAAGCAGTGAATG 3306
Cry8Ka1        CAGTAGATGAGACCTATGAAGCAGAACAAGAT---------------------------- 1992
               ************* ******** ***
```

Fig. 17AJ

| | | | |
|---|---|---|---|
| Sequence_71 | CAAATAATCAAAATGAATATGAAATTATAGATGCGACACCTTCTACTTCTGTATCCAATG | 67 | (SEQ ID NO:47) |
| Sequence_73 | CAAATAATCAAAATGAATATGAAATTATAGATGCGACACCTTCTACTTCTGTATCCAATG | 67 | (SEQ ID NO:48) |
| Sequence_21 | CAAATAATCAAAATGAATATGAAATTATAGATGCGACACCTTCTACTTCTGTATCCAATG | 67 | (SEQ ID NO:32) |
| Sequence_67 | CAAATAATCAAAATGAATATGAAATTATAGATGCGACACCTTCTACTTCTGTATCCAATG | 67 | (SEQ ID NO:45) |
| Sequence_61 | CAAATAATCAAAATGAATATGAAATTATAGATGCGACACCTTCTACTTCTGTATCCAATG | 67 | (SEQ ID NO:44) |
| Sequence_93 | CAAATAATCAAAATGAATATGAAATTATAGATGCGACACCTTCTACTTCTGTATCCAATG | 67 | (SEQ ID NO:55) |
| Sequence_59 | CAAATAATCAAAATGAATATGAAATTATAGATGCGACACCTTCTACTTCTGTATCCAATG | 67 | (SEQ ID NO:43) |
| Sequence_91 | CAAATAATCAAAATGAATATGAAATTATAGATGCGACACCTTCTACTTCTGTATCCAATG | 67 | (SEQ ID NO:54) |
| Sequence_39 | CAAATAATCAAAATGAATATGAAATTATAGATGCGACACCTTCTACTTCTGTATCCAATG | 67 | (SEQ ID NO:36) |
| Sequence_41 | CAAATAATCAAAATGAATATGAAATTATAGATGCGACACCTTCTACTTCTGTATCCAATG | 67 | (SEQ ID NO:37) |
| Sequence_49 | CAAATAATCAAAATGAATATGAAATTATAGATGCGACACCTTCTACTTCTGTATCCAATG | 67 | (SEQ ID NO:41) |
| Sequence_81 | CAAATAATCAAAATGAATATGAAATTATAGATGCGACACCTTCTACTTCTGTATCCAATG | 67 | (SEQ ID NO:52) |
| Sequence_45 | CAAATAATCAAAATGAATATGAAATTATAGATGCGACACCTTCTACTTCTGTATCCAATG | 67 | (SEQ ID NO:39) |
| Sequence_77 | CAAATAATCAAAATGAATATGAAATTATAGATGCGACACCTTCTACTTCTGTATCCAATG | 67 | (SEQ ID NO:50) |
| Sequence_75 | CAAATAATCAAAATGAATATGAAATTATAGATGCGACACCTTCTACTTCTGTATCCAATG | 67 | (SEQ ID NO:49) |
| Sequence_43 | CAAATAATCAAAATGAATATGAAATTATAGATGCGACACCTTCTACTTCTGTATCCAATG | 67 | (SEQ ID NO:38) |
| Sequence_47 | CAAATAATCAAAATGAATATGAAATTATAGATGCGACACCTTCTACTTCTGTATCCAATG | 67 | (SEQ ID NO:40) |
| Sequence_79 | CAAATAATCAAAATGAATATGAAATTATAGATGCGACACCTTCTACTTCTGTATCCAATG | 67 | (SEQ ID NO:51) |
| Sequence_51 | CAAATAATCAAAATGAATATGAAATTATAGATGCGACACCTTCTACTTCTGTATCCAATG | 67 | (SEQ ID NO:42) |

To Fig. 18B

Fig. 18A

From Fig. 18A

```
Sequence_83    CAAATAATCAAAATGAATATGAAATTATAGATGCGACACCTTCTACTTCTGTATCCAATG 67   (SEQ ID NO:53)
Sequence_7     CAAATAATCAAAATGAATATGAAATTATAGATGCGACACCTTCTACTTCTGTATCCAATG 67   (SEQ ID NO:27)
Sequence_25    CAAATAATCAAAATGAATATGAAATTATAGATGCGACACCTTCTACTTCTGTATCCAATG 67   (SEQ ID NO:33)
Sequence_29    CAAATAATCAAAATGAATATGAAATTATAGATGCGACACCTTCTACTTCTGTATCCAATG 67   (SEQ ID NO:34)
Sequence_33    CAAATAATCAAAATGAATATGAAATTATAGATGCGACACCTTCTACTTCTGTATCCAATG 67   (SEQ ID NO:35)
Sequence_69    CAAATAATCAAAATGAATATGAAATTATAGATGCGACACCTTCTACTTCTGTATCCAATG 67   (SEQ ID NO:46)
Sequence_11    CAAATAATCAAAATGAATATGAAATTATAGATGCGACACCTTCTACTTCTGTATCCAATG 67   (SEQ ID NO:28)
Sequence_1     CAAATAATCAAAATGAATATGAAATTATAGATGCGACACCTTCTACTTCTGTATCCAATG 67   (SEQ ID NO:24)
Sequence_17    CAAATAATCAAAATGAATATGAAATTATAGATGCGACACCTTCTACTTCTGTATCCAATG 797  (SEQ ID NO:30)
Sequence_3     CAAATAATCAAAATGAATATGAAATTATAGATGCGACACCTTCTACTTCTGTATCCAATG 67   (SEQ ID NO:25)
Sequence_13    CAAATAATCAAAATGAATATGAAATTATAGATGCGACACCTTCTACTTCTGTATCCAATG 67   (SEQ ID NO:29)
Sequence_18    CAAATAATCAAAATGAATATGAAATTATAGATGCGACACCTTCTACTTCTGTATCCAATG 1320 (SEQ ID NO:31)
Cry8Ka1        CAAATAATCTAAATGAATATGAAATTATAGATGCGACACCTTCTACATCTGTATCTAATG 67   (SEQ ID NO:22)
               ********* ************************************ ******** ****
```

To Fig. 18C

Fig. 18B

From Fig. 18B

```
Sequence_71     ATTCTAACAGATACCCTTTTGCGAATGAGCCAACAAATGCGCTACAAAATATGGATTATA 127
Sequence_73     ATTCTAACAGATACCCTTTTGCGAATGAGCCAACAAATGCGCTACAAAATATGGATTATA 127
Sequence_21     ATTCTAACAGATACCCTTTTGCGAATGAGCCAACAAATGCGCTACAAAATATGGATTATA 127
Sequence_67     ATTCTAACAGATACCCTTTTGCGAATGAGCCAACAAATGCGCTACAAAATATGGATTATA 127
Sequence_61     ATTCTAACAGATACCCTTTTGCGAATGAGCCAACAAATGCGCTACAAAATATGGATTATA 127
Sequence_93     ATTCTAACAGATACCCTTTTGCGAATGAGCCAACAAATGCGCTACAAAATATGGATTATA 127
Sequence_59     ATTCTAACAGATACCCTTTTGCGAATGAGCCAACAAATGCGCTACAAAATATGGATTATA 127
Sequence_91     ATTCTAACAGATACCCTTTTGCGAATGAGCCAACAAATGCGCTACAAAATATGGATTATA 127
Sequence_39     ATTCTAACAGATACCCTTTTGCGAATGAGCCAACAAATGCGCTACAAAATATGGATTATA 127
Sequence_41     ATTCTAACAGATACCCTTTTGCGAATGAGCCAACAAATGCGCTACAAAATATGGATTATA 127
Sequence_49     ATTCTAACAGATACCCTTTTGCGAATGAGCCAACAAATGCGCTACAAAATATGGATTATA 127
Sequence_81     ATTCTAACAGATACCCTTTTGCGAATGAGCCAACAAATGCGCTACAAAATATGGATTATA 127
Sequence_45     ATTCTAACAGATACCCTTTTGCGAATGAGCCAACAAATGCGCTACAAAATATGGATTATA 127
Sequence_77     ATTCTAACAGATACCCTTTTGCGAATGAGCCAACAAATGCGCTACAAAATATGGATTATA 127
Sequence_75     ATTCTAACAGATACCCTTTTGCGAATGAGCCAACAAATGCGCTACAAAATATGGATTATA 127
Sequence_43     ATTCTAACAGATACCCTTTTGCGAATGAGCCAACAAATGCGCTACAAAATATGGATTATA 127
Sequence_47     ATTCTAACAGATACCCTTTTGCGAATGAGCCAACAAATGCGCTACAAAATATGGATTATA 127
Sequence_79     ATTCTAACAGATACCCTTTTGCGAATGAGCCAACAAATGCGCTACAAAATATGGATTATA 127
Sequence_51     ATTCTAACAGATACCCTTTTGCGAATGAGCCAACAAATGCGCTACAAAATATGGATTATA 127
Sequence_83     ATTCTAACAGATACCCTTTTGCGAATGAGCCAACAAATGCGCTACAAAATATGGATTATA 127
Sequence_7      ATTCTAACAGATACCCTTTTGCGAATGAGCCAACAAATGCGCTACAAAATATGGATTATA 127
Sequence_25     ATTCTAACAGATACCCTTTTGCGAATGAGCCAACAAATGCGCTACAAAATATGGATTATA 127
Sequence_29     ATTCTAACAGATACCCTTTTGCGAATGAGCCAACAAATGCGCTACAAAATATGGATTATA 127
Sequence_33     ATTCTAACAGATACCCTTTTGCGAATGAGCCAACAAATGCGCTACAAAATATGGATTATA 127
Sequence_69     ATTCTAACAGATACCCTTTTGCGAATGAGCCAACAAATGCGCTACAAAATATGGATTATA 127
Sequence_11     ATTCTAACAGATACCCTTTTGCGAATGAGCCAACAAATGCGCTACAAAATATGGATTATA 127
Sequence_1      ATTCTAACAGATACCCTTTTGCGAATGAGCCAACAAATGCGCTACAAAATATGGATTATA 127
Sequence_17     ATTCTAACAGATACCCTTTTGCGAATGAGCCAACAAATGCGCTACAAAATATGGATTATA 857
Sequence_3      ATTCTAACAGATACCCTTTTGCGAATGAGCCAACAAATGCGCTACAAAATATGGATTATA 127
Sequence_13     ATTCTAACAGATACCCTTTTGCGAATGAGCCAACAAATGCGCTACAAAATATGGATTATA 127
Sequence_18     ATTCTAACAGATACCCTTTTGCGAATGAGCCAACAAATGCGCTACAAAATATGGATTATA 1380
Cry8Ka1         ATTCTACCAGATACCCTTATGCGAATGAGCCCACAAATGCGTTACAAAATATGAATTATA 127
                ****** *********** ************ ********* *********** ******
```

To Fig. 18D

Fig. 18C

From Fig. 18C

```
Sequence_71      AAGATTATTTAAAAATGTCTGCGGGAAATGCTAGTGAATACCCTGGTTCACCTGAAGTAC 187
Sequence_73      AAGATTATTTAAAAATGTCTGCGGGAAATGCTAGTGAATACCCTGGTTCACCTGAAGTAC 187
Sequence_21      AAGATTATTTAAAAATGTCTGCGGGAAATGCTAGTGAATACCCTGGTTCACCTGAAGTAC 187
Sequence_67      AAGATTATTTAAAAATGTCTGCGGGAAATGCTAGTGAATACCCTGGTTCACCTGAAGTAC 187
Sequence_61      AAGATTATTTAAAAATGTCTGCGGGAAATGCTAGTGAATACCCTGGTTCACCTGAAGTAC 187
Sequence_93      AAGATTATTTAAAAATGTCTGCGGGAAATGCTAGTGAATACCCTGGTTCACCTGAAGTAC 187
Sequence_59      AAGATTATTTAAAAATGTCTGCGGGAAATGCTAGTGAATACCCTGGTTCACCTGAAGTAC 187
Sequence_91      AAGATTATTTAAAAATGTCTGCGGGAAATGCTAGTGAATACCCTGGTTCACCTGAAGTAC 187
Sequence_39      AAGATTATTTAAAAATGTCTGCGGGAAATGCTAGTGAATACCCTGGTTCACCTGAAGTAC 187
Sequence_41      AAGATTATTTAAAAATGTCTGCGGGAAATGCTAGTGAATACCCTGGTTCACCTGAAGTAC 187
Sequence_49      AAGATTATTTAAAAATGTCTGCGGGAAATGCTAGTGAATACCCTGGTTCACCTGAAGTAC 187
Sequence_81      AAGATTATTTAAAAATGTCTGCGGGAAATGCTAGTGAATACCCTGGTTCACCTGAAGTAC 187
Sequence_45      AAGATTATTTAAAAATGTCTGCGGGAAATGCTAGTGAATACCCTGGTTCACCTGAAGTAC 187
Sequence_77      AAGATTATTTAAAAATGTCTGCGGGAAATGCTAGTGAATACCCTGGTTCACCTGAAGTAC 187
Sequence_75      AAGATTATTTAAAAATGTCTGCGGGAAATGCTAGTGAATACCCTGGTTCACCTGAAGTAC 187
Sequence_43      AAGATTATTTAAAAATGTCTGCGGGAAATGCTAGTGAATACCCTGGTTCACCTGAAGTAC 187
Sequence_47      AAGATTATTTAAAAATGTCTGCGGGAAATGCTAGTGAATACCCTGGTTCACCTGAAGTAC 187
Sequence_79      AAGATTATTTAAAAATGTCTGCGGGAAATGCTAGTGAATACCCTGGTTCACCTGAAGTAC 187
Sequence_51      AAGATTATTTAAAAATGTCTGCGGGAAATGCTAGTGAATACCCTGGTTCACCTGAAGTAC 187
Sequence_83      AAGATTATTTAAAAATGTCTGCGGGAAATGCTAGTGAATACCCTGGTTCACCTGAAGTAC 187
Sequence_7       AAGATTATTTAAAAATGTCTGCGGGAAATGCTAGTGAATACCCTGGTTCACCTGAAGTAC 187
Sequence_25      AAGATTATTTAAAAATGTCTGCGGGAAATGCTAGTGAATACCCTGGTTCACCTGAAGTAC 187
Sequence_29      AAGATTATTTAAAAATGTCTGCGGGAAATGCTAGTGAATACCCTGGTTCACCTGAAGTAC 187
Sequence_33      AAGATTATTTAAAAATGTCTGCGGGAAATGCTAGTGAATACCCTGGTTCACCTGAAGTAC 187
Sequence_69      AAGATTATTTAAAAATGTCTGCGGGAAATGCTAGTGAATACCCTGGTTCACCTGAAGTAC 187
Sequence_11      AAGATTATTTAAAAATGTCTGCGGGAAATGCTAGTGAATACCCTGGTTCACCTGAAGTAC 187
Sequence_1       AAGATTATTTAAAAATGTCTGCGGGAAATGCTAGTGAATACCCTGGTTCACCTGAAGTAC 187
Sequence_17      AAGATTATTTAAAAATGTCTGCGGGAAATGCTAGTGAATACCCTGGTTCACCTGAAGTAC 917
Sequence_3       AAGATTATTTAAAAATGTCTGCGGGAAATGCTAGTGAATACCCTGGTTCACCTGAAGTAC 187
Sequence_13      AAGATTATTTAAAAATGTCTGCGGGAAATGCTAGTGAATACCCTGGTTCACCTGAAGTAC 187
Sequence_18      AAGATTATTTAAAAATGTCTGCGGGAAATGCTAGTGAATACCCTGGTTCACCTGAAGTAC 1440
Cry8Ka1_         AGGATTATTTAAGAATGTCTGAAGGTTACGATAATAAATATTTTGCAAATCCTGAAGTGT 187
                 * ********** ********  **  * * ** * ****   **     ********
```

To Fig. 18E

Fig. 18D

From Fig. 18D

```
Sequence_71   TTGTTAGCGGACAAGATGCAGCTAAGGCCGCAATTGATATAGTAGGTAAATTACTATCAG 247
Sequence_73   TTGTTAGCGGACAAGATGCAGCTAAGGCCGCAATTGATATAGTAGGTAAATTACTATCAG 247
Sequence_21   TTGTTAGCGGACAAGATGCAGCTAAGGCCGCAATTGATATAGTAGGTAAATTACTATCAG 247
Sequence_67   TTGTTAGCGGACAAGATGCAGCTAAGGCCGCAATTGATATAGTAGGTAAATTACTATCAG 247
Sequence_61   TTGTTAGCGGACAAGATGCAGCTAAGGCCGCAATTGATATAGTAGGTAAATTACTATCAG 247
Sequence_93   TTGTTAGCGGACAAGATGCAGCTAAGGCCGCAATTGATATAGTAGGTAAATTACTATCAG 247
Sequence_59   TTGTTAGCGGACAAGATGCAGCTAAGGCCGCAATTGATATAGTAGGTAAATTACTATCAG 247
Sequence_91   TTGTTAGCGGACAAGATGCAGCTAAGGCCGCAATTGATATAGTAGGTAAATTACTATCAG 247
Sequence_39   TTGTTAGCGGACAAGATGCAGCTAAGGCCGCAATTGATATAGTAGGTAAATTACTATCAG 247
Sequence_41   TTGTTAGCGGACAAGATGCAGCTAAGGCCGCAATTGATATAGTAGGTAAATTACTATCAG 247
Sequence_49   TTGTTAGCGGACAAGATGCAGCTAAGGCCGCAATTGATATAGTAGGTAAATTACTATCAG 247
Sequence_81   TTGTTAGCGGACAAGATGCAGCTAAGGCCGCAATTGATATAGTAGGTAAATTACTATCAG 247
Sequence_45   TTGTTAGCGGACAAGATGCAGCTAAGGCCGCAATTGATATAGTAGGTAAATTACTATCAG 247
Sequence_77   TTGTTAGCGGACAAGATGCAGCTAAGGCCGCAATTGATATAGTAGGTAAATTACTATCAG 247
Sequence_75   TTGTTAGCGGACAAGATGCAGCTAAGGCCGCAATTGATATAGTAGGTAAATTACTATCAG 247
Sequence_43   TTGTTAGCGGACAAGATGCAGCTAAGGCCGCAATTGATATAGTAGGTAAATTACTATCAG 247
Sequence_47   TTGTTAGCGGACAAGATGCAGCTAAGGCCGCAATTGATATAGTAGGTAAATTACTATCAG 247
Sequence_79   TTGTTAGCGGACAAGATGCAGCTAAGGCCGCAATTGATATAGTAGGTAAATTACTATCAG 247
Sequence_51   TTGTTAGCGGACAAGATGCAGCTAAGGCCGCAATTGATATAGTAGGTAAATTACTATCAG 247
Sequence_83   TTGTTAGCGGACAAGATGCAGCTAAGGCCGCAATTGATATAGTAGGTAAATTACTATCAG 247
Sequence_7    TTGTTAGCGGACAAGATGCAGCTAAGGCCGCAATTGATATAGTAGGTAAATTACTATCAG 247
Sequence_25   TTGTTAGCGGACAAGATGCAGCTAAGGCCGCAATTGATATAGTAGGTAAATTACTATCAG 247
Sequence_29   TTGTTAGCGGACAAGATGCAGCTAAGGCCGCAATTGATATAGTAGGTAAATTACTATCAG 247
Sequence_33   TTGTTAGCGGACAAGATGCAGCTAAGGCCGCAATTGATATAGTAGGTAAATTACTATCAG 247
Sequence_69   TTGTTAGCGGACAAGATGCAGCTAAGGCCGCAATTGATATAGTAGGTAAATTACTATCAG 247
Sequence_11   TTGTTAGCGGACAAGATGCAGCTAAGGCCGCAATTGATATAGTAGGTAAATTACTATCAG 247
Sequence_1    TTGTTAGCGGACAAGATGCAGCTAAGGCCGCAATTGATATAGTAGGTAAATTACTATCAG 247
Sequence_17   TTGTTAGCGGACAAGATGCAGCTAAGGCCGCAATTGATATAGTAGGTAAATTACTATCAG 977
Sequence_3    TTGTTAGCGGACAAGATGCAGCTAAGGCCGCAATTGATATAGTAGGTAAATTACTATCAG 247
Sequence_13   TTGTTAGCGGACAAGATGCAGCTAAGGCCGCAATTGATATAGTAGGTAAATTACTATCAG 247
Sequence_18   TTGTTAGCGGACAAGATGCAGCTAAGGCCGCAATTGATATAGTAGGTAAATTACTATCAG 1500
Cry8Ka1       TTGCT---GCACCAGGTGGGATTACAACTGGAATTACTATAGTTACTAAATTACTGGGGT 244
              ***  *   *  ** **  **   *  ****  ******  ********
```

To Fig. 18F

Fig. 18E

From Fig. 18E

```
Sequence_71     GTTTAGGGGTCCCATTTGTTGGGCCGATAGTGAGTCTTTATACTCAACTTATTGATATTC 307
Sequence_73     GTTTAGGGGTCCCATTTGTTGGGCCGATAGTGAGTCTTTATACTCAACTTATTGATATTC 307
Sequence_21     GTTTAGGGGTCCCATTTGTTGGGCCGATAGTGAGTCTTTATACTCAACTTATTGATATTC 307
Sequence_67     GTTTAGGGGTCCCATTTGTTGGGCCGATAGTGAGTCTTTATACTCAACTTATTGATATTC 307
Sequence_61     GTTTAGGGGTCCCATTTGTTGGGCCGATAGTGAGTCTTTATACTCAACTTATTGATATTC 307
Sequence_93     GTTTAGGGGTCCCATTTGTTGGGCCGATAGTGAGTCTTTATACTCAACTTATTGATATTC 307
Sequence_59     GTTTAGGGGTCCCATTTGTTGGGCCGATAGTGAGTCTTTATACTCAACTTATTGATATTC 307
Sequence_91     GTTTAGGGGTCCCATTTGTTGGGCCGATAGTGAGTCTTTATACTCAACTTATTGATATTC 307
Sequence_39     GTTTAGGGGTCCCATTTGTTGGGCCGATAGTGAGTCTTTATACTCAACTTATTGATATTC 307
Sequence_41     GTTTAGGGGTCCCATTTGTTGGGCCGATAGTGAGTCTTTATACTCAACTTATTGATATTC 307
Sequence_49     GTTTAGGGGTCCCATTTGTTGGGCCGATAGTGAGTCTTTATACTCAACTTATTGATATTC 307
Sequence_81     GTTTAGGGGTCCCATTTGTTGGGCCGATAGTGAGTCTTTATACTCAACTTATTGATATTC 307
Sequence_45     GTTTAGGGGTCCCATTTGTTGGGCCGATAGTGAGTCTTTATACTCAACTTATTGATATTC 307
Sequence_77     GTTTAGGGGTCCCATTTGTTGGGCCGATAGTGAGTCTTTATACTCAACTTATTGATATTC 307
Sequence_75     GTTTAGGGGTCCCATTTGTTGGGCCGATAGTGAGTCTTTATACTCAACTTATTGATATTC 307
Sequence_43     GTTTAGGGGTCCCATTTGTTGGGCCGATAGTGAGTCTTTATACTCAACTTATTGATATTC 307
Sequence_47     GTTTAGGGGTCCCATTTGTTGGGCCGATAGTGAGTCTTTATACTCAACTTATTGATATTC 307
Sequence_79     GTTTAGGGGTCCCATTTGTTGGGCCGATAGTGAGTCTTTATACTCAACTTATTGATATTC 307
Sequence_51     GTTTAGGGGTCCCATTTGTTGGGCCGATAGTGAGTCTTTATACTCAACTTATTGATATTC 307
Sequence_83     GTTTAGGGGTCCCATTTGTTGGGCCGATAGTGAGTCTTTATACTCAACTTATTGATATTC 307
Sequence_7      GTTTAGGGGTCCCATTTGTTGGGCCGATAGTGAGTCTTTATACTCAACTTATTGATATTC 307
Sequence_25     GTTTAGGGGTCCCATTTGTTGGGCCGATAGTGAGTCTTTATACTCAACTTATTGATATTC 307
Sequence_29     GTTTAGGGGTCCCATTTGTTGGGCCGATAGTGAGTCTTTATACTCAACTTATTGATATTC 307
Sequence_33     GTTTAGGGGTCCCATTTGTTGGGCCGATAGTGAGTCTTTATACTCAACTTATTGATATTC 307
Sequence_69     GTTTAGGGGTCCCATTTGTTGGGCCGATAGTGAGTCTTTATACTCAACTTATTGATATTC 307
Sequence_11     GTTTAGGGGTCCCATTTGTTGGGCCGATAGTGAGTCTTTATACTCAACTTATTGATATTC 307
Sequence_1      GTTTAGGGGTCCCATTTGTTGGGCCGATAGTGAGTCTTTATACTCAACTTATTGATATTC 307
Sequence_17     GTTTAGGGGTCCCATTTGTTGGGCCGATAGTGAGTCTTTATACTCAACTTATTGATATTC 1037
Sequence_3      GTTTAGGGGTCCCATTTGTTGGGCCGATAGTGAGTCTTTATACTCAACTTATTGATATTC 307
Sequence_13     GTTTAGGGGTCCCATTTGTTGGGCCGATAGTGAGTCTTTATACTCAACTTATTGATATTC 307
Sequence_18     GTTTAGGGGTCCCATTTGTTGGGCCGATAGTGAGTCTTTATACTCAACTTATTGATATTC 1560
Cry8Ka1_        GGTTAGGACTTCCATTTGCTGGGGAAACAGGGATGGCTCTTAATTTCATTCTAGGTCTAT 304
                * *****  * ******* ****   * ** **    *  ** *    ** * * * *
```

To Fig. 18G

Fig. 18F

From Fig. 18F

```
Sequence_71      TGTGGCCTTCAGGGGAAAAGAGTCAATGGGAAATTTTTATGGAACAAGTAGAAGAACTCA 367
Sequence_73      TGTGGCCTTCAGGGGAAAAGAGTCAATGGGAAATTTTTATGGAACAAGTAGAAGAACTCA 367
Sequence_21      TGTGGCCTTCAGGGGAAAAGAGTCAATGGGAAATTTTTATGGAACAAGTAGAAGAACTCA 367
Sequence_67      TGTGGCCTTCAGGGGAAAAGAGTCAATGGGAAATTTTTATGGAACAAGTAGAAGAACTCA 367
Sequence_61      TGTGGCCTTCAGGGGAAAAGAGTCAATGGGAAATTTTTATGGAACAAGTAGAAGAACTCA 367
Sequence_93      TGTGGCCTTCAGGGGAAAAGAGTCAATGGGAAATTTTTATGGAACAAGTAGAAGAACTCA 367
Sequence_59      TGTGGCCTTCAGGGGAAAAGAGTCAATGGGAAATTTTTATGGAACAAGTAGAAGAACTCA 367
Sequence_91      TGTGGCCTTCAGGGGAAAAGAGTCAATGGGAAATTTTTATGGAACAAGTAGAAGAACTCA 367
Sequence_39      TGTGGCCTTCAGGGGAAAAGAGTCAATGGGAAATTTTTATGGAACAAGTAGAAGAACTCA 367
Sequence_41      TGTGGCCTTCAGGGGAAAAGAGTCAATGGGAAATTTTTATGGAACAAGTAGAAGAACTCA 367
Sequence_49      TGTGGCCTTCAGGGGAAAAGAGTCAATGGGAAATTTTTATGGAACAAGTAGAAGAACTCA 367
Sequence_81      TGTGGCCTTCAGGGGAAAAGAGTCAATGGGAAATTTTTATGGAACAAGTAGAAGAACTCA 367
Sequence_45      TGTGGCCTTCAGGGGAAAAGAGTCAATGGGAAATTTTTATGGAACAAGTAGAAGAACTCA 367
Sequence_77      TGTGGCCTTCAGGGGAAAAGAGTCAATGGGAAATTTTTATGGAACAAGTAGAAGAACTCA 367
Sequence_75      TGTGGCCTTCAGGGGAAAAGAGTCAATGGGAAATTTTTATGGAACAAGTAGAAGAACTCA 367
Sequence_43      TGTGGCCTTCAGGGGAAAAGAGTCAATGGGAAATTTTTATGGAACAAGTAGAAGAACTCA 367
Sequence_47      TGTGGCCTTCAGGGGAAAAGAGTCAATGGGAAATTTTTATGGAACAAGTAGAAGAACTCA 367
Sequence_79      TGTGGCCTTCAGGGGAAAAGAGTCAATGGGAAATTTTTATGGAACAAGTAGAAGAACTCA 367
Sequence_51      TGTGGCCTTCAGGGGAAAAGAGTCAATGGGAAATTTTTATGGAACAAGTAGAAGAACTCA 367
Sequence_83      TGTGGCCTTCAGGGGAAAAGAGTCAATGGGAAATTTTTATGGAACAAGTAGAAGAACTCA 367
Sequence_7       TGTGGCCTTCAGGGGAAAAGAGTCAATGGGAAATTTTTATGGAACAAGTAGAAGAACTCA 367
Sequence_25      TGTGGCCTTCAGGGGAAAAGAGTCAATGGGAAATTTTTATGGAACAAGTAGAAGAACTCA 367
Sequence_29      TGTGGCCTTCAGGGGAAAAGAGTCAATGGGAAATTTTTATGGAACAAGTAGAAGAACTCA 367
Sequence_33      TGTGGCCTTCAGGGGAAAAGAGTCAATGGGAAATTTTTATGGAACAAGTAGAAGAACTCA 367
Sequence_69      TGTGGCCTTCAGGGGAAAAGAGTCAATGGGAAATTTTTATGGAACAAGTAGAAGAACTCA 367
Sequence_11      TGTGGCCTTCAGGGGAAAAGAGTCAATGGGAAATTTTTATGGAACAAGTAGAAGAACTCA 367
Sequence_1       TGTGGCCTTCAGGGGAAAAGAGTCAATGGGAAATTTTTATGGAACAAGTAGAAGAACTCA 367
Sequence_17      TGTGGCCTTCAGGGGAAAAGAGTCAATGGGAAATTTTTATGGAACAAGTAGAAGAACTCA 1097
Sequence_3       TGTGGCCTTCAGGGCAAAAGAGTCAATGGGAGATTTTTATGGAACAAGTAGAAGAACTCA 367
Sequence_13      TGTGGCCTTCAGGGCAAAAGAGTCAATGGGAGATTTTTATGGAACAAGTAGAAGAACTCA 367
Sequence_18      TGTGGCCTTCAGGGCAAAAGAGTCAATGGGAGATTTTTATGGAACAAGTAGAAGAACTCA 1620
Cry8Ka1          TATGGCCAACA---TCAGGAAACCCGTGGGCTGAACTAATGATATTGGTAGAAGAACTCA 361
                 * *****  **     *   *  *  ****      * ***  *   *************
```

To Fig. 18H

Fig. 18G

From Fig. 18G

```
Sequence_71    TTAATCAAAAAATAGCAGAATATGCAAGGAATAAAGCGCTTTCGGAATTAGAAGGATTAG 427
Sequence_73    TTAATCAAAAAATAGCAGAATATGCAAGGAATAAAGCGCTTTCGGAATTAGAAGGATTAG 427
Sequence_21    TTAATCAAAAAATAGCAGAATATGCAAGGAATAAAGCGCTTTCGGAATTAGAAGGATTAG 427
Sequence_67    TTAATCAAAAAATAGCAGAATATGCAAGGAATAAAGCGCTTTCGGAATTAGAAGGATTAG 427
Sequence_61    TTAATCAAAAAATAGCAGAATATGCAAGGAATAAAGCGCTTTCGGAATTAGAAGGATTAG 427
Sequence_93    TTAATCAAAAAATAGCAGAATATGCAAGGAATAAAGCGCTTTCGGAATTAGAAGGATTAG 427
Sequence_59    TTAATCAAAAAATAGCAGAATATGCAAGGAATAAAGCGCTTTCGGAATTAGAAGGATTAG 427
Sequence_91    TTAATCAAAAAATAGCAGAATATGCAAGGAATAAAGCGCTTTCGGAATTAGAAGGATTAG 427
Sequence_39    TTAATCAAAAAATAGCAGAATATGCAAGGAATAAAGCGCTTTCGGAATTAGAAGGATTAG 427
Sequence_41    TTAATCAAAAAATAGCAGAATATGCAAGGAATAAAGCGCTTTCGGAATTAGAAGGATTAG 427
Sequence_49    TTAATCAAAAAATAGCAGAATATGCAAGGAATAAAGCGCTTTCGGAATTAGAAGGATTAG 427
Sequence_81    TTAATCAAAAAATAGCAGAATATGCAAGGAATAAAGCGCTTTCGGAATTAGAAGGATTAG 427
Sequence_45    TTAATCAAAAAATAGCAGAATATGCAAGGAATAAAGCGCTTTCGGAATTAGAAGGATTAG 427
Sequence_77    TTAATCAAAAAATAGCAGAATATGCAAGGAATAAAGCGCTTTCGGAATTAGAAGGATTAG 427
Sequence_75    TTAATCAAAAAATAGCAGAATATGCAAGGAATAAAGCGCTTTCGGAATTAGAAGGATTAG 427
Sequence_43    TTAATCAAAAAATAGCAGAATATGCAAGGAATAAAGCGCTTTCGGAATTAGAAGGATTAG 427
Sequence_47    TTAATCAAAAAATAGCAGAATATGCAAGGAATAAAGCGCTTTCGGAATTAGAAGGATTAG 427
Sequence_79    TTAATCAAAAAATAGCAGAATATGCAAGGAATAAAGCGCTTTCGGAATTAGAAGGATTAG 427
Sequence_51    TTAATCAAAAAATAGCAGAATATGCAAGGAATAAAGCGCTTTCGGAATTAGAAGGATTAG 427
Sequence_83    TTAATCAAAAAATAGCAGAATATGCAAGGAATAAAGCGCTTTCGGAATTAGAAGGATTAG 427
Sequence_7     TTAATCAAAAAATAGCAGAATATGCAAGGAATAAAGCGCTTTCGGAATTAGAAGGATTAG 427
Sequence_25    TTAATCAAAAAATAGCAGAATATGCAAGGAATAAAGCGCTTTCGGAATTAGAAGGATTAG 427
Sequence_29    TTAATCAAAAAATAGCAGAATATGCAAGGAATAAAGCGCTTTCGGAATTAGAAGGATTAG 427
Sequence_33    TTAATCAAAAAATAGCAGAATATGCAAGGAATAAAGCGCTTTCGGAATTAGAAGGATTAG 427
Sequence_69    TTAATCAAAAAATAGCAGAATATGCAAGGAATAAAGCGCTTTCGGAATTAGAAGGATTAG 427
Sequence_11    TTAATCAAAAAATAGCAGAATATGCAAGGAATAAAGCGCTTTCGGAATTAGAAGGATTAG 427
Sequence_1     TTAATCAAAAAATAGCAGAATATGCAAGGAATAAAGCGCTTTCGGAATTAGAAGGATTAG 427
Sequence_17    TTAATCAAAAAATAGCAGAATATGCAAGGAATAAAGCGCTTTCGGAATTAGAAGGATTAG 1157
Sequence_3     TAAATCAAAAAATAGCAGAATATGCAAGGAATAAAGCGCTTTCGGAATTAGAAGGATTAG 427
Sequence_13    TAAATCAAAAAATAGCAGAATATGCAAGGAATAAAGCGCTTTCGGAATTAGAAGGATTAG 427
Sequence_18    TAAATCAAAAAATAGCAGAATATGCAAGGAATAAAGCGCTTTCGGAATTAGAAGGATTAG 1680
Cry8Ka1        TAAATCAAAAAATAGAAGAGACTGTAAGAAACAAAGCACTAGCGGATTTGGGCAATTCAG 421
               * ************* ***   ** *** ** ***** **  **** ** *     * **
```

To Fig. 18I

Fig. 18H

From Fig. 18H

```
Sequence_71    GTAATAATTACCAATTATATCTAACTGCGCTTGAAGAATGGGAAGAAAATCCATTTCGAA 487
Sequence_73    GTAATAATTACCAATTATATCTAACTGCGCTTGAAGAATGGGAAGAAAATCCATTTCGAA 487
Sequence_21    GTAATAATTACCAATTATATCTAACTGCGCTTGAAGAATGGGAAGAAAATCCATTTCGA- 486
Sequence_67    GTAATAATTACCAATTATATCTAACTGCGCTTGAAGAATGGGAAGAAAATCCATTTCGA- 486
Sequence_61    GTAATAATTACCAATTATATCTAACTGCGCTTGAAGAATGGGAAGAAAATCCATTTCGA- 486
Sequence_93    GTAATAATTACCAATTATATCTAACTGCGCTTGAAGAATGGGAAGAAAATCCATTTCGA- 486
Sequence_59    GTAATAATTACCAATTATATCTAACTGCGCTTGAAGAATGGGAAGAAAATCCATTTCGA- 486
Sequence_91    GTAATAATTACCAATTATATCTAACTGCGCTTGAAGAATGGGAAGAAAATCCATTTCGA- 486
Sequence_39    GTAATAATTACCAATTATATCTAACTGCGCTTGAAGAATGGGAAGAAAATCCATTTCGAA 487
Sequence_41    GTAATAATTACCAATTATATCTAACTGCGCTTGAAGAATGGGAAGAAAATCCATTTCGAA 487
Sequence_49    GTAATAATTACCAATTATATCTAACTGCGCTTGAAGAATGGGAAGAAAATCCAAATGGTT 487
Sequence_81    GTAATAATTACCAATTATATCTAACTGCGCTTGAAGAATGGGAAGAAAATCCAAATGGTT 487
Sequence_45    GTAATAATTACCAATTATATCTAACTGCGCTTGAAGAATGGGAAGAAAATCCAAATGGTT 487
Sequence_77    GTAATAATTACCAATTATATCTAACTGCGCTTGAAGAATGGGAAGAAAATCCAAATGGTT 487
Sequence_75    GTAATAATTACCAATTATATCTAACTGCGCTTGAAGAATGGGAAGAAAATCCAAATGGTT 487
Sequence_43    GTAATAATTACCAATTATATCTAACTGCGCTTGAAGAATGGGAAGAAAATCCAAATGGTT 487
Sequence_47    GTAATAATTACCAATTATATCTAACTGCGCTTGAAGAATGGGAAGAAAATCCATTTCGAA 487
Sequence_79    GTAATAATTACCAATTATATCTAACTGCGCTTGAAGAATGGGAAGAAAATCCATTTCGAA 487
Sequence_51    GTAATAATTACCAATTATATCTAACTGCGCTTGAAGAATGGGAAGAAAATCCATTTCGAA 487
Sequence_83    GTAATAATTACCAATTATATCTAACTGCGCTTGAAGAATGGGAAGAAAATCCATTTCGAA 487
Sequence_7     GTAATAATTACCAATTATATCTAACTGCGCTTGAAGAATGGGAAGAAAATCCAAATGGT- 486
Sequence_25    GTAATAATTACCAATTATATCTAACTGCGCTTGAAGAATGGGAAGAAAATCCAAATGGT- 486
Sequence_29    GTAATAATTACCAATTATATCTAACTGCGCTTGAAGAATGGGAAGAAAATCCAAATGGT- 486
Sequence_33    GTAATAATTACCAATTATATCTAACTGCGCTTGAAGAATGGGAAGAAAATCCAAATGGT- 486
Sequence_69    GTAATAATTACCAATTATATCTAACTGCGCTTGAAGAATGGGAAGAAAATCCAAATGGT- 486
Sequence_11    GTAATAATTACCAATTATATCTAACTGCGCTTGAAGAATGGGAAGAAAATCCAAATGGT- 486
Sequence_1     GTAATAATTACCAATTATATCTAACTGCGCTTGAAGAATGGGAAGAAAATCCAAATGGT- 486
Sequence_17    GTAATAATTACCAATTATATCTAACTGCGCTTGAAGAATGGGAAGAAAATCCAAATGGT- 1216
Sequence_3     GTAATAATTACCAATTATATCTAACTGCGCTTGAAGAATGGAAAGAAAATCCAAATGGT- 486
Sequence_13    GTAATAATTACCAATTATATCTAACTGCGCTTGAAGAATGGAAAGAAAATCCAAATGGT- 486
Sequence_18    GTAATAATTACCAATTATATCTAACTGCGCTTGAAGAATGGAAAGAAAATCCAAATGGT- 1739
Cry8Ka1        GTAGAGCCTTACGATCCTATTTAAACGCATTTGAAGATTGGCAAAAAAACCCTAATATCT 481
               ***     *  * **  *** ***  **  ******* *** ** **** **   *
```

To Fig. 18J

Fig. 18I

From Fig. 18I

```
Sequence_71     GTCGAGGTTTTCGAAGTCGAGGTCCA---GCCTTACGAGAT-GTGCGAAATCGATTTGAA 543
Sequence_73     GTCGAGGTTTTCGAAGTCGAGGT------GCCTTACGAGAT-GTGCGAAATCGATTTGAA 540
Sequence_21     --CGAGGTTTTCGA---CGAGGT------GCCTTACGAGAT-GTGCGAAATCGATTTGAA 534
Sequence_67     --CGAGGTTTTCGA---CGAGGT------GCCTTACGAGAT-GTGCGAAATCGATTTGAA 534
Sequence_61     --CGAGGTTTTCGA---CGAGGT------GCCTTACGAGAT-GTGCGAAATCGATTTGAA 534
Sequence_93     --CGAGGTTTTCGA---CGAGGT------GCCTTACGAGAT-GTGCGAAATCGATTTGAA 534
Sequence_59     --CGAGGTTTTCGA---CGAGGT------GCCTTACGAGAT-GTGCGAAATCGATTTGAA 534
Sequence_91     --CGAGGTTTTCGA---CGAGGT------GCCTTACGAGAT-GTGCGAAATCGATTTGAA 534
Sequence_39     GTCGAGGTTTTCGAAGTCGAGGTCCA---GCCTTACGAGAT-GTGCGAAATCGATTTGAA 543
Sequence_41     GTCGAGGTTTTCGAAGTCGAGGT------GCCTTACGAGAT-GTGCGAAATCGATTTGAA 540
Sequence_49     CCCGG---TTTCGAAGTCGA---CAA---GCCTTACGAGAT-GTGCGAAATCGATTTGAA 537
Sequence_81     CCCGG---TTTCGAAGTCGA---CAA---GCCTTACGAGAT-GTGCGAAATCGATTTGAA 537
Sequence_45     CCCGG---TTTCGAAGTCGAGGTCCA---GCCTTACGAGAT-GTGCGAAATCGATTTGAA 540
Sequence_77     CCCGG---TTTCGAAGTCGAGGTCCA---GCCTTACGAGAT-GTGCGAAATCGATTTGAA 540
Sequence_75     CCCGG---TTTCGAAGTCGAG---GT---GCCTTACGAGAT-GTGCGAAATCGATTTGAA 537
Sequence_43     CCCGG---TTTCGAAGTCGAG---GT---GCCTTACGAGAT-GTGCGAAATCGATTTGAA 537
Sequence_47     GTCGAGGT---CCAAATGGTTCCCGG---GCCTTACGAGAT-GTGCGAAATCGATTTGAA 540
Sequence_79     GTCGAGGT---CCAAATGGTTCCCGG---GCCTTACGAGAT-GTGCGAAATCGATTTGAA 540
Sequence_51     GTCGAGGTAGTTTAAATGGTTCCCGGCCAGCCTTACGAGAT-GTGCGAAATCGATTTGAA 546
Sequence_83     GTCGAGGTAGTTTAAATGGTTCCCGGCCAGCCTTACGAGAT-GTGCGAAATCGATTTGAA 546
Sequence_7      -TCAA-------GAAATGGTTCCCGG---GCCTTACGAGAT-GTGCGAAATCGATTTGAA 534
Sequence_25     -TCAA-------GAAATGGTTCCCGG---GCCTTACGAGAT-GTGCGAAATCGATTTGAA 534
Sequence_29     -TCAA-------GAAATGGTTCCCGG---GCCTTACGAGAT-GTGCGAAATCGATTTGAA 534
Sequence_33     -TCAA-------GAAATGGTTCCCGG---GCCTTACGAGAT-GTGCGAAATCGATTTGAA 534
Sequence_69     -TCAA-------GAAATGGTTCCCGG---GCCTTACGAGAT-GTGCGAAATCGATTTGAA 534
Sequence_11     -TCAA-------GA---------------GCCTTACGAGAT-GTGCGAAATCGATTTGAA 522
Sequence_1      -TCAA-------GA---------------GCCTTACGAGAT-GTGCGAAATCGATTTGAA 522
Sequence_17     -TCAA-------GA---------------GCCTTACGAGAT-GTGCGAAATCGATTTGAA 1252
Sequence_3      -TCAA-------GA---------------GCCTTACGAGAT-GTGCGAAATCGATTTGAA 522
Sequence_13     -TCAA-------GA---------------GCCTTACGAGAT-GTGCGAAATCGATTTGAA 522
Sequence_18     -TCAA-------GA---------------GCCTTACGAGAT-GTGCGAAATCGATTTGAA 1775
Cry8Ka1         TTCG-------------------------GAGTAAAGAGTTAGTAAAAGAAAGATTTTCA 516
                  *                          *  * * *** * **   * *  *****  *
```

To Fig. 18K

Fig. 18J

From Fig. 18J

```
Sequence_71       ATCCTGGATAGTTTATTTACGCAAT-ATATGCCATCTTTTAGAGTGACAAATTTTGAAGT 602
Sequence_73       ATCCTGGATAGTTTATTTACGCAAT-ATATGCCATCTTTTAGAGTGACAAATTTTGAAGT 599
Sequence_21       ATCCTGGATAGTTTATTTACGCAAT-ATATGCCATCTTTTAGAGTGACAAATTTTGAAGT 593
Sequence_67       ATCCTGGATAGTTTATTTACGCAAT-ATATGCCATCTTTTAGAGTGACAAATTTTGAAGT 593
Sequence_61       ATCCTGGATAGTTTATTTACGCAAT-ATATGCCATCTTTTAGAGTGACAAATTTTGAAGT 593
Sequence_93       ATCCTGGATAGTTTATTTACGCAAT-ATATGCCATCTTTTAGAGTGACAAATTTTGAAGT 593
Sequence_59       ATCCTGGATAGTTTATTTACGCAAT-ATATGCCATCTTTTAGAGTGACAAATTTTGAAGT 593
Sequence_91       ATCCTGGATAGTTTATTTACGCAAT-ATATGCCATCTTTTAGAGTGACAAATTTTGAAGT 593
Sequence_39       ATCCTGGATAGTTTATTTACGCAAT-ATATGCCATCTTTTAGAGTGACAAATTTTGAAGT 602
Sequence_41       ATCCTGGATAGTTTATTTACGCAAT-ATATGCCATCTTTTAGAGTGACAAATTTTGAAGT 599
Sequence_49       ATCCTGGATAGTTTATTTACGCAAT-ATATGCCATCTTTTAGAGTGACAAATTTTGAAGT 596
Sequence_81       ATCCTGGATAGTTTATTTACGCAAT-ATATGCCATCTTTTAGAGTGACAAATTTTGAAGT 596
Sequence_45       ATCCTGGATAGTTTATTTACGCAAT-ATATGCCATCTTTTAGAGTGACAAATTTTGAAGT 599
Sequence_77       ATCCTGGATAGTTTATTTACGCAAT-ATATGCCATCTTTTAGAGTGACAAATTTTGAAGT 599
Sequence_75       ATCCTGGATAGTTTATTTACGCAAT-ATATGCCATCTTTTAGAGTGACAAATTTTGAAGT 596
Sequence_43       ATCCTGGATAGTTTATTTACGCAAT-ATATGCCATCTTTTAGAGTGACAAATTTTGAAGT 596
Sequence_47       ATCCTGGATAGTTTATTTACGCAAT-ATATGCCATCTTTTAGAGTGACAAATTTTGAAGT 599
Sequence_79       ATCCTGGATAGTTTATTTACGCAAT-ATATGCCATCTTTTAGAGTGACAAATTTTGAAGT 599
Sequence_51       ATCCTGGATAGTTTATTTACGCAAT-ATATGCCATCTTTTAGAGTGACAAATTTTGAAGT 605
Sequence_83       ATCCTGGATAGTTTATTTACGCAAT-ATATGCCATCTTTTAGAGTGACAAATTTTGAAGT 605
Sequence_7        ATCCTGGATAGTTTATTTACGCAAT-ATATGCCATCTTTTAGAGTGACAAATTTTGAAGT 593
Sequence_25       ATCCTGGATAGTTTATTTACGCAAT-ATATGCCATCTTTTAGAGTGACAAATTTTGAAGT 593
Sequence_29       ATCCTGGATAGTTTATTTACGCAAT-ATATGCCATCTTTTAGAGTGACAAATTTTGAAGT 593
Sequence_33       ATCCTGGATAGTTTATTTACGCAAT-ATATGCCATCTTTTAGAGTGACAAATTTTGAAGT 593
Sequence_69       ATCCTGGATAGTTTATTTACGCAAT-ATATGCCATCTTTTAGAGTGACAAATTTTGAAGT 593
Sequence_11       ATCCTGGATAGTTTATTTACGCAAT-ATATGCCATCTTTTAGAGTGACAAATTTTGAAGT 581
Sequence_1        ATCCTGGATAGTTTATTTACGCAAT-ATATGCCATCTTTTAGAGTGACAAATTTTGAAGT 581
Sequence_17       ATCCTGGATAGTTTATTTACGCAAT-ATATGCCATCTTTTAGAGTGACAAATTTTGAAGT 1311
Sequence_3        ATCCTGGATAGTTTATTTACGCAAT-ACATGCCATCTTTTCGAGTGACAAATTTTGAAGT 581
Sequence_13       ATCCTGGATAGTTTATTTACGCAAT-ACATGCCATCTTTTCGAGTGACAAATTTTGAAGT 581
Sequence_18       ATCCTGGATAGTTTATTTACGCAAT-ACATGCCATCTTTTCGAGTGACAAATTTTGAAGT 1834
Cry8Ka1_          AACGCGGAACATTCATT-ACGTACCGAAATGAGTTCTTTTGCCATAAGAGGATTTGAAAT 575
                  * *  ***   ** *** *** *   * ***   ******    * * *   ****** *
```

To Fig. 18L

Fig. 18K

From Fig. 18K

```
Sequence_71     ACCATTCCTTACTGTATATGCAATGGCAGCCAACCTTCATTTACTGTTATTAAAGGACGC 662
Sequence_73     ACCATTCCTTACTGTATATGCAATGGCAGCCAACCTTCATTTACTGTTATTAAAGGACGC 659
Sequence_21     ACCATTCCTTACTGTATATGCAATGGCAGCCAACCTTCATTTACTGTTATTAAAGGACGC 653
Sequence_67     ACCATTCCTTACTGTATATGCAATGGCAGCCAACCTTCATTTACTGTTATTAAAGGACGC 653
Sequence_61     ACCATTCCTTACTGTATATGCAATGGCAGCCAACCTTCATTTACTGTTATTAAAGGACGC 653
Sequence_93     ACCATTCCTTACTGTATATGCAATGGCAGCCAACCTTCATTTACTGTTATTAAAGGACGC 653
Sequence_59     ACCATTCCTTACTGTATATGCAATGGCAGCCAACCTTCATTTACTGTTATTAAAGGACGC 653
Sequence_91     ACCATTCCTTACTGTATATGCAATGGCAGCCAACCTTCATTTACTGTTATTAAAGGACGC 653
Sequence_39     ACCATTCCTTACTGTATATGCAATGGCAGCCAACCTTCATTTACTGTTATTAAAGGACGC 662
Sequence_41     ACCATTCCTTACTGTATATGCAATGGCAGCCAACCTTCATTTACTGTTATTAAAGGACGC 659
Sequence_49     ACCATTCCTTACTGTATATGCAATGGCAGCCAACCTTCATTTACTGTTATTAAAGGACGC 656
Sequence_81     ACCATTCCTTACTGTATATGCAATGGCAGCCAACCTTCATTTACTGTTATTAAAGGACGC 656
Sequence_45     ACCATTCCTTACTGTATATGCAATGGCAGCCAACCTTCATTTACTGTTATTAAAGGACGC 659
Sequence_77     ACCATTCCTTACTGTATATGCAATGGCAGCCAACCTTCATTTACTGTTATTAAAGGACGC 659
Sequence_75     ACCATTCCTTACTGTATATGCAATGGCAGCCAACCTTCATTTACTGTTATTAAAGGACGC 656
Sequence_43     ACCATTCCTTACTGTATATGCAATGGCAGCCAACCTTCATTTACTGTTATTAAAGGACGC 656
Sequence_47     ACCATTCCTTACTGTATATGCAATGGCAGCCAACCTTCATTTACTGTTATTAAAGGACGC 659
Sequence_79     ACCATTCCTTACTGTATATGCAATGGCAGCCAACCTTCATTTACTGTTATTAAAGGACGC 659
Sequence_51     ACCATTCCTTACTGTATATGCAATGGCAGCCAACCTTCATTTACTGTTATTAAAGGACGC 665
Sequence_83     ACCATTCCTTACTGTATATGCAATGGCAGCCAACCTTCATTTACTGTTATTAAAGGACGC 665
Sequence_7      ACCATTCCTTACTGTATATGCAATGGCAGCCAACCTTCATTTACTGTTATTAAAGGACGC 653
Sequence_25     ACCATTCCTTACTGTATATGCAATGGCAGCCAACCTTCATTTACTGTTATTAAAGGACGC 653
Sequence_29     ACCATTCCTTACTGTATATGCAATGGCAGCCAACCTTCATTTACTGTTATTAAAGGACGC 653
Sequence_33     ACCATTCCTTACTGTATATGCAATGGCAGCCAACCTTCATTTACTGTTATTAAAGGACGC 653
Sequence_69     ACCATTCCTTACTGTATATGCAATGGCAGCCAACCTTCATTTACTGTTATTAAAGGACGC 653
Sequence_11     ACCATTCCTTACTGTATATGCAATGGCAGCCAACCTTCATTTACTGTTATTAAAGGACGC 641
Sequence_1      ACCATTCCTTACTGTATATGCAATGGCAGCCAACCTTCATTTACTGTTATTAAAGGACGC 641
Sequence_17     ACCATTCCTTACTGTATATGCAATGGCAGCCAACCTTCATTTACTGTTATTAAAGGACGC 1371
Sequence_3      ACCATTCCTTACAGTATATACACAGGCAGCCAACCTTCATTTACTGTTATTAAAGGACGC 641
Sequence_13     ACCATTCCTTACAGTATATACACAGGCAGCCAACCTTCATTTACTGTTATTAAAGGACGC 641
Sequence_18     ACCATTCCTTACAGTATATACACAGGCAGCCAACCTTCATTTACTGTTATTAAAGGACGC 1894
Cry8Ka1_        TCCTCTTTTAGCAACATATGCACAAGCTGCGAATTTACATTTATTTCTAATTAAAGATAT 635
                 **  *  *  *   **** **   ** ** **  * ****** *  ** * ** **
```

To Fig. 18M

Fig. 18L

From Fig. 18L

```
Sequence_71         GTCAATTTTTGGAGAAGAATGGGGATGGTCAACAACTACTATTAATAACTATTATGATCG 722
Sequence_73         GTCAATTTTTGGAGAAGAATGGGGATGGTCAACAACTACTATTAATAACTATTATGATCG 719
Sequence_21         GTCAATTTTTGGAGAAGAATGGGGATGGTCAACAACTACTATTAATAACTATTATGATCG 713
Sequence_67         GTCAATTTTTGGAGAAGAATGGGGATGGTCAACAACTACTATTAATAACTATTATGATCG 713
Sequence_61         GTCAATTTTTGGAGAAGAATGGGGATGGTCAACAACTACTATTAATAACGTGGTGGATCG 713
Sequence_93         GTCAATTTTTGGAGAAGAATGGGGATGGTCAACAACTACTATTAATAACGTGGTGGATCG 713
Sequence_59         GTCAATTTTTGGAGAAGAATGGGGATGGTCAACAACTACTATTAATAACTATTATGATCG 713
Sequence_91         GTCAATTTTTGGAGAAGAATGGGGATGGTCAACAACTACTATTAATAACTATTATGATCG 713
Sequence_39         GTCAATTTTTGGAGAAGAATGGGGATGGTCAACAACTACTATTAATAACTATTATGATCG 722
Sequence_41         GTCAATTTTTGGAGAAGAATGGGGATGGTCAACAACTACTATTAATAACTATTATGATCG 719
Sequence_49         GTCAATTTTTGGAGAAGAATGGGGATGGTCAACAACTACTATTAATAACTATTATGATCG 716
Sequence_81         GTCAATTTTTGGAGAAGAATGGGGATGGTCAACAACTACTATTAATAACTATTATGATCG 716
Sequence_45         GTCAATTTTTGGAGAAGAATGGGGATGGTCAACAACTACTATTAATAACTATTATGATCG 719
Sequence_77         GTCAATTTTTGGAGAAGAATGGGGATGGTCAACAACTACTATTAATAACTATTATGATCG 719
Sequence_75         GTCAATTTTTGGAGAAGAATGGGGATGGTCAACAACTACTATTAATAACTATTATGATCG 716
Sequence_43         GTCAATTTTTGGAGAAGAATGGGGATGGTCAACAACTACTATTAATAACTATTATGATCG 716
Sequence_47         GTCAATTTTTGGAGAAGAATGGGGATGGTCAACAACTACTATTAATAACTATTATGATCG 719
Sequence_79         GTCAATTTTTGGAGAAGAATGGGGATGGTCAACAACTACTATTAATAACTATTATGATCG 719
Sequence_51         GTCAATTTTTGGAGAAGAATGGGGATGGTCAACAACTACTATTAATAACTATTATGATCG 725
Sequence_83         GTCAATTTTTGGAGAAGAATGGGGATGGTCAACAACTACTATTAATAACTATTATGATCG 725
Sequence_7          GTCAATTTTTGGAGAAGAATGGGGATGGTCAACAACTACTATTAATAACTATTATGATCG 713
Sequence_25         GTCAATTTTTGGAGAAGAATGGGGATGGTCAACAACTACTATTAATAACTATTATGATCG 713
Sequence_29         GTCAATTTTTGGAGAAGAATGGGGATGGTCAACAACTACTATTAATAACTATTATGATCG 713
Sequence_33         GTCAATTTTTGGAGAAGAATGGGGATGGTCAACAACTACTATTAATAACTATTATGATCG 713
Sequence_69         GTCAATTTTTGGAGAAGAATGGGGATGGTCAACAACTACTATTAATAACTATTATGATCG 713
Sequence_11         GTCAATTTTTGGAGAAGAATGGGGATGGTCAACAACTACTATTAATAACTATTATGATCG 701
Sequence_1          GTCAATTTTTGGAGAAGAATGGGGATGGTCAACAACTACTATTAATAACTATTATGATCG 701
Sequence_17         GTCAATTTTTGGAGAAGAATGGGGATGGTCAACAACTACTATTAATAACTATTATGATCG 1431
Sequence_3          TTCAATTTTTGGAGAAGAATGGGGATGGTCTACAACCACTATTAATAACTATTATGATCG 701
Sequence_13         TTCAATTTTTGGAGAAGAATGGGGATGGTCTACAACCACTATTAATAACTATTATGATCG 701
Sequence_18         TTCAATTTTTGGAGAAGAATGGGGATGGTCTACAACCACTATTAATAACTATTATGATCG 1954
Cry8Ka1             TCAAATTTATGGAAAAGAATGGGGATATACTCAAGCCGATATTGACTTATTTTATAGAGA 695
                       ***** **** ************   *   * *   **** *
```

To Fig. 18N

Fig. 18M

From Fig. 18M

```
Sequence_71     TCAAATGAAACTTACTGCAGAATATTCTGATCACTGTGTAAAGTGGTATGAAACTGGTTT 782
Sequence_73     TCAAATGAAACTTACTGCAGAATATTCTGATCACTGTGTAAAGTGGTATGAAACTGGTTT 779
Sequence_21     TCAAATGAAACTTACTGCAGAATATTCTGATCACTGTGTAAAGTGGTATGAAACTGGTTT 773
Sequence_67     TCAAATGAAACTTACTGCAGAATATTCTGATCACTGTGTAAAGTGGTATGAAACTGGTTT 773
Sequence_61     TCAAATGAAACTTACTGCAGAATATTCTGATCACTGTGTAAAGTGGTATGAAACTGGTTT 773
Sequence_93     TCAAATGAAACTTACTGCAGAATATTCTGATCACTGTGTAAAGTGGTATGAAACTGGTTT 773
Sequence_59     TCAAATGAAACTTACTGCAGAATATTCTGATCACTGTGTAAAGTGGTATGAAACTGGTTT 773
Sequence_91     TCAAATGAAACTTACTGCAGAATATTCTGATCACTGTGTAAAGTGGTATGAAACTGGTTT 773
Sequence_39     TCAAATGAAACTTACTGCAGAATATTCTGATCACTGTGTAAAGTGGTATGAAACTGGTTT 782
Sequence_41     TCAAATGAAACTTACTGCAGAATATTCTGATCACTGTGTAAAGTGGTATGAAACTGGTTT 779
Sequence_49     TCAAATGAAACTTACTGCAGAATATTCTGATCACTGTGTAAAGTGGTATGAAACTGGTTT 776
Sequence_81     TCAAATGAAACTTACTGCAGAATATTCTGATCACTGTGTAAAGTGGTATGAAACTGGTTT 776
Sequence_45     TCAAATGAAACTTACTGCAGAATATTCTGATCACTGTGTAAAGTGGTATGAAACTGGTTT 779
Sequence_77     TCAAATGAAACTTACTGCAGAATATTCTGATCACTGTGTAAAGTGGTATGAAACTGGTTT 779
Sequence_75     TCAAATGAAACTTACTGCAGAATATTCTGATCACTGTGTAAAGTGGTATGAAACTGGTTT 776
Sequence_43     TCAAATGAAACTTACTGCAGAATATTCTGATCACTGTGTAAAGTGGTATGAAACTGGTTT 776
Sequence_47     TCAAATGAAACTTACTGCAGAATATTCTGATCACTGTGTAAAGTGGTATGAAACTGGTTT 779
Sequence_79     TCAAATGAAACTTACTGCAGAATATTCTGATCACTGTGTAAAGTGGTATGAAACTGGTTT 779
Sequence_51     TCAAATGAAACTTACTGCAGAATATTCTGATCACTGTGTAAAGTGGTATGAAACTGGTTT 785
Sequence_83     TCAAATGAAACTTACTGCAGAATATTCTGATCACTGTGTAAAGTGGTATGAAACTGGTTT 785
Sequence_7      TCAAATGAAACTTACTGCAGAATATTCTGATCACTGTGTAAAGTGGTATGAAACTGGTTT 773
Sequence_25     TCAAATGAAACTTACTGCAGAATATTCTGATCACTGTGTAAAGTGGTATGAAACTGGTTT 773
Sequence_29     TCAAATGAAACTTACTGCAGAATATTCTGATCACTGTGTAAAGTGGTATGAAACTGGTTT 773
Sequence_33     TCAAATGAAACTTACTGCAGAATATTCTGATCACTGTGTAAAGTGGTATGAAACTGGTTT 773
Sequence_69     TCAAATGAAACTTACTGCAGAATATTCTGATCACTGTGTAAAGTGGTATGAAACTGGTTT 773
Sequence_11     TCAAATGAAACTTACTGCAGAATATTCTGATCACTGTGTAAAGTGGTATGAAACTGGTTT 761
Sequence_1      TCAAATGAAACTTACTGCAGAATATTCTGATCACTGTGTAAAGTGGTATGAAACTGGTTT 761
Sequence_17     TCAAATGAAACTTACTGCAGAATATTCTGATCACTGTGTAAAGTGGTATGAAACTGGTTT 1491
Sequence_3      TCAAATGAAACTTACTGCAGAATATTCTGATCACTGTGTAAAGTGGTATGAAACTGGTTT 761
Sequence_13     TCAAATGAAACTTACTGCAGAATATTCTGATCACTGTGTAAAGTGGTATGAAACTGGTTT 761
Sequence_18     TCAAATGAAACTTACTGCAGAATATTCTGATCACTGTGTAAAGTGGTATGAAACTGGTTT 2014
Cry8Ka1         ACAAGTAGAGTTTACGAAAGAATACACCGAACACTGTATTAATATTTATAATGATGGTTT 755
                 *** *  *  ****   ******  * ** ****** * **    *** *   ******
```

To Fig. 18O

Fig. 18N

From Fig. 18N

```
Sequence_71     AGCAAAATTAAAAGGCACGAGCGCTAAACAATGGGTTGACTATAACCAATTCCGTAGAGA 842
Sequence_73     AGCAAAATTAAAAGGCACGAGCGCTAAACAATGGGTTGACTATAACCAATTCCGTAGAGA 839
Sequence_21     AGCAAAATTAAAAGGCACGAGCGCTAAACAATGGGTTGACTATAACCAATTCCGTAGAGA 833
Sequence_67     AGCAAAATTAAAAGGCACGAGCGCTAAACAATGGGTTGACTATAACCAATTCCGTAGAGA 833
Sequence_61     AGCAAAATTAAAAGGCACGAGCGCTAAACAATGGGTTGACTATAACCAATTCCGTAGAGA 833
Sequence_93     AGCAAAATTAAAAGGCACGAGCGCTAAACAATGGGTTGACTATAACCAATTCCGTAGAGA 833
Sequence_59     AGCAAAATTAAAAGGCACGAGCGCTAAACAATGGGTTGACTATAACCAATTCCGTAGAGA 833
Sequence_91     AGCAAAATTAAAAGGCACGAGCGCTAAACAATGGGTTGACTATAACCAATTCCGTAGAGA 833
Sequence_39     AGCAAAATTAAAAGGCACGAGCGCTAAACAATGGGTTGACTATAACCAATTCCGTAGAGA 842
Sequence_41     AGCAAAATTAAAAGGCACGAGCGCTAAACAATGGGTTGACTATAACCAATTCCGTAGAGA 839
Sequence_49     AGCAAAATTAAAAGGCACGAGCGCTAAACAATGGGTTGACTATAACCAATTCCGTAGAGA 836
Sequence_81     AGCAAAATTAAAAGGCACGAGCGCTAAACAATGGGTTGACTATAACCAATTCCGTAGAGA 836
Sequence_45     AGCAAAATTAAAAGGCACGAGCGCTAAACAATGGGTTGACTATAACCAATTCCGTAGAGA 839
Sequence_77     AGCAAAATTAAAAGGCACGAGCGCTAAACAATGGGTTGACTATAACCAATTCCGTAGAGA 839
Sequence_75     AGCAAAATTAAAAGGCACGAGCGCTAAACAATGGGTTGACTATAACCAATTCCGTAGAGA 836
Sequence_43     AGCAAAATTAAAAGGCACGAGCGCTAAACAATGGGTTGACTATAACCAATTCCGTAGAGA 836
Sequence_47     AGCAAAATTAAAAGGCACGAGCGCTAAACAATGGGTTGACTATAACCAATTCCGTAGAGA 839
Sequence_79     AGCAAAATTAAAAGGCACGAGCGCTAAACAATGGGTTGACTATAACCAATTCCGTAGAGA 839
Sequence_51     AGCAAAATTAAAAGGCACGAGCGCTAAACAATGGGTTGACTATAACCAATTCCGTAGAGA 845
Sequence_83     AGCAAAATTAAAAGGCACGAGCGCTAAACAATGGGTTGACTATAACCAATTCCGTAGAGA 845
Sequence_7      AGCAAAATTAAAAGGCACGAGCGCTAAACAATGGGTTGACTATAACCAATTCCGTAGAGA 833
Sequence_25     AGCAAAATTAAAAGGCACGAGCGCTAAACAATGGGTTGACTATAACCAATTCCGTAGAGA 833
Sequence_29     AGCAAAATTAAAAGGCACGAGCGCTAAACAATGGGTTGACTATAACCAATTCCGTAGAGA 833
Sequence_33     AGCAAAATTAAAAGGCACGAGCGCTAAACAATGGGTTGACTATAACCAATTCCGTAGAGA 833
Sequence_69     AGCAAAATTAAAAGGCACGAGCGCTAAACAATGGGTTGACTATAACCAATTCCGTAGAGA 833
Sequence_11     AGCAAAATTAAAAGGCACGAGCGCTAAACAATGGGTTGACTATAACCAATTCCGTAGAGA 821
Sequence_1      AGCAAAATTAAAAGGCACGAGCGCTAAACAATGGGTTGACTATAACCAATTCCGTAGAGA 821
Sequence_17     AGCAAAATTAAAAGGCACGAGCGCTAAACAATGGGTTGACTATAACCAATTCCGTAGAGA 1551
Sequence_3      AGCAAAATTAAAAGGCACGAGCGCTAAACAATGGGTCGACTATAACCAATTCCGTAGAGA 821
Sequence_13     AGCAAAATTAAAAGGCACGAGCGCTAAACAATGGGTCGACTATAACCAATTCCGTAGAGA 821
Sequence_18     AGCAAAATTAAAAGGCACGAGCGCTAAACAATGGGTCGACTATAACCAATTCCGTAGAGA 2074
Cry8Ka1         AAATCAATTAAAAGGTTCGAATGCTAAGCAATGGATTGCATTTAATCGCTTCCGTAGAGA 815
                *    **********  ***  ***** ****** * *  * *** *  ***********
```

To Fig. 18P

Fig. 18O

From Fig. 18O

```
Sequence_71      AATGACACTGGCGGTTTTAGATGTTGTTGCATTATTCCCAAATTATGACACACGCACGTA 902
Sequence_73      AATGACACTGGCGGTTTTAGATGTTGTTGCATTATTCCCAAATTATGACACACGCACGTA 899
Sequence_21      AATGACACTGGCGGTTTTAGATGTTGTTGCATTATTCCCAAATTATGACACACGCACGTA 893
Sequence_67      AATGACACTGGCGGTTTTAGATGTTGTTGCATTATTCCCAAATTATGACACACGCACGTA 893
Sequence_61      AATGACACTGGCGGTTTTAGATGTTGTTGCATTATTCCCAAATTATGACACAATAACGTA 893
Sequence_93      AATGACACTGGCGGTTTTAGATGTTGTTGCATTATTCCCAAATTATGACACAATAACGTA 893
Sequence_59      AATGACACTGGCGGTTTTAGATGTTGTTGCATTATTCCCAAATTATGACACAATAACGTA 893
Sequence_91      AATGACACTGGCGGTTTTAGATGTTGTTGCATTATTCCCAAATTATGACACAATAACGTA 893
Sequence_39      AATGACACTGGCGGTTTTAGATGTTGTTGCATTATTCCCAAATTATGACACACGCACGTA 902
Sequence_41      AATGACACTGGCGGTTTTAGATGTTGTTGCATTATTCCCAAATTATGACACACGCACGTA 899
Sequence_49      AATGACACTGGCGGTTTTAGATGTTGTTGCATTATTCCCAAATTATGACACACGCACGTA 896
Sequence_81      AATGACACTGGCGGTTTTAGATGTTGTTGCATTATTCCCAAATTATGACACACGCACGTA 896
Sequence_45      AATGACACTGGCGGTTTTAGATGTTGTTGCATTATTCCCAAATTATGACACACGCACGTA 899
Sequence_77      AATGACACTGGCGGTTTTAGATGTTGTTGCATTATTCCCAAATTATGACACACGCACGTA 899
Sequence_75      AATGACACTGGCGGTTTTAGATGTTGTTGCATTATTCCCAAATTATGACACACGCACGTA 896
Sequence_43      AATGACACTGGCGGTTTTAGATGTTGTTGCATTATTCCCAAATTATGACACACGCACGTA 896
Sequence_47      AATGACACTGGCGGTTTTAGATGTTGTTGCATTATTCCCAAATTATGACACACGCACGTA 899
Sequence_79      AATGACACTGGCGGTTTTAGATGTTGTTGCATTATTCCCAAATTATGACACACGCACGTA 899
Sequence_51      AATGACACTGGCGGTTTTAGATGTTGTTGCATTATTCCCAAATTATGACACACGCACGTA 905
Sequence_83      AATGACACTGGCGGTTTTAGATGTTGTTGCATTATTCCCAAATTATGACACACGCACGTA 905
Sequence_7       AATGACACTGGCGGTTTTAGATGTTGTTGCATTATTCCCAAATTATGACACACGCACGTA 893
Sequence_25      AATGACACTGGCGGTTTTAGATGTTGTTGCATTATTCCCAAATTATGACACACGCACGTA 893
Sequence_29      AATGACACTGGCGGTTTTAGATGTTGTTGCATTATTCCCAAATTATGACACACGCACGTA 893
Sequence_33      AATGACACTGGCGGTTTTAGATGTTGTTGCATTATTCCCAAATTATGACACACGCACGTA 893
Sequence_69      AATGACACTGGCGGTTTTAGATGTTGTTGCATTATTCCCAAATTATGACACACGCACGTA 893
Sequence_11      AATGACACTGGCGGTTTTAGATGTTGTTGCATTATTCCCAAATTATGACACACGCACGTA 881
Sequence_1       AATGACACTGGCGGTTTTAGATGTTGTTGCATTATTCCCAAATTATGACACACGCACGTA 881
Sequence_17      AATGACACTGGCGGTTTTAGATGTTGTTGCATTATTCCCAAATTATGACACACGCACGTA 1611
Sequence_3       AATGACACTGACGGTTTTAGATGTTGTTGCATTATTCCCAAATTATGACACACGCACGTA 881
Sequence_13      AATGACACTGACGGTTTTAGATGTTGTTGCATTATTCCCAAATTATGACACACGCACGTA 881
Sequence_18      AATGACACTGACGGTTTTAGATGTTGTTGCATTATTCCCAAATTATGACACACGCACGTA 2134
Cry8Ka1          AATGACATTGACGGTACTGGATGTAGTTGCATTATTCCCGAACTATGATGTACGTATGTA 875
                 ******* ** ****  * ***** ************** ** *****   *   * ***
```

To Fig. 18Q

Fig. 18P

From Fig. 18P

```
Sequence_71      CCCAATGGAAACGAAAGCACAACTAACAAGGGAAGTATATACAGATCCACTGGGCGCGGT 962
Sequence_73      CCCAATGGAAACGAAAGCACAACTAACAAGGGAAGTATATACAGATCCACTGGGCGCGGT 959
Sequence_21      CCCAATGGAAACGAAAGCACAACTAACAAGGGAAGTATATACAGATCCACTGGGCGCGGT 953
Sequence_67      CCCAATGGAAACGAAAGCACAACTAACAAGGGAAGTATATACAGATCCACTGGGCGCGGT 953
Sequence_61      CCCAATAGAAACGAAAGCACAACTAACAAGGGAAGTATATACAGATCCACTGGGCGCGGT 953
Sequence_93      CCCAATAGAAACGAAAGCACAACTAACAAGGGAAGTATATACAGATCCACTGGGCGCGGT 953
Sequence_59      CCCAATGGAAACGAAAGCACAACTAACAAGGGAAGTATATACAGATCCACTGGGCGCGGT 953
Sequence_91      CCCAATGGAAACGAAAGCACAACTAACAAGGGAAGTATATACAGATCCACTGGGCGCGGT 953
Sequence_39      CCCAATGGAAACGAAAGCACAACTAACAAGGGAAGTATATACAGATCCACTGGGCGCGGT 962
Sequence_41      CCCAATGGAAACGAAAGCACAACTAACAAGGGAAGTATATACAGATCCACTGGGCGCGGT 959
Sequence_49      CCCAATGGAAACGAAAGCACAACTAACAAGGGAAGTATATACAGATCCACTGGGCGCGGT 956
Sequence_81      CCCAATGGAAACGAAAGCACAACTAACAAGGGAAGTATATACAGATCCACTGGGCGCGGT 956
Sequence_45      CCCAATGGAAACGAAAGCACAACTAACAAGGGAAGTATATACAGATCCACTGGGCGCGGT 959
Sequence_77      CCCAATGGAAACGAAAGCACAACTAACAAGGGAAGTATATACAGATCCACTGGGCGCGGT 959
Sequence_75      CCCAATGGAAACGAAAGCACAACTAACAAGGGAAGTATATACAGATCCACTGGGCGCGGT 956
Sequence_43      CCCAATGGAAACGAAAGCACAACTAACAAGGGAAGTATATACAGATCCACTGGGCGCGGT 956
Sequence_47      CCCAATGGAAACGAAAGCACAACTAACAAGGGAAGTATATACAGATCCACTGGGCGCGGT 959
Sequence_79      CCCAATGGAAACGAAAGCACAACTAACAAGGGAAGTATATACAGATCCACTGGGCGCGGT 959
Sequence_51      CCCAATGGAAACGAAAGCACAACTAACAAGGGAAGTATATACAGATCCACTGGGCGCGGT 965
Sequence_83      CCCAATGGAAACGAAAGCACAACTAACAAGGGAAGTATATACAGATCCACTGGGCGCGGT 965
Sequence_7       CCCAATGGAAACGAAAGCACAACTAACAAGGGAAGTATATACAGATCCACTGGGCGCGGT 953
Sequence_25      CCCAATGGAAACGAAAGCACAACTAACAAGGGAAGTATATACAGATCCACTGGGCGCGGT 953
Sequence_29      CCCAATGGAAACGAAAGCACAACTAACAAGGGAAGTATATACAGATCCACTGGGCGCGGT 953
Sequence_33      CCCAATGGAAACGAAAGCACAACTAACAAGGGAAGTATATACAGATCCACTGGGCGCGGT 953
Sequence_69      CCCAATGGAAACGAAAGCACAACTAACAAGGGAAGTATATACAGATCCACTGGGCGCGGT 953
Sequence_11      CCCAATGGAAACGAAAGCACAACTAACAAGGGAAGTATATACAGATCCACTGGGCGCGGT 941
Sequence_1       CCCAATGGAAACGAAAGCACAACTAACAAGGGAAGTATATACAGATCCACTGGGCGCGGT 941
Sequence_17      CCCAATGGAAACGAAAGCACAACTAACAAGGGAAGTATATACAGATCCACTGGGCGCGGT 1671
Sequence_3       CCCAATGGAAACGAAAGCACAACTAACAAGGGAAGTATATACAGATCCACTGGGCGCGGT 941
Sequence_13      CCCAATGGAAACGAAAGCACAACTAACAAGGGAAGTATATACAGATCCACTGGGCGCGGT 941
Sequence_18      CCCAATGGAAACGAAAGCACAACTAACAAGGGAAGTATATACAGATCCACTGGGCGCGGT 2194
Cry8Ka1          CCCTATAAAAACAACTACAGAGCTAACGAGAACAATTTATACCGATCCACTTGGTTACAC 935
                 *** **  **** *   ** * ***** **   * * ***** ******** **
```

To Fig. 18R

Fig. 18Q

From Fig. 18Q

```
Sequence_71          AAACGTGTCTTCAATTGGT------TCCTGGTATGACAAAGCACCTTCTTTCGGAGTGAT 1016
Sequence_73          AAACGTGTCTTCAATTGGT------TCCTGGTATGACAAAGCACCTTCTTTCGGAGTGAT 1013
Sequence_21          AAACGTGTCTTCAATTGGT------TCCTGGTATGACAAAGCACCTTCTTTCGGAGTGAT 1007
Sequence_67          AAACGTGTCTTCAATTGGT------TCCTGGTATGACAAAGCACCTTCTTTCGGAGTGAT 1007
Sequence_61          AAACGTGTCTTCAATTGGT------TCCTGGTATGACAAAGCACCTTCTTTCGGAGTGAT 1007
Sequence_93          AAACGTGTCTTCAATTGGT------TCCTGGTATGACAAAGCACCTTCTTTCGGAGTGAT 1007
Sequence_59          AAACGTGTCTTCAATTGGT------TCCTGGTATGACAAAGCACCTTCTTTCGGAGTGAT 1007
Sequence_91          AAACGTGTCTTCAATTGGT------TCCTGGTATGACAAAGCACCTTCTTTCGGAGTGAT 1007
Sequence_39          AAACGTGTCTTCAATTGGT------TCCTGGTATGACAAAGCACCTTCTTTCGGAGTGAT 1016
Sequence_41          AAACGTGTCTTCAATTGGT------TCCTGGTATGACAAAGCACCTTCTTTCGGAGTGAT 1013
Sequence_49          AAACGTGTCTTCAATTGGT------TCCTGGTATGACAAAGCACCTTCTTTCGGAGTGAT 1010
Sequence_81          AAACGTGTCTTCAATTGGT------TCCTGGTATGACAAAGCACCTTCTTTCGGAGTGAT 1010
Sequence_45          AAACGTGTCTTCAATTGGT------TCCTGGTATGACAAAGCACCTTCTTTCGGAGTGAT 1013
Sequence_77          AAACGTGTCTTCAATTGGT------TCCTGGTATGACAAAGCACCTTCTTTCGGAGTGAT 1013
Sequence_75          AAACGTGTCTTCAATTGGT------TCCTGGTATGACAAAGCACCTTCTTTCGGAGTGAT 1010
Sequence_43          AAACGTGTCTTCAATTGGT------TCCTGGTATGACAAAGCACCTTCTTTCGGAGTGAT 1010
Sequence_47          AAACGTGTCTTCAATTGGT------TCCTGGTATGACAAAGCACCTTCTTTCGGAGTGAT 1013
Sequence_79          AAACGTGTCTTCAATTGGT------TCCTGGTATGACAAAGCACCTTCTTTCGGAGTGAT 1013
Sequence_51          AAACGTGTCTTCAATTGGT------TCCTGGTATGACAAAGCACCTTCTTTCGGAGTGAT 1019
Sequence_83          AAACGTGTCTTCAATTGGT------TCCTGGTATGACAAAGCACCTTCTTTCGGAGTGAT 1019
Sequence_7           AAACGTGTCTTCAATTGGT------TCCTGGTATGACAAAGCACCTTCTTTCGGAGTGAT 1007
Sequence_25          AAACGTGTCTTCAATTGGT------TCCTGGTATGACAAAGCACCTTCTTTCGGAGTGAT 1007
Sequence_29          AAACGTGTCTTCAATTGGT------TCCTGGTATGACAAAGCACCTTCTTTCGGAGTGAT 1007
Sequence_33          AAACGTGTCTTCAATTGGT------TCCTGGTATGACAAAGCACCTTCTTTCGGAGTGAT 1007
Sequence_69          AAACGTGTCTTCAATTGGT------TCCTGGTATGACAAAGCACCTTCTTTCGGAGTGAT 1007
Sequence_11          AAACGTGTCTTCAATTGGT------TCCTGGTATGACAAAGCACCTTCTTTCGGAGTGAT 995
Sequence_1           AAACGTGTCTTCAATTGGT------TCCTGGTATGACAAAGCACCTTCTTTCGGAGTGAT 995
Sequence_17          AAACGTGTCTTCAATTGGT------TCCTGGTATGACAAAGCACCTTCTTTCGGAGTGAT 1725
Sequence_3           AAACGTGTCTTCAATTGGT------TCCTGGTATGACAAAGCACCTTCTTTCGGAGTGAT 995
Sequence_13          AAACGTGTCTTCAATTGGT------TCCTGGTATGACAAAGCACCTTCTTTCGGAGTGAT 995
Sequence_18          AAACGTGTCTTCAATTGGT------TCCTGGTATGACAAAGCACCTTCTTTCGGAGTGAT 2248
Cry8Ka1              GAAAACGGGTTCTAGTAGTACACCACCATGGTATAATTATGGATCTAGTTTCTCATATAT 995
                      **   *  *** * * **       * ****** *  * * * **  ****  *   **
```

To Fig. 18S

Fig. 18R

From Fig. 18R

```
Sequence_71    AGAATCATCCGTTATTCGACCACCCCATGTATTTGATTATATAACGGGACTCACAGTGTA 1076
Sequence_73    AGAATCATCCGTTATTCGACCACCCCATGTATTTGATTATATAACGGGACTCACAGTGTA 1073
Sequence_21    AGAATCATCCGTTATTCGACCACCCCATGTATTTGATTATATAACGGGACTCACAGTGTA 1067
Sequence_67    AGAATCATCCGTTATTCGACCACCCCATGTATTTGATTATATAACGGGACTCACAGTGTA 1067
Sequence_61    AGAATCATCCGTTATTCGACCACCCCATGTATTTGATTATATAACGGGACTCACAGTGTA 1067
Sequence_93    AGAATCATCCGTTATTCGACCACCCCATGTATTTGATTATATAACGGGACTCACAGTGTA 1067
Sequence_59    AGAATCATCCGTTATTCGACCACCCCATGTATTTGATTATATAACGGGACTCACAGTGTA 1067
Sequence_91    AGAATCATCCGTTATTCGACCACCCCATGTATTTGATTATATAACGGGACTCACAGTGTA 1067
Sequence_39    AGAATCATCCGTTATTCGACCACCCCATGTATTTGATTATATAACGGGACTCACAGTGTA 1076
Sequence_41    AGAATCATCCGTTATTCGACCACCCCATGTATTTGATTATATAACGGGACTCACAGTGTA 1073
Sequence_49    AGAATCATCCGTTATTCGACCACCCCATGTATTTGATTATATAACGGGACTCACAGTGTA 1070
Sequence_81    AGAATCATCCGTTATTCGACCACCCCATGTATTTGATTATATAACGGGACTCACAGTGTA 1070
Sequence_45    AGAATCATCCGTTATTCGACCACCCCATGTATTTGATTATATAACGGGACTCACAGTGTA 1073
Sequence_77    AGAATCATCCGTTATTCGACCACCCCATGTATTTGATTATATAACGGGACTCACAGTGTA 1073
Sequence_75    AGAATCATCCGTTATTCGACCACCCCATGTATTTGATTATATAACGGGACTCACAGTGTA 1070
Sequence_43    AGAATCATCCGTTATTCGACCACCCCATGTATTTGATTATATAACGGGACTCACAGTGTA 1070
Sequence_47    AGAATCATCCGTTATTCGACCACCCCATGTATTTGATTATATAACGGGACTCACAGTGTA 1073
Sequence_79    AGAATCATCCGTTATTCGACCACCCCATGTATTTGATTATATAACGGGACTCACAGTGTA 1073
Sequence_51    AGAATCATCCGTTATTCGACCACCCCATGTATTTGATTATATAACGGGACTCACAGTGTA 1079
Sequence_83    AGAATCATCCGTTATTCGACCACCCCATGTATTTGATTATATAACGGGACTCACAGTGTA 1079
Sequence_7     AGAATCATCCGTTATTCGACCACCCCATGTATTTGATTATATAACGGGACTCACAGTGTA 1067
Sequence_25    AGAATCATCCGTTATTCGACCACCCCATGTATTTGATTATATAACGGGACTCACAGTGTA 1067
Sequence_29    AGAATCATCCGTTATTCGACCACCCCATGTATTTGATTATATAACGGGACTCACAGTGTA 1067
Sequence_33    AGAATCATCCGTTATTCGACCACCCCATGTATTTGATTATATAACGGGACTCACAGTGTA 1067
Sequence_69    AGAATCATCCGTTATTCGACCACCCCATGTATTTGATTATATAACGGGACTCACAGTGTA 1067
Sequence_11    AGAATCATCCGTTATTCGACCACCCCATGTATTTGATTATATAACGGGACTCACAGTGTA 1055
Sequence_1     AGAATCATCCGTTATTCGACCACCCCATGTATTTGATTATATAACGGGACTCACAGTGTA 1055
Sequence_17    AGAATCATCCGTTATTCGACCACCCCATGTATTTGATTATATAACGGGACTCACAGTGTA 1785
Sequence_3     AGAATCATCCGTTATTCGACCACCCCATGTATTTGATTATATAACGGGACTCACAGTGTA 1055
Sequence_13    AGAATCATCCGTTATTCGACCACCCCATGTATTTGATTATATAACGGGACTCACAGTGTA 1055
Sequence_18    AGAATCATCCGTTATTCGACCACCCCATGTATTTGATTATATAACGGGACTCACAGTGTA 2308
Cry8Ka1        AGAAAGTGTAGCGATTCCAGCCCCTAGTCTGGTTAAGTGGTTAAGTCAGATTGAAATTTA 1055
               ****      *  **** * * **   * *  ** * *   ***      *   * * **
```

To Fig. 18T

Fig. 18S

From Fig. 18S

```
Sequence_71     TACACAATCAAGAAGCATTTCTTCCGCTCGCTATATAAGACATTGGGCTGGTCATCAAAT 1136
Sequence_73     TACACAATCAAGAAGCATTTCTTCCGCTCGCTATATAAGACATTGGGCTGGTCATCAAAT 1133
Sequence_21     TACACAATCAAGAAGCATTTCTTCCGCTCGCTATATAAGACATTGGGCTGGTCATCAAAT 1127
Sequence_67     TACACAATCAAGAAGCATTTCTTCCGCTCGCTATATAAGACATTGGGCTGGTCATCAAAT 1127
Sequence_61     TACACAATCAAGAAGCATTTCTTCCGCTCGCTATATAAGACATTGGGCTGGTCATCAAAT 1127
Sequence_93     TACACAATCAAGAAGCATTTCTTCCGCTCGCTATATAAGACATTGGGCTGGTCATCAAAT 1127
Sequence_59     TACACAATCAAGAAGCATTTCTTCCGCTCGCTATATAAGACATTGGGCTGGTCATCAAAT 1127
Sequence_91     TACACAATCAAGAAGCATTTCTTCCGCTCGCTATATAAGACATTGGGCTGGTCATCAAAT 1127
Sequence_39     TACACAATCAAGAAGCATTTCTTCCGCTCGCTATATAAGACATTGGGCTGGTCATCAAAT 1136
Sequence_41     TACACAATCAAGAAGCATTTCTTCCGCTCGCTATATAAGACATTGGGCTGGTCATCAAAT 1133
Sequence_49     TACACAATCAAGAAGCATTTCTTCCGCTCGCTATATAAGACATTGGGCTGGTCATCAAAT 1130
Sequence_81     TACACAATCAAGAAGCATTTCTTCCGCTCGCTATATAAGACATTGGGCTGGTCATCAAAT 1130
Sequence_45     TACACAATCAAGAAGCATTTCTTCCGCTCGCTATATAAGACATTGGGCTGGTCATCAAAT 1133
Sequence_77     TACACAATCAAGAAGCATTTCTTCCGCTCGCTATATAAGACATTGGGCTGGTCATCAAAT 1133
Sequence_75     TACACAATCAAGAAGCATTTCTTCCGCTCGCTATATAAGACATTGGGCTGGTCATCAAAT 1130
Sequence_43     TACACAATCAAGAAGCATTTCTTCCGCTCGCTATATAAGACATTGGGCTGGTCATCAAAT 1130
Sequence_47     TACACAATCAAGAAGCATTTCTTCCGCTCGCTATATAAGACATTGGGCTGGTCATCAAAT 1133
Sequence_79     TACACAATCAAGAAGCATTTCTTCCGCTCGCTATATAAGACATTGGGCTGGTCATCAAAT 1133
Sequence_51     TACACAATCAAGAAGCATTTCTTCCGCTCGCTATATAAGACATTGGGCTGGTCATCAAAT 1139
Sequence_83     TACACAATCAAGAAGCATTTCTTCCGCTCGCTATATAAGACATTGGGCTGGTCATCAAAT 1139
Sequence_7      TACACAATCAAGAAGCATTTCTTCCGCTCGCTATATAAGACATTGGGCTGGTCATCAAAT 1127
Sequence_25     TACACAATCAAGAAGCATTTCTTCCGCTCGCTATATAAGACATTGGGCTGGTCATCAAAT 1127
Sequence_29     TACACAATCAAGAAGCATTTCTTCCGCTCGCTATATAAGACATTGGGCTGGTCATCAAAT 1127
Sequence_33     TACACAATCAAGAAGCATTTCTTCCGCTCGCTATATAAGACATTGGGCTGGTCATCAAAT 1127
Sequence_69     TACACAATCAAGAAGCATTTCTTCCGCTCGCTATATAAGACATTGGGCTGGTCATCAAAT 1127
Sequence_11     TACACAATCAAGAAGCATTTCTTCCGCTCGCTATATAAGACATTGGGCTGGTCATCAAAT 1115
Sequence_1      TACACAATCAAGAAGCATTTCTTCCGCTCGCTATATAAGACATTGGGCTGGTCATCAAAT 1115
Sequence_17     TACACAATCAAGAAGCATTTCTTCCGCTCGCTATATAAGACATTGGGCTGGTCATCAAAT 1845
Sequence_3      TACACAATCAAGAAGCATTTCTTCCGCTCGCTATATAAGACATTGGGCTGGTCATCAAAT 1115
Sequence_13     TACACAATCAAGAAGCATTTCTTCCGCTCGCTATATAAGACATTGGGCTGGTCATCAAAT 1115
Sequence_18     TACACAATCAAGAAGCATTTCTTCCGCTCGCTATATAAGACATTGGGCTGGTCATCAAAT 2368
Cry8Ka1         TTCGAAATCCGCAAGGGCTACACC---GCAAAGTGCGGATTATTGGGCAGGACATACAAT 1112
                * *  ****   ***   * *  *    *    *       ******* ** ***  ***
```

To Fig. 18U

Fig. 18T

From Fig. 18T

```
Sequence_71    AAGCTACCATCGTGTCAGTAGGGGTAGTAATCTTCAACAAATGTATGGAACTAATCAAAA 1196
Sequence_73    AAGCTACCATCGTGTCAGTAGGGGTAGTAATCTTCAACAAATGTATGGAACTAATCAAAA 1193
Sequence_21    AAGCTACCATCGTGTCAGTAGGGGTAGTAATCTTCAACAAATGTATGGAACTAATCAAAA 1187
Sequence_67    AAGCTACCATCGTGTCAGTAGGGGTAGTAATCTTCAACAAATGTATGGAACTAATCAAAA 1187
Sequence_61    AAGCTACCATCGTGTCAGTAGGGGTAGTAATCTTCAACAAATGTATGGAACTAATCAAAA 1187
Sequence_93    AAGCTACCATCGTGTCAGTAGGGGTAGTAATCTTCAACAAATGTATGGAACTAATCAAAA 1187
Sequence_59    AAGCTACCATCGTGTCAGTAGGGGTAGTAATCTTCAACAAATGTATGGAACTAATCAAAA 1187
Sequence_91    AAGCTACCATCGTGTCAGTAGGGGTAGTAATCTTCAACAAATGTATGGAACTAATCAAAA 1187
Sequence_39    AAGCTACCATCGTGTCAGTAGGGGTAGTAATCTTCAACAAATGTATGGAACTAATCAAAA 1196
Sequence_41    AAGCTACCATCGTGTCAGTAGGGGTAGTAATCTTCAACAAATGTATGGAACTAATCAAAA 1193
Sequence_49    AAGCTACCATCGTGTCAGTAGGGGTAGTAATCTTCAACAAATGTATGGAACTAATCAAAA 1190
Sequence_81    AAGCTACCATCGTGTCAGTAGGGGTAGTAATCTTCAACAAATGTATGGAACTAATCAAAA 1190
Sequence_45    AAGCTACCATCGTGTCAGTAGGGGTAGTAATCTTCAACAAATGTATGGAACTAATCAAAA 1193
Sequence_77    AAGCTACCATCGTGTCAGTAGGGGTAGTAATCTTCAACAAATGTATGGAACTAATCAAAA 1193
Sequence_75    AAGCTACCATCGTGTCAGTAGGGGTAGTAATCTTCAACAAATGTATGGAACTAATCAAAA 1190
Sequence_43    AAGCTACCATCGTGTCAGTAGGGGTAGTAATCTTCAACAAATGTATGGAACTAATCAAAA 1190
Sequence_47    AAGCTACCATCGTGTCAGTAGGGGTAGTAATCTTCAACAAATGTATGGAACTAATCAAAA 1193
Sequence_79    AAGCTACCATCGTGTCAGTAGGGGTAGTAATCTTCAACAAATGTATGGAACTAATCAAAA 1193
Sequence_51    AAGCTACCATCGTGTCAGTAGGGGTAGTAATCTTCAACAAATGTATGGAACTAATCAAAA 1199
Sequence_83    AAGCTACCATCGTGTCAGTAGGGGTAGTAATCTTCAACAAATGTATGGAACTAATCAAAA 1199
Sequence_7     AAGCTACCATCGTGTCAGTAGGGGTAGTAATCTTCAACAAATGTATGGAACTAATCAAAA 1187
Sequence_25    AAGCTACCATCGTGTCAGTAGGGGTAGTAATCTTCAACAAATGTATGGAACTAATCAAAA 1187
Sequence_29    AAGCTACCATCGTGTCAGTAGGGGTAGTAATCTTCAACAAATGTATGGAACTAATCAAAA 1187
Sequence_33    AAGCTACCATCGTGTCAGTAGGGGTAGTAATCTTCAACAAATGTATGGAACTAATCAAAA 1187
Sequence_69    AAGCTACCATCGTGTCAGTAGGGGTAGTAATCTTCAACAAATGTATGGAACTAATCAAAA 1187
Sequence_11    AAGCTACCATCGTGTCAGTAGGGGTAGTAATCTTCAACAAATGTATGGAACTAATCAAAA 1175
Sequence_1     AAGCTACCATCGTGTCAGTAGGGGTAGTAATCTTCAACAAATGTATGGAACTAATCAAAA 1175
Sequence_17    AAGCTACCATCGTGTCAGTAGGGGTAGTAATCTTCAACAAATGTATGGAACTAATCAAAA 1905
Sequence_3     AAGCTATCATCGGATTTTTAGTGATAATATTATAAAACAGATGTATGGAACTAATCAAAA 1175
Sequence_13    AAGCTATCATCGGATTTTTAGTGATAATATTATAAAACAGATGTATGGAACTAATCAAAA 1175
Sequence_18    AAGCTATCATCGGATTTTTAGTGATAATATTATAAAACAGATGTATGGAACTAATCAAAA 2428
Cry8Ka1        AACATATCACTATAGTGGAGATGATGGTCAAGCAGTACCTAATTATGGAGATAGAACGAA 1172
               **  ** **             * *  *        **  *  ******  **     **
```

To Fig. 18V

Fig. 18U

From Fig. 18U

```
Sequence_71    TCTACACAGCACTAGTACCTTTGATTTTACGAATTATGATATTTACAAGACTCTATCAAA 1256
Sequence_73    TCTACACAGCACTAGTACCTTTGATTTTACGAATTATGATATTTACAAGACTCTATCAAA 1253
Sequence_21    TCTACACAGCACTAGTACCTTTGATTTTACGAATTATGATATTTACAAGACTCTATCAAA 1247
Sequence_67    TCTACACAGCACTAGTACCTTTGATTTTACGAATTATGATATTTACAAGACTCTATCAAA 1247
Sequence_61    TCTACACAGCACTAGTACCTTTGATTTTACGAATTATGATATTTACAAGACTCTATCAAA 1247
Sequence_93    TCTACACAGCACTAGTACCTTTGATTTTACGAATTATGATATTTACAAGACTCTATCAAA 1247
Sequence_59    TCTACACAGCACTAGTACCTTTGATTTTACGAATTATGATATTTACAAGACTCTATCAAA 1247
Sequence_91    TCTACACAGCACTAGTACCTTTGATTTTACGAATTATGATATTTACAAGACTCTATCAAA 1247
Sequence_39    TCTACACAGCACTAGTACCTTTGATTTTACGAATTATGATATTTACAAGACTCTATCAAA 1256
Sequence_41    TCTACACAGCACTAGTACCTTTGATTTTACGAATTATGATATTTACAAGACTCTATCAAA 1253
Sequence_49    TCTACACAGCACTAGTACCTTTGATTTTACGAATTATGATATTTACAAGACTCTATCAAA 1250
Sequence_81    TCTACACAGCACTAGTACCTTTGATTTTACGAATTATGATATTTACAAGACTCTATCAAA 1250
Sequence_45    TCTACACAGCACTAGTACCTTTGATTTTACGAATTATGATATTTACAAGACTCTATCAAA 1253
Sequence_77    TCTACACAGCACTAGTACCTTTGATTTTACGAATTATGATATTTACAAGACTCTATCAAA 1253
Sequence_75    TCTACACAGCACTAGTACCTTTGATTTTACGAATTATGATATTTACAAGACTCTATCAAA 1250
Sequence_43    TCTACACAGCACTAGTACCTTTGATTTTACGAATTATGATATTTACAAGACTCTATCAAA 1250
Sequence_47    TCTACACAGCACTAGTACCTTTGATTTTACGAATTATGATATTTACAAGACTCTATCAAA 1253
Sequence_79    TCTACACAGCACTAGTACCTTTGATTTTACGAATTATGATATTTACAAGACTCTATCAAA 1253
Sequence_51    TCTACACAGCACTAGTACCTTTGATTTTACGAATTATGATATTTACAAGACTCTATCAAA 1259
Sequence_83    TCTACACAGCACTAGTACCTTTGATTTTACGAATTATGATATTTACAAGACTCTATCAAA 1259
Sequence_7     TCTACACAGCACTAGTACCTTTGATTTTACGAATTATGATATTTACAAGACTCTATCAAA 1247
Sequence_25    TCTACACAGCACTAGTACCTTTGATTTTACGAATTATGATATTTACAAGACTCTATCAAA 1247
Sequence_29    TCTACACAGCACTAGTACCTTTGATTTTACGAATTATGATATTTACAAGACTCTATCAAA 1247
Sequence_33    TCTACACAGCACTAGTACCTTTGATTTTACGAATTATGATATTTACAAGACTCTATCAAA 1247
Sequence_69    TCTACACAGCACTAGTACCTTTGATTTTACGAATTATGATATTTACAAGACTCTATCAAA 1247
Sequence_11    TCTACACAGCACTAGTACCTTTGATTTTACGAATTATGATATTTACAAGACTCTATCAAA 1235
Sequence_1     TCTACACAGCACTAGTACCTTTGATTTTACGAATTATGATATTTACAAGACTCTATCAAA 1235
Sequence_17    TCTACACAGCACTAGTACCTTTGATTTTACGAATTATGATATTTACAAGACTCTATCAAA 1965
Sequence_3     TCTACACAGCACTAGTACCTTTGATTTTACGAATTATGATATTTACAAGACGTTATCAAA 1235
Sequence_13    TCTACACAGCACTAGTACCTTTGATTTTACGAATTATGATATTTACAAGACGTTATCAAA 1235
Sequence_18    TCTACACAGCACTAGTACCTTTGATTTTACGAATTATGATATTTACAAGACGTTATCAAA 2488
Cry8Ka1        TCCTGTAATTGTAAATCGTTATAATTTTGAGCAGGCTGACATTTATAGAGTTTCATCATC 1232
               **     *     * *   * * *****  * *   *** ***** *       ****
```

To Fig. 18W

Fig. 18V

From Fig. 18V

```
Sequence_71     GGATGCAGTACTCCTTGATATTGTT-TACCCTGGTTATACGTATATATTTTTTGGAATGC 1315
Sequence_73     GGATGCAGTACTCCTTGATATTGTT-TACCCTGGTTATACGTATATATTTTTTGGAATGC 1312
Sequence_21     GGATGCAGTACTCCTTGATATTGTT-TACCCTGGTTATACGTATATATTTTTTGGAATGC 1306
Sequence_67     GGATGCAGTACTCCTTGATATTGTT-TACCCTGGTTATACGTATATATTTTTTGGAATGC 1306
Sequence_61     GGATGCAGTACTCCTTGATATTGTT-TACCCTGGTTATACGTATATATTTTTTGGAATGC 1306
Sequence_93     GGATGCAGTACTCCTTGATATTGTT-TACCCTGGTTATACGTATATATTTTTTGGAATGC 1306
Sequence_59     GGATGCAGTACTCCTTGATATTGTT-TACCCTGGTTATACGTATATATTTTTTGGAATGC 1306
Sequence_91     GGATGCAGTACTCCTTGATATTGTT-TACCCTGGTTATACGTATATATTTTTTGGAATGC 1306
Sequence_39     GGATGCAGTACTCCTTGATATTGTT-TACCCTGGTTATACGTATATATTTTTTGGAATGC 1315
Sequence_41     GGATGCAGTACTCCTTGATATTGTT-TACCCTGGTTATACGTATATATTTTTTGGAATGC 1312
Sequence_49     GGATGCAGTACTCCTTGATATTGTT-TACCCTGGTTATACGTATATATTTTTTGGAATGC 1309
Sequence_81     GGATGCAGTACTCCTTGATATTGTT-TACCCTGGTTATACGTATATATTTTTTGGAATGC 1309
Sequence_45     GGATGCAGTACTCCTTGATATTGTT-TACCCTGGTTATACGTATATATTTTTTGGAATGC 1312
Sequence_77     GGATGCAGTACTCCTTGATATTGTT-TACCCTGGTTATACGTATATATTTTTTGGAATGC 1312
Sequence_75     GGATGCAGTACTCCTTGATATTGTT-TACCCTGGTTATACGTATATATTTTTTGGAATGC 1309
Sequence_43     GGATGCAGTACTCCTTGATATTGTT-TACCCTGGTTATACGTATATATTTTTTGGAATGC 1309
Sequence_47     GGATGCAGTACTCCTTGATATTGTT-TACCCTGGTTATACGTATATATTTTTTGGAATGC 1312
Sequence_79     GGATGCAGTACTCCTTGATATTGTT-TACCCTGGTTATACGTATATATTTTTTGGAATGC 1312
Sequence_51     GGATGCAGTACTCCTTGATATTGTT-TACCCTGGTTATACGTATATATTTTTTGGAATGC 1318
Sequence_83     GGATGCAGTACTCCTTGATATTGTT-TACCCTGGTTATACGTATATATTTTTTGGAATGC 1318
Sequence_7      GGATGCAGTACTCCTTGATATTGTT-TACCCTGGTTATACGTATATATTTTTTGGAATGC 1306
Sequence_25     GGATGCAGTACTCCTTGATATTGTT-TACCCTGGTTATACGTATATATTTTTTGGAATGC 1306
Sequence_29     GGATGCAGTACTCCTTGATATTGTT-TACCCTGGTTATACGTATATATTTTTTGGAATGC 1306
Sequence_33     GGATGCAGTACTCCTTGATATTGTT-TACCCTGGTTATACGTATATATTTTTTGGAATGC 1306
Sequence_69     GGATGCAGTACTCCTTGATATTGTT-TACCCTGGTTATACGTATATATTTTTTGGAATGC 1306
Sequence_11     GGATGCAGTACTCCTTGATATTGTT-TACCCTGGTTATACGTATATATTTTTTGGAATGC 1294
Sequence_1      GGATGCAGTACTCCTTGATATTGTT-TACCCTGGTTATACGTATATATTTTTTGGAATGC 1294
Sequence_17     GGATGCAGTACTCCTTGATATTGTT-TACCCTGGTTATACGTATATATTTTTTGGAATGC 2024
Sequence_3      AGATGCGGTGCTCCTTGATATTGTT-TTTCCTGGTTATACGTATATATTTTTTGGAATGC 1294
Sequence_13     AGATGCGGTGCTCCTTGATATTGTT-TTTCCTGGTTATACGTATATATTTTTTGGAATGC 1294
Sequence_18     AGATGCGGTGCTCCTTGATATTGTT-TTTCCTGGTTATACGTATATATTTTTTGGAATGC 2547
Cry8Ka1         TGTTGCTTCAAGTACAACTAGTGGTGTTAAATTATTAACTACTAAGGCTATATTTGATGG 1292
                 * ***            ** ** * *    *  ***       *   * * *   ***
```

To Fig. 18X

Fig. 18W

From Fig. 18W

```
Sequence_71      CAGAAGTCGAGTTTTTCATGGTAAACCAATTGAATA-ATACCAGAAAGAC-GTTAAAGTA 1373
Sequence_73      CAGAAGTCGAGTTTTTCATGGTAAACCAATTGAATA-ATACCAGAAAGAC-GTTAAAGTA 1370
Sequence_21      CAGAAGTCGAGTTTTTCATGGTAAACCAATTGAATA-ATACCAGAAAGAC-GTTAAAGTA 1364
Sequence_67      CAGAAGTCGAGTTTTTCATGGTAAACCAATTGAATA-ATACCAGAAAGAC-GTTAAAGTA 1364
Sequence_61      CAGAAGTCGAGTTTTTCATGGTAAACCAATTGAATA-ATACCAGAAAGAC-GTTAAAGTA 1364
Sequence_93      CAGAAGTCGAGTTTTTCATGGTAAACCAATTGAATA-ATACCAGAAAGAC-GTTAAAGTA 1364
Sequence_59      CAGAAGTCGAGTTTTTCATGGTAAACCAATTGAATA-ATACCAGAAAGAC-GTTAAAGTA 1364
Sequence_91      CAGAAGTCGAGTTTTTCATGGTAAACCAATTGAATA-ATACCAGAAAGAC-GTTAAAGTA 1364
Sequence_39      CAGAAGTCGAGTTTTTCATGGTAAACCAATTGAATA-ATACCAGAAAGAC-GTTAAAGTA 1373
Sequence_41      CAGAAGTCGAGTTTTTCATGGTAAACCAATTGAATA-ATACCAGAAAGAC-GTTAAAGTA 1370
Sequence_49      CAGAAGTCGAGTTTTTCATGGTAAACCAATTGAATA-ATACCAGAAAGAC-GTTAAAGTA 1367
Sequence_81      CAGAAGTCGAGTTTTTCATGGTAAACCAATTGAATA-ATACCAGAAAGAC-GTTAAAGTA 1367
Sequence_45      CAGAAGTCGAGTTTTTCATGGTAAACCAATTGAATA-ATACCAGAAAGAC-GTTAAAGTA 1370
Sequence_77      CAGAAGTCGAGTTTTTCATGGTAAACCAATTGAATA-ATACCAGAAAGAC-GTTAAAGTA 1370
Sequence_75      CAGAAGTCGAGTTTTTCATGGTAAACCAATTGAATA-ATACCAGAAAGAC-GTTAAAGTA 1367
Sequence_43      CAGAAGTCGAGTTTTTCATGGTAAACCAATTGAATA-ATACCAGAAAGAC-GTTAAAGTA 1367
Sequence_47      CAGAAGTCGAGTTTTTCATGGTAAACCAATTGAATA-ATACCAGAAAGAC-GTTAAAGTA 1370
Sequence_79      CAGAAGTCGAGTTTTTCATGGTAAACCAATTGAATA-ATACCAGAAAGAC-GTTAAAGTA 1370
Sequence_51      CAGAAGTCGAGTTTTTCATGGTAAACCAATTGAATA-ATACCAGAAAGAC-GTTAAAGTA 1376
Sequence_83      CAGAAGTCGAGTTTTTCATGGTAAACCAATTGAATA-ATACCAGAAAGAC-GTTAAAGTA 1376
Sequence_7       CAGAAGTCGAGTTTTTCATGGTAAACCAATTGAATA-ATACCAGAAAGAC-GTTAAAGTA 1364
Sequence_25      CAGAAGTCGAGTTTTTCATGGTAAACCAATTGAATA-ATACCAGAAAGAC-GTTAAAGTA 1364
Sequence_29      CAGAAGTCGAGTTTTTCATGGTAAACCAATTGAATA-ATACCAGAAAGAC-GTTAAAGTA 1364
Sequence_33      CAGAAGTCGAGTTTTTCATGGTAAACCAATTGAATA-ATACCAGAAAGAC-GTTAAAGTA 1364
Sequence_69      CAGAAGTCGAGTTTTTCATGGTAAACCAATTGAATA-ATACCAGAAAGAC-GTTAAAGTA 1364
Sequence_11      CAGAAGTCGAGTTTTTCATGGTAAACCAATTGAATA-ATACCAGAAAGAC-GTTAAAGTA 1352
Sequence_1       CAGAAGTCGAGTTTTTCATGGTAAACCAATTGAATA-ATACCAGAAAGAC-GTTAAAGTA 1352
Sequence_17      CAGAAGTCGAGTTTTTCATGGTAAACCAATTGAATA-ATACCAGAAAGAC-GTTAAAGTA 2082
Sequence_3       CAGAAGTCGAGTTTTTCATGGTAAACCAATTGAATA-ATACCAGAAAGAC-GTTAAAGTA 1352
Sequence_13      CAGAAGTCGAGTTTTTCATGGTAAACCAATTGAATA-ATACCAGAAAGAC-GTTAAAGTA 1352
Sequence_18      CAGAAGTCGAGTTTTTCATGGTAAACCAATTGAATA-ATACCAGAAAGAC-GTTAAAGTA 2605
Cry8Ka1          CATAAGTACAA------ACAATGGACTAGTGAGTTACATGTATGAAAAATTATCGAACTT 1346
                 ** ****  *         *    *   ** * *    ** **    **** *    *  ** *
```

To Fig. 18Y

Fig. 18X

From Fig. 18X

```
Sequence_71    TAATCCAGTTTCCAAAGATATTATAGCGAGTACAAGAGATTCGGAATTAGAAT----TAC 1429
Sequence_73    TAATCCAGTTTCCAAAGATATTATAGCGAGTACAAGAGATTCGGAATTAGAAT----TAC 1426
Sequence_21    TAATCCAGTTTCCAAAGATATTATAGCGAGTACAAGAGATTCGGAATTAGAAT----TAC 1420
Sequence_67    TAATCCAGTTTCCAAAGATATTATAGCGAGTACAAGAGATTCGGAATTAGAAT----TAC 1420
Sequence_61    TAATCCAGTTTCCAAAGATATTATAGCGAGTACAAGAGATTCGGAATTAGAAT----TAC 1420
Sequence_93    TAATCCAGTTTCCAAAGATATTATAGCGAGTACAAGAGATTCGGAATTAGAAT----TAC 1420
Sequence_59    TAATCCAGTTTCCAAAGATATTATAGCGAGTACAAGAGATTCGGAATTAGAAT----TAC 1420
Sequence_91    TAATCCAGTTTCCAAAGATATTATAGCGAGTACAAGAGATTCGGAATTAGAAT----TAC 1420
Sequence_39    TAATCCAGTTTCCAAAGATATTATAGCGAGTACAAGAGATTCGGAATTAGAAT----TAC 1429
Sequence_41    TAATCCAGTTTCCAAAGATATTATAGCGAGTACAAGAGATTCGGAATTAGAAT----TAC 1426
Sequence_49    TAATCCAGTTTCCAAAGATATTATAGCGAGTACAAGAGATTCGGAATTAGAAT----TAC 1423
Sequence_81    TAATCCAGTTTCCAAAGATATTATAGCGAGTACAAGAGATTCGGAATTAGAAT----TAC 1423
Sequence_45    TAATCCAGTTTCCAAAGATATTATAGCGAGTACAAGAGATTCGGAATTAGAAT----TAC 1426
Sequence_77    TAATCCAGTTTCCAAAGATATTATAGCGAGTACAAGAGATTCGGAATTAGAAT----TAC 1426
Sequence_75    TAATCCAGTTTCCAAAGATATTATAGCGAGTACAAGAGATTCGGAATTAGAAT----TAC 1423
Sequence_43    TAATCCAGTTTCCAAAGATATTATAGCGAGTACAAGAGATTCGGAATTAGAAT----TAC 1423
Sequence_47    TAATCCAGTTTCCAAAGATATTATAGCGAGTACAAGAGATTCGGAATTAGAAT----TAC 1426
Sequence_79    TAATCCAGTTTCCAAAGATATTATAGCGAGTACAAGAGATTCGGAATTAGAAT----TAC 1426
Sequence_51    TAATCCAGTTTCCAAAGATATTATAGCGAGTACAAGAGATTCGGAATTAGAAT----TAC 1432
Sequence_83    TAATCCAGTTTCCAAAGATATTATAGCGAGTACAAGAGATTCGGAATTAGAAT----TAC 1432
Sequence_7     TAATCCAGTTTCCAAAGATATTATAGCGAGTACAAGAGATTCGGAATTAGAAT----TAC 1420
Sequence_25    TAATCCAGTTTCCAAAGATATTATAGCGAGTACAAGAGATTCGGAATTAGAAT----TAC 1420
Sequence_29    TAATCCAGTTTCCAAAGATATTATAGCGAGTACAAGAGATTCGGAATTAGAAT----TAC 1420
Sequence_33    TAATCCAGTTTCCAAAGATATTATAGCGAGTACAAGAGATTCGGAATTAGAAT----TAC 1420
Sequence_69    TAATCCAGTTTCCAAAGATATTATAGCGAGTACAAGAGATTCGGAATTAGAAT----TAC 1420
Sequence_11    TAATCCAGTTTCCAAAGATATTATAGCGAGTACAAGAGATTCGGAATTAGAAT----TAC 1408
Sequence_1     TAATCCAGTTTCCAAAGATATTATAGCGAGTACAAGAGATTCGGAATTAGAAT----TAC 1408
Sequence_17    TAATCCAGTTTCCAAAGATATTATAGCGAGTACAAGAGATTCGGAATTAGAAT----TAC 2138
Sequence_3     TAATCCGGTTTCCAAAGATATTATAGCGGGGACAAGAGATTCGGAATTAGAAT----TAC 1408
Sequence_13    TAATCCGGTTTCCAAAGATATTATAGCGGGGACAAGAGATTCGGAATTAGAAT----TAC 1408
Sequence_18    TAATCCGGTTTCCAAAGATATTATAGCGGGGACAAGAGATTCGGAATTAGAAT----TAC 2661
Cry8Ka1_       TTTTAATGAACTAAAAGATACAATTACAGAGCTACCTGTTCAGATATCCAGTCCTCCTAC 1406
               *  *   *     *******  **  *      *   * *  *  **          ***
```

To Fig. 18Z

Fig. 18Y

From Fig. 18Y

```
Sequence_71    CTCCAGAAACTTCAGATCAACCAAATTATGAGTCATATAGCCATAGATTATGTCATATCA 1489
Sequence_73    CTCCAGAAACTTCAGATCAACCAAATTATGAGTCATATAGCCATAGATTATGTCATATCA 1486
Sequence_21    CTCCAGAAACTTCAGATCAACCAAATTATGAGTCATATAGCCATAGATTATGTCATATCA 1480
Sequence_67    CTCCAGAAACTTCAGATCAACCAAATTATGAGTCATATAGCCATAGATTATGTCATATCA 1480
Sequence_61    CTCCAGAAACTTCAGATCAACCAAATTATGAGTCATATAGCCATAGATTATGTCATATCA 1480
Sequence_93    CTCCAGAAACTTCAGATCAACCAAATTATGAGTCATATAGCCATAGATTATGTCATATCA 1480
Sequence_59    CTCCAGAAACTTCAGATCAACCAAATTATGAGTCATATAGCCATAGATTATGTCATATCA 1480
Sequence_91    CTCCAGAAACTTCAGATCAACCAAATTATGAGTCATATAGCCATAGATTATGTCATATCA 1480
Sequence_39    CTCCAGAAACTTCAGATCAACCAAATTATGAGTCATATAGCCATAGATTATGTCATATCA 1489
Sequence_41    CTCCAGAAACTTCAGATCAACCAAATTATGAGTCATATAGCCATAGATTATGTCATATCA 1486
Sequence_49    CTCCAGAAACTTCAGATCAACCAAATTATGAGTCATATAGCCATAGATTATGTCATATCA 1483
Sequence_81    CTCCAGAAACTTCAGATCAACCAAATTATGAGTCATATAGCCATAGATTATGTCATATCA 1483
Sequence_45    CTCCAGAAACTTCAGATCAACCAAATTATGAGTCATATAGCCATAGATTATGTCATATCA 1486
Sequence_77    CTCCAGAAACTTCAGATCAACCAAATTATGAGTCATATAGCCATAGATTATGTCATATCA 1486
Sequence_75    CTCCAGAAACTTCAGATCAACCAAATTATGAGTCATATAGCCATAGATTATGTCATATCA 1483
Sequence_43    CTCCAGAAACTTCAGATCAACCAAATTATGAGTCATATAGCCATAGATTATGTCATATCA 1483
Sequence_47    CTCCAGAAACTTCAGATCAACCAAATTATGAGTCATATAGCCATAGATTATGTCATATCA 1486
Sequence_79    CTCCAGAAACTTCAGATCAACCAAATTATGAGTCATATAGCCATAGATTATGTCATATCA 1486
Sequence_51    CTCCAGAAACTTCAGATCAACCAAATTATGAGTCATATAGCCATAGATTATGTCATATCA 1492
Sequence_83    CTCCAGAAACTTCAGATCAACCAAATTATGAGTCATATAGCCATAGATTATGTCATATCA 1492
Sequence_7     CTCCAGAAACTTCAGATCAACCAAATTATGAGTCATATAGCCATAGATTATGTCATATCA 1480
Sequence_25    CTCCAGAAACTTCAGATCAACCAAATTATGAGTCATATAGCCATAGATTATGTCATATCA 1480
Sequence_29    CTCCAGAAACTTCAGATCAACCAAATTATGAGTCATATAGCCATAGATTATGTCATATCA 1480
Sequence_33    CTCCAGAAACTTCAGATCAACCAAATTATGAGTCATATAGCCATAGATTATGTCATATCA 1480
Sequence_69    CTCCAGAAACTTCAGATCAACCAAATTATGAGTCATATAGCCATAGATTATGTCATATCA 1480
Sequence_11    CTCCAGAAACTTCAGATCAACCAAATTATGAGTCATATAGCCATAGATTATGTCATATCA 1468
Sequence_1     CTCCAGAAACTTCAGATCAACCAAATTATGAGTCATATAGCCATAGATTATGTCATATCA 1468
Sequence_17    CTCCAGAAACTTCAGATCAACCAAATTATGAGTCATATAGCCATAGATTATGTCATATCA 2198
Sequence_3     CTCCAGAAACTTCAGATCAACCAAATTATGAGTCATATAGCCATAGATTATGTCATATCA 1468
Sequence_13    CTCCAGAAACTTCAGATCAACCAAATTATGAGTCATATAGCCATAGATTATGTCATATCA 1468
Sequence_18    CTCCAGAAACTTCAGATCAACCAAATTATGAGTCATATAGCCATAGATTATGTCATATCA 2721
Cry8Ka1_       CTACGGGGA-TGCTGAACAGTACAGTCATCGGCTATCCTAT-GTTTCTAATGCTCCAACA 1464
               ** * *  * * * ** **    * * ** * **        * * ***   * **
```

To Fig. 18AA

Fig. 18Z

From Fig. 18Z

```
Sequence_71      CAAGTATTCCCGCGACGGG--TAACACTACCGGATTAGTACCTGTATTTTCTTGGACACA 1547
Sequence_73      CAAGTATTCCCGCGACGGG--TAACACTACCGGATTAGTACCTGTATTTTCTTGGACACA 1544
Sequence_21      CAAGTATTCCCGCGACGGG--TAACACTACCGGATTAGTACCTGTATTTTCTTGGACACA 1538
Sequence_67      CAAGTATTCCCGCGACGGG--TAACACTACCGGATTAGTACCTGTATTTTCTTGGACACA 1538
Sequence_61      CAAGTATTCCCGCGACGGG--TAACACTACCGGATTAGTACCTGTATTTTCTTGGACACA 1538
Sequence_93      CAAGTATTCCCGCGACGGG--TAACACTACCGGATTAGTACCTGTATTTTCTTGGACACA 1538
Sequence_59      CAAGTATTCCCGCGACGGG--TAACACTACCGGATTAGTACCTGTATTTTCTTGGACACA 1538
Sequence_91      CAAGTATTCCCGCGACGGG--TAACACTACCGGATTAGTACCTGTATTTTCTTGGACACA 1538
Sequence_39      CAAGTATTCCCGCGACGGG--TAACACTACCGGATTAGTACCTGTATTTTCTTGGACACA 1547
Sequence_41      CAAGTATTCCCGCGACGGG--TAACACTACCGGATTAGTACCTGTATTTTCTTGGACACA 1544
Sequence_49      CAAGTATTCCCGCGACGGG--TAACACTACCGGATTAGTACCTGTATTTTCTTGGACACA 1541
Sequence_81      CAAGTATTCCCGCGACGGG--TAACACTACCGGATTAGTACCTGTATTTTCTTGGACACA 1541
Sequence_45      CAAGTATTCCCGCGACGGG--TAACACTACCGGATTAGTACCTGTATTTTCTTGGACACA 1544
Sequence_77      CAAGTATTCCCGCGACGGG--TAACACTACCGGATTAGTACCTGTATTTTCTTGGACACA 1544
Sequence_75      CAAGTATTCCCGCGACGGG--TAACACTACCGGATTAGTACCTGTATTTTCTTGGACACA 1541
Sequence_43      CAAGTATTCCCGCGACGGG--TAACACTACCGGATTAGTACCTGTATTTTCTTGGACACA 1541
Sequence_47      CAAGTATTCCCGCGACGGG--TAACACTACCGGATTAGTACCTGTATTTTCTTGGACACA 1544
Sequence_79      CAAGTATTCCCGCGACGGG--TAACACTACCGGATTAGTACCTGTATTTTCTTGGACACA 1544
Sequence_51      CAAGTATTCCCGCGACGGG--TAACACTACCGGATTAGTACCTGTATTTTCTTGGACACA 1550
Sequence_83      CAAGTATTCCCGCGACGGG--TAACACTACCGGATTAGTACCTGTATTTTCTTGGACACA 1550
Sequence_7       CAAGTATTCCCGCGACGGG--TAACACTACCGGATTAGTACCTGTATTTTCTTGGACACA 1538
Sequence_25      CAAGTATTCCCGCGACGGG--TAACACTACCGGATTAGTACCTGTATTTTCTTGGACACA 1538
Sequence_29      CAAGTATTCCCGCGACGGG--TAACACTACCGGATTAGTACCTGTATTTTCTTGGACACA 1538
Sequence_33      CAAGTATTCCCGCGACGGG--TAACACTACCGGATTAGTACCTGTATTTTCTTGGACACA 1538
Sequence_69      CAAGTATTCCCGCGACGGG--TAACACTACCGGATTAGTACCTGTATTTTCTTGGACACA 1538
Sequence_11      CAAGTATTCCCGCGACGGG--TAACACTACCGGATTAGTACCTGTATTTTCTTGGACACA 1526
Sequence_1       CAAGTATTCCCGCGACGGG--TAACACTACCGGATTAGTACCTGTATTTTCTTGGACACA 1526
Sequence_17      CAAGTATTCCCGCGACGGG--TAACACTACCGGATTAGTACCTGTATTTTCTTGGACACA 2256
Sequence_3       CAAGTATTCCCGCGACGGG--TTCAACTACCGGATTAGTACCTGTATTTTCTTGGACACA 1526
Sequence_13      CAAGTATTCCCGCGACGGG--TTCAACTACCGGATTAGTACCTGTATTTTCTTGGACACA 1526
Sequence_18      CAAGTATTCCCGCGACGGG--TTCAACTACCGGATTAGTACCTGTATTTTCTTGGACACA 2779
Cry8Ka1          -GAGTACTCTTCGGGCGGACATTTAATTTTGGGACTAATCCCAGTACTGGGTTGGACGCA 1523
                   **** **    * ***   *   * *   *** ** * ** *** *   ****** **
```

To Fig. 18AB

Fig. 18AA

From Fig. 18AA

```
Sequence_71    TCGAAGTGCAGATTTAAACAATACAATATATTCAGATAAAATCACTCAAATTCCGGCCGT 1607
Sequence_73    TCGAAGTGCAGATTTAAACAATACAATATATTCAGATAAAATCACTCAAATTCCGGCCGT 1604
Sequence_21    TCGAAGTGCAGATTTAAACAATACAATATATTCAGATAAAATCACTCAAATTCCGGCCGT 1598
Sequence_67    TCGAAGTGCAGATTTAAACAATACAATATATTCAGATAAAATCACTCAAATTCCGGCCGT 1598
Sequence_61    TCGAAGTGCAGATTTAAACAATACAATATATTCAGATAAAATCACTCAAATTCCGGCCGT 1598
Sequence_93    TCGAAGTGCAGATTTAAACAATACAATATATTCAGATAAAATCACTCAAATTCCGGCCGT 1598
Sequence_59    TCGAAGTGCAGATTTAAACAATACAATATATTCAGATAAAATCACTCAAATTCCGGCCGT 1598
Sequence_91    TCGAAGTGCAGATTTAAACAATACAATATATTCAGATAAAATCACTCAAATTCCGGCCGT 1598
Sequence_39    TCGAAGTGCAGATTTAAACAATACAATATATTCAGATAAAATCACTCAAATTCCGGCCGT 1607
Sequence_41    TCGAAGTGCAGATTTAAACAATACAATATATTCAGATAAAATCACTCAAATTCCGGCCGT 1604
Sequence_49    TCGAAGTGCAGATTTAAACAATACAATATATTCAGATAAAATCACTCAAATTCCGGCCGT 1601
Sequence_81    TCGAAGTGCAGATTTAAACAATACAATATATTCAGATAAAATCACTCAAATTCCGGCCGT 1601
Sequence_45    TCGAAGTGCAGATTTAAACAATACAATATATTCAGATAAAATCACTCAAATTCCGGCCGT 1604
Sequence_77    TCGAAGTGCAGATTTAAACAATACAATATATTCAGATAAAATCACTCAAATTCCGGCCGT 1604
Sequence_75    TCGAAGTGCAGATTTAAACAATACAATATATTCAGATAAAATCACTCAAATTCCGGCCGT 1601
Sequence_43    TCGAAGTGCAGATTTAAACAATACAATATATTCAGATAAAATCACTCAAATTCCGGCCGT 1601
Sequence_47    TCGAAGTGCAGATTTAAACAATACAATATATTCAGATAAAATCACTCAAATTCCGGCCGT 1604
Sequence_79    TCGAAGTGCAGATTTAAACAATACAATATATTCAGATAAAATCACTCAAATTCCGGCCGT 1604
Sequence_51    TCGAAGTGCAGATTTAAACAATACAATATATTCAGATAAAATCACTCAAATTCCGGCCGT 1610
Sequence_83    TCGAAGTGCAGATTTAAACAATACAATATATTCAGATAAAATCACTCAAATTCCGGCCGT 1610
Sequence_7     TCGAAGTGCAGATTTAAACAATACAATATATTCAGATAAAATCACTCAAATTCCGGCCGT 1598
Sequence_25    TCGAAGTGCAGATTTAAACAATACAATATATTCAGATAAAATCACTCAAATTCCGGCCGT 1598
Sequence_29    TCGAAGTGCAGATTTAAACAATACAATATATTCAGATAAAATCACTCAAATTCCGGCCGT 1598
Sequence_33    TCGAAGTGCAGATTTAAACAATACAATATATTCAGATAAAATCACTCAAATTCCGGCCGT 1598
Sequence_69    TCGAAGTGCAGATTTAAACAATACAATATATTCAGATAAAATCACTCAAATTCCGGCCGT 1598
Sequence_11    TCGAAGTGCAGATTTAAACAATACAATATATTCAGATAAAATCACTCAAATTCCGGCCGT 1586
Sequence_1     TCGAAGTGCAGATTTAAACAATACAATATATTCAGATAAAATCACTCAAATTCCGGCCGT 1586
Sequence_17    TCGAAGTGCAGATTTAAACAATACAATATATTCAGATAAAATCACTCAAATTCCGGCCGT 2316
Sequence_3     TCGGAGTGCCGATCTTATAAATGCAGTTCATTCAGATAAAATTACTCAGATTCCGGTCGT 1586
Sequence_13    TCGGAGTGCCGATCTTATAAATGCAGTTCATTCAGATAAAATTACTCAGATTCCGGTCGT 1586
Sequence_18    TCGGAGTGCCGATCTTATAAATGCAGTTCATTCAGATAAAATTACTCAGATTCCGGTCGT 2839
Cry8Ka1        TACTAGTTTAACTCAAACAAATCAGATACATTCTGACTCAATTACTCAAATTCCAGCTGT 1583
               *   ***     *   *  ***    *  **** **   *** ***** ***** *  **
```

To Fig. 18AC

Fig. 18AB

From Fig. 18AB

```
Sequence_71     TAAATGTTGGGATAATTTACCGTTTGTTCCAGTGGT----AAAAGGACCAGGACATACAG 1663
Sequence_73     TAAATGTTGGGATAATTTACCGTTTGTTCCAGTGGT----AAAAGGACCAGGACATACAG 1660
Sequence_21     TAAATGTTGGGATAATTTACCGTTTGTTCCAGTGGT----AAAAGGACCAGGACATACAG 1654
Sequence_67     TAAATGTTGGGATAATTTACCGTTTGTTCCAGTGGT----AAAAGGACCAGGACATACAG 1654
Sequence_61     TAAATGTTGGGATAATTTACCGTTTGTTCCAGTGGT----AAAAGGACCAGGACATACAG 1654
Sequence_93     TAAATGTTGGGATAATTTACCGTTTGTTCCAGTGGT----AAAAGGACCAGGACATACAG 1654
Sequence_59     TAAATGTTGGGATAATTTACCGTTTGTTCCAGTGGT----AAAAGGACCAGGACATACAG 1654
Sequence_91     TAAATGTTGGGATAATTTACCGTTTGTTCCAGTGGT----AAAAGGACCAGGACATACAG 1654
Sequence_39     TAAATGTTGGGATAATTTACCGTTTGTTCCAGTGGT----AAAAGGACCAGGACATACAG 1663
Sequence_41     TAAATGTTGGGATAATTTACCGTTTGTTCCAGTGGT----AAAAGGACCAGGACATACAG 1660
Sequence_49     TAAATGTTGGGATAATTTACCGTTTGTTCCAGTGGT----AAAAGGACCAGGACATACAG 1657
Sequence_81     TAAATGTTGGGATAATTTACCGTTTGTTCCAGTGGT----AAAAGGACCAGGACATACAG 1657
Sequence_45     TAAATGTTGGGATAATTTACCGTTTGTTCCAGTGGT----AAAAGGACCAGGACATACAG 1660
Sequence_77     TAAATGTTGGGATAATTTACCGTTTGTTCCAGTGGT----AAAAGGACCAGGACATACAG 1660
Sequence_75     TAAATGTTGGGATAATTTACCGTTTGTTCCAGTGGT----AAAAGGACCAGGACATACAG 1657
Sequence_43     TAAATGTTGGGATAATTTACCGTTTGTTCCAGTGGT----AAAAGGACCAGGACATACAG 1657
Sequence_47     TAAATGTTGGGATAATTTACCGTTTGTTCCAGTGGT----AAAAGGACCAGGACATACAG 1660
Sequence_79     TAAATGTTGGGATAATTTACCGTTTGTTCCAGTGGT----AAAAGGACCAGGACATACAG 1660
Sequence_51     TAAATGTTGGGATAATTTACCGTTTGTTCCAGTGGT----AAAAGGACCAGGACATACAG 1666
Sequence_83     TAAATGTTGGGATAATTTACCGTTTGTTCCAGTGGT----AAAAGGACCAGGACATACAG 1666
Sequence_7      TAAATGTTGGGATAATTTACCGTTTGTTCCAGTGGT----AAAAGGACCAGGACATACAG 1654
Sequence_25     TAAATGTTGGGATAATTTACCGTTTGTTCCAGTGGT----AAAAGGACCAGGACATACAG 1654
Sequence_29     TAAATGTTGGGATAATTTACCGTTTGTTCCAGTGGT----AAAAGGACCAGGACATACAG 1654
Sequence_33     TAAATGTTGGGATAATTTACCGTTTGTTCCAGTGGT----AAAAGGACCAGGACATACAG 1654
Sequence_69     TAAATGTTGGGATAATTTACCGTTTGTTCCAGTGGT----AAAAGGACCAGGACATACAG 1654
Sequence_11     TAAATGTTGGGATAATTTACCGTTTGTTCCAGTGGT----AAAAGGACCAGGACATACAG 1642
Sequence_1      TAAATGTTGGGATAATTTACCGTTTGTTCCAGTGGT----AAAAGGACCAGGACATACAG 1642
Sequence_17     TAAATGTTGGGATAATTTACCGTTTGTTCCAGTGGT----AAAAGGACCAGGACATACAG 2372
Sequence_3      AAAGGTTTCTGATTTGGCTCCCTCTATAACAGGAGGGCCAAATAATACCGTTGTATCGGG 1646
Sequence_13     AAAGGTTTCTGATTTGGCTCCCTCTATAACAGGAGGGCCAAATAATACCGTTGTATCGGG 1646
Sequence_18     AAAGGTTTCTGATTTGGCTCCCTCTATAACAGGAGGGCCAAATAATACCGTTGTATCGGG 2899
Cry8Ka1         TAAAGCAAATAGTGTTAGTTCTTATGT------------------TACTGTTGAAAAGGG 1625
                 **         *       * * * *                   **      *    *
```

To Fig. 18AD

Fig. 18AC

From Fig. 18AC

```
Sequence_71       GAGGGGATTTATTACAGT----ATAATAGAAGTACTG-GTTCTGTAGGAACCTTATTTCT 1718
Sequence_73       GAGGGGATTTATTACAGT----ATAATAGAAGTACTG-GTTCTGTAGGAACCTTATTTCT 1715
Sequence_21       GAGGGGATTTATTACAGT----ATAATAGAAGTACTG-GTTCTGTAGGAACCTTATTTCT 1709
Sequence_67       GAGGGGATTTATTACAGT----ATAATAGAAGTACTG-GTTCTGTAGGAACCTTATTTCT 1709
Sequence_61       GAGGGGATTTATTACAGT----ATAATAGAAGTACTG-GTTCTGTAGGAACCTTATTTCT 1709
Sequence_93       GAGGGGATTTATTACAGT----ATAATAGAAGTACTG-GTTCTGTAGGAACCTTATTTCT 1709
Sequence_59       GAGGGGATTTATTACAGT----ATAATAGAAGTACTG-GTTCTGTAGGAACCTTATTTCT 1709
Sequence_91       GAGGGGATTTATTACAGT----ATAATAGAAGTACTG-GTTCTGTAGGAACCTTATTTCT 1709
Sequence_39       GAGGGGATTTATTACAGT----ATAATAGAAGTACTG-GTTCTGTAGGAACCTTATTTCT 1718
Sequence_41       GAGGGGATTTATTACAGT----ATAATAGAAGTACTG-GTTCTGTAGGAACCTTATTTCT 1715
Sequence_49       GAGGGGATTTATTACAGT----ATAATAGAAGTACTG-GTTCTGTAGGAACCTTATTTCT 1712
Sequence_81       GAGGGGATTTATTACAGT----ATAATAGAAGTACTG-GTTCTGTAGGAACCTTATTTCT 1712
Sequence_45       GAGGGGATTTATTACAGT----ATAATAGAAGTACTG-GTTCTGTAGGAACCTTATTTCT 1715
Sequence_77       GAGGGGATTTATTACAGT----ATAATAGAAGTACTG-GTTCTGTAGGAACCTTATTTCT 1715
Sequence_75       GAGGGGATTTATTACAGT----ATAATAGAAGTACTG-GTTCTGTAGGAACCTTATTTCT 1712
Sequence_43       GAGGGGATTTATTACAGT----ATAATAGAAGTACTG-GTTCTGTAGGAACCTTATTTCT 1712
Sequence_47       GAGGGGATTTATTACAGT----ATAATAGAAGTACTG-GTTCTGTAGGAACCTTATTTCT 1715
Sequence_79       GAGGGGATTTATTACAGT----ATAATAGAAGTACTG-GTTCTGTAGGAACCTTATTTCT 1715
Sequence_51       GAGGGGATTTATTACAGT----ATAATAGAAGTACTG-GTTCTGTAGGAACCTTATTTCT 1721
Sequence_83       GAGGGGATTTATTACAGT----ATAATAGAAGTACTG-GTTCTGTAGGAACCTTATTTCT 1721
Sequence_7        GAGGGGATTTATTACAGT----ATAATAGAAGTACTG-GTTCTGTAGGAACCTTATTTCT 1709
Sequence_25       GAGGGGATTTATTACAGT----ATAATAGAAGTACTG-GTTCTGTAGGAACCTTATTTCT 1709
Sequence_29       GAGGGGATTTATTACAGT----ATAATAGAAGTACTG-GTTCTGTAGGAACCTTATTTCT 1709
Sequence_33       GAGGGGATTTATTACAGT----ATAATAGAAGTACTG-GTTCTGTAGGAACCTTATTTCT 1709
Sequence_69       GAGGGGATTTATTACAGT----ATAATAGAAGTACTG-GTTCTGTAGGAACCTTATTTCT 1709
Sequence_11       GAGGGGATTTATTACAGT----ATAATAGAAGTACTG-GTTCTGTAGGAACCTTATTTCT 1697
Sequence_1        GAGGGGATTTATTACAGT----ATAATAGAAGTACTG-GTTCTGTAGGAACCTTATTTCT 1697
Sequence_17       GAGGGGATTTATTACAGT----ATAATAGAAGTACTG-GTTCTGTAGGAACCTTATTTCT 2427
Sequence_3        TCCTGGATTTACAGGGGGGGGGATAATAAAAGTAATAAGAAATGGAGTAATTATATCACA 1706
Sequence_13       TCCTGGATTTACAGGGGGGGGGATAATAAAAGTAATAAGAAATGGAGTAATTATATCACA 1706
Sequence_18       TCCTGGATTTACAGGGGGGGGGATAATAAAAGTAATAAGAAATGGAGTAATTATATCACA 2959
Cry8Ka1           AACAGGCTTTACAGGTGGAGATTTAGTGAAATTCTCC---ACTGGATTCATGTCTACAGG 1682
                      ** ****     *      ** *  ** *         ** *   *
```

To Fig. 18AE

Fig. 18AD

From Fig. 18AD

```
Sequence_71         AGCTCGATATGGCCTAGCATTAGAAAAAGCAGGGAAATATCGTGTAAGACTGAGATATGC 1778
Sequence_73         AGCTCGATATGGCCTAGCATTAGAAAAAGCAGGGAAATATCGTGTAAGACTGAGATATGC 1775
Sequence_21         AGCTCGATATGGCCTAGCATTAGAAAAAGCAGGGAAATATCGTGTAAGACTGAGATATGC 1769
Sequence_67         AGCTCGATATGGCCTAGCATTAGAAAAAGCAGGGAAATATCGTGTAAGACTGAGATATGC 1769
Sequence_61         AGCTCGATATGGCCTAGCATTAGAAAAAGCAGGGAAATATCGTGTAAGACTGAGATATGC 1769
Sequence_93         AGCTCGATATGGCCTAGCATTAGAAAAAGCAGGGAAATATCGTGTAAGACTGAGATATGC 1769
Sequence_59         AGCTCGATATGGCCTAGCATTAGAAAAAGCAGGGAAATATCGTGTAAGACTGAGATATGC 1769
Sequence_91         AGCTCGATATGGCCTAGCATTAGAAAAAGCAGGGAAATATCGTGTAAGACTGAGATATGC 1769
Sequence_39         AGCTCGATATGGCCTAGCATTAGAAAAAGCAGGGAAATATCGTGTAAGACTGAGATATGC 1778
Sequence_41         AGCTCGATATGGCCTAGCATTAGAAAAAGCAGGGAAATATCGTGTAAGACTGAGATATGC 1775
Sequence_49         AGCTCGATATGGCCTAGCATTAGAAAAAGCAGGGAAATATCGTGTAAGACTGAGATATGC 1772
Sequence_81         AGCTCGATATGGCCTAGCATTAGAAAAAGCAGGGAAATATCGTGTAAGACTGAGATATGC 1772
Sequence_45         AGCTCGATATGGCCTAGCATTAGAAAAAGCAGGGAAATATCGTGTAAGACTGAGATATGC 1775
Sequence_77         AGCTCGATATGGCCTAGCATTAGAAAAAGCAGGGAAATATCGTGTAAGACTGAGATATGC 1775
Sequence_75         AGCTCGATATGGCCTAGCATTAGAAAAAGCAGGGAAATATCGTGTAAGACTGAGATATGC 1772
Sequence_43         AGCTCGATATGGCCTAGCATTAGAAAAAGCAGGGAAATATCGTGTAAGACTGAGATATGC 1772
Sequence_47         AGCTCGATATGGCCTAGCATTAGAAAAAGCAGGGAAATATCGTGTAAGACTGAGATATGC 1775
Sequence_79         AGCTCGATATGGCCTAGCATTAGAAAAAGCAGGGAAATATCGTGTAAGACTGAGATATGC 1775
Sequence_51         AGCTCGATATGGCCTAGCATTAGAAAAAGCAGGGAAATATCGTGTAAGACTGAGATATGC 1781
Sequence_83         AGCTCGATATGGCCTAGCATTAGAAAAAGCAGGGAAATATCGTGTAAGACTGAGATATGC 1781
Sequence_7          AGCTCGATATGGCCTAGCATTAGAAAAAGCAGGGAAATATCGTGTAAGACTGAGATATGC 1769
Sequence_25         AGCTCGATATGGCCTAGCATTAGAAAAAGCAGGGAAATATCGTGTAAGACTGAGATATGC 1769
Sequence_29         AGCTCGATATGGCCTAGCATTAGAAAAAGCAGGGAAATATCGTGTAAGACTGAGATATGC 1769
Sequence_33         AGCTCGATATGGCCTAGCATTAGAAAAAGCAGGGAAATATCGTGTAAGACTGAGATATGC 1769
Sequence_69         AGCTCGATATGGCCTAGCATTAGAAAAAGCAGGGAAATATCGTGTAAGACTGAGATATGC 1769
Sequence_11         AGCTCGATATGGCCTAGCATTAGAAAAAGCAGGGAAATATCGTGTAAGACTGAGATATGC 1757
Sequence_1          AGCTCGATATGGCCTAGCATTAGAAAAAGCAGGGAAATATCGTGTAAGACTGAGATATGC 1757
Sequence_17         AGCTCGATATGGCCTAGCATTAGAAAAAGCAGGGAAATATCGTGTAAGACTGAGATATGC 2487
Sequence_3          TATGCG---TGTTAAAATTTCAGACATTAACAAAGAATATAGTATGAGGATTCGGTATGC 1763
Sequence_13         TATGCG---TGTTAAAATTTCAGACATTAACAAAGAATATAGTATGAGGATTCGGTATGC 1763
Sequence_18         TATGCG---TGTTAAAATTTCAGACATTAACAAAGAATATAGTATGAGGATTCGGTATGC 3016
Cry8Ka1             AATACAGTTTAATTTAAAGATAGAAGAAAGAAAGCGTTATCGTATCCGTATACGATATGC 1742
                        *    *     *     ***             *** ** *  *  *  * *****
```

To Fig. 18AF

Fig. 18AE

From Fig. 18AE

```
Sequence_71    TACTGATGCAGATATTGTATTGCATGTAAAC------------GATGCTCAGATTCAGAT 1826
Sequence_73    TACTGATGCAGATATTGTATTGCATGTAAAC------------GATGCTCAGATTCAGAT 1823
Sequence_21    TACTGATGCAGATATTGTATTGCATGTAAAC------------GATGCTCAGATTCAGAT 1817
Sequence_67    TACTGATGCAGATATTGTATTGCATGTAAAC------------GATGCTCAGATTCAGAT 1817
Sequence_61    TACTGATGCAGATATTGTATTGCATGTAAAC------------GATGCTCAGATTCAGAT 1817
Sequence_93    TACTGATGCAGATATTGTATTGCATGTAAAC------------GATGCTCAGATTCAGAT 1817
Sequence_59    TACTGATGCAGATATTGTATTGCATGTAAAC------------GATGCTCAGATTCAGAT 1817
Sequence_91    TACTGATGCAGATATTGTATTGCATGTAAAC------------GATGCTCAGATTCAGAT 1817
Sequence_39    TACTGATGCAGATATTGTATTGCATGTAAAC------------GATGCTCAGATTCAGAT 1826
Sequence_41    TACTGATGCAGATATTGTATTGCATGTAAAC------------GATGCTCAGATTCAGAT 1823
Sequence_49    TACTGATGCAGATATTGTATTGCATGTAAAC------------GATGCTCAGATTCAGAT 1820
Sequence_81    TACTGATGCAGATATTGTATTGCATGTAAAC------------GATGCTCAGATTCAGAT 1820
Sequence_45    TACTGATGCAGATATTGTATTGCATGTAAAC------------GATGCTCAGATTCAGAT 1823
Sequence_77    TACTGATGCAGATATTGTATTGCATGTAAAC------------GATGCTCAGATTCAGAT 1823
Sequence_75    TACTGATGCAGATATTGTATTGCATGTAAAC------------GATGCTCAGATTCAGAT 1820
Sequence_43    TACTGATGCAGATATTGTATTGCATGTAAAC------------GATGCTCAGATTCAGAT 1820
Sequence_47    TACTGATGCAGATATTGTATTGCATGTAAAC------------GATGCTCAGATTCAGAT 1823
Sequence_79    TACTGATGCAGATATTGTATTGCATGTAAAC------------GATGCTCAGATTCAGAT 1823
Sequence_51    TACTGATGCAGATATTGTATTGCATGTAAAC------------GATGCTCAGATTCAGAT 1829
Sequence_83    TACTGATGCAGATATTGTATTGCATGTAAAC------------GATGCTCAGATTCAGAT 1829
Sequence_7     TACTGATGCAGATATTGTATTGCATGTAAAC------------GATGCTCAGATTCAGAT 1817
Sequence_25    TACTGATGCAGATATTGTATTGCATGTAAAC------------GATGCTCAGATTCAGAT 1817
Sequence_29    TACTGATGCAGATATTGTATTGCATGTAAAC------------GATGCTCAGATTCAGAT 1817
Sequence_33    TACTGATGCAGATATTGTATTGCATGTAAAC------------GATGCTCAGATTCAGAT 1817
Sequence_69    TACTGATGCAGATATTGTATTGCATGTAAAC------------GATGCTCAGATTCAGAT 1817
Sequence_11    TACTGATGCAGATATTGTATTGCATGTAAAC------------GATGCTCAGATTCAGAT 1805
Sequence_1     TACTGATGCAGATATTGTATTGCATGTAAAC------------GATGCTCAGATTCAGAT 1805
Sequence_17    TACTGATGCAGATATTGTATTGCATGTAAAC------------GATGCTCAGATTCAGAT 2535
Sequence_3     TTCCGCTAATAATACTGAATTTTATATAAATCCTTCTGAAGAAAACGTTAAATCTCACGC 1823
Sequence_13    TTCCGCTAATAATACTGAATTTTATATAAATCCTTCTGAAGAAAACGTTAAATCTCACGC 1823
Sequence_18    TTCCGCTAATAATACTGAATTTTATATAAATCCTTCTGAAGAAAACGTTAAATCTCACGC 3076
Cry8Ka1        CGCTGATGTTAATGCT--ACTCTATCTGCACTTGGATTAA-ATGATGCATTTATTAACAT 1799
                 * * *    **  *  * *  ** *  *            * *       * *
```

To Fig. 18AG

Fig. 18AF

From Fig. 18AF

```
Sequence_71         GCCAAAAACAATGAACCCAGGTGAGGATCTGACATCTAAAACTTTTAAAGTTGCAGATGC 1886
Sequence_73         GCCAAAAACAATGAACCCAGGTGAGGATCTGACATCTAAAACTTTTAAAGTTGCAGATGC 1883
Sequence_21         GCCAAAAACAATGAACCCAGGTGAGGATCTGACATCTAAAACTTTTAAAGTTGCAGATGC 1877
Sequence_67         GCCAAAAACAATGAACCCAGGTGAGGATCTGACATCTAAAACTTTTAAAGTTGCAGATGC 1877
Sequence_61         GCCAAAAACAATGAACCCAGGTGAGGATCTGACATCTAAAACTTTTAAAGTTGCAGATGC 1877
Sequence_93         GCCAAAAACAATGAACCCAGGTGAGGATCTGACATCTAAAACTTTTAAAGTTGCAGATGC 1877
Sequence_59         GCCAAAAACAATGAACCCAGGTGAGGATCTGACATCTAAAACTTTTAAAGTTGCAGATGC 1877
Sequence_91         GCCAAAAACAATGAACCCAGGTGAGGATCTGACATCTAAAACTTTTAAAGTTGCAGATGC 1877
Sequence_39         GCCAAAAACAATGAACCCAGGTGAGGATCTGACATCTAAAACTTTTAAAGTTGCAGATGC 1886
Sequence_41         GCCAAAAACAATGAACCCAGGTGAGGATCTGACATCTAAAACTTTTAAAGTTGCAGATGC 1883
Sequence_49         GCCAAAAACAATGAACCCAGGTGAGGATCTGACATCTAAAACTTTTAAAGTTGCAGATGC 1880
Sequence_81         GCCAAAAACAATGAACCCAGGTGAGGATCTGACATCTAAAACTTTTAAAGTTGCAGATGC 1880
Sequence_45         GCCAAAAACAATGAACCCAGGTGAGGATCTGACATCTAAAACTTTTAAAGTTGCAGATGC 1883
Sequence_77         GCCAAAAACAATGAACCCAGGTGAGGATCTGACATCTAAAACTTTTAAAGTTGCAGATGC 1883
Sequence_75         GCCAAAAACAATGAACCCAGGTGAGGATCTGACATCTAAAACTTTTAAAGTTGCAGATGC 1880
Sequence_43         GCCAAAAACAATGAACCCAGGTGAGGATCTGACATCTAAAACTTTTAAAGTTGCAGATGC 1880
Sequence_47         GCCAAAAACAATGAACCCAGGTGAGGATCTGACATCTAAAACTTTTAAAGTTGCAGATGC 1883
Sequence_79         GCCAAAAACAATGAACCCAGGTGAGGATCTGACATCTAAAACTTTTAAAGTTGCAGATGC 1883
Sequence_51         GCCAAAAACAATGAACCCAGGTGAGGATCTGACATCTAAAACTTTTAAAGTTGCAGATGC 1889
Sequence_83         GCCAAAAACAATGAACCCAGGTGAGGATCTGACATCTAAAACTTTTAAAGTTGCAGATGC 1889
Sequence_7          GCCAAAAACAATGAACCCAGGTGAGGATCTGACATCTAAAACTTTTAAAGTTGCAGATGC 1877
Sequence_25         GCCAAAAACAATGAACCCAGGTGAGGATCTGACATCTAAAACTTTTAAAGTTGCAGATGC 1877
Sequence_29         GCCAAAAACAATGAACCCAGGTGAGGATCTGACATCTAAAACTTTTAAAGTTGCAGATGC 1877
Sequence_33         GCCAAAAACAATGAACCCAGGTGAGGATCTGACATCTAAAACTTTTAAAGTTGCAGATGC 1877
Sequence_69         GCCAAAAACAATGAACCCAGGTGAGGATCTGACATCTAAAACTTTTAAAGTTGCAGATGC 1877
Sequence_11         GCCAAAAACAATGAACCCAGGTGAGGATCTGACATCTAAAACTTTTAAAGTTGCAGATGC 1865
Sequence_1          GCCAAAAACAATGAACCCAGGTGAGGATCTGACATCTAAAACTTTTAAAGTTGCAGATGC 1865
Sequence_17         GCCAAAAACAATGAACCCAGGTGAGGATCTGACATCTAAAACTTTTAAAGTTGCAGATGC 2595
Sequence_3          TCAAAAAACTATGAATAGAGGTGAAGCTTTAACATATAATAAATTTAATTATGC-GACTT 1882
Sequence_13         TCAAAAAACTATGAATAGAGGTGAAGCTTTAACATATAATAAATTTAATTATGC-GACTT 1882
Sequence_18         TCAAAAAACTATGAATAGAGGTGAAGCTTTAACATATAATAAATTTAATTATGC-GACTT 3135
Cry8Ka1             TAAATCGACAATGTCTCAAGACACACCATTGAAGTATAACGATTTCCAATATGCAGAAGC 1859
                       *   ** ***     **         * *  * ***    **  *   *** **
```

To Fig. 18AH

Fig. 18AG

From Fig. 18AG

```
Sequence_71     TATCACAACAGTTAATTTA--GCAACAGATAGTTCGGTTGCAGTTAAA--CATAATTTAG 1942
Sequence_73     TATCACAACAGTTAATTTA--GCAACAGATAGTTCGGTTGCAGTTAAA--CATAATTTAG 1939
Sequence_21     TATCACAACAGTAAATTTA--GCAACAGATAGTTCGGTAGCAGTGAAA--CATAATGTAG 1933
Sequence_67     TATCACAACAGTAAATTTA--GCAACAGATAGTTCGGTAGCAGTGAAA--CATAATTTAG 1933
Sequence_61     TATCACAACAGTTAATTTA--GCAACAGATAGTTCGGTTGCAGTTAAA--CATAATGTAG 1933
Sequence_93     TATCACAACAGTTAATTTA--GCAACAGATAGTTCGGTTGCAGTTAAA--CATAATTTAG 1933
Sequence_59     TATCACAACAGTTAATTTA--GCAACAGATAGTTCGGTTGCAGTTAAA--CATAATGTAG 1933
Sequence_91     TATCACAACAGTTAATTTA--GCAACAGATAGTTCGGTTGCAGTTAAA--CATAATTTAG 1933
Sequence_39     TATCACAACAGTTAATTTA--GCAACAGATAGTTCGGTTGCAGTTAAA--CATAATGTAG 1942
Sequence_41     TATCACAACAGTTAATTTA--GCAACAGATAGTTCGGTTGCAGTTAAA--CATAATGTAG 1939
Sequence_49     TATCACAACAGTTAATTTA--GCAACAGATAGTTCGGTTGCAGTTAAA--CATAATGTAG 1936
Sequence_81     TATCACAACAGTTAATTTA--GCAACAGATAGTTCGGTTGCAGTTAAA--CATAATTTAG 1936
Sequence_45     TATCACAACAGTTAATTTA--GCAACAGATAGTTCGGTTGCAGTTAAA--CATAATGTAG 1939
Sequence_77     TATCACAACAGTTAATTTA--GCAACAGATAGTTCGGTTGCAGTTAAA--CATAATTTAG 1939
Sequence_75     TATCACAACAGTTAATTTA--GCAACAGATAGTTCGGTTGCAGTTAAA--CATAATTTAG 1936
Sequence_43     TATCACAACAGTTAATTTA--GCAACAGATAGTTCGGTTGCAGTTAAA--CATAATGTAG 1936
Sequence_47     TATCACAACAGTTAATTTA--GCAACAGATAGTTCGGTTGCAGTTAAA--CATAATGTAG 1939
Sequence_79     TATCACAACAGTTAATTTA--GCAACAGATAGTTCGGTTGCAGTTAAA--CATAATTTAG 1939
Sequence_51     TATCACAACAGTTAATTTA--GCAACAGATAGTTCGGTTGCAGTTAAA--CATAATGTAG 1945
Sequence_83     TATCACAACAGTTAATTTA--GCAACAGATAGTTCGGTTGCAGTTAAA--CATAATTTAG 1945
Sequence_7      TATCACAACATTAAATTTA--GCAACAGATAGTTCGCTAGCATTGAAA--CATAATTTAG 1933
Sequence_25     TATCACAACATTAAATTTA--GCAACAGATAGTTCGCTAGCATTGAAA--CATAATGTAG 1933
Sequence_29     TATCACAACATTAAATTTA--GCAACAGATAGTTCGCTAGCAGTGAAA--CATAATGTAG 1933
Sequence_33     TATCACAACAGTAAATTTA--GCAACAGATAGTTCGGTAGCAGTGAAA--CATAATGTAG 1933
Sequence_69     TATCACAACAGTAAATTTA--GCAACAGATAGTTCGGTAGCAGTGAAA--CATAATTTAG 1933
Sequence_11     TATCACAACATTAAATTTA--GCAACAGATAGTTCGCTAGCATTGAAA--CATAATTTAG 1921
Sequence_1      TATCACAACATTAAATTTA--GCAACAGATAGTTCGCTAGCATTGAAA--CATAATTTAG 1921
Sequence_17     TATCACAACATTAAATTTA--GCAACAGATAGTTCGCTAGCATTGAAA--CATAATTTAG 2651
Sequence_3      TGCCCCC-TATTAAATTTACGACAACCGAACCTTTCATTACTCTAGGGGCTATATTTGAA 1941
Sequence_13     TGCCCCC-TATTAAATTTACGACAACCGAACCTTTCATTACTCTAGGGGCTATATTTGAA 1941
Sequence_18     TGCCCCC-TATTAAATTTACGACAACCGAACCTTTCATTACTCTAGGGGCTATATTTGAA 3194
Cry8Ka1         TGACAAAACAGTGCATTTA-----TACAATCCTCGTTTTTCTTTA-----TATTTAGAAA 1909
                *  *     * *  *****     *   *   *  *  *      **    *
```

To Fig. 18AI

Fig. 18AH

From Fig. 18AH

| | | |
|---|---|---|
| Sequence_71 | GTGAAGACCCTAATTCAACATTATCTGGTATAGTTTACGTTGACCGAATCGAATTCATCC | 2002 |
| Sequence_73 | GTGAAGACCCTAATTCAACATTATCTGGTATAGTTTACGTTGACCGAATCGAATTCATCC | 1999 |
| Sequence_21 | GTGAAGACCCTAATTCAACATTATCTGGTATAGTTTACGTTGACCGAATCGAATTCATCC | 1993 |
| Sequence_67 | GTGAAGACCCTAATTCAACATTATCTGGTATAGTTTACGTTGACCGAATCGAATTCATCC | 1993 |
| Sequence_61 | GTGAAGACCCTAATTCAACATTATCTGGTATAGTTTACGTTGACCGAATCGAATTCATCC | 1993 |
| Sequence_93 | GTGAAGACCCTAATTCAACATTATCTGGTATAGTTTACGTTGACCGAATCGAATTCATCC | 1993 |
| Sequence_59 | GTGAAGACCCTAATTCAACATTATCTGGTATAGTTTACGTTGACCGAATCGAATTCATCC | 1993 |
| Sequence_91 | GTGAAGACCCTAATTCAACATTATCTGGTATAGTTTACGTTGACCGAATCGAATTCATCC | 1993 |
| Sequence_39 | GTGAAGACCCTAATTCAACATTATCTGGTATAGTTTACGTTGACCGAATCGAATTCATCC | 2002 |
| Sequence_41 | GTGAAGACCCTAATTCAACATTATCTGGTATAGTTTACGTTGACCGAATCGAATTCATCC | 1999 |
| Sequence_49 | GTGAAGACCCTAATTCAACATTATCTGGTATAGTTTACGTTGACCGAATCGAATTCATCC | 1996 |
| Sequence_81 | GTGAAGACCCTAATTCAACATTATCTGGTATAGTTTACGTTGACCGAATCGAATTCATCC | 1996 |
| Sequence_45 | GTGAAGACCCTAATTCAACATTATCTGGTATAGTTTACGTTGACCGAATCGAATTCATCC | 1999 |
| Sequence_77 | GTGAAGACCCTAATTCAACATTATCTGGTATAGTTTACGTTGACCGAATCGAATTCATCC | 1999 |
| Sequence_75 | GTGAAGACCCTAATTCAACATTATCTGGTATAGTTTACGTTGACCGAATCGAATTCATCC | 1996 |
| Sequence_43 | GTGAAGACCCTAATTCAACATTATCTGGTATAGTTTACGTTGACCGAATCGAATTCATCC | 1996 |
| Sequence_47 | GTGAAGACCCTAATTCAACATTATCTGGTATAGTTTACGTTGACCGAATCGAATTCATCC | 1999 |
| Sequence_79 | GTGAAGACCCTAATTCAACATTATCTGGTATAGTTTACGTTGACCGAATCGAATTCATCC | 1999 |
| Sequence_51 | GTGAAGACCCTAATTCAACATTATCTGGTATAGTTTACGTTGACCGAATCGAATTCATCC | 2005 |
| Sequence_83 | GTGAAGACCCTAATTCAACATTATCTGGTATAGTTTACGTTGACCGAATCGAATTCATCC | 2005 |
| Sequence_7 | GTGAAGACCCTAATTCAACATTATCTGGTATAGTTTACGTTGACCGAATCGAATTCATCC | 1993 |
| Sequence_25 | GTGAAGACCCTAATTCAACATTATCTGGTATAGTTTACGTTGACCGAATCGAATTCATCC | 1993 |
| Sequence_29 | GTGAAGACCCTAATTCAACATTATCTGGTATAGTTTACGTTGACCGAATCGAATTCATCC | 1993 |
| Sequence_33 | GTGAAGACCCTAATTCAACATTATCTGGTATAGTTTACGTTGACCGAATCGAATTCATCC | 1993 |
| Sequence_69 | GTGAAGACCCTAATTCAACATTATCTGGTATAGTTTACGTTGACCGAATCGAATTCATCC | 1993 |
| Sequence_11 | GTGAAGACCCTAATTCAACATTATCTGGTATAGTTTACGTTGACCGAATCGAATTCATCC | 1981 |
| Sequence_1 | GTGAAGACCCTAATTCAACATTATCTGGTATAGTTTACGTTGACCGAATCGAATTCATCC | 1981 |
| Sequence_17 | GTGAAGACCCTAATTCAACATTATCTGGTATAGTTTACGTTGACCGAATCGAATTCATCC | 2711 |
| Sequence_3 | GCGGAAGACTTTCTTGGAATTGA--------AGCTTATATAGACCGAATCGAATTTATCC | 1993 |
| Sequence_13 | GCGGAAGACTTTCTTGGAATTGA--------AGCTTATATAGACCGAATCGAATTTATCC | 1993 |
| Sequence_18 | GCGGAAGACTTTCTTGGAATTGA--------AGCTTATATAGACCGAATCGAATTTATCC | 3246 |
| Cry8Ka1 | ATTCAGATCAATCCGGGAAAAGT---------ATTTATATAGATCGAATCGAATTCATCC | 1960 |
| | *  *    *              *** * ** ********** ****** | |

To Fig. 18AJ

Fig. 18AI

From Fig. 18AI

```
Sequence_71    CAGTAGATGAGACATATGAAGCGGAA---------------------------------- 2028
Sequence_73    CAGTAGATGAGACATATGAAGCGGAA---------------------------------- 2025
Sequence_21    CAGTAGATGAGACATATGAAGCGGAATAA------------------------------- 2022
Sequence_67    CAGTAGATGAGACATATGAAGCGGAATAA------------------------------- 2022
Sequence_61    CAGTAGATGAGACATATGAAGCGGAA---------------------------------- 2019
Sequence_93    CAGTAGATGAGACATATGAAGCGGAA---------------------------------- 2019
Sequence_59    CAGTAGATGAGACATATGAAGCGGAA---------------------------------- 2019
Sequence_91    CAGTAGATGAGACATATGAAGCGGAA---------------------------------- 2019
Sequence_39    CAGTAGATGAGACATATGAAGCGGAA---------------------------------- 2028
Sequence_41    CAGTAGATGAGACATATGAAGCGGAA---------------------------------- 2025
Sequence_49    CAGTAGATGAGACATATGAAGCGGAA---------------------------------- 2022
Sequence_81    CAGTAGATGAGACATATGAAGCGGAA---------------------------------- 2022
Sequence_45    CAGTAGATGAGACATATGAAGCGGAA---------------------------------- 2025
Sequence_77    CAGTAGATGAGACATATGAAGCGGAA---------------------------------- 2025
Sequence_75    CAGTAGATGAGACATATGAAGCGGAA---------------------------------- 2022
Sequence_43    CAGTAGATGAGACATATGAAGCGGAA---------------------------------- 2022
Sequence_47    CAGTAGATGAGACATATGAAGCGGAA---------------------------------- 2025
Sequence_79    CAGTAGATGAGACATATGAAGCGGAA---------------------------------- 2025
Sequence_51    CAGTAGATGAGACATATGAAGCGGAA---------------------------------- 2031
Sequence_83    CAGTAGATGAGACATATGAAGCGGAA---------------------------------- 2031
Sequence_7     CAGTAGATGAGACATATGAAGCGGAATAA------------------------------- 2022
Sequence_25    CAGTAGATGAGACATATGAAGCGGAATAA------------------------------- 2022
Sequence_29    CAGTAGATGAGACATATGAAGCGGAATAA------------------------------- 2022
Sequence_33    CAGTAGATGAGACATATGAAGCGGAATAA------------------------------- 2022
Sequence_69    CAGTAGATGAGACATATGAAGCGGAATAA------------------------------- 2022
Sequence_11    CAGTAGATGAGACATATGAAGCGGAATAA------------------------------- 2010
Sequence_1     CAGTAGATGAGACATATGAAGCGGAACAAGATTTAGAAGCAGCGAAGAAAGCAGTGAATG 2041
Sequence_17    CAGTAGATGAGACATATGAAGCGGAACAAGATTTAGAAGCAGCGAAGAAAGCAGTGAATG 2771
Sequence_3     CAGTAGATGAGACATATGAAGCGGAACAAGATTTAGAAGCAGCGAAGAAAGCAGTGAATG 2053
Sequence_13    CAGTAGATGAGACATATGAAGCGGAATAA------------------------------- 2022
Sequence_18    CAGTAGATGAGACATATGAAGCGGAACAAGATTTAGAAGCAGCGAAGAAAGCAGTGAATG 3306
Cry8Ka1_       CAGTAGATGAGACCTATGAAGCAGAACAAGAT---------------------------- 1992
               ************* ******** ***
```

Fig. 18AJ

```
Cry8Ba1      MSPNNQNEYEIIDATPSTSVSNDSNRYPFANEPTNALQNMDYKDYLKMSAGNVSEYPGSP 60  (SEQ ID NO:56)
50c_b        MSPNNQNEYEIIDATPSTSVSNDSNRYPFANEPTNALQNMDYKDYLKMSAGNVSEYPGSP 60  (SEQ ID NO:57)
Cry8Bb1      MSPNNQNEYEIIDATPSTSVSNDSNRYPFANEPTNALQNMDYKDYLKMSAGNASEYPGSP 60  (SEQ ID NO:58)
Cry8Bc1      MSPNNQNEYEIIDATPSTSVSNDSNRYPFANEPTNALQNMDYKDYLKMSAGNASEYPGSP 60  (SEQ ID NO:59)
Cry8Aa1      MSPNNQNEYEIIDATPSTSVSSDSNRYPFANEPTDALQNMNYKDYLKMSGGENPELFGNP 60  (SEQ ID NO:60)
Cry8AB001.1  MSPNNQNEYEIIDATPSTSVSNDSNRYPFANEPTNALQNMNYKDYLRMSEGYDSEYSGSP 60  (SEQ ID NO:61)
Cry8Da1      MSPNNQNEYEILDASSSTSVSDNSVRYPLANDQTTTLQNMNYKDYLRMSEGENPELFGNP 60  (SEQ ID NO:62)
Cry8Da3      MSPNNQNEYEILDASSSTSVSDNSVRYPLANDQTTTLQNMNYKDYLRMSEGENPELFGNP 60  (SEQ ID NO:63)
Cry8Da2      MSPNNQNEYEILDASSSTSVSDNSVRYPLANDQTTTLQNMNYKDYLRMSEGENPELFGNP 60  (SEQ ID NO:64)
Cry8Ca1      MSPNNQNEYEIIDALSPTSVSDNSIRYPLANDQTNTLQNMNYKDYLKMTESTNAELSRNP 60  (SEQ ID NO:65)
Cry8Ca2      MSPNNQNEYEIIDALSPTSVSDNSIRYPLANDQTNTLQNMNYKDYLKMTESTNAELSRNP 60  (SEQ ID NO:66)
Cry8Ka1      MSPNNLNEYEIIDATPSTSVSNDSTRYPYANEPTNALQNMNYKDYLRMSEGYDNKYFANP 60  (SEQ ID NO:4)
             ***** *****:** ..****.:* *** **: * :****:*****:*: .   :    .*

Cry8Ba1      EVFLSEQDAVKAAIDIVGKLLTGLGVPFVGPIVSLYTQLIDILWPSKQKSQWEIFMEQVE 120
50c_b        EVFLSEQDAVKAAIDIVGKLLTGLGVPFVGPIVSLYTQLIDILWPSKQKSQWEIFMEQVE 120
Cry8Bb1      EVLVSGQDAAKAAIDIVGKLLSGLGVPFVGPIVSLYTQLIDILWPSGEKSQWEIFMEQVE 120
Cry8Bc1      EVLVSGQDAAKAAIDIVGKLLSGLGVPFVGPIVSLYTQLIDILWPSGQKSQWEIFMEQVE 120
Cry8Aa1      ETFISS-STIQTGIGIVGRILGALGVPFASQIASFYSFIVGQLWPSKSVDIWGEIMERVE 119
Cry8AB001.1  GALVSGKQAIKVGIDIVGNILGKLGVPFASQIVSFYNFILDQLWPSNSVSVWEQIMTLVE 120
```

To Fig. 19B

Fig. 19A

From Fig. 19A

```
Cry8Da1         ETFISSS-TVQTGIGIVGQVLGALGVPFAGQIASFYSFIVGQLWPSSTVSVWEMIMKQVE 119
Cry8Da3         ETFISSS-TVQTGIGIVGQVLGALGVPFAGQIASFYSFIVGQLWPSSTVSVWEMIMKQVE 119
Cry8Da2         ETFISSS-TVQTGIGIVGQVLGALGVPFAGQIASFYSFIVGQLWPSSTVSVWEMIMKQVE 119
Cry8Ca1         GTFISAQDAVGTGIDIVSTIISGLGIPVLGEVFSILGSLIGLLWPSNNENVWQIFMNRVE 120
Cry8Ca2         GTFISAQDAVGTGIDIVSTIISGLGIPVLGEVFSILGSLIGLLWPSNNENVWQIFMNRVE 120
Cry8Ka1         EVFAAPG-GITTGITIVTKLLGWLGLPFAGETGMALNFILGLLWPTSG-NPWAELMILVE 118
                 .: :      ..* **  ::  **:*. .        ::. ***:   . *  :*  **

Cry8Ba1         ELINQKIAEYARNKALSELEGLGNNYQLYLTALEEWKENPNGSRALRDVRNRFEILDSLF 180
50c b           ELINQKIAEYARNKALSELEGLGNNYQLYLTALEEWKENPNGSRALRDVRNRFEILDSLF 180
Cry8Bb1         ELINQKIAEYARNKALSELEGLGNNYQLYLTALEEWEENPNGSRALRDVRNRFEILDSLF 180
Cry8Bc1         ELINQKIAEYARNKALSELEGLGNNYQLYLTALEEWKENPNGSRALRDVRNRFEILDSLF 180
Cry8Aa1         ELVDQKIEKYVKDKALAELKGLGNALDVYQQSLEDWLENRNDARTRSVVSNQFIALDLNF 179
Cry8AB001.1     ELVDQKITEYARNKALAELKGLGDALGVYQQSLEAWLENRNDTRARSVVSNQFIALELDF 180
Cry8Da1         DLIDQKITDSVRKTALAGLQGLGDGLDVYQKSLKNWLENRNDTRARSVVVTQYIALELDF 179
Cry8Da3         DLIDQKITDSVRKTALAGLQGLGDGLDVYQKSLKNWLENRNDTRARSVVVTQYIALELDF 179
Cry8Da2         DLIDQKITDSVRKTALAGLQGLGDGLDVYQKSLKNWLENRNDTRARSVVVTQYIALELDF 179
Cry8Ca1         ELIDQKILDSVRSRAIADLANSRIAVEYYQNALEDWRKNPHSTRSAALVKERFGNAEAIL 180
Cry8Ca2         ELIDQKILDSVRSRAIADLANSRIAVEYYQNALEDWRKNPHSTRSAALVKERFGNAEAIL 180
Cry8Ka1         ELINQKIEETVRNKALADLGNSGRALRSYLNAFEDWQKNPNIFRSKELVKERFSNAEHSL 178
                :*::*** . .:. *:: * .       *  ::: * :* :  *:   *  ::   :  :

Cry8Ba1         TQYMPSFRVTNFEVPFLTVYTMAANLHLLLLRDASIFGEEWGLSTSTINNYYNRQMKLTA 240
50c b           TQYMPSFRVTNFEVPFLTVYTMAANLHLLLLRDASIFGEEWGLSTSTINNYYNRQMKLTA 240
Cry8Bb1         TQYMPSFRVTNFEVPFLTVYAMAANLHLLLLKDASIFGEEWGWSTTTINNYYDRQMKLTA 240
Cry8Bc1         TQYMPSFRVTNFEVPFLTVYTQAANLHLLLLKDASIFGEEWGWSTTTINNYYDRQMKLTA 240
Cry8Aa1         VSSIPSFAVSGHEVLLLAVYAQAVNLHLLLLRDASIFGEEWGFTPGEISRFYNRQVQLTA 239
Cry8AB001.1     VGAIPSFAVSGQEVPLLAVYAQAVNMHLLLLRDASIFGEEWGFTSSEISTYYNRQVQLTS 240
Cry8Da1         VAKIPSFAISGQEVPLLSVYAQAANLHLLLLRDASIFGAEWGFTPGEISTFYDRQVTRTA 239
Cry8Da3         VAKIPSFAISGQEVPLLSVYAQAANLHLLLLRDASIFGAEWGFTPGEISTFYDRQVTRTA 239
Cry8Da2         VAKIPSFAISGQEVPLLSVYAQAANLHLLLLRDASIFGAEWGFTPGEISTFYDRQVTRTA 239
Cry8Ca1         RTNMGSFSQTNYETPLLPTYAQAASLHLLVMRDVQIYGKEWGYPQNDIDLFYKEQVSYTA 240
Cry8Ca2         RTNMGSFSQTNYETPLLPTYAQAASLHLLVMRDVQIYGKEWGYPQNDIDLFYKEQVSYTA 240
```

To Fig. 19C

Fig. 19B

From Fig. 19B

```
Cry8Ka1        RTEMSSFAIRGFEIPLLATYAQAANLHLFLIKDIQIYGKEWGYTQADIDLFYREQVEFTK 238
                  : **   .  *  :*..*: *...**:::*  .*:* ***  .    *. :*  .*:   *

Cry8Ba1        EYSDHCVKWYETGLAKLKGSSAKQWIDYNQFRREMTLTVLDVVALFSNYDTRTYPLATTA 300
50c_b          EYSDHCVKWYETGLAKLKGSSAKQWIDYNQFRREMTLTVLDVVALFSNYDTRTYPLATTA 300
Cry8Bb1        EYSDHCVKWYETGLAKLKGTSAKQWVDYNQFRREMTLAVLDVVALFPNYDTRTYPMETKA 300
Cry8Bc1        EYSDHCVKWYETGLAKLKGTSAKQWVDYNQFRREMTLTVLDVVALFPNYDTRTYPMETKA 300
Cry8Aa1        EYSDYCVKWYKIGLDKLKGTTSKSWLNYHQFRREMTLLVLDLVALFPNYDTHMYPIETTA 299
Cry8AB001.1    QYSDYCVKWYDTGLQKLKGTSAESWLEYHQFRREMTFMVLDLVALFPNYDTHTYPLETKA 300
Cry8Da1        QYSDYCVKWYNTGLDKLKGTNAASWLKYHQFRREMTLLVLDLVALFPNYDTRTYPIETTA 299
Cry8Da3        QYSDYCVKWYNTGLDKLKGTNAASWLKYHQFRREMTLLVLDLVALFPNYDTRTYPIETTA 299
Cry8Da2        QYSDYCVKWYNTGLDKLKGTNAASWLKYHQFRREMTLLVLDLVALFPNYDTRTYPIETTA 299
Cry8Ca1        RYSDHCVQWYNAGLNKLRGTGAKQWVDYNRFRREMNVMVLDLVALFPNYDARIYPLETNA 300
Cry8Ca2        RYSDHCVQWYNAGLNKLRGTGAKQWVDYNRFRREMNVMVLDLVALFPNYDARIYPLETNA 300
Cry8Ka1        EYTEHCINIYNDGLNQLKGSNAKQWIAFNRFRREMTLTVLDVVALFPNYDVRMYPIKTTT 298
               .*:::*:: *. ** :*:*: : .*: :::*****.. ***:****.***.: **: *.:

Cry8Ba1        QLTREVYTDPLGAVDVPNIG---SWYDKAP----SFSEIEKAAIRPPHVFDYITGLTVYT 353
50c_b          QLTREVYTDPLGAVDVPNIG---SWYDKAP----SFSEIEKAAIRPPHVFDYITGLTVYT 353
Cry8Bb1        QLTREVYTDPLGAVNVSSIG---SWYDKAP----SFGVIESSVIRPPHVFDYITGLTVYT 353
Cry8Bc1        QLTREVYTDPLGAVNVSSIG---SWYDKAP----SFGVIESSVIRPPHVFDYITGLTVYT 353
Cry8Aa1        QLTRDVYTDPIAFNIVTSTG---FCNPWSTHSGILFYEVENNVIRPPHLFDILSSVEINT 356
Cry8AB001.1    QLTREVYTDPIAFNLSGAAG---FCSPWSKYTGISFSEIENDVIRPPHLFNLLRSLEINT 357
Cry8Da1        QLTREVYTDPI-VFNRETSGGFCRRWSLN--SDISFSEVESAVIRSPHLFDILSEIEFYT 356
Cry8Da3        QLTREVYTDPI-VFNRETSGGFCRRWSLN--SDISFSEVESAVIRSPHLFDILSEIEFYT 356
Cry8Da2        QLTREVYTDPI-VFNRETSGGFCRRWSLN--SDISFSEVESAVIRSPHLFDILSEIEFYT 356
Cry8Ca1        ELTREIFTDPVGSYVTGQSSTLISWYDMIPAALPSFSTLEN-LLRKPDFFTLLQEIRMYT 359
Cry8Ca2        ELTREIFTDPVGSYVTGQSSTLISWYDMIPAALPSFSTLEN-LLRKPDFFTLLQEIRMYT 359
Cry8Ka1        ELTRTIYTDPLGYTKTGSSSTP-PWYNYGS----SFSYIESVAIPAPSLVKWLSQIEIYS 353
               :***  ::***:        .                 *  :*.  :  *..  :  : . :

Cry8Ba1        KKRSFTS--DRYMRYWAGHQISYKHIGTSSTFTQMYGTNQNLQSTSNFDFTNYDIYKTLS 411
50c_b          KKRSFTS--DRYMRYWAGHQISYKHIGTSSTFTQMYGTNQNLQSTSNFDFTNYDIYKTLS 411
Cry8Bb1        QSRSISS--ARYIRHWAGHQISYHRVSRGSNLQQMYGTNQNLHSTSTFDFTNYDIYKTLS 411
```

To Fig. 19D

Fig. 19C

From Fig. 19C

```
Cry8Bc1         QSRSISS--ARYIRHWAGHQISYHRIFSDNIIKQMYGTNQNLHSTSTFDFTNYDIYKTLS 411
Cry8Aa1         SRGGITLNNDAYINYWSGHTLKYRRTADSTVTYTAN-YGRITSEKNSFALEDRDIFEINS 415
Cry8AB001.1     VRGTILGNTKDYLNYWSGHSLQYN-FIGKTIVRESN-YGYLTSEKTRIELDTRDIFEINS 415
Cry8Da1         TRAGLPLNNTEYLEYWVGHSIKYKNTNASS-ALERNYGTITSNKIKYYDLANKDIFQVRS 415
Cry8Da3         TRAGLPLNNTEYLEYWVGHSIKYKNTNASS-ALERNYGTITSNKIKYYDLANKDIFQVRS 415
Cry8Da2         TRAGLPLNNTEYLEYWVGHSIKYKNTNASS-ALERNYGTITSNKIKYYDLANKDIFQVRS 415
Cry8Ca1         SFR--QNGTIEYYNYWGGQRLTLSYIYGSS-FNK--YSGVLAGAEDIIPVGQNDIYRV-- 412
Cry8Ca2         SFR--QNGTIEYYNYWGGQRLTLSYIYGSS-FNK--YSGVLAGAEDIIPVGQNDIYRV-- 412
Cry8Ka1         KSARATP---QSADYWAGHTITYHYSGDDGQAVPNYGDRTNPVIVNRYNFEQADIYRVSS 410
                              :* *: :                            .   **:.

Cry8Ba1         NGAVLLDIVYPGYTYTFFGMPETEFFMVNQLNNTRKT-LTYKPASKDIID---RTRDSEL 467
50c b           NGAVLLDIVYPGYTYTFFGMPETEFFMVNQLNNTRKT-LTYKPASKDIID---RTRDSEL 467
Cry8Bb1         KDAVLLDIVYPGYTYIFFGMPEVEFFMVNQLNNTRKT-LKYNPVSKDIIA---STRDSEL 467
Cry8Bc1         KDAVLLDIVFPGYTYIFFGMPEVEFFMVNQLNNTRKT-LKYNPVSKDIIA---GTRDSEL 467
Cry8Aa1         TVANLAN-----YYQKAYGVPGSWFHMVKRG-TSSTT-AYLYSKTHTALQGCTQVYESSD 468
Cry8AB001.1     TAASLAN-----YYQETYGVPESRLHLVRWASPYYTS-SHLYSKTHTTGEGCTQVYESSE 469
Cry8Da1         LGADLAN-----YYAQVYGVPYASFTLLDKNTGSGSVGGFTYSKPHTTMQVCTQNYNTID 470
Cry8Da3         LGADLAN-----YYAQVYGVPYASFTLLDKNTGSGSVGGFTYSKPHTTMQVCTQNYNTID 470
Cry8Da2         LGADLAN-----YYAQVYGVPYASFTLLDKNTGSGSVGGFTYSKPHTTMQVCTQNYNTID 470
Cry8Ca1         VWTYIGR-----YTNSLLGVNPVTFYFSNNTQK-------TYSKPKQ-FAGGIKTIDSGE 459
Cry8Ca2         VWTYIGR-----YTNSLLGVNPVTFYFSNNTQK-------TYSKPKQ-FAGGIKTIDSGE 459
Cry8Ka1         SVASSTT------SGVKLLTTKAIFDGISTNNGLVSY---MYEKLSNFFN---ELKDTIT 458
                   :                     :                               ::

Cry8Ba1         ELPPETSG---QPNYESYSHRLGHITFIYSS------STSTYVPVFSWTHRSADLTNTVK 518
50c b           ELPPETSG---QPNYESYSHRLGHITFIYSS------STSTYVPVFSWTHRSADLTNTVK 518
Cry8Bb1         ELPPETSD---QPNYESYSHRLCHITSIPATG-----NTTGLVPVFSWTHRSADLNNTIY 519
Cry8Bc1         ELPPETSD---QPNYESYSHRLCHITSIPATG-----STTGLVPVFSWTHRSADLINAVH 519
Cry8Aa1         EIPLDRT----VPVAESYSHRLSHITSHSFSKNGSAYY--GSFPVFVWTHTSADLNNTIY 522
Cry8AB001.1     EIPVDRT----VPINEGYSHRLSYVTALFFQKIINTFYRNGTLPVFVWTHRSADLTNTIY 525
Cry8Da1         EIPPENE-----PLSRGYSHRLSHITSYSFSKNASSPARYGNLPVFAWTHRSADVTNTVY 525
Cry8Da3         EIPPENE-----PLSRGYSHRLSHITSYSFSKNASSPARYGNLPVFAWTHRSADVTNTVY 525
Cry8Da2         EIPPENE-----PLSRGYSHRLSHITSYSFSKNASSPARYGNLPVFAWTHRSADVTNTVY 525
```

To Fig. 19E

Fig. 19D

From Fig. 19D

```
Cry8Ca1        ELTYEN--------YQSYSHRVSYIT--SFEIKSTGGTVLGVVPIFGWTHSSASRNNFIY 509
Cry8Ca2        ELTYEN--------YQSYSHRVSYIT--SFEIKSTGGTVLGVVPIFGWTHSSASRNNFIY 509
Cry8Ka1        ELPVQISSPPTYGDAEQYSHRLSYVSNAPTEYSSGGHLILGLIPVLGWTHTSLTQTNQIH 518
               *:. :           . ****: :.:                 .*.: *** *     * :

Cry8Ba1        SGEITQIPGGKSSTIGRNTY-------IIKGRG-YTGGDLVALTDRIG------SCEFQM 564
50c_b          SGEITQIPGGKSSTIGRNTY-------IIKGRG-YTGGDLVALTDRIG------SCEFQM 564
Cry8Bb1        SDKITQIPAVKCWDNLPFVP-------VVKGPG-HTGGDLLQYNRSTGSVGTLFLARYGL 571
Cry8Bc1        SDKITQIPVVKVSDLAPSITG-GPNNTVVSGPG-FTGGGIIKVIRN----GVIISHMRVK 573
Cry8Aa1        SDKITQIPAVKGDML-------YLGGSVVQGPG-FTGGDILKRTNPSIL----GTFAVTV 570
Cry8AB001.1    PDVITQIPVVKAYELGSSILPDSPSPTIVPGPG-FTGGDIIQLLANTKG----IANMNFE 580
Cry8Da1        SDKITQIPVVKAHTLVSGTT-------VIKGPG-FTGGNILKRTSSGP----LAYTSVSV 573
Cry8Da3        SDKITQIPVVKAHTLVSGTT-------VIKGPG-FTGGNILKRTSSGP----LAYTSVSV 573
Cry8Da2        SDKITQIPVVKAHTLVSGTT-------VIKGPG-FTGGNILKRTSSGP----LAYTSVSV 573
Cry8Ca1        ATKISQIPINKASRTSGGAV-------WNFQEGLYNGGPVMKLSGSGSQ--VINLRVATD 560
Cry8Ca2        ATKISQIPINKASRTSGGAV-------WNFQEGLYNGGPVMKLSGSGSQ--VINLRVATD 560
Cry8Ka1        SDSITQIPAVKANSVSSYVT-------VEKGTG-FTGGDLVKFSTGFMS----TGIQFNL 566
               .  *:***  *                       *  ..** :.

Cry8Ba1        IFPESQRFRIRIRYASNETSYISLYGLN----QSGTLKFNQTYSNKNENDLTYNDFKYIE 620
50c_b          IFPESQRFRIRIRYASNETSYISLYGLN----QSGTLKFNQTYSNKNENDLTYNDFKYIE 620
Cry8Bb1        ALEKAGKYRVRLRYATDADIVLHVN--------DAQIQMPKTMN--PGEDLTSKTFKVAD 621
Cry8Bc1        ISDINKEYSMRIRYASANNTEFYINPSE----ENVKSHAQKTMN--RGEALTYNKFNYAT 627
Cry8Aa1        NGSLSQRYRVRIRYASTTDFEFTLYLGD----TIE--KNRFNKTMDNGASLTYETFKFAS 624
Cry8AB001.1    IQDINKEYIMRIRYASAANPEFNIAVGT----SGERVSTSAQKTMNPGDILTFNKFNYAT 636
Cry8Da1        KSPLSQRYRARIRYASTTNLRLFVTISG-----TRIYSINVNKTMNKGDDLTFNTFDLAT 628
Cry8Da3        KSPLSQRYRARIRYASTTNLRLFVTISG-----TRIYSINVNKTMNKGDDLTFNTFDLAT 628
Cry8Da2        KSPLSQRYRARIRYASTTNLRLFVTISG-----TRIYSINVNKTMNKGDDLTFNTFDLAT 628
Cry8Ca1        AKGASQRYRIRIRYASDRAGKFTISSRSPENPATYSASIAYTNTMSTNASLTYSTFAYAE 620
Cry8Ca2        AKGASQRYRIRIRYASDRAGKFTISSRSPENPATYSASIAYTNTMSTNASLTYSTFAYAE 620
Cry8Ka1        KIEERKRYRIRIRYAADVNATLSALGLN-------DAFINIKSTMSQDTPLKYNDFQYAE 619
                    .:  *:***:     :                     .        *. . *

Cry8Ba1        YPRVISVNASSNIQRLSIG----IQTNTNLFILDRIEFIPVDETYEAETDLEAAKKAVNA 676
```

To Fig. 19F

Fig. 19E

From Fig. 19E

```
50c_b          YPRVISVNASSNIQRLSIG----IQTNTNLFILDRIEFIPVDETYEAETDLEAAKKAVNA 676
Cry8Bb1        AITTLNLATDSSLALKHNLGEDPNSTLSGIVYVDRIEFIPVDETYEAEQDLEAAKKAVNA 681
Cry8Bc1        LPPIKFTTTEPFITLGAIF--EAEDFLGIEAYIDRIEFIPVDETYEAEQDLEAAKKAVNA 685
Cry8Aa1        FITDFQFRETQDKILLS---MGDFSS-GQEVYIDRIEFIPVDETYEAEQDLEAAKKAVNA 680
Cry8AB001.1    FPP-IKFNSTKISIMLTAR-LAAFASTLLETYIDRIEFIPVDETYEAETDLETAKKAVNA 694
Cry8Da1        IG--TAFTFSNYSDSLTVG--ADSFASGGEVYVDKFELIPVNATFEAEEDLDVAKKAVK- 683
Cry8Da3        IG--TAFTFSNYSDSLTVG--ADSFASGGEVYVDKFELIPVNATFEAEEDLDVAKKAVNG 684
Cry8Da2        IG--TAFTFSNYSDSLTVG--ADSFASGGEVYVDKFELIPVNATFEAEEDLDVAKKAVNG 684
Cry8Ca1        SGP-INLGISGSSRTFDIS--ITKEAGAANLYIDRIEFIPVNTLFEAEEDLDVAKKAVNG 677
Cry8Ca2        SGP-INLGISGSSRTFDIS--ITKEAGAANLYIDRIEFIPVNTLFEAEEDLDVAKKAVNG 677
Cry8Ka1        ADKTVHLYNPRFSLYLENS-----DQSGKSIYIDRIEFIPVDETYEAEQDLE-------- 666
                                              :*::*:***:  :*** **:

Cry8Ba1        LFTNTKDGLQPGVTDYEVNQAANLVECLSDDLYPNEKRLLFDAVREAKRLSEARNLLQDP 736
50c_b          LFTNTKDGLQPGVTDYEVNQAANLVECLSDDLYPNEKRLLFDAVREAKRLSEARNLLQDP 736
Cry8Bb1        LFTNTKDGLRPGVTDYEVNQAANLVECLSDDLYPNEKRLLFDAVREAKRLSEARNLLQDP 741
Cry8Bc1        LFTNTKDGLRPGVTDYEVNQAANLVECLSDDLYPNEKRLLFDAVREAKRLSEARNLLQDP 745
Cry8Aa1        LFTNTKDGLRPGVTDYEVNQAANLVECLSDDLYPNEKRLLFDAVREAKRLSGARNLLQDP 740
Cry8AB001.1    LFTNTKDGLRPGVTDYEVNQAANLV----------------------------------- 719
Cry8Da1        ----------------------NLVECLSDELYPNEKRMLWDAVKEAKRLVQARNLLQDT 721
Cry8Da3        LFTSKKDALQTSVTDYQVNQAANLVECLSDELYPNEKRMLWDAVKEAKRLVQARNLLQDT 744
Cry8Da2        LFTSKKDALQTSVTDYQVNQAANLVECLSDELYPNEKRMLWDAVKEAKRLVQARNLLQDT 744
Cry8Ca1        LFTNEKDALQTSVTDYQVNQAANLIECLSDELYPNEKRMLWDAVKEAKRLVQARNLLQDT 737
Cry8Ca2        LFTNEKDALQTSVTDYQVNQAANLIECLSDELYPNEKRMLWDAVKEAKRLVQARNLLQDT 737
Cry8Ka1        ------------------------------------------------------------

Cry8Ba1        DFQEINGENGWTASTGIEVIEGDAVFKGRYLRLPGAREIDTETYPTYLYQKVEEGVLKPY 796
50c_b          DFQEINGENGWTASTGIEVIEGDAVFKGRYLRLPGAREIDTETYPTYLYQKVEEGVLKPY 796
Cry8Bb1        DFQEINGENGWTASTGIEVIEGDALFKGRYLRLPGAREIDTETYPTYLYQKVEEGVLKPY 801
Cry8Bc1        DFQEINGENGWTASTGIEVIEGDALFKGRYLRLPGAREIDTETYPTYLYQKVEEGVLKPY 805
Cry8Aa1        DFQEINGENGWAASTGIEIVEGDAVFKGRYLRLPGAREIDTETYPTYLYQKVEEGVLKPY 800
Cry8AB001.1    ------------------------------------------------------------
Cry8Da1        GFNRINGENGWTGSTGIEVAEGDVLFKDRSLRLTSAREIDTETYPTYLYQQIDESLLKPY 781
```

To Fig. 19G

Fig. 19F

From Fig. 19F

```
Cry8Da3      GFNRINGENGWTGSTGIEVAEGDVLFKDRSLRLTSAREIDTETYPTYLYQQIDESLLKPY 804
Cry8Da2      GFNRINGENGWTGSTGIEVAEGDVLFKDRSLRLTSAREIDTETYPTYLYQQIDESLLKPY 804
Cry8Ca1      GFNRINGENGWTGSTGIEVVEGDVLFKDRSLRLTSAREIDTETYPTYLYQQIDESLLKPY 797
Cry8Ca2      GFNRINGENGWTGSTGIEVVEGDVLFKDRSLRLTNAREIDTETYPTYLYQQIDESLLKPY 797
Cry8Ka1      ------------------------------------------------------------

Cry8Ba1      TRYRLRGFVGSSQGLEIYTIRHQTNRIVKNVPDDLLPDVPPVNNDGRINRCSEQKYVNSR 856
50c b        TRYRLRGFVGSSQGLEIYTIRHQTNRIVKNVPDDLLPDVPPVNNDGRINRCSEQKYVNSR 856
Cry8Bb1      TRYRLRGFVGSSQGLEIFTIRHQTNRIVKNVPDDLLPDVSPVNSDGSINRCSEQKYVNSR 861
Cry8Bc1      TRYRLRGFVGSSQGLEIFTIRHQTNRIVKNVPDDLLPDVSPVNSDGSINRCSEQKYVNSR 865
Cry8Aa1      TRYRLRGFVGSSQGLEIYTIRHQTNRIVKNVPDDLLPDVSPVNSDGSINRCSEQKYVNSR 860
Cry8AB001.1  ------------------------------------------------------------
Cry8Da1      TRYKLKGFIGSSQDLEIKLIRHRANQIVKNVPDNLLPDVLPVNSCGGIDRCSEQQYVDAN 841
Cry8Da3      TRYKLKGFIGSSQDLEIKLIRHRANQIVKNVPDNLLPDVLPVNSCGGIDRCSEQQYVDAN 864
Cry8Da2      TRYKLKGFIGSSQDLEIKLIRHRANQIVKNVPDNLLPDVLPVNSCGGIDRCSEQQYVDAN 864
Cry8Ca1      TRYKLKGFIGSSQDLEIKLIRHRANQIVKNVPDNLLPDVRPVNSCGGVDRCSEQQYVDAN 857
Cry8Ca2      TRYKLKGFIGSSQDLEIKLIRHRANQIVKNVPDNLLPDVRPVNSCGGVDRCSEQQYVDAN 857
Cry8Ka1      ------------------------------------------------------------

Cry8Ba1      LEVENR------SGEAHEFSIPIDTGELDYNENAGIWVGFKITDPEGYATLGNLELVEEG 910
50c b        LEVENR------SGEAHEFSIPIDTGELDYNENAGIWVGFKITDPEGYATLGNLELVEEG 910
Cry8Bb1      LEVENR------SGEAHEFSIPIDTGEIDYNENAGIWVGFKITDPEGYATLGNLELVEEG 915
Cry8Bc1      LEVENR------SGEAHEFSIPIDTGEIDYNENAGIWVGFKITDPEGYATLGNLELVEEG 919
Cry8Aa1      LEGENR------SGDAHEFSLPIDIGELDYNENAGIWVGFKITDPEGYATLGNLELVEEG 914
Cry8AB001.1  ------------------------------------------------------------
Cry8Da1      LALENNGENGNMSSDSHAFSFHIDTGEIDLNENTGIWVVFKIPTTNGYATLGNLELVEEG 901
Cry8Da3      LALENNGENGNMSSDSHAFSFHIDTGEIDLNENTGIWVVFKIPTTNGYATLGNLELVEEG 924
Cry8Da2      LALENNGENGNMSSDSHAFSFHIDTGEIDLNENTGIWVVFKIPTTNGYATLGNLELVEEG 924
Cry8Ca1      LALENNGENGNMSSDSHAFSFHIDTGEIDLNENTGIWIVFKIPTTNGNATLGNLEFVEEG 917
Cry8Ca2      LALENNGENGNMSSDSHAFSFHIDTGEIDLNENTGIWIVFKIPTTNGNATLGNLEFVEEG 917
Cry8Ka1      ------------------------------------------------------------
```

To Fig. 19H

Fig. 19G

From Fig. 19G

```
Cry8Ba1      PLSGDALERLQKEEQQWKIQMTRRREETDRRYMASKQAVDRLYADYQDQQLNPNVEITDL 970
50c b        PLSGDALERLQKEEQQWKIQMTRRREETDRRYMASKQAVDRLYADYQDQQLNPNVEITDL 970
Cry8Bb1      PLSGDALERLQREEQQWKIQMTRRREETDRRYMASKQAVDRLYADYQDQQLNPDVEITDL 975
Cry8Bc1      PLSGDALERLQREEQQWKIQMTRRREETDRRYMASKQAVDRLYADYQDQQLNPDVEITDL 979
Cry8Aa1      PLSGDALERLQREEQQWKIQMTRRREETDRRYMASKQAVDRLYADYQDQQLNPDVEITDL 974
Cry8AB001.1  ------------------------------------------------------------
Cry8Da1      PLSGETLERAQQQEQQWQDKMARKRGASEKAYYAAKQAIDRLFADYQDQKLNSGVEMSDM 961
Cry8Da3      PLSGETLERAQQQEQQWQDKMARKRGASEKAYYAAKQAIDRLFADYQDQKLNSGVEMSDM 984
Cry8Da2      PLSGETLERAQQQEQQWQDKMARKRGASEKAYYAAKQAIDRLFADYQDQKLNSGVEMSDM 984
Cry8Ca1      PLSGETLEWAQQQEQQWQDKMARKRAASEKTYYAAKQAIDRLFADYQDQKLNSGVEMSDL 977
Cry8Ca2      PLSGETLEWAQQQEQQWQDKMARKRAASEKTYYAAKQAIDRLFADYQDQKLNSGVEMSDL 977
Cry8Ka1      ------------------------------------------------------------

Cry8Ba1      TAAQDLIQSIPYVYNEMFPEIPGMNYTKFTELTDRLQQAWGLYDQRNAIPNGDYRNELSN 1030
50c b        TAAQDLIQSIPYVYNEMFPEIPGMNYTKFTELTDRLQQAWGLYDQRNAIPNGDYRNELSN 1030
Cry8Bb1      TAAQDLIQSIPYVYNEMFPEIPGMNYTKFTELTDRLQQAWSLYDQRNAIPNGDFRNGLSN 1035
Cry8Bc1      TAAQDLIQSIPYVYNEMFPEIPGMNYTKFTELTDRLQQAWSLYDQRNAIPNGDFRNGLSN 1039
Cry8Aa1      TAAQDLIQSIPYVYNEMFPEIPGMNYTKFTELTDRLQQAWNLYDQRNAIPNGDFRNGLSN 1034
Cry8AB001.1  ------------------------------------------------------------
Cry8Da1      LAAQNLVQSIPYVYNDALPEIPGMNYTSFTELTNRLQQAWNLYDLRNAIPNGDFRNGLSD 1021
Cry8Da3      LAAQNLVQSIPYVYNDALPEIPGMNYTSFTELTNRLQQAWNLYDLRNAIPNGDFRNGLSD 1044
Cry8Da2      LAAQNLVQSIPYVYNDALPEIPGMNYTSFTELTNRLQQAWNLYDLRNAIPNGDFRNGLSD 1044
Cry8Ca1      LAAQNLVQSIPYVYNDALPEIPGMNYTSFTELTNRLQQAWNLYDLQNAIPNGDFRNGLSN 1037
Cry8Ca2      LAAQNLVQSIPYVYNDALPEIPGMNYTSFTELTNRLQQAWNLYDLQNAIPNGDFRNGLSN 1037
Cry8Ka1      ------------------------------------------------------------

Cry8Ba1      WNTTSGVNVQQINHTSVLVIPNWNEQVSQKFTVQPNQRYVLRVTARKEGVGNGYVSIRDG 1090
50c b        WNTTSGVNVQQINHTSVLVIPNWNEQVSQKFTVQPNQRYVLRVTARKEGVGNGYVSIRDG 1090
Cry8Bb1      WNATPGVEVQQINHTSVLVIPNWDEQVSQQFTVQPNQRYVLRVTARKEGVGNGYVSIRDG 1095
Cry8Bc1      WNATPGVEVQQINHTSVLVIPNWDEQVSQQFTVQPNQRYVLRVTARKEGVGNGYVSIRDG 1099
Cry8Aa1      WNATPGVEVQQINHTSVLVIPNWDEQVSQQFTVQPNQRYVLRVTARKEGVGNGYVSIRDG 1094
Cry8AB001.1  ------------------------------------------------------------
```

To Fig. 19I

Fig. 19H

From Fig. 19H

```
Cry8Da1      WNATSDVNVQQLSDTSVLVIPNWNSQVSQQFTVQPNYRYVLRVTARKEGVGDGYVIIRDG 1081
Cry8Da3      WNATSDVNVQQLSDTSVLVIPNWNSQVSQQFTVQPNYRYVLRVTARKEGVGDGYVIIRDG 1104
Cry8Da2      WNATSDVNVQQLSDTSVLVIPNWNSQVSQQFTVQPNYRYVLRVTARKEGVGDGYVIIRDG 1104
Cry8Ca1      WNATSDVNVQQLSDTSVLVIPNWNSQVSQQFTVQPNYRYVLRVTARKEGVGDGYVIIRDG 1097
Cry8Ca2      WNATSDVNVQQLSDTSVLVIPNWNSQVSQQFTVQPNYRYVLRVTARKEGVGDGYVIIRDG 1097
Cry8Ka1      ------------------------------------------------------------

Cry8Ba1      GNQSETLTFSASDYDTNGMYDTQASNTNGYNTNSVYMIKPAISR---------------- 1134
50c b        GNQSETLTFSASDYDTNGMYDTQASNTNGYNTNSVYMIKPAISR---------------- 1134
Cry8Bb1      GNQTETLTFSASDYDTNGMYNTQVSNTNGYNTNNAYNTQASSTNGYNANNMYNTQASNTN 1155
Cry8Bc1      GNQTETLTFSASDYDTNGMYNTQVSNTNGYNTNNAYNTQASSTNGYNANNMYNTQASNTN 1159
Cry8Aa1      GNQSETLTFSASDYDTNGVYNDQTGYIT-------------------------------- 1122
Cry8AB001.1  ------------------------------------------------------------
Cry8Da1      ANQTETLTFNICDDDTGVLSADQTSYIT-------------------------------- 1109
Cry8Da3      ANQTETLTFNICDDDTGVLSADQTSYIT-------------------------------- 1132
Cry8Da2      ANQTETLTFNICDDDTGVLSADQTSYIT-------------------------------- 1132
Cry8Ca1      ANQTETLTFNICDDDTGVLSTDQTSYIT-------------------------------- 1125
Cry8Ca2      ANQTETLTFNICDDDTGVLSTDQTSYIT-------------------------------- 1125
Cry8Ka1      ------------------------------------------------------------

Cry8Ba1      ----------------KTVDISSVYNQMWIEISETEGTFYIESVELIVDVE 1169
50c b        ----------------KTVDISSVYNQMWIEISETEGTFYIESVELIVDVE 1169
Cry8Bb1      GYNTNSVYNDQTGYITKTVTFIPYTDQMWIEMSETEGTFYIESVELIVDVE 1206
Cry8Bc1      GYNTNSVYNDQTGYITKTVTFIPYTDQMWIEMSETEGTFYIESVELIVDVE 1210
Cry8Aa1      ----------------KTVTFIPYTDQMWIEISETEGTFYIESVELIVDVE 1157
Cry8AB001.1  ---------------------------------------------------
Cry8Da1      ----------------KTVEFTPSTEQVWIDMSETEGVFNIESVELVLEEE 1144
Cry8Da3      ----------------KTVEFTPSTEQVWIDMSETEGVFNIESVELVLEEE 1167
Cry8Da2      ----------------KTVEFTPSTEQVWIDMSETEGVFNIESVELVLEEE 1167
Cry8Ca1      ----------------KTVEFTPSTEQVWIDMSETEGVFNIESVELVLEEE 1160
Cry8Ca2      ----------------KTVEFTPSTEQVWIDMSETEGVFNIESVELVLEEE 1160
Cry8Ka1      ---------------------------------------------------
```

Fig. 19I

SEQUENCE LISTING

```
<160> NUMBER OF SEQ ID NOS: 74

<210> SEQ ID NO 1
<211> LENGTH: 2710
<212> TYPE: DNA
<213> ORGANISM: Bacillus thuringiensis
<220> FEATURE:
<221> NAME/KEY: misc_feature
<223> OTHER INFORMATION: Bacillus thuringiensis Cry8Ka1 gene

<400> SEQUENCE: 1

atgagtccaa ataatctaaa tgaatatgaa attatagatg cgacaccttc tacatctgta     60
tctaatgatt ctaccagata cccttatgcg aatgagccca caaatgcgtt acaaaatatg    120
aattataagg attatttaag aatgtctgaa ggttacgata ataaatattt tgcaaatcct    180
gaagtgtttg ctgcaccagg tgggattaca actggaatta ctatagttac taaattactg    240
gggtggttag gacttccatt tgctggggaa acagggatgg ctcttaattt cattctaggt    300
ctattatggc caacatcagg aaacccgtgg gctgaactaa tgatattggt agaagaactc    360
ataaatcaaa aaatagaaga gactgtaaga aacaaagcac tagcggattt gggcaattca    420
ggtagagcct tacgatccta tttaaacgca tttgaagatt ggcaaaaaaa ccctaatatc    480
tttcggagta aagagttagt aaaagaaaga ttttcaaacg cggaacattc attacgtacc    540
gaaatgagtt cttttgccat aagaggattt gaaattcctc ttttagcaac atatgcacaa    600
gctgcgaatt tacatttatt tctaattaaa gatattcaaa tttatggaaa agaatgggga    660
tatactcaag ccgatattga cttattttat agagaacaag tagagtttac gaaagaatac    720
accgaacact gtattaatat ttataatgat ggtttaaatc aattaaaagg ttcgaatgct    780
aagcaatgga ttgcatttaa tcgcttccgt agagaaatga cattgacggt actggatgta    840
gttgcattat tcccgaacta tgatgtacgt atgtacccta taaaaacaac tacagagcta    900
acgagaacaa tttataccga tccacttggt tacacgaaaa cgggttctag tagtacacca    960
ccatggtata attatggatc tagtttctca tatatagaaa gtgtagcgat tccagcccct   1020
agtctggtta agtggttaag tcagattgaa atttattcga aatccgcaag ggctacaccg   1080
caaagtgcgg attattgggc aggacataca ataacatatc actatagtgg agatgatggt   1140
caagcagtac ctaattatgg agatagaacg aatcctgtaa ttgtaaatcg ttataatttt   1200
gagcaggctg acatttatag agtttcatca tctgttgctt caagtacaac tagtggtgtt   1260
aaattattaa ctactaaggc tatatttgat ggcataagta caaacaatgg actagtgagt   1320
tacatgtatg aaaaattatc gaactttttt aatgaactaa aagatacaat tacagagcta   1380
cctgttcaga tatccagtcc tcctacctac ggggatgctg aacagtacag tcatcggcta   1440
tcctatgttt ctaatgctcc aacagagtac tcttcgggcg gacatttaat tttgggacta   1500
atcccagtac tgggttggac gcatactagt ttaactcaaa caaatcagat acattctgac   1560
tcaattactc aaattccagc tgttaaagca aatagtgtta gttcttatgt tactgttgaa   1620
aagggaacag gctttacagg tggagattta gtgaaattct ccactggatt catgtctaca   1680
ggaatacagt ttaatttaaa gatagaagaa agaaagcgtt atcgtatccg tatacgatat   1740
```

gccgctgatg ttaatgctac tctatctgca cttggattaa atgatgcatt tattaacatt 1800
aaatcgacaa tgtctcaaga cacaccattg aagtataacg atttccaata tgcagaagct 1860
gacaaaacag tgcatttata caatcctcgt ttttctttat atttagaaaa ttcagatcaa 1920
tccgggaaaa gtatttatat agatcgaatc gaattcatcc cagtagatga gacctatgaa 1980
gcagaacaag atcttgaaaa tgcaaagaaa gcagtgaatg ctttgtttac gaatacaaaa 2040
gatggattac gaccaggcgt aacggattat gaagtaaatc aagcggcaaa cttagtcgaa 2100
tgcctatcag atgatttgta tccaaatgaa aaacgcttgt tatttgatgc agtcagagag 2160
gcaaaacgac ttagcgaggc acgaaacctg cttcaagatc cagatttcca agagataaat 2220
ggagaaaatg gatggactgc aagtacagga attgaggttg tagaagggga cgctttattt 2280
aaagggcgtt atctacgcct accgggtgca cgacaaattg atacggaaac gtatccaacg 2340
tatttgtatc aaaaaattga cgaaggtgta ttaaagccat acacaagata tagactgaga 2400
ggctttgtcg gaagaagtca aggattagaa atttatacga ttcgtcacca aacgaatcga 2460
attgtaaaaa atgtaccgga taatttattg ccagatgcat ctcctggaaa tgctggtgat 2520
ggaatcaatc gatgcagcga acaaaagtat gtaaatagtc gtctagaagg agaaaaaggc 2580
ttaccaaatg gcagtcgttc tgctgaagcg catgagttct caatccctat cgatacaggt 2640
gaaatcgatt acaatgaaaa tgcaggaata tgggttgggt ttaagattac ggacccagag 2700
caaaaacaac 2710

<210> SEQ ID NO 2
<211> LENGTH: 903
<212> TYPE: PRT
<213> ORGANISM: Bacillus thuringiensis
<220> FEATURE:
<221> NAME/KEY: misc_feature
<223> OTHER INFORMATION: Bacillus thuringiensis Cry8Ka1 protein

<400> SEQUENCE: 2

Met Ser Pro Asn Asn Leu Asn Glu Tyr Glu Ile Ile Asp Ala Thr Pro
1 5 10 15

Ser Thr Ser Val Ser Asn Asp Ser Thr Arg Tyr Pro Tyr Ala Asn Glu
20 25 30

Pro Thr Asn Ala Leu Gln Asn Met Asn Tyr Lys Asp Tyr Leu Arg Met
35 40 45

Ser Glu Gly Tyr Asp Asn Lys Tyr Phe Ala Asn Pro Glu Val Phe Ala
50 55 60

Ala Pro Gly Gly Ile Thr Thr Gly Ile Thr Ile Val Thr Lys Leu Leu
65 70 75 80

Gly Trp Leu Gly Leu Pro Phe Ala Gly Glu Thr Gly Met Ala Leu Asn
85 90 95

Phe Ile Leu Gly Leu Leu Trp Pro Thr Ser Gly Asn Pro Trp Ala Glu
100 105 110

Leu Met Ile Leu Val Glu Glu Leu Ile Asn Gln Lys Ile Glu Glu Thr
115 120 125

Val Arg Asn Lys Ala Leu Ala Asp Leu Gly Asn Ser Gly Arg Ala Leu
130 135 140

Arg Ser Tyr Leu Asn Ala Phe Glu Asp Trp Gln Lys Asn Pro Asn Ile
145 150 155 160

Phe Arg Ser Lys Glu Leu Val Lys Glu Arg Phe Ser Asn Ala Glu His
165 170 175

Ser Leu Arg Thr Glu Met Ser Ser Phe Ala Ile Arg Gly Phe Glu Ile

```
            180                 185                 190

Pro Leu Leu Ala Thr Tyr Ala Gln Ala Ala Asn Leu His Leu Phe Leu
        195                 200                 205

Ile Lys Asp Ile Gln Ile Tyr Gly Lys Glu Trp Gly Tyr Thr Gln Ala
    210                 215                 220

Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
            260                 265                 270

Met Thr Leu Thr Val Leu Asp Val Val Ala Leu Phe Pro Asn Tyr Asp
        275                 280                 285

Val Arg Met Tyr Pro Ile Lys Thr Thr Thr Glu Leu Thr Arg Thr Ile
    290                 295                 300

Tyr Thr Asp Pro Leu Gly Tyr Thr Lys Thr Gly Ser Ser Ser Thr Pro
305                 310                 315                 320

Pro Trp Tyr Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
            340                 345                 350

Ser Lys Ser Ala Arg Ala Thr Pro Gln Ser Ala Asp Tyr Trp Ala Gly
        355                 360                 365

His Thr Ile Thr Tyr His Tyr Ser Gly Asp Asp Gly Gln Ala Val Pro
    370                 375                 380

Asn Tyr Gly Asp Arg Thr Asn Pro Val Ile Val Asn Arg Tyr Asn Phe
385                 390                 395                 400

Glu Gln Ala Asp Ile Tyr Arg Val Ser Ser Ser Val Ala Ser Ser Thr
                405                 410                 415

Thr Ser Gly Val Lys Leu Leu Thr Thr Lys Ala Ile Phe Asp Gly Ile
            420                 425                 430

Ser Thr Asn Asn Gly Leu Val Ser Tyr Met Tyr Glu Lys Leu Ser Asn
        435                 440                 445

Phe Phe Asn Glu Leu Lys Asp Thr Ile Thr Glu Leu Pro Val Gln Ile
    450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Ser Ser Gly Gly His Leu
                485                 490                 495

Ile Leu Gly Leu Ile Pro Val Leu Gly Trp Thr His Thr Ser Leu Thr
            500                 505                 510

Gln Thr Asn Gln Ile His Ser Asp Ser Ile Thr Gln Ile Pro Ala Val
        515                 520                 525

Lys Ala Asn Ser Val Ser Ser Tyr Val Thr Val Glu Lys Gly Thr Gly
    530                 535                 540

Phe Thr Gly Gly Asp Leu Val Lys Phe Ser Thr Gly Phe Met Ser Thr
545                 550                 555                 560

Gly Ile Gln Phe Asn Leu Lys Ile Glu Glu Arg Lys Arg Tyr Arg Ile
                565                 570                 575

Arg Ile Arg Tyr Ala Ala Asp Val Asn Ala Thr Leu Ser Ala Leu Gly
            580                 585                 590

Leu Asn Asp Ala Phe Ile Asn Ile Lys Ser Thr Met Ser Gln Asp Thr
        595                 600                 605
```

```
Pro Leu Lys Tyr Asn Asp Phe Gln Tyr Ala Glu Ala Asp Lys Thr Val
    610                 615                 620

His Leu Tyr Asn Pro Arg Phe Ser Leu Tyr Leu Glu Asn Ser Asp Gln
625                 630                 635                 640

Ser Gly Lys Ser Ile Tyr Ile Asp Arg Ile Glu Phe Ile Pro Val Asp
                645                 650                 655

Glu Thr Tyr Glu Ala Glu Gln Asp Leu Glu Asn Ala Lys Lys Ala Val
            660                 665                 670

Asn Ala Leu Phe Thr Asn Thr Lys Asp Gly Leu Arg Pro Gly Val Thr
        675                 680                 685

Asp Tyr Glu Val Asn Gln Ala Ala Asn Leu Val Glu Cys Leu Ser Asp
    690                 695                 700

Asp Leu Tyr Pro Asn Glu Lys Arg Leu Leu Phe Asp Ala Val Arg Glu
705                 710                 715                 720

Ala Lys Arg Leu Ser Glu Ala Arg Asn Leu Leu Gln Asp Pro Asp Phe
                725                 730                 735

Gln Glu Ile Asn Gly Glu Asn Gly Trp Thr Ala Ser Thr Gly Ile Glu
            740                 745                 750

Val Val Glu Gly Asp Ala Leu Phe Lys Gly Arg Tyr Leu Arg Leu Pro
        755                 760                 765

Gly Ala Arg Gln Ile Asp Thr Glu Thr Tyr Pro Thr Tyr Leu Tyr Gln
    770                 775                 780

Lys Ile Asp Glu Gly Val Leu Lys Pro Tyr Thr Arg Tyr Arg Leu Arg
785                 790                 795                 800

Gly Phe Val Gly Arg Ser Gln Gly Leu Glu Ile Tyr Thr Ile Arg His
                805                 810                 815

Gln Thr Asn Arg Ile Val Lys Asn Val Pro Asp Asn Leu Leu Pro Asp
            820                 825                 830

Ala Ser Pro Gly Asn Ala Gly Asp Gly Ile Asn Arg Cys Ser Glu Gln
        835                 840                 845

Lys Tyr Val Asn Ser Arg Leu Glu Gly Glu Lys Gly Leu Pro Asn Gly
    850                 855                 860

Ser Arg Ser Ala Glu Ala His Glu Phe Ser Ile Pro Ile Asp Thr Gly
865                 870                 875                 880

Glu Ile Asp Tyr Asn Glu Asn Ala Gly Ile Trp Val Gly Phe Lys Ile
                885                 890                 895

Thr Asp Pro Glu Gln Lys Gln
            900


<210> SEQ ID NO 3
<211> LENGTH: 2001
<212> TYPE: DNA
<213> ORGANISM: Artificial sequence
<220> FEATURE:
<223> OTHER INFORMATION: Synthetic Cry8Ka1 gene sequence

<400> SEQUENCE: 3

atgagtccaa acaaccttaa cgaatatgag attatcgatg ctacccccttc tacatctgtt      60

tctaacgatt ctaccagata cccttatgct aacgagccta caaatgcttt gcagaacatg     120

aattacaagg attacttgag aatgtccgag ggttacgaca acaagtattt cgcaaaccct     180

gaggtgttcg ctgcaccagg tgggatcaca actggaatta ctatcgttac taagttgctt     240

ggttggttgg gacttccatt cgctggggag accggtatgg ctcttaactt cattcttggt     300

cttttgtggc caacatcagg aaacccttgg gctgagctta tgatcttggt tgaagagctc     360
```

```
atcaaccaga agatcgaaga gactgtgaga aacaaggcac ttgctgattt gggcaattca    420

ggtagagcct tgagatccta cttgaacgca ttcgaggatt ggcagaagaa ccctaacatc    480

ttcaggagta aggagttggt taaagaaaga ttctcaaacg ctgaacattc cttgcgtacc    540

gagatgagct ctttcgccat cagaggattc gagattcctc ttttggcaac atatgctcaa    600

gctgctaact tgcatttgtt cctcatcaag gatattcaaa tctacggaaa ggagtgggga    660

tacactcaag ccgatattga cttgttctac agagagcaag tggagtttac taaggagtac    720

accgagcact gtatcaatat ctataacgat ggtttgaacc agttgaaggg ttctaatgct    780

aagcaatgga ttgctttcaa taggttccgt agggaaatga ccttgactgt tcttgatgtg    840

gttgccttgt tccctaacta cgatgttcgt atgtacccta tcaagacaac tacagagctt    900

accagaacaa tctacaccga tccacttggt tacactaaga ccggttctag tagcacacca    960

ccatggtaca actatggatc tagtttctcc tacatcgaaa gtgttgctat tccagcccct   1020

agtcttgtta agtggttgag tcagattgag atctattcta agtccgcaag ggctacacct   1080

caaagtgctg attactgggc aggacatacc atcacatacc actacagcgg agatgatggt   1140

caagcagttc ctaactatgg agatagaact aatcctgtga ttgtgaaccg ttacaacttc   1200

gagcaggctg acatctacag agtttcatcc tctgttgctt ccagtacaac tagtggtgtt   1260

aagttgttga ctactaaggc tatcttcgat ggtatcagta ccaacaatgg acttgtgagt   1320

tacatgtatg agaagttgtc taacttcttt aacgaactca aggatacaat tacagagctt   1380

cctgttcaga tctccagtcc tcctacctac ggtgatgctg agcagtacag ccataggctt   1440

tcctacgttt ctaacgctcc aacagagtac tcttctggtg gacacttgat tttgggactt   1500

atcccagttc ttggttggac ccataccagt ttgactcaga caaaccagat ccattctgac   1560

tcaattactc agattccagc tgttaaggca aacagtgtta gctcttacgt tactgttgag   1620

aagggaacag gcttcacagg tggagatttg gtgaagttct ccaccggatt catgtctacc   1680

ggaatccagt tcaacttgaa gatcgaagag agaaagcgtt accgtatccg tattagatat   1740

gctgctgatg ttaatgctac tctctctgca cttggattga atgatgcatt cattaacatt   1800

aagtccacaa tgtctcagga caccccttg aagtacaacg atttccaata tgcagaggct    1860

gacaagacag tgcatttgta caaccctcgt ttctctttgt acttggaaaa ctcagatcaa   1920

tccgggaaga gtatctacat cgatagaatc gagttcatcc cagtggatga gacctacgag   1980

gcagagcaag atcttgaatg a                                              2001
```

<210> SEQ ID NO 4
<211> LENGTH: 666
<212> TYPE: PRT
<213> ORGANISM: Artificial sequence
<220> FEATURE:
<223> OTHER INFORMATION: Synthetic Cry8Ka1

<400> SEQUENCE: 4

```
Met Ser Pro Asn Asn Leu Asn Glu Tyr Glu Ile Ile Asp Ala Thr Pro
1               5                   10                  15

Ser Thr Ser Val Ser Asn Asp Ser Thr Arg Tyr Pro Tyr Ala Asn Glu
            20                  25                  30

Pro Thr Asn Ala Leu Gln Asn Met Asn Tyr Lys Asp Tyr Leu Arg Met
        35                  40                  45

Ser Glu Gly Tyr Asp Asn Lys Tyr Phe Ala Asn Pro Glu Val Phe Ala
    50                  55                  60
```

-continued

```
Ala Pro Gly Gly Ile Thr Thr Gly Ile Thr Ile Val Thr Lys Leu Leu
65                  70                  75                  80

Gly Trp Leu Gly Leu Pro Phe Ala Gly Glu Thr Gly Met Ala Leu Asn
                85                  90                  95

Phe Ile Leu Gly Leu Leu Trp Pro Thr Ser Gly Asn Pro Trp Ala Glu
            100                 105                 110

Leu Met Ile Leu Val Glu Glu Leu Ile Asn Gln Lys Ile Glu Glu Thr
        115                 120                 125

Val Arg Asn Lys Ala Leu Ala Asp Leu Gly Asn Ser Gly Arg Ala Leu
    130                 135                 140

Arg Ser Tyr Leu Asn Ala Phe Glu Asp Trp Gln Lys Asn Pro Asn Ile
145                 150                 155                 160

Phe Arg Ser Lys Glu Leu Val Lys Glu Arg Phe Ser Asn Ala Glu His
                165                 170                 175

Ser Leu Arg Thr Glu Met Ser Ser Phe Ala Ile Arg Gly Phe Glu Ile
            180                 185                 190

Pro Leu Leu Ala Thr Tyr Ala Gln Ala Ala Asn Leu His Leu Phe Leu
        195                 200                 205

Ile Lys Asp Ile Gln Ile Tyr Gly Lys Glu Trp Gly Tyr Thr Gln Ala
    210                 215                 220

Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
            260                 265                 270

Met Thr Leu Thr Val Leu Asp Val Val Ala Leu Phe Pro Asn Tyr Asp
        275                 280                 285

Val Arg Met Tyr Pro Ile Lys Thr Thr Thr Glu Leu Thr Arg Thr Ile
    290                 295                 300

Tyr Thr Asp Pro Leu Gly Tyr Thr Lys Thr Gly Ser Ser Ser Thr Pro
305                 310                 315                 320

Pro Trp Tyr Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
            340                 345                 350

Ser Lys Ser Ala Arg Ala Thr Pro Gln Ser Ala Asp Tyr Trp Ala Gly
        355                 360                 365

His Thr Ile Thr Tyr His Tyr Ser Gly Asp Asp Gly Gln Ala Val Pro
    370                 375                 380

Asn Tyr Gly Asp Arg Thr Asn Pro Val Ile Val Asn Arg Tyr Asn Phe
385                 390                 395                 400

Glu Gln Ala Asp Ile Tyr Arg Val Ser Ser Ser Val Ala Ser Ser Thr
                405                 410                 415

Thr Ser Gly Val Lys Leu Leu Thr Thr Lys Ala Ile Phe Asp Gly Ile
            420                 425                 430

Ser Thr Asn Asn Gly Leu Val Ser Tyr Met Tyr Glu Lys Leu Ser Asn
        435                 440                 445

Phe Phe Asn Glu Leu Lys Asp Thr Ile Thr Glu Leu Pro Val Gln Ile
    450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Ser Ser Gly Gly His Leu
```

-continued

```
                485                 490                 495

Ile Leu Gly Leu Ile Pro Val Leu Gly Trp Thr His Thr Ser Leu Thr
            500                 505                 510

Gln Thr Asn Gln Ile His Ser Asp Ser Ile Thr Gln Ile Pro Ala Val
        515                 520                 525

Lys Ala Asn Ser Val Ser Ser Tyr Val Thr Val Glu Lys Gly Thr Gly
    530                 535                 540

Phe Thr Gly Gly Asp Leu Val Lys Phe Ser Thr Gly Phe Met Ser Thr
545                 550                 555                 560

Gly Ile Gln Phe Asn Leu Lys Ile Glu Glu Arg Lys Arg Tyr Arg Ile
                565                 570                 575

Arg Ile Arg Tyr Ala Ala Asp Val Asn Ala Thr Leu Ser Ala Leu Gly
            580                 585                 590

Leu Asn Asp Ala Phe Ile Asn Ile Lys Ser Thr Met Ser Gln Asp Thr
        595                 600                 605

Pro Leu Lys Tyr Asn Asp Phe Gln Tyr Ala Glu Ala Asp Lys Thr Val
    610                 615                 620

His Leu Tyr Asn Pro Arg Phe Ser Leu Tyr Leu Glu Asn Ser Asp Gln
625                 630                 635                 640

Ser Gly Lys Ser Ile Tyr Ile Asp Arg Ile Glu Phe Ile Pro Val Asp
                645                 650                 655

Glu Thr Tyr Glu Ala Glu Gln Asp Leu Glu
            660                 665


<210> SEQ ID NO 5
<211> LENGTH: 1982
<212> TYPE: DNA
<213> ORGANISM: Artificial sequence
<220> FEATURE:
<223> OTHER INFORMATION: Cry8Ka2 (Synthetic Cry8Ka1 Variant) coding
      sequence

<400> SEQUENCE: 5

atgagaccaa ataatctaaa tgaatatgaa attatagatg cgacaccttc tacatctgta      60

tctaatgatt ctaccagata cccttatgcg aatgagccca caaatgcgtt acagaatatg     120

aattataagg attacttaag aatgtctgaa ggttacgata ataaatattt tgcaaatcct     180

gaagtgtttg ctgcaccagg tgggattaca actggaatta ctatagttac taaattactg     240

gggtggttag gacttccatt tgctggggaa acagggatgg ctcttaattt cattctaggt     300

ctattatggc caacaccagg aaacccgtgg gctgaactaa tgatattggt agaagaactc     360

ataaatcaaa aaatagaaga gactgtaaga aacaaagcac tagcggattt gggcaattca     420

ggtagagcct tacaatccta tttaaacgca tttgaagatt ggcaaaaaaa ccctaatatc     480

tttcggagta aagagttagt aaaagaaaga ttttcaaacg cggaacattc attacgtacc     540

gaaatgagtt cttttgccat aagaggattt gaaattcctc ttttagcaac atatgcacaa     600

gctgcgaatt tacatttatt tctaattaaa gatattcaaa tttatggaaa agaatgggga     660

tatactcaag ccgatattga cttattttat agagaacaag tagagtttac gaaagaatac     720

accgaacact gtattaatat ttataatgat ggtttaaatc aattaaaagg ttcgaatgct     780

aagcaatgga ttgcatttaa tcgcttccgt agagaaatga cattgacggt actggatgta     840

gttgcattat tcccgaacta tgatgtacgt atgtacccta taaaaacaac tacagagcta     900

acgagaacaa tttataccga tccacttggt tacacgaaaa cgggttctag tagtacacca     960

ccatggtgta attatggatc tagtttctca tatatagaaa gtgtagcgat tccagcccct    1020
```

```
agtctggtta agtggttaag tcagattgaa atttattcga aatccgcaag ggctacaccg   1080

caaagtgcgg attattgggc aggacataca ataacatatc actatagtgg agatgatggt   1140

cgagcagtag ctaattatgg agatagaacg aatcctgtaa ttgtaaatcg ttataatttt   1200

gagcaggctg acatttatag agtttcatca tctgttgctt caagtacaac tagtggtgtt   1260

aaattattaa ctactaaggc tatatttgat ggcataagta caaacaatgg acttgtgagt   1320

tacatgtatg agaagttgtc taacttcttt aacgaactca aggatacaat tacagagctt   1380

cctgttcaga tctccagtcc tcctacctac ggtgatgctg agcagtacag ccataggctt   1440

tcctacgttt ctaacgctcc aacagagtac tcttctggtg gacacttgat tttgggactt   1500

atcccagttc ttggttggac ccataccagt ttgactcaga caaaccagat ccattctgac   1560

tcaattactc agattccagc tgttaaggca aacagtgtta gctcttacgt tactgttgag   1620

aaagggacag gctttacagg tggagatttg gaaatttcca ctggattcat gttcacagga   1680

atacagttta atttaaagat agaagaagga aagcgttatc gtatccgtat acgatatgcc   1740

gctgatgtta atgctactct atctgcactt ggattaaatg gtgcatttat taacattgaa   1800

tcgacaatgt ctcaagacac accattgaag tataacgatt tccaatatgc agaagctgac   1860

aaaacagtgc atttatacaa tcctcgtttt tctttatatt tagaaaattc agatcaatcc   1920

gggaaaagta tttatataga tcgaatcgaa ttcatcccag tagataacgg ttccttgaac   1980

gg                                                                  1982


<210> SEQ ID NO 6
<211> LENGTH: 660
<212> TYPE: PRT
<213> ORGANISM: Artificial sequence
<220> FEATURE:
<223> OTHER INFORMATION: Cry8Ka2 (Synthetic Cry8Ka1 Variant)

<400> SEQUENCE: 6

Met Arg Pro Asn Asn Leu Asn Glu Tyr Glu Ile Ile Asp Ala Thr Pro
1               5                   10                  15

Ser Thr Ser Val Ser Asn Asp Ser Thr Arg Tyr Pro Tyr Ala Asn Glu
            20                  25                  30

Pro Thr Asn Ala Leu Gln Asn Met Asn Tyr Lys Asp Tyr Leu Arg Met
        35                  40                  45

Ser Glu Gly Tyr Asp Asn Lys Tyr Phe Ala Asn Pro Glu Val Phe Ala
    50                  55                  60

Ala Pro Gly Gly Ile Thr Thr Gly Ile Thr Ile Val Thr Lys Leu Leu
65                  70                  75                  80

Gly Trp Leu Gly Leu Pro Phe Ala Gly Glu Thr Gly Met Ala Leu Asn
                85                  90                  95

Phe Ile Leu Gly Leu Leu Trp Pro Thr Pro Gly Asn Pro Trp Ala Glu
            100                 105                 110

Leu Met Ile Leu Val Glu Glu Leu Ile Asn Gln Lys Ile Glu Glu Thr
        115                 120                 125

Val Arg Asn Lys Ala Leu Ala Asp Leu Gly Asn Ser Gly Arg Ala Leu
    130                 135                 140

Gln Ser Tyr Leu Asn Ala Phe Glu Asp Trp Gln Lys Asn Pro Asn Ile
145                 150                 155                 160

Phe Arg Ser Lys Glu Leu Val Lys Glu Arg Phe Ser Asn Ala Glu His
                165                 170                 175

Ser Leu Arg Thr Glu Met Ser Ser Phe Ala Ile Arg Gly Phe Glu Ile
```

-continued

```
            180                 185                 190

Pro Leu Leu Ala Thr Tyr Ala Gln Ala Ala Asn Leu His Leu Phe Leu
        195                 200                 205

Ile Lys Asp Ile Gln Ile Tyr Gly Lys Glu Trp Gly Tyr Thr Gln Ala
    210                 215                 220

Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
            260                 265                 270

Met Thr Leu Thr Val Leu Asp Val Val Ala Leu Phe Pro Asn Tyr Asp
        275                 280                 285

Val Arg Met Tyr Pro Ile Lys Thr Thr Thr Glu Leu Thr Arg Thr Ile
    290                 295                 300

Tyr Thr Asp Pro Leu Gly Tyr Thr Lys Thr Gly Ser Ser Ser Thr Pro
305                 310                 315                 320

Pro Trp Cys Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
            340                 345                 350

Ser Lys Ser Ala Arg Ala Thr Pro Gln Ser Ala Asp Tyr Trp Ala Gly
        355                 360                 365

His Thr Ile Thr Tyr His Tyr Ser Gly Asp Asp Gly Arg Ala Val Ala
    370                 375                 380

Asn Tyr Gly Asp Arg Thr Asn Pro Val Ile Val Asn Arg Tyr Asn Phe
385                 390                 395                 400

Glu Gln Ala Asp Ile Tyr Arg Val Ser Ser Ser Val Ala Ser Ser Thr
                405                 410                 415

Thr Ser Gly Val Lys Leu Leu Thr Thr Lys Ala Ile Phe Asp Gly Ile
            420                 425                 430

Ser Thr Asn Asn Gly Leu Val Ser Tyr Met Tyr Glu Lys Leu Ser Asn
        435                 440                 445

Phe Phe Asn Glu Leu Lys Asp Thr Ile Thr Glu Leu Pro Val Gln Ile
    450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Ser Ser Gly Gly His Leu
                485                 490                 495

Ile Leu Gly Leu Ile Pro Val Leu Gly Trp Thr His Thr Ser Leu Thr
            500                 505                 510

Gln Thr Asn Gln Ile His Ser Asp Ser Ile Thr Gln Ile Pro Ala Val
        515                 520                 525

Lys Ala Asn Ser Val Ser Ser Tyr Val Thr Val Glu Lys Gly Thr Gly
    530                 535                 540

Phe Thr Gly Gly Asp Leu Glu Ile Ser Thr Gly Phe Met Phe Thr Gly
545                 550                 555                 560

Ile Gln Phe Asn Leu Lys Ile Glu Glu Gly Lys Arg Tyr Arg Ile Arg
                565                 570                 575

Ile Arg Tyr Ala Ala Asp Val Asn Ala Thr Leu Ser Ala Leu Gly Leu
            580                 585                 590

Asn Gly Ala Phe Ile Asn Ile Glu Ser Thr Met Ser Gln Asp Thr Pro
        595                 600                 605
```

```
Leu Lys Tyr Asn Asp Phe Gln Tyr Ala Glu Ala Asp Lys Thr Val His
    610                 615                 620

Leu Tyr Asn Pro Arg Phe Ser Leu Tyr Leu Glu Asn Ser Asp Gln Ser
625                 630                 635                 640

Gly Lys Ser Ile Tyr Ile Asp Arg Ile Glu Phe Ile Pro Val Asp Asn
                645                 650                 655

Gly Ser Leu Asn
            660
```

```
<210> SEQ ID NO 7
<211> LENGTH: 1991
<212> TYPE: DNA
<213> ORGANISM: Artificial sequence
<220> FEATURE:
<223> OTHER INFORMATION: Cry8Ka3 (Synthetic Cry8Ka1 Variant) coding
      sequence

<400> SEQUENCE: 7

atgagaccaa ataatctaaa tgaatatgaa attatagatg cgacaccttc tacatctgta     60

tctaatgatt ctaccagata cccttatgcg aatgagccca caaatgcgtt acaaaatatg    120

aattataagg attacttaag aatgtctgaa ggttacgata ataaatattt tgcaaatcct    180

gaagtgtttg ctgcaccagg tgggattaca actggaatta ctatagttac taagttactg    240

gggtggttag gacttccatt tgctggggaa acagggatgg ctcttaattt cattctaggt    300

ctattatggc caacatcagg aaacccgtgg gctgaactaa tgatattggt agaggaactc    360

ataaatcaaa aaatagaaga gactgtaaga aacaaagcac tagcggattt gggcaattca    420

ggtagagcct tacaatccta tttaaacgca tttgaagatt ggcaaaaaaa ccctaatatc    480

tttcggagta aagagttagt aaaagaaaga ttttcaaacg cggaacactc attacgtacc    540

gaaatgagtt cttttgccat aagaggattt gaaattcctc ttttagcaac atatgcacaa    600

gctgcgaatt tacatttatt tctaattaaa gatattcaaa tttatggaaa agaatgggga    660

tatactcaag ccgatattga cttattttat agagaacaag tagagtttac gaaagaatac    720

accgaacact gtattaatat ttataatgat ggtttaaatc aattaaaagg ttcgaatgct    780

aagcaatgga ttgcatttaa tcgcttccgt agagaaatga cattgacggt actggatgta    840

gttgcattat tcccgaacta tgatgtacgt atgtacccta taaaaacaac tacagagcta    900

acgagaacaa tttataccga tccacttggt tacacgaaaa cgggttctag tagtacacca    960

ccatggtgta attatggatc tagtttctca tatatagaaa gtgtagcgat tccagccccc   1020

agtctggtta agtggttaag tcagattgaa atttattcga aatccgcaag ggctacaccg   1080

caaagtgcgg attattgggc aggacataca ataacatatc actatagtgg agatgatggt   1140

caagcagtag ctaattatgg agatagaacg aatcctgtaa ttgtaaatcg ttataatttt   1200

gagcaggctg acatttatag agtttcatca tctgttgctt caagtacaac taggggtgtt   1260

aaattattaa ctactaaggc tatcttcgat ggtatcagta ccaacaatgg acttgtgagt   1320

tacatgtatg agaagttgtc taacttcttt aacgaactca aggatacaat tacagagctt   1380

cctgttcaga tctccagtcc tcctacctac ggtgatgctg agcagtacag ccataggctt   1440

tcctacgttt ctaacgctcc aacagagtac tcttctggtg gacacttgat tttgggactt   1500

atcccagttc ttggttggac ccataccagt ttgactcaga caaaccagat ccattctgac   1560

tcaattactc aaattccagc tgttaaagca aatagtttag tgttagttct tatgttactg   1620

ttagaaaagg gaacaggctt tacaggtgga gatttagtga aattctccac tggattcatg   1680
```

-continued

```
tctacaggaa tacagtttaa tttaaagata gaagaaggaa agcgttatcg tatccgtata   1740

cgatatgccg ctgatgttaa tgctactcta tctgcacttg gattaaatga tgcatttatt   1800

aacattgaat cgacaatgtc tcaagacaca ccattgaagt ataacgattt ccaatatgca   1860

gaagctgaca aaacagtgca tttatacaat cctcgttttt ctttatattt agaaaattca   1920

gatcaatccg ggaaaagtat ttatatagat cgaatcgaat tcatcccagt agataacggt   1980

tccttgaacg g                                                        1991
```

```
<210> SEQ ID NO 8
<211> LENGTH: 663
<212> TYPE: PRT
<213> ORGANISM: Artificial sequence
<220> FEATURE:
<223> OTHER INFORMATION: Cry8Ka3 (Synthetic Cry8Ka1 Variant)

<400> SEQUENCE: 8

Met Arg Pro Asn Asn Leu Asn Glu Tyr Glu Ile Ile Asp Ala Thr Pro
1               5                   10                  15

Ser Thr Ser Val Ser Asn Asp Ser Thr Arg Tyr Pro Tyr Ala Asn Glu
            20                  25                  30

Pro Thr Asn Ala Leu Gln Asn Met Asn Tyr Lys Asp Tyr Leu Arg Met
        35                  40                  45

Ser Glu Gly Tyr Asp Asn Lys Tyr Phe Ala Asn Pro Glu Val Phe Ala
    50                  55                  60

Ala Pro Gly Gly Ile Thr Thr Gly Ile Thr Ile Val Thr Lys Leu Leu
65                  70                  75                  80

Gly Trp Leu Gly Leu Pro Phe Ala Gly Glu Thr Gly Met Ala Leu Asn
                85                  90                  95

Phe Ile Leu Gly Leu Leu Trp Pro Thr Ser Gly Asn Pro Trp Ala Glu
            100                 105                 110

Leu Met Ile Leu Val Glu Glu Leu Ile Asn Gln Lys Ile Glu Glu Thr
        115                 120                 125

Val Arg Asn Lys Ala Leu Ala Asp Leu Gly Asn Ser Gly Arg Ala Leu
    130                 135                 140

Gln Ser Tyr Leu Asn Ala Phe Glu Asp Trp Gln Lys Asn Pro Asn Ile
145                 150                 155                 160

Phe Arg Ser Lys Glu Leu Val Lys Glu Arg Phe Ser Asn Ala Glu His
                165                 170                 175

Ser Leu Arg Thr Glu Met Ser Ser Phe Ala Ile Arg Gly Phe Glu Ile
            180                 185                 190

Pro Leu Leu Ala Thr Tyr Ala Gln Ala Ala Asn Leu His Leu Phe Leu
        195                 200                 205

Ile Lys Asp Ile Gln Ile Tyr Gly Lys Glu Trp Gly Tyr Thr Gln Ala
    210                 215                 220

Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
            260                 265                 270

Met Thr Leu Thr Val Leu Asp Val Val Ala Leu Phe Pro Asn Tyr Asp
        275                 280                 285

Val Arg Met Tyr Pro Ile Lys Thr Thr Thr Glu Leu Thr Arg Thr Ile
    290                 295                 300
```

```
Tyr Thr Asp Pro Leu Gly Tyr Thr Lys Thr Gly Ser Ser Ser Thr Pro
305                 310                 315                 320

Pro Trp Cys Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
            340                 345                 350

Ser Lys Ser Ala Arg Ala Thr Pro Gln Ser Ala Asp Tyr Trp Ala Gly
        355                 360                 365

His Thr Ile Thr Tyr His Tyr Ser Gly Asp Asp Gly Gln Ala Val Ala
    370                 375                 380

Asn Tyr Gly Asp Arg Thr Asn Pro Val Ile Val Asn Arg Tyr Asn Phe
385                 390                 395                 400

Glu Gln Ala Asp Ile Tyr Arg Val Ser Ser Ser Val Ala Ser Ser Thr
                405                 410                 415

Thr Arg Gly Val Lys Leu Leu Thr Thr Lys Ala Ile Phe Asp Gly Ile
            420                 425                 430

Ser Thr Asn Asn Gly Leu Val Ser Tyr Met Tyr Glu Lys Leu Ser Asn
        435                 440                 445

Phe Phe Asn Glu Leu Lys Asp Thr Ile Thr Glu Leu Pro Val Gln Ile
    450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Ser Ser Gly Gly His Leu
                485                 490                 495

Ile Leu Gly Leu Ile Pro Val Leu Gly Trp Thr His Thr Ser Leu Thr
            500                 505                 510

Gln Thr Asn Gln Ile His Ser Asp Ser Ile Thr Gln Ile Pro Ala Val
        515                 520                 525

Lys Ala Asn Ser Leu Val Leu Val Leu Met Leu Leu Leu Glu Lys Gly
    530                 535                 540

Thr Gly Phe Thr Gly Gly Asp Leu Val Lys Phe Ser Thr Gly Phe Met
545                 550                 555                 560

Ser Thr Gly Ile Gln Phe Asn Leu Lys Ile Glu Glu Gly Lys Arg Tyr
                565                 570                 575

Arg Ile Arg Ile Arg Tyr Ala Ala Asp Val Asn Ala Thr Leu Ser Ala
            580                 585                 590

Leu Gly Leu Asn Asp Ala Phe Ile Asn Ile Glu Ser Thr Met Ser Gln
        595                 600                 605

Asp Thr Pro Leu Lys Tyr Asn Asp Phe Gln Tyr Ala Glu Ala Asp Lys
    610                 615                 620

Thr Val His Leu Tyr Asn Pro Arg Phe Ser Leu Tyr Leu Glu Asn Ser
625                 630                 635                 640

Asp Gln Ser Gly Lys Ser Ile Tyr Ile Asp Arg Ile Glu Phe Ile Pro
                645                 650                 655

Val Asp Asn Gly Ser Leu Asn
            660
```

<210> SEQ ID NO 9
<211> LENGTH: 1989
<212> TYPE: DNA
<213> ORGANISM: Artificial sequence
<220> FEATURE:
<223> OTHER INFORMATION: Cry8Ka3 (Synthetic Cry8Ka1 Variant) coding sequence -continued

<400> SEQUENCE: 9

```
atgagaccaa ataatctaaa tgaatatgaa attatagatg cgacaccttc tacatctgta     60
tctaatgatt ctaccagata cccttatgcg aatgagccca caaatgcgtt acaaaatatg    120
aattataagg attacttaag aatgtctgaa ggttacgata ataaatattt tgcaaatcct    180
gaagtgtttg ctgcaccagg tgggattaca actggaatta ctatagttac taaattactg    240
gggtggttag gacttccatt tgctggggaa acagggatgg ctcttaattt cattctaggt    300
ctattatggc caacatcagg aaacccgtgg gctgaactaa tgatattggt agaagaactc    360
ataaatcaaa aaatagaaga gactgtaaga aacaaagcac tagcggattt gggcaattca    420
ggtagagcct tacaatccta tttaaacgca tttgaagatt ggcaaaaaaa ccctaatatc    480
tttcggagta aagagttagt aaaagaaaga ttttcaaacg cggaacattc attacgtacc    540
gaaatgagtt cttttgccat aagaggattt gaaattcctc ttttagcaac atatgcacaa    600
gctgcgaatt tacatttatt tctaattaaa gatattcaaa tttatggaaa agaatgggga    660
tatactcaag ccgatattga cttattttat agagaacaag tagagtttac gaaagaatac    720
accgaacact gtattaatat ttataatgat ggtttaaatc aattaaaagg ttcgaatgct    780
aagcaatgga ttgcatttaa tcgcttccgt agagaaatga cattgacggt actggatgta    840
gttgcattat tcccgaacta tgatgtacgt atgtacccta taaaaacaac tacagagcta    900
acgagaacaa tttataccga tccacttggt tacacgaaaa cgggttctag tagtacacca    960
ccatggtgta attatggatc tagtttctca tatatagaaa gtgtagcgat tccagcccct   1020
agtctggtta agtggttaag tcagattgaa atttattcga aatccgcaag ggctacaccg   1080
caaagtgcgg attattgggc aggacataca ataacatatc actatagtgg agatgatggt   1140
caagcagtac ctaattatgg agatagaacg aatcctgtaa ttgtaaatcg ttataatttt   1200
gagcaggctg acatttatag agtttcatca tctgttgctt caagtacaac tagtggtgtt   1260
aaattattaa ctactaaggc tatatttgat ggcataagta caaacaatgg actagtgagt   1320
tacatgtatg agaagttgtc taacttcttt aacgaactca aggatacaat tacagagctt   1380
cctgttcaga tctccagtcc tcctacctac ggtgatgctg agcagtacag ccataggctt   1440
tcctacgttt ctaacgctcc aacagagtat ttttcgggcg gacattttaa ttttgggact   1500
aattccccag tacttggttg gacgcatact agtttaactc caaaccaaat cagataccat   1560
tctgactcaa ttactcaaat tccagctgtt aaagcaaata gtgttagttc ttatgttact   1620
gttgaaaagg gaacaggctt tacaggtgga gatttagtga aattctccac tggattcatg   1680
tctacaggaa tacagtttaa tttaaagata gaagaaggaa agcgttatcg tatccgtata   1740
cgatatgccg ctgatgttaa tgctactcta tctgcacttg gattaaatga tgcatttatt   1800
aacattgaat cgacaatgtc tcaagacaca ccattgaagt ataacgattt ccaatatgca   1860
gaagctgaca aaacagtgca tttatacaat cctcgttttt ctttatattt agaaaattca   1920
gatcaatccg ggaaaagtat ttatatagat cgaatcgaat tcatcccagt agataacggt   1980
tccttgaac                                                           1989
```

<210> SEQ ID NO 10
<211> LENGTH: 663
<212> TYPE: PRT
<213> ORGANISM: Artificial sequence
<220> FEATURE:
<223> OTHER INFORMATION: Cry8Ka4 (Synthetic Cry8Ka1 Variant)

<400> SEQUENCE: 10

-continued

```
Met Arg Pro Asn Asn Leu Asn Glu Tyr Glu Ile Ile Asp Ala Thr Pro
1               5                   10                  15

Ser Thr Ser Val Ser Asn Asp Ser Thr Arg Tyr Pro Tyr Ala Asn Glu
            20                  25                  30

Pro Thr Asn Ala Leu Gln Asn Met Asn Tyr Lys Asp Tyr Leu Arg Met
        35                  40                  45

Ser Glu Gly Tyr Asp Asn Lys Tyr Phe Ala Asn Pro Glu Val Phe Ala
    50                  55                  60

Ala Pro Gly Gly Ile Thr Thr Gly Ile Thr Ile Val Thr Lys Leu Leu
65                  70                  75                  80

Gly Trp Leu Gly Leu Pro Phe Ala Gly Glu Thr Gly Met Ala Leu Asn
                85                  90                  95

Phe Ile Leu Gly Leu Leu Trp Pro Thr Ser Gly Asn Pro Trp Ala Glu
            100                 105                 110

Leu Met Ile Leu Val Glu Glu Leu Ile Asn Gln Lys Ile Glu Glu Thr
        115                 120                 125

Val Arg Asn Lys Ala Leu Ala Asp Leu Gly Asn Ser Gly Arg Ala Leu
    130                 135                 140

Gln Ser Tyr Leu Asn Ala Phe Glu Asp Trp Gln Lys Asn Pro Asn Ile
145                 150                 155                 160

Phe Arg Ser Lys Glu Leu Val Lys Glu Arg Phe Ser Asn Ala Glu His
                165                 170                 175

Ser Leu Arg Thr Glu Met Ser Ser Phe Ala Ile Arg Gly Phe Glu Ile
            180                 185                 190

Pro Leu Leu Ala Thr Tyr Ala Gln Ala Ala Asn Leu His Leu Phe Leu
        195                 200                 205

Ile Lys Asp Ile Gln Ile Tyr Gly Lys Glu Trp Gly Tyr Thr Gln Ala
    210                 215                 220

Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
            260                 265                 270

Met Thr Leu Thr Val Leu Asp Val Val Ala Leu Phe Pro Asn Tyr Asp
        275                 280                 285

Val Arg Met Tyr Pro Ile Lys Thr Thr Thr Glu Leu Thr Arg Thr Ile
    290                 295                 300

Tyr Thr Asp Pro Leu Gly Tyr Thr Lys Thr Gly Ser Ser Ser Thr Pro
305                 310                 315                 320

Pro Trp Cys Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
            340                 345                 350

Ser Lys Ser Ala Arg Ala Thr Pro Gln Ser Ala Asp Tyr Trp Ala Gly
        355                 360                 365

His Thr Ile Thr Tyr His Tyr Ser Gly Asp Asp Gly Gln Ala Val Pro
    370                 375                 380

Asn Tyr Gly Asp Arg Thr Asn Pro Val Ile Val Asn Arg Tyr Asn Phe
385                 390                 395                 400

Glu Gln Ala Asp Ile Tyr Arg Val Ser Ser Ser Val Ala Ser Ser Thr
                405                 410                 415
```

-continued

```
Thr Ser Gly Val Lys Leu Leu Thr Thr Lys Ala Ile Phe Asp Gly Ile
            420                 425                 430

Ser Thr Asn Asn Gly Leu Val Ser Tyr Met Tyr Glu Lys Leu Ser Asn
        435                 440                 445

Phe Phe Asn Glu Leu Lys Asp Thr Ile Thr Glu Leu Pro Val Gln Ile
    450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Phe Ser Gly Gly His Phe
                485                 490                 495

Asn Phe Gly Thr Asn Ser Pro Val Leu Gly Trp Thr His Thr Ser Leu
            500                 505                 510

Thr Pro Asn Gln Ile Arg Tyr His Ser Asp Ser Ile Thr Gln Ile Pro
        515                 520                 525

Ala Val Lys Ala Asn Ser Val Ser Ser Tyr Val Thr Val Glu Lys Gly
    530                 535                 540

Thr Gly Phe Thr Gly Gly Asp Leu Val Lys Phe Ser Thr Gly Phe Met
545                 550                 555                 560

Ser Thr Gly Ile Gln Phe Asn Leu Lys Ile Glu Glu Gly Lys Arg Tyr
                565                 570                 575

Arg Ile Arg Ile Arg Tyr Ala Ala Asp Val Asn Ala Thr Leu Ser Ala
            580                 585                 590

Leu Gly Leu Asn Asp Ala Phe Ile Asn Ile Glu Ser Thr Met Ser Gln
        595                 600                 605

Asp Thr Pro Leu Lys Tyr Asn Asp Phe Gln Tyr Ala Glu Ala Asp Lys
    610                 615                 620

Thr Val His Leu Tyr Asn Pro Arg Phe Ser Leu Tyr Leu Glu Asn Ser
625                 630                 635                 640

Asp Gln Ser Gly Lys Ser Ile Tyr Ile Asp Arg Ile Glu Phe Ile Pro
                645                 650                 655

Val Asp Asn Gly Ser Leu Asn
            660
```

<210> SEQ ID NO 11
<211> LENGTH: 1947
<212> TYPE: DNA
<213> ORGANISM: Artificial sequence
<220> FEATURE:
<223> OTHER INFORMATION: Cry8Ka5 (Synthetic Cry8Ka1 Variant) coding sequence

<400> SEQUENCE: 11

```
atgcgacacc ttctacatct gtatctaatg attctaccag atacccttat gcgaatgaga      60

ccaaataatg cgttacaaaa tatgaattat aaggattact taagaatgtc tgaaggttac     120

gataataaat attttgcaaa tcctgaagtg tttgctgcac caggtgggat tacaactgga     180

attactatag ttactaaatt actggggtgg ttaggacttc catttgctgg ggaaacaggg     240

atggctctta atttcattct aggtctatta tggccaacat caggaaaccc gtgggctgaa     300

ctaatgatat tggtagaaga actcataaat caaaaaatag aagagactgt aagaaacaaa     360

gcactagcgg atttgggcaa ttcaggtaga gccttacaat cctatttaaa cgcatttgaa     420

gattggcaaa aaaaccctaa tatctttcgg agtaaagagt tagtaaaaga aagattttca     480

aacgcggaac attcattacg taccgaaatg agttcttttg ccataagagg atttgaaatt     540

cctcttttag caacatatgc acaagctgcg aatttacatt tatttctaat taaagatatt     600
```

-continued

```
caaatttatg gaaaagaatg gggatatact caagccgata ttgacttatt ctatagagaa    660

caagtagagt ttacgaaaga atacaccgaa cactgtatta atatttataa tgatggttta    720

aatcaattaa aggttcgaa tgctaagcaa tggattgcat ttaatcgctt ccgtagagaa    780

atgacattga cggtactgga tgtagttgca ttattcccga actatgatgt acgtatgtac    840

cctataaaaa caactacaga gctaacgaga acaatttata ccgatccact tggttacacg    900

aaaacgggtt ctagtagtac accaccatgg tgtaattatg gatctagttt ctcatatata    960

gaaagtgtag cgattccagc ccctagtctg gttaagtggt taagtcagat tgaaatttat   1020

tcgaaatccg caagggctac accgcaaagt gcggattatt gggcaggaca tacaataaca   1080

tatcactata gtggagatga tggtcaagca gtagctaatt atggagatag aacgaatcct   1140

gtaattgtaa atcgttataa ttttgagcag gctgacattt atagagtttc atcatctgtt   1200

gcttcaagta caactagtgg tgttaaatta ttaactacta aggctatatt tgatggcata   1260

agtacaaaca atggactagt gagttacatg tatgaaaaat tatcgaactt ttttaatgaa   1320

ctaaaagata caattacaga gctacctgtt cagatatcca gtcctcctac ctacggggat   1380

gctgaacagt acagtcatcg gctatcctat gtttctaatg ctccaacaga gtactcttcg   1440

ggcggacatt taattttggg actaatccca gtactgggtt ggacgcatac tagtttaact   1500

caaacaaatc agatacattc tgactcaatt actcaaattc cagctgttaa agcaaatagt   1560

gttagttctt atgttactgt tgaaaaggga acaggcttta caggtggaga tttagtgaaa   1620

ttctccactg gattcatgtc tacaggaata cagtttaatt taaagataga agaagggaag   1680

cgttatcgta tccgtatacg atatgccgct gatgttaatg ctactctatc tgcacttgga   1740

ttaaatgatg catttattaa cattgaatcg acaatgtctc aagacacacc attgaagtat   1800

aacgatttcc aatatgcaga agctgacaaa acagtgcatt tatacaatcc tcgtttttct   1860

ttatatttag aaaattcaga tcaatccggg aaaagtattt atatagatcg aatcgaattc   1920

atcccagtag ataacggttc cttgaac                                       1947
```

<210> SEQ ID NO 12
<211> LENGTH: 649
<212> TYPE: PRT
<213> ORGANISM: Artificial sequence
<220> FEATURE:
<223> OTHER INFORMATION: Cry8Ka5 (Synthetic Cry8Ka1 Variant)

<400> SEQUENCE: 12

```
Met Arg His Leu Leu His Leu Tyr Leu Met Ile Leu Pro Asp Thr Leu
1               5                   10                  15

Met Arg Met Arg Pro Asn Asn Ala Leu Gln Asn Met Asn Tyr Lys Asp
            20                  25                  30

Tyr Leu Arg Met Ser Glu Gly Tyr Asp Asn Lys Tyr Phe Ala Asn Pro
        35                  40                  45

Glu Val Phe Ala Ala Pro Gly Gly Ile Thr Thr Gly Ile Thr Ile Val
    50                  55                  60

Thr Lys Leu Leu Gly Trp Leu Gly Leu Pro Phe Ala Gly Glu Thr Gly
65                  70                  75                  80

Met Ala Leu Asn Phe Ile Leu Gly Leu Leu Trp Pro Thr Ser Gly Asn
                85                  90                  95

Pro Trp Ala Glu Leu Met Ile Leu Val Glu Glu Leu Ile Asn Gln Lys
            100                 105                 110

Ile Glu Glu Thr Val Arg Asn Lys Ala Leu Ala Asp Leu Gly Asn Ser
        115                 120                 125
```

```
Gly Arg Ala Leu Gln Ser Tyr Leu Asn Ala Phe Glu Asp Trp Gln Lys
    130                 135                 140

Asn Pro Asn Ile Phe Arg Ser Lys Glu Leu Val Lys Glu Arg Phe Ser
145                 150                 155                 160

Asn Ala Glu His Ser Leu Arg Thr Glu Met Ser Ser Phe Ala Ile Arg
                165                 170                 175

Gly Phe Glu Ile Pro Leu Leu Ala Thr Tyr Ala Gln Ala Ala Asn Leu
            180                 185                 190

His Leu Phe Leu Ile Lys Asp Ile Gln Ile Tyr Gly Lys Glu Trp Gly
        195                 200                 205

Tyr Thr Gln Ala Asp Ile Asp Leu Phe Tyr Arg Glu Gln Val Glu Phe
    210                 215                 220

Thr Lys Glu Tyr Thr Glu His Cys Ile Asn Ile Tyr Asn Asp Gly Leu
225                 230                 235                 240

Asn Gln Leu Lys Gly Ser Asn Ala Lys Gln Trp Ile Ala Phe Asn Arg
                245                 250                 255

Phe Arg Arg Glu Met Thr Leu Thr Val Leu Asp Val Val Ala Leu Phe
            260                 265                 270

Pro Asn Tyr Asp Val Arg Met Tyr Pro Ile Lys Thr Thr Thr Glu Leu
        275                 280                 285

Thr Arg Thr Ile Tyr Thr Asp Pro Leu Gly Tyr Thr Lys Thr Gly Ser
    290                 295                 300

Ser Ser Thr Pro Pro Trp Cys Asn Tyr Gly Ser Ser Phe Ser Tyr Ile
305                 310                 315                 320

Glu Ser Val Ala Ile Pro Ala Pro Ser Leu Val Lys Trp Leu Ser Gln
                325                 330                 335

Ile Glu Ile Tyr Ser Lys Ser Ala Arg Ala Thr Pro Gln Ser Ala Asp
            340                 345                 350

Tyr Trp Ala Gly His Thr Ile Thr Tyr His Tyr Ser Gly Asp Asp Gly
        355                 360                 365

Gln Ala Val Ala Asn Tyr Gly Asp Arg Thr Asn Pro Val Ile Val Asn
    370                 375                 380

Arg Tyr Asn Phe Glu Gln Ala Asp Ile Tyr Arg Val Ser Ser Ser Val
385                 390                 395                 400

Ala Ser Ser Thr Thr Ser Gly Val Lys Leu Leu Thr Thr Lys Ala Ile
                405                 410                 415

Phe Asp Gly Ile Ser Thr Asn Asn Gly Leu Val Ser Tyr Met Tyr Glu
            420                 425                 430

Lys Leu Ser Asn Phe Phe Asn Glu Leu Lys Asp Thr Ile Thr Glu Leu
        435                 440                 445

Pro Val Gln Ile Ser Ser Pro Pro Thr Tyr Gly Asp Ala Glu Gln Tyr
    450                 455                 460

Ser His Arg Leu Ser Tyr Val Ser Asn Ala Pro Thr Glu Tyr Ser Ser
465                 470                 475                 480

Gly Gly His Leu Ile Leu Gly Leu Ile Pro Val Leu Gly Trp Thr His
                485                 490                 495

Thr Ser Leu Thr Gln Thr Asn Gln Ile His Ser Asp Ser Ile Thr Gln
            500                 505                 510

Ile Pro Ala Val Lys Ala Asn Ser Val Ser Ser Tyr Val Thr Val Glu
        515                 520                 525

Lys Gly Thr Gly Phe Thr Gly Gly Asp Leu Val Lys Phe Ser Thr Gly
    530                 535                 540
```

```
Phe Met Ser Thr Gly Ile Gln Phe Asn Leu Lys Ile Glu Glu Gly Lys
545                 550                 555                 560

Arg Tyr Arg Ile Arg Ile Arg Tyr Ala Ala Asp Val Asn Ala Thr Leu
                565                 570                 575

Ser Ala Leu Gly Leu Asn Asp Ala Phe Ile Asn Ile Glu Ser Thr Met
            580                 585                 590

Ser Gln Asp Thr Pro Leu Lys Tyr Asn Asp Phe Gln Tyr Ala Glu Ala
        595                 600                 605

Asp Lys Thr Val His Leu Tyr Asn Pro Arg Phe Ser Leu Tyr Leu Glu
    610                 615                 620

Asn Ser Asp Gln Ser Gly Lys Ser Ile Tyr Ile Asp Arg Ile Glu Phe
625                 630                 635                 640

Ile Pro Val Asp Asn Gly Ser Leu Asn
                645
```

<210> SEQ ID NO 13
<211> LENGTH: 5753
<212> TYPE: DNA
<213> ORGANISM: Artificial sequence
<220> FEATURE:
<223> OTHER INFORMATION: pET101 D/TOPO vector
<220> FEATURE:
<221> NAME/KEY: promoter
<222> LOCATION: (209)..(225)
<223> OTHER INFORMATION: T7 promoter
<220> FEATURE:
<221> NAME/KEY: misc_feature
<222> LOCATION: (228)..(252)
<223> OTHER INFORMATION: lac operator (lacO)
<220> FEATURE:
<221> NAME/KEY: misc_feature
<222> LOCATION: (282)..(288)
<223> OTHER INFORMATION: Ribosome binding site (RBS)
<220> FEATURE:
<221> NAME/KEY: misc_feature
<222> LOCATION: (292)..(296)
<223> OTHER INFORMATION: Ribosome binding site (RBS)
<220> FEATURE:
<221> NAME/KEY: misc_feature
<222> LOCATION: (297)..(310)
<223> OTHER INFORMATION: TOPO cloning site (directional)
<220> FEATURE:
<221> NAME/KEY: misc_feature
<222> LOCATION: (333)..(374)
<223> OTHER INFORMATION: V5 epitope
<220> FEATURE:
<221> NAME/KEY: misc_feature
<222> LOCATION: (384)..(401)
<223> OTHER INFORMATION: Polyhistidine (6xHis) region
<220> FEATURE:
<221> NAME/KEY: terminator
<222> LOCATION: (416)..(544)
<220> FEATURE:
<221> NAME/KEY: primer_bind
<222> LOCATION: (455)..(474)
<220> FEATURE:
<221> NAME/KEY: promoter
<222> LOCATION: (845)..(943)
<223> OTHER INFORMATION: bla promoter
<220> FEATURE:
<221> NAME/KEY: misc_feature
<222> LOCATION: (944)..(1804)
<223> OTHER INFORMATION: Ampicillin (bla) resistance gene (ORF)
<220> FEATURE:
<221> NAME/KEY: rep_origin
<222> LOCATION: (1949)..(2622)
<223> OTHER INFORMATION: pBR322 origin
<220> FEATURE:
<221> NAME/KEY: misc_feature
<222> LOCATION: (2990)..(3181)
<223> OTHER INFORMATION: ROP ORF (complementary strand)
<220> FEATURE:

-continued

<221> NAME/KEY: misc_feature
<222> LOCATION: (4493)..(5584)
<223> OTHER INFORMATION: lacI ORF (complementary strand)

<400> SEQUENCE: 13
caaggagatg gcgcccaaca gtcccccggc cacggggcct gccaccatac ccacgccgaa 60
acaagcgctc atgagcccga agtggcgagc ccgatcttcc ccatcggtga tgtcggcgat 120
ataggcgcca gcaaccgcac ctgtggcgcc ggtgatgccg gccacgatgc gtccggcgta 180
gaggatcgag atctcgatcc cgcgaaatta atacgactca ctatagggga attgtgagcg 240
gataacaatt cccctctaga aataattttg tttaacttta agaaggaatt caggagccct 300
tcaccaaggg cgagctcaat tcgaagcttg aaggtaagcc tatccctaac cctctcctcg 360
gtctcgattc tacgcgtacc ggtcatcatc accatcacca ttgagtttga tccggctgct 420
aacaaagccc gaaaggaagc tgagttggct gctgccaccg ctgagcaata actagcataa 480
ccccttgggg cctctaaacg ggtcttgagg ggttttttgc tgaaaggagg aactatatcc 540
ggatatcccg caagaggccc ggcagtaccg gcataaccaa gcctatgcct acagcatcca 600
gggtgacggt gccgaggatg acgatgagcg cattgttaga tttcatacac ggtgcctgac 660
tgcgttagca atttaactgt gataaactac cgcattaaag cttatcgatg ataagctgtc 720
aaacatgaga attaattctt gaagacgaaa gggcctcgtg atacgcctat ttttataggt 780
taatgtcatg ataataatgg tttcttagac gtcaggtggc acttttcggg gaaatgtgcg 840
cggaacccct atttgtttat ttttctaaat acattcaaat atgtatccgc tcatgagaca 900
ataaccctga taaatgcttc aataatattg aaaaaggaag agtatgagta ttcaacattt 960
ccgtgtcgcc cttattccct tttttgcggc attttgcctt cctgtttttg ctcacccaga 1020
aacgctggtg aaagtaaaag atgctgaaga tcagttgggt gcacgagtgg gttacatcga 1080
actggatctc aacagcggta agatccttga gagttttcgc cccgaagaac gttttccaat 1140
gatgagcact tttaaagttc tgctatgtgg cgcggtatta tcccgtgttg acgccgggca 1200
agagcaactc ggtcgccgca tacactattc tcagaatgac ttggttgagt actcaccagt 1260
cacagaaaag catcttacgg atggcatgac agtaagagaa ttatgcagtg ctgccataac 1320
catgagtgat aacactgcgg ccaacttact tctgacaacg atcggaggac cgaaggagct 1380
aaccgctttt ttgcacaaca tgggggatca tgtaactcgc cttgatcgtt gggaaccgga 1440
gctgaatgaa gccataccaa acgacgagcg tgacaccacg atgcctgcag caatggcaac 1500
aacgttgcgc aaactattaa ctggcgaact acttactcta gcttcccggc aacaattaat 1560
agactggatg gaggcggata aagttgcagg accacttctg cgctcggccc ttccggctgg 1620
ctggtttatt gctgataaat ctggagccgg tgagcgtggg tctcgcggta tcattgcagc 1680
actggggcca gatggtaagc cctcccgtat cgtagttatc tacacgacgg ggagtcaggc 1740
aactatggat gaacgaaata gacagatcgc tgagataggt gcctcactga ttaagcattg 1800
gtaactgtca gaccaagttt actcatatat actttagatt gatttaaaac ttcattttta 1860
atttaaaagg atctaggtga agatcctttt tgataatctc atgaccaaaa tcccttaacg 1920
tgagttttcg ttccactgag cgtcagaccc cgtagaaaag atcaaaggat cttcttgaga 1980 tcctttttt ctgcgcgtaa tctgctgctt gcaaacaaaa aaaccaccgc taccagcggt 2040
ggtttgtttg ccggatcaag agctaccaac tctttttccg aaggtaactg gcttcagcag 2100
agcgcagata ccaaatactg tccttctagt gtagccgtag ttaggccacc acttcaagaa 2160
ctctgtagca ccgcctacat acctcgctct gctaatcctg ttaccagtgg ctgctgccag 2220

-continued tggcgataag tcgtgtctta ccgggttgga ctcaagacga tagttaccgg ataaggcgca 2280
gcggtcgggc tgaacggggg gttcgtgcac acagcccagc ttggagcgaa cgacctacac 2340
cgaactgaga tacctacagc gtgagctatg agaaagcgcc acgcttcccg aagggagaaa 2400
ggcggacagg tatccggtaa gcggcagggt cggaacagga gagcgcacga gggagcttcc 2460
agggggaaac gcctggtatc tttatagtcc tgtcgggttt cgccacctct gacttgagcg 2520
tcgatttttg tgatgctcgt caggggggcg gagcctatgg aaaaacgcca gcaacgcggc 2580
ctttttacgg ttcctggcct tttgctggcc ttttgctcac atgttctttc ctgcgttatc 2640
ccctgattct gtggataacc gtattaccgc ctttgagtga gctgataccg ctcgccgcag 2700
ccgaacgacc gagcgcagcg agtcagtgag cgaggaagcg gaagagcgcc tgatgcggta 2760
ttttctcctt acgcatctgt gcggtatttc acaccgcaat ggtgcactct cagtacaatc 2820
tgctctgatg ccgcatagtt aagccagtat acactccgct atcgctacgt gactgggtca 2880
tggctgcgcc ccgacacccg ccaacacccg ctgacgcgcc ctgacgggct tgtctgctcc 2940
cggcatccgc ttacagacaa gctgtgaccg tctccgggag ctgcatgtgt cagaggtttt 3000
caccgtcatc accgaaacgc gcgaggcagc tgcggtaaag ctcatcagcg tggtcgtgaa 3060
gcgattcaca gatgtctgcc tgttcatccg cgtccagctc gttgagtttc tccagaagcg 3120
ttaatgtctg gcttctgata aagcgggcca tgttaagggc ggtttttcc tgtttggtca 3180
ctgatgcctc cgtgtaaggg ggatttctgt tcatgggggt aatgataccg atgaaacgag 3240
agaggatgct cacgatacgg gttactgatg atgaacatgc ccggttactg gaacgttgtg 3300
agggtaaaca actggcggta tggatgcggc gggaccagag aaaaatcact cagggtcaat 3360
gccagcgctt cgttaataca gatgtaggtg ttccacaggg tagccagcag catcctgcga 3420
tgcagatccg gaacataatg gtgcagggcg ctgacttccg cgtttccaga ctttacgaaa 3480
cacggaaacc gaagaccatt catgttgttg ctcaggtcgc agacgttttg cagcagcagt 3540
cgcttcacgt tcgctcgcgt atcggtgatt cattctgcta accagtaagg caaccccgcc 3600
agcctagccg ggtcctcaac gacaggagca cgatcatgcg cacccgtggc caggacccaa 3660
cgctgcccga gatgcgccgc gtgcggctgc tggagatggc ggacgcgatg gatatgttct 3720
gccaagggtt ggtttgcgca ttcacagttc tccgcaagaa ttgattggct ccaattcttg 3780
gagtggtgaa tccgttagcg aggtgccgcc ggcttccatt caggtcgagg tggcccggct 3840
ccatgcaccg cgacgcaacg cggggaggca gacaaggtat agggcggcgc ctacaatcca 3900
tgccaacccg ttccatgtgc tcgccgaggc ggcataaatc gccgtgacga tcagcggtcc 3960
aatgatcgaa gttaggctgg taagagccgc gagcgatcct tgaagctgtc cctgatggtc 4020
gtcatctacc tgcctggaca gcatggcctg caacgcgggc atcccgatgc cgccggaagc 4080
gagaagaatc ataatgggga aggccatcca gcctcgcgtc gcgaacgcca gcaagacgta 4140
gcccagcgcg tcggccgcca tgccggcgat aatggcctgc ttctcgccga aacgtttggt 4200
ggcgggacca gtgacgaagg cttgagcgag ggcgtgcaag attccgaata ccgcaagcga 4260
caggccgatc atcgtcgcgc tccagcgaaa gcggtcctcg ccgaaaatga cccagagcgc 4320
tgccggcacc tgtcctacga gttgcatgat aaagaagaca gtcataagtg cggcgacgat 4380
agtcatgccc cgcgcccacc ggaaggagct gactgggttg aaggctctca agggcatcgg 4440
tcgagatccc ggtgcctaat gagtgagcta acttacatta attgcgttgc gctcactgcc 4500
cgctttccag tcgggaaacc tgtcgtgcca gctgcattaa tgaatcggcc aacgcgcggg 4560

-continued

```
gagaggcggt ttgcgtattg ggcgccaggg tggtttttct tttcaccagt gagacgggca   4620

acagctgatt gcccttcacc gcctggccct gagagagttg cagcaagcgg tccacgctgg   4680

tttgccccag caggcgaaaa tcctgtttga tggtggttaa cggcgggata taacatgagc   4740

tgtcttcggt atcgtcgtat cccactaccg agatatccgc accaacgcgc agcccggact   4800

cggtaatggc gcgcattgcg cccagcgcca tctgatcgtt ggcaaccagc atcgcagtgg   4860

gaacgatgcc ctcattcagc atttgcatgg tttgttgaaa accggacatg gcactccagt   4920

cgccttcccg ttccgctatc ggctgaattt gattgcgagt gagatattta tgccagccag   4980

ccagacgcag acgcgccgag acagaactta atgggcccgc taacagcgcg atttgctggt   5040

gacccaatgc gaccagatgc tccacgccca gtcgcgtacc gtcttcatgg gagaaaataa   5100

tactgttgat gggtgtctgg tcagagacat caagaaataa cgccggaaca ttagtgcagg   5160

cagcttccac agcaatggca tcctggtcat ccagcggata gttaatgatc agcccactga   5220

cgcgttgcgc gagaagattg tgcaccgccg ctttacaggc ttcgacgccg cttcgttcta   5280

ccatcgacac caccacgctg gcacccagtt gatcggcgcg agatttaatc gccgcgacaa   5340

tttgcgacgg cgcgtgcagg gccagactgg aggtggcaac gccaatcagc aacgactgtt   5400

tgcccgccag ttgttgtgcc acgcggttgg gaatgtaatt cagctccgcc atcgccgctt   5460

ccactttttc ccgcgttttc gcagaaacgt ggctggcctg gttcaccacg cgggaaacgg   5520

tctgataaga gacaccggca tactctgcga catcgtataa cgttactggt ttcacattca   5580

ccaccctgaa ttgactctct tccgggcgct atcatgccat accgcgaaag gttttgcgcc   5640

attcgatggt gtccgggatc tcgacgctct ccccttatgcg actcctgcat taggaagcag   5700

cccagtagta ggttgaggcc gttgagcacc gccgccgcaa ggaatggtgc atg          5753
```

<210> SEQ ID NO 14
<211> LENGTH: 13
<212> TYPE: DNA
<213> ORGANISM: Artificial Sequence
<220> FEATURE:
<223> OTHER INFORMATION: SFiI restriction site
<220> FEATURE:
<221> NAME/KEY: misc_feature
<222> LOCATION: (5)..(9)
<223> OTHER INFORMATION: n is a, c, g, or t

<400> SEQUENCE: 14

```
ggccnnnnng gcc                                                        13
```

<210> SEQ ID NO 15
<211> LENGTH: 30
<212> TYPE: DNA
<213> ORGANISM: Artificial sequence
<220> FEATURE:
<223> OTHER INFORMATION: 5' oligonucleotide : SfiI F primer

<400> SEQUENCE: 15

```
cccggcccag gcggccgacc acgcgtatcg                                      30
```

<210> SEQ ID NO 16
<211> LENGTH: 31
<212> TYPE: DNA
<213> ORGANISM: Artificial sequence
<220> FEATURE:
<223> OTHER INFORMATION: 3' oligonucleotide : SfiI R primer

<400> SEQUENCE: 16

```
cccggccggc ctggccgttc aaggaaccgt t                                    31
```

<210> SEQ ID NO 17
<211> LENGTH: 2022
<212> TYPE: DNA
<213> ORGANISM: Bacillus thuringiensis
<220> FEATURE:
<221> NAME/KEY: misc_feature
<223> OTHER INFORMATION: Cry8Bb1_Seq15

<400> SEQUENCE: 17

```
atgagtccaa ataatcaaaa tgaatatgaa attatagatg cgacaccttc tacttctgta     60
tccaatgatt ctaacagata cccttttgcg aatgagccaa caaatgcgct acaaaatatg    120
gattataaag attatttaaa aatgtctgcg ggaaatgcta gtgaataccc tggttcacct    180
gaagtacttg ttagcggaca agatgcagct aaggccgcaa ttgatatagt aggtaaatta    240
ctatcaggtt taggggtccc atttgttggg ccgatagtga gtctttatac tcaacttatt    300
gatattctgt ggccttcagg ggaaaagagt caatgggaaa tttttatgga acaagtagaa    360
gaactcatta atcaaaaaat agcagaatat gcaaggaata aagcgctttc ggaattagaa    420
ggattaggta ataattacca attatatcta actgcgcttg aagaatggga agaaaatcca    480
tttcgacgag gttttcgacg aggtgcctta cgagatgtgc gaaatcgatt tgaaatcctg    540
gatagtttat ttacgcaata tatgccatct tttagagtga caaattttga agtaccattc    600
cttactgtat atgcaatggc agccaacctt catttactgt tattaaagga cgcgtcaatt    660
tttggagaag aatggggatg gtcaacaact actattaata actattatga tcgtcaaatg    720
aaacttactg cagaatattc tgatcactgt gtaaagtggt atgaaactgg tttagcaaaa    780
ttaaaaggca cgagcgctaa acaatgggtt gactataacc aattccgtag agaaatgaca    840
ctggcggttt tagatgttgt tgcattattc ccaaattatg acacacgcac gtacccaatg    900
gaaacgaaag cacaactaac aagggaagta tatacagatc cactgggcgc ggtaaacgtg    960
tcttcaattg gttcctggta tgacaaagca ccttctttcg gagtgataga atcatccgtt   1020
attcgaccac cccatgtatt tgattatata acgggactca cagtgtatac acaatcaaga   1080
agcatttctt ccgctcgcta tataagacat tgggctggtc atcaaataag ctaccatcgt   1140
gtcagtaggg gtagtaatct tcaacaaatg tatggaacta atcaaaatct acacagcact   1200
agtacctttg attttacgaa ttatgatatt tacaagactc tatcaaagga tgcagtactc   1260
cttgatattg tttaccctgg ttatacgtat atattttttg gaatgccaga agtcgagttt   1320
ttcatggtaa accaattgaa taataccaga aagacgttaa agtataatcc agtttccaaa   1380
gatattatag cgagtacaag agattcggaa ttagaattac ctccagaaac ttcagatcaa   1440
ccaaattatg agtcatatag ccatagatta tgtcatatca caagtattcc cgcgacgggt   1500
aacactaccg gattagtacc tgtattttct tggacacatc gaagtgcaga tttaaacaat   1560
acaatatatt cagataaaat cactcaaatt ccggccgtta aatgttggga taatttaccg   1620
tttgttccag tggtaaaagg accaggacat acaggagggg atttattaca gtataataga   1680
agtactggtt ctgtaggaac cttatttcta gctcgatatg gcctagcatt agaaaaagca   1740
gggaaatatc gtgtaagact gagatatgct actgatgcag atattgtatt gcatgtaaac   1800
gatgctcaga ttcagatgcc aaaaaacaatg aacccaggtg aggatctgac atctaaaact   1860
tttaaagttg cagatgctat cacaacagta aatttagcaa cagatagttc ggtagcagtg   1920
aaacataatt taggtgaaga ccctaattca acattatctg gtatagttta cgttgaccga   1980
atcgaattca tcccagtaga tgagacatat gaagcggaat aa                      2022
```

<210> SEQ ID NO 18
<211> LENGTH: 2022
<212> TYPE: DNA
<213> ORGANISM: Bacillus thuringiensis
<220> FEATURE:
<221> NAME/KEY: misc_feature
<223> OTHER INFORMATION: Cry8Bb1_Seq17

<400> SEQUENCE: 18
atgagtccaa ataatcaaaa tgaatatgaa attatagatg cgacaccttc tacttctgta 60
tccaatgatt ctaacagata cccttttgcg aatgagccaa caaatgcgct acaaaatatg 120
gattataaag attatttaaa aatgtctgcg ggaaatgcta gtgaataccc tggttcacct 180
gaagtacttg ttagcggaca agatgcagct aaggccgcaa ttgatatagt aggtaaatta 240
ctatcaggtt taggggtccc atttgttggg ccgatagtga gtctttatac tcaacttatt 300
gatattctgt ggccttcagg ggaaaagagt caatgggaaa tttttatgga acaagtagaa 360
gaactcatta atcaaaaaat agcagaatat gcaaggaata aagcgctttc ggaattagaa 420
ggattaggta ataattacca attatatcta actgcgcttg aagaatggga agaaaatcca 480
tttcgacgag gttttcgacg aggtgcctta cgagatgtgc gaaatcgatt tgaaatcctg 540
gatagtttat ttacgcaata tatgccatct tttagagtga caaattttga agtaccattc 600
cttactgtat atgcaatggc agccaacctt catttactgt tattaaagga cgcgtcaatt 660
tttggagaag aatggggatg gtcaacaact actattaata actattatga tcgtcaaatg 720
aaacttactg cagaatattc tgatcactgt gtaaagtggt atgaaactgg tttagcaaaa 780
ttaaaaggca cgagcgctaa acaatgggtt gactataacc aattccgtag agaaatgaca 840
ctggcggttt tagatgttgt tgcattattc ccaaattatg acacacgcac gtacccaatg 900
gaaacgaaag cacaactaac aagggaagta tatacagatc cactgggcgc ggtaaacgtg 960
tcttcaattg gttcctggta tgacaaagca ccttctttcg gagtgataga atcatccgtt 1020
attcgaccac cccatgtatt tgattatata acgggactca cagtgtatac acaatcaaga 1080
agcatttctt ccgctcgcta tataagacat tgggctggtc atcaaataag ctaccatcgt 1140
gtcagtaggg gtagtaatct tcaacaaatg tatggaacta atcaaaatct acacagcact 1200
agtacctttg attttacgaa ttatgatatt tacaagactc tatcaaagga tgcagtactc 1260
cttgatattg tttaccctgg ttatacgtat atattttttg gaatgccaga agtcgagttt 1320
ttcatggtaa accaattgaa taataccaga aagacgttaa agtataatcc agtttccaaa 1380
gatattatag cgagtacaag agattcggaa ttagaattac ctccagaaac ttcagatcaa 1440
ccaaattatg agtcatatag ccatagatta tgtcatatca caagtattcc cgcgacgggt 1500
aacactaccg gattagtacc tgtattttct tggacacatc gaagtgcaga tttaaacaat 1560
acaatatatt cagataaaat cactcaaatt ccggccgtta aatgttggga taatttaccg 1620
tttgttccag tggtaaaagg accaggacat acaggagggg atttattaca gtataataga 1680
agtactggtt ctgtaggaac cttatttcta gctcgatatg gcctagcatt agaaaaagca 1740
gggaaatatc gtgtaagact gagatatgct actgatgcag atattgtatt gcatgtaaac 1800
gatgctcaga ttcagatgcc aaaaaacaatg aacccaggtg aggatctgac atctaaaact 1860
tttaaagttg cagatgctat cacaacagta aatttagcaa cagatagttc ggtagcagtg 1920
aaacataatg taggtgaaga ccctaattca acattatctg gtatagttta cgttgaccga 1980
atcgaattca tcccagtaga tgagacatat gaagcggaat aa 2022

<210> SEQ ID NO 19
<211> LENGTH: 2068
<212> TYPE: DNA
<213> ORGANISM: Bacillus thuringiensis
<220> FEATURE:
<221> NAME/KEY: misc_feature
<223> OTHER INFORMATION: Cry8AB00.1_Seq_5

<400> SEQUENCE: 19

```
atgagtccaa ataatcaaaa tgaatatgaa attatagatg cgacaccttc tacttctgta     60
tccaatgatt ctaacagata cccttttgcg aatgagccaa caaatgcgct acaaaatatg    120
gattataaag attatttaaa aatgtctgcg ggaaatgcta gtgaataccc tggttcacct    180
gaagtacttg ttagcggaca agatgcagct aaggccgcaa ttgatatagt aggtaaatta    240
ctatcaggtt taggggtccc atttgttggg ccgatagtga gtctttatac tcaacttatt    300
gatattctgt ggccttcagg ggaaaagagt caatgggaaa tttttatgga acaagtagaa    360
gaactcatta atcaaaaaat agcagaatat gcaaggaata aagcgctttc ggaattagaa    420
ggattaggta ataattacca attatatcta actgcgcttg aagaatggga agaaaatcca    480
aatggttcaa gagccttacg agatgtgcga aatcgatttg aaatcctgga tagtttattt    540
acgcaatata tgccatcttt tagagtgaca aattttgaag taccattcct tactgtatat    600
gcaatggcag ccaaccttca tttactgtta ttaaaggacg cgtcaatttt tggagaagaa    660
tggggatggt caacaactac tattaataac tattatgatc gtcaaatgaa acttactgca    720
gaatattctg atcactgtgt aaagtggtat gaaactggtt tagcaaaatt aaaaggcacg    780
agcgctaaac aatgggttga ctataaccaa ttccgtagag aaatgacact ggcggtttta    840
gatgttgttg cattattccc aaattatgac acacgcacgt acccaatgga aacgaaagca    900
caactaacaa gggaagtata tacagatcca ctgggcgcgg taaacgtgtc ttcaattggt    960
tcctggtatg acaaagcacc ttctttcgga gtgatagaat catccgttat tcgaccaccc   1020
catgtatttg attatataac gggactcaca gtgtatacac aatcaagaag catttcttcc   1080
gctcgctata taagacattg ggctggtcat caaataagct accatcgtgt cagtaggggt   1140
agtaatcttc aacaaatgta tggaactaat caaaatctac acagcactag tacctttgat   1200
tttacgaatt atgatattta caagactcta tcaaaggatg cagtactcct tgatattgtt   1260
taccctggtt atacgtatat attttttgga atgccagaag tcgagttttt catggtaaac   1320
caattgaata ataccagaaa gacgttaaag tataatccag tttccaaaga tattatagcg   1380
agtacaagag attcggaatt agaattacct ccagaaactt cagatcaacc aaattatgag   1440
tcatatagcc atagattatg tcatatcaca agtattcccg cgacgggtaa cactaccgga   1500
ttagtacctg tattttcttg gacacatcga agtgcagatt taaacaatac aatatattca   1560
gataaaatca ctcaaattcc ggccgttaaa tgttgggata atttaccgtt tgttccagtg   1620
gtaaaaggac caggacatac aggaggggat ttattacagt ataatagaag tactggttct   1680
gtaggaacct tatttctagc tcgatatggc ctagcattag aaaaagcagg gaaatatcgt   1740
gtaagactga gatatgctac tgatgcagat attgtattgc atgtaaacga tgctcagatt   1800
cagatgccaa aaacaatgaa cccaggtgag gatctgacat ctaaaacttt taaagttgca   1860
gatgctatca caacattaaa tttagcaaca gatagttcgc tagcattgaa acataattta   1920
ggtgaagacc ctaattcaac attatctggt atagtttacg ttgaccgaat cgaattcatc   1980
ccagtagatg agacatatga agcggaacaa gatttagaag cagcgaagaa agcagtgaat   2040
```

gccttgttta cgaatacaaa agatggct 2068

<210> SEQ ID NO 20
<211> LENGTH: 2053
<212> TYPE: DNA
<213> ORGANISM: Bacillus thuringiensis
<220> FEATURE:
<221> NAME/KEY: misc_feature
<223> OTHER INFORMATION: 50C_b_

<400> SEQUENCE: 20
atgagtccaa ataatcaaaa tgaatatgaa attatagatg cgacaccttc tacatctgta 60
tccaatgatt ctaacagata cccttttgcg aatgagccaa caaatgcgct acaaaatatg 120
gattataaag attatttaaa aatgtctgcg ggaaatgtta gtgaataccc tggttcacct 180
gaggtatttc taagcgagca agatgcagtt aaggccgcaa ttgatatagt aggtaaatta 240
ctaacaggtt taggggttcc atttgttggg ccgatagtga gtctttatac tcaacttatt 300
gatattctgt ggccttcaaa acaaaagagt caatgggaaa tttttatgga acaagtagaa 360
gaactcatta atcaaaaaat agcagaatat gcaaggaata aagcgctttc ggaattggaa 420
gggctaggga ataattacca attatatcta actgcgcttg aagagtggaa agaaaatcca 480
aatggttcaa gagccttacg agatgttcga aatcgatttg aaatcctgga tagtttattt 540
acgcaatata tgccatcttt tcgagtgaca aattttgaag taccattcct tacagtatat 600
acaatggcag caaacctaca tttactttta ttaagggacg catcaatttt tggagaagaa 660
tggggattgt ctacaagcac tattaataac tactataatc gtcaaatgaa acttactgca 720
gaatattctg accactgtgt aaagtggtat gaaactggtt tagcaaaatt aaaaggctcg 780
agcgctaaac aatggattga ctataaccaa ttccgtagag aaatgacatt gacggtgtta 840
gacgttgttg cattattttc aaactatgat acgcgtacgt atccactggc aacaacagct 900
cagcttacaa gggaagtata tacagatcca cttggcgcgg tagatgtgcc taatattggc 960
tcctggtatg acaaagcacc ttctttctca gaaatagaaa aagcggctat tcgtccacct 1020
catgtgtttg attatataac gggactcaca gtttatacaa aaaaacgtag cttcacttct 1080
gatcgttata tgagatattg ggctggtcat caaataagct ataagcatat cggtacgagt 1140
agtacccttta cacagatgta tggaaccaat caaaatttac aaagtactag caattttgat 1200
tttacgaatt acgatattta caagacttta tcaaatggtg cagtactcct tgatatagtt 1260
taccctggtt atacgtatac attttttgga atgccagaaa ccgagttttt tatggtaaat 1320
caattgaata ataccagaaa gacgttaacg tataaaccag cttccaaaga tattatagat 1380
cggacaagag attcggaatt agaattgcct ccagaaactt caggtcaacc aaattacgag 1440
tcatatagcc atagattagg tcatattaca tttatttact ccagttcaac tagcacgtat 1500
gtacctgtat tttcttggac acatcggagt gcagatctaa caaatacagt taaaagtggc 1560
gaaatcaccc aaataccagg gggcaagtct agcaccatag gcagaaatac ttatataata 1620
aaagggcgtg gttatacagg gggagactta gtggctttaa cggaccgcat cggaagttgt 1680
gagtttcaga tgatctttcc agagtctcaa cgattccgta ttcggattcg ttacgcttct 1740
aatgaaacta gttatattag tttatacgga ctaaaccaaa gcggaacttt aaaattcaac 1800
cagacatatt ctaataaaaa tgaaaatgat ttaacatata atgatttcaa atatatagaa 1860
tatccaagag tcatttcagt aaatgcttct tcaaacatac agaggttatc tataggtata 1920
caaacgaata caaatttatt tattttagac cgaatcgaat tcatcccagt agatgagaca 1980

```
tatgaagcgg aaacggattt agaagcggca aagaaagcag tgaatgcctt gtttacgaat   2040

acaaaagatg gat                                                       2053
```

<210> SEQ ID NO 21
<211> LENGTH: 2107
<212> TYPE: DNA
<213> ORGANISM: Bacillus thuringiensis
<220> FEATURE:
<221> NAME/KEY: misc_feature
<223> OTHER INFORMATION: Cry8AB00.1_Seq_3

<400> SEQUENCE: 21

```
atgagtccaa ataatcaaaa tgaatatgaa attatagatg cgacaccttc tacttctgta     60

tccaatgatt ctaacagata cccttttgcg aatgagccaa caaatgcatt acaaaatatg    120

aattataagg attatttaag aatgtctgag ggtatgata gtgaatattc tggttcacct     180

ggagcacttg ttagtggaaa acaagcaatt aaggttggaa tcgatattgt cggcaacata    240

ttaggtaagt taggagttcc gtttgctagt cagatagtaa gtttttataa ttttattctc    300

gatcagctat ggccatcaaa ttctgtgagt gtatgggaac agattatgac gctagtggaa    360

gaacttgtag atcaaaaaat aacagaatat gcaagaaata aagcactcgc tgaattaaaa    420

ggattaggag atgctttggg tgtatatcag caatcacttg aagcttggtt ggaaaatcgc    480

aatgacacga gagctagaag tgttgtttct aatcaattta tagccttaga actggatttt    540

gttggagcaa ttccatcctt tgcagtatcc gggcaggaag taccattatt agcagtatat    600

gcacaggctg tgaacatgca cttattgtta ctaagagacg cttctatttt tggagaagag    660

tggggattca catcatctga aatttccact tactacaacc gtcaagtgca actcacttct    720

caatattccg attattgtgt gaagtggtac gataccggtt tacagaaatt aaaaggtacg    780

agcgctgaga gttggctgga gtatcatcaa ttccgcagag agatgacttt catggtatta    840

gatttggttg cattatttcc aaactacgat acacacacgt atccacttga aacaaaggct    900

caacttacac gagaagtata tacggatccg atcgccttta atctttctgg ggcagcgggt    960

ttttgtagcc cttggtcaaa gtatactggt atttcctttt cggagattga aaatgatgta   1020

attcgtccgc ctcatttatt taatctactc agaagtttag agattaatac agttaggggg   1080

acaattttag gtaatactaa agattaccta aactattggt caggtcattc tctacaatat   1140

aattttatag gtaagacaat agtcagggaa agtaattatg gatatcttac ttcagaaaaa   1200

actaggattg aattagacac tagagatatt tttgaaatta attcaactgc cgcaagctta   1260

gcgaattact atcaagagac ttatggtgtg ccagaatcta ggctccattt ggtgagatgg   1320

gctagcccat attatacatc atctcatctt tattctaaaa cacatacaac tggagaaggt   1380

tgtacacaag tttatgaatc aagtgaggaa atacctgtag acagaaccgt accgataaat   1440

gaaggttata gtcacagact atcgtatgtc accgctctct tttccagaa aattattaat    1500

actttttata gaaatggaac tctacctgtc tttgtttgga cacatcgaag tgcagatctt   1560

acaaatacaa tttatccaga tgtaattact caaataccag tggtaaaggc ctatgaattg   1620

ggtagctcca tcttaccaga tagtccatca cctactattg tgccagggcc tggatttaca   1680

ggggggggata taatacaatt actggcgaat acaaaaggta tagcaaatat gaattttgaa  1740

attcaagaca ttaataaaga atatattatg agaattcggt atgcttccgc tgcaaatcct   1800

gaattcaata tagctgttgg tactagtgga gaaagagtta gtactagtgc tcaaaaaact   1860

atgaatccag ggatatttt aacatttaat aaatttaatt acgcaacttt ccctcccatt    1920
```

aaatttaatt caactaaaat ttcgataatg ttaacagcaa gattggctgc ttttgcaagc 1980
acattattgg aaacctatat agatagaatc gaattcatcc cagtagatga aacatacgag 2040
gcggagacag atttagaaac ggcgaagaaa gcagtgaatg ccttgtttac gaatacaaaa 2100
gatggct 2107

<210> SEQ ID NO 22
<211> LENGTH: 1992
<212> TYPE: DNA
<213> ORGANISM: Bacillus thuringiensis
<220> FEATURE:
<221> NAME/KEY: misc_feature
<223> OTHER INFORMATION: Cry8Ka1

<400> SEQUENCE: 22
atgagtccaa ataatctaaa tgaatatgaa attatagatg cgacaccttc tacatctgta 60
tctaatgatt ctaccagata cccttatgcg aatgagccca caaatgcgtt acaaaatatg 120
aattataagg attatttaag aatgtctgaa ggttacgata ataaatattt tgcaaatcct 180
gaagtgtttg ctgcaccagg tgggattaca actggaatta ctatagttac taaattactg 240
gggtggttag gacttccatt tgctggggaa acagggatgg ctcttaattt cattctaggt 300
ctattatggc caacatcagg aaacccgtgg gctgaactaa tgatattggt agaagaactc 360
ataaatcaaa aaatagaaga gactgtaaga aacaaagcac tagcggattt gggcaattca 420
ggtagagcct tacgatccta tttaaacgca tttgaagatt ggcaaaaaaa ccctaatatc 480
tttcggagta aagagttagt aaaagaaaga ttttcaaacg cggaacattc attacgtacc 540
gaaatgagtt cttttgccat aagaggattt gaaattcctc ttttagcaac atatgcacaa 600
gctgcgaatt tacatttatt tctaattaaa gatattcaaa tttatggaaa agaatgggga 660
tatactcaag ccgatattga cttattttat agagaacaag tagagtttac gaaagaatac 720
accgaacact gtattaatat ttataatgat ggtttaaatc aattaaaagg ttcgaatgct 780
aagcaatgga ttgcatttaa tcgcttccgt agagaaatga cattgacggt actggatgta 840
gttgcattat tcccgaacta tgatgtacgt atgtacccta taaaaacaac tacagagcta 900
acgagaacaa tttataccga tccacttggt tacacgaaaa cgggttctag tagtacacca 960
ccatggtata attatggatc tagtttctca tatatagaaa gtgtagcgat tccagcccct 1020
agtctggtta agtggttaag tcagattgaa atttattcga aatccgcaag ggctacaccg 1080
caaagtgcgg attattgggc aggacataca ataacatatc actatagtgg agatgatggt 1140
caagcagtac ctaattatgg agatagaacg aatcctgtaa ttgtaaatcg ttataatttt 1200
gagcaggctg acatttatag agtttcatca tctgttgctt caagtacaac tagtggtgtt 1260
aaattattaa ctactaaggc tatatttgat ggcataagta caaacaatgg actagtgagt 1320
tacatgtatg aaaaattatc gaactttttt aatgaactaa aagatacaat tacagagcta 1380
cctgttcaga tatccagtcc tcctacctac ggggatgctg aacagtacag tcatcggcta 1440
tcctatgttt ctaatgctcc aacagagtac tcttcgggcg gacatttaat tttgggacta 1500
atcccagtac tgggttggac gcatactagt ttaactcaaa caaatcagat acattctgac 1560
tcaattactc aaattccagc tgttaaagca aatagtgtta gttcttatgt tactgttgaa 1620
aagggaacag gctttacagg tggagattta gtgaaattct ccactggatt catgtctaca 1680
ggaatacagt ttaatttaaa gatagaagaa agaaagcgtt atcgtatccg tatacgatat 1740
gccgctgatg ttaatgctac tctatctgca cttggattaa atgatgcatt tattaacatt 1800

```
aaatcgacaa tgtctcaaga cacaccattg aagtataacg atttccaata tgcagaagct   1860

gacaaaacag tgcatttata caatcctcgt ttttctttat atttagaaaa ttcagatcaa   1920

tccgggaaaa gtatttatat agatcgaatc gaattcatcc cagtagatga gacctatgaa   1980

gcagaacaag at                                                        1992


<210> SEQ ID NO 23
<211> LENGTH: 1992
<212> TYPE: DNA
<213> ORGANISM: Bacillus thuringiensis
<220> FEATURE:
<221> NAME/KEY: misc_feature
<223> OTHER INFORMATION: Cry8Ha1

<400> SEQUENCE: 23

atgagtccaa ataatctaaa tgaatatgaa attatagatg cgacaccttc tacatctgta     60

tctaatgatt ctaccagata cccttatgcg aatgagccca caaatgcgtt acaaaatatg    120

aattataagg attatttaag aatgtctgaa ggttacgata ataaatattt tgcaaatcct    180

gaagtgtttg ctgcaccagg tgggattaca actggaatta ctatagttac taaattactg    240

gggtggttag gacttccatt tgctggggaa acagggatgg ctcttaattt cattctaggt    300

ctattatggc caacatcagg aaacccgtgg gctgaactaa tgatattggt agaagaactc    360

ataaatcaaa aaatagaaga gactgtaaga aacaaagcac tagcggattt gggcaattca    420

ggtagagcct tacgatccta tttaaacgca tttgaagatt ggcaaaaaaa ccctaatatc    480

tttcggagta aagagttagt aaaagaaaga ttttcaaacg cggaacattc attacgtacc    540

gaaatgagtt cttttgccat aagaggattt gaaattcctc ttttagcaac atatgcacaa    600

gctgcgaatt tacatttatt tctaattaaa gatattcaaa tttatggaaa agaatgggga    660

tatactcaag ccgatattga cttattttat agagaacaag tagagtttac gaaagaatac    720

accgaacact gtattaatat ttataatgat ggtttaaatc aattaaaagg ttcgaatgct    780

aagcaatgga ttgcatttaa tcgcttccgt agagaaatga cattgacggt actggatgta    840

gttgcattat tcccgaacta tgatgtacgt atgtacccta taaaaacaac tacagagcta    900

acgagaacaa tttataccga tccacttggt tacacgaaaa cgggttctag tagtacacca    960

ccatggtata attatggatc tagtttctca tatatagaaa gtgtagcgat tccagcccct   1020

agtctggtta agtggttaag tcagattgaa atttattcga aatccgcaag ggctacaccg   1080

caaagtgcgg attattgggc aggacataca ataacatatc actatagtgg agatgatggt   1140

caagcagtac ctaattatgg agatagaacg aatcctgtaa ttgtaaatcg ttataatttt   1200

gagcaggctg acatttatag agtttcatca tctgttgctt caagtacaac tagtggtgtt   1260

aaattattaa ctactaaggc tatatttgat ggcataagta caaacaatgg actagtgagt   1320

tacatgtatg aaaaattatc gaactttttt aatgaactaa aagatacaat tacagagcta   1380

cctgttcaga tatccagtcc tcctacctac ggggatgctg aacagtacag tcatcggcta   1440

tcctatgttt ctaatgctcc aacagagtac tcttcgggcg gacatttaat tttgggacta   1500

atcccagtac tgggttggac gcatactagt ttaactcaaa caaatcagat acattctgac   1560

tcaattactc aaattccagc tgttaaagca aatagtgtta gttcttatgt tactgttgaa   1620

aagggaacag gctttacagg tggagattta gtgaaattct ccactggatt catgtctaca   1680

ggaatacagt ttaatttaaa gatagaagaa agaaagcgtt atcgtatccg tatacgatat   1740

gccgctgatg ttaatgctac tctatctgca cttggattaa atgatgcatt tattaacatt   1800
```

-continued

```
aaatcgacaa tgtctcaaga cacaccattg aagtataacg atttccaata tgcagaagct   1860

gacaaaacag tgcatttata caatcctcgt ttttctttat atttagaaaa ttcagatcaa   1920

tccgggaaaa gtatttatat agatcgaatc gaattcatcc cagtagatga gacctatgaa   1980

gcagaacaag at                                                       1992
```

<210> SEQ ID NO 24
<211> LENGTH: 2041
<212> TYPE: DNA
<213> ORGANISM: Bacillus thuringiensis
<220> FEATURE:
<221> NAME/KEY: misc_feature
<223> OTHER INFORMATION: Sequence_1 of Figures 16, 17 and 18

<400> SEQUENCE: 24

```
atgagtccaa ataatcaaaa tgaatatgaa attatagatg cgacaccttc tacttctgta     60

tccaatgatt ctaacagata cccttttgcg aatgagccaa caaatgcgct acaaaatatg    120

gattataaag attatttaaa aatgtctgcg ggaaatgcta gtgaataccc tggttcacct    180

gaagtacttg ttagcggaca agatgcagct aaggccgcaa ttgatatagt aggtaaatta    240

ctatcaggtt taggggtccc atttgttggg ccgatagtga gtctttatac tcaacttatt    300

gatattctgt ggccttcagg ggaaaagagt caatgggaaa tttttatgga acaagtagaa    360

gaactcatta atcaaaaaat agcagaatat gcaaggaata aagcgctttc ggaattagaa    420

ggattaggta ataattacca attatatcta actgcgcttg aagaatggga agaaaatcca    480

aatggttcaa gagccttacg agatgtgcga aatcgatttg aaatcctgga tagtttattt    540

acgcaatata tgccatcttt tagagtgaca aattttgaag taccattcct tactgtatat    600

gcaatggcag ccaaccttca tttactgtta ttaaaggacg cgtcaatttt tggagaagaa    660

tggggatggt caacaactac tattaataac tattatgatc gtcaaatgaa acttactgca    720

gaatattctg atcactgtgt aaagtggtat gaaactggtt tagcaaaatt aaaaggcacg    780

agcgctaaac aatgggttga ctataaccaa ttccgtagag aaatgacact ggcggtttta    840

gatgttgttg cattattccc aaattatgac acacgcacgt acccaatgga aacgaaagca    900

caactaacaa gggaagtata tacagatcca ctgggcgcgg taaacgtgtc ttcaattggt    960

tcctggtatg acaaagcacc ttctttcgga gtgatagaat catccgttat tcgaccaccc   1020

catgtatttg attatataac gggactcaca gtgtatacac aatcaagaag catttcttcc   1080

gctcgctata taagacattg ggctggtcat caaataagct accatcgtgt cagtaggggt   1140

agtaatcttc aacaaatgta tggaactaat caaaatctac acagcactag tacctttgat   1200

tttacgaatt atgatattta caagactcta tcaaaggatg cagtactcct tgatattgtt   1260

taccctggtt atacgtatat attttttgga atgccagaag tcgagttttt catggtaaac   1320

caattgaata ataccagaaa gacgttaaag tataatccag tttccaaaga tattatagcg   1380

agtacaagag attcggaatt agaattacct ccagaaactt cagatcaacc aaattatgag   1440

tcatatagcc atagattatg tcatatcaca agtattcccg cgacgggtaa cactaccgga   1500

ttagtacctg tattttcttg gacacatcga agtgcagatt taaacaatac aatatattca   1560

gataaaatca ctcaaattcc ggccgttaaa tgttgggata atttaccgtt tgttccagtg   1620

gtaaaaggac caggacatac aggaggggat ttattacagt ataatagaag tactggttct   1680

gtaggaacct tatttctagc tcgatatggc ctagcattag aaaaagcagg gaaatatcgt   1740

gtaagactga gatatgctac tgatgcagat attgtattgc atgtaaacga tgctcagatt   1800
```

```
cagatgccaa aaacaatgaa cccaggtgag gatctgacat ctaaaacttt taaagttgca   1860

gatgctatca caacattaaa tttagcaaca gatagttcgc tagcattgaa acataattta   1920

ggtgaagacc ctaattcaac attatctggt atagtttacg ttgaccgaat cgaattcatc   1980

ccagtagatg agacatatga agcggaacaa gatttagaag cagcgaagaa agcagtgaat   2040

g                                                                   2041
```

<210> SEQ ID NO 25
<211> LENGTH: 2053
<212> TYPE: DNA
<213> ORGANISM: Bacillus thuringiensis
<220> FEATURE:
<221> NAME/KEY: misc_feature
<223> OTHER INFORMATION: Sequence_3 of Figures 16, 17 and 18

<400> SEQUENCE: 25

```
atgagtccaa ataatcaaaa tgaatatgaa attatagatg cgacaccttc tacttctgta     60

tccaatgatt ctaacagata cccttttgcg aatgagccaa caaatgcgct acaaaatatg    120

gattataaag attatttaaa aatgtctgcg ggaaatgcta gtgaataccc tggttcacct    180

gaagtacttg ttagcggaca agatgcagct aaggccgcaa ttgatatagt aggtaaatta    240

ctatcaggtt taggggtccc atttgttggg ccgatagtga gtctttatac tcaacttatt    300

gatattctgt ggccttcagg gcaaaagagt caatgggaga tttttatgga acaagtagaa    360

gaactcataa atcaaaaaat agcagaatat gcaaggaata aagcgctttc ggaattagaa    420

ggattaggta ataattacca attatatcta actgcgcttg aagaatggaa agaaaatcca    480

aatggttcaa gagccttacg agatgtgcga aatcgatttg aaatcctgga tagtttattt    540

acgcaataca tgccatcttt tcgagtgaca aattttgaag taccattcct tacagtatat    600

acacaggcag ccaaccttca tttactgtta ttaaaggacg cttcaatttt tggagaagaa    660

tggggatggt ctacaaccac tattaataac tattatgatc gtcaaatgaa acttactgca    720

gaatattctg atcactgtgt aaagtggtat gaaactggtt tagcaaaatt aaaaggcacg    780

agcgctaaac aatgggtcga ctataaccaa ttccgtagag aaatgacact gacggtttta    840

gatgttgttg cattattccc aaattatgac acacgcacgt acccaatgga aacgaaagca    900

caactaacaa gggaagtata tacagatcca ctgggcgcgg taaacgtgtc ttcaattggt    960

tcctggtatg acaaagcacc ttctttcgga gtgatagaat catccgttat tcgaccaccc   1020

catgtatttg attatataac gggactcaca gtgtatacac aatcaagaag catttcttcc   1080

gctcgctata taagacattg ggctggtcat caaataagct atcatcggat ttttagtgat   1140

aatattataa aacagatgta tggaactaat caaaatctac acagcactag tacctttgat   1200

tttacgaatt atgatattta caagacgtta tcaaaagatg cggtgctcct tgatattgtt   1260

tttcctggtt atacgtatat attttttgga atgccagaag tcgagttttt catggtaaac   1320

caattgaata ataccagaaa gacgttaaag tataatccgg tttccaaaga tattatagcg   1380

gggacaagag attcggaatt agaattacct ccagaaactt cagatcaacc aaattatgag   1440

tcatatagcc atagattatg tcatatcaca agtattcccg cgacgggttc aactaccgga   1500

ttagtacctg tattttcttg gacacatcgg agtgccgatc ttataaatgc agttcattca   1560

gataaaatta ctcagattcc ggtcgtaaag gtttctgatt tggctccctc tataacagga   1620

gggccaaata ataccgttgt atcgggtcct ggatttacag gggggggat aataaaagta   1680

ataagaaatg gagtaattat atcacatatg cgtgttaaaa tttcagacat taacaaagaa   1740
```

```
tatagtatga ggattcggta tgcttccgct aataatactg aattttatat aaatccttct   1800

gaagaaaacg ttaaatctca cgctcaaaaa actatgaata gaggtgaagc tttaacatat   1860

aataaattta attatgcgac tttgccccct attaaattta cgacaaccga acctttcatt   1920

actctagggg ctatatttga agcggaagac tttcttggaa ttgaagctta tatagaccga   1980

atcgaattta tcccagtaga tgagacatat gaagcggaac aagatttaga agcagcgaag   2040

aaagcagtga atg                                                      2053
```

<210> SEQ ID NO 26
<211> LENGTH: 2034
<212> TYPE: DNA
<213> ORGANISM: Bacillus thuringiensis
<220> FEATURE:
<221> NAME/KEY: misc_feature
<223> OTHER INFORMATION: Sequence_5 of Figure 16

<400> SEQUENCE: 26

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

caagagcctt acgagatgtg cgaaatcgat ttgaaatcct ggatagttta tttacgcaat    540

atatgccatc ttttagagtg acaaattttg aagtaccatt ccttactgta tatgcaatgg    600

cagccaacct tcatttactg ttattaaagg acgcgtcaat tttggagaa gaatggggat    660

ggtcaacaac tactattaat aactattatg atcgtcaaat gaaacttact gcagaatatt    720

ctgatcactg tgtaaagtgg tatgaaactg gtttagcaaa attaaaaggc acgagcgcta    780

aacaatgggt tgactataac caattccgta gagaaatgac actggcggtt ttagatgttg    840

ttgcattatt cccaaattat gacacacgca cgtacccaat ggaaacgaaa gcacaactaa    900

caagggaagt atatacagat ccactgggcg cggtaaacgt gtcttcaatt ggttcctggt    960

atgacaaagc accttctttc ggagtgatag aatcatccgt tattcgacca ccccatgtat   1020

ttgattatat aacgggactc acagtgtata cacaatcaag aagcatttct tccgctcgct   1080

atataagaca ttgggctggt catcaaataa gctaccatcg tgtcagtagg ggtagtaatc   1140

ttcaacaaat gtatggaact aatcaaaatc tacacagcac tagtaccttt gattttacga   1200

attatgatat ttacaagact ctatcaaagg atgcagtact ccttgatatt gtttaccctg   1260

gttatacgta tatatttttt ggaatgccag aagtcgagtt tttcatggta aaccaattga   1320

ataataccag aaagacgtta aagtataatc cagtttccaa agatattata gcgagtacaa   1380

gagattcgga attagaatta cctccagaaa cttcagatca accaaattat gagtcatata   1440

gccatagatt atgtcatatc acaagtattc ccgcgacggg taacactacc ggattagtac   1500

ctgtattttc ttggacacat cgaagtgcag atttaaacaa tacaatatat tcagataaaa   1560

tcactcaaat tccggccgtt aaatgttggg ataatttacc gtttgttcca gtggtaaaag   1620

gaccaggaca tacaggaggg gatttattac agtataatag aagtactggt tctgtaggaa   1680
```

ccttatttct agctcgatat ggcctagcat tagaaaaagc agggaaatat cgtgtaagac 1740
tgagatatgc tactgatgca gatattgtat tgcatgtaaa cgatgctcag attcagatgc 1800
caaaaacaat gaacccaggt gaggatctga catctaaaac ttttaaagtt gcagatgcta 1860
tcacaacatt aaatttagca acagatagtt cgctagcatt gaaacataat ttaggtgaag 1920
accctaattc aacattatct ggtatagttt acgttgaccg aatcgaattc atcccagtag 1980
atgagacata tgaagcggaa caagatttag aagcagcgaa gaaagcagtg aatg 2034

<210> SEQ ID NO 27
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_7 of Figures 16, 17 and 18

<400> SEQUENCE: 27
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccaaatggtt 480
caagaaatgg ttcccgggcc ttacgagatg tgcgaaatcg atttgaaatc ctggatagtt 540
tatttacgca atatatgcca tcttttagag tgacaaattt tgaagtacca ttccttactg 600
tatatgcaat ggcagccaac cttcatttac tgttattaaa ggacgcgtca atttttggag 660
aagaatgggg atggtcaaca actactatta ataactatta tgatcgtcaa atgaaactta 720
ctgcagaata ttctgatcac tgtgtaaagt ggtatgaaac tggtttagca aaattaaaag 780
gcacgagcgc taaacaatgg gttgactata accaattccg tagagaaatg acactggcgg 840
ttttagatgt tgttgcatta ttcccaaatt atgacacacg cacgtaccca atggaaacga 900
aagcacaact aacaagggaa gtatatacag atccactggg cgcggtaaac gtgtcttcaa 960
ttggttcctg gtatgacaaa gcaccttctt tcggagtgat agaatcatcc gttattcgac 1020
caccccatgt atttgattat ataacgggac tcacagtgta tacacaatca agaagcattt 1080
cttccgctcg ctatataaga cattgggctg gtcatcaaat aagctaccat cgtgtcagta 1140
ggggtagtaa tcttcaacaa atgtatggaa ctaatcaaaa tctacacagc actagtacct 1200
ttgattttac gaattatgat atttacaaga ctctatcaaa ggatgcagta ctccttgata 1260
ttgtttaccc tggttatacg tatatatttt ttggaatgcc agaagtcgag tttttcatgg 1320
taaaccaatt gaataatacc agaaagacgt taaagtataa tccagtttcc aaagatatta 1380
tagcgagtac aagagattcg gaattagaat tacctccaga aacttcagat caaccaaatt 1440
atgagtcata tagccataga ttatgtcata tcacaagtat tcccgcgacg ggtaacacta 1500
ccggattagt acctgtattt tcttggacac atcgaagtgc agatttaaac aatacaatat 1560
attcagataa aatcactcaa attccggccg ttaaatgttg ggataattta ccgtttgttc 1620
cagtggtaaa aggaccagga catacaggag gggatttatt acagtataat agaagtactg 1680

```
gttctgtagg aaccttattt ctagctcgat atggcctagc attagaaaaa gcagggaaat   1740
atcgtgtaag actgagatat gctactgatg cagatattgt attgcatgta aacgatgctc   1800
agattcagat gccaaaaaca atgaacccag gtgaggatct gacatctaaa acttttaaag   1860
ttgcagatgc tatcacaaca ttaaatttag caacagatag ttcgctagca ttgaaacata   1920
atttaggtga agaccctaat tcaacattat ctggtatagt ttacgttgac cgaatcgaat   1980
tcatcccagt agatgagaca tatgaagcgg aataa                              2015
```

```
<210> SEQ ID NO 28
<211> LENGTH: 2003
<212> TYPE: DNA
<213> ORGANISM: Bacillus thuringiensis
<220> FEATURE:
<221> NAME/KEY: misc_feature
<223> OTHER INFORMATION: Sequence_11 of Figures 16, 17 and 18

<400> SEQUENCE: 28

caaataatca aaatgaatat gaaattatag atgcgacacc ttctacttct gtatccaatg     60
attctaacag ataccctttt gcgaatgagc caacaaatgc gctacaaaat atggattata    120
aagattattt aaaaatgtct gcgggaaatg ctagtgaata ccctggttca cctgaagtac    180
ttgttagcgg acaagatgca gctaaggccg caattgatat agtaggtaaa ttactatcag    240
gtttaggggt cccatttgtt gggccgatag tgagtcttta tactcaactt attgatattc    300
tgtggccttc aggggaaaag agtcaatggg aaatttttat ggaacaagta gaagaactca    360
ttaatcaaaa aatagcagaa tatgcaagga ataaagcgct ttcggaatta gaaggattag    420
gtaataatta ccaattatat ctaactgcgc ttgaagaatg ggaagaaaat ccaaatggtt    480
caagagcctt acgagatgtg cgaaatcgat ttgaaatcct ggatagttta tttacgcaat    540
atatgccatc ttttagagtg acaaattttg aagtaccatt ccttactgta tatgcaatgg    600
cagccaacct tcatttactg ttattaaagg acgcgtcaat tttggagaa gaatggggat    660
ggtcaacaac tactattaat aactattatg atcgtcaaat gaaacttact gcagaatatt    720
ctgatcactg tgtaaagtgg tatgaaactg gtttagcaaa attaaaaggc acgagcgcta    780
aacaatgggt tgactataac caattccgta gagaaatgac actggcggtt ttagatgttg    840
ttgcattatt cccaaattat gacacacgca cgtacccaat ggaaacgaaa gcacaactaa    900
caagggaagt atatacagat ccactgggcg cggtaaacgt gtcttcaatt ggttcctggt    960
atgacaaagc accttctttc ggagtgatag aatcatccgt tattcgacca ccccatgtat   1020
ttgattatat aacgggactc acagtgtata cacaatcaag aagcatttct tccgcacgct   1080
atataagaca ttgggctggt catcaaataa gctaccatcg tgtcagtagg ggtagtaatc   1140
ttcaacaaat gtatggaact aatcaaaatc tacacagcac tagtaccttt gattttacga   1200
attatgatat ttacaagact ctatcaaagg atgcagtact ccttgatatt gtttaccctg   1260
gttatacgta tatatttttt ggaatgccag aagtcgagtt tttcatggta aaccaattga   1320
ataataccag aaagacgtta aagtataatc cagtttccaa agatattata gcgagtacaa   1380
gagattcgga attagaatta cctccagaaa cttcagatca accaaattat gagtcatata   1440
gccatagatt atgtcatatc acaagtattc ccgcgacggg taacactacc ggattagtac   1500
ctgtattttc ttggacacat cgaagtgcag atttaaacaa tacaatatat tcagataaaa   1560
tcactcaaat tccggccgtt aaatgttggg ataatttacc gtttgttcca gtggtaaaag   1620
gaccaggaca tacaggaggg gatttattac agtataatag aagtactggt tctgtaggaa   1680
```

ccttatttct agctcgatat ggcctagcat tagaaaaagc agggaaatat cgtgtaagac 1740
tgagatatgc tactgatgca gatattgtat tgcatgtaaa cgatgctcag attcagatgc 1800
caaaaacaat gaacccaggt gaggatctga catctaaaac ttttaaagtt gcagatgcta 1860
tcacaacatt aaatttagca acagatagtt cgctagcatt gaaacataat ttaggtgaag 1920
accctaattc aacattatct ggtatagttt acgttgaccg aatcgaattc atcccagtag 1980
atgagacata tgaagcggaa taa 2003

<210> SEQ ID NO 29
<211> LENGTH: 2022
<212> TYPE: DNA
<213> ORGANISM: Bacillus thuringiensis
<220> FEATURE:
<221> NAME/KEY: misc_feature
<223> OTHER INFORMATION: Sequence_13 of Figures 16, 17 and 18

<400> SEQUENCE: 29
atgagtccaa ataatcaaaa tgaatatgaa attatagatg cgacaccttc tacttctgta 60
tccaatgatt ctaacagata cccttttgcg aatgagccaa caaatgcgct acaaaatatg 120
gattataaag attatttaaa aatgtctgcg ggaaatgcta gtgaataccc tggttcacct 180
gaagtacttg ttagcggaca agatgcagct aaggccgcaa ttgatatagt aggtaaatta 240
ctatcaggtt taggggtccc atttgttggg ccgatagtga gtctttatac tcaacttatt 300
gatattctgt ggccttcagg gcaaaagagt caatgggaga tttttatgga acaagtagaa 360
gaactcataa atcaaaaaat agcagaatat gcaaggaata aagcgctttc ggaattagaa 420
ggattaggta ataattacca attatatcta actgcgcttg aagaatggaa agaaaatcca 480
aatggttcaa gagccttacg agatgtgcga aatcgatttg aaatcctgga tagtttattt 540
acgcaataca tgccatcttt tcgagtgaca aattttgaag taccattcct tacagtatat 600
acacaggcag ccaaccttca tttactgtta ttaaaggacg cttcaatttt tggagaagaa 660
tggggatggt ctacaaccac tattaataac tattatgatc gtcaaatgaa acttactgca 720
gaatattctg atcactgtgt aaagtggtat gaaactggtt tagcaaaatt aaaaggcacg 780
agcgctaaac aatgggtcga ctataaccaa ttccgtagag aaatgacact gacggtttta 840
gatgttgttg cattattccc aaattatgac acacgcacgt acccaatgga aacgaaagca 900
caactaacaa gggaagtata tacagatcca ctgggcgcgg taaacgtgtc ttcaattggt 960
tcctggtatg acaaagcacc ttctttcgga gtgatagaat catccgttat tcgaccaccc 1020
catgtatttg attatataac gggactcaca gtgtatacac aatcaagaag catttcttcc 1080
gctcgctata taagacattg ggctggtcat caaataagct atcatcggat ttttagtgat 1140
aatattataa aacagatgta tggaactaat caaaatctac acagcactag tacctttgat 1200
tttacgaatt atgatattta caagacgtta tcaaaagatg cggtgctcct tgatattgtt 1260
tttcctggtt atacgtatat attttttgga atgccagaag tcgagttttt catggtaaac 1320
caattgaata ataccagaaa gacgttaaag tataatccgg tttccaaaga tattatagcg 1380
gggacaagag attcggaatt agaattacct ccagaaactt cagatcaacc aaattatgag 1440
tcatatagcc atagattatg tcatatcaca agtattcccg cgacgggttc aactaccgga 1500
ttagtacctg tattttcttg gacacatcgg agtgccgatc ttataaatgc agttcattca 1560
gataaaatta ctcagattcc ggtcgtaaag gtttctgatt tggctccctc tataacagga 1620
gggccaaata ataccgttgt atcgggtcct ggatttacag gggggggat aataaaagta 1680 ataagaaatg gagtaattat atcacatatg cgtgttaaaa tttcagacat taacaaagaa 1740
tatagtatga ggattcggta tgcttccgct aataatactg aattttatat aaatccttct 1800
gaagaaaacg ttaaatctca cgctcaaaaa actatgaata gaggtgaagc tttaacatat 1860
aataaattta attatgcgac tttgcccct attaaattta cgacaaccga acctttcatt 1920
actctagggg ctatatttga agcggaagac tttcttggaa ttgaagctta tatagaccga 1980
atcgaattta tcccagtaga tgagacatat gaagcggaat aa 2022

<210> SEQ ID NO 30
<211> LENGTH: 2094
<212> TYPE: DNA
<213> ORGANISM: Bacillus thuringiensis
<220> FEATURE:
<221> NAME/KEY: misc_feature
<223> OTHER INFORMATION: Sequence_17 of Figures 16, 17 and 18

<400> SEQUENCE: 30
aaaagaaagt gtaaaaaatc tttgtatctt gtatatgtat aggaggaaaa tagatgagtc 60
caaataatca aaatgaatat gaaattatag atgcgacacc ttctacttct gtatccaatg 120
attctaacag ataccctttt gcgaatgagc caacaaatgc gctacaaaat atggattata 180
aagattattt aaaaatgtct gcgggaaatg ctagtgaata ccctggttca cctgaagtac 240
ttgttagcgg acaagatgca gctaaggccg caattgatat agtaggtaaa ttactatcag 300
gtttaggggt cccatttgtt gggccgatag tgagtcttta tactcaactt attgatattc 360
tgtggccttc aggggaaaag agtcaatggg aaatttttat ggaacaagta gaagaactca 420
ttaatcaaaa aatagcagaa tatgcaagga ataaagcgct ttcggaatta gaaggattag 480
gtaataatta ccaattatat ctaactgcgc ttgaagaatg ggaagaaaat ccaaatggtt 540
caagagcctt acgagatgtg cgaaatcgat ttgaaatcct ggatagttta tttacgcaat 600
atatgccatc ttttagagtg acaaattttg aagtaccatt ccttactgta tatgcaatgg 660
cagccaacct tcatttactg ttattaaagg acgcgtcaat ttttggagaa gaatggggat 720
ggtcaacaac tactattaat aactattatg atcgtcaaat gaaacttact gcagaatatt 780
ctgatcactg tgtaaagtgg tatgaaactg gtttagcaaa attaaaaggc acgagcgcta 840
aacaatgggt tgactataac caattccgta gagaaatgac actggcggtt ttagatgttg 900
ttgcattatt cccaaattat gacacacgca cgtacccaat ggaaacgaaa gcacaactaa 960
caagggaagt atatacagat ccactgggcg cggtaaacgt gtcttcaatt ggttcctggt 1020
atgacaaagc accttctttc ggagtgatag aatcatccgt tattcgacca ccccatgtat 1080
ttgattatat aacgggactc acagtgtata cacaatcaag aagcatttct tccgctcgct 1140
atataagaca ttgggctggt catcaaataa gctaccatcg tgtcagtagg ggtagtaatc 1200
ttcaacaaat gtatggaact aatcaaaatc tacacagcac tagtaccttt gattttacga 1260
attatgatat ttacaagact ctatcaaagg atgcagtact ccttgatatt gtttaccctg 1320
gttatacgta tatatttttt ggaatgccag aagtcgagtt tttcatggta aaccaattga 1380
ataataccag aaagacgtta aagtataatc cagtttccaa agatattata gcgagtacaa 1440
gagattcgga attagaatta cctccagaaa cttcagatca accaaattat gagtcatata 1500
gccatagatt atgtcatatc acaagtattc ccgcgacggg taacactacc ggattagtac 1560
ctgtattttc ttggacacat cgaagtgcag atttaaacaa tacaatatat tcagataaaa 1620
tcactcaaat tccggccgtt aaatgttggg ataatttacc gtttgttcca gtggtaaaag 1680
gaccaggaca tacaggaggg gatttattac agtataatag aagtactggt tctgtaggaa 1740
ccttatttct agctcgatat ggcctagcat tagaaaaagc agggaaatat cgtgtaagac 1800
tgagatatgc tactgatgca gatattgtat tgcatgtaaa cgatgctcag attcagatgc 1860
caaaaacaat gaacccaggt gaggatctga catctaaaac ttttaaagtt gcagatgcta 1920
tcacaacatt aaatttagca acagatagtt cgctagcatt gaaacataat ttaggtgaag 1980
accctaattc aacattatct ggtatagttt acgttgaccg aatcgaattc atcccagtag 2040
atgagacata tgaagcggaa caagatttag aagcagcgaa gaaagcagtg aatg 2094

<210> SEQ ID NO 31
<211> LENGTH: 2106
<212> TYPE: DNA
<213> ORGANISM: Bacillus thuringiensis
<220> FEATURE:
<221> NAME/KEY: misc_feature
<223> OTHER INFORMATION: Sequence_18 of Figures 16, 17 and 18

<400> SEQUENCE: 31
ttaaaaaaag tgtaagaaat tttatatctt ttgtatgtat aggaggaaaa tagatgagtc 60
caaataatca aaatgaatat gaaattatag atgcgacacc ttctacttct gtatccaatg 120
attctaacag ataccctttt gcgaatgagc caacaaatgc gctacaaaat atggattata 180
aagattattt aaaaatgtct gcgggaaatg ctagtgaata ccctggttca cctgaagtac 240
ttgttagcgg acaagatgca gctaaggccg caattgatat agtaggtaaa ttactatcag 300
gtttaggggt cccatttgtt gggccgatag tgagtcttta tactcaactt attgatattc 360
tgtggccttc agggcaaaag agtcaatggg agatttttat ggaacaagta gaagaactca 420
taaatcaaaa aatagcagaa tatgcaagga ataaagcgct ttcggaatta gaaggattag 480
gtaataatta ccaattatat ctaactgcgc ttgaagaatg gaaagaaaat ccaaatggtt 540
caagagcctt acgagatgtg cgaaatcgat ttgaaatcct ggatagttta tttacgcaat 600
acatgccatc ttttcgagtg acaaattttg aagtaccatt ccttacagta tatacacagg 660
cagccaacct tcatttactg ttattaaagg acgcttcaat tttggagaa gaatggggat 720
ggtctacaac cactattaat aactattatg atcgtcaaat gaaacttact gcagaatatt 780
ctgatcactg tgtaaagtgg tatgaaactg gtttagcaaa attaaaaggc acgagcgcta 840
aacaatgggt cgactataac caattccgta gagaaatgac actgacggtt ttagatgttg 900
ttgcattatt cccaaattat gacacacgca cgtacccaat ggaaacgaaa gcacaactaa 960
caagggaagt atatacagat ccactgggcg cggtaaacgt gtcttcaatt ggttcctggt 1020
atgacaaagc accttctttc ggagtgatag aatcatccgt tattcgacca ccccatgtat 1080
ttgattatat aacgggactc acagtgtata cacaatcaag aagcatttct tccgctcgct 1140
atataagaca ttgggctggt catcaaataa gctatcatcg gatttttagt gataatatta 1200
taaaacagat gtatggaact aatcaaaatc tacacagcac tagtaccttt gattttacga 1260
attatgatat ttacaagacg ttatcaaaag atgcggtgct ccttgatatt gtttttcctg 1320
gttatacgta tatatttttt ggaatgccag aagtcgagtt tttcatggta aaccaattga 1380
ataataccag aaagacgtta aagtataatc cggtttccaa agatattata gcggggacaa 1440
gagattcgga attagaatta cctccagaaa cttcagatca accaaattat gagtcatata 1500
gccatagatt atgtcatatc acaagtattc ccgcgacggg ttcaactacc ggattagtac 1560
ctgtattttc ttggacacat cggagtgccg atcttataaa tgcagttcat tcagataaaa 1620
ttactcagat tccggtcgta aaggtttctg atttggctcc ctctataaca ggagggccaa 1680
ataataccgt tgtatcgggt cctggattta caggggggggg gataataaaa gtaataagaa 1740
atggagtaat tatatcacat atgcgtgtta aaatttcaga cattaacaaa gaatatagta 1800
tgaggattcg gtatgcttcc gctaataata ctgaatttta tataaatcct tctgaagaaa 1860
acgttaaatc tcacgctcaa aaaactatga atagaggtga agctttaaca tataataaat 1920
ttaattatgc gactttgccc cctattaaat ttacgacaac cgaacctttc attactctag 1980
gggctatatt tgaagcggaa gactttcttg gaattgaagc ttatatagac cgaatcgaat 2040
ttatcccagt agatgagaca tatgaagcgg aacaagattt agaagcagcg aagaaagcag 2100
tgaatg 2106

<210> SEQ ID NO 32
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_21 of Figures 16, 17 and 18

<400> SEQUENCE: 32
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccatttcgac 480
gaggttttcg acgaggtgcc ttacgagatg tgcgaaatcg atttgaaatc ctggatagtt 540
tatttacgca atatatgcca tcttttagag tgacaaattt tgaagtacca ttccttactg 600
tatatgcaat ggcagccaac cttcatttac tgttattaaa ggacgcgtca atttttggag 660
aagaatgggg atggtcaaca actactatta ataactatta tgatcgtcaa atgaaactta 720
ctgcagaata ttctgatcac tgtgtaaagt ggtatgaaac tggtttagca aaattaaaag 780
gcacgagcgc taaacaatgg gttgactata accaattccg tagagaaatg acactggcgg 840
ttttagatgt tgttgcatta ttcccaaatt atgacacacg cacgtaccca atggaaacga 900
aagcacaact aacaagggaa gtatatacag atccactggg cgcggtaaac gtgtcttcaa 960
ttggttcctg gtatgacaaa gcaccttctt tcggagtgat agaatcatcc gttattcgac 1020
caccccatgt atttgattat ataacgggac tcacagtgta tacacaatca agaagcattt 1080
cttccgctcg ctatataaga cattgggctg gtcatcaaat aagctaccat cgtgtcagta 1140
ggggtagtaa tcttcaacaa atgtatggaa ctaatcaaaa tctacacagc actagtacct 1200
ttgattttac gaattatgat atttacaaga ctctatcaaa ggatgcagta ctccttgata 1260
ttgtttaccc tggttatacg tatatatttt ttggaatgcc agaagtcgag tttttcatgg 1320
taaaccaatt gaataatacc agaaagacgt taaagtataa tccagtttcc aaagatatta 1380
tagcgagtac aagagattcg gaattagaat tacctccaga aacttcagat caaccaaatt 1440
atgagtcata tagccataga ttatgtcata tcacaagtat tcccgcgacg ggtaacacta 1500

-continued

```
ccggattagt acctgtattt tcttggacac atcgaagtgc agatttaaac aatacaatat   1560
attcagataa aatcactcaa attccggccg ttaaatgttg ggataattta ccgtttgttc   1620
cagtggtaaa aggaccagga catacaggag ggatttatt acagtataat agaagtactg   1680
gttctgtagg aaccttattt ctagctcgat atggcctagc attagaaaaa gcagggaaat   1740
atcgtgtaag actgagatat gctactgatg cagatattgt attgcatgta aacgatgctc   1800
agattcagat gccaaaaaca atgaacccag gtgaggatct gacatctaaa acttttaaag   1860
ttgcagatgc tatcacaaca gtaaatttag caacagatag ttcggtagca gtgaaacata   1920
atgtaggtga agaccctaat tcaacattat ctggtatagt ttacgttgac cgaatcgaat   1980
tcatcccagt agatgagaca tatgaagcgg aataa                              2015
```

<210> SEQ ID NO 33
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_25 of Figures 16, 17 and 18

<400> SEQUENCE: 33

```
caaataatca aaatgaatat gaaattatag atgcgacacc ttctacttct gtatccaatg     60
attctaacag atacccttt gcgaatgagc caacaaatgc gctacaaaat atggattata    120
aagattattt aaaaatgtct gcgggaaatg ctagtgaata ccctggttca cctgaagtac    180
ttgttagcgg acaagatgca gctaaggccg caattgatat agtaggtaaa ttactatcag    240
gtttaggggt cccatttgtt gggccgatag tgagtcttta tactcaactt attgatattc    300
tgtggccttc aggggaaaag agtcaatggg aaattttat ggaacaagta gaagaactca    360
ttaatcaaaa aatagcagaa tatgcaagga ataaagcgct ttcggaatta gaaggattag    420
gtaataatta ccaattatat ctaactgcgc ttgaagaatg ggaagaaaat ccaaatggtt    480
caagaaatgg ttcccgggcc ttacgagatg tgcgaaatcg atttgaaatc ctggatagtt    540
tatttacgca atatatgcca tcttttagag tgacaaattt tgaagtacca ttccttactg    600
tatatgcaat ggcagccaac cttcatttac tgttattaaa ggacgcgtca atttttggag    660
aagaatgggg atggtcaaca actactatta ataactatta tgatcgtcaa atgaaactta    720
ctgcagaata ttctgatcac tgtgtaaagt ggtatgaaac tggtttagca aaattaaaag    780
gcacgagcgc taaacaatgg gttgactata accaattccg tagagaaatg acactggcgg    840
ttttagatgt tgttgcatta ttcccaaatt atgacacacg cacgtaccca atggaaacga    900
aagcacaact aacaagggaa gtatatacag atccactggg cgcggtaaac gtgtcttcaa    960
ttggttcctg gtatgacaaa gcaccttctt tcggagtgat agaatcatcc gttattcgac   1020
caccccatgt atttgattat ataacgggac tcacagtgta tacacaatca agaagcattt   1080
cttccgctcg ctatataaga cattgggctg gtcatcaaat aagctaccat cgtgtcagta   1140
ggggtagtaa tcttcaacaa atgtatggaa ctaatcaaaa tctacacagc actagtacct   1200
ttgattttac gaattatgat atttacaaga ctctatcaaa ggatgcagta ctccttgata   1260
ttgtttaccc tggttatacg tatatatttt ttggaatgcc agaagtcgag tttttcatgg   1320
taaaccaatt gaataatacc agaaagacgt taaagtataa tccagtttcc aaagatatta   1380
tagcgagtac aagagattcg gaattagaat tacctccaga aacttcagat caaccaaatt   1440
atgagtcata tagccataga ttatgtcata tcacaagtat tcccgcgacg ggtaacacta   1500
```

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt acagtataat agaagtactg   1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca ttaaatttag caacagatag ttcgctagca ttgaaacata   1920

atgtaggtga agaccctaat tcaacattat ctggtatagt ttacgttgac cgaatcgaat   1980

tcatcccagt agatgagaca tatgaagcgg aataa                              2015
```

<210> SEQ ID NO 34
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_29 of Figures 16, 17 and 18

<400> SEQUENCE: 34

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

caagaaatgg ttcccgggcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataactatta tgatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacacg cacgtaccca atggaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt acagtataat agaagtactg   1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca ttaaatttag caacagatag ttcgctagca gtgaaacata   1920

atgtaggtga agaccctaat tcaacattat ctggtatagt ttacgttgac cgaatcgaat   1980

tcatcccagt agatgagaca tatgaagcgg aataa                              2015
```

<210> SEQ ID NO 35
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_33 of Figures 16, 17 and 18

<400> SEQUENCE: 35

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

caagaaatgg ttcccgggcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataactatta tgatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacacg cacgtaccca atggaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

ccggattagt acctgtattt tcttggacac atcgaagtgc agatttaaac aatacaatat 1560
attcagataa aatcactcaa attccggccg ttaaatgttg ggataattta ccgtttgttc 1620
cagtggtaaa aggaccagga catacaggag ggatttatt acagtataat agaagtactg 1680
gttctgtagg aaccttattt ctagctcgat atggcctagc attagaaaaa gcagggaaat 1740
atcgtgtaag actgagatat gctactgatg cagatattgt attgcatgta aacgatgctc 1800
agattcagat gccaaaaaca atgaacccag gtgaggatct gacatctaaa acttttaaag 1860
ttgcagatgc tatcacaaca gtaaatttag caacagatag ttcggtagca gtgaaacata 1920
atgtaggtga agaccctaat tcaacattat ctggtatagt ttacgttgac cgaatcgaat 1980
tcatcccagt agatgagaca tatgaagcgg aataa 2015

<210> SEQ ID NO 36
<211> LENGTH: 2021
<212> TYPE: DNA
<213> ORGANISM: Bacillus thuringiensis
<220> FEATURE:
<221> NAME/KEY: misc_feature
<223> OTHER INFORMATION: Sequence_39 of Figures 16, 17 and 18

<400> SEQUENCE: 36
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccatttcgaa 480
gtcgaggttt tcgaagtcga ggtccagcct tacgagatgt gcgaaatcga tttgaaatcc 540
tggatagttt atttacgcaa tatatgccat cttttagagt gacaaatttt gaagtaccat 600
tccttactgt atatgcaatg gcagccaacc ttcatttact gttattaaag gacgcgtcaa 660
tttttggaga agaatgggga tggtcaacaa ctactattaa taactattat gatcgtcaaa 720
tgaaacttac tgcagaatat tctgatcact gtgtaaagtg gtatgaaact ggtttagcaa 780
aattaaaagg cacgagcgct aaacaatggg ttgactataa ccaattccgt agagaaatga 840
cactggcggt tttagatgtt gttgcattat tcccaaatta tgacacacgc acgtacccaa 900
tggaaacgaa agcacaacta acaagggaag tatatacaga tccactgggc gcggtaaacg 960
tgtcttcaat tggttcctgg tatgacaaag caccttcttt cggagtgata gaatcatccg 1020
ttattcgacc accccatgta tttgattata taacgggact cacagtgtat acacaatcaa 1080
gaagcatttc ttccgctcgc tatataagac attgggctgg tcatcaaata agctaccatc 1140
gtgtcagtag ggtagtaat cttcaacaaa tgtatggaac taatcaaaat ctacacagca 1200
ctagtacctt tgattttacg aattatgata tttacaagac tctatcaaag gatgcagtac 1260
tccttgatat tgtttaccct ggttatacgt atatattttt tggaatgcca gaagtcgagt 1320
ttttcatggt aaaccaattg aataatacca gaaagacgtt aaagtataat ccagtttcca 1380
aagatattat agcgagtaca agagattcgg aattagaatt acctccagaa acttcagatc 1440
aaccaaatta tgagtcatat agccatagat tatgtcatat cacaagtatt cccgcgacgg 1500
gtaacactac cggattagta cctgtatttt cttggacaca tcgaagtgca gatttaaaca 1560
atacaatata ttcagataaa atcactcaaa ttccggccgt taaatgttgg gataatttac 1620
cgtttgttcc agtggtaaaa ggaccaggac atacaggagg ggatttatta cagtataata 1680
gaagtactgg ttctgtagga accttatttc tagctcgata tggcctagca ttagaaaaag 1740
cagggaaata tcgtgtaaga ctgagatatg ctactgatgc agatattgta ttgcatgtaa 1800
acgatgctca gattcagatg ccaaaaacaa tgaacccagg tgaggatctg acatctaaaa 1860
cttttaaagt tgcagatgct atcacaacag ttaatttagc aacagatagt tcggttgcag 1920
ttaaacataa tgtaggtgaa gaccctaatt caacattatc tggtatagtt tacgttgacc 1980
gaatcgaatt catcccagta gatgagacat atgaagcgga a 2021

<210> SEQ ID NO 37
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_41 of Figures 16, 17 and 18

<400> SEQUENCE: 37
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccatttcgaa 480
gtcgaggttt tcgaagtcga ggtgccttac gagatgtgcg aaatcgattt gaaatcctgg 540
atagtttatt tacgcaatat atgccatctt ttagagtgac aaattttgaa gtaccattcc 600
ttactgtata tgcaatggca gccaaccttc atttactgtt attaaaggac gcgtcaattt 660
ttggagaaga atggggatgg tcaacaacta ctattaataa ctattatgat cgtcaaatga 720
aacttactgc agaatattct gatcactgtg taaagtggta tgaaactggt ttagcaaaat 780
taaaaggcac gagcgctaaa caatgggttg actataacca attccgtaga gaaatgacac 840
tggcggtttt agatgttgtt gcattattcc caaattatga cacacgcacg tacccaatgg 900
aaacgaaagc acaactaaca agggaagtat atacagatcc actgggcgcg gtaaacgtgt 960
cttcaattgg ttcctggtat gacaaagcac cttctttcgg agtgatagaa tcatccgtta 1020
ttcgaccacc ccatgtattt gattatataa cgggactcac agtgtataca caatcaagaa 1080
gcatttcttc cgctcgctat ataagacatt gggctggtca tcaaataagc taccatcgtg 1140
tcagtagggg tagtaatctt caacaaatgt atggaactaa tcaaaatcta cacagcacta 1200
gtacctttga ttttacgaat tatgatattt acaagactct atcaaaggat gcagtactcc 1260
ttgatattgt ttaccctggt tatacgtata tatttttttgg aatgccagaa gtcgagtttt 1320
tcatggtaaa ccaattgaat aataccagaa agacgttaaa gtataatcca gtttccaaag 1380
atattatagc gagtacaaga gattcggaat tagaattacc tccagaaact tcagatcaac 1440
caaattatga gtcatatagc catagattat gtcatatcac aagtattccc gcgacgggta 1500
acactaccgg attagtacct gtattttctt ggacacatcg aagtgcagat ttaaacaata 1560
caatatattc agataaaatc actcaaattc cggccgttaa atgttgggat aatttaccgt 1620
ttgttccagt ggtaaaagga ccaggacata caggagggga tttattacag tataatagaa 1680
gtactggttc tgtaggaacc ttatttctag ctcgatatgg cctagcatta gaaaaagcag 1740
ggaaatatcg tgtaagactg agatatgcta ctgatgcaga tattgtattg catgtaaacg 1800
atgctcagat tcagatgcca aaaacaatga acccaggtga ggatctgaca tctaaaactt 1860
ttaaagttgc agatgctatc acaacagtta atttagcaac agatagttcg gttgcagtta 1920
aacataatgt aggtgaagac cctaattcaa cattatctgg tatagtttac gttgaccgaa 1980
tcgaattcat cccagtagat gagacatatg aagcggaa 2018

<210> SEQ ID NO 38
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_43 of Figures 16, 17 and 18

<400> SEQUENCE: 38
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccaaatggtt 480
cccggtttcg aagtcgaggt gccttacgag atgtgcgaaa tcgatttgaa atcctggata 540
gtttatttac gcaatatatg ccatctttta gagtgacaaa ttttgaagta ccattcctta 600
ctgtatatgc aatggcagcc aaccttcatt tactgttatt aaaggacgcg tcaatttttg 660
gagaagaatg gggatggtca acaactacta ttaataacta ttatgatcgt caaatgaaac 720
ttactgcaga atattctgat cactgtgtaa agtggtatga aactggttta gcaaaattaa 780
aaggcacgag cgctaaacaa tggggttgact ataaccaatt ccgtagagaa atgacactgg 840
cggttttaga tgttgttgca ttattcccaa attatgacac acgcacgtac ccaatggaaa 900
cgaaagcaca actaacaagg gaagtatata cagatccact gggcgcggta aacgtgtctt 960
caattggttc ctggtatgac aaagcacctt ctttcggagt gatagaatca tccgttattc 1020
gaccacccca tgtatttgat tatataacgg gactcacagt gtatacacaa tcaagaagca 1080
tttcttccgc tcgctatata agacattggg ctggtcatca aataagctac catcgtgtca 1140
gtaggggtag taatcttcaa caaatgtatg gaactaatca aaatctacac agcactagta 1200
cctttgattt tacgaattat gatatttaca agactctatc aaaggatgca gtactccttg 1260
atattgttta ccctggttat acgtatatat tttttggaat gccagaagtc gagtttttca 1320
tggtaaacca attgaataat accagaaaga cgttaaagta taatccagtt tccaaagata 1380
ttatagcgag tacaagagat tcggaattag aattacctcc agaaacttca gatcaaccaa 1440
attatgagtc atatagccat agattatgtc atatcacaag tattcccgcg acgggtaaca 1500
ctaccggatt agtacctgta ttttcttgga cacatcgaag tgcagattta aacaatacaa 1560
tatattcaga taaaatcact caaattccgg ccgttaaatg ttgggataat ttaccgtttg 1620
ttccagtggt aaaaggacca ggacatacag gaggggattt attacagtat aatagaagta 1680
ctggttctgt aggaacctta tttctagctc gatatggcct agcattagaa aaagcaggga 1740
aatatcgtgt aagactgaga tatgctactg atgcagatat tgtattgcat gtaaacgatg 1800
ctcagattca gatgccaaaa acaatgaacc caggtgagga tctgacatct aaaactttta 1860
aagttgcaga tgctatcaca acagttaatt tagcaacaga tagttcggtt gcagttaaac 1920
ataatgtagg tgaagaccct aattcaacat tatctggtat agtttacgtt gaccgaatcg 1980
aattcatccc agtagatgag acatatgaag cggaa 2015

<210> SEQ ID NO 39
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_45 of Figures 16, 17 and 18

<400> SEQUENCE: 39
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaattttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccaaatggtt 480
cccggtttcg aagtcgaggt ccagccttac gagatgtgcg aaatcgattt gaaatcctgg 540
atagtttatt tacgcaatat atgccatctt ttagagtgac aaattttgaa gtaccattcc 600
ttactgtata tgcaatggca gccaaccttc atttactgtt attaaaggac gcgtcaattt 660
ttggagaaga atggggatgg tcaacaacta ctattaataa ctattatgat cgtcaaatga 720
aacttactgc agaatattct gatcactgtg taaagtggta tgaaactggt ttagcaaaat 780
taaaaggcac gagcgctaaa caatgggttg actataacca attccgtaga gaaatgacac 840
tggcggtttt agatgttgtt gcattattcc caaattatga cacacgcacg tacccaatgg 900
aaacgaaagc acaactaaca agggaagtat atacagatcc actgggcgcg gtaaacgtgt 960
cttcaattgg ttcctggtat gacaaagcac cttctttcgg agtgatagaa tcatccgtta 1020
ttcgaccacc ccatgtattt gattatataa cgggactcac agtgtataca caatcaagaa 1080
gcatttcttc cgctcgctat ataagacatt gggctggtca tcaaataagc taccatcgtg 1140
tcagtagggg tagtaatctt caacaaatgt atggaactaa tcaaaatcta cacagcacta 1200
gtacctttga ttttacgaat tatgatattt acaagactct atcaaaggat gcagtactcc 1260
ttgatattgt ttaccctggt tatacgtata tattttttgg aatgccagaa gtcgagtttt 1320
tcatggtaaa ccaattgaat aataccagaa agacgttaaa gtataatcca gtttccaaag 1380
atattatagc gagtacaaga gattcggaat tagaattacc tccagaaact tcagatcaac 1440
caaattatga gtcatatagc catagattat gtcatatcac aagtattccc gcgacgggta 1500

```
acactaccgg attagtacct gtattttctt ggacacatcg aagtgcagat ttaaacaata   1560

caatatattc agataaaatc actcaaattc cggccgttaa atgttgggat aatttaccgt   1620

ttgttccagt ggtaaaagga ccaggacata caggaggga tttattacag tataatagaa   1680

gtactggttc tgtaggaacc ttatttctag ctcgatatgg cctagcatta gaaaaagcag   1740

ggaaatatcg tgtaagactg agatatgcta ctgatgcaga tattgtattg catgtaaacg   1800

atgctcagat tcagatgcca aaaacaatga acccaggtga ggatctgaca tctaaaactt   1860

ttaaagttgc agatgctatc acaacagtta atttagcaac agatagttcg gttgcagtta   1920

aacataatgt aggtgaagac cctaattcaa cattatctgg tatagtttac gttgaccgaa   1980

tcgaattcat cccagtagat gagacatatg aagcggaa                           2018
```

<210> SEQ ID NO 40
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_47 of Figures 16, 17 and 18

<400> SEQUENCE: 40

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgaa    480

gtcgaggtcc aaatggttcc cgggccttac gagatgtgcg aaatcgattt gaaatcctgg    540

atagtttatt tacgcaatat atgccatctt ttagagtgac aaattttgaa gtaccattcc    600

ttactgtata tgcaatggca gccaaccttc atttactgtt attaaaggac gcgtcaattt    660

ttggagaaga atggggatgg tcaacaacta ctattaataa ctattatgat cgtcaaatga    720

aacttactgc agaatattct gatcactgtg taaagtggta tgaaactggt ttagcaaaat    780

taaaaggcac gagcgctaaa caatgggttg actataacca attccgtaga gaaatgacac    840

tggcggtttt agatgttgtt gcattattcc caaattatga cacacgcacg tacccaatgg    900

aaacgaaagc acaactaaca agggaagtat atacagatcc actgggcgcg gtaaacgtgt    960

cttcaattgg ttcctggtat gacaaagcac cttctttcgg agtgatagaa tcatccgtta   1020

ttcgaccacc ccatgtattt gattatataa cgggactcac agtgtataca caatcaagaa   1080

gcatttcttc cgctcgctat ataagacatt gggctggtca tcaaataagc taccatcgtg   1140

tcagtagggg tagtaatctt caacaaatgt atggaactaa tcaaaatcta cacagcacta   1200

gtacctttga ttttacgaat tatgatattt acaagactct atcaaaggat gcagtactcc   1260

ttgatattgt ttaccctggt tatacgtata tatttttttgg aatgccagaa gtcgagtttt   1320

tcatggtaaa ccaattgaat aataccagaa agacgttaaa gtataatcca gtttccaaag   1380

atattatagc gagtacaaga gattcggaat tagaattacc tccagaaact tcagatcaac   1440

caaattatga gtcatatagc catagattat gtcatatcac aagtattccc gcgacgggta   1500
```

-continued acactaccgg attagtacct gtattttctt ggacacatcg aagtgcagat ttaaacaata 1560
caatatattc agataaaatc actcaaattc cggccgttaa atgttgggat aatttaccgt 1620
ttgttccagt ggtaaaagga ccaggacata caggagggga tttattacag tataatagaa 1680
gtactggttc tgtaggaacc ttatttctag ctcgatatgg cctagcatta gaaaaagcag 1740
ggaaatatcg tgtaagactg agatatgcta ctgatgcaga tattgtattg catgtaaacg 1800
atgctcagat tcagatgcca aaaacaatga acccaggtga ggatctgaca tctaaaactt 1860
ttaaagttgc agatgctatc acaacagtta atttagcaac agatagttcg gttgcagtta 1920
aacataatgt aggtgaagac cctaattcaa cattatctgg tatagtttac gttgaccgaa 1980
tcgaattcat cccagtagat gagacatatg aagcggaa 2018

<210> SEQ ID NO 41
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_49 of Figures 16, 17 and 18

<400> SEQUENCE: 41
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccaaatggtt 480
cccggtttcg aagtcgacaa gccttacgag atgtgcgaaa tcgatttgaa atcctggata 540
gtttatttac gcaatatatg ccatctttta gagtgacaaa ttttgaagta ccattcctta 600
ctgtatatgc aatggcagcc aaccttcatt tactgttatt aaaggacgcg tcaatttttg 660
gagaagaatg gggatggtca acaactacta ttaataacta ttatgatcgt caaatgaaac 720
ttactgcaga atattctgat cactgtgtaa agtggtatga aactggttta gcaaaattaa 780
aaggcacgag cgctaaacaa tggggttgact ataaccaatt ccgtagagaa atgacactgg 840
cggttttaga tgttgttgca ttattcccaa attatgacac acgcacgtac ccaatggaaa 900
cgaaagcaca actaacaagg gaagtatata cagatccact gggcgcggta aacgtgtctt 960
caattggttc ctggtatgac aaagcacctt ctttcggagt gatagaatca tccgttattc 1020
gaccacccca tgtatttgat tatataacgg gactcacagt gtatacacaa tcaagaagca 1080
tttcttccgc tcgctatata agacattggg ctggtcatca aataagctac catcgtgtca 1140
gtaggggtag taatcttcaa caaatgtatg gaactaatca aaatctacac agcactagta 1200
cctttgattt tacgaattat gatatttaca agactctatc aaaggatgca gtactccttg 1260
atattgttta ccctggttat acgtatatat tttttggaat gccagaagtc gagtttttca 1320
tggtaaacca attgaataat accagaaaga cgttaaagta taatccagtt tccaaagata 1380
ttatagcgag tacaagagat tcggaattag aattacctcc agaaacttca gatcaaccaa 1440
attatgagtc atatagccat agattatgtc atatcacaag tattcccgcg acgggtaaca 1500

```
ctaccggatt agtacctgta ttttcttgga cacatcgaag tgcagattta aacaatacaa   1560

tatattcaga taaaatcact caaattccgg ccgttaaatg ttgggataat ttaccgtttg   1620

ttccagtggt aaaaggacca ggacatacag gaggggattt attacagtat aatagaagta   1680

ctggttctgt aggaacctta tttctagctc gatatggcct agcattagaa aaagcaggga   1740

aatatcgtgt aagactgaga tatgctactg atgcagatat tgtattgcat gtaaacgatg   1800

ctcagattca gatgccaaaa acaatgaacc caggtgagga tctgacatct aaaactttta   1860

aagttgcaga tgctatcaca acagttaatt tagcaacaga tagttcggtt gcagttaaac   1920

ataatgtagg tgaagaccct aattcaacat tatctggtat agtttacgtt gaccgaatcg   1980

aattcatccc agtagatgag acatatgaag cggaa                              2015
```

<210> SEQ ID NO 42
<211> LENGTH: 2024
<212> TYPE: DNA
<213> ORGANISM: Bacillus thuringiensis
<220> FEATURE:
<221> NAME/KEY: misc_feature
<223> OTHER INFORMATION: Sequence_51 of Figures 16, 17 and 18

<400> SEQUENCE: 42

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgaa    480

gtcgaggtag tttaaatggt tcccggccag ccttacgaga tgtgcgaaat cgatttgaaa    540

tcctggatag tttatttacg caatatatgc catcttttag agtgacaaat tttgaagtac    600

cattccttac tgtatatgca atggcagcca accttcattt actgttatta aaggacgcgt    660

caatttttgg agaagaatgg ggatggtcaa caactactat taataactat tatgatcgtc    720

aaatgaaact tactgcagaa tattctgatc actgtgtaaa gtggtatgaa actggtttag    780

caaaattaaa aggcacgagc gctaaacaat gggttgacta taaccaattc cgtagagaaa    840

tgacactggc ggttttagat gttgttgcat tattcccaaa ttatgacaca cgcacgtacc    900

caatggaaac gaaagcacaa ctaacaaggg aagtatatac agatccactg ggcgcggtaa    960

acgtgtcttc aattggttcc tggtatgaca aagcaccttc tttcggagtg atagaatcat   1020

ccgttattcg accaccccat gtatttgatt atataacggg actcacagtg tatacacaat   1080

caagaagcat ttcttccgct cgctatataa gacattgggc tggtcatcaa ataagctacc   1140

atcgtgtcag taggggtagt aatcttcaac aaatgtatgg aactaatcaa aatctacaca   1200

gcactagtac ctttgatttt acgaattatg atatttacaa gactctatca aaggatgcag   1260

tactccttga tattgtttac cctggttata cgtatatatt ttttggaatg ccagaagtcg   1320

agtttttcat ggtaaaccaa ttgaataata ccagaaagac gttaaagtat aatccagttt   1380

ccaaagatat tatagcgagt acaagagatt cggaattaga attacctcca gaaacttcag   1440

atcaaccaaa ttatgagtca tatagccata gattatgtca tatcacaagt attcccgcga   1500
```

```
cgggtaacac taccggatta gtacctgtat tttcttggac acatcgaagt gcagatttaa   1560
acaatacaat atattcagat aaaatcactc aaattccggc cgttaaatgt tgggataatt   1620
taccgtttgt tccagtggta aaaggaccag gacatacagg aggggattta ttacagtata   1680
atagaagtac tggttctgta ggaaccttat ttctagctcg atatggccta gcattagaaa   1740
aagcagggaa atatcgtgta agactgagat atgctactga tgcagatatt gtattgcatg   1800
taaacgatgc tcagattcag atgccaaaaa caatgaaccc aggtgaggat ctgacatcta   1860
aaacttttaa agttgcagat gctatcacaa cagttaattt agcaacagat agttcggttg   1920
cagttaaaca taatgtaggt gaagacccta attcaacatt atctggtata gtttacgttg   1980
accgaatcga attcatccca gtagatgaga catatgaagc ggaa                    2024
```

<210> SEQ ID NO 43
<211> LENGTH: 2012
<212> TYPE: DNA
<213> ORGANISM: Bacillus thuringiensis
<220> FEATURE:
<221> NAME/KEY: misc_feature
<223> OTHER INFORMATION: Sequence_59 of Figures 16, 17 and 18

<400> SEQUENCE: 43

```
caaataatca aaatgaatat gaaattatag atgcgacacc ttctacttct gtatccaatg     60
attctaacag ataccctttt gcgaatgagc caacaaatgc gctacaaaat atggattata    120
aagattattt aaaaatgtct gcgggaaatg ctagtgaata ccctggttca cctgaagtac    180
ttgttagcgg acaagatgca gctaaggccg caattgatat agtaggtaaa ttactatcag    240
gtttaggggt cccatttgtt gggccgatag tgagtcttta tactcaactt attgatattc    300
tgtggccttc aggggaaaag agtcaatggg aaatttttat ggaacaagta gaagaactca    360
ttaatcaaaa aatagcagaa tatgcaagga ataaagcgct ttcggaatta gaaggattag    420
gtaataatta ccaattatat ctaactgcgc ttgaagaatg ggaagaaaat ccatttcgac    480
gaggttttcg acgaggtgcc ttacgagatg tgcgaaatcg atttgaaatc ctggatagtt    540
tatttacgca atatatgcca tcttttagag tgacaaattt tgaagtacca ttccttactg    600
tatatgcaat ggcagccaac cttcatttac tgttattaaa ggacgcgtca atttttggag    660
aagaatgggg atggtcaaca actactatta ataactatta tgatcgtcaa atgaaactta    720
ctgcagaata ttctgatcac tgtgtaaagt ggtatgaaac tggtttagca aaattaaaag    780
gcacgagcgc taaacaatgg gttgactata accaattccg tagagaaatg acactggcgg    840
ttttagatgt tgttgcatta ttcccaaatt atgacacaat aacgtaccca atggaaacga    900
aagcacaact aacaagggaa gtatatacag atccactggg cgcggtaaac gtgtcttcaa    960
ttggttcctg gtatgacaaa gcaccttctt tcggagtgat agaatcatcc gttattcgac   1020
caccccatgt atttgattat ataacgggac tcacagtgta tacacaatca agaagcattt   1080
cttccgctcg ctatataaga cattgggctg gtcatcaaat aagctaccat cgtgtcagta   1140
ggggtagtaa tcttcaacaa atgtatggaa ctaatcaaaa tctacacagc actagtacct   1200
ttgattttac gaattatgat atttacaaga ctctatcaaa ggatgcagta ctccttgata   1260
ttgtttaccc tggttatacg tatatatttt ttggaatgcc agaagtcgag tttttcatgg   1320
taaaccaatt gaataatacc agaaagacgt taaagtataa tccagtttcc aaagatatta   1380
tagcgagtac aagagattcg gaattagaat tacctccaga aacttcagat caaccaaatt   1440
atgagtcata tagccataga ttatgtcata tcacaagtat tcccgcgacg ggtaacacta   1500
```

```
ccggattagt acctgtattt tcttggacac atcgaagtgc agatttaaac aatacaatat   1560
attcagataa aatcactcaa attccggccg ttaaatgttg ggataattta ccgtttgttc   1620
cagtggtaaa aggaccagga catacaggag ggatttatt acagtataat agaagtactg    1680
gttctgtagg aaccttattt ctagctcgat atggcctagc attagaaaaa gcagggaaat   1740
atcgtgtaag actgagatat gctactgatg cagatattgt attgcatgta aacgatgctc   1800
agattcagat gccaaaaaca atgaacccag gtgaggatct gacatctaaa acttttaaag   1860
ttgcagatgc tatcacaaca gttaatttag caacagatag ttcggttgca gttaaacata   1920
atgtaggtga agaccctaat tcaacattat ctggtatagt ttacgttgac cgaatcgaat   1980
tcatcccagt agatgagaca tatgaagcgg aa                                 2012
```

<210> SEQ ID NO 44
<211> LENGTH: 2012
<212> TYPE: DNA
<213> ORGANISM: Bacillus thuringiensis
<220> FEATURE:
<221> NAME/KEY: misc_feature
<223> OTHER INFORMATION: Sequence_61 of Figures 16, 17 and 18

<400> SEQUENCE: 44

```
caaataatca aaatgaatat gaaattatag atgcgacacc ttctacttct gtatccaatg     60
attctaacag atacccttt gcgaatgagc caacaaatgc gctacaaaat atggattata    120
aagattattt aaaaatgtct gcgggaaatg ctagtgaata ccctggttca cctgaagtac   180
ttgttagcgg acaagatgca gctaaggccg caattgatat agtaggtaaa ttactatcag   240
gtttaggggt cccatttgtt gggccgatag tgagtcttta tactcaactt attgatattc   300
tgtggccttc aggggaaaag agtcaatggg aaatttttat ggaacaagta gaagaactca   360
ttaatcaaaa aatagcagaa tatgcaagga ataaagcgct ttcggaatta gaaggattag   420
gtaataatta ccaattatat ctaactgcgc ttgaagaatg ggaagaaaat ccatttcgac   480
gaggttttcg acgaggtgcc ttacgagatg tgcgaaatcg atttgaaatc ctggatagtt   540
tatttacgca atatatgcca tcttttagag tgacaaattt tgaagtacca ttccttactg   600
tatatgcaat ggcagccaac cttcatttac tgttattaaa ggacgcgtca atttttggag   660
aagaatgggg atggtcaaca actactatta ataacgtggt ggatcgtcaa atgaaactta   720
ctgcagaata ttctgatcac tgtgtaaagt ggtatgaaac tggtttagca aaattaaaag   780
gcacgagcgc taaacaatgg gttgactata accaattccg tagagaaatg acactggcgg   840
ttttagatgt tgttgcatta ttcccaaatt atgacacaat aacgtaccca atagaaacga   900
aagcacaact aacaagggaa gtatatacag atccactggg cgcggtaaac gtgtcttcaa   960
ttggttcctg gtatgacaaa gcaccttctt tcggagtgat agaatcatcc gttattcgac  1020
caccccatgt atttgattat ataacgggac tcacagtgta tacacaatca agaagcattt  1080
cttccgctcg ctatataaga cattgggctg gtcatcaaat aagctaccat cgtgtcagta  1140
ggggtagtaa tcttcaacaa atgtatggaa ctaatcaaaa tctacacagc actagtacct  1200
ttgattttac gaattatgat atttacaaga ctctatcaaa ggatgcagta ctccttgata  1260
ttgtttaccc tggttatacg tatatatttt ttggaatgcc agaagtcgag tttttcatgg  1320
taaaccaatt gaataatacc agaaagacgt taaagtataa tccagtttcc aaagatatta  1380
tagcgagtac aagagattcg gaattagaat tacctccaga aacttcagat caaccaaatt  1440
atgagtcata tagccataga ttatgtcata tcacaagtat tcccgcgacg ggtaacacta  1500
```

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt acagtataat agaagtactg   1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca gttaatttag caacagatag ttcggttgca gttaaacata   1920

atgtaggtga agaccctaat tcaacattat ctggtatagt ttacgttgac cgaatcgaat   1980

tcatcccagt agatgagaca tatgaagcgg aa                                 2012
```

<210> SEQ ID NO 45
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_67 of Figures 16, 17 and 18

<400> SEQUENCE: 45

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgac    480

gaggttttcg acgaggtgcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataactatta tgatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacacg cacgtaccca atggaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt  acagtataat agaagtactg   1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca gtaaatttag caacagatag ttcggtagca gtgaaacata   1920

atttaggtga agaccctaat tcaacattat ctggtatagt ttacgttgac cgaatcgaat   1980

tcatcccagt agatgagaca tatgaagcgg aataa                              2015


<210> SEQ ID NO 46
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_69 of Figures 16, 17 and 18

<400> SEQUENCE: 46

caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

caagaaatgg ttcccgggcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataactatta tgatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacacg cacgtaccca atggaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

-continued

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt acagtataat agaagtactg    1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca gtaaatttag caacagatag ttcggtagca gtgaaacata   1920

atttaggtga agaccctaat tcaacattat ctggtatagt ttacgttgac cgaatcgaat   1980

tcatcccagt agatgagaca tatgaagcgg aataa                              2015
```

<210> SEQ ID NO 47
<211> LENGTH: 2021
<212> TYPE: DNA
<213> ORGANISM: Bacillus thuringiensis
<220> FEATURE:
<221> NAME/KEY: misc_feature
<223> OTHER INFORMATION: Sequence_71 of Figures 16, 17 and 18

<400> SEQUENCE: 47

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgaa    480

gtcgaggttt tcgaagtcga ggtccagcct tacgagatgt gcgaaatcga tttgaaatcc    540

tggatagttt atttacgcaa tatatgccat cttttagagt gacaaatttt gaagtaccat    600

tccttactgt atatgcaatg gcagccaacc ttcatttact gttattaaag gacgcgtcaa    660

tttttggaga agaatgggga tggtcaacaa ctactattaa taactattat gatcgtcaaa    720

tgaaacttac tgcagaatat tctgatcact gtgtaaagtg gtatgaaact ggtttagcaa    780

aattaaaagg cacgagcgct aaacaatggg ttgactataa ccaattccgt agagaaatga    840

cactggcggt tttagatgtt gttgcattat tcccaaatta tgacacacgc acgtacccaa    900

tggaaacgaa agcacaacta acaagggaag tatatacaga tccactgggc gcggtaaacg    960

tgtcttcaat tggttcctgg tatgacaaag caccttcttt cggagtgata gaatcatccg   1020

ttattcgacc accccatgta tttgattata taacgggact cacagtgtat acacaatcaa   1080

gaagcatttc ttccgctcgc tatataagac attgggctgg tcatcaaata agctaccatc   1140

gtgtcagtag ggtagtaat cttcaacaaa tgtatggaac taatcaaaat ctacacagca    1200

ctagtacctt tgattttacg aattatgata tttacaagac tctatcaaag gatgcagtac   1260

tccttgatat tgtttaccct ggttatacgt atatattttt tggaatgcca gaagtcgagt   1320

ttttcatggt aaaccaattg aataatacca gaaagacgtt aaagtataat ccagtttcca   1380

aagatattat agcgagtaca agagattcgg aattagaatt acctccagaa acttcagatc   1440

aaccaaatta tgagtcatat agccatagat tatgtcatat cacaagtatt cccgcgacgg   1500
```

```
gtaacactac cggattagta cctgtatttt cttggacaca tcgaagtgca gatttaaaca   1560
atacaatata ttcagataaa atcactcaaa ttccggccgt taaatgttgg gataatttac   1620
cgtttgttcc agtggtaaaa ggaccaggac atacaggagg ggatttatta cagtataata   1680
gaagtactgg ttctgtagga accttatttc tagctcgata tggcctagca ttagaaaaag   1740
cagggaaata tcgtgtaaga ctgagatatg ctactgatgc agatattgta ttgcatgtaa   1800
acgatgctca gattcagatg ccaaaaacaa tgaacccagg tgaggatctg acatctaaaa   1860
cttttaaagt tgcagatgct atcacaacag ttaatttagc aacagatagt tcggttgcag   1920
ttaaacataa tttaggtgaa gaccctaatt caacattatc tggtatagtt tacgttgacc   1980
gaatcgaatt catcccagta gatgagacat atgaagcgga a                       2021
```

<210> SEQ ID NO 48
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_73 of Figures 16, 17 and 18

<400> SEQUENCE: 48

```
caaataatca aaatgaatat gaaattatag atgcgacacc ttctacttct gtatccaatg     60
attctaacag ataccctttt gcgaatgagc caacaaatgc gctacaaaat atggattata    120
aagattattt aaaaatgtct gcgggaaatg ctagtgaata ccctggttca cctgaagtac    180
ttgttagcgg acaagatgca gctaaggccg caattgatat agtaggtaaa ttactatcag    240
gtttaggggt cccatttgtt gggccgatag tgagtcttta tactcaactt attgatattc    300
tgtggccttc aggggaaaag agtcaatggg aaatttttat ggaacaagta gaagaactca    360
ttaatcaaaa aatagcagaa tatgcaagga ataaagcgct ttcggaatta gaaggattag    420
gtaataatta ccaattatat ctaactgcgc ttgaagaatg ggaagaaaat ccatttcgaa    480
gtcgaggttt tcgaagtcga ggtgccttac gagatgtgcg aaatcgattt gaaatcctgg    540
atagtttatt tacgcaatat atgccatctt ttagagtgac aaattttgaa gtaccattcc    600
ttactgtata tgcaatggca gccaaccttc atttactgtt attaaaggac gcgtcaattt    660
ttggagaaga atggggatgg tcaacaacta ctattaataa ctattatgat cgtcaaatga    720
aacttactgc agaatattct gatcactgtg taaagtggta tgaaactggt ttagcaaaat    780
taaaaggcac gagcgctaaa caatgggttg actataacca attccgtaga gaaatgacac    840
tggcggtttt agatgttgtt gcattattcc caaattatga cacacgcacg tacccaatgg    900
aaacgaaagc acaactaaca agggaagtat atacagatcc actgggcgcg gtaaacgtgt    960
cttcaattgg ttcctggtat gacaaagcac cttctttcgg agtgatagaa tcatccgtta   1020
ttcgaccacc ccatgtattt gattatataa cgggactcac agtgtataca caatcaagaa   1080
gcatttcttc cgctcgctat ataagacatt gggctggtca tcaaataagc taccatcgtg   1140
tcagtagggg tagtaatctt caacaaatgt atggaactaa tcaaaatcta cacagcacta   1200
gtacctttga ttttacgaat tatgatattt acaagactct atcaaaggat gcagtactcc   1260
ttgatattgt ttaccctggt tatacgtata tatttttgg aatgccagaa gtcgagtttt   1320
tcatggtaaa ccaattgaat aataccagaa agacgttaaa gtataatcca gtttccaaag   1380
atattatagc gagtacaaga gattcggaat tagaattacc tccagaaact tcagatcaac   1440
caaattatga gtcatatagc catagattat gtcatatcac aagtattccc gcgacgggta   1500
```

```
acactaccgg attagtacct gtattttctt ggacacatcg aagtgcagat ttaaacaata   1560

caatatattc agataaaatc actcaaattc cggccgttaa atgttgggat aatttaccgt   1620

ttgttccagt ggtaaaagga ccaggacata caggaggga tttattacag tataatagaa    1680

gtactggttc tgtaggaacc ttatttctag ctcgatatgg cctagcatta gaaaaagcag   1740

ggaaatatcg tgtaagactg agatatgcta ctgatgcaga tattgtattg catgtaaacg   1800

atgctcagat tcagatgcca aaaacaatga acccaggtga ggatctgaca tctaaaactt   1860

ttaaagttgc agatgctatc acaacagtta atttagcaac agatagttcg gttgcagtta   1920

aacataattt aggtgaagac cctaattcaa cattatctgg tatagtttac gttgaccgaa   1980

tcgaattcat cccagtagat gagacatatg aagcggaa                           2018
```

<210> SEQ ID NO 49
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_75 of Figures 16, 17 and 18

<400> SEQUENCE: 49

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

cccggtttcg aagtcgaggt gccttacgag atgtgcgaaa tcgatttgaa atcctggata    540

gtttatttac gcaatatatg ccatctttta gagtgacaaa ttttgaagta ccattcctta    600

ctgtatatgc aatggcagcc aaccttcatt tactgttatt aaaggacgcg tcaatttttg    660

gagaagaatg ggatggtca acaactacta ttaataacta ttatgatcgt caaatgaaac     720

ttactgcaga atattctgat cactgtgtaa agtggtatga aactggttta gcaaaattaa    780

aaggcacgag cgctaaacaa tggttgact ataaccaatt ccgtagagaa atgacactgg     840

cggttttaga tgttgttgca ttattcccaa attatgacac acgcacgtac ccaatggaaa    900

cgaaagcaca actaacaagg gaagtatata cagatccact gggcgcggta aacgtgtctt    960

caattggttc ctggtatgac aaagcacctt ctttcggagt gatagaatca tccgttattc   1020

gaccacccca tgtatttgat tatataacgg gactcacagt gtatacacaa tcaagaagca   1080

tttcttccgc tcgctatata agacattggg ctggtcatca aataagctac catcgtgtca   1140

gtaggggtag taatcttcaa caaatgtatg gaactaatca aaatctacac agcactagta   1200

cctttgattt tacgaattat gatatttaca agactctatc aaaggatgca gtactccttg   1260

atattgttta ccctggttat acgtatatat tttttggaat gccagaagtc gagtttttca   1320

tggtaaacca attgaataat accagaaaga cgttaaagta taatccagtt tccaaagata   1380

ttatagcgag tacaagagat tcggaattag aattacctcc agaaacttca gatcaaccaa   1440

attatgagtc atatagccat agattatgtc atatcacaag tattcccgcg acgggtaaca   1500
```

ctaccggatt agtacctgta ttttcttgga cacatcgaag tgcagattta aacaatacaa 1560
tatattcaga taaaatcact caaattccgg ccgttaaatg ttgggataat ttaccgtttg 1620
ttccagtggt aaaaggacca ggacatacag gaggggattt attacagtat aatagaagta 1680
ctggttctgt aggaacctta tttctagctc gatatggcct agcattagaa aaagcaggga 1740
aatatcgtgt aagactgaga tatgctactg atgcagatat tgtattgcat gtaaacgatg 1800
ctcagattca gatgccaaaa acaatgaacc caggtgagga tctgacatct aaaactttta 1860
aagttgcaga tgctatcaca acagttaatt tagcaacaga tagttcggtt gcagttaaac 1920
ataatttagg tgaagaccct aattcaacat tatctggtat agtttacgtt gaccgaatcg 1980
aattcatccc agtagatgag acatatgaag cggaa 2015

<210> SEQ ID NO 50
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_77 of Figures 16, 17 and 18

<400> SEQUENCE: 50
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaatttttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccaaatggtt 480
cccggtttcg aagtcgaggt ccagccttac gagatgtgcg aaatcgattt gaaatcctgg 540
atagtttatt tacgcaatat atgccatctt ttagagtgac aaattttgaa gtaccattcc 600
ttactgtata tgcaatggca gccaaccttc atttactgtt attaaaggac gcgtcaattt 660
ttggagaaga atggggatgg tcaacaacta ctattaataa ctattatgat cgtcaaatga 720
aacttactgc agaatattct gatcactgtg taaagtggta tgaaactggt ttagcaaaat 780
taaaaggcac gagcgctaaa caatgggttg actataacca attccgtaga gaaatgacac 840
tggcggtttt agatgttgtt gcattattcc caaattatga cacacgcacg tacccaatgg 900
aaacgaaagc acaactaaca agggaagtat atacagatcc actgggcgcg gtaaacgtgt 960
cttcaattgg ttcctggtat gacaaagcac cttctttcgg agtgatagaa tcatccgtta 1020
ttcgaccacc ccatgtattt gattatataa cgggactcac agtgtataca caatcaagaa 1080
gcatttcttc cgctcgctat ataagacatt gggctggtca tcaaataagc taccatcgtg 1140
tcagtagggg tagtaatctt caacaaatgt atggaactaa tcaaaatcta cacagcacta 1200
gtacctttga ttttacgaat tatgatattt acaagactct atcaaaggat gcagtactcc 1260
ttgatattgt ttaccctggt tatacgtata tatttttgg aatgccagaa gtcgagtttt 1320
tcatggtaaa ccaattgaat aataccagaa agacgttaaa gtataatcca gtttccaaag 1380
atattatagc gagtacaaga gattcggaat tagaattacc tccagaaact tcagatcaac 1440
caaattatga gtcatatagc catagattat gtcatatcac aagtattccc gcgacgggta 1500
acactaccgg attagtacct gtattttctt ggacacatcg aagtgcagat ttaaacaata 1560
caatatattc agataaaatc actcaaattc cggccgttaa atgttgggat aatttaccgt 1620
ttgttccagt ggtaaaagga ccaggacata caggagggga tttattacag tataatagaa 1680
gtactggttc tgtaggaacc ttatttctag ctcgatatgg cctagcatta gaaaaagcag 1740
ggaaatatcg tgtaagactg agatatgcta ctgatgcaga tattgtattg catgtaaacg 1800
atgctcagat tcagatgcca aaaacaatga acccaggtga ggatctgaca tctaaaactt 1860
ttaaagttgc agatgctatc acaacagtta atttagcaac agatagttcg gttgcagtta 1920
aacataattt aggtgaagac cctaattcaa cattatctgg tatagtttac gttgaccgaa 1980
tcgaattcat cccagtagat gagacatatg aagcggaa 2018

<210> SEQ ID NO 51
<211> LENGTH: 2018
<212> TYPE: DNA
<213> ORGANISM: Bacillus thuringiensis
<220> FEATURE:
<221> NAME/KEY: misc_feature
<223> OTHER INFORMATION: Sequence_79 of Figures 16, 17 and 18

<400> SEQUENCE: 51
caaataatca aaatgaatat gaaattatag atgcgacacc ttctacttct gtatccaatg 60
attctaacag ataccctttt gcgaatgagc caacaaatgc gctacaaaat atggattata 120
aagattattt aaaaatgtct gcgggaaatg ctagtgaata ccctggttca cctgaagtac 180
ttgttagcgg acaagatgca gctaaggccg caattgatat agtaggtaaa ttactatcag 240
gtttaggggt cccatttgtt gggccgatag tgagtcttta tactcaactt attgatattc 300
tgtggccttc aggggaaaag agtcaatggg aaattttat ggaacaagta gaagaactca 360
ttaatcaaaa aatagcagaa tatgcaagga ataaagcgct ttcggaatta gaaggattag 420
gtaataatta ccaattatat ctaactgcgc ttgaagaatg ggaagaaaat ccatttcgaa 480
gtcgaggtcc aaatggttcc cgggccttac gagatgtgcg aaatcgattt gaaatcctgg 540
atagtttatt tacgcaatat atgccatctt ttagagtgac aaattttgaa gtaccattcc 600
ttactgtata tgcaatggca gccaaccttc atttactgtt attaaaggac gcgtcaattt 660
ttggagaaga atggggatgg tcaacaacta ctattaataa ctattatgat cgtcaaatga 720
aacttactgc agaatattct gatcactgtg taaagtggta tgaaactggt ttagcaaaat 780
taaaaggcac gagcgctaaa caatgggttg actataacca attccgtaga gaaatgacac 840
tggcggtttt agatgttgtt gcattattcc caaattatga cacacgcacg tacccaatgg 900
aaacgaaagc acaactaaca agggaagtat atacagatcc actgggcgcg gtaaacgtgt 960
cttcaattgg ttcctggtat gacaaagcac cttctttcgg agtgatagaa tcatccgtta 1020
ttcgaccacc ccatgtattt gattatataa cgggactcac agtgtataca caatcaagaa 1080
gcatttcttc cgctcgctat ataagacatt gggctggtca tcaaataagc taccatcgtg 1140
tcagtagggg tagtaatctt caacaaatgt atggaactaa tcaaaatcta cacagcacta 1200
gtacctttga ttttacgaat tatgatattt acaagactct atcaaaggat gcagtactcc 1260
ttgatattgt ttaccctggt tatacgtata tattttttgg aatgccagaa gtcgagtttt 1320
tcatggtaaa ccaattgaat aataccagaa agacgttaaa gtataatcca gtttccaaag 1380
atattatagc gagtacaaga gattcggaat tagaattacc tccagaaact tcagatcaac 1440
caaattatga gtcatatagc catagattat gtcatatcac aagtattccc gcgacgggta 1500

```
acactaccgg attagtacct gtattttctt ggacacatcg aagtgcagat ttaaacaata   1560

caatatattc agataaaatc actcaaattc cggccgttaa atgttgggat aatttaccgt   1620

ttgttccagt ggtaaaagga ccaggacata caggaggga tttattacag tataatagaa   1680

gtactggttc tgtaggaacc ttatttctag ctcgatatgg cctagcatta gaaaaagcag   1740

ggaaatatcg tgtaagactg agatatgcta ctgatgcaga tattgtattg catgtaaacg   1800

atgctcagat tcagatgcca aaaacaatga acccaggtga ggatctgaca tctaaaactt   1860

ttaaagttgc agatgctatc acaacagtta atttagcaac agatagttcg gttgcagtta   1920

aacataattt aggtgaagac cctaattcaa cattatctgg tatagtttac gttgaccgaa   1980

tcgaattcat cccagtagat gagacatatg aagcggaa                           2018
```

<210> SEQ ID NO 52
<211> LENGTH: 2015
<212> TYPE: DNA
<213> ORGANISM: Bacillus thuringiensis
<220> FEATURE:
<221> NAME/KEY: misc_feature
<223> OTHER INFORMATION: Sequence_81 of Figures 16, 17 and 18

<400> SEQUENCE: 52

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccaaatggtt    480

cccggtttcg aagtcgacaa gccttacgag atgtgcgaaa tcgatttgaa atcctggata    540

gtttatttac gcaatatatg ccatctttta gagtgacaaa ttttgaagta ccattcctta    600

ctgtatatgc aatggcagcc aaccttcatt tactgttatt aaaggacgcg tcaatttttg    660

gagaagaatg ggatggtca acaactacta ttaataacta ttatgatcgt caaatgaaac    720

ttactgcaga atattctgat cactgtgtaa agtggtatga aactggttta gcaaaattaa    780

aaggcacgag cgctaaacaa tggttgact ataaccaatt ccgtagagaa atgacactgg    840

cggttttaga tgttgttgca ttattcccaa attatgacac acgcacgtac ccaatggaaa    900

cgaaagcaca actaacaagg gaagtatata cagatccact gggcgcggta aacgtgtctt    960

caattggttc ctggtatgac aaagcacctt ctttcggagt gatagaatca tccgttattc   1020

gaccacccca tgtatttgat tatataacgg gactcacagt gtatacacaa tcaagaagca   1080

tttcttccgc tcgctatata agacattggg ctggtcatca aataagctac catcgtgtca   1140

gtaggggtag taatcttcaa caaatgtatg gaactaatca aaatctacac agcactagta   1200

cctttgattt tacgaattat gatatttaca agactctatc aaaggatgca gtactccttg   1260

atattgttta ccctggttat acgtatatat tttttggaat gccagaagtc gagtttttca   1320

tggtaaacca attgaataat accagaaaga cgttaaagta taatccagtt tccaaagata   1380

ttatagcgag tacaagagat tcggaattag aattacctcc agaaacttca gatcaaccaa   1440

attatgagtc atatagccat agattatgtc atatcacaag tattcccgcg acgggtaaca   1500
```

```
ctaccggatt agtacctgta ttttcttgga cacatcgaag tgcagattta aacaatacaa   1560

tatattcaga taaaatcact caaattccgg ccgttaaatg ttgggataat ttaccgtttg   1620

ttccagtggt aaaaggacca ggacatacag gaggggattt attacagtat aatagaagta   1680

ctggttctgt aggaacctta tttctagctc gatatggcct agcattagaa aaagcaggga   1740

aatatcgtgt aagactgaga tatgctactg atgcagatat tgtattgcat gtaaacgatg   1800

ctcagattca gatgccaaaa acaatgaacc caggtgagga tctgacatct aaaactttta   1860

aagttgcaga tgctatcaca acagttaatt tagcaacaga tagttcggtt gcagttaaac   1920

ataatttagg tgaagaccct aattcaacat tatctggtat agtttacgtt gaccgaatcg   1980

aattcatccc agtagatgag acatatgaag cggaa                             2015
```

<210> SEQ ID NO 53
<211> LENGTH: 2024
<212> TYPE: DNA
<213> ORGANISM: Bacillus thuringiensis
<220> FEATURE:
<221> NAME/KEY: misc_feature
<223> OTHER INFORMATION: Sequence_83 of Figures 16, 17 and 18

<400> SEQUENCE: 53

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgaa    480

gtcgaggtag tttaaatggt tcccggccag ccttacgaga tgtgcgaaat cgatttgaaa    540

tcctggatag tttatttacg caatatatgc catcttttag agtgacaaat tttgaagtac    600

cattccttac tgtatatgca atggcagcca accttcattt actgttatta aaggacgcgt    660

caatttttgg agaagaatgg ggatggtcaa caactactat taataactat tatgatcgtc    720

aaatgaaact tactgcagaa tattctgatc actgtgtaaa gtggtatgaa actggtttag    780

caaaattaaa aggcacgagc gctaaacaat gggttgacta taaccaattc cgtagagaaa    840

tgacactggc ggttttagat gttgttgcat tattcccaaa ttatgacaca cgcacgtacc    900

caatggaaac gaaagcacaa ctaacaaggg aagtatatac agatccactg ggcgcggtaa    960

acgtgtcttc aattggttcc tggtatgaca aagcaccttc tttcggagtg atagaatcat   1020

ccgttattcg accaccccat gtatttgatt atataacggg actcacagtg tatacacaat   1080

caagaagcat ttcttccgct cgctatataa gacattgggc tggtcatcaa ataagctacc   1140

atcgtgtcag taggggtagt aatcttcaac aaatgtatgg aactaatcaa aatctacaca   1200

gcactagtac ctttgatttt acgaattatg atatttacaa gactctatca aaggatgcag   1260

tactccttga tattgtttac cctggttata cgtatatatt ttttggaatg ccagaagtcg   1320

agtttttcat ggtaaaccaa ttgaataata ccagaaagac gttaaagtat aatccagttt   1380

ccaaagatat tatagcgagt acaagagatt cggaattaga attacctcca gaaacttcag   1440

atcaaccaaa ttatgagtca tatagccata gattatgtca tatcacaagt attcccgcga   1500
```

```
cgggtaacac taccggatta gtacctgtat tttcttggac acatcgaagt gcagatttaa   1560

acaatacaat atattcagat aaaatcactc aaattccggc cgttaaatgt tgggataatt   1620

taccgtttgt tccagtggta aaaggaccag gacatacagg aggggattta ttacagtata   1680

atagaagtac tggttctgta ggaaccttat ttctagctcg atatggccta gcattagaaa   1740

aagcagggaa atatcgtgta agactgagat atgctactga tgcagatatt gtattgcatg   1800

taaacgatgc tcagattcag atgccaaaaa caatgaaccc aggtgaggat ctgacatcta   1860

aaacttttaa agttgcagat gctatcacaa cagttaattt agcaacagat agttcggttg   1920

cagttaaaca taatttaggt gaagacccta attcaacatt atctggtata gtttacgttg   1980

accgaatcga attcatccca gtagatgaga catatgaagc ggaa                    2024
```

<210> SEQ ID NO 54
<211> LENGTH: 2012
<212> TYPE: DNA
<213> ORGANISM: Bacillus thuringiensis
<220> FEATURE:
<221> NAME/KEY: misc_feature
<223> OTHER INFORMATION: Sequence_91 of Figures 16, 17 and 18

<400> SEQUENCE: 54

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgac    480

gaggttttcg acgaggtgcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataactatta tgatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacaat aacgtaccca atggaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

```
ccggattagt acctgtattt tcttggacac atcgaagtgc agatttaaac aatacaatat   1560

attcagataa aatcactcaa attccggccg ttaaatgttg ggataattta ccgtttgttc   1620

cagtggtaaa aggaccagga catacaggag ggatttatt acagtataat agaagtactg   1680

gttctgtagg aaccttattt ctagctcgat atggcctagc attagaaaaa gcagggaaat   1740

atcgtgtaag actgagatat gctactgatg cagatattgt attgcatgta aacgatgctc   1800

agattcagat gccaaaaaca atgaacccag gtgaggatct gacatctaaa acttttaaag   1860

ttgcagatgc tatcacaaca gttaatttag caacagatag ttcggttgca gttaaacata   1920

atttaggtga agaccctaat tcaacattat ctggtatagt ttacgttgac cgaatcgaat   1980

tcatcccagt agatgagaca tatgaagcgg aa                                 2012
```

<210> SEQ ID NO 55
<211> LENGTH: 2012
<212> TYPE: DNA
<213> ORGANISM: Bacillus thuringiensis
<220> FEATURE:
<221> NAME/KEY: misc_feature
<223> OTHER INFORMATION: Sequence_93 of Figures 16, 17 and 18

<400> SEQUENCE: 55

```
caaataatca aaatgaatat gaaattatag atgcgacacc ttctacttct gtatccaatg     60

attctaacag ataccctttt gcgaatgagc caacaaatgc gctacaaaat atggattata    120

aagattattt aaaaatgtct gcgggaaatg ctagtgaata ccctggttca cctgaagtac    180

ttgttagcgg acaagatgca gctaaggccg caattgatat agtaggtaaa ttactatcag    240

gtttaggggt cccatttgtt gggccgatag tgagtcttta tactcaactt attgatattc    300

tgtggccttc aggggaaaag agtcaatggg aaatttttat ggaacaagta gaagaactca    360

ttaatcaaaa aatagcagaa tatgcaagga ataaagcgct ttcggaatta gaaggattag    420

gtaataatta ccaattatat ctaactgcgc ttgaagaatg ggaagaaaat ccatttcgac    480

gaggttttcg acgaggtgcc ttacgagatg tgcgaaatcg atttgaaatc ctggatagtt    540

tatttacgca atatatgcca tcttttagag tgacaaattt tgaagtacca ttccttactg    600

tatatgcaat ggcagccaac cttcatttac tgttattaaa ggacgcgtca atttttggag    660

aagaatgggg atggtcaaca actactatta ataacgtggt ggatcgtcaa atgaaactta    720

ctgcagaata ttctgatcac tgtgtaaagt ggtatgaaac tggtttagca aaattaaaag    780

gcacgagcgc taaacaatgg gttgactata accaattccg tagagaaatg acactggcgg    840

ttttagatgt tgttgcatta ttcccaaatt atgacacaat aacgtaccca atagaaacga    900

aagcacaact aacaagggaa gtatatacag atccactggg cgcggtaaac gtgtcttcaa    960

ttggttcctg gtatgacaaa gcaccttctt tcggagtgat agaatcatcc gttattcgac   1020

caccccatgt atttgattat ataacgggac tcacagtgta tacacaatca agaagcattt   1080

cttccgctcg ctatataaga cattgggctg gtcatcaaat aagctaccat cgtgtcagta   1140

ggggtagtaa tcttcaacaa atgtatggaa ctaatcaaaa tctacacagc actagtacct   1200

ttgattttac gaattatgat atttacaaga ctctatcaaa ggatgcagta ctccttgata   1260

ttgtttaccc tggttatacg tatatatttt ttggaatgcc agaagtcgag tttttcatgg   1320

taaaccaatt gaataatacc agaaagacgt taaagtataa tccagtttcc aaagatatta   1380

tagcgagtac aagagattcg gaattagaat tacctccaga aacttcagat caaccaaatt   1440

atgagtcata tagccataga ttatgtcata tcacaagtat tcccgcgacg ggtaacacta   1500
```

```
ccggattagt acctgtattt tcttggacac atcgaagtgc agatttaaac aatacaatat      1560

attcagataa aatcactcaa attccggccg ttaaatgttg ggataattta ccgtttgttc      1620

cagtggtaaa aggaccagga catacaggag gggatttatt acagtataat agaagtactg      1680

gttctgtagg aaccttattt ctagctcgat atggcctagc attagaaaaa gcagggaaat      1740

atcgtgtaag actgagatat gctactgatg cagatattgt attgcatgta aacgatgctc      1800

agattcagat gccaaaaaca atgaacccag gtgaggatct gacatctaaa acttttaaag      1860

ttgcagatgc tatcacaaca gttaatttag caacagatag ttcggttgca gttaaacata      1920

atttaggtga agaccctaat tcaacattat ctggtatagt ttacgttgac cgaatcgaat      1980

tcatcccagt agatgagaca tatgaagcgg aa                                   2012
```

<210> SEQ ID NO 56
<211> LENGTH: 1169
<212> TYPE: PRT
<213> ORGANISM: Bacillus thuringiensis
<220> FEATURE:
<221> NAME/KEY: MISC_FEATURE
<223> OTHER INFORMATION: Cry8Ba1

<400> SEQUENCE: 56

```
Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Val Ser Glu Tyr Pro Gly Ser Pro Glu Val Phe Leu
    50                  55                  60

Ser Glu Gln Asp Ala Val Lys Ala Ala Ile Asp Ile Val Gly Lys Leu
65                  70                  75                  80

Leu Thr Gly Leu Gly Val Pro Phe Val Gly Pro Ile Val Ser Leu Tyr
                85                  90                  95

Thr Gln Leu Ile Asp Ile Leu Trp Pro Ser Lys Gln Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Met Ala Ala Asn Leu His Leu
        195                 200                 205

Leu Leu Leu Arg Asp Ala Ser Ile Phe Gly Glu Glu Trp Gly Leu Ser
    210                 215                 220

Thr Ser Thr Ile Asn Asn Tyr Tyr Asn Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Ser Ser Ala Lys Gln Trp Ile Asp Tyr Asn Gln Phe Arg
```

-continued

```
            260                 265                 270

Arg Glu Met Thr Leu Thr Val Leu Asp Val Val Ala Leu Phe Ser Asn
        275                 280                 285

Tyr Asp Thr Arg Thr Tyr Pro Leu Ala Thr Thr Ala Gln Leu Thr Arg
    290                 295                 300

Glu Val Tyr Thr Asp Pro Leu Gly Ala Val Asp Val Pro Asn Ile Gly
305                 310                 315                 320

Ser Trp Tyr Asp Lys Ala Pro Ser Phe Ser Glu Ile Glu Lys Ala Ala
                325                 330                 335

Ile Arg Pro Pro His Val Phe Asp Tyr Ile Thr Gly Leu Thr Val Tyr
            340                 345                 350

Thr Lys Lys Arg Ser Phe Thr Ser Asp Arg Tyr Met Arg Tyr Trp Ala
        355                 360                 365

Gly His Gln Ile Ser Tyr Lys His Ile Gly Thr Ser Ser Thr Phe Thr
    370                 375                 380

Gln Met Tyr Gly Thr Asn Gln Asn Leu Gln Ser Thr Ser Asn Phe Asp
385                 390                 395                 400

Phe Thr Asn Tyr Asp Ile Tyr Lys Thr Leu Ser Asn Gly Ala Val Leu
                405                 410                 415

Leu Asp Ile Val Tyr Pro Gly Tyr Thr Tyr Thr Phe Phe Gly Met Pro
            420                 425                 430

Glu Thr Glu Phe Phe Met Val Asn Gln Leu Asn Asn Thr Arg Lys Thr
        435                 440                 445

Leu Thr Tyr Lys Pro Ala Ser Lys Asp Ile Ile Asp Arg Thr Arg Asp
    450                 455                 460

Ser Glu Leu Glu Leu Pro Pro Glu Thr Ser Gly Gln Pro Asn Tyr Glu
465                 470                 475                 480

Ser Tyr Ser His Arg Leu Gly His Ile Thr Phe Ile Tyr Ser Ser Ser
                485                 490                 495

Thr Ser Thr Tyr Val Pro Val Phe Ser Trp Thr His Arg Ser Ala Asp
            500                 505                 510

Leu Thr Asn Thr Val Lys Ser Gly Glu Ile Thr Gln Ile Pro Gly Gly
        515                 520                 525

Lys Ser Ser Thr Ile Gly Arg Asn Thr Tyr Ile Ile Lys Gly Arg Gly
    530                 535                 540

Tyr Thr Gly Gly Asp Leu Val Ala Leu Thr Asp Arg Ile Gly Ser Cys
545                 550                 555                 560

Glu Phe Gln Met Ile Phe Pro Glu Ser Gln Arg Phe Arg Ile Arg Ile
                565                 570                 575

Arg Tyr Ala Ser Asn Glu Thr Ser Tyr Ile Ser Leu Tyr Gly Leu Asn
            580                 585                 590

Gln Ser Gly Thr Leu Lys Phe Asn Gln Thr Tyr Ser Asn Lys Asn Glu
        595                 600                 605

Asn Asp Leu Thr Tyr Asn Asp Phe Lys Tyr Ile Glu Tyr Pro Arg Val
    610                 615                 620

Ile Ser Val Asn Ala Ser Ser Asn Ile Gln Arg Leu Ser Ile Gly Ile
625                 630                 635                 640

Gln Thr Asn Thr Asn Leu Phe Ile Leu Asp Arg Ile Glu Phe Ile Pro
                645                 650                 655

Val Asp Glu Thr Tyr Glu Ala Glu Thr Asp Leu Glu Ala Ala Lys Lys
            660                 665                 670

Ala Val Asn Ala Leu Phe Thr Asn Thr Lys Asp Gly Leu Gln Pro Gly
        675                 680                 685
```

```
Val Thr Asp Tyr Glu Val Asn Gln Ala Ala Asn Leu Val Glu Cys Leu
    690                 695                 700

Ser Asp Asp Leu Tyr Pro Asn Glu Lys Arg Leu Leu Phe Asp Ala Val
705                 710                 715                 720

Arg Glu Ala Lys Arg Leu Ser Glu Ala Arg Asn Leu Leu Gln Asp Pro
                725                 730                 735

Asp Phe Gln Glu Ile Asn Gly Glu Asn Gly Trp Thr Ala Ser Thr Gly
            740                 745                 750

Ile Glu Val Ile Glu Gly Asp Ala Val Phe Lys Gly Arg Tyr Leu Arg
        755                 760                 765

Leu Pro Gly Ala Arg Glu Ile Asp Thr Glu Thr Tyr Pro Thr Tyr Leu
    770                 775                 780

Tyr Gln Lys Val Glu Glu Gly Val Leu Lys Pro Tyr Thr Arg Tyr Arg
785                 790                 795                 800

Leu Arg Gly Phe Val Gly Ser Ser Gln Gly Leu Glu Ile Tyr Thr Ile
                805                 810                 815

Arg His Gln Thr Asn Arg Ile Val Lys Asn Val Pro Asp Asp Leu Leu
            820                 825                 830

Pro Asp Val Pro Pro Val Asn Asn Asp Gly Arg Ile Asn Arg Cys Ser
        835                 840                 845

Glu Gln Lys Tyr Val Asn Ser Arg Leu Glu Val Glu Asn Arg Ser Gly
    850                 855                 860

Glu Ala His Glu Phe Ser Ile Pro Ile Asp Thr Gly Glu Leu Asp Tyr
865                 870                 875                 880

Asn Glu Asn Ala Gly Ile Trp Val Gly Phe Lys Ile Thr Asp Pro Glu
                885                 890                 895

Gly Tyr Ala Thr Leu Gly Asn Leu Glu Leu Val Glu Glu Gly Pro Leu
            900                 905                 910

Ser Gly Asp Ala Leu Glu Arg Leu Gln Lys Glu Glu Gln Gln Trp Lys
        915                 920                 925

Ile Gln Met Thr Arg Arg Arg Glu Glu Thr Asp Arg Arg Tyr Met Ala
    930                 935                 940

Ser Lys Gln Ala Val Asp Arg Leu Tyr Ala Asp Tyr Gln Asp Gln Gln
945                 950                 955                 960

Leu Asn Pro Asn Val Glu Ile Thr Asp Leu Thr Ala Ala Gln Asp Leu
                965                 970                 975

Ile Gln Ser Ile Pro Tyr Val Tyr Asn Glu Met Phe Pro Glu Ile Pro
            980                 985                 990

Gly Met Asn Tyr Thr Lys Phe Thr  Glu Leu Thr Asp Arg  Leu Gln Gln
        995                 1000                1005

Ala Trp  Gly Leu Tyr Asp Gln  Arg Asn Ala Ile Pro  Asn Gly Asp
    1010                1015                1020

Tyr Arg  Asn Glu Leu Ser Asn  Trp Asn Thr Thr Ser  Gly Val Asn
    1025                1030                1035

Val Gln  Gln Ile Asn His Thr  Ser Val Leu Val Ile  Pro Asn Trp
    1040                1045                1050

Asn Glu  Gln Val Ser Gln Lys  Phe Thr Val Gln Pro  Asn Gln Arg
    1055                1060                1065

Tyr Val  Leu Arg Val Thr Ala  Arg Lys Glu Gly Val  Gly Asn Gly
    1070                1075                1080

Tyr Val  Ser Ile Arg Asp Gly  Gly Asn Gln Ser Glu  Thr Leu Thr
    1085                1090                1095
```

-continued

Phe Ser Ala Ser Asp Tyr Asp Thr Asn Gly Met Tyr Asp Thr Gln
1100 1105 1110

Ala Ser Asn Thr Asn Gly Tyr Asn Thr Asn Ser Val Tyr Met Ile
1115 1120 1125

Lys Pro Ala Ile Ser Arg Lys Thr Val Asp Ile Ser Ser Val Tyr
1130 1135 1140

Asn Gln Met Trp Ile Glu Ile Ser Glu Thr Glu Gly Thr Phe Tyr
1145 1150 1155

Ile Glu Ser Val Glu Leu Ile Val Asp Val Glu
1160 1165

<210> SEQ ID NO 57
<211> LENGTH: 1169
<212> TYPE: PRT
<213> ORGANISM: Bacillus thuringiensis
<220> FEATURE:
<221> NAME/KEY: MISC_FEATURE
<223> OTHER INFORMATION: 50c_b_

<400> SEQUENCE: 57

Met Ser Pro Asn Asn Gln Asn Glu Tyr Glu Ile Ile Asp Ala Thr Pro
1 5 10 15

Ser Thr Ser Val Ser Asn Asp Ser Asn Arg Tyr Pro Phe Ala Asn Glu
20 25 30

Pro Thr Asn Ala Leu Gln Asn Met Asp Tyr Lys Asp Tyr Leu Lys Met
35 40 45

Ser Ala Gly Asn Val Ser Glu Tyr Pro Gly Ser Pro Glu Val Phe Leu
50 55 60

Ser Glu Gln Asp Ala Val Lys Ala Ala Ile Asp Ile Val Gly Lys Leu
65 70 75 80

Leu Thr Gly Leu Gly Val Pro Phe Val Gly Pro Ile Val Ser Leu Tyr
85 90 95

Thr Gln Leu Ile Asp Ile Leu Trp Pro Ser Lys Gln Lys Ser Gln Trp
100 105 110

Glu Ile Phe Met Glu Gln Val Glu Glu Leu Ile Asn Gln Lys Ile Ala
115 120 125

Glu Tyr Ala Arg Asn Lys Ala Leu Ser Glu Leu Glu Gly Leu Gly Asn
130 135 140

Asn Tyr Gln Leu Tyr Leu Thr Ala Leu Glu Glu Trp Lys Glu Asn Pro
145 150 155 160

Asn Gly Ser Arg Ala Leu Arg Asp Val Arg Asn Arg Phe Glu Ile Leu
165 170 175

Asp Ser Leu Phe Thr Gln Tyr Met Pro Ser Phe Arg Val Thr Asn Phe
180 185 190

Glu Val Pro Phe Leu Thr Val Tyr Thr Met Ala Ala Asn Leu His Leu
195 200 205

Leu Leu Leu Arg Asp Ala Ser Ile Phe Gly Glu Glu Trp Gly Leu Ser
210 215 220

Thr Ser Thr Ile Asn Asn Tyr Tyr Asn Arg Gln Met Lys Leu Thr Ala
225 230 235 240

Glu Tyr Ser Asp His Cys Val Lys Trp Tyr Glu Thr Gly Leu Ala Lys
245 250 255

Leu Lys Gly Ser Ser Ala Lys Gln Trp Ile Asp Tyr Asn Gln Phe Arg
260 265 270

Arg Glu Met Thr Leu Thr Val Leu Asp Val Val Ala Leu Phe Ser Asn
275 280 285

```
Tyr Asp Thr Arg Thr Tyr Pro Leu Ala Thr Thr Ala Gln Leu Thr Arg
    290                 295                 300

Glu Val Tyr Thr Asp Pro Leu Gly Ala Val Asp Val Pro Asn Ile Gly
305                 310                 315                 320

Ser Trp Tyr Asp Lys Ala Pro Ser Phe Ser Glu Ile Glu Lys Ala Ala
                325                 330                 335

Ile Arg Pro Pro His Val Phe Asp Tyr Ile Thr Gly Leu Thr Val Tyr
            340                 345                 350

Thr Lys Lys Arg Ser Phe Thr Ser Asp Arg Tyr Met Arg Tyr Trp Ala
        355                 360                 365

Gly His Gln Ile Ser Tyr Lys His Ile Gly Thr Ser Ser Thr Phe Thr
    370                 375                 380

Gln Met Tyr Gly Thr Asn Gln Asn Leu Gln Ser Thr Ser Asn Phe Asp
385                 390                 395                 400

Phe Thr Asn Tyr Asp Ile Tyr Lys Thr Leu Ser Asn Gly Ala Val Leu
                405                 410                 415

Leu Asp Ile Val Tyr Pro Gly Tyr Thr Tyr Thr Phe Phe Gly Met Pro
            420                 425                 430

Glu Thr Glu Phe Phe Met Val Asn Gln Leu Asn Asn Thr Arg Lys Thr
        435                 440                 445

Leu Thr Tyr Lys Pro Ala Ser Lys Asp Ile Ile Asp Arg Thr Arg Asp
    450                 455                 460

Ser Glu Leu Glu Leu Pro Pro Glu Thr Ser Gly Gln Pro Asn Tyr Glu
465                 470                 475                 480

Ser Tyr Ser His Arg Leu Gly His Ile Thr Phe Ile Tyr Ser Ser Ser
                485                 490                 495

Thr Ser Thr Tyr Val Pro Val Phe Ser Trp Thr His Arg Ser Ala Asp
            500                 505                 510

Leu Thr Asn Thr Val Lys Ser Gly Glu Ile Thr Gln Ile Pro Gly Gly
        515                 520                 525

Lys Ser Ser Thr Ile Gly Arg Asn Thr Tyr Ile Ile Lys Gly Arg Gly
    530                 535                 540

Tyr Thr Gly Gly Asp Leu Val Ala Leu Thr Asp Arg Ile Gly Ser Cys
545                 550                 555                 560

Glu Phe Gln Met Ile Phe Pro Glu Ser Gln Arg Phe Arg Ile Arg Ile
                565                 570                 575

Arg Tyr Ala Ser Asn Glu Thr Ser Tyr Ile Ser Leu Tyr Gly Leu Asn
            580                 585                 590

Gln Ser Gly Thr Leu Lys Phe Asn Gln Thr Tyr Ser Asn Lys Asn Glu
        595                 600                 605

Asn Asp Leu Thr Tyr Asn Asp Phe Lys Tyr Ile Glu Tyr Pro Arg Val
    610                 615                 620

Ile Ser Val Asn Ala Ser Ser Asn Ile Gln Arg Leu Ser Ile Gly Ile
625                 630                 635                 640

Gln Thr Asn Thr Asn Leu Phe Ile Leu Asp Arg Ile Glu Phe Ile Pro
                645                 650                 655

Val Asp Glu Thr Tyr Glu Ala Glu Thr Asp Leu Glu Ala Ala Lys Lys
            660                 665                 670

Ala Val Asn Ala Leu Phe Thr Asn Thr Lys Asp Gly Leu Gln Pro Gly
        675                 680                 685

Val Thr Asp Tyr Glu Val Asn Gln Ala Ala Asn Leu Val Glu Cys Leu
    690                 695                 700
```

-continued

```
Ser Asp Asp Leu Tyr Pro Asn Glu Lys Arg Leu Leu Phe Asp Ala Val
705                 710                 715                 720

Arg Glu Ala Lys Arg Leu Ser Glu Ala Arg Asn Leu Leu Gln Asp Pro
                725                 730                 735

Asp Phe Gln Glu Ile Asn Gly Glu Asn Gly Trp Thr Ala Ser Thr Gly
            740                 745                 750

Ile Glu Val Ile Glu Gly Asp Ala Val Phe Lys Gly Arg Tyr Leu Arg
        755                 760                 765

Leu Pro Gly Ala Arg Glu Ile Asp Thr Glu Thr Tyr Pro Thr Tyr Leu
    770                 775                 780

Tyr Gln Lys Val Glu Glu Gly Val Leu Lys Pro Tyr Thr Arg Tyr Arg
785                 790                 795                 800

Leu Arg Gly Phe Val Gly Ser Ser Gln Gly Leu Glu Ile Tyr Thr Ile
                805                 810                 815

Arg His Gln Thr Asn Arg Ile Val Lys Asn Val Pro Asp Asp Leu Leu
            820                 825                 830

Pro Asp Val Pro Pro Val Asn Asn Asp Gly Arg Ile Asn Arg Cys Ser
        835                 840                 845

Glu Gln Lys Tyr Val Asn Ser Arg Leu Glu Val Glu Asn Arg Ser Gly
    850                 855                 860

Glu Ala His Glu Phe Ser Ile Pro Ile Asp Thr Gly Glu Leu Asp Tyr
865                 870                 875                 880

Asn Glu Asn Ala Gly Ile Trp Val Gly Phe Lys Ile Thr Asp Pro Glu
                885                 890                 895

Gly Tyr Ala Thr Leu Gly Asn Leu Glu Leu Val Glu Glu Gly Pro Leu
            900                 905                 910

Ser Gly Asp Ala Leu Glu Arg Leu Gln Lys Glu Glu Gln Gln Trp Lys
        915                 920                 925

Ile Gln Met Thr Arg Arg Arg Glu Glu Thr Asp Arg Arg Tyr Met Ala
    930                 935                 940

Ser Lys Gln Ala Val Asp Arg Leu Tyr Ala Asp Tyr Gln Asp Gln Gln
945                 950                 955                 960

Leu Asn Pro Asn Val Glu Ile Thr Asp Leu Thr Ala Ala Gln Asp Leu
                965                 970                 975

Ile Gln Ser Ile Pro Tyr Val Tyr Asn Glu Met Phe Pro Glu Ile Pro
            980                 985                 990

Gly Met Asn Tyr Thr Lys Phe Thr  Glu Leu Thr Asp Arg  Leu Gln Gln
        995                 1000                1005

Ala Trp  Gly Leu Tyr Asp Gln  Arg Asn Ala Ile Pro  Asn Gly Asp
    1010                 1015                 1020

Tyr Arg  Asn Glu Leu Ser Asn  Trp Asn Thr Thr Ser  Gly Val Asn
    1025                 1030                 1035

Val Gln  Gln Ile Asn His Thr  Ser Val Leu Val Ile  Pro Asn Trp
    1040                 1045                 1050

Asn Glu  Gln Val Ser Gln Lys  Phe Thr Val Gln Pro  Asn Gln Arg
    1055                 1060                 1065

Tyr Val  Leu Arg Val Thr Ala  Arg Lys Glu Gly Val  Gly Asn Gly
    1070                 1075                 1080

Tyr Val  Ser Ile Arg Asp Gly  Gly Asn Gln Ser Glu  Thr Leu Thr
    1085                 1090                 1095

Phe Ser  Ala Ser Asp Tyr Asp  Thr Asn Gly Met Tyr  Asp Thr Gln
    1100                 1105                 1110

Ala Ser  Asn Thr Asn Gly Tyr  Asn Thr Asn Ser Val  Tyr Met Ile
```

```
    1115                1120                1125

Lys Pro  Ala Ile Ser Arg Lys  Thr Val Asp Ile Ser  Ser Val Tyr
    1130                1135                1140

Asn Gln  Met Trp Ile Glu Ile  Ser Glu Thr Glu Gly  Thr Phe Tyr
    1145                1150                1155

Ile Glu  Ser Val Glu Leu Ile  Val Asp Val Glu
    1160                1165


<210> SEQ ID NO 58
<211> LENGTH: 1206
<212> TYPE: PRT
<213> ORGANISM: Bacillus thuringiensis
<220> FEATURE:
<221> NAME/KEY: MISC_FEATURE
<223> OTHER INFORMATION: Cry8Bb1

<400> SEQUENCE: 58

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Glu Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Ala Met Ala Ala Asn Leu His Leu
        195                 200                 205

Leu Leu Leu Lys Asp Ala Ser Ile Phe Gly Glu Glu Trp Gly Trp Ser
    210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Ala Val Leu Asp Val Val Ala Leu Phe Pro Asn
        275                 280                 285

Tyr Asp Thr Arg Thr Tyr Pro Met Glu Thr Lys Ala Gln Leu Thr Arg
    290                 295                 300
```

-continued

```
Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Val Ser Arg Gly Ser Asn Leu Gln
    370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Tyr Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Lys Tyr Asn Pro Val Ser Lys Asp Ile Ile Ala Ser Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Asn Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Cys Trp Asp Asn Leu Pro Phe Val Pro Val Val Lys Gly Pro
    530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
                565                 570                 575

Gly Lys Tyr Arg Val Arg Leu Arg Tyr Ala Thr Asp Ala Asp Ile Val
            580                 585                 590

Leu His Val Asn Asp Ala Gln Ile Gln Met Pro Lys Thr Met Asn Pro
        595                 600                 605

Gly Glu Asp Leu Thr Ser Lys Thr Phe Lys Val Ala Asp Ala Ile Thr
    610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655

Ile Glu Phe Ile Pro Val Asp Glu Thr Tyr Glu Ala Glu Gln Asp Leu
            660                 665                 670

Glu Ala Ala Lys Lys Ala Val Asn Ala Leu Phe Thr Asn Thr Lys Asp
        675                 680                 685

Gly Leu Arg Pro Gly Val Thr Asp Tyr Glu Val Asn Gln Ala Ala Asn
    690                 695                 700

Leu Val Glu Cys Leu Ser Asp Asp Leu Tyr Pro Asn Glu Lys Arg Leu
705                 710                 715                 720

Leu Phe Asp Ala Val Arg Glu Ala Lys Arg Leu Ser Glu Ala Arg Asn
```

```
                725                 730                 735

Leu Leu Gln Asp Pro Asp Phe Gln Glu Ile Asn Gly Glu Asn Gly Trp
            740                 745                 750

Thr Ala Ser Thr Gly Ile Glu Val Ile Glu Gly Asp Ala Leu Phe Lys
        755                 760                 765

Gly Arg Tyr Leu Arg Leu Pro Gly Ala Arg Glu Ile Asp Thr Glu Thr
    770                 775                 780

Tyr Pro Thr Tyr Leu Tyr Gln Lys Val Glu Glu Gly Val Leu Lys Pro
785                 790                 795                 800

Tyr Thr Arg Tyr Arg Leu Arg Gly Phe Val Gly Ser Ser Gln Gly Leu
                805                 810                 815

Glu Ile Phe Thr Ile Arg His Gln Thr Asn Arg Ile Val Lys Asn Val
            820                 825                 830

Pro Asp Asp Leu Leu Pro Asp Val Ser Pro Val Asn Ser Asp Gly Ser
        835                 840                 845

Ile Asn Arg Cys Ser Glu Gln Lys Tyr Val Asn Ser Arg Leu Glu Val
    850                 855                 860

Glu Asn Arg Ser Gly Glu Ala His Glu Phe Ser Ile Pro Ile Asp Thr
865                 870                 875                 880

Gly Glu Ile Asp Tyr Asn Glu Asn Ala Gly Ile Trp Val Gly Phe Lys
                885                 890                 895

Ile Thr Asp Pro Glu Gly Tyr Ala Thr Leu Gly Asn Leu Glu Leu Val
            900                 905                 910

Glu Glu Gly Pro Leu Ser Gly Asp Ala Leu Glu Arg Leu Gln Arg Glu
        915                 920                 925

Glu Gln Gln Trp Lys Ile Gln Met Thr Arg Arg Arg Glu Glu Thr Asp
    930                 935                 940

Arg Arg Tyr Met Ala Ser Lys Gln Ala Val Asp Arg Leu Tyr Ala Asp
945                 950                 955                 960

Tyr Gln Asp Gln Gln Leu Asn Pro Asp Val Glu Ile Thr Asp Leu Thr
                965                 970                 975

Ala Ala Gln Asp Leu Ile Gln Ser Ile Pro Tyr Val Tyr Asn Glu Met
            980                 985                 990

Phe Pro Glu Ile Pro Gly Met Asn  Tyr Thr Lys Phe Thr  Glu Leu Thr
        995                 1000                1005

Asp Arg  Leu Gln Gln Ala Trp  Ser Leu Tyr Asp Gln  Arg Asn Ala
    1010                 1015                 1020

Ile Pro  Asn Gly Asp Phe Arg  Asn Gly Leu Ser Asn  Trp Asn Ala
    1025                 1030                 1035

Thr Pro  Gly Val Glu Val Gln  Gln Ile Asn His Thr  Ser Val Leu
    1040                 1045                 1050

Val Ile  Pro Asn Trp Asp Glu  Gln Val Ser Gln Gln  Phe Thr Val
    1055                 1060                 1065

Gln Pro  Asn Gln Arg Tyr Val  Leu Arg Val Thr Ala  Arg Lys Glu
    1070                 1075                 1080

Gly Val  Gly Asn Gly Tyr Val  Ser Ile Arg Asp Gly  Gly Asn Gln
    1085                 1090                 1095

Thr Glu  Thr Leu Thr Phe Ser  Ala Ser Asp Tyr Asp  Thr Asn Gly
    1100                 1105                 1110

Met Tyr  Asn Thr Gln Val Ser  Asn Thr Asn Gly Tyr  Asn Thr Asn
    1115                 1120                 1125

Asn Ala  Tyr Asn Thr Gln Ala  Ser Ser Thr Asn Gly  Tyr Asn Ala
    1130                 1135                 1140
```

```
Asn Asn  Met Tyr Asn Thr Gln  Ala Ser Asn Thr Asn  Gly Tyr Asn
    1145                 1150                 1155

Thr Asn  Ser Val Tyr Asn Asp  Gln Thr Gly Tyr Ile  Thr Lys Thr
    1160                 1165                 1170

Val Thr  Phe Ile Pro Tyr Thr  Asp Gln Met Trp Ile  Glu Met Ser
    1175                 1180                 1185

Glu Thr  Glu Gly Thr Phe Tyr  Ile Glu Ser Val Glu  Leu Ile Val
    1190                 1195                 1200

Asp Val  Glu
    1205


<210> SEQ ID NO 59
<211> LENGTH: 1210
<212> TYPE: PRT
<213> ORGANISM: Bacillus thuringiensis
<220> FEATURE:
<221> NAME/KEY: MISC_FEATURE
<223> OTHER INFORMATION: Cry8Bc1

<400> SEQUENCE: 59

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Gln Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Gln Ala Ala Asn Leu His Leu
        195                 200                 205

Leu Leu Leu Lys Asp Ala Ser Ile Phe Gly Glu Glu Trp Gly Trp Ser
    210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Thr Val Leu Asp Val Val Ala Leu Phe Pro Asn
```

-continued

```
        275                 280                 285

Tyr Asp Thr Arg Thr Tyr Pro Met Glu Thr Lys Ala Gln Leu Thr Arg
    290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Ile Phe Ser Asp Asn Ile Ile Lys
    370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Phe Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Lys Tyr Asn Pro Val Ser Lys Asp Ile Ile Ala Gly Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Ile Asn Ala Val His Ser Asp Lys Ile Thr Gln Ile Pro Val
        515                 520                 525

Val Lys Val Ser Asp Leu Ala Pro Ser Ile Thr Gly Gly Pro Asn Asn
    530                 535                 540

Thr Val Val Ser Gly Pro Gly Phe Thr Gly Gly Gly Ile Ile Lys Val
545                 550                 555                 560

Ile Arg Asn Gly Val Ile Ile Ser His Met Arg Val Lys Ile Ser Asp
                565                 570                 575

Ile Asn Lys Glu Tyr Ser Met Arg Ile Arg Tyr Ala Ser Ala Asn Asn
            580                 585                 590

Thr Glu Phe Tyr Ile Asn Pro Ser Glu Glu Asn Val Lys Ser His Ala
        595                 600                 605

Gln Lys Thr Met Asn Arg Gly Glu Ala Leu Thr Tyr Asn Lys Phe Asn
    610                 615                 620

Tyr Ala Thr Leu Pro Pro Ile Lys Phe Thr Thr Thr Glu Pro Phe Ile
625                 630                 635                 640

Thr Leu Gly Ala Ile Phe Glu Ala Glu Asp Phe Leu Gly Ile Glu Ala
                645                 650                 655

Tyr Ile Asp Arg Ile Glu Phe Ile Pro Val Asp Glu Thr Tyr Glu Ala
            660                 665                 670

Glu Gln Asp Leu Glu Ala Ala Lys Lys Ala Val Asn Ala Leu Phe Thr
        675                 680                 685

Asn Thr Lys Asp Gly Leu Arg Pro Gly Val Thr Asp Tyr Glu Val Asn
    690                 695                 700
```

```
Gln Ala Ala Asn Leu Val Glu Cys Leu Ser Asp Asp Leu Tyr Pro Asn
705                 710                 715                 720

Glu Lys Arg Leu Leu Phe Asp Ala Val Arg Glu Ala Lys Arg Leu Ser
                725                 730                 735

Glu Ala Arg Asn Leu Leu Gln Asp Pro Asp Phe Gln Glu Ile Asn Gly
            740                 745                 750

Glu Asn Gly Trp Thr Ala Ser Thr Gly Ile Glu Val Ile Glu Gly Asp
        755                 760                 765

Ala Leu Phe Lys Gly Arg Tyr Leu Arg Leu Pro Gly Ala Arg Glu Ile
    770                 775                 780

Asp Thr Glu Thr Tyr Pro Thr Tyr Leu Tyr Gln Lys Val Glu Glu Gly
785                 790                 795                 800

Val Leu Lys Pro Tyr Thr Arg Tyr Arg Leu Arg Gly Phe Val Gly Ser
                805                 810                 815

Ser Gln Gly Leu Glu Ile Phe Thr Ile Arg His Gln Thr Asn Arg Ile
            820                 825                 830

Val Lys Asn Val Pro Asp Asp Leu Leu Pro Asp Val Ser Pro Val Asn
        835                 840                 845

Ser Asp Gly Ser Ile Asn Arg Cys Ser Glu Gln Lys Tyr Val Asn Ser
    850                 855                 860

Arg Leu Glu Val Glu Asn Arg Ser Gly Glu Ala His Glu Phe Ser Ile
865                 870                 875                 880

Pro Ile Asp Thr Gly Glu Ile Asp Tyr Asn Glu Asn Ala Gly Ile Trp
                885                 890                 895

Val Gly Phe Lys Ile Thr Asp Pro Glu Gly Tyr Ala Thr Leu Gly Asn
            900                 905                 910

Leu Glu Leu Val Glu Glu Gly Pro Leu Ser Gly Asp Ala Leu Glu Arg
        915                 920                 925

Leu Gln Arg Glu Glu Gln Gln Trp Lys Ile Gln Met Thr Arg Arg Arg
    930                 935                 940

Glu Glu Thr Asp Arg Arg Tyr Met Ala Ser Lys Gln Ala Val Asp Arg
945                 950                 955                 960

Leu Tyr Ala Asp Tyr Gln Asp Gln Gln Leu Asn Pro Asp Val Glu Ile
                965                 970                 975

Thr Asp Leu Thr Ala Ala Gln Asp Leu Ile Gln Ser Ile Pro Tyr Val
            980                 985                 990

Tyr Asn Glu Met Phe Pro Glu Ile  Pro Gly Met Asn Tyr  Thr Lys Phe
        995                 1000                1005

Thr Glu  Leu Thr Asp Arg Leu  Gln Gln Ala Trp Ser  Leu Tyr Asp
    1010                1015                1020

Gln Arg  Asn Ala Ile Pro Asn  Gly Asp Phe Arg Asn  Gly Leu Ser
    1025                1030                1035

Asn Trp  Asn Ala Thr Pro Gly  Val Glu Val Gln Gln  Ile Asn His
    1040                1045                1050

Thr Ser  Val Leu Val Ile Pro  Asn Trp Asp Glu Gln  Val Ser Gln
    1055                1060                1065

Gln Phe  Thr Val Gln Pro Asn  Gln Arg Tyr Val Leu  Arg Val Thr
    1070                1075                1080

Ala Arg  Lys Glu Gly Val Gly  Asn Gly Tyr Val Ser  Ile Arg Asp
    1085                1090                1095

Gly Gly  Asn Gln Thr Glu Thr  Leu Thr Phe Ser Ala  Ser Asp Tyr
    1100                1105                1110
```

```
Asp Thr  Asn Gly Met Tyr Asn  Thr Gln Val Ser Asn  Thr Asn Gly
    1115                 1120                 1125

Tyr Asn  Thr Asn Asn Ala Tyr  Asn Thr Gln Ala Ser  Ser Thr Asn
    1130                 1135                 1140

Gly Tyr  Asn Ala Asn Asn Met  Tyr Asn Thr Gln Ala  Ser Asn Thr
    1145                 1150                 1155

Asn Gly  Tyr Asn Thr Asn Ser  Val Tyr Asn Asp Gln  Thr Gly Tyr
    1160                 1165                 1170

Ile Thr  Lys Thr Val Thr Phe  Ile Pro Tyr Thr Asp  Gln Met Trp
    1175                 1180                 1185

Ile Glu  Met Ser Glu Thr Glu  Gly Thr Phe Tyr Ile  Glu Ser Val
    1190                 1195                 1200

Glu Leu  Ile Val Asp Val Glu
    1205                 1210


<210> SEQ ID NO 60
<211> LENGTH: 1157
<212> TYPE: PRT
<213> ORGANISM: Bacillus thuringiensis
<220> FEATURE:
<221> NAME/KEY: MISC_FEATURE
<223> OTHER INFORMATION: Cry8Aa1

<400> SEQUENCE: 60

Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
            20                  25                  30

Pro Thr Asp Ala Leu Gln Asn Met Asn Tyr Lys Asp Tyr Leu Lys Met
        35                  40                  45

Ser Gly Gly Glu Asn Pro Glu Leu Phe Gly Asn Pro Glu Thr Phe Ile
    50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
            100                 105                 110

Glu Ile Met Glu Arg Val Glu Glu Leu Val Asp Gln Lys Ile Glu Lys
        115                 120                 125

Tyr Val Lys Asp Lys Ala Leu Ala Glu Leu Lys Gly Leu Gly Asn Ala
    130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
            180                 185                 190

Val Leu Leu Leu Ala Val Tyr Ala Gln Ala Val Asn Leu His Leu Leu
        195                 200                 205

Leu Leu Arg Asp Ala Ser Ile Phe Gly Glu Glu Trp Gly Phe Thr Pro
    210                 215                 220

Gly Glu Ile Ser Arg Phe Tyr Asn Arg Gln Val Gln Leu Thr Ala Glu
225                 230                 235                 240

Tyr Ser Asp Tyr Cys Val Lys Trp Tyr Lys Ile Gly Leu Asp Lys Leu
                245                 250                 255
```

```
Lys Gly Thr Thr Ser Lys Ser Trp Leu Asn Tyr His Gln Phe Arg Arg
            260                 265                 270

Glu Met Thr Leu Leu Val Leu Asp Leu Val Ala Leu Phe Pro Asn Tyr
        275                 280                 285

Asp Thr His Met Tyr Pro Ile Glu Thr Thr Ala Gln Leu Thr Arg Asp
    290                 295                 300

Val Tyr Thr Asp Pro Ile Ala Phe Asn Ile Val Thr Ser Thr Gly Phe
305                 310                 315                 320

Cys Asn Pro Trp Ser Thr His Ser Gly Ile Leu Phe Tyr Glu Val Glu
                325                 330                 335

Asn Asn Val Ile Arg Pro Pro His Leu Phe Asp Ile Leu Ser Ser Val
            340                 345                 350

Glu Ile Asn Thr Ser Arg Gly Gly Ile Thr Leu Asn Asn Asp Ala Tyr
        355                 360                 365

Ile Asn Tyr Trp Ser Gly His Thr Leu Lys Tyr Arg Arg Thr Ala Asp
    370                 375                 380

Ser Thr Val Thr Tyr Thr Ala Asn Tyr Gly Arg Ile Thr Ser Glu Lys
385                 390                 395                 400

Asn Ser Phe Ala Leu Glu Asp Arg Asp Ile Phe Glu Ile Asn Ser Thr
                405                 410                 415

Val Ala Asn Leu Ala Asn Tyr Tyr Gln Lys Ala Tyr Gly Val Pro Gly
            420                 425                 430

Ser Trp Phe His Met Val Lys Arg Gly Thr Ser Ser Thr Thr Ala Tyr
        435                 440                 445

Leu Tyr Ser Lys Thr His Thr Ala Leu Gln Gly Cys Thr Gln Val Tyr
    450                 455                 460

Glu Ser Ser Asp Glu Ile Pro Leu Asp Arg Thr Val Pro Val Ala Glu
465                 470                 475                 480

Ser Tyr Ser His Arg Leu Ser His Ile Thr Ser His Ser Phe Ser Lys
                485                 490                 495

Asn Gly Ser Ala Tyr Tyr Gly Ser Phe Pro Val Phe Val Trp Thr His
            500                 505                 510

Thr Ser Ala Asp Leu Asn Asn Thr Ile Tyr Ser Asp Lys Ile Thr Gln
        515                 520                 525

Ile Pro Ala Val Lys Gly Asp Met Leu Tyr Leu Gly Gly Ser Val Val
    530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
            580                 585                 590

Thr Leu Tyr Leu Gly Asp Thr Ile Glu Lys Asn Arg Phe Asn Lys Thr
        595                 600                 605

Met Asp Asn Gly Ala Ser Leu Thr Tyr Glu Thr Phe Lys Phe Ala Ser
    610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
            660                 665                 670
```

```
Ala Ala Lys Lys Ala Val Asn Ala Leu Phe Thr Asn Thr Lys Asp Gly
        675                 680                 685

Leu Arg Pro Gly Val Thr Asp Tyr Glu Val Asn Gln Ala Ala Asn Leu
    690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gly Trp Ala
            740                 745                 750

Ala Ser Thr Gly Ile Glu Ile Val Glu Gly Asp Ala Val Phe Lys Gly
        755                 760                 765

Arg Tyr Leu Arg Leu Pro Gly Ala Arg Glu Ile Asp Thr Glu Thr Tyr
    770                 775                 780

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Ser Gln Gly Leu Glu
                805                 810                 815

Ile Tyr Thr Ile Arg His Gln Thr Asn Arg Ile Val Lys Asn Val Pro
            820                 825                 830

Asp Asp Leu Leu Pro Asp Val Ser Pro Val Asn Ser Asp Gly Ser Ile
        835                 840                 845

Asn Arg Cys Ser Glu Gln Lys Tyr Val Asn Ser Arg Leu Glu Gly Glu
    850                 855                 860

Asn Arg Ser Gly Asp Ala His Glu Phe Ser Leu Pro Ile Asp Ile Gly
865                 870                 875                 880

Glu Leu Asp Tyr Asn Glu Asn Ala Gly Ile Trp Val Gly Phe Lys Ile
                885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
        915                 920                 925

Gln Gln Trp Lys Ile Gln Met Thr Arg Arg Arg Glu Glu Thr Asp Arg
    930                 935                 940

Arg Tyr Met Ala Ser Lys Gln Ala Val Asp Arg Leu Tyr Ala Asp Tyr
945                 950                 955                 960

Gln Asp Gln Gln Leu Asn Pro Asp Val Glu Ile Thr Asp Leu Thr Ala
                965                 970                 975

Ala Gln Asp Leu Ile Gln Ser Ile Pro Tyr Val Tyr Asn Glu Met Phe
            980                 985                 990

Pro Glu Ile Pro Gly Met Asn Tyr  Thr Lys Phe Thr Glu  Leu Thr Asp
        995                 1000                1005

Arg Leu  Gln Gln Ala Trp Asn  Leu Tyr Asp Gln Arg  Asn Ala Ile
    1010                1015                1020

Pro Asn  Gly Asp Phe Arg Asn  Gly Leu Ser Asn Trp  Asn Ala Thr
    1025                1030                1035

Pro Gly  Val Glu Val Gln Gln  Ile Asn His Thr Ser  Val Leu Val
    1040                1045                1050

Ile Pro  Asn Trp Asp Glu Gln  Val Ser Gln Gln Phe  Thr Val Gln
    1055                1060                1065

Pro Asn  Gln Arg Tyr Val Leu  Arg Val Thr Ala Arg  Lys Glu Gly
    1070                1075                1080

Val Gly  Asn Gly Tyr Val Ser  Ile Arg Asp Gly Gly  Asn Gln Ser
```

1085 1090 1095

Glu Thr Leu Thr Phe Ser Ala Ser Asp Tyr Asp Thr Asn Gly Val
1100 1105 1110

Tyr Asn Asp Gln Thr Gly Tyr Ile Thr Lys Thr Val Thr Phe Ile
1115 1120 1125

Pro Tyr Thr Asp Gln Met Trp Ile Glu Ile Ser Glu Thr Glu Gly
1130 1135 1140

Thr Phe Tyr Ile Glu Ser Val Glu Leu Ile Val Asp Val Glu
1145 1150 1155

<210> SEQ ID NO 61
<211> LENGTH: 719
<212> TYPE: PRT
<213> ORGANISM: Bacillus thuringiensis
<220> FEATURE:
<221> NAME/KEY: MISC_FEATURE
<223> OTHER INFORMATION: Cry8AB001.1

<400> SEQUENCE: 61

Met Ser Pro Asn Asn Gln Asn Glu Tyr Glu Ile Ile Asp Ala Thr Pro
1 5 10 15

Ser Thr Ser Val Ser Asn Asp Ser Asn Arg Tyr Pro Phe Ala Asn Glu
20 25 30

Pro Thr Asn Ala Leu Gln Asn Met Asn Tyr Lys Asp Tyr Leu Arg Met
35 40 45

Ser Glu Gly Tyr Asp Ser Glu Tyr Ser Gly Ser Pro Gly Ala Leu Val
50 55 60

Ser Gly Lys Gln Ala Ile Lys Val Gly Ile Asp Ile Val Gly Asn Ile
65 70 75 80

Leu Gly Lys Leu Gly Val Pro Phe Ala Ser Gln Ile Val Ser Phe Tyr
85 90 95

Asn Phe Ile Leu Asp Gln Leu Trp Pro Ser Asn Ser Val Ser Val Trp
100 105 110

Glu Gln Ile Met Thr Leu Val Glu Glu Leu Val Asp Gln Lys Ile Thr
115 120 125

Glu Tyr Ala Arg Asn Lys Ala Leu Ala Glu Leu Lys Gly Leu Gly Asp
130 135 140

Ala Leu Gly Val Tyr Gln Gln Ser Leu Glu Ala Trp Leu Glu Asn Arg
145 150 155 160

Asn Asp Thr Arg Ala Arg Ser Val Val Ser Asn Gln Phe Ile Ala Leu
165 170 175

Glu Leu Asp Phe Val Gly Ala Ile Pro Ser Phe Ala Val Ser Gly Gln
180 185 190

Glu Val Pro Leu Leu Ala Val Tyr Ala Gln Ala Val Asn Met His Leu
195 200 205

Leu Leu Leu Arg Asp Ala Ser Ile Phe Gly Glu Glu Trp Gly Phe Thr
210 215 220

Ser Ser Glu Ile Ser Thr Tyr Tyr Asn Arg Gln Val Gln Leu Thr Ser
225 230 235 240

Gln Tyr Ser Asp Tyr Cys Val Lys Trp Tyr Asp Thr Gly Leu Gln Lys
245 250 255

Leu Lys Gly Thr Ser Ala Glu Ser Trp Leu Glu Tyr His Gln Phe Arg
260 265 270

Arg Glu Met Thr Phe Met Val Leu Asp Leu Val Ala Leu Phe Pro Asn
275 280 285

-continued

```
Tyr Asp Thr His Thr Tyr Pro Leu Glu Thr Lys Ala Gln Leu Thr Arg
    290                 295                 300

Glu Val Tyr Thr Asp Pro Ile Ala Phe Asn Leu Ser Gly Ala Ala Gly
305                 310                 315                 320

Phe Cys Ser Pro Trp Ser Lys Tyr Thr Gly Ile Ser Phe Ser Glu Ile
                325                 330                 335

Glu Asn Asp Val Ile Arg Pro Pro His Leu Phe Asn Leu Leu Arg Ser
            340                 345                 350

Leu Glu Ile Asn Thr Val Arg Gly Thr Ile Leu Gly Asn Thr Lys Asp
        355                 360                 365

Tyr Leu Asn Tyr Trp Ser Gly His Ser Leu Gln Tyr Asn Phe Ile Gly
    370                 375                 380

Lys Thr Ile Val Arg Glu Ser Asn Tyr Gly Tyr Leu Thr Ser Glu Lys
385                 390                 395                 400

Thr Arg Ile Glu Leu Asp Thr Arg Asp Ile Phe Glu Ile Asn Ser Thr
                405                 410                 415

Ala Ala Ser Leu Ala Asn Tyr Tyr Gln Glu Thr Tyr Gly Val Pro Glu
            420                 425                 430

Ser Arg Leu His Leu Val Arg Trp Ala Ser Pro Tyr Tyr Thr Ser Ser
        435                 440                 445

His Leu Tyr Ser Lys Thr His Thr Thr Gly Glu Gly Cys Thr Gln Val
    450                 455                 460

Tyr Glu Ser Ser Glu Glu Ile Pro Val Asp Arg Thr Val Pro Ile Asn
465                 470                 475                 480

Glu Gly Tyr Ser His Arg Leu Ser Tyr Val Thr Ala Leu Phe Phe Gln
                485                 490                 495

Lys Ile Ile Asn Thr Phe Tyr Arg Asn Gly Thr Leu Pro Val Phe Val
            500                 505                 510

Trp Thr His Arg Ser Ala Asp Leu Thr Asn Thr Ile Tyr Pro Asp Val
        515                 520                 525

Ile Thr Gln Ile Pro Val Val Lys Ala Tyr Glu Leu Gly Ser Ser Ile
    530                 535                 540

Leu Pro Asp Ser Pro Ser Pro Thr Ile Val Pro Gly Pro Gly Phe Thr
545                 550                 555                 560

Gly Gly Asp Ile Ile Gln Leu Leu Ala Asn Thr Lys Gly Ile Ala Asn
                565                 570                 575

Met Asn Phe Glu Ile Gln Asp Ile Asn Lys Glu Tyr Ile Met Arg Ile
            580                 585                 590

Arg Tyr Ala Ser Ala Ala Asn Pro Glu Phe Asn Ile Ala Val Gly Thr
        595                 600                 605

Ser Gly Glu Arg Val Ser Thr Ser Ala Gln Lys Thr Met Asn Pro Gly
    610                 615                 620

Asp Ile Leu Thr Phe Asn Lys Phe Asn Tyr Ala Thr Phe Pro Pro Ile
625                 630                 635                 640

Lys Phe Asn Ser Thr Lys Ile Ser Ile Met Leu Thr Ala Arg Leu Ala
                645                 650                 655

Ala Phe Ala Ser Thr Leu Leu Glu Thr Tyr Ile Asp Arg Ile Glu Phe
            660                 665                 670

Ile Pro Val Asp Glu Thr Tyr Glu Ala Glu Thr Asp Leu Glu Thr Ala
        675                 680                 685

Lys Lys Ala Val Asn Ala Leu Phe Thr Asn Thr Lys Asp Gly Leu Arg
    690                 695                 700

Pro Gly Val Thr Asp Tyr Glu Val Asn Gln Ala Ala Asn Leu Val
```

705 710 715

<210> SEQ ID NO 62
<211> LENGTH: 1144
<212> TYPE: PRT
<213> ORGANISM: Bacillus thuringiensis
<220> FEATURE:
<221> NAME/KEY: MISC_FEATURE
<223> OTHER INFORMATION: Cry8Da1

<400> SEQUENCE: 62

Met Ser Pro Asn Asn Gln Asn Glu Tyr Glu Ile Leu Asp Ala Ser Ser
1 5 10 15

Ser Thr Ser Val Ser Asp Asn Ser Val Arg Tyr Pro Leu Ala Asn Asp
20 25 30

Gln Thr Thr Thr Leu Gln Asn Met Asn Tyr Lys Asp Tyr Leu Arg Met
35 40 45

Ser Glu Gly Glu Asn Pro Glu Leu Phe Gly Asn Pro Glu Thr Phe Ile
50 55 60

Ser Ser Ser Thr Val Gln Thr Gly Ile Gly Ile Val Gly Gln Val Leu
65 70 75 80

Gly Ala Leu Gly Val Pro Phe Ala Gly Gln Ile Ala Ser Phe Tyr Ser
85 90 95

Phe Ile Val Gly Gln Leu Trp Pro Ser Ser Thr Val Ser Val Trp Glu
100 105 110

Met Ile Met Lys Gln Val Glu Asp Leu Ile Asp Gln Lys Ile Thr Asp
115 120 125

Ser Val Arg Lys Thr Ala Leu Ala Gly Leu Gln Gly Leu Gly Asp Gly
130 135 140

Leu Asp Val Tyr Gln Lys Ser Leu Lys Asn Trp Leu Glu Asn Arg Asn
145 150 155 160

Asp Thr Arg Ala Arg Ser Val Val Val Thr Gln Tyr Ile Ala Leu Glu
165 170 175

Leu Asp Phe Val Ala Lys Ile Pro Ser Phe Ala Ile Ser Gly Gln Glu
180 185 190

Val Pro Leu Leu Ser Val Tyr Ala Gln Ala Ala Asn Leu His Leu Leu
195 200 205

Leu Leu Arg Asp Ala Ser Ile Phe Gly Ala Glu Trp Gly Phe Thr Pro
210 215 220

Gly Glu Ile Ser Thr Phe Tyr Asp Arg Gln Val Thr Arg Thr Ala Gln
225 230 235 240

Tyr Ser Asp Tyr Cys Val Lys Trp Tyr Asn Thr Gly Leu Asp Lys Leu
245 250 255

Lys Gly Thr Asn Ala Ala Ser Trp Leu Lys Tyr His Gln Phe Arg Arg
260 265 270

Glu Met Thr Leu Leu Val Leu Asp Leu Val Ala Leu Phe Pro Asn Tyr
275 280 285

Asp Thr Arg Thr Tyr Pro Ile Glu Thr Thr Ala Gln Leu Thr Arg Glu
290 295 300

Val Tyr Thr Asp Pro Ile Val Phe Asn Arg Glu Thr Ser Gly Gly Phe
305 310 315 320

Cys Arg Arg Trp Ser Leu Asn Ser Asp Ile Ser Phe Ser Glu Val Glu
325 330 335

Ser Ala Val Ile Arg Ser Pro His Leu Phe Asp Ile Leu Ser Glu Ile
340 345 350

```
Glu Phe Tyr Thr Thr Arg Ala Gly Leu Pro Leu Asn Asn Thr Glu Tyr
        355                 360                 365

Leu Glu Tyr Trp Val Gly His Ser Ile Lys Tyr Lys Asn Thr Asn Ala
    370                 375                 380

Ser Ser Ala Leu Glu Arg Asn Tyr Gly Thr Ile Thr Ser Asn Lys Ile
385                 390                 395                 400

Lys Tyr Tyr Asp Leu Ala Asn Lys Asp Ile Phe Gln Val Arg Ser Leu
                405                 410                 415

Gly Ala Asp Leu Ala Asn Tyr Tyr Ala Gln Val Tyr Gly Val Pro Tyr
            420                 425                 430

Ala Ser Phe Thr Leu Leu Asp Lys Asn Thr Gly Ser Gly Ser Val Gly
        435                 440                 445

Gly Phe Thr Tyr Ser Lys Pro His Thr Thr Met Gln Val Cys Thr Gln
    450                 455                 460

Asn Tyr Asn Thr Ile Asp Glu Ile Pro Pro Glu Asn Glu Pro Leu Ser
465                 470                 475                 480

Arg Gly Tyr Ser His Arg Leu Ser His Ile Thr Ser Tyr Ser Phe Ser
                485                 490                 495

Lys Asn Ala Ser Ser Pro Ala Arg Tyr Gly Asn Leu Pro Val Phe Ala
            500                 505                 510

Trp Thr His Arg Ser Ala Asp Val Thr Asn Thr Val Tyr Ser Asp Lys
        515                 520                 525

Ile Thr Gln Ile Pro Val Val Lys Ala His Thr Leu Val Ser Gly Thr
    530                 535                 540

Thr Val Ile Lys Gly Pro Gly Phe Thr Gly Gly Asn Ile Leu Lys Arg
545                 550                 555                 560

Thr Ser Ser Gly Pro Leu Ala Tyr Thr Ser Val Ser Val Lys Ser Pro
                565                 570                 575

Leu Ser Gln Arg Tyr Arg Ala Arg Ile Arg Tyr Ala Ser Thr Thr Asn
            580                 585                 590

Leu Arg Leu Phe Val Thr Ile Ser Gly Thr Arg Ile Tyr Ser Ile Asn
        595                 600                 605

Val Asn Lys Thr Met Asn Lys Gly Asp Asp Leu Thr Phe Asn Thr Phe
    610                 615                 620

Asp Leu Ala Thr Ile Gly Thr Ala Phe Thr Phe Ser Asn Tyr Ser Asp
625                 630                 635                 640

Ser Leu Thr Val Gly Ala Asp Ser Phe Ala Ser Gly Gly Glu Val Tyr
                645                 650                 655

Val Asp Lys Phe Glu Leu Ile Pro Val Asn Ala Thr Phe Glu Ala Glu
            660                 665                 670

Glu Asp Leu Asp Val Ala Lys Lys Ala Val Lys Asn Leu Val Glu Cys
        675                 680                 685

Leu Ser Asp Glu Leu Tyr Pro Asn Glu Lys Arg Met Leu Trp Asp Ala
    690                 695                 700

Val Lys Glu Ala Lys Arg Leu Val Gln Ala Arg Asn Leu Leu Gln Asp
705                 710                 715                 720

Thr Gly Phe Asn Arg Ile Asn Gly Glu Asn Gly Trp Thr Gly Ser Thr
                725                 730                 735

Gly Ile Glu Val Ala Glu Gly Asp Val Leu Phe Lys Asp Arg Ser Leu
            740                 745                 750

Arg Leu Thr Ser Ala Arg Glu Ile Asp Thr Glu Thr Tyr Pro Thr Tyr
        755                 760                 765

Leu Tyr Gln Gln Ile Asp Glu Ser Leu Leu Lys Pro Tyr Thr Arg Tyr
```

-continued

```
    770                 775                 780

Lys Leu Lys Gly Phe Ile Gly Ser Ser Gln Asp Leu Glu Ile Lys Leu
785                 790                 795                 800

Ile Arg His Arg Ala Asn Gln Ile Val Lys Asn Val Pro Asp Asn Leu
                805                 810                 815

Leu Pro Asp Val Leu Pro Val Asn Ser Cys Gly Gly Ile Asp Arg Cys
            820                 825                 830

Ser Glu Gln Gln Tyr Val Asp Ala Asn Leu Ala Leu Glu Asn Asn Gly
        835                 840                 845

Glu Asn Gly Asn Met Ser Ser Asp Ser His Ala Phe Ser Phe His Ile
    850                 855                 860

Asp Thr Gly Glu Ile Asp Leu Asn Glu Asn Thr Gly Ile Trp Val Val
865                 870                 875                 880

Phe Lys Ile Pro Thr Thr Asn Gly Tyr Ala Thr Leu Gly Asn Leu Glu
                885                 890                 895

Leu Val Glu Glu Gly Pro Leu Ser Gly Glu Thr Leu Glu Arg Ala Gln
            900                 905                 910

Gln Gln Glu Gln Gln Trp Gln Asp Lys Met Ala Arg Lys Arg Gly Ala
        915                 920                 925

Ser Glu Lys Ala Tyr Tyr Ala Ala Lys Gln Ala Ile Asp Arg Leu Phe
    930                 935                 940

Ala Asp Tyr Gln Asp Gln Lys Leu Asn Ser Gly Val Glu Met Ser Asp
945                 950                 955                 960

Met Leu Ala Ala Gln Asn Leu Val Gln Ser Ile Pro Tyr Val Tyr Asn
                965                 970                 975

Asp Ala Leu Pro Glu Ile Pro Gly Met Asn Tyr Thr Ser Phe Thr Glu
            980                 985                 990

Leu Thr Asn Arg Leu Gln Gln Ala  Trp Asn Leu Tyr Asp  Leu Arg Asn
        995                 1000                1005

Ala Ile  Pro Asn Gly Asp Phe  Arg Asn Gly Leu Ser  Asp Trp Asn
    1010                1015                1020

Ala Thr  Ser Asp Val Asn Val  Gln Gln Leu Ser Asp  Thr Ser Val
    1025                1030                1035

Leu Val  Ile Pro Asn Trp Asn  Ser Gln Val Ser Gln  Gln Phe Thr
    1040                1045                1050

Val Gln  Pro Asn Tyr Arg Tyr  Val Leu Arg Val Thr  Ala Arg Lys
    1055                1060                1065

Glu Gly  Val Gly Asp Gly Tyr  Val Ile Ile Arg Asp  Gly Ala Asn
    1070                1075                1080

Gln Thr  Glu Thr Leu Thr Phe  Asn Ile Cys Asp Asp  Asp Thr Gly
    1085                1090                1095

Val Leu  Ser Ala Asp Gln Thr  Ser Tyr Ile Thr Lys  Thr Val Glu
    1100                1105                1110

Phe Thr  Pro Ser Thr Glu Gln  Val Trp Ile Asp Met  Ser Glu Thr
    1115                1120                1125

Glu Gly  Val Phe Asn Ile Glu  Ser Val Glu Leu Val  Leu Glu Glu
    1130                1135                1140

Glu
```

<210> SEQ ID NO 63
<211> LENGTH: 1167
<212> TYPE: PRT
<213> ORGANISM: Bacillus thuringiensis
<220> FEATURE:

<221> NAME/KEY: MISC_FEATURE
<223> OTHER INFORMATION: Cry8Da3

<400> SEQUENCE: 63

```
Met Ser Pro Asn Asn Gln Asn Glu Tyr Glu Ile Leu Asp Ala Ser Ser
1               5                   10                  15

Ser Thr Ser Val Ser Asp Asn Ser Val Arg Tyr Pro Leu Ala Asn Asp
            20                  25                  30

Gln Thr Thr Thr Leu Gln Asn Met Asn Tyr Lys Asp Tyr Leu Arg Met
        35                  40                  45

Ser Glu Gly Glu Asn Pro Glu Leu Phe Gly Asn Pro Glu Thr Phe Ile
    50                  55                  60

Ser Ser Ser Thr Val Gln Thr Gly Ile Gly Ile Val Gly Gln Val Leu
65                  70                  75                  80

Gly Ala Leu Gly Val Pro Phe Ala Gly Gln Ile Ala Ser Phe Tyr Ser
                85                  90                  95

Phe Ile Val Gly Gln Leu Trp Pro Ser Ser Thr Val Ser Val Trp Glu
            100                 105                 110

Met Ile Met Lys Gln Val Glu Asp Leu Ile Asp Gln Lys Ile Thr Asp
        115                 120                 125

Ser Val Arg Lys Thr Ala Leu Ala Gly Leu Gln Gly Leu Gly Asp Gly
    130                 135                 140

Leu Asp Val Tyr Gln Lys Ser Leu Lys Asn Trp Leu Glu Asn Arg Asn
145                 150                 155                 160

Asp Thr Arg Ala Arg Ser Val Val Val Thr Gln Tyr Ile Ala Leu Glu
                165                 170                 175

Leu Asp Phe Val Ala Lys Ile Pro Ser Phe Ala Ile Ser Gly Gln Glu
            180                 185                 190

Val Pro Leu Leu Ser Val Tyr Ala Gln Ala Ala Asn Leu His Leu Leu
        195                 200                 205

Leu Leu Arg Asp Ala Ser Ile Phe Gly Ala Glu Trp Gly Phe Thr Pro
    210                 215                 220

Gly Glu Ile Ser Thr Phe Tyr Asp Arg Gln Val Thr Arg Thr Ala Gln
225                 230                 235                 240

Tyr Ser Asp Tyr Cys Val Lys Trp Tyr Asn Thr Gly Leu Asp Lys Leu
                245                 250                 255

Lys Gly Thr Asn Ala Ala Ser Trp Leu Lys Tyr His Gln Phe Arg Arg
            260                 265                 270

Glu Met Thr Leu Leu Val Leu Asp Leu Val Ala Leu Phe Pro Asn Tyr
        275                 280                 285

Asp Thr Arg Thr Tyr Pro Ile Glu Thr Thr Ala Gln Leu Thr Arg Glu
    290                 295                 300

Val Tyr Thr Asp Pro Ile Val Phe Asn Arg Glu Thr Ser Gly Gly Phe
305                 310                 315                 320

Cys Arg Arg Trp Ser Leu Asn Ser Asp Ile Ser Phe Ser Glu Val Glu
                325                 330                 335

Ser Ala Val Ile Arg Ser Pro His Leu Phe Asp Ile Leu Ser Glu Ile
            340                 345                 350

Glu Phe Tyr Thr Thr Arg Ala Gly Leu Pro Leu Asn Asn Thr Glu Tyr
        355                 360                 365

Leu Glu Tyr Trp Val Gly His Ser Ile Lys Tyr Lys Asn Thr Asn Ala
    370                 375                 380

Ser Ser Ala Leu Glu Arg Asn Tyr Gly Thr Ile Thr Ser Asn Lys Ile
385                 390                 395                 400
```

```
Lys Tyr Tyr Asp Leu Ala Asn Lys Asp Ile Phe Gln Val Arg Ser Leu
                405                 410                 415

Gly Ala Asp Leu Ala Asn Tyr Tyr Ala Gln Val Tyr Gly Val Pro Tyr
            420                 425                 430

Ala Ser Phe Thr Leu Leu Asp Lys Asn Thr Gly Ser Gly Ser Val Gly
        435                 440                 445

Gly Phe Thr Tyr Ser Lys Pro His Thr Thr Met Gln Val Cys Thr Gln
    450                 455                 460

Asn Tyr Asn Thr Ile Asp Glu Ile Pro Pro Glu Asn Glu Pro Leu Ser
465                 470                 475                 480

Arg Gly Tyr Ser His Arg Leu Ser His Ile Thr Ser Tyr Ser Phe Ser
                485                 490                 495

Lys Asn Ala Ser Ser Pro Ala Arg Tyr Gly Asn Leu Pro Val Phe Ala
            500                 505                 510

Trp Thr His Arg Ser Ala Asp Val Thr Asn Thr Val Tyr Ser Asp Lys
        515                 520                 525

Ile Thr Gln Ile Pro Val Val Lys Ala His Thr Leu Val Ser Gly Thr
    530                 535                 540

Thr Val Ile Lys Gly Pro Gly Phe Thr Gly Gly Asn Ile Leu Lys Arg
545                 550                 555                 560

Thr Ser Ser Gly Pro Leu Ala Tyr Thr Ser Val Ser Val Lys Ser Pro
                565                 570                 575

Leu Ser Gln Arg Tyr Arg Ala Arg Ile Arg Tyr Ala Ser Thr Thr Asn
            580                 585                 590

Leu Arg Leu Phe Val Thr Ile Ser Gly Thr Arg Ile Tyr Ser Ile Asn
        595                 600                 605

Val Asn Lys Thr Met Asn Lys Gly Asp Asp Leu Thr Phe Asn Thr Phe
    610                 615                 620

Asp Leu Ala Thr Ile Gly Thr Ala Phe Thr Phe Ser Asn Tyr Ser Asp
625                 630                 635                 640

Ser Leu Thr Val Gly Ala Asp Ser Phe Ala Ser Gly Gly Glu Val Tyr
                645                 650                 655

Val Asp Lys Phe Glu Leu Ile Pro Val Asn Ala Thr Phe Glu Ala Glu
            660                 665                 670

Glu Asp Leu Asp Val Ala Lys Lys Ala Val Asn Gly Leu Phe Thr Ser
        675                 680                 685

Lys Lys Asp Ala Leu Gln Thr Ser Val Thr Asp Tyr Gln Val Asn Gln
    690                 695                 700

Ala Ala Asn Leu Val Glu Cys Leu Ser Asp Glu Leu Tyr Pro Asn Glu
705                 710                 715                 720

Lys Arg Met Leu Trp Asp Ala Val Lys Glu Ala Lys Arg Leu Val Gln
                725                 730                 735

Ala Arg Asn Leu Leu Gln Asp Thr Gly Phe Asn Arg Ile Asn Gly Glu
            740                 745                 750

Asn Gly Trp Thr Gly Ser Thr Gly Ile Glu Val Ala Glu Gly Asp Val
        755                 760                 765

Leu Phe Lys Asp Arg Ser Leu Arg Leu Thr Ser Ala Arg Glu Ile Asp
    770                 775                 780

Thr Glu Thr Tyr Pro Thr Tyr Leu Tyr Gln Gln Ile Asp Glu Ser Leu
785                 790                 795                 800

Leu Lys Pro Tyr Thr Arg Tyr Lys Leu Lys Gly Phe Ile Gly Ser Ser
                805                 810                 815
```

```
Gln Asp Leu Glu Ile Lys Leu Ile Arg His Arg Ala Asn Gln Ile Val
            820                 825                 830

Lys Asn Val Pro Asp Asn Leu Leu Pro Asp Val Leu Pro Val Asn Ser
        835                 840                 845

Cys Gly Gly Ile Asp Arg Cys Ser Glu Gln Gln Tyr Val Asp Ala Asn
    850                 855                 860

Leu Ala Leu Glu Asn Asn Gly Glu Asn Gly Asn Met Ser Ser Asp Ser
865                 870                 875                 880

His Ala Phe Ser Phe His Ile Asp Thr Gly Glu Ile Asp Leu Asn Glu
                885                 890                 895

Asn Thr Gly Ile Trp Val Val Phe Lys Ile Pro Thr Thr Asn Gly Tyr
            900                 905                 910

Ala Thr Leu Gly Asn Leu Glu Leu Val Glu Glu Gly Pro Leu Ser Gly
        915                 920                 925

Glu Thr Leu Glu Arg Ala Gln Gln Gln Glu Gln Gln Trp Gln Asp Lys
    930                 935                 940

Met Ala Arg Lys Arg Gly Ala Ser Glu Lys Ala Tyr Tyr Ala Ala Lys
945                 950                 955                 960

Gln Ala Ile Asp Arg Leu Phe Ala Asp Tyr Gln Asp Gln Lys Leu Asn
                965                 970                 975

Ser Gly Val Glu Met Ser Asp Met Leu Ala Ala Gln Asn Leu Val Gln
            980                 985                 990

Ser Ile Pro Tyr Val Tyr Asn Asp  Ala Leu Pro Glu Ile  Pro Gly Met
        995                 1000                 1005

Asn Tyr  Thr Ser Phe Thr Glu  Leu Thr Asn Arg Leu  Gln Gln Ala
    1010                 1015                 1020

Trp Asn  Leu Tyr Asp Leu Arg  Asn Ala Ile Pro Asn  Gly Asp Phe
    1025                 1030                 1035

Arg Asn  Gly Leu Ser Asp Trp  Asn Ala Thr Ser Asp  Val Asn Val
    1040                 1045                 1050

Gln Gln  Leu Ser Asp Thr Ser  Val Leu Val Ile Pro  Asn Trp Asn
    1055                 1060                 1065

Ser Gln  Val Ser Gln Gln Phe  Thr Val Gln Pro Asn  Tyr Arg Tyr
    1070                 1075                 1080

Val Leu  Arg Val Thr Ala Arg  Lys Glu Gly Val Gly  Asp Gly Tyr
    1085                 1090                 1095

Val Ile  Ile Arg Asp Gly Ala  Asn Gln Thr Glu Thr  Leu Thr Phe
    1100                 1105                 1110

Asn Ile  Cys Asp Asp Asp Thr  Gly Val Leu Ser Ala  Asp Gln Thr
    1115                 1120                 1125

Ser Tyr  Ile Thr Lys Thr Val  Glu Phe Thr Pro Ser  Thr Glu Gln
    1130                 1135                 1140

Val Trp  Ile Asp Met Ser Glu  Thr Glu Gly Val Phe  Asn Ile Glu
    1145                 1150                 1155

Ser Val  Glu Leu Val Leu Glu  Glu Glu
    1160                 1165
```

<210> SEQ ID NO 64
<211> LENGTH: 1167
<212> TYPE: PRT
<213> ORGANISM: Bacillus thuringiensis
<220> FEATURE:
<221> NAME/KEY: MISC_FEATURE
<223> OTHER INFORMATION: Cry8Da2

<400> SEQUENCE: 64

-continued

```
Met Ser Pro Asn Asn Gln Asn Glu Tyr Glu Ile Leu Asp Ala Ser Ser
1               5                   10                  15

Ser Thr Ser Val Ser Asp Asn Ser Val Arg Tyr Pro Leu Ala Asn Asp
            20                  25                  30

Gln Thr Thr Thr Leu Gln Asn Met Asn Tyr Lys Asp Tyr Leu Arg Met
        35                  40                  45

Ser Glu Gly Glu Asn Pro Glu Leu Phe Gly Asn Pro Glu Thr Phe Ile
    50                  55                  60

Ser Ser Ser Thr Val Gln Thr Gly Ile Gly Ile Val Gly Gln Val Leu
65                  70                  75                  80

Gly Ala Leu Gly Val Pro Phe Ala Gly Gln Ile Ala Ser Phe Tyr Ser
                85                  90                  95

Phe Ile Val Gly Gln Leu Trp Pro Ser Ser Thr Val Ser Val Trp Glu
            100                 105                 110

Met Ile Met Lys Gln Val Glu Asp Leu Ile Asp Gln Lys Ile Thr Asp
        115                 120                 125

Ser Val Arg Lys Thr Ala Leu Ala Gly Leu Gln Gly Leu Gly Asp Gly
    130                 135                 140

Leu Asp Val Tyr Gln Lys Ser Leu Lys Asn Trp Leu Glu Asn Arg Asn
145                 150                 155                 160

Asp Thr Arg Ala Arg Ser Val Val Val Thr Gln Tyr Ile Ala Leu Glu
                165                 170                 175

Leu Asp Phe Val Ala Lys Ile Pro Ser Phe Ala Ile Ser Gly Gln Glu
            180                 185                 190

Val Pro Leu Leu Ser Val Tyr Ala Gln Ala Ala Asn Leu His Leu Leu
        195                 200                 205

Leu Leu Arg Asp Ala Ser Ile Phe Gly Ala Glu Trp Gly Phe Thr Pro
    210                 215                 220

Gly Glu Ile Ser Thr Phe Tyr Asp Arg Gln Val Thr Arg Thr Ala Gln
225                 230                 235                 240

Tyr Ser Asp Tyr Cys Val Lys Trp Tyr Asn Thr Gly Leu Asp Lys Leu
                245                 250                 255

Lys Gly Thr Asn Ala Ala Ser Trp Leu Lys Tyr His Gln Phe Arg Arg
            260                 265                 270

Glu Met Thr Leu Leu Val Leu Asp Leu Val Ala Leu Phe Pro Asn Tyr
        275                 280                 285

Asp Thr Arg Thr Tyr Pro Ile Glu Thr Thr Ala Gln Leu Thr Arg Glu
    290                 295                 300

Val Tyr Thr Asp Pro Ile Val Phe Asn Arg Glu Thr Ser Gly Gly Phe
305                 310                 315                 320

Cys Arg Arg Trp Ser Leu Asn Ser Asp Ile Ser Phe Ser Glu Val Glu
                325                 330                 335

Ser Ala Val Ile Arg Ser Pro His Leu Phe Asp Ile Leu Ser Glu Ile
            340                 345                 350

Glu Phe Tyr Thr Thr Arg Ala Gly Leu Pro Leu Asn Asn Thr Glu Tyr
        355                 360                 365

Leu Glu Tyr Trp Val Gly His Ser Ile Lys Tyr Lys Asn Thr Asn Ala
    370                 375                 380

Ser Ser Ala Leu Glu Arg Asn Tyr Gly Thr Ile Thr Ser Asn Lys Ile
385                 390                 395                 400

Lys Tyr Tyr Asp Leu Ala Asn Lys Asp Ile Phe Gln Val Arg Ser Leu
                405                 410                 415
```

-continued

```
Gly Ala Asp Leu Ala Asn Tyr Tyr Ala Gln Val Tyr Gly Val Pro Tyr
            420                 425                 430

Ala Ser Phe Thr Leu Leu Asp Lys Asn Thr Gly Ser Gly Ser Val Gly
        435                 440                 445

Gly Phe Thr Tyr Ser Lys Pro His Thr Thr Met Gln Val Cys Thr Gln
    450                 455                 460

Asn Tyr Asn Thr Ile Asp Glu Ile Pro Pro Glu Asn Glu Pro Leu Ser
465                 470                 475                 480

Arg Gly Tyr Ser His Arg Leu Ser His Ile Thr Ser Tyr Ser Phe Ser
                485                 490                 495

Lys Asn Ala Ser Ser Pro Ala Arg Tyr Gly Asn Leu Pro Val Phe Ala
            500                 505                 510

Trp Thr His Arg Ser Ala Asp Val Thr Asn Thr Val Tyr Ser Asp Lys
        515                 520                 525

Ile Thr Gln Ile Pro Val Val Lys Ala His Thr Leu Val Ser Gly Thr
    530                 535                 540

Thr Val Ile Lys Gly Pro Gly Phe Thr Gly Gly Asn Ile Leu Lys Arg
545                 550                 555                 560

Thr Ser Ser Gly Pro Leu Ala Tyr Thr Ser Val Ser Val Lys Ser Pro
                565                 570                 575

Leu Ser Gln Arg Tyr Arg Ala Arg Ile Arg Tyr Ala Ser Thr Thr Asn
            580                 585                 590

Leu Arg Leu Phe Val Thr Ile Ser Gly Thr Arg Ile Tyr Ser Ile Asn
        595                 600                 605

Val Asn Lys Thr Met Asn Lys Gly Asp Asp Leu Thr Phe Asn Thr Phe
    610                 615                 620

Asp Leu Ala Thr Ile Gly Thr Ala Phe Thr Phe Ser Asn Tyr Ser Asp
625                 630                 635                 640

Ser Leu Thr Val Gly Ala Asp Ser Phe Ala Ser Gly Gly Glu Val Tyr
                645                 650                 655

Val Asp Lys Phe Glu Leu Ile Pro Val Asn Ala Thr Phe Glu Ala Glu
            660                 665                 670

Glu Asp Leu Asp Val Ala Lys Lys Ala Val Asn Gly Leu Phe Thr Ser
        675                 680                 685

Lys Lys Asp Ala Leu Gln Thr Ser Val Thr Asp Tyr Gln Val Asn Gln
    690                 695                 700

Ala Ala Asn Leu Val Glu Cys Leu Ser Asp Glu Leu Tyr Pro Asn Glu
705                 710                 715                 720

Lys Arg Met Leu Trp Asp Ala Val Lys Glu Ala Lys Arg Leu Val Gln
                725                 730                 735

Ala Arg Asn Leu Leu Gln Asp Thr Gly Phe Asn Arg Ile Asn Gly Glu
            740                 745                 750

Asn Gly Trp Thr Gly Ser Thr Gly Ile Glu Val Ala Glu Gly Asp Val
        755                 760                 765

Leu Phe Lys Asp Arg Ser Leu Arg Leu Thr Ser Ala Arg Glu Ile Asp
    770                 775                 780

Thr Glu Thr Tyr Pro Thr Tyr Leu Tyr Gln Gln Ile Asp Glu Ser Leu
785                 790                 795                 800

Leu Lys Pro Tyr Thr Arg Tyr Lys Leu Lys Gly Phe Ile Gly Ser Ser
                805                 810                 815

Gln Asp Leu Glu Ile Lys Leu Ile Arg His Arg Ala Asn Gln Ile Val
            820                 825                 830

Lys Asn Val Pro Asp Asn Leu Leu Pro Asp Val Leu Pro Val Asn Ser
```

835 840 845

Cys Gly Gly Ile Asp Arg Cys Ser Glu Gln Gln Tyr Val Asp Ala Asn
850 855 860

Leu Ala Leu Glu Asn Asn Gly Glu Asn Gly Asn Met Ser Ser Asp Ser
865 870 875 880

His Ala Phe Ser Phe His Ile Asp Thr Gly Glu Ile Asp Leu Asn Glu
885 890 895

Asn Thr Gly Ile Trp Val Val Phe Lys Ile Pro Thr Thr Asn Gly Tyr
900 905 910

Ala Thr Leu Gly Asn Leu Glu Leu Val Glu Glu Gly Pro Leu Ser Gly
915 920 925

Glu Thr Leu Glu Arg Ala Gln Gln Gln Glu Gln Gln Trp Gln Asp Lys
930 935 940

Met Ala Arg Lys Arg Gly Ala Ser Glu Lys Ala Tyr Tyr Ala Ala Lys
945 950 955 960

Gln Ala Ile Asp Arg Leu Phe Ala Asp Tyr Gln Asp Gln Lys Leu Asn
965 970 975

Ser Gly Val Glu Met Ser Asp Met Leu Ala Ala Gln Asn Leu Val Gln
980 985 990

Ser Ile Pro Tyr Val Tyr Asn Asp Ala Leu Pro Glu Ile Pro Gly Met
995 1000 1005

Asn Tyr Thr Ser Phe Thr Glu Leu Thr Asn Arg Leu Gln Gln Ala
1010 1015 1020

Trp Asn Leu Tyr Asp Leu Arg Asn Ala Ile Pro Asn Gly Asp Phe
1025 1030 1035

Arg Asn Gly Leu Ser Asp Trp Asn Ala Thr Ser Asp Val Asn Val
1040 1045 1050

Gln Gln Leu Ser Asp Thr Ser Val Leu Val Ile Pro Asn Trp Asn
1055 1060 1065

Ser Gln Val Ser Gln Gln Phe Thr Val Gln Pro Asn Tyr Arg Tyr
1070 1075 1080

Val Leu Arg Val Thr Ala Arg Lys Glu Gly Val Gly Asp Gly Tyr
1085 1090 1095

Val Ile Ile Arg Asp Gly Ala Asn Gln Thr Glu Thr Leu Thr Phe
1100 1105 1110

Asn Ile Cys Asp Asp Asp Thr Gly Val Leu Ser Ala Asp Gln Thr
1115 1120 1125

Ser Tyr Ile Thr Lys Thr Val Glu Phe Thr Pro Ser Thr Glu Gln
1130 1135 1140

Val Trp Ile Asp Met Ser Glu Thr Glu Gly Val Phe Asn Ile Glu
1145 1150 1155

Ser Val Glu Leu Val Leu Glu Glu Glu
1160 1165

<210> SEQ ID NO 65
<211> LENGTH: 1160
<212> TYPE: PRT
<213> ORGANISM: Bacillus thuringiensis
<220> FEATURE:
<221> NAME/KEY: MISC_FEATURE
<223> OTHER INFORMATION: Cry8Ca1

<400> SEQUENCE: 65

Met Ser Pro Asn Asn Gln Asn Glu Tyr Glu Ile Ile Asp Ala Leu Ser
1 5 10 15

-continued

```
Pro Thr Ser Val Ser Asp Asn Ser Ile Arg Tyr Pro Leu Ala Asn Asp
            20                  25                  30

Gln Thr Asn Thr Leu Gln Asn Met Asn Tyr Lys Asp Tyr Leu Lys Met
        35                  40                  45

Thr Glu Ser Thr Asn Ala Glu Leu Ser Arg Asn Pro Gly Thr Phe Ile
    50                  55                  60

Ser Ala Gln Asp Ala Val Gly Thr Gly Ile Asp Ile Val Ser Thr Ile
65                  70                  75                  80

Ile Ser Gly Leu Gly Ile Pro Val Leu Gly Glu Val Phe Ser Ile Leu
                85                  90                  95

Gly Ser Leu Ile Gly Leu Leu Trp Pro Ser Asn Asn Glu Asn Val Trp
            100                 105                 110

Gln Ile Phe Met Asn Arg Val Glu Glu Leu Ile Asp Gln Lys Ile Leu
        115                 120                 125

Asp Ser Val Arg Ser Arg Ala Ile Ala Asp Leu Ala Asn Ser Arg Ile
    130                 135                 140

Ala Val Glu Tyr Tyr Gln Asn Ala Leu Glu Asp Trp Arg Lys Asn Pro
145                 150                 155                 160

His Ser Thr Arg Ser Ala Ala Leu Val Lys Glu Arg Phe Gly Asn Ala
                165                 170                 175

Glu Ala Ile Leu Arg Thr Asn Met Gly Ser Phe Ser Gln Thr Asn Tyr
            180                 185                 190

Glu Thr Pro Leu Leu Pro Thr Tyr Ala Gln Ala Ala Ser Leu His Leu
        195                 200                 205

Leu Val Met Arg Asp Val Gln Ile Tyr Gly Lys Glu Trp Gly Tyr Pro
    210                 215                 220

Gln Asn Asp Ile Asp Leu Phe Tyr Lys Glu Gln Val Ser Tyr Thr Ala
225                 230                 235                 240

Arg Tyr Ser Asp His Cys Val Gln Trp Tyr Asn Ala Gly Leu Asn Lys
                245                 250                 255

Leu Arg Gly Thr Gly Ala Lys Gln Trp Val Asp Tyr Asn Arg Phe Arg
            260                 265                 270

Arg Glu Met Asn Val Met Val Leu Asp Leu Val Ala Leu Phe Pro Asn
        275                 280                 285

Tyr Asp Ala Arg Ile Tyr Pro Leu Glu Thr Asn Ala Glu Leu Thr Arg
    290                 295                 300

Glu Ile Phe Thr Asp Pro Val Gly Ser Tyr Val Thr Gly Gln Ser Ser
305                 310                 315                 320

Thr Leu Ile Ser Trp Tyr Asp Met Ile Pro Ala Ala Leu Pro Ser Phe
                325                 330                 335

Ser Thr Leu Glu Asn Leu Leu Arg Lys Pro Asp Phe Phe Thr Leu Leu
            340                 345                 350

Gln Glu Ile Arg Met Tyr Thr Ser Phe Arg Gln Asn Gly Thr Ile Glu
        355                 360                 365

Tyr Tyr Asn Tyr Trp Gly Gly Gln Arg Leu Thr Leu Ser Tyr Ile Tyr
    370                 375                 380

Gly Ser Ser Phe Asn Lys Tyr Ser Gly Val Leu Ala Gly Ala Glu Asp
385                 390                 395                 400

Ile Ile Pro Val Gly Gln Asn Asp Ile Tyr Arg Val Val Trp Thr Tyr
                405                 410                 415

Ile Gly Arg Tyr Thr Asn Ser Leu Leu Gly Val Asn Pro Val Thr Phe
            420                 425                 430

Tyr Phe Ser Asn Asn Thr Gln Lys Thr Tyr Ser Lys Pro Lys Gln Phe
```

-continued

```
        435                 440                 445

Ala Gly Gly Ile Lys Thr Ile Asp Ser Gly Glu Glu Leu Thr Tyr Glu
    450                 455                 460

Asn Tyr Gln Ser Tyr Ser His Arg Val Ser Tyr Ile Thr Ser Phe Glu
465                 470                 475                 480

Ile Lys Ser Thr Gly Gly Thr Val Leu Gly Val Val Pro Ile Phe Gly
                485                 490                 495

Trp Thr His Ser Ser Ala Ser Arg Asn Asn Phe Ile Tyr Ala Thr Lys
            500                 505                 510

Ile Ser Gln Ile Pro Ile Asn Lys Ala Ser Arg Thr Ser Gly Gly Ala
        515                 520                 525

Val Trp Asn Phe Gln Glu Gly Leu Tyr Asn Gly Gly Pro Val Met Lys
    530                 535                 540

Leu Ser Gly Ser Gly Ser Gln Val Ile Asn Leu Arg Val Ala Thr Asp
545                 550                 555                 560

Ala Lys Gly Ala Ser Gln Arg Tyr Arg Ile Arg Ile Arg Tyr Ala Ser
                565                 570                 575

Asp Arg Ala Gly Lys Phe Thr Ile Ser Ser Arg Ser Pro Glu Asn Pro
            580                 585                 590

Ala Thr Tyr Ser Ala Ser Ile Ala Tyr Thr Asn Thr Met Ser Thr Asn
        595                 600                 605

Ala Ser Leu Thr Tyr Ser Thr Phe Ala Tyr Ala Glu Ser Gly Pro Ile
    610                 615                 620

Asn Leu Gly Ile Ser Gly Ser Ser Arg Thr Phe Asp Ile Ser Ile Thr
625                 630                 635                 640

Lys Glu Ala Gly Ala Ala Asn Leu Tyr Ile Asp Arg Ile Glu Phe Ile
                645                 650                 655

Pro Val Asn Thr Leu Phe Glu Ala Glu Glu Asp Leu Asp Val Ala Lys
            660                 665                 670

Lys Ala Val Asn Gly Leu Phe Thr Asn Glu Lys Asp Ala Leu Gln Thr
        675                 680                 685

Ser Val Thr Asp Tyr Gln Val Asn Gln Ala Ala Asn Leu Ile Glu Cys
    690                 695                 700

Leu Ser Asp Glu Leu Tyr Pro Asn Glu Lys Arg Met Leu Trp Asp Ala
705                 710                 715                 720

Val Lys Glu Ala Lys Arg Leu Val Gln Ala Arg Asn Leu Leu Gln Asp
                725                 730                 735

Thr Gly Phe Asn Arg Ile Asn Gly Glu Asn Gly Trp Thr Gly Ser Thr
            740                 745                 750

Gly Ile Glu Val Val Glu Gly Asp Val Leu Phe Lys Asp Arg Ser Leu
        755                 760                 765

Arg Leu Thr Ser Ala Arg Glu Ile Asp Thr Glu Thr Tyr Pro Thr Tyr
    770                 775                 780

Leu Tyr Gln Gln Ile Asp Glu Ser Leu Leu Lys Pro Tyr Thr Arg Tyr
785                 790                 795                 800

Lys Leu Lys Gly Phe Ile Gly Ser Ser Gln Asp Leu Glu Ile Lys Leu
                805                 810                 815

Ile Arg His Arg Ala Asn Gln Ile Val Lys Asn Val Pro Asp Asn Leu
            820                 825                 830

Leu Pro Asp Val Arg Pro Val Asn Ser Cys Gly Gly Val Asp Arg Cys
        835                 840                 845

Ser Glu Gln Gln Tyr Val Asp Ala Asn Leu Ala Leu Glu Asn Asn Gly
    850                 855                 860
```

Glu Asn Gly Asn Met Ser Ser Asp Ser His Ala Phe Ser Phe His Ile
865 870 875 880

Asp Thr Gly Glu Ile Asp Leu Asn Glu Asn Thr Gly Ile Trp Ile Val
885 890 895

Phe Lys Ile Pro Thr Thr Asn Gly Asn Ala Thr Leu Gly Asn Leu Glu
900 905 910

Phe Val Glu Glu Gly Pro Leu Ser Gly Glu Thr Leu Glu Trp Ala Gln
915 920 925

Gln Gln Glu Gln Gln Trp Gln Asp Lys Met Ala Arg Lys Arg Ala Ala
930 935 940

Ser Glu Lys Thr Tyr Tyr Ala Ala Lys Gln Ala Ile Asp Arg Leu Phe
945 950 955 960

Ala Asp Tyr Gln Asp Gln Lys Leu Asn Ser Gly Val Glu Met Ser Asp
965 970 975

Leu Leu Ala Ala Gln Asn Leu Val Gln Ser Ile Pro Tyr Val Tyr Asn
980 985 990

Asp Ala Leu Pro Glu Ile Pro Gly Met Asn Tyr Thr Ser Phe Thr Glu
995 1000 1005

Leu Thr Asn Arg Leu Gln Gln Ala Trp Asn Leu Tyr Asp Leu Gln
1010 1015 1020

Asn Ala Ile Pro Asn Gly Asp Phe Arg Asn Gly Leu Ser Asn Trp
1025 1030 1035

Asn Ala Thr Ser Asp Val Asn Val Gln Gln Leu Ser Asp Thr Ser
1040 1045 1050

Val Leu Val Ile Pro Asn Trp Asn Ser Gln Val Ser Gln Gln Phe
1055 1060 1065

Thr Val Gln Pro Asn Tyr Arg Tyr Val Leu Arg Val Thr Ala Arg
1070 1075 1080

Lys Glu Gly Val Gly Asp Gly Tyr Val Ile Ile Arg Asp Gly Ala
1085 1090 1095

Asn Gln Thr Glu Thr Leu Thr Phe Asn Ile Cys Asp Asp Asp Thr
1100 1105 1110

Gly Val Leu Ser Thr Asp Gln Thr Ser Tyr Ile Thr Lys Thr Val
1115 1120 1125

Glu Phe Thr Pro Ser Thr Glu Gln Val Trp Ile Asp Met Ser Glu
1130 1135 1140

Thr Glu Gly Val Phe Asn Ile Glu Ser Val Glu Leu Val Leu Glu
1145 1150 1155

Glu Glu
1160

<210> SEQ ID NO 66
<211> LENGTH: 1160
<212> TYPE: PRT
<213> ORGANISM: Bacillus thuringiensis
<220> FEATURE:
<221> NAME/KEY: MISC_FEATURE
<223> OTHER INFORMATION: Cry8Ca2

<400> SEQUENCE: 66

Met Ser Pro Asn Asn Gln Asn Glu Tyr Glu Ile Ile Asp Ala Leu Ser
1 5 10 15

Pro Thr Ser Val Ser Asp Asn Ser Ile Arg Tyr Pro Leu Ala Asn Asp
20 25 30

Gln Thr Asn Thr Leu Gln Asn Met Asn Tyr Lys Asp Tyr Leu Lys Met

-continued

```
        35                  40                  45

Thr Glu Ser Thr Asn Ala Glu Leu Ser Arg Asn Pro Gly Thr Phe Ile
    50                  55                  60

Ser Ala Gln Asp Ala Val Gly Thr Gly Ile Asp Ile Val Ser Thr Ile
65                  70                  75                  80

Ile Ser Gly Leu Gly Ile Pro Val Leu Gly Glu Val Phe Ser Ile Leu
                85                  90                  95

Gly Ser Leu Ile Gly Leu Leu Trp Pro Ser Asn Asn Glu Asn Val Trp
            100                 105                 110

Gln Ile Phe Met Asn Arg Val Glu Glu Leu Ile Asp Gln Lys Ile Leu
        115                 120                 125

Asp Ser Val Arg Ser Arg Ala Ile Ala Asp Leu Ala Asn Ser Arg Ile
    130                 135                 140

Ala Val Glu Tyr Tyr Gln Asn Ala Leu Glu Asp Trp Arg Lys Asn Pro
145                 150                 155                 160

His Ser Thr Arg Ser Ala Ala Leu Val Lys Glu Arg Phe Gly Asn Ala
                165                 170                 175

Glu Ala Ile Leu Arg Thr Asn Met Gly Ser Phe Ser Gln Thr Asn Tyr
            180                 185                 190

Glu Thr Pro Leu Leu Pro Thr Tyr Ala Gln Ala Ala Ser Leu His Leu
        195                 200                 205

Leu Val Met Arg Asp Val Gln Ile Tyr Gly Lys Glu Trp Gly Tyr Pro
    210                 215                 220

Gln Asn Asp Ile Asp Leu Phe Tyr Lys Glu Gln Val Ser Tyr Thr Ala
225                 230                 235                 240

Arg Tyr Ser Asp His Cys Val Gln Trp Tyr Asn Ala Gly Leu Asn Lys
                245                 250                 255

Leu Arg Gly Thr Gly Ala Lys Gln Trp Val Asp Tyr Asn Arg Phe Arg
            260                 265                 270

Arg Glu Met Asn Val Met Val Leu Asp Leu Val Ala Leu Phe Pro Asn
        275                 280                 285

Tyr Asp Ala Arg Ile Tyr Pro Leu Glu Thr Asn Ala Glu Leu Thr Arg
    290                 295                 300

Glu Ile Phe Thr Asp Pro Val Gly Ser Tyr Val Thr Gly Gln Ser Ser
305                 310                 315                 320

Thr Leu Ile Ser Trp Tyr Asp Met Ile Pro Ala Ala Leu Pro Ser Phe
                325                 330                 335

Ser Thr Leu Glu Asn Leu Leu Arg Lys Pro Asp Phe Phe Thr Leu Leu
            340                 345                 350

Gln Glu Ile Arg Met Tyr Thr Ser Phe Arg Gln Asn Gly Thr Ile Glu
        355                 360                 365

Tyr Tyr Asn Tyr Trp Gly Gly Gln Arg Leu Thr Leu Ser Tyr Ile Tyr
    370                 375                 380

Gly Ser Ser Phe Asn Lys Tyr Ser Gly Val Leu Ala Gly Ala Glu Asp
385                 390                 395                 400

Ile Ile Pro Val Gly Gln Asn Asp Ile Tyr Arg Val Val Trp Thr Tyr
                405                 410                 415

Ile Gly Arg Tyr Thr Asn Ser Leu Leu Gly Val Asn Pro Val Thr Phe
            420                 425                 430

Tyr Phe Ser Asn Asn Thr Gln Lys Thr Tyr Ser Lys Pro Lys Gln Phe
        435                 440                 445

Ala Gly Gly Ile Lys Thr Ile Asp Ser Gly Glu Glu Leu Thr Tyr Glu
    450                 455                 460
```

```
Asn Tyr Gln Ser Tyr Ser His Arg Val Ser Tyr Ile Thr Ser Phe Glu
465                 470                 475                 480

Ile Lys Ser Thr Gly Gly Thr Val Leu Gly Val Val Pro Ile Phe Gly
                485                 490                 495

Trp Thr His Ser Ser Ala Ser Arg Asn Asn Phe Ile Tyr Ala Thr Lys
            500                 505                 510

Ile Ser Gln Ile Pro Ile Asn Lys Ala Ser Arg Thr Ser Gly Gly Ala
        515                 520                 525

Val Trp Asn Phe Gln Glu Gly Leu Tyr Asn Gly Gly Pro Val Met Lys
    530                 535                 540

Leu Ser Gly Ser Gly Ser Gln Val Ile Asn Leu Arg Val Ala Thr Asp
545                 550                 555                 560

Ala Lys Gly Ala Ser Gln Arg Tyr Arg Ile Arg Ile Arg Tyr Ala Ser
                565                 570                 575

Asp Arg Ala Gly Lys Phe Thr Ile Ser Ser Arg Ser Pro Glu Asn Pro
            580                 585                 590

Ala Thr Tyr Ser Ala Ser Ile Ala Tyr Thr Asn Thr Met Ser Thr Asn
        595                 600                 605

Ala Ser Leu Thr Tyr Ser Thr Phe Ala Tyr Ala Glu Ser Gly Pro Ile
    610                 615                 620

Asn Leu Gly Ile Ser Gly Ser Ser Arg Thr Phe Asp Ile Ser Ile Thr
625                 630                 635                 640

Lys Glu Ala Gly Ala Ala Asn Leu Tyr Ile Asp Arg Ile Glu Phe Ile
                645                 650                 655

Pro Val Asn Thr Leu Phe Glu Ala Glu Glu Asp Leu Asp Val Ala Lys
            660                 665                 670

Lys Ala Val Asn Gly Leu Phe Thr Asn Glu Lys Asp Ala Leu Gln Thr
        675                 680                 685

Ser Val Thr Asp Tyr Gln Val Asn Gln Ala Ala Asn Leu Ile Glu Cys
    690                 695                 700

Leu Ser Asp Glu Leu Tyr Pro Asn Glu Lys Arg Met Leu Trp Asp Ala
705                 710                 715                 720

Val Lys Glu Ala Lys Arg Leu Val Gln Ala Arg Asn Leu Leu Gln Asp
                725                 730                 735

Thr Gly Phe Asn Arg Ile Asn Gly Glu Asn Gly Trp Thr Gly Ser Thr
            740                 745                 750

Gly Ile Glu Val Val Glu Gly Asp Val Leu Phe Lys Asp Arg Ser Leu
        755                 760                 765

Arg Leu Thr Asn Ala Arg Glu Ile Asp Thr Glu Thr Tyr Pro Thr Tyr
    770                 775                 780

Leu Tyr Gln Gln Ile Asp Glu Ser Leu Leu Lys Pro Tyr Thr Arg Tyr
785                 790                 795                 800

Lys Leu Lys Gly Phe Ile Gly Ser Ser Gln Asp Leu Glu Ile Lys Leu
                805                 810                 815

Ile Arg His Arg Ala Asn Gln Ile Val Lys Asn Val Pro Asp Asn Leu
            820                 825                 830

Leu Pro Asp Val Arg Pro Val Asn Ser Cys Gly Gly Val Asp Arg Cys
        835                 840                 845

Ser Glu Gln Gln Tyr Val Asp Ala Asn Leu Ala Leu Glu Asn Asn Gly
    850                 855                 860

Glu Asn Gly Asn Met Ser Ser Asp Ser His Ala Phe Ser Phe His Ile
865                 870                 875                 880
```

```
Asp Thr Gly Glu Ile Asp Leu Asn Glu Asn Thr Gly Ile Trp Ile Val
                885                 890                 895

Phe Lys Ile Pro Thr Thr Asn Gly Asn Ala Thr Leu Gly Asn Leu Glu
            900                 905                 910

Phe Val Glu Glu Gly Pro Leu Ser Gly Glu Thr Leu Glu Trp Ala Gln
        915                 920                 925

Gln Gln Glu Gln Gln Trp Gln Asp Lys Met Ala Arg Lys Arg Ala Ala
    930                 935                 940

Ser Glu Lys Thr Tyr Tyr Ala Ala Lys Gln Ala Ile Asp Arg Leu Phe
945                 950                 955                 960

Ala Asp Tyr Gln Asp Gln Lys Leu Asn Ser Gly Val Glu Met Ser Asp
                965                 970                 975

Leu Leu Ala Ala Gln Asn Leu Val Gln Ser Ile Pro Tyr Val Tyr Asn
            980                 985                 990

Asp Ala Leu Pro Glu Ile Pro Gly  Met Asn Tyr Thr Ser  Phe Thr Glu
        995                 1000                1005

Leu Thr  Asn Arg Leu Gln Gln  Ala Trp Asn Leu Tyr  Asp Leu Gln
    1010                 1015                 1020

Asn Ala  Ile Pro Asn Gly Asp  Phe Arg Asn Gly Leu  Ser Asn Trp
    1025                 1030                 1035

Asn Ala  Thr Ser Asp Val Asn  Val Gln Gln Leu Ser  Asp Thr Ser
    1040                 1045                 1050

Val Leu  Val Ile Pro Asn Trp  Asn Ser Gln Val Ser  Gln Gln Phe
    1055                 1060                 1065

Thr Val  Gln Pro Asn Tyr Arg  Tyr Val Leu Arg Val  Thr Ala Arg
    1070                 1075                 1080

Lys Glu  Gly Val Gly Asp Gly  Tyr Val Ile Ile Arg  Asp Gly Ala
    1085                 1090                 1095

Asn Gln  Thr Glu Thr Leu Thr  Phe Asn Ile Cys Asp  Asp Asp Thr
    1100                 1105                 1110

Gly Val  Leu Ser Thr Asp Gln  Thr Ser Tyr Ile Thr  Lys Thr Val
    1115                 1120                 1125

Glu Phe  Thr Pro Ser Thr Glu  Gln Val Trp Ile Asp  Met Ser Glu
    1130                 1135                 1140

Thr Glu  Gly Val Phe Asn Ile  Glu Ser Val Glu Leu  Val Leu Glu
    1145                 1150                 1155

Glu Glu
    1160
```

<210> SEQ ID NO 67
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(22)
<223> OTHER INFORMATION: n is a, c, g, or t
<220> FEATURE:
<221> NAME/KEY: UNSURE
<222> LOCATION: (11)..(19)

<400> SEQUENCE: 67
caccatgnnn nnnnnnnnnn nn 22

<210> SEQ ID NO 68
<211> LENGTH: 22

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(22)
<223> OTHER INFORMATION: n is a, c, g, or t
<220> FEATURE:
<221> NAME/KEY: unsure
<222> LOCATION: (11)..(19)

<400> SEQUENCE: 68
gtggtacnnn nnnnnnnnnn nn 22

<210> SEQ ID NO 69
<211> LENGTH: 32
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (13)..(27)
<223> OTHER INFORMATION: n is a, c, g, or t
<220> FEATURE:
<221> NAME/KEY: UNSURE
<222> LOCATION: (16)..(24)

<400> SEQUENCE: 69
cccttcacca tgnnnnnnnn nnnnnnnaag gg 32

<210> SEQ ID NO 70
<211> LENGTH: 32
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (13)..(27)
<223> OTHER INFORMATION: n is a, c, g, or t
<220> FEATURE:
<221> NAME/KEY: unsure
<222> LOCATION: (16)..(24)

<400> SEQUENCE: 70
gggaagtggt acnnnnnnnn nnnnnnnttc cc 32

<210> SEQ ID NO 71
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 71

Gly Lys Pro Ile Pro Asn Pro Leu Leu Gly Leu Asp Ser Thr
1 5 10

<210> SEQ ID NO 72
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 72
cccggcccag gcggccgacc acgcgtatcg a 31

-continued

```
<210> SEQ ID NO 73
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 73

cccggccggc ctggccgttc aaggaaccgt t                                 31


<210> SEQ ID NO 74
<211> LENGTH: 13
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(9)
<223> OTHER INFORMATION: n is a, c, g, or t

<400> SEQUENCE: 74

ggccnnnnng gcc                                                     13
```

GENETIC CONSTRUCT EXPRESSING INSECTICIDAL TOXIN AND THE METHOD OF USING THEREOF

CROSS REFERENCE TO RELATED APPLICATION

This application is a National Stage of International Application No. PCT/BR2010/000242, filed on Jul. 26, 2010, claiming priority based on Brazilian Patent Application No. PI 0906128-2, filed Jul. 24, 2009, the contents of all of which are incorporated herein by reference in their entirety.

FIELD OF THE INVENTION

The following specification of the patent of invention refers to the field of controlling insect-pests which attack crops, using methods and compositions that comprise δ-endotoxins derived from the microorganism *Bacillus thuringiensis*.

BACKGROUND OF THE ART

Of all the domestic and cultivatable plants, cotton is one of the most attacked by diseases and insect-pests, besides being highly sensitive to the occurrence imposed by weed plants (Beltrão, E. M., Souza, J. G. O. agronegócio do algodão no Brasil. Embrapa: Brasília, v. 01, 1999). Among the main insect-pests comes the boll weevil, *Anthonomus grandis* (Boheman, C. H. Description of new species. In Schoenherr, Genera et species *Curculionidum cum synonymia hujus* Familiae, vol. 7, pt. 2. Paris: Roret. 461 p., 1843), considered one of the most serious pests for cotton cultivation, being prevalent across Mexico, Cuba, Haiti, Venezuela, Colombia, Paraguay and Brazil. This insect uses the flower buds and fruits of its host as a source of food and place for development, causing direct prejudice to the commercialization of cotton fiber. Levels of infestation grow rapidly and up to 100% of production can be affected unless adequate control measures are taken. This insect represents potentially major damage, being considered a key pest in the planning and control of insects that are harmful to crops, mainly due to the difficulty of control by chemical insecticides.

The cotton plant and its pests have co-existed for a long evolutionary period.

Plant and insect form an interdependent and competitive morphological and biochemical system, most often resulting in the use of part of the plant by the insect. This part used represents the damage caused by the insect to the plant, and depends on the size of the pest population, and the plant's ability to resist the attack and to recover from the damage sustained (Beltrão, E. M., Souza, J. G. O. agronegócio do algodão no Brasil. Embrapa: Brasília, v. 01, 1999).

The plant versus insect interaction can be visualized in at least two ways: from the point of view of the insect, with the plant varying from suitable to completely unsuitable as host and, on the other hand, from the point of view of the plant where, the lower the number of species and abundance of insects associated thereto, and the lesser the effect that these insects exert thereover, the greater their resistance to these insects (Santos, W. J. Identificação, biologia, amostragem e controle das pragas do algodoeiro. In: Embrapa Agropecuária Oeste; Embrapa Algodão. Algodão: tecnologia de produção., p. 296 p. 2002).

Between one extreme and another of plant resistance to insect-pests, there is a complete and extensive arsenal of mechanisms to attack and counter-attack the action of insects, which include from a simple morphological impediment to complex phytochemical components, which interfere directly in the metabolic process involved in the use of the plant as insect host. In practical terms, the resistance of the cotton plant to insect-pests represents the ability of certain crops to produce better quality cotton in a greater amount than other crops, under attack from the same population of insect-pests (Freire, E. C. Cultivares e produção de semente na melhoria da qualidade do algodão no nordeste e centro-oeste do Brasil. Boletim informativo Embrapa/CNPA. 1997).

In most countries where cotton is cultivated, vulnerability to pests represents the main problem of this crop. Having no alternatives for more effective control, the producers routinely continue to believe that chemical insecticides are the only way to protect the crops. Though efficient, they are expensive, potentially harmful to man, to the environment and, in the long term, trigger resistance processes, pest's resurgence and reduction in the incidence of natural enemies (Panizzi, A. R. Efeito de insecticides na população das principais pragas da soja. An. Soc. Entomol. Brasil, v. 6, p. 264-275. 1977). Under these circumstances, the objective of the present invention is to increase the resistance of plants, generating transgenic plants, which are capable of expressing genes with high entomotoxic activity, whereby solving the problem of the abusive use of chemical insecticides.

The stable introduction of exogenous genes into cotton plants, with the purpose of inducing resistance to insect-pests, is an excellent alternative to reduce a large part of the problems associated to chemical methods. This technology comprises various advantages, chiefly because it does not pollute the environment. General data demonstrate that transformed cotton plants does not present negative effects to the environment, the characteristics being inheritable and expressed normally in the plant (Adamczyk, J. J., L. C. Adams L. C., Hardee, D. D. Field efficacy and seasonal expression profiles for terminal leaves of single and double *Bacillus thuringiensis* toxin cotton genotypes. Journal of Economic Entomology, v. 94, n.6, DEC, p. 1589-1593. 2001).

The availability of microorganisms and organic compounds in nature for biological use is very widespread, and they supply a wide variety of raw materials for the development of new products, having greater pathogenicity against the insect and broad action spectrum. Among these micro-organisms, a major discovery was the soil bacteria *Bacillus thuringiensis*, which is widely used as a biological control agent and as a source of potential molecules for biotechnological programs, destined to obtain transgenic plants resistant to insect-pests. With this strategy, it is possible to reduce populations of agricultural pests of economic interest to tolerable levels (Perlak, F. J., R. W. Deaton, T. A. Armstrong, R. L. Fuchs, S. R. Sims, J. T. Greenplate and D. A. Fischhoff. Insect resistant cotton plants. Biotechnology (NY), v. 8, n. 10, p. 939-943. 1990).

Although some δ-endotoxins with activity on the boll weevil have already been identified and described, the endophytic habit of this pest hampers or even prevents the use of these toxins by conventional means, which are commercialized as bioinsecticides, such as, for example, protein formulations containing Cry toxins. They present instability in the environment, low yield in purification from natural sources, in addition to easy loss of the activity of these toxins by weather conditions such as rain and sun.

Faced with this problem, the most efficient strategy is the use of Cry toxin-encoding genes in the generation of genetically-modified plants.

The use of encoding genes for this type of entomotoxic proteins and the expression of same in heterologous systems (bacteria or transgenic plants) overcomes the difficulties caused by the use of bioinsecticides. This strategy has gained prominence in recent years in the field of transgenia, due to the specificity of these toxins in relation to the insect-pests, efficiency, driven expression and innocuity to animals and humans. Accordingly, genetically-modified plants with specific resistance to insect-pest can be generated in high efficiency systems.

There are some Bt genes and transgenes with activity for coleoptera, such as, for example, the plants expressing a cry8 gene by the company DU PONT DE MENOURS with toxicity for *Leptinotarsa decemlineata* (US20030177528), the transgenic corn with a cry8-like gene by PIONEER & DU PONT with toxicity for *Diabrotica virgifera, Diabrotica undecimpunctata howardi, Leptinotarsa decemlineata* and *Anthonomus grandis* (US20060021096, as also mentioned in U.S. Pat. No. 7,105,332 and US2005166284), Feng, S et al., 2005 also describe a modified cry8 gene, cry8Ca, with specific activity for coleoptera insects (CN1609220-A) and, more recently, PIONEER & DU PONT describes a synthetic cry8 gene with toxicity for *Diabrotica virgifera virgifera* in monocot plants such as, for example, corn plants (as mentioned in patent application US20060288448).

Currently, plants expressing genes Bt of the cry8 type are, in their totality, monocot (eg.: corn). This being the case, to-date, no invention has described a gene of this nature, with potential application in dicot plants, as is the case of the cotton plant.

Modern techniques of molecular biology, such as the construction of combinatorial libraries, are used to develop and identify analog mutant genes with specific objectives.

Construction of variant analog genes libraries using molecular evolution technology in vitro, have been used over the last three decades. This fact is due to the appearance of biotechnological tools, which act as a platform for genetic engineering in the development of new molecules with improved activity, mainly intended for agriculture and the pharmaceuticals industry (Ling Yuan, L. Kurek, I., English, J. and Keenan, R. Laboratory-directed protein evolution. Microbiology and Molecular Biology Review. Vol. 69, No. 3, p. 373-392, 2005). There are various techniques which can be applied to generate mutations in a genic sequence, and of particular importance in the present invention is the DNA shuffling technique (Rosic, N. N., Huang, W., Johnston, W. A., James J. Devoss, J. J., Gillam, E. M. J. Extending the diversity of cytochrome P450 enzymes by DNA family shuffling. Gene, Vol. 35762, No of Pages 9, 2007; Ling Yuan, L. Kurek, I., English, J. and Keenan, R. Laboratory-directed protein evolution. Microbiology and Molecular Biology Reviews, Vol. 69, No. 3, p. 373-392, 2005; Abécassis, V., Pompon, D. and Truan, G. High efficiency family shuffling based on multistep PCR and in vivo DNA recombination in yeast: statistical analysis of a combinatorial library between human cytochrome P450 1A1 and 1A2. Nucleic Acids Research, Vol. 28, No. 20: E 88, 2000; Zhao, H. and Arnold, F. H. Functional and nonfunctional mutations distinguished by random recombination of homologous genes. Proc. Natl. Acad. Sci. U.S.A., Vol. 94, p. 7997-8000, 1997; Stemmer, W. P. C. Rapid evolution of a protein in vitro By DNA shuffling. Nature. London, Vol. 370, p. 389-391, 1994).

The technique of DNA shuffling consists of a directed molecular evolution, which generates punctual changes in the primary structure of the DNA molecules by means of random mutations (Ling Yuan, L. Kurek, I., English, J. and Keenan, R. Laboratory-directed protein evolution. Microbiology and Molecular Biology Reviews, Vol. 69, No. 3, p. 373-392, 2005; Stemmer, W. P. C. Rapid evolution of a protein in vitro By DNA shuffling. Nature. London, Vol. 370, p. 389-391, 1994, U.S. Pat. Nos. 5,605,793, 5,811,238, 5,830,721). Firstly, the gene of interest is randomly fragmented into small sequences of 30-50 base pairs, and this product is recombined in a PCR reaction (Polymerase Chain Reaction), which is conducted without the addition of oligonucleotides. In a second consecutive reaction, the products of the first reaction and specific oligonucleotides are added. Thus, a population of analog mutant/variant genes can be amplified (Stemmer, W. P. C. Rapid evolution of a protein in vitro by DNA shuffling. Nature. London, Vol. 370, p. 389-391, 1994; Zhao, H. and Arnold, F. H. Functional and nonfunctional mutations distinguished by random recombination of homologous genes. Proc. Natl. Acad. Sci. U.S.A., Vol. 94, p. 7997-8000, 1997).

The efficiency of the technique in producing analog molecules with greater biological activity has been proven in various works such as, for example, in Jager et al (Jager, S. A. W., Jekel, P. A. and Janssen, D. B. Hybrid penicillin acylases with improved properties for synthesis of β-lactam antibiotics. Enzyme And Microbial Technology, Vol. 40, p. 1335-1344, 2007), where the enzyme activity of the penicillin acyclase increased by 90%. The technique can use a single gene or more homologous genes and its success depends on a delicate arrangement between the size of the library, the biological diversity of origin, and a selection methodology of the variants having the desired characteristic (Ling Yuan, L. Kurek, I., English, J. and Keenan, R. Laboratory-directed protein evolution. Microbiology and Molecular Biology Reviews, Vol. 69, No. 3, p. 373-392, 2005).

The association of DNA shuffling techniques (creation of combinatorial libraries) and presentation of proteins on the surface of bacteriophages—*Phage Display*, makes selecting and expressing new molecules much more efficient (Stoop, A. A., Jespers, L., Lasters, I., Eldering, E. And Pannekoek, H. High-density mutagenesis by combined DNA shuffling and phage display to assign essential amino acid residues in protein-protein interactions: application to study structure-function of plasminogen activation inhibitor 1 (PAI-I). J. Mol. Biol., Vol. 301, p. 1135-1147, 2000).

SUMMARY OF THE INVENTION

The present invention provides molecules that encode new natural δ-endotoxins, mutant analogs and synthetic analogs for controlling insect-pests, particularly the boll weevil (*Anthonomus grandis*), which presents susceptibility to the new toxins.

Aspects of the invention also include genic constructs containing the nucleic acid molecules for encoding δ-endotoxins, transformation and expression vectors, cells and transgenic organisms, methods for the heterologous expression of the new δ-endotoxins in transgenic organisms, as well as the use of same in the control of pests. The invention also comprises a method of obtaining a transgenic plant characterized by comprising the following steps: a) transform a plant cell with a genic construct according to claim 4; b) cultivate the transformed cell, containing a genic construct of interest stably inserted into its genome, under ideal growth conditions in cell culture; and c) regenerate a transgenic plant expressing the product of the inserted construct, from the transformed cell and of obtaining transgenic plants.

The invention also provides synthetic analog genes, which are optimized for transformation and expression of same in plants, particularly in cotton plants.

Another embodiment of the invention refers to synthetic peptides of δ-endotoxins used for the treatment of infected plants, in controlling insect-pests and the use thereof in the preparation of biodegradable pesticide compositions.

SUMMARY DESCRIPTION OF THE DRAWINGS

FIG. 1: Amplification of the cry8 gene. Amplification reaction by PCR, using specific oligonucleotides described by Bravo et al (1998). Agarose gel 1.0% stained with ethidium bromide (A) First round with the oligonucleotides described by Bravo et al (1998). Line 1. Molecular weight marker 1 Kb ladder plus. Line 2. Amplified bands of approximately 400 bp with the oligonucleotides cry8b, $2^{nd}$ round. The arrow indicates the probable desired product. Line 3. Oligonucleotides cry8a, $2^{nd}$ round. Line 4. Oligonucleotides cry8geral. Line 5. Oligonucleotides cry8a, $1^{st}$ Round. Line 6. Oligonucleotides cry8geral, $1^{st}$ Round. (B) Second round with the oligonucleotide cry8b Line 1. Molecular weight marker 1 Kb ladder plus. Line 2 and 3. Amplification using 1 μL of the reaction 1 (FIG. A) and sample of line 2 with the band of approximately 450 pb.

Figure 2:
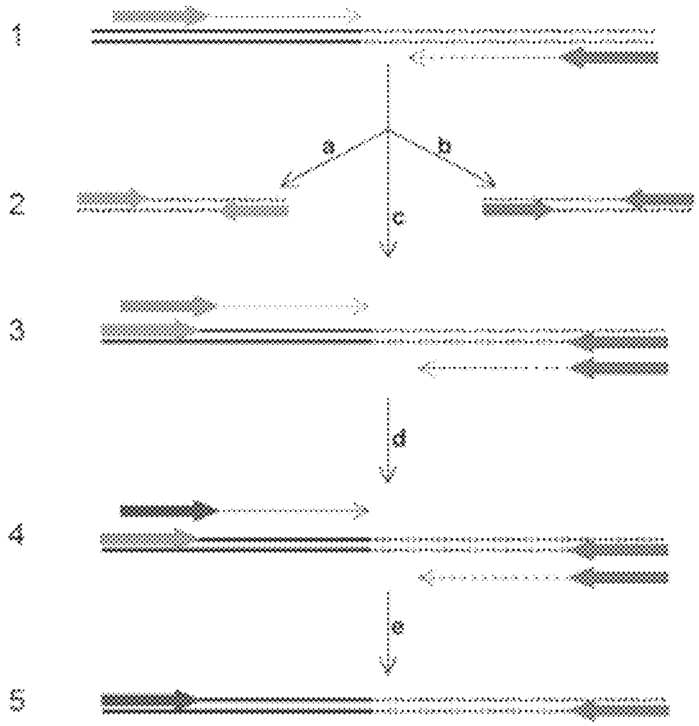

FIG. 2: TAIL-PCR. Schematic representation of the TAIL-PCR technique (Liu et al., 1995). 1. First amplification with the specific 1 and arbitrary oligonucleotides. 2. Result of the first amplification generating unspecific products (a, b) and the specific product (c). 3. Second amplification with the same arbitrary oligonucleotide and specific more internal oligonucleotide generating the second specific product (d). 4. Third amplification with the same arbitrary oligonucleotide and the specific oligonucleotide 3 generating the final product (e). 5. Final specific product.

Figure 3:
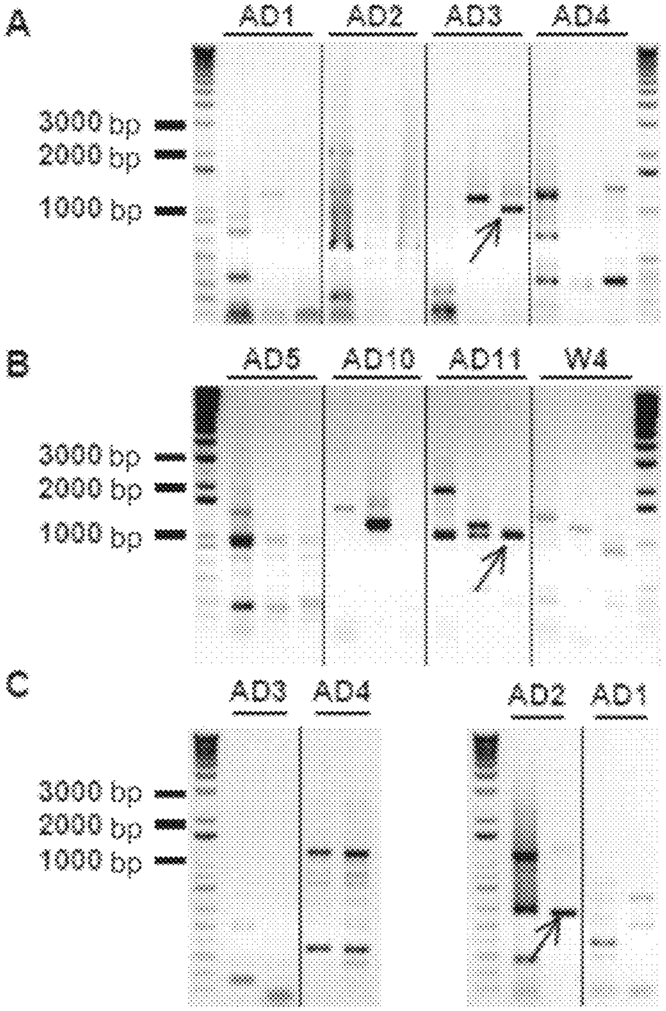

FIG. 3: Cloning of cry8 gene of strain S811 by TAIL-PCR. Agarose gels 1.0% stained with ethidium bromide and molecular weight marker 1 Kb ladder plus. (A) First TAIL-PCR using the arbitrary oligonucleotides AD1, AD2, AD3, AD4, showing the successive rounds of amplifications with each specific oligonucleotide. (B) First TAIL-PCR using the arbitrary oligonucleotide AD5, AD10, AD11, W4, showing the successive rounds of amplifications with each specific oligonucleotide. (C) Second TAIL-PCR using the arbitrary oligonucleotide AD3, AD4, AD2 and AD1, showing the successive rounds of amplifications with each specific oligonucleotide. The arrows indicate the potentially positive products that were subsequently cloned and sequenced.

Figure 4:
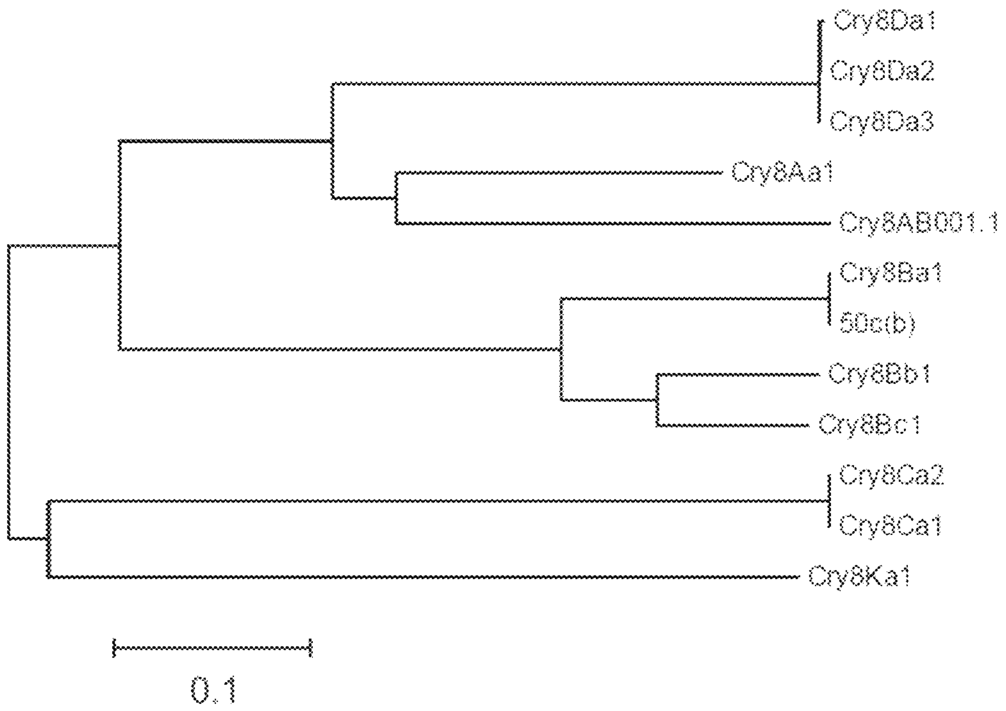

FIG. 4: Dendrogram of the new toxin Cry8Ka1 alignment, obtained after two rounds of TAIL-PCR. Analysis with the other Cry8 toxins filed at the data bank to-date, showing the high identity between them and that the cloned gene encodes a protein distinct from the others. The scale indicates that in the space represented, there is an exchange of 0.1 aa. The dendrogram was produced using the program MEGA4 (Tamura K, Dudley J, Nei M & Kumar S (2007) MEGA4: Molecular Evolutionary Genetics Analysis (MEGA) software version 4.0. Molecular Biology and Evolution 24:1596-1599).

Figure 5:
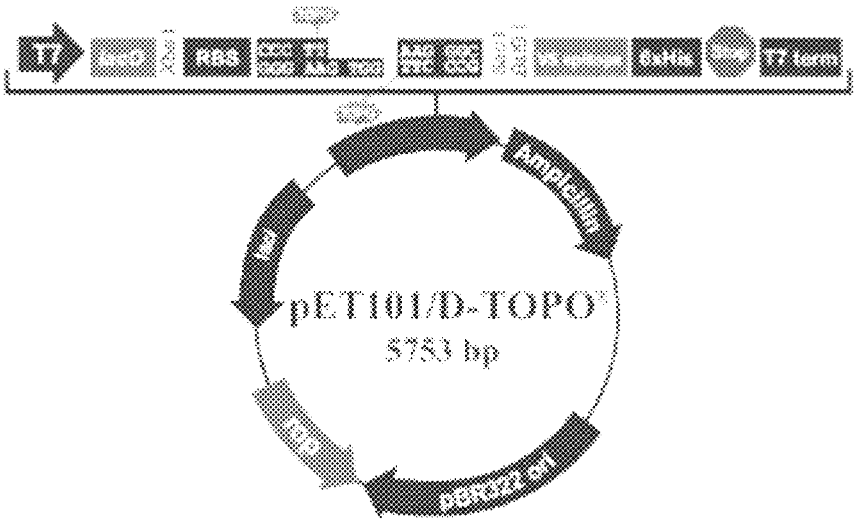

FIG. 5: Map of the commercial vector pET101/D-TOPO for heterologous expression in *Escherichia coli*. Schematic representation of the vector, including the promoter pT7. Pomoter T7: Induced by IPTG allows the large-scale expression in some strains of *Escherichia coli*; Lac Operon (lacO): binding site of the lac repressor important to the basal expression reduction of the recombinant proteins (their function can be regulated by the presence or absence of glucose in the culture medium); RBS: Ribosome Binding Site, located upstream the 5' region of the gene to be cloned in the ideal position to begin the translation process; Cloning site TOPO: Region that comprises the exact location where the insert will be cloned; Epitope V5 (Gly- Lys-Pro-Ile-Pro-Asn-Pro-Leu-Leu- Gly-Leu-Asp-Ser-Thr (SEQ ID NO: 71)): Used to detect recombinant proteins by western blot using antibodies anti-V5; 6His C-terminal: Important to purify proteins, using for such resins which have a coupled metal; Terminater T7: Sequence of bacteriophage T7 which allows the finalization of the transcription of the genes; Promoter bla: Promoter of the ampicillin resistance gene; β-lactamase ampicillin resistance gene): Selects the resistant plasmides in *E.coli*; pBR322 Origin of Replication (ori): Replication element and maintenance of the plasmide in *E.coli.*

Figure 6:
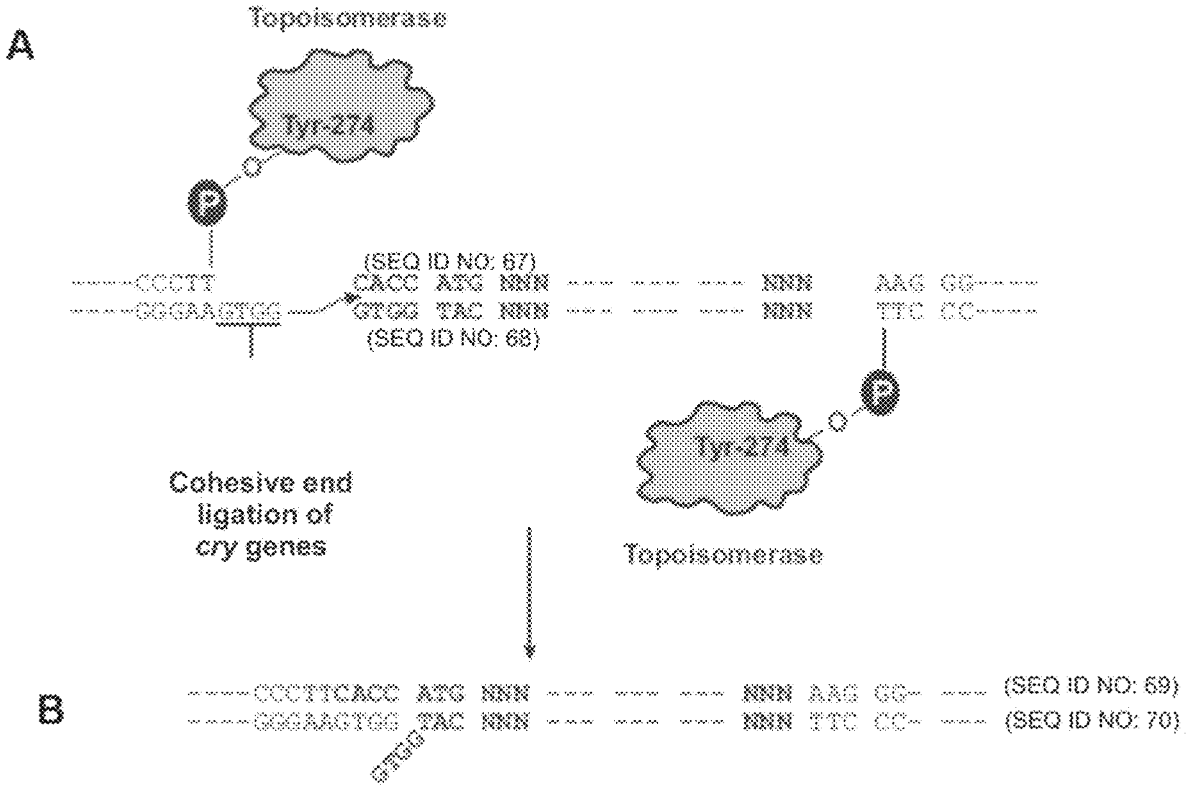

FIG. 6: Ligation system scheme of the PCR product into the pET101/D-TOPO vector of. (A) The cohesive end of the vector where the PCR product will be cloned is demonstrated jointly with the presence of the topoisomerase enzyme. (B) The PCR product is directly cloned by adding 4 base pairs of the direct orientation oligonucleotide. The cohesive end of the cloning vector (GTGG) invades the end 5' of the PCR product, annealing with the four added bases (CACC) and stabilizing the PCR product in the correct orientation. The topoisomerase then cleaves the protruding part of the PCR product so that the ink is effective.

Figure 7:
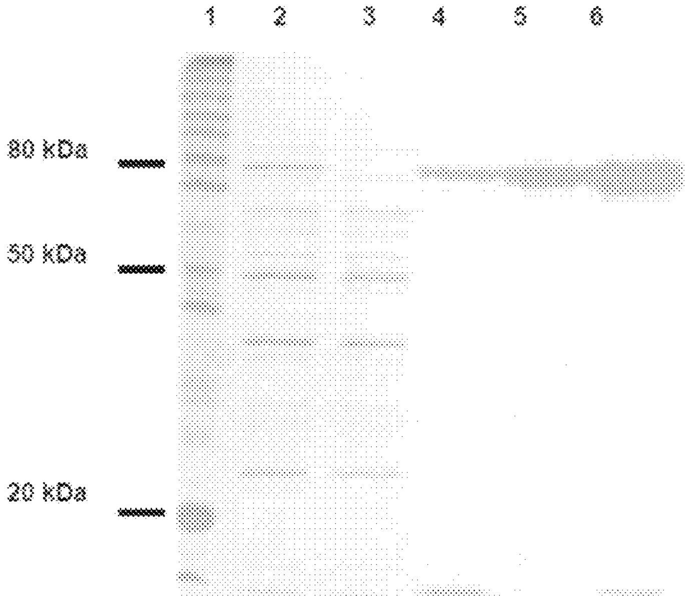

FIG. 7: Analysis by SDS-PAGE 12% of the recombinant protein Cry8Ka1 purified by affinity chromatography (Ni-NTA). Line 1. Molecular weight marker. Line 2. Total extract of *E. coli* expressing the recombinant protein Cry8Ka1. Line 3. Ni-NTA resin Pass-through fraction. Lines 4, 5 and 6. Protein Cry8Ka1 eluted from the Ni-NTA resin in different concentrations to confirm the purity thereof. 5 μg (lines 2, 3 and 4), 10 μg (line 5) and 15 μg (line 6) of samples were added to the sample buffer, submitted to SDS-PAGE 12%, at 25 mA and stained with silver nitrate.

Figure 8:
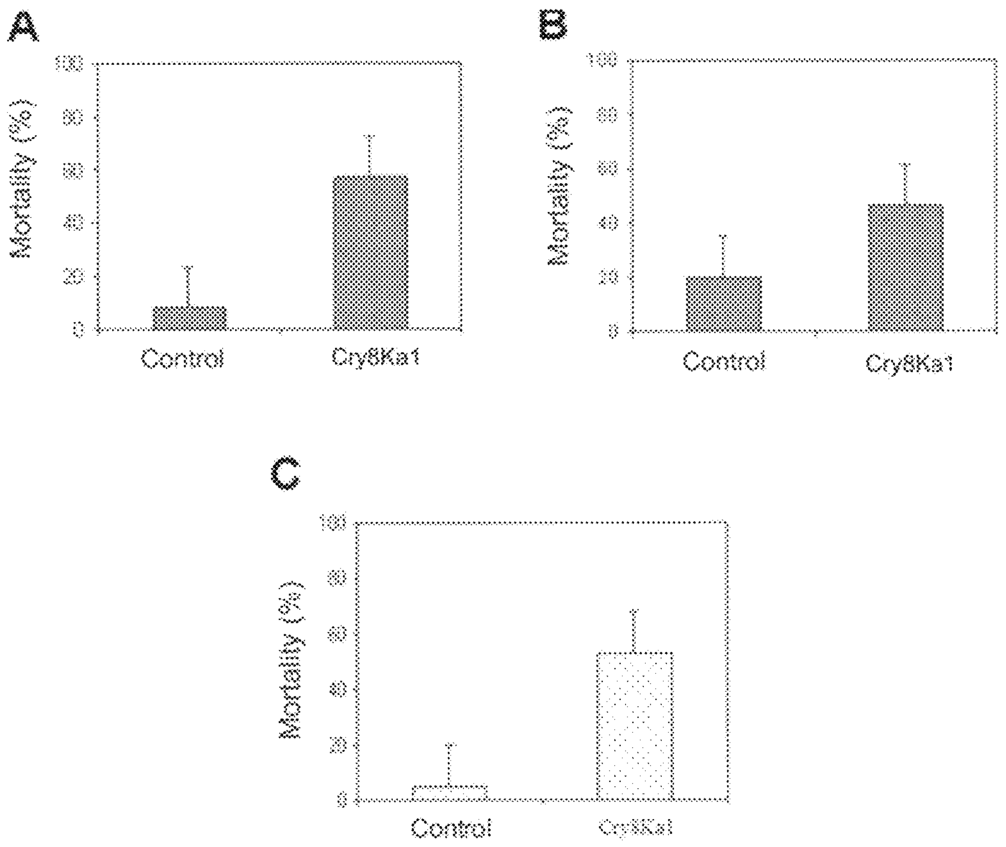

FIG. 8: Bioassays against *A. grandis* and *S. frugiperda* with recombinant toxins Cry8Ka1 and Cry8Ka1. (A) Bioassay against *S. frugiperda* using Cry8Ka1. Surface diet showing mortality of 50% in the concentration of 5 μg/mL. (B) Bioassay against *A. grandis* using Cry8Ka1. Diet incorporated demonstrating mortality of 50% in the concentration of 230 μg/mL. (C) Bioassay against *A. grandis* using Cry8Ka1. Diet incorporated demonstrating mortality of 50% in the concentration of 160 μg/mL. The dialysis water to which the proteins were submitted was used as control. All the experiments were carried out in triplicate with 30 insects of *A. grandis* and 90 of *S. frugiperda.*

Figure 9:
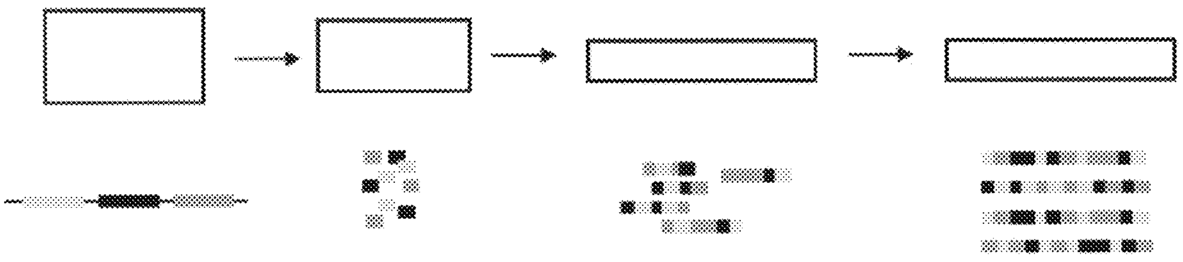

FIG. 9. Scheme of DNA shuffling technique using a single gene as substrate. Scheme of amplifying the cry8Ka1 gene with specific oligonucleotides for inserting the restriction site of the SfiI enzyme. Fragmentations, amplifications and reconstruction of the mutant analog genes.

Figure 10:
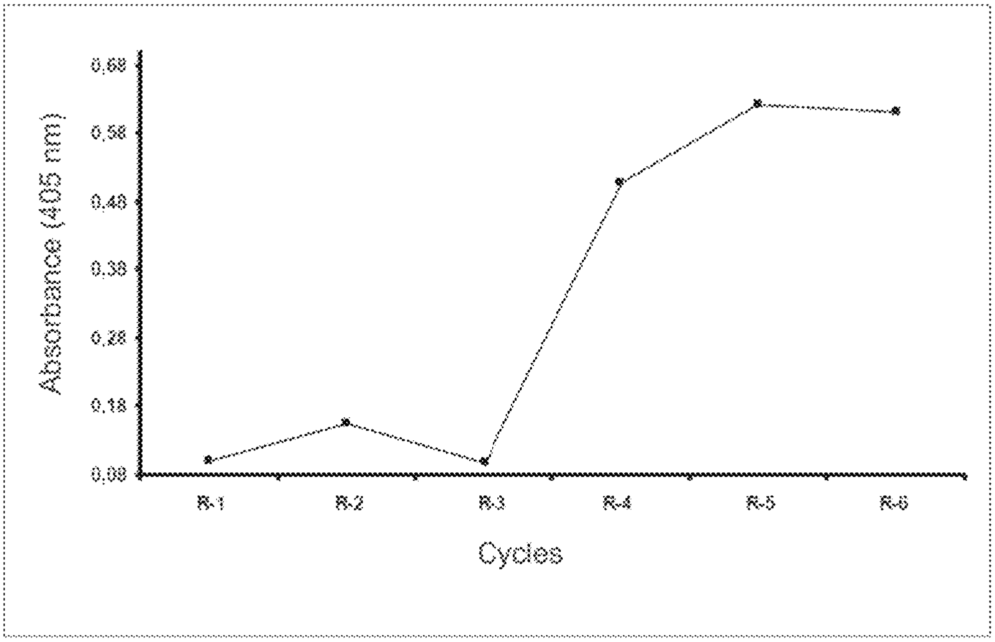

FIG. 10. Interaction between BBMVs of *A. grandis* and fusion phages. For absorbency reading, the wavelength of 405 nm was used. R-1 to R-6—Selection cycles and the number of washes per cycle. The greater absorbency, that is, the number of fusion phages with specificity on BBMVs of the insect *A. grandis*, occurred as of the $5^{th}$ cycle of the selection.

Figure 11:
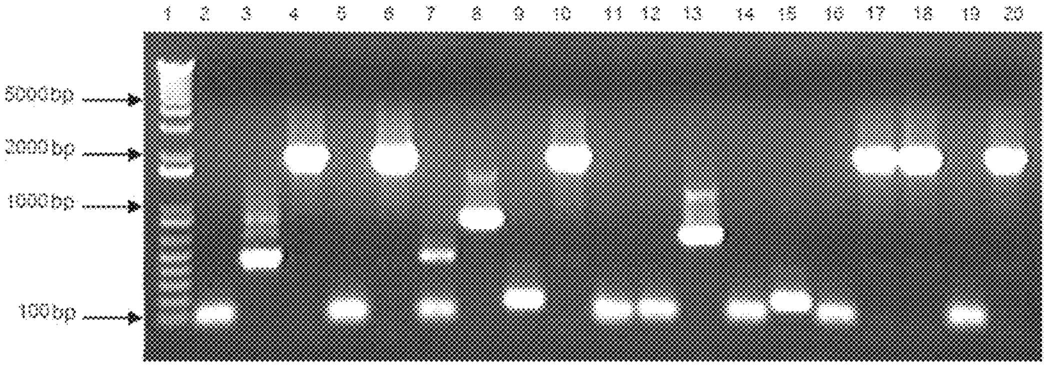

FIG. 11. PCR of variant colony BI using specific initiator oligonucleotides. Photo of agarose gel 1% exhibiting amplified DNA in the expected size of approximately 2000 bp. In this gel, five colonies, in addition to the positive control, presented the expected size (4, 6, 10, 17 and 18). 1—Marker 1 Kb Plus® (INVITROGEN). 2 to 18—Variants of cry8Ka1 gene. 19—Negative control (PCR without DNA). 20—Positive control, cry8Ka1 gene with specific initiator oligonucleotides.

Figure 12:
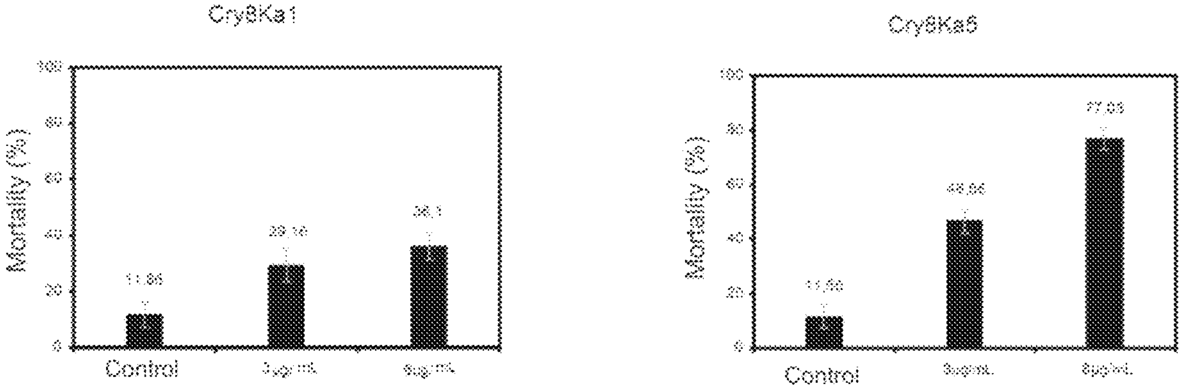

FIG. 12. Bioassay with neonate larvae of *A. grandis* to determine the insecticide activity of proteins Cry8Ka1 and Cry8Ka5 (mutant). Control—Negative control, diet without the addition of proteins under study. A—Mortality of larvae fed with Cry8Ka1; B—Mortality of larvae fed with Cry8Ka5. In the concentration of 6 μg/mL of diet, a twofold increase was noted in the insecticide activity of the new molecule.

Figure 13:
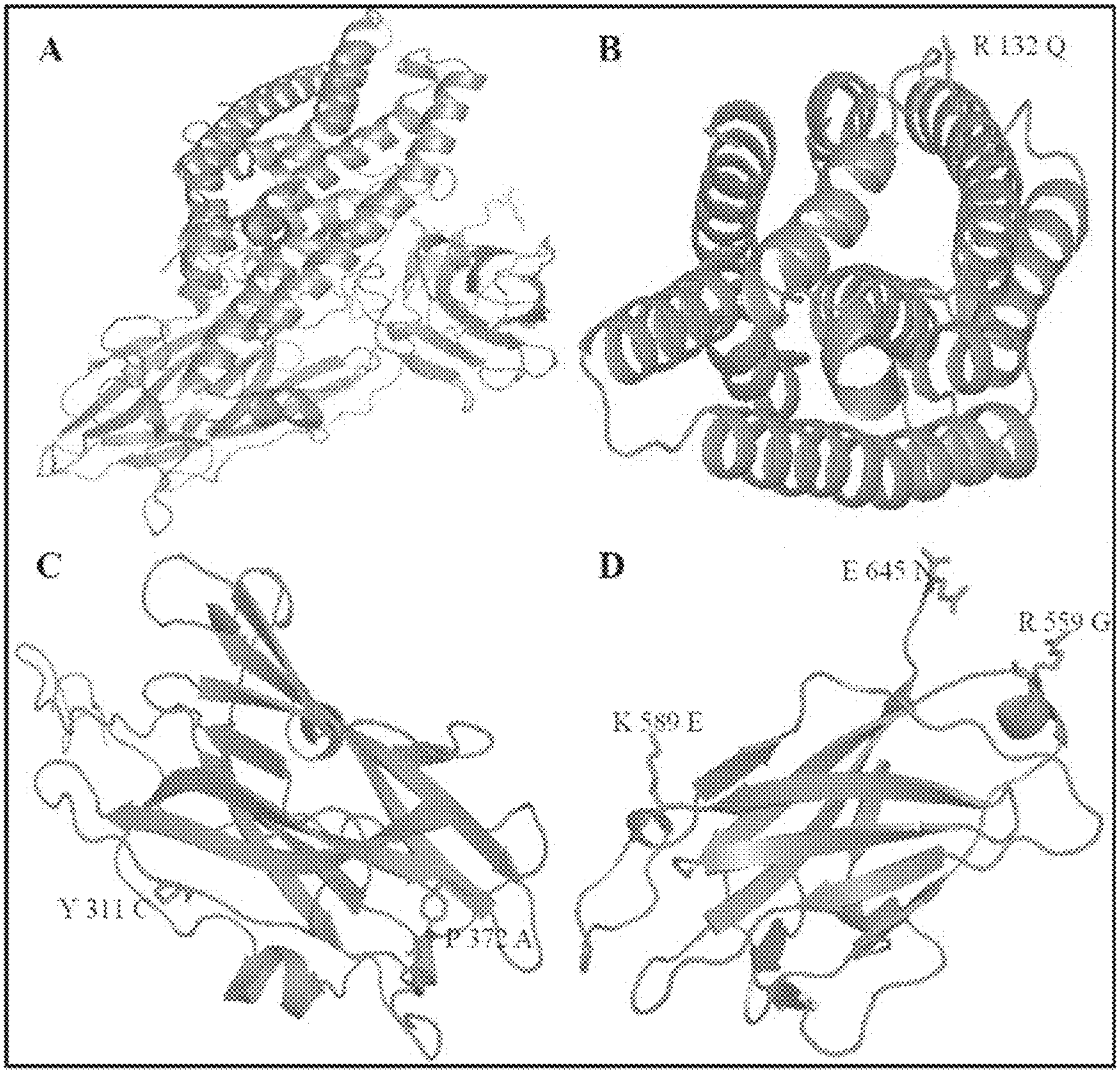

FIG. 13. Representation of modeled structure of the native toxin Cry8Ka1 using the Modeller program and visualized by PyMOL (Delano, W. L. The PyMOL Molecular Graphics System (2002) on World Wide Web http://www.pymol.org). In the analog Cry8Ka5, the structure skeleton remains the same, being just the side chains of the residues Cry8Ka1 substituted amino acids. The Figure indicates the residues of amino acids of Cry8Ka1 that were substituted in the sequence of analog Cry8Ka5. In A, representation of the molecule with the three domains I, II and III. In B, prominence is given to the domain I, formed by seven α-helix. The arginin 132 substituted for glutamine is located in helix 3. In C, prominence is given to the three anti-parallel β-sheets of domain II, with indication of the residues of native Cry 8 substituted in the analog molecule: tyrosine 311 substituted in Cry8Ka5 for cysteine and proline 372 by alanine. In D, the β sandwich of Domain III, and indication of the three residues substituted in the analog molecule (arginin 559 for glycine, lysine 589 for glutamic acid and glutamic acid 645 for asparagine).

Figure 14:
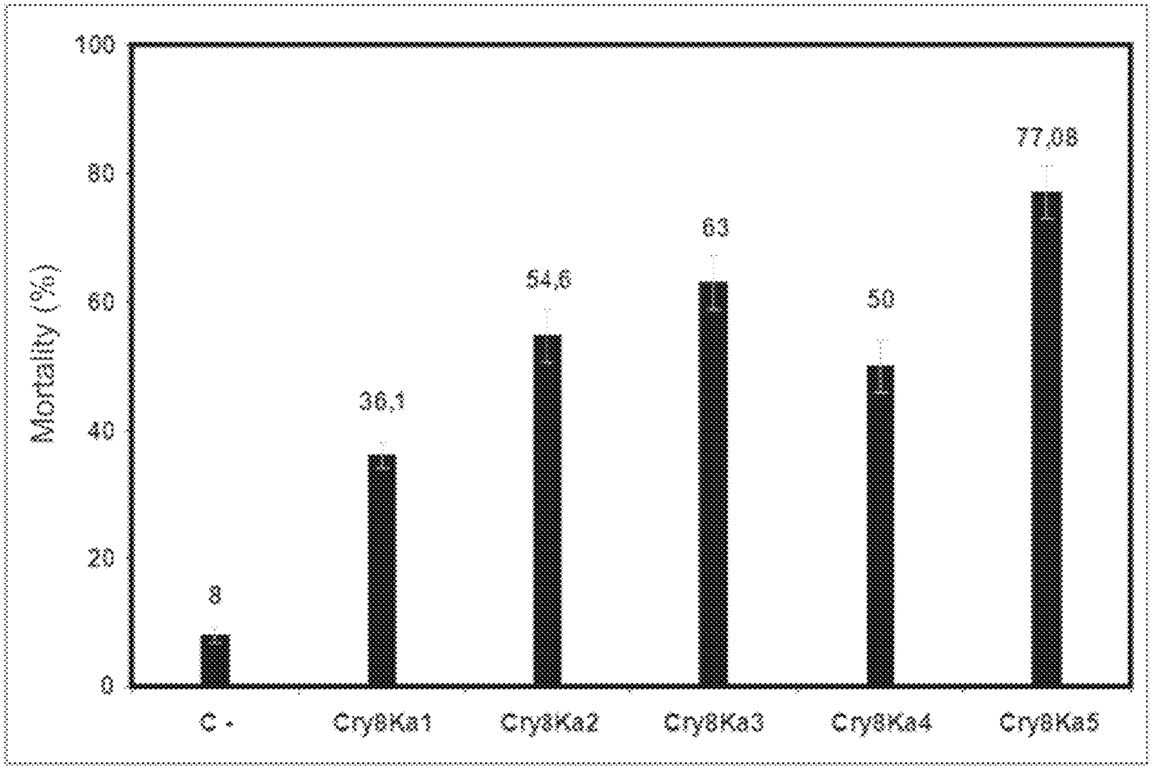

FIG. 14. Graph of entomotoxic activity of the cry8 analog genes to the native cry8Ka1 gene. The bioassay was conducted with the fusion phages. Legend: C- —Negative control using phages HELPER. Cry8Ka1—Original protein expressed in the phage system. Cry8Ka2, Cry8Ka3, Cry8Ka4 and Cry8Ka5—Variants of toxin Cry8 expressed in the phage system.

FIG. 15. Alignment of the Cry8Ka1 nucleotides sequence with the Cry8AB00.1, 50C (b) and Cry8Bb1 sequences. The first line represents the Cry8Ka1 sequence; the second line, Cry8AB00.1, sequence 3 of U.S. Pat. No. 7,329,7361; the third line, Cry8AB00.1, sequence 5 of U.S. Pat. No. 7,339,092; the fourth line, 50C sequence (b) of U.S. Pat. No. 5,554,534; the fifth line, Cry8Bb1, sequence 15 of patent WO2005083095; the sixth line, Cry8Bb1, sequence 17 of patent WO2005083095. The numbers above the alignments refer to the position of each nucleotide in the sequence. The sequences were aligned using the program CLUSTALW2. (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404). The full-length alignment of the sequences can be seen in the corresponding Brazilian Patent Application filed under number 012090001018.

FIG. 16. Cry8Ka1 nucleotides sequence alignment with Cry8Bb1. The first line represents a the Cry8Ka1 sequence; from the second line to the 32$^{nd}$ line, Cry8Bb1, sequences 1, 3, 5, 7, 11, 13, 17, 18, 21, 25, 29, 33, 39, 41, 43, 45, 47, 49, 51, 59, 61, 67, 69, 71, 73, 75, 77, 79, 81, 83, 91 and 93 of patent WO2005063996. The alignment numbers above refer to the position of each nucleotide in the sequence. The sequences were aligned using the program CLUSTALW2. (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404). The full-length alignment of the sequences can be seen in the corresponding Brazilian Patent Application filed under number 012090001018.

FIG. 17. Cry8Ka1 nucleotides sequence alignment with Cry8Bb1. The first line represents the Cry8Ka1 sequence; from the second line to the 31$^{st}$ line, Cry8Bb1, sequences 1, 3, 7, 11, 13, 17, 18, 21, 25, 29, 33, 39, 41, 43, 45, 47, 49, 51, 59, 61, 67, 69, 71, 73, 75, 77, 79, 81, 83, 91 and 93 of U.S. Pat. No. 7,105,332. The numbers above the alignment refer to the position of each nucleotide in the sequence. The sequences were aligned using the program CLUSTALW2. (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404). The full-length alignment of the sequences can be seen in the corresponding Brazilian Patent Application filed under number 012090001018.

FIG. 18. Alignment of the sequence of nucleotides of Cry8Ka1 with Cry8Bb1. The first line represents a sequence of Cry8Ka1; from the second line to the 31$^{st}$ line, Cry8Bb1, sequences 1, 3, 7, 11, 13, 17, 18, 21, 25, 29, 33, 39, 41, 43, 45, 47, 49, 51, 59, 61, 67, 69, 71, 73, 75, 77, 79, 81, 83, 91 and 93 of U.S. Pat. No. 7,378,499. The alignment numbers above refer to the position of each nucleotide in the sequence. The sequences were aligned using the program CLUSTALW2. (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404). The full-length alignment of the sequences can be seen in the corresponding Brazilian Patent Application filed under number 012090001018.

FIG. 19. Alignment of the new δ-endotoxin Cry8Ka1 amino acids sequences with sequences of Cry8. The sequences were aligned using the program CLUSTALW2 (http://www.ebi.ac.uk/Tools/clustalw2/) (Larkin, M A; Blackshields, G; Brown, N P; Chenna, R; McGettigan, P A; McWilliam, H; Valentin, F; Wallace, I M; Wilm, A; Lopez, R; Thompson, J D; Gibson, T J; Higgins, D G. ClustalW and ClustalX version 2. Bioinformatics. 2007; 23:2947-2948. doi: 10.1093/bioinformatics/btm404). The residues containing * are conserved amino acids; :, conservative substitutions; ., semiconservative substitutions. The full-length alignment of the sequences can be seen in the corresponding Brazilian Patent Application filed under number 012090001018.

DETAILED DESCRIPTION OF THE INVENTION

In the present invention, a new gene belonging to the family cry8, with high toxicity against coleopteran insects, specifically the boll weevil, was identified and cloned. The codons of this sequence were optimized for their expression in plants, specifically for cotton plants. Additionally, a combinatorial library was constructed using the DNA shuffling technique, with the aim of developing mutant analog genes, which also encodes the protein of the Cry8 family. The mutant analog genes generated, as well as the original gene, have a potential effect in controlling the boll weevil.

To achieve the desired objective, that is, δ-endotoxin genes with activity on the cotton boll weevil, initially a scanning was performed in the *B. thuringiensis* germplasm bank of Embrapa Recursos Genéticos e Biotecnologia, with the aim of identifying strains with activity on the boll weevil. The effective strains had their genetic material extracted and submitted to molecular biology techniques for identification, characterization and subsequent cloning of the cry genes. This scanning identified a strain, called S811, highly effective against the boll weevil.

In order to clone the cry genes of strain S811 (Germoplasm Bank, Embrapa Recursos Genéticos e Biotecnologia) an initial amplification by PCR was made with specific oligonucleotides for various of δ-endotoxins families. The amplification with specific oligonucleotides for the Cry8 family resulting in a fragment of about 500 bp corresponding to 5' end of a new cry8 family gene. The TAIL-PCR technique (Thermal Assymetric Interlacing Polymerase Chain Reaction) was used to obtain the full-length sequence of the gene, with specific oligonucleotides derived from previously amplified sequences and eight arbitrary initiator oligonucleotides. The TAIL-PCR consists of applying the PCR technique that allows the isolation of DNA segments adjacent to known sequences (Liu & Whittier, Efficient isolation and mapping of *Arabidopsis thaliana* T-DNA insert junctions by thermal asymmetric interlaced PCR. Plant J. 8: 457-463. 1995).

In short, three PCR reactions are done in sequence using three specific sequential oligonucleotides on one side and an arbitrary sequence oligonucleotide on the another side. An initial low stringency cycle is performed so as to enable the annealing of the arbitrary oligonucleotide with the unknown target sequence segment, followed by some high stringency cycles to favor the annealing of the specific oligonucleotide and the linear amplification of the target sequence. By alternating high and low stringency cycles, double strand molecules are formed and the amplification of the target sequence becomes logarithmic. In a second and third cycle of amplifications, non-specific products are not amplified and are eliminated.

Amplified fragments resulted from TAIL-PCR and, potentially positive, were cloned and sequenced in both directions in an automatic sequencer. In total, two TAIL-PCR sequence reactions were carried out and amplified 2688 bp (SEQ ID No 1) equivalent to 896 amino acids (SEQ ID No 2) of a new gene of *B. thuringiensis* belonging to the family of δ-endotoxins Cry8. The predicted protein sequence of the new gene, called cry8Ka1 (official nomenclature according to http://www.lifesci.sussex.ac.uk/home/Neil_Crickmore/Bt/), presents the three structural domains characteristic of the activated N-terminal end of the δ-endotoxins and 240 amino acids of the C-terminal extension. This original sequence served as a template to generate analogs with improved entomotoxic activity.

To obtain cry analog genes, with high entomotoxicity for the boll weevil, the cry8Ka1 gene isolated from strain S811 of *B. thuringiensis* was used. This gene was used as substrate in the process of originating variant genes by the DNA shuffling technique. The variants were selected for their ability to bind receptors present in the membrane of the middle intestine of the boll weevil (BBMVs), by the technique of presenting proteins on the surface of bacteriophages—*Phage display* (Barbas III, C. F.; Burton, D. R.; Scott, J. K.; Silverman, G. J. Selection from antibody libraries. In: *Phage display*—A laboratory manual—USA: Cold Spring Laboratory, p. 10.1-10.20, 2001).

To select variants of the cry8 gene of the present invention, we used the technique of presenting proteins on the surface of bacteriophages—*Phage Display* (Zhang, Q., Bai, G., Cheng, J., Yu, Y., Tian, W. and Yang, W. Use of an enhanced green fluorescence protein linked to a single chain fragment variable antibody to localize *Bursaphelenchus xylophilus* cellulose. Biosci. Biotechnol. Biochem, Vol. 71, No 6, p. 1514-1520, 2007; Andris-Widhopf, J., Rader, C., Steinberger, P., Fuller, R., Barbas III, C. F. Methods for the generation of chicken monoclonal antibody fragments by *Phage display*. Journal of Immunological Methods, Vol. 242, p. 159-181, 2000; Stoop, A. A., Jespers, L., Lasters, I., Eldering, E. and Pannekoek, H. High-density mutagenesis by combined DNA shuffling and Phage display to assign essential amino acid residues in protein-protein interactions: application to study structure-function of plasminogen activation inhibitor 1 (PAI-I). J. Mol. Biol., Vol. 301, p. 1135-1147, 2000; Barbas III, C. F., Bain, J. D., Hoekstra, D. M., And Lerner, R. A. Semisynthetic combinatorial antibody libraries: A chemical solution to the diversity problem. Proc. Natl. Acad. Sci. USA, Vol. 89, p. 4457-4461, 1992).

Lastly, the native toxin Cry8Ka1, its mutant and synthetic analogs had their entomotoxic effects evaluated in vitro, by means of selective bioassays. To do so, the selected analog genes were cloned in vectors of heterologous expression (*Escherichia coli*) and the recombinant toxins generated was used in bioassays against the insect-pests of the cotton plant (SEQ ID No 5 to 12).

The invention describes new entomotoxins and methods which enable the generation of technologies capable of controlling insect-pests of major economic interest. More specifically, the nucleic acids (genes) of the present invention, including fragments and variants of same, comprise nucleotide sequences, which encode entomotoxic proteins (polypeptides). The entomotoxic proteins described are biologically active against certain insect-pests belonging to the order Coleoptera, such as, for example: the boll weevil, *Anthonomus grandis*; the western corn root worm, *Diabrotica virgifera virgifera*; northern corn rootworm, *Diabrotica longicornis barberi*; southern corn rootworm, *Diabrotica undecimpunctata howardi*. Additional pests include: larvae of elater beetles such as *Melanotus, Eleodes, Conoderus*, and *Aeolus* spp; Japanese beetle, *Popillia japonica*; white grub, *Phyllophaga crinita*; corn flea beetle, *Chaetocnema pulicaria*; sunflower stem weevil, *Cylindrocupturus adspersus*; grey sunflower seed weevil, *Smicronyx sordidus*; sunflower beetle, *Zygogramma exclamationis*; lesser clover leaf weevil, *Hypera nigrirostris*; cabbage flea beetle, *Phyllotreta cruciferae*; Colorado potato weevil, *Leptinotarsa decemlineata*; striped flea beetle, *Phyllotreta striolata*; yellow-striped flea beetle, *Phyllotreta nemorum* and the common pollen beetle, *Meligethes aeneus.*

Besides the nucleotide sequences, the present invention also describes an expression vector comprising the sequences encoding protein genes with high entomotoxic activity.

The nucleotide sequences of the invention have direct use in the methods of controlling insect-pests, particularly of the order Coleoptera. The present invention provides new techniques, which do not depend on the use of traditional synthetic chemical pesticides. The invention relates to biodegradable pesticides occurring naturally and genes encoding the same.

In certain embodiments, the invention provides an encoding gene for δ-endotoxins of the family of Cry8, obtained from natural sources, called cry8Ka1 (as per the official nomenclature of these genes; www.http://epunix.biols.susx-.ac.uk/Home/Neil_Crickmore/Bt.html). Mutant analog genes and synthetic genes to the native gene were created by mutation in vitro, and also δ-endotoxin-encoding genes. In other embodiments, the invention provides genetically modified microorganisms and plants capable of expressing (producing) the new δ-endotoxins, as well as methods involving the use of nucleic acids in compositions and/or pesticide products to act against the insect-pests in question. The invention is also related to possible encoding sequences or to δ-endotoxins encoding variant fragments.

In the description that follows, various terms are used extensively. The following definitions are provided to facilitate the understanding of the invention.

As described herein, the term "analog" describes nucleotide or protein sequences different to the original sequences specifically identified, where one or more nucleotides or residues of amino acids were deleted, substituted and/or added. These sequences can be characterized by the percentage of identity of their sequences, by algorithms commonly used in the state of the art, with the nucleotide (SEQ ID NOs: 1 and 3) or protein SEQ ID NOs: 2 and 4) sequences described herein. The percentual identity is determined by aligning the two sequences to be compared, determining the number of identical residues in the aligned portion, dividing this number by the total number of residues in the sequence surveyed and multiplying the result by 100. This alignment can be done by public domain tools, such as BLASTN and BLASTP, available on the web site page of the National Center for Bio-technology Information (NCBI) (www.ncbi.nlm.nih.gov). The sequence alignment and the percentage of identity calculation of the present invention was performed as described with the sequences filed at the Bank Genes. FIGS. 15-19 show the sequence alignment of the present invention (Cry8Ka1) with the sequences described in the state of the art.

As used herein, the terms "nucleic acid" and "nucleotide sequences" refer to a double-stranded desoxyribonucleotide polymer (DNA), encompassing known analogs having the essential nature of natural nucleotides and they hybridize specifically to single-stranded n nucleic acids in a manner similar to the naturally-occurring nucleotides.

The term "oligonucleotide" is referred herein as 'primers' and 'probes' of the present invention, and is defined as a molecule of nucleic acid comprising from ten to thirty deoxyribonucleotides, preferably more than eight. The exact size of the oligonucleotides depends on the particular experimental factors of each step of the process.

As used in the present invention, the terms "encoding" or "encoded" mean that a nucleotide sequence has information, which will be biologically translated from the sequence of nucleotide into a specific protein sequence. The encoded information of a protein is specified by the codons expressed in the nucleotide sequence. These codons are exploited by each live organism in a different manner, and parts of different nucleotide sequences may be biologically translated to identical peptides.

As used herein, the term "antisense", used in the context of a nucleotide sequence orientation refers to a complementary sequence of an encoding polynucleotide sequence that is operably linked in the sense 3'-5', from 5' end of a gene. The antisense strand is complementary to the sense orientation strand generating a final mRNA capable of hybridizing with the mRNA produced from the transcription of the original sequence.

The term "gene" corresponds to a specific nucleotide sequence located in a particular region of the chromosome, and is responsible for encoding a specific final product. The gene also carries in its primary structure all the information needed for the transcription and biological translation processes, such as, for example, promoter and regulatory regions of the transcription. In the case of the present invention, gene comprises an encoding nucleotide sequence corresponding to the Cry toxins from *Bacillus thuringiensis.*

The term "vector" refers to a replicon, such as plasmide, phage or virus, in which other genetic sequences or elements (be they DNA or RNA) can be linked. Accordingly, the genes can be replicated jointly with the vector. Preferably one of the vectors of interest of the present invention refers to the phagemide. The term "phagemide" refers to a vector that contains sequence for replication into phage and into bacteria, this vector has characteristics that meet the specifications of the host cell as well as selector and promoter agents. One example is the phagemide pComb3X (Andris-Widhopf, J.; Rader, C.; Steinberger, P.; Fuller, R., Barbas III, C. F. Methods for the generation of chicken monoclonal antibody fragments by *Phage display. Journal of Immunological Methods,* 242: 159-181, 2000), which has the characteristic of fusioning a sequence of interest to the gene of protein III, of the filamentous bacteriophage M13, located in viral capside. The term "recombinant vector" results from the combination of a commercial vector with genes of the present invention operably linked to an endogenous and/or heterologous polynucleotide of interest which in turn is operably linked to a termination signal. Said vectors can be obtained commercially, including those supplied by Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). Some examples of vectors used in the present invention, but not limited, are the vectors pGEM-T easy (Promega Corporation), pET101/D-TOPO (Invitrogen), pComb3X (Andris-Widhopf, J.; Rader, C.; Steinberger, P.; Fuller, R., Barbas III, C. F. Methods for the generation of chicken monoclonal antibody fragments by *Phage display. Journal of Immunological Methods,* 242: 159-181, 2000). Obtaining recombinant vectors comprising promoters linked to nucleic acids is known in the state of the art and can be found in Sambrook et al. (Sambrook, J., Russell, D. W., Molecular Cloning, A Laboratory Manual, $2^{nd}$ ed., Cold Spring Harbor Laboratory Press. 1989).

An "expression vector" is a specialized vector that contains a gene with regulatory regions necessary for expression in a host cell. Said vectors can be obtained commercially, including those supplied by Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). The term "operably linked" means that the regulatory sequences necessary for expressing the encoding sequence are placed in the DNA molecule in suitable positions such that when attached to the encoding sequence, it maintains the suitable reading frame for the effect of its expression. This same definition is sometimes applied for the arrangement of encoding sequences and transcription control elements (for example, promoters enhancers and termination elements) in the expression vector. An exogenous encoding region is typically flanked by regulatory regions operably linked that regulate the expression of the exogenous encoding region in a transformed cell (and may be a microorganism, plant or animal). A typical regulatory region operably linked to an exogenous encoding region includes a promoter, that is, a nucleic acid fragment that can cause transcription of exogenous encoding regions, positioned at 5' region of the exogenous encoding region.

The present invention is not limited to the use of any promoter. Promoters may be inducible, constitutive and tissue-specific. Preferably, the promoter of the present invention is from the group of promoters of cotton fiber genes, and may be, but is not limited to, E6, H6S, Rac13, LTP, ACP, Expansine, CAP, Anexine, FbL2A and actine 2.

The promoter may contain "enhancer" elements. An "enhancer" is a DNA sequence that can stimulate the activity of a promoter. It may be an innate element of the promoter or a heterologous element inserted to increase the level and/or the tissue-specificity of a promoter. "Constitutive promoters" refer to those that drive the genic expression in all the tissue and for the entire time. "Tissue-specific" or "development-specific" promoters are those that drive the genic expression almost exclusively in specific tissues, such as leaves, roots, stalks, flowers, fruits or seeds, or in specific stages of the development of a tissue, such as at the beginning or the end of embryo-genesis.

As described previously, the term "expression vectors" may comprise an inducible promoter operably linked to a sequence of nucleic acid encoding the pesticidal protein of the present invention. "Inducible" promoters may drive the expression of a polynucleotide with which they are operably linked, in a tissue or specific stage of the development or in response to environmental conditions. In one of the aspects of the invention, expression vectors comprise an inducible promoter firmly regulated and operably linked to a nucleic acid molecule encoding a pesticidal protein. Said expression vector may additionally comprise a selection marker gene (for example, a gene encoding a protein that confers antibiotic resistance) operably linked to a constitutive promoter or to an inducible promoter firmly regulated. Depending on the application, it may benefit the expression of a nucleic acid sequence encoding a pesticidal protein by way of an insect-pest inducible promoter. In one aspect of the present invention it may be advantageous to use promoters that are expressed locally or near to the pest infection site.

In one of the aspects of the invention, the promoter is a promoter expressed in plants. As used herein, the term "promoter expressed in plants" means a DNA sequence that is capable of starting and/or controlling transcription in a plant cell. This includes any promoter of plant origin; any promoter of non-plant origin that is capable of directing the synthesis of the gene present in the T-DNA of *Agrobacterium*; tissue-specific or organ-specific promoters, including but not limited to seed-specific promoters (WO8903887), specific promoters of primordial organs (as mentioned in patent application US20030175783, An, Y. Q., Huang, S., McDowell, J. M., McKinney, E. C., Meagher, R. B., Conserved expression of the *Arabidopsis* ACT1 and ACT3 actin subclass in organ primordia and mature pollen. The Plant Cell 8, 15-30, 1996), stem-specific promoters (as mentioned in patent application US20030175783, Keller, B., Sauer, N., Lamb, C. J., Glycine-rich cell wall proteins in bean: Gene structure and association of the protein with the vascular system. EMBO J. 7: 3625-3633, 1988), leaf-specific promoters (as mentioned in patent application US20030175783, Hudspeth, R. L., Grula, J. W., Structure and expression of the maize gene encoding the phosphoenolpyruvate carboxylase involved in $C_4$ photosynthesis. Plant Mol Biol 12:579-589, 1989), mosophile-specific promoters, root-specific promoters (as mentioned in patent application US20030175783, Keller, B., Lamb, C. J., Specific expression of a novel cell wall hydroxyproline-rich glycoprotein gene in lateral root initiation. Genes Devel. 3:1639-1646, 1989), tuber-specific promoters (as mentioned in patent application US20030175783, Keil, M., Sanchez-Serrano, J. J., Willmitzer, L., Both wound-inducible and tuber-specific expression are mediated by the promoter of a single member of the potato proteinase inhibitor II gene family. EMBO J. 8: 1323:1330, 1989), vascular tissue-specific promoters (as mentioned in patent application US20030175783, Peleman J., Saito, K., Cottyn, B., Engler, G., Seurinck, J., Van Montagu, M., Inze, D., Structure and expression analyses of the S-adenosylmethionine synthetase gene family in *Arabidopsis thaliana*. Gene 84: 359-369, 1989), stamen-specific promoters (WO8910396, WO9213956), dehiscence zone-specific promoters (WO9713865); and the like.

A "leader sequence" or "signal sequence" in the present invention means a sequence of nucleic acid which, when operably linked to a nucleic acid molecule, allows the secretion of the product of the nucleic acid molecule. The leader sequence is preferably located in region 5' of the nucleic acid molecule. Preferably, the lead sequence is obtained from the same gene that the promoter used to drive the transcription of the nucleic acid molecule, or is obtained from the gene where the nucleic acid molecule is derived. Preferably, the present invention uses the signal sequence originating from a crop of Brazilian cotton.

The termination signal of the transcription and the polyadenylation region of the present invention includes, but is not limited to, termination signal SV40, adenylation signal HSV TK, termination signal of the nopaline synthetase gene of *Agrobacterium tumefasciens* (NOS), termination signal of the octopine synthetase gene, termination signal of the gene 19S and 35S of CaMV, termination signal of the alcohol dehydrogenase gene of maize, termination signal of the manopine synthetase gene, termination signal of the beta-phaseolin gene, termination signal of the ssRUBISCO gene, termination signal of the sucrose synthetase gene, termination signal of the virus that attacks *Trifolium subterranean* (SCSV), termination signal of the trpC gene of *Aspergillus nidulans*, and other similar.

The terms "polypeptide", "peptide" and "protein" are used interchangeably herein to refer to a polymer of amino acids residues. The terms apply to amino acid polymers in which one amino acid residue is an artificial chemical analog of a corresponding naturally-occurring amino acid, as well as to naturally-occurring amino acid polymers.

Polypeptides of the invention can be produced either through a nucleic acid described herein, or by using standard techniques of molecular biology. For example, a truncated protein of the invention can be produced by the expression of a recombinant nucleic acid of the invention in an appropriate host cell, or alternatively by the combination of procedures, such as digestion using protease and purification.

The term "substantially pure" refers to preparations comprising at least 50-60% by weight of the component of interest (for example, nucleic acid, oligonucleotide, polypeptide, protein, etc). More preferably, the preparation comprises at least 75% by weight, and more preferably 90-99% by weight of the component of interest. The purity is measured by way of methods appropriate for the component of interest (for example, mass spectometry and the like).

The term "isolated protein" or "isolated and purified protein" is often used in the present invention. This term refers to a protein produced by the expression of an isolated nucleic acid molecule of the present invention. Alternatively, this term may refer to a protein that was sufficiently separated from other proteins to which it may be naturally associated, as it exists in its "substantially pure" form. The term "isolated" does not exclude synthetic or artificial mixtures with other compounds or materials, or the presence of impurities which do not interfere with the fundamental activity of the protein, and which may be present, for example, in an incomplete purification, addition of stabilizers, or combined therein, for example, in an agriculturally acceptable composition.

The term "agriculturally acceptable vehicle" refers to solution in which a pesticidal protein or a nucleic acid sequence encoding a pesticidal protein can be kept without altering functional properties of the protein molecute described herein for agricultural use. The vehicles used in the present invention can be liquid or solid. Liquid vehicles that can be used to form compositions using recombinant protein of the present invention include, but are not limited to, water or organic solvents, such as polyols, esters, methylene chloride, alcohol, or vegetable oil. Other components that can be included in the formulation include humectants, preservatives, thickeners, antimicrobial agents, antioxidants, emulsifiers, film-forming polymers and mixtures thereof. Humectants may include polyols, sugars (such as molasses), glycols and hydroscopic salts. Vitreous membranes, film-forming polymers include rosin gum, latex, polyvinyl pyrrolidone, polyvinyl alcohol, polyvinyl chloride, polyethylene, polyvinyl acetate, and mixtures thereof. Additional optional additives include methyl, metalcrylate, and mixtures thereof.

The terms "peptide analog" or "mutant analog" mean a natural analog or mutant of a protein, comprising a series of linear or discontinuous fragments of that protein and in which there may be one or more amino acids replaced with (an) other amino acid(s) and may have its biological activity altered, assisted, increased or decreased when compared to the native parental or non-mutated protein.

The term "biological activity" refers to a function or a group of functions executed by a molecule in a biological context (that is, in an organism or substitute in vitro or any other similar model). For the entomotoxic proteins, the biological activity is characterized by the physical-chemical properties such as, for example, structuring in highly hydrophobic domains, able to form oligomers, and affinity by biological membranes, causing the destruction of the same. This membranes affinity may be caused by the presence of specific receptors as well as by the simple chemical interaction between both.

As used herein, the term "impacting insect-pests" refers to effecting changes in insect feeding, growth and/or behavior at any stage of, including, but not limited to: killing the insect; retarding growth; preventing reproductive capability; antifeedant activity; and the like.

The terms "pesticide activity" and "insecticide activity" are used synonymously to refer to the activity of an organism or a substance (eg.: a protein) which can be measured by, but is not limited to, the mortality of the pest, weight loss of the pest, repellence to pests, and other behaviors and physical changes of a pest after feeding and exposure for a suitable period of time. Accordingly, the impact of the pesticidal activity should have at least a measurable parameter of pest fitness. For example, "pesticidal proteins" are proteins that display pesticidal activity by themselves or in combination with other proteins. Endotoxins and δ-endotoxin are pesticidal proteins. Other examples of pesticidal proteins include, for example, pentina-1 and jaburetox.

The term "pesticideally effective amount" connotes a quantity of a substance or organism that has pesticidal activity when present in the environment of a pest. For each substance or organism, the pesticideally effective amount is determined empirically for each pest affected in a specific environment. Similarly, the term "insecticideally effective amount" may be used to refer to a "pesticidally effective amount" when a pest is an insect-pest.

The term "recombinantly engineered" or "engineered" connotes the use of recombinant DNA technology to generate (engineer) a change in the protein structure based on an understanding of the protein's mechanism of action, in which the amino acids may be introduced, deleted or substituted.

The term "DNA shuffling" is used to describe a method employed in directed molecular evolution in vitro to generate variants of a single genic sequence, or two or more homologous sequences by means of recombinations of randomly-generated fragments, with recovery of modified sequences and with consequent modification of amino acids residues in the protein encoded by the mutant analog.

The term "presentation of proteins on the surface of bacteriophages—Phage display" refers to a system of expression and interaction of proteins fusioned to bacteriophages that allow a scanning of cells, tissue or organs in search of receptor-ligand pairs, and these ligands are proteins that bind to the receptors present in the target in study.

As used herein, the term "mutant nucleotide sequence" or "mutation" or "mutagenized nucleotide sequence" connotes a nucleotide sequence that has been mutagenized or altered to contain one or more nucleotide residues (eg.: base pairs) that are not present in the wild-type or non-mutagenize sequence. Such mutagenesis or alteration consists of one or more additions, deletions, or substitutions or replacement of nucleic acids residues.

The term "analog" or "mutant" is used to identify a gene that was altered by mutation and which makes it different from the wild-type or from the normal variation of the population.

As used herein, the term "improved insecticide activity" or "improved pesticide activity" characterizes a polypeptide or a δ-endotoxin of the invention that has pesticide activity against coleoptera improved in relation to other δ-endotoxins that are effective against insects. To measure the improvement of the pesticide or insecticide activity requires a demonstration of the increase in toxicity of at least 10%, against the target insect, and more preferably 20%, 25%, 30%, 35%, 40%, 45%, 50%, 60%, 70%, 100%, 200% or a greater increase in toxicity in relation to the insecticide activity of the existing δ-endotoxins Cry8 that are active against the same insect.

The term "toxin" or "endotoxin" relates to a polypeptide, which presents insecticide toxic activity. It is known, in the state of the art, that naturally-occurring δ-endotoxins are synthesized by *B. thuringiensis*, which sporulate releasing the protein crystalline inclusion containing the δ-endotoxin.

For a particular interest of the invention, sequences encoding pesticidal proteins of this invention were optimized. As used herein, the terms "optimized nucleotide sequences" or "synthetic sequences" refer to nucleic acids that are optimized for expression in a particular organism. Optimized nucleotide sequences include those sequences which were highly modified that the GC content of the nucleotide sequence becomes altered. Said modification in the nucleotide sequence may or may not comprise an encoding region. Where the modified nucleotide sequence comprises an encoding region, alterations in the GC content can be made considering another genetic phenomenon, such as, for example, the preference of one codon for a particular organism or the trend of the GC content in the encoding region.

In some embodiments of the invention, where the optimized nucleotide sequence comprises an encoding region, alteration in the GC content does not result in a change in the protein encoded by the nucleotide sequence. In other embodiments, alteration in the GC content results in changes in the encoded protein that may be changes in conserved amino acids that may not significantly alter the function of the encoded protein. The GC content of a nucleotide sequence may differ from the native nucleotide sequence by at least 1%, 2%, 3%, 4%, 5%, 6%, 7%, 8%, 9%, 10%, or 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%, or more. Hence, the GC content of an optimized nucleotide sequence may be 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%, or more.

A specialist in the art knows that advances in the field of molecular biology such as a site-specific or random mutagenesis, polymerase chain reaction methodology (PCR), and protein engineering techniques provide an extensive collection of tools and protocols suitable for use to alter or engineer both the amino acid sequences and underlying genetic sequences of proteins of agricultural interest. Therefore, the pesticide proteins of the invention can be altered in various ways, including the substitution of amino acid, deletions, truncations, and insertions. Methods for such manipulations are generally known in the art. For example, amino acid sequence variants of the pesticidal protein of the present invention can be prepared by introducing a mutations into a synthetic nucleic acid (eg.: DNA molecule). Methods for mutagenesis and nucleic acid alterations are well described in the state of the art.

The design of the synthetic gene was carried out based on the original sequence of the gene, including the N-terminal portion of the protein with the three domains responsible for the insecticidal activity. In the design of the synthetic gene, 262 base pairs were modified, resulting in the elimination of 25 possible polyadenylation signals, 17 instability motifs, 95 codons hardly used in plants and in the increase of the GC content from 35.6 to 43.8%. The final protein sequence of the synthetic gene is identical to the original sequence, that is, it remained unaltered.

It is understood that the polypeptides of the invention can be produced both by the expression of a nucleic acid described herein, or by the use of standard molecular biology techniques.

It is known that pesticidal proteins can be oligomeric and vary in molecular weight, number of residues, peptide components, activity against particular pests, and other characteristics. However, by the methods set forth herein, proteins active against a variety of pests may be isolated and characterized. The pesticidal proteins of the invention can be used in combination with Bt δ-endotoxins or other insecticidal proteins to increase insect target range. Furthermore, the use of the pesticidal proteins of the present invention in combination with Bt δ-endotoxins or other insecticidal principles of a distinct nature may have a particular utility for the prevention and/or management of insect resistance. Other insecticidal agents include, but are not limited to, protease inhibitors (both serine and cysteine), lectins, alphaamylase, and peroxidase.

The invention also refers to microorganisms transformed with at least one nucleic acid of the present invention, with a chimeric gene comprising the nucleic acid, or with an expression vector comprising the chimeric gene. Preferably, the microorganism is one that multiplies in plants. More preferably, the microorganism is a root-colonizing bacteria. An embodiment of the present invention refers to an encapsulated pesticidal protein which comprises a transformed microorganism comprising at least one pesticidal protein of the invention.

The invention also provides pesticide compositions comprising a transformed organism of the invention. Preferably, the transformed microorganism is present in the pesticidal composition in a pesticidally effective amount, together with an acceptable carrier vehicle. The invention also comprises pesticidal compositions comprising an isolated protein of the invention, alone or in combination with a transformed organism of the invention and/or an encapsulated pesticidal protein of the invention, in an insecticidally effective amount, together with an acceptable vehicle.

The invention also provides a method to increase the reach of the target insect through the use of pesticidal proteins of the invention in combination with at least a second pesticidal protein that is different to the pesticidal protein of the invention. Any pesticidal protein known in the state of the art can be used in the method of the present invention. Said pesticidal proteins include, but are not limited to Bt δ-endotoxins, protease inhibitors, lectines, alpha amylases, lipid acyl hydrolases, and peroxidase.

The invention also comprises transgenic or transformed plants comprising at least a nucleotide sequence of the invention. Preferably, the plant is stably transformed with a chimerical gene comprising at least a nucleotide sequence of the invention operably linked to a promoter that drives expression in plant cells. As used herein, the term "transgenic plants" or "transformed plants" refers to a plant that comprises a heterologous polynucleotide inside its genome. Generally, the heterologous polynucleotide is incorporated into the genome of a transgenic plant, in a stable manner so that the polynucleotide is passed on to successive generations. The heterologous polynucleotide can be incorporated into the genome alone or as part of a recombinant vector.

As used herein, the term "transgenic" includes any cell, cell line, callus, tissue, part of a plant, or plant genotype of which has been altered by the presence of heterologous nucleic acid including those transgenics initially highly altered as well as those created by sexual crosses or sexual propagation of the sexual transgenic.

The term "plants" refer to photosynthetic organisms, both eukaryotes and prokaryotes, where the term "developed plants" refers to eukaryote plants. The term refers to whole plants, plant organs (eg.: leaves, stalks, roots, flowers, and the like), seeds, plant cells, and progeny of same. Parts of the transgenic plants are also included within the scope of the invention comprising, for example, plant cells, protoplasts, tissues, callus, embryos, as well as flowers, ovules, stalks, fruits, leaves, roots originating in transgenic plants or their progeny previously transformed with a DNA molecule of the invention and, therefore, consisting of at least part of the transgenic cells, are also the object of the present invention. The nucleic acids of the invention can be used to confer desired treatments to essentially any plant. Therefore, the invention has use on various species of plants, including species of the genera *Anona, Arachis, Artocarpus, Aspara-*

*gus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna*, and *Zea*. Particularly, the present invention refers to cotton plants transformed with the nucleotide sequences of the present invention as well as fragments and derivatives of same, more specifically plants transformed de *Gossypium hirsutum.*

Transformation protocols as well as protocols for introducing nucleotide sequences into plants may vary depending on the type of plant or plant cell, for example, monocot or dicot, targeted for transformation. Suitable methods of introducing nucleotide sequences into plant cells and subsequent insertion into the plant genome are well described in the state of the art and can be, but are not limited to techniques such as electroporation and microinjection of plant cell protoplasts, or the construct can be introduced directly into the plant tissue using ballistic methods, such as bombarding with DNA-coated particles.

Microinjection techniques are known in the state of the art and well described in scientific and patent literature (Zhou, G., Wang, J., Zeng, Y., Huang, J., Qian, S., Liu, G., Introduction of exogenous DNA into cotton embryos. Meth. in Enzymol., 101, 433-448, 1983) (as mentioned in patent application U.S. Pat. No. 4,743,548). The introduction of genic constructs using precipitations of glycol polyethylene is described in Paszkowski et al. (Paszkowski, J., Shillito, R. D., Saul, M., Mandák, V., Hohn, T. Hohn, B., Potrykus, I., Direct gene transfer to plants. Embo J. 3: 2717-2722, 1984) (as mentioned in patent application US20020152501). Electroporation techniques are described in Fromm et al (Fromm, M. E., Taylor, L. P. Walbot, V., Expression of genes electroporated into monocot and dicot plant cells. Proc. Natl. Acad. Sci. USA 82:5824, 1985) (as mentioned in patent application US20020152501). Ballistic transformation techniques are described in Klein et al (Klein, T. M., Wolf., E. D., Wu, R., Sanford, J. C., High velocity microprojectiles for delivering nucleic acids into living cells. Nature 327:70-73, 1987) (as mentioned in patent application US20020152501).

Alternatively, the genic constructs can be combined with suitable T-DNA-flanking regions that are introduced into a conventional vector, the host *Agrobacterium tumefaciens*. The virulence function of the host *Agrobacterium tumefaciens* will direct the insertion of the genic constructs and adjacent marker inside the DNA of the plant cell when the cell is infected by the bacteria. Transformation techniques mediated by *Agrobacterium tumefaciens*, including disarmament and the use of binary vectors, are well described in scientific literature (as mentioned in patent application US 20020152501, Horsch, R. B., Fraley, R. T., Rogers, S. G., Sanders, P. R., Lloyd, A., Hoffmann, N. Inheritance of functional foreign genes in plants. Science 233:496-498, 1984; and Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., Woo, S. C. Expression of bacterial genes in plant cells. Proc. Natl. Acad. Sci. USA 80:4803, 1983).

Cells from transformed plants derived from any of the transformation techniques described above can be cultivated to regenerate an entire plant that has its genotype transformed and then the desired phenotype, such as resistance to insects. Said regeneration techniques include the manipulation of certain phytohormones in a tissue culture growth medium, typically containing a biocide and/or herbicide marker, which should be introduced with the desired nucleotides sequence. Regeneration of plants based on the protoplasts culture is described in Evans et al (Evans, D. E., and Bravo, J. E., Protoplasts Isolation and Culture, Handbook of Plant Cell Culture, vol. 1, 124-176, MacMillilan Publishing Company, New York, 1983); and Binding 1985 (Binding, H., Regeneration of Plants, Plant Protoplasts, pp. 21-73, CRC Press, Boca Raton, 1985) (as mentioned in patent application US20020152501). Regeneration can also be obtained by way of plant callus, explants, organs, or part of same. Said regeneration techniques are generally described in Klee et al (Klee, H., Horsch, R., Rogers, S., *Agrobacterium*-mediated plant transformation and its further applications to plant biology. Ann. Ver. Of Plant Phys. 38:467-486, 1987 (as mentioned in patent application US20020152501).

It is recognized that the genes encoding the pesticidal proteins can be used to transform insect pathogenic organisms. Such organisms include baculoviruses, fungi, protozoa, bacteria, and nematodes.

A gene encoding a pesticidal protein of the invention may be introduced via a suitable vector into a microbial host, and said host applied to the environment, or to plants or animals. The term "introduced" in the context of inserting a nucleic acid into a cell means "transfection" or "transformation" or "transduction" and includes the incorporation of a nucleic acid into a prokaryotic or eukaryotic cell where the nucleic acid may be incorporated into the genome of the cell (eg.: chromosome, plasmid, plastid, or mitochondrial DNA), converted into an autonomous replicon, or transiently expressed (eg.: transfected mRNA).

Microorganism hosts that are known to occupy the "phytosphere" (phylloplane, phyllosphere, rhizosphere, and/or rhizoplana) of one or more crops of interest may be selected. These microorganisms of interest are selected to be capable of successfully competing in a particular environment with the wild-type microorganisms, providing for the stable maintenance and expression of the gene expressing the pesticidal protein, and desirably, improve protection of the pesticide from environmental degradation and inactivation.

Such microorganisms include, but are not limited to, bacteria, algae and fungi. Particularly, the microorganisms include bacteria such as *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, for example, *Saccharomyces, Cryptococcus, Kluyveromyces, Sporobolomyces, Rhodotorula*, and *Aureobasidium*. Of particular interest are bacterial species of the phytosphere, such as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and yeast species of the phytosphere such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans.*

There are various viable methods for introducing a gene expressing a pesticidal protein into a microorganism host under conditions that allow the stable maintenance and expression of the gene. For example, expression of vectors can be constructed containing a nucleotide sequence of interest operably linked to the transcription and translational regulatory signals for expression of the nucleotide sequence. When a homologous sequence of nucleotide inside the organism detects a sequence in the expression vector, there may be a recombination between them and the gene that encodes a pesticidal protein will stably incorporate into the genome of the host organism.

Suitable host cells, where the pesticidal protein-containing cells will be treated to prolong the activity of the pesticidal proteins in the cell when the treated cell is applied to the environment of the target pest, may include prokaryote or eukaryote cells, normally being limited to those cells that do not produce toxic substances to higher organisms. However, organisms that produce substances toxic to higher organisms could be used, whereas the toxin is unstable or the level of application is sufficiently low to avoid any possibility of toxicity to a mammalian host. Particularly, the hosts are less developed prokaryotes and eukaryotes such as fungi. Illustrative prokaryotes, both gram-negative and gram-positive, include, but are not limited to *Enterobacteriaceae*, such as *Escherichia, Erwinia, Shigella, Salmonella*, and *Proteus; Bacillaceae; Rhizobiceae*, such as *Rhizobium; Spirillaceae*, such as *Photobacterium, Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes*, such as *Rhodotorula, Aureobasidium, Sporobolomyces*, and the like.

Characteristics of particular interest in selecting a host cell for purposes of pesticidal protein production include ease of introducing a pesticidal protein gene into the expression system, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

In the present invention, the transformed microorganism (containing an encoding sequence of the pesticidal protein of the invention) or an isolated pesticide protein can be formulated as an acceptable carrier vehicle inside a pesticidal composition, which may be, for example, a suspension, a solution, an emulsion, a powder, a dispersible granule, a wettable powder, an emulsifiable concentrate, an aerosol, an impregnated granule, an adjuvant, a coated capsule, and also encapsulation in, for example, polymeric substances.

Such compositions disclosed above may be obtained by the addition of a surface-active agent, an inert carrier vehicle, a preservative, a humectant, a feeding stimulant, an attractant, an encapsulating agent, a binder, an emulsifier, a dye, a UV protectant, a buffer, a flow agent or fertilizer, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, for example, natural or regenerated mineral substances, solvents, dispersants, wetting agents, binders, or fertilizers. The active ingredients of the present invention are normally applied in the form of compositions and can be applied to the crop area, plants, or seed to be treated. For example, the compositions of the present invention may be applied to grain in preparation for or during storage in a grain silo. The compositions of the present invention may be applied simultaneously or in succession with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and rate of application depend on the intensity of the infestation by the corresponding pest.

Examples of inert materials include but are not limited to inorganic minerals such as kaolin, phyllosilicates, carbonates, sulfates, phosphates, or botanical materials such as cork, powdered corncobs, peanut hulls, rice hulls and walnut shells.

The compositions of the present invention can be in a suitable form for direct application or as a concentrate of primary composition that requires dilution with a suitable amount of water or other diluent before application. The pesticidal concentration will vary depending upon the nature of the particular formulation, specifically, whether it is a concentrate or to be used directly. The composition may contain 1 to 98% of a solid or liquid inert carrier, and 0 to 50%, preferably 0.1% to 50% of a surfactant. These compositions will be administered at the labeled rate for the commercial product, preferably about 0.01 lb-5.0 lb per acre when in dry form and at about 0.01 pts-10 pts per acre when in liquid form.

The embodiments of the present invention may be effective against a variety of pests. For the purposes of the present invention, pests include, but are not limited to, insects, fungi, bacteria, nematodes, acarids, protozoal pathogenes, animal parasites, and the like. Pests of particular interest are insect-pests, particularly insect-pests that cause significant damage to agricultural plants. "Insect-pests" are understood to be insects and other similar pests such as, for example, insects of the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, especially *Anthonomus grandis, Diabrotica virgifera* and *Lepidoptera*. Insect-pests of the present invention of most crops include, but are not limited to Maize: *Ostrinia nubilalis, Agrotis ipsilon, Helicoverpa zea, Spodoptera frugiperda, Diatraea grandiosella, Elasmopalpus lignosellus, Diatraea saccharalis, Diabrotica virgifera virgifera, Diabrotica longicomis barberi, Diabrotica undecimpunctata howardi, Melanotus* spp., *Cyclocephala borealis, Cyclocephala immaculata, Popillia japonica, Chaetocnema pulicaria, Sphenophorus maidis, Rhopalosiphum maidis, Anuraphis maidiradicis, Blissus leucopterus leucopterus, Melanoplus femurrubrum,*

*Melanoplus sanguinipes, Hylemya platura, Agromyza parvicornis, Anaphothrips obscrurus, Solenopsis milesta, Tetranychus urticae*; Sorgo: *Chilo partellus, Spodoptera frugiperda, Helicoverpa zea, Elasmopalpus lignosellus, Feltia subterranea, Phyllophaga crinita, Eleodes, Conoderus*, and *Aeolus* spp., *Oulema melanopus, Chaetocnema pulicaria, Sphenophorus maidis, Rhopalosiphum maidis, Sipha flava, Blissus leucopterus leucopterus, Contarinia sorghicola, Tetranychus cinnabarinus, Tetranychus urticae*; Wheat: *Pseudaletia unipunctata, Spodoptera frugiperda, Elasmopalpus lignosellus, Agrotis orthogonia, Elasmopalpus lignosellus, Oulema melanopus, Hypera punctata, Diabrotica undecimpunctata howardi, Schizaphis graminum, Macrosiphum avenae, Melanoplus femurrubrum, Melanoplus differentialis, Melanoplus sanguinipes, Mayetiola destructor, Sitodiplosis mosellana, Meromyza americana, Hylemya coarctata, Frankliniella fusca, Cephus cinctus, Aceria tulipae*; Sunflower: *Cylindrocupturus adspersus, Smicronyx fulus, Smicronyx sordidus, Suleima helianthana, Homoeosoma electellum, Zygogramma exclamationis, Bothyrus gibbosus, Neolasioptera murtfeldtiana*; Cotton: *Heliothis virescens*, tobacco budworm; *Helicoverpa zea*, corn earworm; *Spodoptera exigua*, fall armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandwinged whitefly *Bemisia tabaci; Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider; *Tetranychus urticae*, two-spotted spider mite; Rice: *Diatraea saccharalis, Spodoptera frugiperda, Helicoverpa zea, Colaspis brunnea, Lissorhoptrus oryzophilus, Sitophilus oryzae, Nephotettix nigropictus, Blissus leucopterus leucopterus, Acrosternum hilare*; Soja: *Pseudoplusia includens, Anticarsia gemmatalis, Plathypena scabra, Ostrinia nubilalis, Agrotis ipsilon, Spodoptera exigua, Heliothis virescens, Helicoverpa zea, Epilachna varivestis, Myzus persicae, Empoasca fabae, Acrosternum hilare, Melanoplus femurrubrum, Melanoplus differentialis, Hylemya platura, Sericothrips variabilis, Thrips tabaci, Tetranychus turkestani, Tetranychus urticae*; Barley: *Ostrinia nubilalis, Agrotis ipsilon, Schizaphis graminum, Blissus leucopterus leucopterus; Acrosternum hilare, Euschistus servus, Jylemya platura, Mayetiola destructor, Petrobia latens*; Canola: *Vrevicoryne brassicae, Phyllotreta cruciferae, Phyllotreta striolata, Phyllotreta nemorum, Meligethes aeneus, Meligethes rufimanus, Meligethes nigrescens, Meligethes canadianus*, and *Meligethes viridescens*; Potato, *Leptinotarsa decemlineata.*

The examples below are provided to illustrate and better clarify the invention and should not be seen as limiting to the present invention.

EXAMPLES

Usual techniques of molecular biology (eg.: transformation of bacteria and agarose gel electrophoresis of nucleic acids) are described by means of terms commonly used. Details of the practice of such techniques are described in Sambrook et al (Sambrook, J., Russell, D. W., Molecular Cloning, A Laboratory Manual, $2^{nd}$ ed., Cold Spring Harbor Laboratory Press. 1989).

Example 1

Selection of *Bacillus thuringiensis* Strain S811 from the Germoplasm Bank of Embrapa Recursos Genéticos e Biotecnológicos In a previous work by Silva-Werneck et al. (Monerat, R. G., Silva, S. F., Silva-Werneck, J. O. Catálogo do banco de germoplasma de bactérias do gênero *Bacillus*. Brasília: Embrapa-Cenargen, Documentos 60, 65 p., 2001), various strains belonging to the Microbial Germoplasm Bank of Embrapa Recursos Genéticos e Biotecnologia were identified and characterized. Among these, strain S811 was selected due to its high entomotoxic activity against insects of the Coleoptera order, such as, for example, *Anthonomus grandis*. Toxicity was evaluated by means of selective bioassays, using the total protein extract of the bacteria *Bacillus thuringiensis* S811 as substrate.

To obtain the gross protein extract, the strain was cultivated in a nutrient broth culture medium (MCCN; nutrient broth 8 g/L, yeast extract 1 g/L and 1 g/L of potassium phosphate monobasic) at 30° C., under agitation at 200 rpm. After culturing for 12 hours, with the culture in vegetative phase and after 48-72 hours with complete sporulation, it is possible to obtain the genetic material and the gross protein extract, respectively.

Example 2

Identification, Isolation and Characterization of the Cry8 Gene of the *Bacillus thuringiensis* Strain S811

Extraction of the total DNA from *Bacillus thuringiensis* S811 was performed according to protocol CTAB (2% CTAB, 0.2% of β-mercaptoethanol). After 12 hours of cultivation, 30 mL of the culture, in vegetative phase, was centrifuged at 5000 rpm for 20 minutes. The pellet was frozen in liquid nitrogen and soaked following the protocol described by Romano, E. (Romano, E. Extração de DNA de tecidos vegetais. In: Manual de transformação genética de plantas. A. C. M. Brasileiro & V. T. C. Carneiro (Eds). Embrapa Recursos Genéticos e Biotecnologia, Brasília, 1998). The final product was dried and resuspended in 50 μL of Milli-Q water and subsequently stored at −20° C.

The PCR (Polymerase Chain Reaction) technique was used to identify Cry toxin-encoding genes in strain S811. The amplifications were carried out using specific oligonucleotides to detect genes of the cry1 subgroup (Cerón, J.; Covarrubias, L.; Quintero, R.; Ortiz, A.; Ortiz, M.; Aranda, E.; Lina, L., Bravo, A. PCR analysis of the cryI insecticidal crystal family genes from *Bacillus thuringiensis*. Appl. Environ. Microbiol., 60, 353-356, 1994; Ceroń, J.; Ortiz, A.; Quintero, R.; Güereca, L., Bravo, A. Specific PCR primers directed to identify cryI and cryIII genes within a *Bacillus thuringiensis* strain collection. Appl. Environ. Microbiol., 61, 3826-3831, 1995) and cry8 (Bravo, A.; Sarabia, S.; Lopez, L.; Ontiveros, H.; Abarca, C.; Ortiz, A.; Ortiz, M.; Lina, L.; Villalobos, F. J.; Peña, G.; Nuñez-Valdez, M. E.; Soberon, M.; Quintero, R. Characterization of cry Genes in a Mexican *Bacillus thuringiensis* Strain Collection. Appl. Environ. Microbiol., v. 64, p. 4965-4972, 1998). The PCR reaction conditions containing oligonucleotides of the cry1 group were described by Cerón et al (Cerón, J.; Covarrubias, L.; Quintero, R.; Ortiz, A.; Ortiz, M.; Aranda, E.; Lina, L., Bravo, A. PCR analysis of the cryI insecticidal crystal family genes from *Bacillus thuringiensis*. Appl. Environ. Microbiol., 60, 353-356, 1994) and the PCR reaction conditions containing oligonucleotides of the cry8 group were described by Bravo et al (Bravo, A.; Sarabia, S.; Lopez, L.; Ontiveros, H.; Abarca, C.; Ortiz, A.; Ortiz, M.; Lina, L.; Villalobos, F. J.; Peña, G.; Nuñez-Valdez, M. E.; Soberón, M.; Quintero, R. Characterization of cry Genes in a Mexican *Bacillus thuringiensis* Strain Collection. Appl. Environ. Microbiol., v. 64, p. 4965-4972, 1998). All the reactions were carried out in volumes of 25 μL containing 2.5 μg of total DNA, 10 mM Tris-HCl pH 8.4, 2 mM of $MgCl_2$, 50 mM KCl, 200 mM of each dNTP (deoxynucleotides triphosphate), 500 nM of each oligonucleotide and 0.1 U/μL of Taq DNA polymerase for each DNA sample. The amplification was carried out in a thermocycler (MasterCicle Gradient Eppendorf) under the following conditions: prior denaturation at 94° C. for 2 minutes, repetition and 30 cycles at 94° C. for 45 seconds (denaturation), annealing of the oligonucleotides for 45 seconds (specific temperature for each oligonucleotide), 72° C. for 2 minutes (extension of DNA polymerase) and at the end, a final extension, 72° C. for 5 minutes. The fragments amplified by PCR were separated and visualized in 0.8% of agarose gel. The DNA fragments were excised from the gel and purified using kit GeneClean (Bio101 System) and quantified by spectrophotometry. The purified fragments were then cloned into 50 ng of commercial vector pGEMT-easy (PROMEGA), at a molar ratio of 3:1 (insert:vector) with 4 U/μL T4 DNA ligase and buffer 1× in the final volume of 15 μL. The vectors generated were used to transform competent cells of *Escherichia coli* by electroporation. The positive clones were identified by colony PCR and had their plasmidial DNA extracted. The plasmidial DNAs obtained were sequenced in an automatic ABI sequencer, using general oligonucleotides T7, SP6, reverse and universal (Nag, D. K., Huang, H. V. and Berg, D. E. Bidirectional Chaintermination Nucleotide Sequencing: Transposon Tn5seq1 as a Móbile Source of Primer Sites. Gene 64, 135-145. 1988).

The sequences obtained were compared with the sequences of the Databases (GeneBank and SwissProt) by the program BLAST (http://www.ncbi.nlm.nih.gov/BLAST/). The multiple alignment of the sequences of the clones obtained carried out with the most similar sequences filed in the Database (GeneBank) was performed by CLUSTALW (http://www.ebi.ac.uk/clustalw/) (Thompson, J. D., D. G. Higgins e T. J. Gibson. CLUSTALW: improving the sensitivity of progressive multiple sequence alignment through sequence weighting, position specific gap penalties and weight matrix choice. Nucleic Acids Res, v. 22, n. 22, November 11, p. 4673-4680. 1994).

The first reaction of amplification by PCR with the specific oligonucleotides for the cry8 family, Bravo et al, 1998, resulted in a fragment of 442 bp (FIG. 1) corresponding to the 5' end of a new gene belonging to the cry8 family (SEQ. ID NO. 1). Aiming to obtaining the full-length sequence of the gene cry8, two rounds of amplification by TAIL-PCR technique were carried out (Polymerase Chain Reaction by Assymetric Thermal Interlacing) (Liu, Y.; Whittier, R. F. Thermal asymmetric interlaced PCR: Automatable amplification and sequencing of insert end fragments from P1 and YAC clones for chromosome walking. Genomics, v. 25, p. 674-681, 1995) (FIG. 2). This consists applying the PCR technique which allows the isolation of the DNA segments adjacent to known sequences, using for such the genomic DNA of the organism. The technique uses specific sequential oligonucleotides, in conjunction with small arbitrary degenerated oligonucleotide to thermally control the efficiency of amplification in relation to specific and unspecific products. Interspersing cycles of high and low stringencies, specific products are preferably amplified on nonspecific products.

In short, having carried out three sequential PCR reactions using specific oligonucleotides derived from the sequences previously amplified from one side (Bravo, A.; Sarabia, S.; Lopez, L.; Ontiveros, H.; Abarca, C.; Ortiz, A.; Ortiz, M.; Lina, L.; Villalobos, F. J.; Peña, G.; Nuñez-Valdez, M. E.; Soberón, M.; Quintero, R. Characterization of cry Genes in a Mexican *Bacillus thuringiensis* Strain Collection. Appl. Environ. Microbiol., v. 64, p. 4965-4972, 1998) and eight arbitrary oligonucleotide on the other (Liu, Y.; Whittier, R. F. Thermal asymmetric interlaced PCR: Automatable amplification and sequencing of insert end fragments from P1 and YAC clones for chromosome walking. Genomics, v. 25, p. 674-681, 1995). Fragments were amplified, cloned, sequenced and analyzed under the same conditions described previously for the initial identification of the gene.

The final product, obtained by the TAIL-PCR technique, contains 2688 bp amplified (SEQ ID No 1) and encodes a new δ-endotoxin of 896 amino acids (SEQ ID No 2). The analysis of the nucleotide sequence by the program BLASTn, having as search standard the data base of patents filed at NCBI, identified the sequence of the present invention as being corresponding to the Cry8 family, presenting over 90% identity, as demonstrated in the alignments (FIGS. 18, 19, 20 and 21).

Analyses of the predicted protein sequence of the new Cry8 gene show the presence of three structural domains characteristic of the δ-endotoxins, in its N-terminal portion. The analyses also demonstrate the presence of over 240 amino acids of the C-terminal extension of the new δ-endotoxin (FIG. 3).

The alignment of the sequences of amino acids of the present invention with other patented proteins of the Cry8 family shows that the new δ-endotoxin differs 80% from the other sequences of amino acids, presenting about 150 conserved amino acids (FIG. 19).

When compared to other δ-endotoxins, the new δ-endotoxin Cry8 presented greater similarity to the cry8Aa gene (53% identity and 67% similarity), followed by the cry8Ba genes (53% identity and 66% similarity) and cry8Ca (49% identity and 65% similarity). FIG. 4 presents a dendogram of the new toxin Cry8 alignment of the with the other toxins Cry8 filed in the data base to-date. FIG. 4 shows the high identity between the toxins. The scale indicates that in the space represented, there is an exchange of at least 0.1 aa.

The N-terminal and C-terminal ends of the new δ-endotoxin Cry8Ka1 present high identity with other δ-endotoxins Cry8, while the three structural domains are less conserved, particularly the second and third domains (Table 1), which are involved with receptor binding, suggesting new insecticide activities/specificities for the isolated gene.

TABLE 1

Average identity between the domains of δ-endotoxin Cry8Ga and the corresponding domains in other δ-endotoxin Cry8.

| | Cry8Ka1 | | | | |
|---|---|---|---|---|---|
| | N-terminal | Domain I | Domain II | Domain III | C-terminal |
| Cry8Aa | 87.7% | 48.6% | 29.8% | 35.5% | 90.7% |
| Cry8Ba | 89.8% | 47.7% | 31.3% | 37.6% | 91.1% |
| Cry8Ca | 73.5% | 57.7% | 31.6% | 33.3% | 68.6% |

Example 3

Construction of the Expression Vector Containing the New Cry8Ka1 Gene and Obtainment of the Recombinant Toxin For the expression of the heterologous protein, the commercial expression vector pET101-D/TOPO (Invitrogen—

FIG. 5) was used. The vector was acquired in its linearized form with one abrupt end and the other cohesive, complementary to the end of the amplified gene insert. In this system, the PCR product is directly cloned by adding the four base pairs of the sense oligonucleotide. The cohesive end of the cloning vector (GTGG) invades 5"end of the PCR product, annealing with the four added (CACC) and stabilizes the PCR product in the correct sense. Topoisomerase then cleaves the protruding part of the PCR product so that the ligation is effective (FIG. 6). The inserts can be cloned in this manner with 90% efficiency.

To amplify the gene cry8 with the complementary ends, oligonucleotides were designed based on the initiation codon (ATG) of the genes, with addition of the sequence CACC in 5' region of the sense oligonucleotide, according to instructions from the manufacturer of the system pET Directional TOPO cloning (Invitrogen). The antisense oligonucleotide does not have the termination codon, as it is found soon after the poly-hystidine tail (FIG. 5). These oligonucleotides were then used in a PCR reaction with final volume of 25 μL, containing 400 nM of each oligonucleotide, 200 mM of dNTPs, 1× enzyme pfu buffer, 2.5 U of DNA polymerase pfu (Stratagene) and 10 ng of the cry genes cloned in the vector pGEMT-easy (Invitrogen). The amplification was carried out in a thermocycler (Mastercycler Gradient-Eppendorf) under the following conditions: prior denaturation at 94° C. for 1.5 minute a repetition of 30 cycles at 94° C. for 1 minute (denaturation); 55° C. for 1 minute (annealing of oligonucleotides) and 72° C. for 2 minutes (Extent of DNA polymerase) and at the end an extension at 72° C. for 5 minutes.

The product generated was then submitted to a link reaction under the following conditions: 10 ng of the PCR product, 200 mM of NaCl, 10 mM of MgCl2, 1 μL of the vector pET101. The mixture was incubated at room temperature, 25° C., for 30 minutes. *E. coli* competent cells of TOP10 were transformed with 3 μL of the ligation system (10 ng) by heat shock. For this procedure, the 10 ng of DNA were mixed at 200 μL of competent cells and the mixture was incubated on ice for 30 min. The heat shock was carried out for 3 minutes at 42° C. The cells were immediately transferred to the ice and 500 μL of culture medium SOC (2% triptone; 0.5% yeast extract; 0.05% NaCl; 2.5 mM KCl; 20 mM MgCl2) was subsequently added. Subsequently, the cells were inoculated in 10 mL of Luria-Bertani agar culture medium containing 100 μM of ampicillin/mL and grown for 16 hours at 37° C. To verify the positive clones, a colony PCR was carried out, using DNA of the transformed bacteria as template the DNA and the same conditions described for cloning genes. The positive clones were then inoculated in 5 mL of Luria-Bertani agar medium containing 100 μM of ampicillin/mL.

To express the new gene, the plasmides generated were transformed by heat shock in *Escherichia coli* BL21 cells (DE) Star (Invitrogen). Then 10 ng of the pET101/cry8Ka1 vectors were added to 200 μL of competent cells and the mixture was incubated on ice for 30 minutes. The heat shock was carried out for 3 minutes at 42° C. and, soon afterwards the cells mixture of placed on ice. Next, 250 μL of SOC medium was added and incubated for 30 minutes at 37° C., with stirring of 200 rpm. After this period the cells were inoculated in 10 mL of LB-amp medium and grown for 16 hours. This culture was then used with pre-inoculum for the expression. For each 100 mL of Luria-Bertoni medium, 5 mL of pre-inoculum was added. The material was incubated at 37° C., with stirring of 200 rpm. Once the culture reaches $OD_{600}$ between 0.6-0.8, the inducer (IPTG) was added in the concentration of 1 mM and the culture remained at 37° C. for a further 16 hours in order to obtain the recombinant toxin Cry8Ka1. Having determined the ideal culture conditions for improved yield of the recombinant protein expression, the cells were inoculated in volumes of 500 mL. After 18 hours of cultivation, the group of cells was centrifuged for 10 minutes at 4000 g and the supernatant was discarded. The cells precipitate was resuspended in 10 mL of lise buffer (50 mM of phosphate buffer pH 7.8; 300 mM NaCl, 10% glycerol, 0.5% triton X-100 whether or not containing 2 mg/mL lysozyme) and the cells were lised by ultra-sound (3×5 min). The lysated product was then centrifuged for 15 minutes at 10000 g. The supernatant was then withdrawn, quantified by the methodology described by Lowry et al. (Lowry, O. H., N. J. Rosebrough, A. L. Farr e R. J. Randall. Protein measurement with the Folin phenol reagent. J Biol Chem, v. 193, n. 1, November, p. 265-275. 1951).

With the aim of obtaining the purified recombinant toxin, the supernatant obtained was submitted to Nickel affinity chromatography (Ni), using 5 ml of resin Ni-NTA (nickel-nitrilotriacetic acid), with the capacity of retaining 5-10 mg of recombinant protein with poly-hystidine tail. The resin was then packaged in a glass column and balanced with 4 column volumes with balance solution (50 mM sodium phosphate buffer pH 7.8; 300 mM NaCl and 10 mM imidazole). The sample was added (not exceeding the total capacity of the resin) and the portion not retained, reserved and quantified for analysis. The excess material was retained with the addition of 3 column volumes of buffer solution. Washing was performed with 6 column volumes of wash solution (50 mM of phosphate buffer pH 7.8; 300 mM NaCl and 20 mM imidazole). The protein was eluted with two column volumes of elution buffer (50 mM of phosphate buffer pH 7.8; 300 mM NaCl and 250 mM imidazole). The eluted material was then dialyzed against 15 mM carbonate buffer (1.59 g of $Na_2CO_3$ and 2.93 g of $NaHCO_3$), quantified by Lowry and submitted to unidimensional electrophoresis in polyacrylamide gel 12% (FIG. 7). FIG. 7 shows the entire process of expression and purification of the new δ-endotoxin, in polyacrylamide gel 12%.

Example 4

Selective Bioassays Against the Boll Weevil for Determination of the Entomotoxic Activity of the New Recombinant δ-endotoxin reCry8Ka1

With the aim of verifying the activity of the recombinant toxins, selective bioassays were carried out against the insect-pests of interest. The selective bioassays were performed according to Praça et al (Praça, L. B., Batista, A. C., Martins, E. S., Siqueira, C. B., Dias, D. G. S., Gomes, A. C. M. M., Falcão, R., Monnerat, G. R. Estirpes De *Bacillus thuringiensis* Efetivas Contra Insetos Das Ordens Lepidoptera, Coleoptera E Diptera. Brasília: Embrapa-Cenargen. 2004, Vol. 39, No 1, p. 11-16), incorporating 50 μg/mL, 100 μg/mL, 200 μg/mL of the new recombinant toxin Cry8Ka1 in 5 mL of artificial diet (at 50° C.), poured into 6 wells Cell Plates NUNC™. After solidification of the diet, 15 holes were made having approximately 0.6 $mm^2$, where the neonate larvae (one per hole) were inserted, and a reading was taken on the seventh day (Monnerat, R. G., Dias, S. C., Oliveira Neto, O. B. de, Nobre, S. D., Silva-Werneck, J. O. E Sa, M. F. G. de. Criação Massal Do Boll weevil *Anthonomus Grandis* Em Laboratório. Brasília: Embrapa-Cenargen, 2000. 4 p. Comunicado Técnico, 46). The bioassays were repeated three times and cultures of *Bacillus thuringi-*

*ensis* strain S811, containing the native cry8 gene was used as positive control, and 15 mM carbonate buffer as negative control.

As external control to the experiment, bioassays were carried out on neonate larvae of *Spodoptera frugiperda*. The bioassays showed significant toxic activity of the culture of *Bacillus thuringiensis* expressing the native toxin Cry8Ka1, as well as the pure recombinant toxin, on *Anthonomus grandis* (FIG. 8). Accordingly, the entomotoxic activity of the cry8Ka1 gene was confirmed.

Example 5

Generation of Mutant Genes, Analog to Native Cry8Ka1 Gene, Highly Effective in Controlling *Anthonomus grandis* by the DNA Shuffling Technique The construction of a library of recombinant genes analog to new cry8 gene is an important biotechnological strategy, making an important contribution to plant improvement programs, via genetic transformation for the generation of transgenics. This technology provides a variety of new molecules with potential use in transforming plants viewing the control of the target insect, as well as improved insecticidal activity of new proteins encoded by the recombinant genes. This factor gains further important when considering the low expression levels of these heterologous proteins in genetically-transformed plants.

Once the entomotoxic activity of the new δ-endotoxin Cry8Ka1 against the insect-pest *Anthonomus grandis* is confirmed, the strategy was then to obtain new genes in vitro, analog to cry8 gene, encoding for the same Cry8Ka1 toxin. To do so, the native cry8Ka1 gene was re-amplified by PCR with specific oligonucleotides for the genic sequence in question, which contains the sequence of the restriction enzyme SfiI (5'GGCCNN NNNGGCC3' (SEQ ID NO: 74)). These oligonucleotides were designed in our laboratory using the native genic sequence cry8Ka1 as template and introduced to the 5' and 3' ends of the native gene a sequence of the enzyme in question (5' oligonucleotide: SfiI F-5'"CCCGGCCCAGGC GGCCGACCACGCGTATCGA 3' (SEQ ID NO: 72) and 3' oligonucleotide: SfiI R-5'CCCG-GCCGGCCT GGCCGTTCAAGGAACCGTT 3' (SEQ ID NO: 73)). These oligonucleotides were then used in a PCR reaction with final volume of 25 μL containing 300nM of each specific oligonucleotide, 200 nM of dNTPs, 1 X enzyme taq buffer for the (PHT), 1 U of DNA polymerase taq (PHT) and 400 ng of active DNA cry8Ka1. The amplification was performed in a thermocycler (Mastercycler Gradient—Eppendorf) under the following conditions: prior denaturation at 95° C. for 5 minutes; a repetition of 29 cycles at 95° C. for 40 seconds (denaturation), 45° C. for 40 seconds (annealing of the oligonucleotides) and 72° C. for 40 seconds (extension of the DNA polymerase) and at the end an extension of 72° C. for 2 minutes.

The reaction generated a product of 2000 bp (base pairs), which was submitted to electrophoresis in agarose gel 1%, at 100 Volts for 90 minutes. The genic fragment was excised and eluted from the agarose gel using the kit Geneclean® II (Qbiogene). A total of 100 μg of the new DNA product (SfiI/cry8Ka1/SfiI) were digested with the enzyme SfiI for 24 hours at 50° C. The product of the enzymatic digestion was submitted to electrophoresis in agarose gel 1%, excised and eluted from the gel. Finally, approximately 40 μg of the new DNA product (SfiI/cry8Ka1/SfiI) digested with SfiI was obtained.

According to the protocol of the DNA shuffling technique described by Stemmer, W. P. C. et al., (Stemmer, W. P. C. Rapid evolution of a protein in vitro By DNA shuffling. Nature. London, 1994, Vol. 370, p. 389-391; Zhao, H. and Arnold, F. H. Functional and nonfunctional mutations distinguished by random recombination of homologous genes. Proc. Natl. Acad. Sci. USA., 1997, Vol. 94, p. 7997-8000), the digestion was carried out, with the nuclease DNAseI, of 10 μg of the new DNA product (Sfillcry8Ka1/SfiI) digested with SfiI. The reaction was conducted in a specific buffer of the enzyme with 10 U of the same and interrupted by adding 26 mM of EDTA (Acid 4-acetic 2-amino ethylene). After this stage, the genic product was completely fragmented generating small genic pieces of 30 to 50 bp, which were purified with the Kit High Pure PCR Product Purification® (Roche). The purified fragments were used in a PCR reaction, in accordance with the following conditions: 100 ng of pure product digested with DNAseI, 1× Taq Platinum buffer, 2.5 mM of dNTPs, 0.5 mM of $MgSO_4$, 2.5 U of Taq Platinum High Fidelity DNA polymerase. The PCR reaction was carried out in a thermocycler (Mastercycler Gradient—Eppendorf) under the following conditions: prior denaturation at 95° C. for 2 minutes, a repetition of 43 cycles at 95° C. for 1 minute (denaturation); 44° C. for 1 minute (annealing of the fragments) and 72° C. for 1 minute with the addition of 5 seconds per cycle (Extension of DNA polymerase) and finally an extension of 72° C. for 7 minutes.

This DNA shuffling reaction is conducted without the addition of oligonucleotides, which ultimately generates an amount of fragments of various sizes. This new product is then used in the second PCR reaction as a template, in the following conditions: ⅓ of the volume of the product of the first reaction (template), 1× Taq Platinum buffer, 0.2 mM dNTPs, 0.8 μM of the specific oligonucleotides SfiI F and SfiI R, 2 mM of $MgSO_4$ and 25 U in the mixture of 1:1 Taq Platinum High Fidelity (Invitrogen)/Taq PHT. The amplification reaction was carried out in a thermocycler (Mastercycler Gradient—Eppendorf) under the following conditions: prior denaturation at 95° C. for 2 minutes, a repetition of 10 cycles at 95° C. for 30 seconds (denaturation); 45° C. for 30 seconds (annealing of the fragments), 72° C. for 1 minute (extension of DNA polymerase), another repetition of 14 cycles at 95° C. for 30 seconds (denaturation), 43° C. for 30 seconds (annealing of the product), 72° C. for 42 seconds (extension of DNA polymerase) with an addition of 20 seconds per cycle and finally an extension 72° C. for 7 minutes.

Accordingly, the original gene is reconstituted with modifications in its nucleotide structure, either by introduction, deletion or substitution of nucleotides. This final product, reconstructed was submitted to electrophoresis in agarose gel 1%, at 100 Volts for 90 minutes, excised and eluted from the gel with the Kit Geneclean® II (Qbiogene). The purified product, approximately 25 μg, was then digested with the restriction enzyme SfiI (prior conditions) and submitted to electrophoresis in agarose gel 1%, at 100 Volts for 90 minutes. The band in the approximate size of the original gene (approximately 2000 pb) was excised from the gel and the DNA eluted by Geneclean® II Kit (Qbiogene) (FIG. 9).

The final product (population of recombined genes) with specific adapters becomes apt for cloning in the vector pCOMB3X (Andris-Widhopf, J.; Rader, C.; Steinberger, P.; Fuller, R., Barbas III, C. F. Methods for the generation of chicken monoclonal antibody fragments by *Phage display. Journal of Immunological Methods,* 242: 159-181, 2000). Hence, the new reconstructed genes (analogs to the native cry8Ka1 gene) were cloned in the vector with the assistance of the enzyme T4 DNA Ligase® (Invitrogen) and this used to transform cells of *Escherichia coli* XL1-Blue® (Stratagene), via electroporation, under the following conditions: capacitancy 25 uFD, resistance 200Ω, voltage 2.5 KVolts. The transformants were then seeded on plates containing culture medium Luria-Bertani Agar and Ampicillin® USB (100 μg/mL). After 17 hours at 37° C. the colonies grown in the selective medium indicate the title of the library containing $10^5$ transformants.

This library of analogs of cry8Ka1 generated by DNA shuffling and fusioned to protein III of the filamentous phage M13 capside (fusion phages) was then selected by the technique of presentation of proteins on the surface of bacteriophages—*Phage Display* (Barbas III, C. F.; Burton, D. R., Scott, J. K., Silverman, G. J. Selection from antibody libraries. In: *Phage display*—A Laboratory Manual—USA: Cold Spring Laboratory, 10.1-10.20, 2001) using as binders BBMVs of *A. grandis* (Francis, B. R., Maaty, W. S. A., Bulla-Jr, L. A. Effects of Midgut-Protein-Preparative and Ligand Binding Procedures on the Toxin Binding Characteristics of BT-R1, a Common High-Affinity Receptor in *Manduca sexta* for Cry1A *Bacillus thuringiensis* Toxins. Applied and Environmental Microbiology. June 1998, Vol. 64, No. 6, p. 2158-2165).

The culture of *E. coli* XL1-Blue transformed cells, in SB medium containing 100 μg mL$^-$carbenicillin, 5 μg mL$^{-1}$ tetracycline, was incubated at 37° C. under stirring until reaching an optical density of $A_{550}$=0.6-0.8. Then, 1x$10^{12}$ pfu mL$^{-1}$ of the auxiliary phage (VCSM13® Stratagene) was added to produce fusion phages containing the analogs of cry8Ka1, incubated for 2 hours at 37° C. 100 μg mL$^{-1}$ of Kanamycin was added, and the incubation followed for 12 hours at 37° C. The cells collected by centrifugation were kept at −20° C. for subsequent DNA preparation. The fusion phages were precipitated with PEG-8000 (4% p/v) for 30 minutes on ice and after centrifugation resuspended in 2 mL of 1% (p/v) BSA (bovine serum albumine) in saline solution. Collected after centrifugation, the preparation of fusion phages is used in selection cycles.

In the procedure of selection by ligation affinity, the fusioned phages were deposited in wells of a microtitration plate previously sensitized with BBMVs (100 μg μL$^{-1}$), extracted from the membrane of the intestine of boll weevil larvae. Upon each selection cycle, the wells are washed with PBS-Tween solution (137 mM NaCl, 2.7 mM KCl, 12 mM $Na_2HPO_4$, 1.2 mM $KH_2PO_4$ and 0.05% Tween 20®) and, the specific phages, eluted at low pH, are used to transfect new cells of *E. coli*. The amplified particles of phages are used in the successive selection cycle. The procedure involved five washing cycles, elution and amplification. The titration of the colonies collected in each cycle is made by colony plating in serial dilutions in SB-agar medium containing carbenicillin 100 μg mL$^{-1}$. The colonies isolated from the amount of eluted specific phages in the fifth selection cycle (presenting the major title and, therefore, representing the enrichment cycle of specific phages) FIG. 10 were amplified with specific oligonucleotides for the cry8Ka1 gene. Colonies showing amplification in PCR and containing approximately 2000 bp (size of original gene) were selected for expression in phages FIG. 11.

The cry8Ka1 gene and the analog genes selected in the fifth selection cycle were expressed in a selective medium (1% MOPS, 2% Yeast extract, 3% tryptone, 100 μg mL$^{-1}$ ampicillin, 5 μg mL$^{-1}$ tetracycline, 100 μg mL$^{-1}$ Kanamycin, pH 7.0) containing the auxiliary phage VCSM13, with 18 hours of incubation at 37° C. The culture was centrifuged and the phages collected were precipitated with solution PEG-NaCl (20% Polyethylene-Glycol 8000, 15% Sodium Chloride) for 30 minutes on ice. After centrifugation, the phages were resuspended in saline solution TBS (5 mM Tris-HCl, 15 mM NaCl, pH 7.5), centrifuged again, collected and stored at 4° C. for immediate use in bioassays.

The selected analogs were evaluated by means of selective bioassays against the larvae of *Anthonomus grandis*, and those exhibiting greater entomotoxic activity were submitted to a sequencing reaction under the following conditions: 400-800 ng of DNA plasmidial containing the analogs and 4 pM of specific oligonucleotides (SfiI R and SfiI F) in an automatic sequencer model 3130 xL Genetic Analyzer (APPLIED BIOSYSTEMS).

Lastly, four analog sequences to the new cry8Ka1 gene were selected (discriminated in Table 2). The new molecules generated by the recombination of the cry8Ka1 gene presented significant differences of 13.29 to 16.33% base pairs and of 2.10 to 5.11% in residues of modified amino acids (Table 2). In the analysis of the sequences and classification of same as analogs of the native cry8Ka1 gene, these molecules were grouped by identity of nucleotide sequences obeying the nomenclature system for toxins Cry (http://www.lifesci.sussex.ac.uk/home/Neil_Crickmore/Bt/). Due to a variation≤5% between the analog toxins and the native toxin Cry8Ka1, the new sequences were classified in the Cry8 family of toxins, being subsequently named Cry8Ka2, Cry8Ka3, Cry8Ka4 and Cry8Ka5 (Table 2) (SEQ ID No 5-12).

TABLE 2

Modifications of nucleotide bases and residues of amino acids generated by the DNA shuffling technique in the cry8Ka1 gene and mortality of neonate larvae of *Anthonomus grandis* fed with the proteins expressed in the phage system.

| | Nucleotides | | Amino acids | | |
|---|---|---|---|---|---|
| Gene | Base pairs | Modified (%) | Residues | Modified (%) | DL 50 (%) |
| cry8Ka1 | 2001 | — | 666 | — | 36.1 |
| cry8Ka2 | 1982 | 13.29 | 660 | 2.1 | 54.6 |
| cry8Ka3 | 1991 | 13.25 | 663 | 2.84 | 63 |
| cry8Ka4 | 1989 | 14.1 | 663 | 2.99 | 50 |
| cry8Ka5 | 1947 | 16.33 | 649 | 5.11 | 77.08 |

In spite of the high number of nucleotide mutations in the sequences generated (from 13 to 16%), there were few modifications of residues of amino acids (from 2 to 5%), the deletion of amino acid residues at end 5' of the variants also being generated. The new molecule Cry8Ka5 proved approximately 3 times more active that the original molecule (Cry8Ka1) exhibiting a mortality of 77% of the neonate larvae fed on a diet containing 6 μg of protein per mL of diet (FIG. 12).

Example 6

Determining the Tertiary Structure in Silico of the Native Cry8Ka1 and Analog Cry8Ka5 Toxins The tertiary structures of the toxins Cry8Ka1 and of the analog Cry8Ka5 were predicted in silico, being modeled by molecular modeling using as template the crystal structures of the toxins Cry3Bb1 and Cry3A (1ji6.pdb; Galitsky, N., Cody, V.; Wojtczak, A.; Ghosh, D.; Luft, J. R.; Pangborn, W. & English, L. Structure of insecticidal bacterial δ-endotoxin Cry3Bb1 of *Bacillus thuringiensis*. Acta Crystallographica, Section D, Biological Crystallography, 57: 1101-1109, 2001) and Cry3A (1dlc.pdb; Li, J.; Carrol, J., Ellar, D. J. Crystal structure of insecticidal δ-endotoxin from *Bacillus thuringiensis* at 2.5 A resolution. Nature, 353: 815-821, 1991) filed in the Protein Structure Data Base (PDB). The alignment of the multiple sequences containing the sequences of the template structures and the toxins for modeling was submitted for the program Modeller Version 9.2 (Sali A, Blundell T L: Comparative protein modeling by satisfaction of spatial restraints. *J Mol Biol* 1993, 234(3): 779-815.

The models obtained by the Modeller program were analyzed in terms of their stereochemical properties by the PROCHECK program (Laskowski R A, Macarthur M W, Moss D S, Thornton J M: Procheck—a Program to Check the Stereochemical Quality of Protein Structures. *Journal of Applied Crystallography* 1993, 26:283-291).

The Cry8Ka1 and analog Cry8Ka5 models showed the same structural skeleton, and differences were only noted in the side chains of the amino acids substituted in the analog. The original and analog Cry8Ka5 structures present three conserved functional domains (I, II, and III), typical of Cry toxins, and all the mutations and/or substitutions are located in the outer surface of the molecule (FIG. 13).

Example 7

Selective Bioassays Against the Boll Weevil for Determining the Entomotoxic Activity of the New Recombinant δ-endotoxin Cry8Ka1 and its Analogs Cry8Ka2, Cry8Ka3, Cry8Ka4 and Cry8Ka5

The selective bioassays were carried out in accordance with the same conditions previously described in example 3 of this invention. FIG. 14 demonstrates the results relating to certain entomotoxic activities.

Example 8

Design of a Synthetic, Optimized Cry8Ka1 Gene for Expression in Cotton Plants

The design of the synthetic cry8Ka1 gene was based on the sequence of the native cry8Ka1 gene, including the three domains responsible for the insecticide activity, comprised of 666 amino acids. In the design of the synthetic cry8Ka1 gene, 262 base pairs were modified, resulting in the elimination of 25 possible polyadenylation signals, 17 instability motifs, 95 codons little used in plants and in the increase in the GC content from 35.6 to 43.8%. The final protein sequence of the synthetic cry8Ka1 gene (SEQ ID No 4) is identical to the original sequence (SEQ ID No 2). A summary of the modifications introduced is presented in Table 3.

TABLE 3

Modification introduced into the nucleotide sequence of the synthetic cry8Ka1 gene and the parameters taken into consideration for modifications of the sequence (SEQS ID 03 and 04).

|  | Segment N-terminal domains I, II & III of the Cry8Ka1 gene | synthetic Cry8Ka1 |
| --- | --- | --- |
| Base pairs (pb) | 1998 bp = 666 aa | 1998 bp = 666 aa |
| A | 690 | 558 |
| T | 597 | 565 |
| C | 333 | 441 |
| G | 378 | 434 |

TABLE 3-continued

Modification introduced into the nucleotide sequence of the synthetic cry8Ka1 gene and the parameters taken into consideration for modifications of the sequence (SEQS ID 03 and 04).

|  | Segment N-terminal domains I, II & III of the Cry8Ka1 gene | synthetic Cry8Ka1 |
| --- | --- | --- |
| A + T | 1287 (64.4%) | 1123 (56.2%) |
| C + G | 711 (35.6%) | 875 (43.8%) |
| Modified bp | 0 | 262 (13%) |
| Modified codons | 0 | 261 (39%) |
| Base pairs (pb) | 1998 bp = 666 aa | 1998 bp = 666 aa |
| ATTTA Motive | 17 | 0 |
| Putative polyadenylation sites | 26 | 1 |
| NCG codons | 23 | 0 |
| NTA codons | 72 | 0 |

To modify the sequence of the cry8Ka1 gene, the Template Directed Ligation by Polymerase Chain Reaction—TDL-PCR methodology was used, as described by Strizhov et al. (Strizhov, N.; Keller, M.; Mathur, J.; Koncz-Kálmán, K.; Bosch, D.; Prudovsky, E.; Schell, J.; Sneh, B.; Koncz, C.; Zilberstein, A. A synthetic cryIC gene, encoding a *Bacillus thuringiensis* endotoxin, confers *Spodoptera* resistance in alfalfa and tobacco. Proc. Natl. Acad. Sci. USA, v. 93, p. 15012-15017, 1996)

The sequence of the cry8Ka1 gene was divided into three blocks called A, B and C with 595, 665 and 753 bp, respectively. Blocks A and B are delimited by an Nde I site and blocks B and C by an Spe I site. For the synthesis of block A, 6 'oligonucleotides' were designed, for block B, 7 'oligonucleotides' and for block C, 9 'oligonucleotides'. The oligonucleotides at the ends of each block contain unique sequences non-complementary to the original gene, for subsequent selective amplification by PCR. Inside each block there is no overlapping in the sequence of the oligonucleotides.

Example 9

Construction of the Synthetic Gene Cry8Ka1 Optimized for Expression in Cotton Plants In short, the methodology used, 'template directed ligation-PCR'—TDL-PCR, described by Strizhov et al. (Strizhov, N.; Keller, M.; Mathur, J.; Koncz-Kalman, K.; Bosch, D.; Prudovsky, E.; Schell, J.; Sneh, B.; Koncz, C.; Zilberstein, A. A synthetic cryIC gene, encoding a *Bacillus thuringiensis* endotoxin, confers *Spodoptera* resistance in alfalfa and tobacco. Proc. Natl. Acad. Sci. USA, v. 93, p. 15012-15017, 1996), consists of the following stages: (1) Analysis of the sequence and chemical synthesis of the oligonucleotides with the modifications to be introduced; (2) Production of simple DNA strand of the gene sequence, and which will be used as template in the subsequent stage; (3) Annealing of the oligonucleotides with the single DNA strand template, partially complementary, derived from the original gene, and the ligation of the oligos using DNA ligase; (4) Selective amplification and synthesis of the second strand of the synthetic DNA by PCR, with complementary oligonucleotides only to the synthetic DNA; (5) Assembly of the gene, subcloning and sequencing.

Table 3 shows the modifications introduced into the nucleotide sequence of the synthetic cry8Ka1 gene. The table also shows the parameters taken into consideration for sequence modifications.

Modifications of the embodiments presented herein, related with the present invention, may be idealized by specialists in the art to which this invention refers, based on the teachings disclosed in the present description and respective drawings. Therefore, it is understood that the invention is not limited to the embodiments specifically disclosed and any modifications and other embodiments may be included within the scope of the invention disclosed herein.

All the publications and patent applications mentioned in the specification are indicative of the state of the art to which this invention pertains. All the publications and the patent applications are incorporated herein by reference.

The invention claimed is:

1. A nucleic acid molecule, wherein said nucleic acid molecule comprises a polynucleotide sequence encoding a protein having at least 95% identity to SEQ ID NO: 2 and which has activity on insect-pests, linked to a heterologous nucleotide sequence.

2. The nucleic acid molecule according to claim 1, wherein the insect-pest is boll weevil.

3. An isolated nucleic acid molecule comprising the nucleotide sequence of SEQ ID NO: 3.

4. A genic construct comprising:

a) a polynucleotide comprising the sequence of SEQ ID NO: 3; and b) an active promoter, operably linked to the polynucleotide defined in (a).

5. A vector comprising the nucleic acid molecule according to claim 1.

6. The vector according to claim 5, wherein said vector is capable of promoting the expression of said protein.

7. A transgenic cell containing an optimized polynucleotide sequence for expression in plants, wherein the polynucleotide comprises the sequence of SEQ ID NO: 3.

8. The transgenic cell according to claim 7, wherein the cell is a plant cell.

9. The transgenic cell according to claim 7, wherein the cell is a microbial cell.

10. A method of obtaining a transgenic cell, comprising the following steps:

a) transforming a cell with the genic construct of claim 4; and b) regenerating the transformed cell containing a genic construct of interest stably inserted into its genome, under suitable growth conditions in cell culture; and c) expressing the genic product of the construct inserted into the regenerated cell.

11. The method according to claim 10, wherein the cell is a microorganism.

12. The method according to claim 11, wherein the microorganism is a root-colonizing bacteria.

13. The method according to claim 10, wherein the cell is a plant cell.

14. A method of obtaining a transgenic plant comprising the following steps:

a) transforming a plant cell with the genic construct of claim 4;

b) cultivating the transformed cell containing a genic construct of interest stably inserted into its genome under suitable growth conditions in cell culture; and c) regenerating a transgenic plant expressing the product of the construct inserted from the transformed cell.

15. The method according to claim 14, wherein the plant is monocot or dicot.

16. The method according to claim 15, wherein the dicot is a cotton plant.

17. A method of obtaining transgenic strains resistant to an insect pest, comprising the following steps:

a) transforming a crop of interest with the genic construct of claim 4;

b) regenerating transgenic strains containing said construct stably incorporated into their genomes;

c) selecting the transgenic strains with the highest expression levels of δ-endotoxin of the invention.

18. The transgenic cell according to claim 9, wherein the transgenic microbial cell is a species of the genus *Rhizobium.*

* * * * *